US009675593B2

(12) United States Patent
Buckman et al.

(10) Patent No.: US 9,675,593 B2
(45) Date of Patent: Jun. 13, 2017

(54) ANTI-FIBROTIC PYRIDINONES

(71) Applicant: InterMune, Inc., South San Francisco, CA (US)

(72) Inventors: Brad Owen Buckman, Oakland, CA (US); John Beamond Nicholas, Redwood City, CA (US); Johnnie Y. Ramphal, Union City, CA (US); Kumaraswamy Emayan, Albany, CA (US); Scott D. Seiwert, Seattle, WA (US)

(73) Assignee: INTERMUNE, Inc., Brisbane, CA (US)

( * ) Notice: Subject to any disclaimer, the term of this patent is extended or adjusted under 35 U.S.C. 154(b) by 0 days.

(21) Appl. No.: 15/162,214

(22) Filed: May 23, 2016

(65) Prior Publication Data
US 2016/0263090 A1 Sep. 15, 2016

Related U.S. Application Data

(62) Division of application No. 14/043,121, filed on Oct. 1, 2013, now Pat. No. 9,359,379.

(60) Provisional application No. 61/872,157, filed on Aug. 30, 2013, provisional application No. 61/777,499, filed on Mar. 12, 2013, provisional application No. 61/709,075, filed on Oct. 2, 2012.

(51) Int. Cl.
| | |
|---|---|
| *A61K 31/437* | (2006.01) |
| *C07D 513/04* | (2006.01) |
| *C07D 495/04* | (2006.01) |
| *C07D 211/86* | (2006.01) |
| *C07D 401/04* | (2006.01) |
| *C07D 221/04* | (2006.01) |
| *C07D 471/04* | (2006.01) |
| *C07D 498/04* | (2006.01) |
| *C07D 295/125* | (2006.01) |
| *C07D 401/14* | (2006.01) |
| *C07D 405/14* | (2006.01) |
| *C07D 413/14* | (2006.01) |
| *C07D 223/10* | (2006.01) |
| *C07D 405/04* | (2006.01) |
| *C07D 409/14* | (2006.01) |
| *C07D 413/04* | (2006.01) |
| *C07D 417/04* | (2006.01) |
| *C07D 213/64* | (2006.01) |
| *C07D 217/24* | (2006.01) |
| *A61K 9/00* | (2006.01) |

(52) U.S. Cl.
CPC ............ *A61K 31/437* (2013.01); *A61K 9/007* (2013.01); *C07D 211/86* (2013.01); *C07D 213/64* (2013.01); *C07D 217/24* (2013.01); *C07D 221/04* (2013.01); *C07D 223/10* (2013.01); *C07D 295/125* (2013.01); *C07D 401/04* (2013.01); *C07D 401/14* (2013.01); *C07D 405/04* (2013.01); *C07D 405/14* (2013.01); *C07D 409/14* (2013.01); *C07D 413/04* (2013.01); *C07D 413/14* (2013.01); *C07D 417/04* (2013.01); *C07D 471/04* (2013.01); *C07D 495/04* (2013.01); *C07D 498/04* (2013.01); *C07D 513/04* (2013.01)

(58) Field of Classification Search
CPC .................................................... A61K 31/437
USPC ........................................................ 514/303
See application file for complete search history.

(56) References Cited

U.S. PATENT DOCUMENTS

| | | | |
|---|---|---|---|
| 3,014,034 | A | 12/1961 | Druey et al. |
| 3,622,340 | A | 11/1971 | Lamon |
| 3,759,924 | A | 9/1973 | Jeanmart et al. |
| 3,839,346 | A | 10/1974 | Gadekar et al. |
| 3,974,281 | A | 8/1976 | Gadekar |
| 4,042,699 | A | 8/1977 | Gadekar |
| 4,052,509 | A | 10/1977 | Gadekar |
| 4,256,640 | A | 3/1981 | Makisumi et al. |
| 4,258,052 | A | 3/1981 | Yu et al. |
| 4,325,863 | A | 4/1982 | Hinsken et al. |
| 4,397,854 | A | 8/1983 | Sircar |
| 4,404,203 | A | 9/1983 | Sircar |
| 4,473,696 | A | 9/1984 | Hartmann et al. |
| 4,576,942 | A | 3/1986 | Youssefyeh |
| 4,645,839 | A | 2/1987 | Kruse et al. |
| 4,650,804 | A | 3/1987 | Kitaura et al. |
| 4,698,349 | A | 10/1987 | Kitaura et al. |
| 4,820,309 | A | 4/1989 | Holliger |
| 4,898,654 | A | 2/1990 | Toda et al. |
| 5,019,365 | A | 5/1991 | Bedell |
| 5,077,142 | A | 12/1991 | Sakon et al. |
| 5,080,710 | A | 1/1992 | Rueb et al. |
| 5,167,941 | A | 12/1992 | Bedell |
| 5,241,065 | A | 8/1993 | Berger et al. |
| 5,310,562 | A | 5/1994 | Margolin |

(Continued)

FOREIGN PATENT DOCUMENTS

| | | |
|---|---|---|
| AT | 333774 B | 12/1976 |
| AU | 4610372 | 3/1974 |

(Continued)

OTHER PUBLICATIONS

CAS Database Accession No. 2000:723577, "Electroluminescent devices"; Daigo Aoki ; Dai Nippon Printing Co., Ltd., Japan; XP-002756228; 1 page.

(Continued)

*Primary Examiner* — Niloofar Rahmani
(74) *Attorney, Agent, or Firm* — Marshall, Gerstein & Borun LLP

(57) ABSTRACT

Disclosed are pyridinone compounds, method for preparing these compounds, and methods for treating fibrotic disorders.

24 Claims, No Drawings

(56) References Cited

U.S. PATENT DOCUMENTS

| | | |
|---|---|---|
| 5,356,904 A | 10/1994 | Freidinger et al. |
| 5,401,738 A | 3/1995 | Mederski et al. |
| 5,457,099 A | 10/1995 | Shogaki et al. |
| 5,466,697 A | 11/1995 | Wilhelm et al. |
| 5,518,729 A | 5/1996 | Margolin |
| 5,543,521 A | 8/1996 | Chan et al. |
| 5,552,409 A | 9/1996 | Michelotti et al. |
| 5,716,632 A | 2/1998 | Margolin |
| 5,719,155 A | 2/1998 | Cho et al. |
| 5,731,106 A | 3/1998 | Tsutsumi et al. |
| 5,741,793 A | 4/1998 | Young et al. |
| 5,808,015 A | 9/1998 | Hamprecht |
| 5,817,700 A | 10/1998 | Dube et al. |
| 5,859,041 A | 1/1999 | Liverton et al. |
| 5,962,478 A | 10/1999 | Margolin |
| 6,090,822 A | 7/2000 | Margolin |
| 6,114,353 A | 9/2000 | Margolin |
| 6,117,973 A | 9/2000 | Batz et al. |
| 6,174,901 B1 | 1/2001 | Mantlo et al. |
| 6,225,052 B1 | 5/2001 | Batz et al. |
| 6,265,350 B1 | 7/2001 | Schnatterer et al. |
| 6,300,349 B1 | 10/2001 | Margolin |
| 6,307,047 B1 | 10/2001 | Black et al. |
| 6,509,354 B1 | 1/2003 | Toriyabe et al. |
| 6,521,656 B1 | 2/2003 | Kaneko et al. |
| 6,551,963 B1 | 4/2003 | Linker et al. |
| 6,586,447 B1 | 7/2003 | Lyssikatos et al. |
| 6,602,826 B1 | 8/2003 | Andree et al. |
| 6,750,232 B2 | 6/2004 | Harada et al. |
| 6,949,571 B2 | 9/2005 | Nagato et al. |
| 7,067,540 B2 | 6/2006 | Devadas et al. |
| 7,728,013 B2 | 6/2010 | Blatt et al. |
| 7,825,133 B2 | 11/2010 | Yi |
| 7,939,549 B2 | 5/2011 | Nagato et al. |
| 8,377,932 B2 | 2/2013 | Hu et al. |
| 8,741,936 B2 | 6/2014 | Blatt et al. |
| 8,969,347 B2 | 3/2015 | Kossen et al. |
| 2002/0077486 A1 | 6/2002 | Scarborough et al. |
| 2003/0065175 A1 | 4/2003 | Natsan et al. |
| 2003/0162130 A1 | 8/2003 | Murota |
| 2003/0194748 A1 | 10/2003 | Nagasaki |
| 2003/0199692 A1 | 10/2003 | Biediger et al. |
| 2003/0220368 A1 | 11/2003 | Ozaki et al. |
| 2004/0006082 A1 | 1/2004 | Harada et al. |
| 2004/0014986 A1 | 1/2004 | Hendel et al. |
| 2004/0023973 A1 | 2/2004 | Nagato et al. |
| 2004/0048902 A1 | 3/2004 | Kiyonaka et al. |
| 2004/0058964 A1 | 3/2004 | Devadas et al. |
| 2004/0063955 A1 | 4/2004 | Biediger et al. |
| 2004/0082619 A1 | 4/2004 | Tada et al. |
| 2004/0097560 A1 | 5/2004 | Warshakoon et al. |
| 2004/0102494 A1 | 5/2004 | Selvakumar et al. |
| 2004/0142950 A1 | 7/2004 | Bunker et al. |
| 2004/0157738 A1 | 8/2004 | Tsukamoto et al. |
| 2004/0180906 A1 | 9/2004 | Flynn et al. |
| 2004/0235886 A1 | 11/2004 | Charifson et al. |
| 2004/0259864 A1 | 12/2004 | Geneste et al. |
| 2004/0259865 A1 | 12/2004 | Harada et al. |
| 2005/0004149 A1 | 1/2005 | Harada et al. |
| 2005/0020594 A1 | 1/2005 | Hepperle et al. |
| 2005/0038247 A1 | 2/2005 | Charifson et al. |
| 2005/0054631 A1 | 3/2005 | Jiang et al. |
| 2005/0065144 A1 | 3/2005 | Feng et al. |
| 2005/0101590 A1 | 5/2005 | Yasui et al. |
| 2005/0130943 A1 | 6/2005 | Wallace et al. |
| 2005/0130976 A1 | 6/2005 | Wallace et al. |
| 2005/0153941 A1 | 7/2005 | Miyabayashi et al. |
| 2005/0153942 A1 | 7/2005 | Wallace et al. |
| 2005/0176775 A1 | 8/2005 | Devadas et al. |
| 2005/0245581 A1 | 11/2005 | Nagato et al. |
| 2005/0250782 A1 | 11/2005 | Marlow et al. |
| 2005/0256123 A1 | 11/2005 | Marlow et al. |
| 2005/0256136 A1 | 11/2005 | Charifson et al. |
| 2005/0288286 A1 | 12/2005 | Flynn et al. |
| 2006/0025337 A1 | 2/2006 | Sinclair et al. |
| 2006/0025424 A1 | 2/2006 | Charifson et al. |
| 2006/0069260 A1 | 3/2006 | Zhang et al. |
| 2006/0084135 A1 | 4/2006 | Howitz et al. |
| 2006/0100193 A1 | 5/2006 | Zhu et al. |
| 2006/0111355 A1 | 5/2006 | Garrick et al. |
| 2006/0160862 A1 | 7/2006 | Charrier et al. |
| 2006/0189616 A1 | 8/2006 | Pelletier et al. |
| 2006/0189617 A1 | 8/2006 | Pelletier et al. |
| 2006/0211577 A1 | 9/2006 | Hamprecht et al. |
| 2006/0247269 A1 | 11/2006 | Brookings et al. |
| 2006/0258861 A1 | 11/2006 | Anderskewitz et al. |
| 2006/0287319 A1 | 12/2006 | Jiang et al. |
| 2007/0037808 A1 | 2/2007 | Flynn et al. |
| 2007/0037822 A1 | 2/2007 | Letourneau et al. |
| 2007/0037973 A1 | 2/2007 | Momiyama et al. |
| 2007/0049624 A1 | 3/2007 | Yi |
| 2007/0092488 A1 | 4/2007 | Strieter et al. |
| 2007/0105890 A1 | 5/2007 | Nakahira et al. |
| 2007/0112038 A1 | 5/2007 | Marlow et al. |
| 2007/0117841 A1 | 5/2007 | Ozes et al. |
| 2007/0142640 A1 | 6/2007 | Arimoto et al. |
| 2007/0149513 A1 | 6/2007 | Chen et al. |
| 2007/0179165 A1 | 8/2007 | Gyorkos et al. |
| 2007/0185092 A1 | 8/2007 | Zhu et al. |
| 2007/0191336 A1 | 8/2007 | Flynn et al. |
| 2007/0219182 A1 | 9/2007 | Lubisch et al. |
| 2007/0259924 A1 | 11/2007 | Song et al. |
| 2007/0265308 A1 | 11/2007 | Nakai et al. |
| 2008/0020010 A1 | 1/2008 | Nair et al. |
| 2008/0081825 A1 | 4/2008 | Nakai et al. |
| 2008/0103139 A1 | 5/2008 | Ishizuka et al. |
| 2008/0114033 A1 | 5/2008 | Borzilleri et al. |
| 2008/0139557 A1 | 6/2008 | Blomgren et al. |
| 2008/0161361 A1 | 7/2008 | Wu et al. |
| 2008/0234332 A1 | 9/2008 | Cai et al. |
| 2008/0249090 A1 | 10/2008 | Hu et al. |
| 2008/0255083 A1 | 10/2008 | Stenkamp et al. |
| 2008/0269287 A1 | 10/2008 | Ohtake et al. |
| 2008/0280917 A1 | 11/2008 | Albrecht et al. |
| 2008/0280930 A1 | 11/2008 | Yao |
| 2008/0306053 A1 | 12/2008 | Tachdjian et al. |
| 2008/0306093 A1 | 12/2008 | Servant et al. |
| 2008/0312284 A1 | 12/2008 | Omae et al. |
| 2008/0319026 A1 | 12/2008 | Gant et al. |
| 2009/0023702 A1 | 1/2009 | Wacker et al. |
| 2009/0029994 A1 | 1/2009 | Nakamura et al. |
| 2009/0030017 A1 | 1/2009 | Hanada et al. |
| 2009/0030036 A1 | 1/2009 | Dalton et al. |
| 2009/0042919 A1 | 2/2009 | Wacker et al. |
| 2009/0088574 A1 | 4/2009 | Urawa et al. |
| 2009/0131485 A1 | 5/2009 | Liu et al. |
| 2009/0170861 A1 | 7/2009 | Ting et al. |
| 2009/0246198 A1 | 10/2009 | Dong et al. |
| 2009/0247566 A1 | 10/2009 | Kornienko et al. |
| 2009/0318455 A1 | 12/2009 | Kossen et al. |
| 2010/0063104 A1 | 3/2010 | Nakai et al. |
| 2010/0120862 A1 | 5/2010 | Tafesse |
| 2010/0137317 A1 | 6/2010 | Ripka et al. |
| 2010/0190731 A1 | 7/2010 | Olgin et al. |
| 2010/0197651 A1 | 8/2010 | Taniguchi et al. |
| 2010/0222592 A1 | 9/2010 | Takabe et al. |
| 2010/0233710 A1 | 9/2010 | McDougall et al. |
| 2010/0240704 A1 | 9/2010 | Blatt et al. |
| 2010/0266717 A1 | 10/2010 | Asolkar et al. |
| 2010/0267767 A1 | 10/2010 | Narayanan et al. |
| 2010/0298293 A1 | 11/2010 | Allerheiligen et al. |
| 2010/0305326 A1 | 12/2010 | Sem |
| 2011/0009407 A1 | 1/2011 | Xu et al. |
| 2011/0034495 A1 | 2/2011 | Seiwert et al. |
| 2011/0067612 A1 | 3/2011 | Ito et al. |
| 2011/0105509 A1 | 5/2011 | Kaila et al. |
| 2011/0144164 A1 | 6/2011 | Khanzhin et al. |
| 2011/0172277 A1 | 7/2011 | Bradford et al. |
| 2011/0224265 A1 | 9/2011 | Magana Castro et al. |
| 2012/0014917 A1 | 1/2012 | Kossen et al. |
| 2012/0015984 A1 | 1/2012 | Radhakrishnan et al. |
| 2012/0016133 A1 | 1/2012 | Pyles et al. |
| 2012/0046321 A1 | 2/2012 | Olgin et al. |
| 2012/0077850 A1 | 3/2012 | Bradford et al. |

(56) References Cited

U.S. PATENT DOCUMENTS

| | | |
|---|---|---|
| 2012/0129859 A1 | 5/2012 | Hu et al. |
| 2012/0142688 A1 | 6/2012 | Hu et al. |
| 2012/0149698 A1 | 6/2012 | Gottschling et al. |
| 2012/0192861 A1 | 8/2012 | Surber |
| 2012/0225896 A1 | 9/2012 | Miura et al. |
| 2012/0258924 A1 | 10/2012 | Blatt et al. |
| 2013/0102597 A1 | 4/2013 | Kossen et al. |
| 2013/0252934 A1 | 9/2013 | Blake et al. |
| 2013/0310424 A1 | 11/2013 | Surber et al. |
| 2014/0094456 A1 | 4/2014 | Buckman et al. |
| 2014/0228310 A1 | 8/2014 | Blatt et al. |
| 2014/0235637 A1 | 8/2014 | Kossen et al. |
| 2015/0266899 A1 | 9/2015 | Buckman et al. |

FOREIGN PATENT DOCUMENTS

| | | | |
|---|---|---|---|
| CA | 1085857 A | | 9/1980 |
| CA | 2603763 A1 | | 10/2006 |
| CH | 312530 A | | 12/1955 |
| CH | 312531 A | | 12/1955 |
| CH | 333366 | | 10/1958 |
| CN | 1349982 | | 5/2002 |
| CN | 1386737 | | 12/2002 |
| CN | 1417209 | | 5/2003 |
| CN | 1676518 A | | 10/2005 |
| CN | 1817862 | | 8/2006 |
| CN | 1927923 | | 3/2007 |
| CN | 1962642 A | | 5/2007 |
| CN | 101235030 | | 8/2008 |
| DE | 1070639 | | 4/1964 |
| DE | 2112026 A1 | | 9/1971 |
| DE | 2143744 A1 | | 3/1973 |
| DE | 2557342 A1 | | 6/1977 |
| DE | 2707268 A1 | | 8/1978 |
| DE | 149666 A1 | | 7/1981 |
| DE | 4423934 A1 | | 3/1995 |
| DE | 19754348 A1 | | 6/1998 |
| DE | 19821263 A1 | | 11/1998 |
| DE | 19726241 A1 | | 12/1998 |
| DE | 19729061 | | 1/1999 |
| DE | 19918725 A1 | | 10/2000 |
| DE | 10024938 | | 11/2001 |
| DE | 10345648 A1 | | 4/2005 |
| EP | 0104860 A1 | | 4/1984 |
| EP | 0241006 A2 | | 10/1987 |
| EP | 0259048 A2 | | 3/1988 |
| EP | 0311010 A2 | | 4/1989 |
| EP | 0319957 A2 | | 6/1989 |
| EP | 0381374 A1 | | 8/1990 |
| EP | 0393936 A1 | | 10/1990 |
| EP | 0409435 A1 | | 1/1991 |
| EP | 0478195 A1 | | 4/1992 |
| EP | 0531578 A1 | | 3/1993 |
| EP | 0548680 A1 | | 6/1993 |
| EP | 0577325 A1 | | 1/1994 |
| EP | 0579059 A1 | | 1/1994 |
| EP | 0602515 A1 | | 6/1994 |
| EP | 0626377 A1 | | 11/1994 |
| EP | 0648760 A2 | | 4/1995 |
| EP | 0733629 A1 | | 9/1996 |
| EP | 0738716 A2 | | 10/1996 |
| EP | 0760208 A2 | | 3/1997 |
| EP | 0835865 A1 | | 4/1998 |
| EP | 0856255 A2 | | 8/1998 |
| EP | 1186318 A2 | | 3/2002 |
| EP | 1213288 A1 | | 6/2002 |
| EP | 1400243 A1 | | 3/2004 |
| EP | 1544194 A1 | | 6/2005 |
| FR | 2046068 A5 | | 3/1971 |
| FR | 2774986 A1 | | 8/1999 |
| FR | 2797629 A1 | | 2/2001 |
| GB | 0788393 | | 1/1958 |
| GB | 0889317 | | 2/1962 |
| GB | 1388001 A | | 3/1975 |
| GB | 1458048 A | | 12/1976 |
| GB | 1458049 A | | 12/1976 |
| GB | 1596887 A | | 9/1981 |
| JP | 42002264 | | 2/1967 |
| JP | 51128438 A | | 11/1976 |
| JP | 57021388 A | | 2/1982 |
| JP | 57077671 A | | 5/1982 |
| JP | 63290821 A | | 11/1988 |
| JP | 3043744 | | 2/1991 |
| JP | 4223457 A | | 8/1992 |
| JP | 6256187 A | | 9/1994 |
| JP | 7128793 A | | 5/1995 |
| JP | 7233072 A | | 9/1995 |
| JP | 7295165 A | | 11/1995 |
| JP | 7295166 A | | 11/1995 |
| JP | 8134371 A | | 5/1996 |
| JP | H08-510251 | | 10/1996 |
| JP | 9244235 A | | 9/1997 |
| JP | 9249567 A | | 9/1997 |
| JP | 9319023 A | | 12/1997 |
| JP | 11049755 A | | 2/1999 |
| JP | H11-501911 | | 2/1999 |
| JP | 11180952 A | | 7/1999 |
| JP | 2002371078 | | 12/2002 |
| JP | 2003012645 A | | 1/2003 |
| JP | 2003238611 A | | 8/2003 |
| JP | 2003261535 A | | 9/2003 |
| JP | 2004269469 A | | 9/2004 |
| JP | 2004315594 A | | 11/2004 |
| JP | 2004359641 | | 12/2004 |
| JP | 2005013152 A | | 1/2005 |
| JP | 2005145882 A | | 6/2005 |
| JP | 2005255675 A | | 9/2005 |
| JP | 2006142666 A | | 6/2006 |
| JP | 2007063268 A | | 3/2007 |
| JP | 2007145819 | | 6/2007 |
| JP | 2008039883 | | 2/2008 |
| JP | 2008076948 | | 4/2008 |
| JP | 2008214225 A | | 9/2008 |
| KR | 20080045538 A | | 5/2008 |
| WO | WO 91/14674 | | 10/1991 |
| WO | WO 92/13451 | | 8/1992 |
| WO | WO 92/20642 | | 11/1992 |
| WO | WO 92/20816 | | 11/1992 |
| WO | WO 93/21185 | | 10/1993 |
| WO | WO 93/23404 | | 11/1993 |
| WO | WO 94/17059 | | 8/1994 |
| WO | WO 94/26249 | | 11/1994 |
| WO | WO 95/16712 | | 6/1995 |
| WO | WO 95/18128 | | 7/1995 |
| WO | WO 96/18770 | | 6/1996 |
| WO | WO 96/27374 | | 9/1996 |
| WO | WO 96/33994 | | 10/1996 |
| WO | WO 97/05109 | | 2/1997 |
| WO | WO 97/05137 | | 2/1997 |
| WO | WO 97/10712 | | 3/1997 |
| WO | WO 97/29107 | | 8/1997 |
| WO | WO 97/36863 | | 10/1997 |
| WO | WO 97/41830 | | 11/1997 |
| WO | WO 98/13361 | | 4/1998 |
| WO | WO 98/29119 | | 7/1998 |
| WO | WO 98/51772 | | 11/1998 |
| WO | WO 98/52948 | | 11/1998 |
| WO | WO 99/02501 | | 1/1999 |
| WO | WO 99/05123 | | 2/1999 |
| WO | WO 99/05125 | | 2/1999 |
| WO | WO 99/05913 | | 2/1999 |
| WO | WO 99/10331 | | 3/1999 |
| WO | WO 99/10332 | | 3/1999 |
| WO | WO 99/12903 | | 3/1999 |
| WO | WO 99/21837 | | 5/1999 |
| WO | WO 99/26944 | | 6/1999 |
| WO | WO 99/28313 | | 6/1999 |
| WO | WO 99/32448 | | 7/1999 |
| WO | WO 99/38857 | | 8/1999 |
| WO | WO 99/47140 | | 9/1999 |
| WO | WO 99/50263 | | 10/1999 |
| WO | WO 99/52878 | | 10/1999 |
| WO | WO 99/55676 | | 11/1999 |
| WO | WO 99/62900 | | 12/1999 |

(56) References Cited

FOREIGN PATENT DOCUMENTS

| | | |
|---|---|---|
| WO | WO 00/16775 | 3/2000 |
| WO | WO 00/25789 | 5/2000 |
| WO | WO 00/44381 | 8/2000 |
| WO | WO 00/68188 | 11/2000 |
| WO | WO 01/12600 | 2/2001 |
| WO | WO 01/56992 | 8/2001 |
| WO | WO 01/57019 | 8/2001 |
| WO | WO 01/57021 | 8/2001 |
| WO | WO 01/57037 | 8/2001 |
| WO | WO 01/58448 | 8/2001 |
| WO | WO 01/62253 | 8/2001 |
| WO | WO 01/70746 | 9/2001 |
| WO | WO 01/72708 | 10/2001 |
| WO | WO 02/06244 | 1/2002 |
| WO | WO 02/22587 | 3/2002 |
| WO | WO 02/24650 | 3/2002 |
| WO | WO 02/40448 | 5/2002 |
| WO | WO 02/067675 | 9/2002 |
| WO | WO 02/085858 | 10/2002 |
| WO | WO 02/090334 | 11/2002 |
| WO | WO 02/098853 | 12/2002 |
| WO | WO 03/014087 | 2/2003 |
| WO | WO 03/033502 | 4/2003 |
| WO | WO 03/035650 | 5/2003 |
| WO | WO 03/045912 | 6/2003 |
| WO | WO 03/047347 | 6/2003 |
| WO | WO 03/047577 | 6/2003 |
| WO | WO 03/059871 | 7/2003 |
| WO | WO 03/059891 | 7/2003 |
| WO | WO 03/068230 | 8/2003 |
| WO | WO 03/076405 | 9/2003 |
| WO | WO 03/082265 | 10/2003 |
| WO | WO 03/093273 | 11/2003 |
| WO | WO 03/097062 | 11/2003 |
| WO | WO 03/106452 | 12/2003 |
| WO | WO 2004/000355 | 12/2003 |
| WO | WO 2004/000846 | 12/2003 |
| WO | WO 2004/005286 | 1/2004 |
| WO | WO 2004/006906 | 1/2004 |
| WO | WO 2004/009560 | 1/2004 |
| WO | WO 2004/014859 | 2/2004 |
| WO | WO 2004/014892 | 2/2004 |
| WO | WO 2004/019863 | 3/2004 |
| WO | WO 2004/024078 | 3/2004 |
| WO | WO 2004/024152 | 3/2004 |
| WO | WO 2004/031145 | 4/2004 |
| WO | WO 2004/031188 | 4/2004 |
| WO | WO 2004/037159 | 5/2004 |
| WO | WO 2004/048314 | 6/2004 |
| WO | WO 2004/058256 | 7/2004 |
| WO | WO 2004/060306 | 7/2004 |
| WO | WO 2004/072033 | 8/2004 |
| WO | WO 2004/073628 | 9/2004 |
| WO | WO 2004/074282 | 9/2004 |
| WO | WO 2004/078174 | 9/2004 |
| WO | WO 2004/103296 | 12/2004 |
| WO | WO 2004/105684 | 12/2004 |
| WO | WO 2004/110245 | 12/2004 |
| WO | WO 2004/113347 | 12/2004 |
| WO | WO 2005/000227 | 1/2005 |
| WO | WO 2005/000818 | 1/2005 |
| WO | WO 2005/002672 | 1/2005 |
| WO | WO 2005/007632 | 1/2005 |
| WO | WO 2005/012288 | 2/2005 |
| WO | WO 2005/013917 | 2/2005 |
| WO | WO 2005/018557 | 3/2005 |
| WO | WO 2005/026123 | 3/2005 |
| WO | WO 2005/026124 | 3/2005 |
| WO | WO 2005/039598 | 5/2005 |
| WO | WO 2005/040758 | 5/2005 |
| WO | WO 2005/073222 | 8/2005 |
| WO | WO 2005/075438 | 8/2005 |
| WO | WO 2005/085200 | 9/2005 |
| WO | WO 2005/090294 | 9/2005 |
| WO | WO 2005/096784 | 10/2005 |
| WO | WO 2005/097750 | 10/2005 |
| WO | WO 2005/099688 | 10/2005 |
| WO | WO 2005/105743 | 11/2005 |
| WO | WO 2005/105790 | 11/2005 |
| WO | WO 2005/123687 | 12/2005 |
| WO | WO 2006/004107 | 1/2006 |
| WO | WO 2006/011024 | 2/2006 |
| WO | WO 2006/017443 | 2/2006 |
| WO | WO 2006/020145 | 2/2006 |
| WO | WO 2006/026305 | 3/2006 |
| WO | WO 2006/030032 | 3/2006 |
| WO | WO 2006/032631 | 3/2006 |
| WO | WO 2006/038734 | 4/2006 |
| WO | WO 2006/044405 | 4/2006 |
| WO | WO 2006/055918 | 5/2006 |
| WO | WO 2006/056427 | 6/2006 |
| WO | WO 2006/060122 | 6/2006 |
| WO | WO 2006/066079 A2 | 6/2006 |
| WO | WO 2006/072037 | 7/2006 |
| WO | WO 2006/072039 | 7/2006 |
| WO | WO 2006/076681 | 7/2006 |
| WO | WO 2006/079021 | 7/2006 |
| WO | WO 2006/107859 | 10/2006 |
| WO | WO 2006/107860 | 10/2006 |
| WO | WO 2006/108354 | 10/2006 |
| WO | WO 2006/116713 | 11/2006 |
| WO | WO 2006/122154 | 11/2006 |
| WO | WO 2006/129076 | 12/2006 |
| WO | WO 2006/131186 | 12/2006 |
| WO | WO 2006/133147 | 12/2006 |
| WO | WO 2006/138418 | 12/2006 |
| WO | WO 2007/006591 | 1/2007 |
| WO | WO 2007/008548 | 1/2007 |
| WO | WO 2007/024021 | 3/2007 |
| WO | WO 2007/026950 | 3/2007 |
| WO | WO 2007/037543 | 4/2007 |
| WO | WO 2007/044796 | 4/2007 |
| WO | WO 2007/048065 | 4/2007 |
| WO | WO 2007/053685 | 5/2007 |
| WO | WO 2007/057329 | 5/2007 |
| WO | WO 2007/058392 | 5/2007 |
| WO | WO 2007/062167 | 5/2007 |
| WO | WO 2007/064797 | 6/2007 |
| WO | WO 2007/088996 | 8/2007 |
| WO | WO 2007/100990 | 9/2007 |
| WO | WO 2007/104034 | 9/2007 |
| WO | WO 2007/107545 | 9/2007 |
| WO | WO 2007/108968 | 9/2007 |
| WO | WO 2007/117482 | 10/2007 |
| WO | WO 2007/117559 | 10/2007 |
| WO | WO 2007/117778 | 10/2007 |
| WO | WO 2007/120842 | 10/2007 |
| WO | WO 2007/127474 | 11/2007 |
| WO | WO 2007/127475 | 11/2007 |
| WO | WO 2007/129040 | 11/2007 |
| WO | WO 2007/139150 | 12/2007 |
| WO | WO 2007/146712 | 12/2007 |
| WO | WO 2007/147297 | 12/2007 |
| WO | WO 2007/148093 | 12/2007 |
| WO | WO 2008/002490 | 1/2008 |
| WO | WO 2008/013838 | 1/2008 |
| WO | WO 2008/016239 | 2/2008 |
| WO | WO 2008/077550 | 3/2008 |
| WO | WO 2008/065428 | 6/2008 |
| WO | WO 2008/068265 | 6/2008 |
| WO | WO 2008/072784 | 6/2008 |
| WO | WO 2008/076562 | 6/2008 |
| WO | WO 2008/079277 | 7/2008 |
| WO | WO 2008/079787 | 7/2008 |
| WO | WO 2008/080056 | 7/2008 |
| WO | WO 2008/086188 | 7/2008 |
| WO | WO 2008/091555 | 7/2008 |
| WO | WO 2008/099000 | 8/2008 |
| WO | WO 2008/103277 | 8/2008 |
| WO | WO 2008/106202 | 9/2008 |
| WO | WO 2008/107480 | 9/2008 |
| WO | WO 2008/110793 | 9/2008 |
| WO | WO 2008/112715 | 9/2008 |
| WO | WO 2008/121407 | 10/2008 |

(56) References Cited

FOREIGN PATENT DOCUMENTS

| WO | WO 2008/121877 | 10/2008 |
|---|---|---|
| WO | WO 2008/124323 | 10/2008 |
| WO | WO 2008/124575 | 10/2008 |
| WO | WO 2008/124582 | 10/2008 |
| WO | WO 2008/132155 | 11/2008 |
| WO | WO 2008/140066 | 11/2008 |
| WO | WO 2008/141119 | 11/2008 |
| WO | WO 2008/144720 | 11/2008 |
| WO | WO 2008/147169 | 12/2008 |
| WO | WO 2008/147170 | 12/2008 |
| WO | WO 2008/157786 | 12/2008 |
| WO | WO 2009/011410 | 1/2009 |
| WO | WO 2009/011411 | 1/2009 |
| WO | WO 2009/011412 | 1/2009 |
| WO | WO 2009/012275 | 1/2009 |
| WO | WO 2009/016118 | 2/2009 |
| WO | WO 2009/026816 | 3/2009 |
| WO | WO 2009/029625 | 3/2009 |
| WO | WO 2009/033703 | 3/2009 |
| WO | WO 2009/035598 | 3/2009 |
| WO | WO 2009/039773 | 4/2009 |
| WO | WO 2009/054543 | 4/2009 |
| WO | WO 2009/054544 | 4/2009 |
| WO | WO 2009/057827 | 5/2009 |
| WO | WO 2009/060835 | 5/2009 |
| WO | WO 2009/073620 | 6/2009 |
| WO | WO 2009/074810 | 6/2009 |
| WO | WO 2009/076529 | 6/2009 |
| WO | WO 2009/082038 | 7/2009 |
| WO | WO 2009/082039 | 7/2009 |
| WO | WO 2009/094427 | 7/2009 |
| WO | WO 2009/097309 | 8/2009 |
| WO | WO 2009/108499 | 9/2009 |
| WO | WO 2009/111785 | 9/2009 |
| WO | WO 2009/124119 | 10/2009 |
| WO | WO 2009/124553 | 10/2009 |
| WO | WO 2009/135299 | 11/2009 |
| WO | WO 2009/142732 | 11/2009 |
| WO | WO 2009/149188 | 12/2009 |
| WO | WO 2009/156484 | 12/2009 |
| WO | WO 2009/158393 | 12/2009 |
| WO | WO 2009/158473 | 12/2009 |
| WO | WO 2010/006191 | 1/2010 |
| WO | WO 2010/009183 | 1/2010 |
| WO | WO 2010/021693 | 2/2010 |
| WO | WO 2010/025087 | 3/2010 |
| WO | WO 2010/027567 | 3/2010 |
| WO | WO 2010/029299 | 3/2010 |
| WO | WO 2010/044885 | 4/2010 |
| WO | WO 2010/048716 | 5/2010 |
| WO | WO 2010/065755 | 6/2010 |
| WO | WO 2010/066028 | 6/2010 |
| WO | WO 2010/068253 | 6/2010 |
| WO | WO 2010/075561 | 7/2010 |
| WO | WO 2010/077680 | 7/2010 |
| WO | WO 2010/080795 | 7/2010 |
| WO | WO 2010/085805 | 7/2010 |
| WO | WO 2010/088177 | 8/2010 |
| WO | WO 2010/104818 | 9/2010 |
| WO | WO 2010/104830 | 9/2010 |
| WO | WO 2010/108652 | 9/2010 |
| WO | WO 2010/126104 | 11/2010 |
| WO | WO 2010/129467 | 11/2010 |
| WO | WO 2010/135470 | 11/2010 |
| WO | WO 2010/141538 | 12/2010 |
| WO | WO 2010/141539 | 12/2010 |
| WO | WO 2010/141540 | 12/2010 |
| WO | WO 2010/141545 | 12/2010 |
| WO | WO 2011/133722 | 10/2011 |
| WO | WO 2012/000595 | 1/2012 |
| WO | WO 2013/018685 | 2/2012 |
| WO | WO 2012/035078 | 3/2012 |
| WO | WO 2012/059041 | 5/2012 |
| WO | WO 2012/075917 | 6/2012 |
| WO | WO 2012/102580 | 8/2012 |
| WO | WO 2012/102583 | 8/2012 |
| WO | WO 2012/106382 | 8/2012 |
| WO | WO 2012/107831 | 8/2012 |
| WO | WO 2012/120195 | 9/2012 |
| WO | WO 2012/122165 | 9/2012 |
| WO | WO 2012/162592 | 11/2012 |
| WO | WO 2012/167600 | 12/2012 |
| WO | WO 2012/175514 | 12/2012 |
| WO | WO 2013/012307 | 1/2013 |
| WO | WO 2013/023250 | 2/2013 |
| WO | WO 2013/142390 | 9/2013 |
| WO | WO 2014/012360 | 1/2014 |
| WO | WO 2014/018668 | 1/2014 |

OTHER PUBLICATIONS

CAS Database Accession No. 2004:117844, "4-Aryl-5-hydroxyisoquinolinones, their preparation, and poly(ADP-ribose) polymerase inhibitors containing them", Asano et al.; Jpn. Kokai Tokkyo Koho, Japan; XP-002756230; 15 pages.

CAS Database Accession No. 2004:252487, "Preparation of 4-(substituted aryl)-5-hydroxyisoquinolinone derivatives aas poly(ADP-ribose) polymerase inhibitors" Shiga et al., Kyorin Pharmaceutical Co., Ltd. Japan; XP-002756231; 30 pages.

CAS Database Accession No. 2010:416736, "New methodologies for the synthesis of 3-acylpyridone metabolites"; Jones RCF et al., Synlett (2010) 4:654-658., XP-002756232; 6 pages.

CAS Database Accession No. 2011:1110104; "A three-component reaction forming naphtyridones—synthesis of lophocladine analogs", Sellstedt M. et al., XP-002756229; 6 pages.

CAS Database Accession No. 2011:1626681; "Method for synthesizing furan '3,2-c]pyridin-4(5h)-one compound", Dong et al., Changun Institute of Applied Chem., XP-002750130; 5 pages.

Chemical Abstracts Services; CAS Registry No. 1243878-27-4; 1,6-Naphthyridin-5(6H)-one, 6,8-bis(1,3-benzodioxol-5-yl)-; Entered Sep. 30, 2010; 1 page.

Chemical Abstracts Services; CAS Registry No. 1243878-50-3; 1,6-Naphthyridin-5(6H)-one, 6,8-bis(2,3-dihydro-1,4-benzodioxin-6-yl)-; Entered Sep. 30, 2010; 1 page.

Chemical Abstracts Services; CAS Registry No. 1401534-66-4; 4-Isopquinolinecarboxamide, 2-(1,3-benzodioxol-5-yl-)-1,2-dihydro-n-(2-methoxyethyl)-1-oxo; Entered Oct. 22, 2012; 1 page.

Chemical Abstracts Services; CAS Registry No. 1401568-76-0; 4-22 Isopquinolinecarboxamide, 2-(benzo[d][1,3]dioxol-5-yl-)-N-isopropyl-1-oxo-1,2-dihydroisoquinoline-4-carboxamide; Entered Oct. 22, 2012; 1 page.

Chemical Abstracts Services; CAS Registry No. 1401579-39-2; methyl 3-(2-(benzo[d][1,3]dioxol-5-yl-)-1-oxo-1,2-dihydroisoquinoline-4-carboxamido)propanoate; Entered Oct. 22, 2012; 1 page.

Chemical Abstracts Services; CAS Registry No. 1401581-78-9; 4-Isoquinolinecarboxomide 2-(1,3-benzodioxol-5-yl)-1,2-dihydro-N-(2-methylpropyl)-1-oxo-; Entered Oct. 22, 2012; 1 page.

Chemical Abstracts Services; CAS Registry No. 1401587-71-0; methyl (2-(benzo[d][1,3]dioxol-5-yl)-1-oxo-1,2-dihydroisoquinoline-4-carbonyl)glycinate; Entered Oct. 22, 2012; 1 page.

Chemical Abstracts Services; CAS Registry No. 1429901-74-5; 4-Isoquinolinecarboxylic acid, 2-(1,3-benzodioxol-5-yl)-1-2-dihydro-1-oxo-; Entered May 3, 2013; 1 page.

Clive et al., "Studies related to furopyridinone antibiotics. Synthesis of 2-epi-CJ-16,170", Tetrahedron (2002) 58: 10243-10250.

Gentile et al., "Identification of 2-(4-pyridyl)thienopyridinones as GSK-3beta inhibitors", Bioorg Med Chem Ltrs. (2011) 21: 4823-4827.

Majumdar et al., "Palladium-Mediated Direct Synthesis of N-Substituted 4-Methyl- and 4-Ethylisoquinolone Derivates", Synthesis, (Aug. 2008) Issue 18, 2991-2995.

Zhang et al., "Convenient Synthesis of 2,7-Naphthyridine Lophocladines A and B and their Analogues", J Comb Chem (2007) 9: 916-919.

Eurasian Office Action dated Feb. 2, 2016 for Application No. 201590477, filed Mar. 30, 2015.

(56) References Cited

OTHER PUBLICATIONS

European Search Report dated Aug. 8, 2016 for Application No. 13843717.3, filed Apr. 29, 2015.
Singapore Search Report and Written Opinion dated Nov. 12, 2015 for Application No. 11201501751R, filed Mar. 9, 2015.
Singapore 2nd Written Opinion dated Jun. 24, 2016 for Application No. 11201501751R, filed Mar. 9, 2015.
Altman et al., Orthogonal Pd-and Cu-based catalyst systems for C- and N-arylation of oxindoles, J Am Chem Soc. (Jul. 2008) 130(29): 9613-9620.
Ammar et al., Cyanoacetanilides Intermediates in Heterocyclic Syntheses. Part 1: A Facile Synthesis of Polysubstituted and Condensed Pyridones. J Chinese Chem Society (2004) 51: 975-981.
Ammar et al., Novel Pirfenidone Analogues: Synthesis of Pyridin-2-ones for the Treatment of Pulmonary Fibrosis, Arch Pharm Chem Life Sci., (Apr. 2006) 339(8): 429-426.
Anonymous, Verfahren zur Hestellung von 6-Arylyridazinon-3 Verbindungen, (Mar. 1999), Research Disclosure No. 311123, The Industry Standard Disclosure Publication Service, Questel Ireland Ltd., pp. 1-5.
Azuma et al., A placebo control and double blind phase II clinical study of pirfenidone in patients with idiopathic pulmonary fibrosis in Japan, Am J Respir Crit Care Med., (2002) 165: A729.
Badger et al., Pharmacological profile of SB 203580, a selective inhibitor of cytokine suppressive binding protein/p38 kinase, in animal models of arthritis, bone resorption, endotoxin shock and immune function. J Pharmacol Exp Ther., (Dec. 1996) 279(3): 1453-1461.
Barluenga et al., Easy Preparation of 2-Methyl-1,3-Dimorpholino-1,3-Butadiene and an Overview of Its Synthetic Applications. Tetrahed Lttrs. (1995) 36(36): 6551-6554.
Beccalli et al., Pd-catalyzed intramolecular cyclization of pyrrolo-2carboxamindes: regiodivergent routes to pyrrolo-pyrazines and pyrrolo-pyridines. Tetrahedron (2005) 61: 1077-1082.
Boehm et al., New Inhibitors of p38 Kinase. Expert Opin Ther Pat (2000), 10(1): 25-37.
Border et al., Transforming growth factor beta in tissue fibrosis, N Engl J Med., (1994) 331(19): 1286-1292.
Brinkman et al., Engagement of Tumor Necrosis Factor (TNF) Receptor 1 Leads to ATF-2- and p38 Mitogen-activated Protein Kinase-dependent TNF-alpha Gene Expression, J Biol Chem., (Oct. 1999) 274(43): 20882-30886.
Buysens et al., Intramolecular Diels-Alder Reactions of 2(1H)-Pyrazinones: Synthesis of New Furo/Pyrano-pyridinones and -pyridines. Tetrahedron (1995) 51(45): 12463-12478.
Cambpell et al., A Novel Mechanism for TNF-alpha Regulation by p38 MAPK: Involvement of NF-kB with Implications for Therapy in Rheumatoid Arthritis, J Immunol., 173(11): 6928-6937.
CAS Registry No. 1011358-02-3, STN Entry Date: Apr. 1, 2008, 1-cyclopoyl-N-[2-(diethylamino)ethyl]-1,2,5,6,7,8-hexahydro-4-hydroxy-2-oxo-3quinolinecarboxamide, 1 page.
CAS Registry No. 1374546-93-6, STN Entry Date: May 25, 2012, 2-cyclopoyl-1,2-dihydro-1-oxo-N-[(1,3,5-trimethyl-1H-pyrazol-4-yl)methyl]-4-isoquinolinecarboxamide, 1 page.
CAS Registry No. 586387-14-6, STN Entry Date: Sep. 16, 2003, 1-Benzyl-4-(benzylthio)-5-methylpyridin-2(1H)-one, 1 page.
Chemical Abstracts Services; CAS Registry No. 102718-41-2; 3,4-Pyridinedicarboxylic acid, 1,6--dihydro-1-(2-hydroxyphenyl)-6-oxo-, 3,4-dimethyl ester; Entered: Jun. 14, 1986; 1 page.
Chemical Abstracts Services; CAS Registry No. 1073610-66-8; 2(1H)-Pyridinone, 1-(3-chlorophenyl)-5-methyl; Entered: Nov. 21, 2008; 1 page.
Chemical Abstracts Services; CAS Registry No. 1076199-03-5; 2(1H)-Pyridinone, 1-[4-(phenylmethoxy) phenyl]; Entered Nov. 26, 2008; 1 page.
Chemical Abstracts Services; CAS Registry No. 1099106-04-3; 2(1H)-Pyridinone, 1-[3-(difluoromethoxy) phenyl]-5-methyl; Entered: Feb. 1, 2009; 1 page.
Chemical Abstracts Services; CAS Registry No. 1099106-08-7; 2(1H)-Pyridinone, 5-methyl-1-[3-(trifluoromethoxy) phenyl]; Entered: Feb. 1, 2009; 1 page.
Chemical Abstracts Services; CAS Registry No. 1099106-10-1; 2(1H)-Pyridinone, 5-ethyl-1-[trifluoromethoxy)phenyl]; Entered: Feb. 1, 2009; 1 page.
Chemical Abstracts Services; CAS Registry No. 1139505-10-4; 4-Pyridinecarbonitrile, 1-[4-chloro-2-fluoro-5-[(1-methyl-2-propyn-1-yl) oxy] phenyl]-1,2-dihydro-2-oxo; Entered: Apr. 27, 2009; 1 page.
Chemical Abstracts Services; CAS Registry No. 1139505-78-4; Acetic acid, 2-[2-chloro-4-fluoro-5-[5-methyl-2-oxo-4-(trifluoromethyl)-1(2H)-pyridinyl]phenoxy', ethyl ester; Entered Apr. 27, 2009; 1 page.
Chemical Abstracts Services; CAS Registry No. 1139505-80-8; 2(1H)-Pyridinone, 1-[4-chloro-2-fluoro-5-[C1-methyl-2-propyn-1-yl) oxy] phenyl]-5-methyl-4-(trifluoromethyl); Entered: Apr. 27, 2009; 1 page.
Chemical Abstracts Services; CAS Registry No. 1139505-81-9; 2(1H)-Pyridinone, 1-[4-chloro-2-fluoro--5-(2-propen-1-yloxy)phenyl]-5-methyl-4-(trifluoromethyl); Entered: Apr. 27, 2009; 1 page.
Chemical Abstracts Services; CAS Registry No. 1139505-83-1; 2(1H)-Pyridinone, 5-chloro-1-[4-chloro-2-fluoro-5-(1-methylethoxy) phenyl]-4-(trifluoromethyl); Entered Apr. 27, 2009; 1 page.
Chemical Abstracts Services; CAS Registry No. 1139505-84-2; 2(1H)-Pyridinone, 5-chloro-1-[4-chloro-2-fluoro-5-[1-methyl-2-propyn-1yl) oxy] phenyl]-4-(trifluoromethyl); Entered: Apr. 27, 2009; 1 page.
Chemical Abstracts Services; CAS Registry No. 1139505-85-3; 2(1H)-Pyridinone, 5-chloro-1-[4-chloro-2-fluoro-5-(2-propen-1-yloxy) phenyl]-4-(trifluoromethyl); Entered Apr. 27, 2009; 1 page.
Chemical Abstracts Services; CAS Registry No. 1139505-86-4; Propanoic acid, 2-[2-chloro-5p[5-chloro-2-oxo-4-(trifluoromethyl)-1(2H)-pyridinyl]-4-fluorophenoxy], ethyl ester; Entered: Apr. 27, 2009; 1 page.
Chemical Abstracts Services; CAS Registry No. 1139505-90-0; 2(1H)-Pyridinone, 1-[4-chloro-2-fluoro-5-(1-methylethoxy) phenyl]-4-(trifluoromethyl); Entered: Apr. 27, 2009; 1 page.
Chemical Abstracts Services; CAS Registry No. 1139505-91-1; 2(1H)-Pyridinone, 1-[4-chloro-2-fluoro-5-(2-propen-1-yloxy) phenyl]-4-(trifluoromethyl); Entered: Feb. 10, 2006; 1 page.
Chemical Abstracts Services; CAS Registry No. 1139505-92-2; 2(1H)-Pyridinone, 1-(4-chloro-2-fluoro-5-[(1-methyl-2-propyn-1-yl) oxy]phenyl]-4-(trifluoromethyl); Entered Apr. 27, 2009; 1 page.
Chemical Abstracts Services; CAS Registry No. 1139506-08-3; Acetic Acid, 2-[2-chloro-4-fluoro-5-[2-oxo-4-(trifluoromethyl)-1(2H)-pyridinyl] phenoxyl], methyl ester; Entered: Apr. 27, 2009; 1 page.
Chemical Abstracts Services; CAS Registry No. 1139506-09-4; Acetic acid, 2-{2-chloro-4-5-[2-oxo-4-(trifluoromethyl)-1(2H)-pyridinyl] phenoxy], ethyl ester; Entered: Apr. 27, 2009; 1 page.
Chemical Abstracts Services; CAS Registry No. 1139506-10-7; Acetic acid, 2-[2-chloro-4-fluoro-5- [2-oxo-4-(trifluoromethyl)-1(2H)-pyridinyl] phenoxy], propyl ester; Entered: Apr. 27, 2009; 1 page.
Chemical Abstracts Services; CAS Registry No. 1139506-11-8; Acetic acid, 2-[2-chloro-4-fluoro-5-[2-oxo-4-(trifluoromethyl)-1(2H)-pyridinyl] phenoxyl', 1-methylethyl ester; Entered: Apr. 27, 2009; 1 page.
Chemical Abstracts Services; CAS Registry No. 1139506-12-9; Propanoic acid, 2-[2-chloro-4-fluoro-5-[2-oxo-4-(trifluoromethyl)-1(2H)-pyridinyl] phenoxy], methyl ester; Entered: Apr. 27, 2009; 1 page.
Chemical Abstracts Services; CAS Registry No. 1139506-13-0; Propanoic acid, 2-[2-chloro-4-fluoro-5-[2-oxo-4-(trifluoromethyl)-1(2H)-pyridinyl] phenoxyl], ethyl ester; Entered: Apr. 27, 2009; 1 page.
Chemical Abstracts Services; CAS Registry No. 1139506-14-1; 2(1H)-Pyridinone, 1-(4-chloro-2-fluoro-5-(methoxymethoxy) phenyl]-4-(trifluoromethyl); Entered: Apr. 27, 2009; 1 page.

(56) References Cited

OTHER PUBLICATIONS

Chemical Abstracts Services; CAS Registry No. 1139506-15-2; 2(1H)-Pyridinone, 1-(4-chloro-2-fluoro-5-hydroxyphenyl)-4-(trifluoromethyl); Entered Apr. 27, 2009; 1 page.
Chemical Abstracts Services; CAS Registry No. 1139506-16-3; 2(1H)-Pyridinone, 1-(4-chloro-2-fluoro-5-phenoxyphenyl)-4-(trifluoromethyl); Entered: Apr. 27, 2009; 1 page.
Chemical Abstracts Services; CAS Registry No. 1139506-17-4; 2(1H)-Pyridinone, 1-[4-chloro-2-fluoro-5-(2-fluoropheoxy)phenyl]-4-(trifluoromethyl); Entered: Apr. 27, 2009; 1 page.
Chemical Abstracts Services; CAS Registry No. 115551-60-5; 2(1H)-Pyridinone, 1-(2,3,4,5,6-pentafluorophenyl)-4-(trifluoromethyl); Entered: Jul. 30, 1988; 1 page.
Chemical Abstracts Services; CAS Registry No. 115551-94-5; 2(1H)-Pyridinone, 1-(4-chloro-2-fluoro-5-hydroxyphenyl)-4-(trifluoromethyl); Entered Apr. 27, 2009; 1 page.
Chemical Abstracts Services; CAS Registry No. 1239505-79-5; Propanoic acid, 2-[2-chloro-4-fluoro-5-[5-methyl-2-oxo-4-(trifluoromethyl)-1(2H)-pyridinyl ]phenoxy], ethyl ester; Entered: Apr. 27, 2009; 1 page.
Chemical Abstracts Services; CAS Registry No. 130879-34-4; 3,4-Pyridinedicarboxylic acid, 5-chloro-1, 6-dihydro-1-(4-methoxyphenyl)-6-0x0, 3,4-dimethyl ester; Entered: Dec. 7, 1990; 1 page.
Chemical Abstracts Services; CAS Registry No. 13179-26-5; 2(1H)-Pyridinone, 1-(4-chlorophenyl); Entered: Nov. 16, 1984; 1 page.
Chemical Abstracts Services; CAS Registry No. 145705-06-2; 2(1H)-Pyridinone, 1-(2-fluoro-4-hydroxyphenyl)-4-(trifluoromethyl); Entered: Feb. 4, 1993; 1 page.
Chemical Abstracts Services; CAS Registry No. 145705-07-3; 2(1H)-Pyridinone, 1-(2-fluoro-4-hydroxyphenyl)-5-methyl-4-(trifluoromethyl); Entered: Feb. 4, 1993; 1 page.
Chemical Abstracts Services; CAS Registry No. 145705-09-5; 2(1H)-Pyridinone, 5-chloro-1-(2-fluoro-4-hydroxyphenyl)-4-(trifluoromethyl phenyl]; Entered: Feb. 4, 1993; 1 page.
Chemical Abstracts Services; CAS Registry No. 145705-10-8; 2(1H)-Pyridinone, 5-bromo-1-(2-fluoro-4-hydroxyphenyl)-4-(trifluoromethyl); Entered: Feb. 4, 1993; 1 page.
Chemical Abstracts Services; CAS Registry No. 145705-11-9; 2(1H)-Pyridinone, 5-ETHYL-1-(2-fluoro-4hydroxyphenyl)-4-(trifluoromethyl); Entered: Feb. 4, 1993; 1 page.
Chemical Abstracts Services; CAS Registry No. 222978-30-5; 2(1H)-Pyridinone, 1-(2-methoxyphenyl); Entered: May 14, 1999; 1 page.
Chemical Abstracts Services; CAS Registry No. 222978-31-6; 2(1H)-Pyridinone, 1-(2-hydroxyphenyl); Entered: May 14, 1999; 1 page.
Chemical Abstracts Services; CAS Registry No. 3512-19-4; 2(1H)-Pyridinone, 1-(3-chloropheyl); Entered: Nov. 16, 1984; 1 page.
Chemical Abstracts Services; CAS Registry No. 3512-20-7; 2(1H)-Pyridinone, 1-(3-bromophenyl); Entered: Nov. 16, 1984; 1 page.
Chemical Abstracts Services; CAS Registry No. 3534-60-9; 2(1H)-Pyridinone, 1-(3-hydroxyphenyl); Entered: Nov. 16, 1984; 1 page.
Chemical Abstracts Services; CAS Registry No. 53427-77-3; 2(1H)-Pyridinone, 1-(4-methoxyphenyl) -5-methyl; Entered: Nov. 16, 1984; 1 page.
Chemical Abstracts Services; CAS Registry No. 53427-80-8; 2(1H)-Pyridinone, 1-(4-chlorophenyl)-5-methyl; Entered: Nov. 16, 1984; 1 page.
Chemical Abstracts Services; CAS Registry No. 60532-42-5; 2(1H)-Pyridinone, 1-(4-fluoropheyl); Entered: Nov. 16, 1984; 1 page.
Chemical Abstracts Services; CAS Registry No. 725256-34-8; 2(1H)-Pyridinone, 1-(3-methoxyphenyl); Entered: Aug. 11, 2004; 1 page.
Chemical Abstracts Services; CAS Registry No. 725256-35-9; 2(1H)-Pyridinone, 1-(3-methoxyphenyl)-5-methyl; Entered: Aug. 11, 2004; 1 page.

Chemical Abstracts Services; CAS Registry No. 725256-36-0; 2(1H)-Pyridinone, 5-chloro-1-(4-methoxyphenyl); Entered: Aug. 11, 2004; American Chemical Society; 1 page.
Chemical Abstracts Services; CAS Registry No. 725256-37-1; 3-Pyridinecarboxylic acid, 1,6-dihydro-1-(3-methoxyphenyl)-6-oxo, ethyl ester; Entered: Aug. 11, 2004; 1 page.
Chemical Abstracts Services; CAS Registry No. 725256-38-2; 2(1H)-Pyridinone, 5-chloro-1-(3-methoxyphenyl); Entered: Aug. 11, 2004; 1 page.
Chemical Abstracts Services; CAS Registry No. 725256-40-6; 2(1H)-Pyridinone, 1-(4-methoxyphenyl); Entered: Aug. 11, 2004; 1 page.
Chemical Abstracts Services; CAS Registry No. 725256-41-7; 2(1H)-Pyridinone, 5-methoxy-1-(4-methoxyphenyl); Entered: Aug. 11, 2004; 1 page.
Chemical Abstracts Services; CAS Registry No. 725256-42-8; 3-Pyridinecarbosylic acid, 1,6-dihydro-1-(4-methoxyphenyl)-64-oxo-, ethyl ester; Entered: Aug. 11, 2004; 1 page.
Chemical Abstracts Services; CAS Registry No. 725256-43-9; 2(1h)-Pyridinone, 5-chloro-1-(4-methoxyphenyl); Entered: Aug. 11, 2004; American Chemical Society; 1 page.
Chemical Abstracts Services; CAS Registry No. 725256-50-8; 2(1H)-Pyridinone, 1-(4-chlorophenyl)-5-methoxy; Entered: Aug. 11, 2004; 1 page.
Chemical Abstracts Services; CAS Registry No. 725256-51-9; 3-Pyridinecarboxylic acid, 1-(4-chlorophenyl)-1,6-dihydro-6-oxo-, ethyl ester; Entered: Aug. 11, 2004; 1 page.
Chemical Abstracts Services; CAS Registry No. 725256-52-0; 2(1H)-Pyridinone, 5-chloro-1-(4-chlorophenyl); Entered: Aug. 11, 2004; 1 page.
Chemical Abstracts Services; CAS Registry No. 766556-75-6; 2(1H)-Pyridinone, 1-(4-iodophenyl); Entered: Oct. 21, 2004; 1 page.
Chemical Abstracts Services; CAS Registry No. 77095-38-6; 3-Pyridinecarboxylic acid, 5-bromo-(5-bromophenyl)-1,6-dihydro-4-methyl-6-oxo; Entered: Nov. 16, 1984; 1 page.
Chemical Abstracts Services; CAS Registry No. 848353-85-5; 2(1H)-Pyridinone, 1-(3-fluorophenyl)-5-methyl; Entered: Apr. 12, 2005; 1 page.
Chemical Abstracts Services; CAS Registry No. 851518-71-3; 2(1H)-Pyridinone, 1-(4-hydoxyphenyl)-5-methyl; Entered: Jun. 2, 2005; 1 page.
Chemical Abstracts Services; CAS Registry No. 859538-51-5; 2(1H)-Pyridinone, 1-(4-hydroxyphenyl); Entered Aug. 11, 2005; 1 page.
Chemical Abstracts Services; CAS Registry No. 873969-21-2; 2(1H)-Pyridinone, 1-(2,5-dimethoxyphenyl); Entered: Feb. 10, 2006; 1 page.
Chemical Abstracts Services; CAS Registry No. 873969-22-3; 2(1H)-Pyridinone, 1-(2,3-dimethoxyphenyl); Entered: Feb. 10, 2006; 1 page.
Chemical Abstracts Services; CAS Registry No. 912570-13-9; 2(1H)-Pyridinone, 1-(3-bromophenyl)-5-methyl; Entered: Nov. 7, 2006; 1 page.
Chen et al., "Synthesis and structure-activity relationship of 5-substituent-2(1H)-pyridone derivatives as anti-fibrosis agents", Bioorg Med Chem Lttrs. (Jan. 2012) 22: 2300-2302.
Dong et al., MAP kinases in the immune response, Annu Rev Immunol., (2002) 20: 55-72.
Eiden et al., 6-Styryl-4-methoxy-2-pyridon-Derivate. Archiv der Pharmazie & Berichte der Deutschen Pharmazeutischen Gesellschaft (1971) 304(10): 723-729.
Elbashir et al., Duplexes of 21-nucleotide RNAs mediate RNA interference in cultured mammalian cells, Nature (2001) 411(6836): 494-498.
English et al., Pharmacological inhibitors of MAPK pathways, Trends Pharmacol Sci., (2002) 23(1): 40-45.
Erian et al., Beta-Enaminonitriles in heterocyclic synthesis; Pyridines, pyrimidines and pyrazoles as antibacterial agents, Scientia Pharmaceutica (Dec. 1999) 67(4): 253-261.
Fitzgerald et al., Structural basis for p38alpha MAP kinase quinazolinone and pyridol-pyrimidine inhibitor specificity, Nat Struct Biol (2003) 10(9): 764-769.

(56) References Cited

OTHER PUBLICATIONS

Fuchs et al., Stability of the ATF2 Transcription Factor is Regulated by Phosphorylation and Dephosphorylation, J Biol Chem., (Apr. 2000), 275(17): 12560-12564.

Furukawa et al., p38 MAPK mediates fibrogenic signal through Smad3 phosphorylation in rat myofibroblasts, Hepatology (2003) 38(4): 879-889.

Gahl et al., Effect of pirfenidone on the pulmonary fibrosis of Hermansky-Pudlak syndrome, Mol Genet Metab., (Jul. 2002) 76(3): 234-242.

Giri et al., Pharmacokinetics and Metabolism of a Novel Antifibrotic Drug Pirfenidone, in Mice Following Intravenous Administration, Biopharm Drug Disp. (2002) 23: 203-211.

Grattendick et al., Effects of 5-ethyl-1-phenyl-2-(1H) pyridone on serum biomarkers of multiorgan dysfunction and mortality in lipopolysaccharide/glactosamine and cecal ligation and puncture models of septic shock in mice. Res Commun Mol Pathol Pharmacol. (2009-2010) 122-123(1-6): 27-50.

Grattendick et al., Effects of Two Anti-TNF-alpha Compounds: Etanercept and 5-Ethyl-1-phenyl-2-(1H)-pyridone on Secreted and Cell-Associated TNF-alpha in Vitro. Pharmacol Pharmacy (2011) 2: 238-247.

Greene et al, Protective Groups in Organic Synthesis. John Wiley & Sons, 3rd Edition, 1999, Table of Contents Only.

Griswold et al., Differentiation in vivo of Classical Non-Steroidal Antiinflammatory Drugs from Cytokine Suppressive Antiinflammatory Drugs and other Pharmacological Classes Using Mouse Tumour Necrosis Factor Alpha Production, Drugs Exp Clin Res. (1993) 19(6): 243-248.

Higuchi et al., Pro-drugs as a Novel Drug Delivery System, (1975) vol. 14, A.C.S. Symposium Series, Table of Content Only.

Hoogenband van den, et al., An efficient synthesis of 4-bromo-N-substituted oxindoles by an intramolecular copper-catalyzed amidation reaction, Tetra Lttrs. (May 2007) 48(26): 4461-4465.

Jiang et al., Characterization of the Structure and Function of a New Mitogen-activated Protein Kinase (p38-beta). J Biol Chem. (Jul. 1996) 271(30): 17920-17926.

Joe et al., Animal Models of Rheumatoid Arthritis and Related Inflammation, Curr Rheumatol Rep. 1: 139-148.

Kaminska et al., TGF beta signaling and its role in tumor pathogenesis, Acta Biochim Pol., (Jun. 2005) 52(2): 329-337.

Kane et al., "Reactions of Diazenediyl Compounds with Pyridones: A Novel [4+2] Cycloaddition." J Heter Chem. (1976) 13(3): 673-674.

Kappe et al., Syntheses of Heterocycles, CLXII: The Synthesis of N-Malonylheterocycles., Monatsheft Chemie (1972); 103(2): 586-598.

Katritzky et al., J Hetero Chem., Synthesis and Some Transformations 4-Benzotriazolyl-3,4-dihydropyrid-2-ones (1996) 33(6): 2031-2036.

Kisteneva, Azomethine Dyes from Oxindole Derivatives. I, The Journal of General Chemistry of the U.S.S.R. (1956) 26(3): 1327-1332.

Kisteneva, Azomethine Dyes from Oxindole Derivatives. II, The Journal of General Chemistry of the U.S.S.R. (1956) 26(7): 2251-2255.

Ko et al., "A New and Facile Synthesis of 2-Pyridones", Bull Korean Chem Soc. (2001) 22(2): 234-236.

Korb et al., Differential tissue expression and activation of p38 MAPK alpha, beta, gamma, and delta isoforms in rheumatoid arthritis, Arthritis & Rheumatism (Sep. 2006) 54(9): 2745-2756.

Kumar et al., Novel Homologues of CSBP/P38 MAP Kinase: Activation, Substrate, Specificity and Sensitivity to Inhibition by Pyridinyl Imidazoles, Biochem Biophys Res Comm., (1997) 235: 533-538.

Lam et al., Copper-catalyzed general C—N and C—O bond cross-coupling with arylboronic acid, Tetrahedron Lett. (2001) 42: 3415-3418.

Lam et al., Copper-promoted C—N bond cross-coupling with phenylstannane, Tetrahedron Lettrs (2002) 43: 3091-3094.

Laufer et al., An in-vitro screening assay for the detection of inhibitors of proinflammatory cytokine synthesis: a useful tool for the development of new antiarthritic and disease modifying drugs, Osteoarth Cartilage (2002) 10: 961-967.

Laufer et al., From Imidazoles to Pyrimidines: New Inhibitors of Cytokine Release, J Med Chem., (2002) 45: 2733-2740.

Laurent, Biochemical pathways leading to collagen deposition in pulmonary fibrosis, Ciba Found Symp. (1985) 114: 222-233.

Lee et al., A protein kinase involved in the regulation of inflammatory cytokine biosynthesis, Nature (Dec. 1994), 372(22): 740-746.

Lee et al., Bicyclic imidazoles as a novel class of cytokine biosynthesis inhibitors, Ann NY Acad Sci., (1993) 696: 149-170.

Lee et al., Inhibition of Monocyte IL-1 Production by the Anti-inflammatory Compound, SK&F 86002, Int J Immunopharmac., (1988) 10(7): 835-843.

Lee et al., Inhibition of p38 MAP Kinase as a Therapeutic Strategy, Immunopharmaco (2000) 47: 185-201.

Lee et al., MAP Kinase p38 Inhibitors: Clinical Results and an Intimate Look at Their Interactions with p38alpha Protein, Curr Med Chem. (2005) 12: 2979-2994.

Lee et al., p38 Mitogen-activated Protein Kinase Inhibitors—Mechanisms and Therapeutic Potentials, Pharmacol. Ther., (1999) 82(2-3): 389-397.

Lee et al., Pirfenidone: A Novel Pharmacological Agent That Inhibits Leiomyoma Cell Proliferation and Collagen Production, J Clin Endocrinol Metab. (1998) 83(1): 219-223.

Li et al., The Primary Structure of p38gamma: A New Member of p38 Group of MAP Kinases, Biochem Biophys Res Comm., (1996) 228: 334-340.

Liverton et al., Design and Synthesis of Potent, Selective, and Orally Bioavailable Tetrasubstituted Imidazole Inhibitors of p38 Mitogen-Activated Protein Kinase, J Med Chem. (1999) 42(12): 2180-2190.

Lou et al., "Design, Synthesis and Antifibrotic Activities of Carbohydrate-Modified 1-(Substituted aryl)-5-trifluoromethyl-2(1H) Pyridones," Molecules (Jan. 2012) 17: 884-896.

Lowery et al., Transcreener: screening enzymes involved in covalent regulation, Expert Opin Ther Targets (Feb. 2006) 10(1): 179-190.

Ma et al., "Synthesis and biological evaluation of the pirfenidone derivatives as antifibrotic agents", Bioorg Med Chem Lttrs (2013)—Available Online Nov. 25, 2013 at http://dx.doi.org/10.1016/j.bmcl.2013.11.038; 14 pages.

Matsuoka, et al., A p38 MAPK inhibitor, FR-167653, ameliorates murine bleomycin-induced pulmonary fibrosis, Am J Physiol Lung Cell Mol Physiol., (2002) 283: L103-L112.

Mayer et al., p38 MAP kinase inhibitors: A future therapy for inflammatory diseases, Drug Discovery Today: Therapeutic Strategies/Immunological disorders and autoimmunity, (2006) 3(1): 50-54.

McIntyre et al., Pyridazine Based Inhibitors of p38 MAPK, Bioorg Med Chem Lttr., (2002) 12: 689-692.

Mederski et al., N-Aryl Heterocycles via Coupling Reactions with Arylboronic Acids, Tetrahedron (1999) 55(44): 12757-12770.

Muddu et al., Resolving fibrosis in the diseased liver: translating the scientific promise to the clinic, Int J Biochem Cell Biol., (2007) 39(4): 695-714 [Online Oct. 7, 2006].

Nagai et al., Open-label Compassionate Use One Year-treatment with Pirfenidone to Patients with Chronic Pulmonary Fibrosis, Intern Med., (2002) 41(12): 1118-1123.

Newton et al., New aspects of p38 mitogen activated protein kinase (MAPK) biology in lung inflammation, Drug Discovery Today: Disease Mechanisms, (2006) 3: 53-61.

Noble et al., Idiopathic pulmonary fibrosis: new insights into pathogenesis, Clin Chest Med. (2004) 25(4): 749-758.

Ono et al., The p38 Signal Transduction Pathway Activation and Function, Cell Signal., (2000) 12: 1-13.

Ozes et al., 697 Preclinical activity of pirfenidone (5-methyl-1phenyl-2(lH)-pyridone) in cell-based models of nonalcoholic steatohepatitis, Hepatology, (2003) 38: 495.

Pargellis et al., Inhibition of p38 MAP kinase by utilizing a novel allosteric binding site, Nat Struct Biol. (2002) 9(4): 268-272.

(56) References Cited

OTHER PUBLICATIONS

Patani et al., Bioisosterism: A Rational Approach in Drug Design. Chem. Rev. (1996), 96(8): 3147-3176.

Pednekar et al., Synthesis of Substituted Pyridazinones and Some Novel Fused Heterocycles from Pyran-2-One and Pyridin-2-One Systems, Indian J Heter Chem. (1998) 8(2): 89-94.

Przheval'skii et al., Mono(m-substituted) Chloroacetyldiarylamines in the Stollé Reaction, Chem Heterocycl Compd. (1982) 18(7): 716-719.

Raghu et al., Treatment of Idiopathic Pulmonary Fibrosis with a New Antifibrotic Agent, Pirfenidone—Results of a Prospective, Open-label Phase II Study, Am J Respir Crit Care Med, (1999) 159: 1061-1069.

Raingeaud et al., Pro-inflammatory Cytokines and Environmental Stress Cause p38 Mitogen-activated Protein Kinase Activation by Dual Phosphorylation on Tyrosine and Threonine, J Biol Chem., (1995) 270(13): 7420-7426.

Results from Chemical Abstract Services Search of Sep. 4, 2013 in Registry/Caplus 1907-date, Casreact, 1840-date, and WPINDEX DCR 1999-date. Answers 1-130 are to patent documents and answers 131-214 are to non-patent literature. One exemplary structure was displaced for Answers 1-130; pp. 291.

Results from Chemical Abstract Services Search of Sep. 4, 2013 showing 3161 structures that were registered from other sources such as chemical libraries and do not have any literature associated with them. Each compound is identified by CA Index name, molecular formula, and structure; pp. 1051.

Richards et al., Biochemical and cellular mechanisms of pulmonary fibrosis, Toxicol Pathol. (1991) 19: 526-539.

Roche et al. (Eds.), Bioreversible Carriers in Drug Design, American Pharmaceutical Association and Pergamon Press (1987) Table of Contents Only.

Salituro et al., Inhibitors of p38 MAP Kinase: Therapeutic Intervention in Cytokine-Mediated Diseases, Curr Med Chem., (1999) 6: 807-823.

Sarges et al., A Novel Class of "GABAergic" Agents: 1-Aryl-3-(aminoalkylidene)oxindoles, (1989) 32(2): 437-444.

Shi-Wen et al., Endothelin-1 Induces Expression of Matrix-associated Genes in Lung Fibroblasts through MEK/ERK. J Biol Chem. (Mar. 23, 2004) 279(22): 23098-23103.

Simonsen et al., Ethyl 6-Methyl-2-pyrone-3, 5-dicarboxylate and its derivatives. J Chem Soc Trans. (1908) 93: 1022-1032.

Stambe et al., The Role of p38alpha Mitogen-Activated Protein Kinase Activation in Renal Fibrosis, J Am Soc Nephrol., (2004) 15: 370-379.

Stein et al., p38-2, a Novel Mitogen-activated Protein Kinase with Distinct Properties, J Biol Chem., (1997) 272(31): 19509-19517.

Stollé, Über N-substituierte Oxindole und Isatine, Journal für Praktische Chemie, (1930), 128: 1-43.

Sugahara et al., A facile copper-catalyzed Ullmann condensation: N-arylation of heterocyclic compounds containing an -NHCO-moiety, Chem Pharm Bull., (1997) 45(4): 719-721.

Ting et al., Substituted 1,3-Dihydro-2H-pyrrolo[2,3-b]pyridin-2-ones as Potential Antiinflammatory Agents, J Med Chem. (1990) 33(10): 2697-2706.

Trifilieff et al., CGH2466, a combined adenosine receptor antagonist, p38 mitogen-activated protein kinase and phosphodiesterase type 4 inhibitor with potent in vitro and in vivo anti-inflammatory activities, Br J Pharmacol., (Jan. 2005) 144: 1002-1010.

Underwood et al., Inhibition of p38 MAP Kinase, Prog Respir Res., (2001) 3'1: 342-345.

Underwood et al., SB 239063, A p38 MAPK inhibitor, reduces neutrophilia, inflammatory cytokines, MMP-9, and fibrosis in lung, Am J Physiol Lung Cell Mol Physiol., (2000) 279: L895-L902.

Vippagunta et al., Crystalline solids, Advanced Drug Delivery Reviews (2001) 48: 3-26.

Wang et al., An improved Ullmann-Ukita-Buchwald-Li conditions for CuI-catalyzed coupling reaction of 2-pyridones with aryl halides, Tetrahedron (2005) 61(11): 2931-2939.

Wang et al., Molecular Cloning and Characterization of a Novel p38 Mitogen-activated Protein Kinase, J Biol Chem., (1997) 272(38): 23668-23674.

Wang et al., Requirement of Mitogen-activated Protein Kinase Kinase 3 (MKK3) for Activation of p38α and p38δ MAPK Isoforms of TGF-β1 in Murine Mesangial Cells (2002) 277: 47257-47262.

Yan et al., Pirfenidone effect and mechanism in the treatment of fibrotic diseases. West China Medical Journal (2004) 19(1):169-170.

Zohdi et al., Heterocyclic Synthesis with Isothiocyanate and sulfur: A novel route for the synthesis of Pyridino[2,3-d]Pyridazine and Thiazolo[4,5-b]Isoquinoline derivatives. Phosphorus, Sulfur, and Silicon (1995) 101(1-4): 179-187.

International Search Report and Written Opinion dated Dec. 23, 2013 in Application No. PCT/US2013/062910, filed Oct. 1, 2013.

International Written Opinion under Rule 66 mailed Sep. 4, 2014 in Application No. PCT/US2013/062910, filed Oct. 1, 2013.

International Written Opinion (Rule 66) dated Nov. 26, 2014 in Application No. PCT/US2013/062910, filed Oct. 1, 2013.

International Preliminary Report on Patentability dated Feb. 2, 2015 in Application No. PCT/US2013/062910, filed Oct. 1, 2013.

ANTI-FIBROTIC PYRIDINONES

CROSS-REFERENCE TO RELATED APPLICATIONS

The present application is a divisional of U.S. application Ser. No. 14/043,121, filed Oct. 1, 2013, which claims the benefit of priority to U.S. Appl. No. 61/709,075, filed Oct. 2, 2012, U.S. Appl. No. 61/777,499, filed Mar. 12, 2013 and U.S. Appl. No. 61/872,157, filed Aug. 30, 2013, all of which are hereby incorporated by references in their entireties.

BACKGROUND

Field

Pyridinone compounds, method of making such compounds, pharmaceutical compositions and medicaments comprising such compounds, and methods of using such compounds to treat, prevent or diagnose diseases, disorders, or conditions associated with fibrosis are provided.

Description

Fibrosis is the formation of excess fibrous connective tissue in an organ or tissue in a reparative or reactive process. Examples of fibrosis include, but are not limited to pulmonary fibrosis, liver fibrosis, dermal fibrosis, and renal fibrosis. Pulmonary fibrosis, also called idiopathic pulmonary fibrosis (IPF), interstitial diffuse pulmonary fibrosis, inflammatory pulmonary fibrosis, or fibrosing alveolitis, is a lung disorder and a heterogeneous group of conditions characterized by abnormal formation of fibrous tissue between alveoli caused by alveolitis comprising cellular infiltration into the alveolar septae with resulting fibrosis. The effects of IPF are chronic, progressive, and often fatal.

There continues to be a need for safe and effective drugs to treat fibrotic conditions such as idiopathic pulmonary fibrosis.

SUMMARY

Some embodiments of the present application provide a compound having the structure of formula (I):

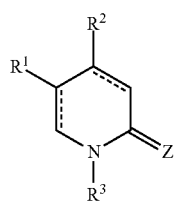

(I)

or a pharmaceutically acceptable salt thereof, wherein
$R^1$ is selected from the group consisting of halogen, —CN, —C(O)$R^8$, —SO$_2R^{16}$, $C_{1-6}$ alkyl optionally substituted with one or more $R^4$, $C_{2-6}$ alkenyl optionally substituted with one or more $R^4$, $C_{2-6}$ alkynyl optionally substituted with one or more $R^4$, $C_{6-10}$ aryl optionally substituted with one or more $R^4$, 5-10 membered heteroaryl optionally substituted with one or more $R^4$, $C_{3-10}$ carbocyclyl optionally substituted with one or more $R^4$, and 3-10 membered heterocyclyl optionally substituted with one or more $R^4$;
$R^2$ is selected from the group consisting of halogen, —CN, —O$R^5$, —S$R^5$, —N$R^6R^7$, and —C(O)$R^8$;
$R^3$ is selected from the group consisting of hydrogen, —(CH$_2)_n$—(C$_{6-10}$ aryl), —(CH$_2)_n$-(5-10 membered heteroaryl), —(CH$_2)_n$—(C$_{3-10}$ carbocyclyl), and —(CH$_2)_n$-(3-10 membered heterocyclyl), each optionally substituted with one or more $R^9$;
each $R^4$ is independently selected from the group consisting of halogen, —CN, —OH, —C(O)$R^8$, —SO$_2R^{16}$, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{6-10}$ aryl optionally substituted with one or more $R^{11}$, $C_{7-14}$ aralkyl optionally substituted with one or more $R^{11}$, 5-10 membered heteroaryl optionally substituted with one or more $R^{11}$, or independently two geminal $R^4$ together are oxo;
each $R^5$ is independently selected from the group consisting of hydrogen, optionally substituted $C_{1-6}$ alkyl, optionally substituted $C_{2-6}$ alkenyl, optionally substituted $C_{2-6}$ alkynyl, optionally substituted $C_{2-8}$ alkoxyalkyl, $C_{6-10}$ aryl optionally substituted with one or more $R^{11}$, $C_{7-14}$ aralkyl optionally substituted with one or more $R^{11}$, and —(CH$_2)_n$-(3-10 membered heterocyclyl) optionally substituted with one or more $R^{10}$;
$R^6$ is selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, (5-10 membered heteroaryl)alkyl optionally substituted with one or more $R^{11}$, —C(O)$R^8$, and —C(O)O$R^5$;
$R^7$ is selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, (5-10 membered heteroaryl)alkyl optionally substituted with one or more $R^{11}$, —C(O)$R^8$, and —C(O)O$R^5$;
or $R^6$ and $R^7$ together with the nitrogen to which they are attached form a 3-10 membered heterocyclyl optionally substituted with one or more $R^{10}$;
each $R^8$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —N$R^{12}R^{13}$, and —O$R^5$;
each $R^9$ is independently selected from the group consisting of hydroxy, halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, —O$R^5$, —N$R^{14}R^{15}$, —C(O)$R^8$, —CN, —SO$_2R^{16}$, and —NO$_2$;
each $R^{10}$ is independently selected from the group consisting of optionally substituted $C_{1-6}$ alkyl, optionally substituted $C_{2-6}$ alkenyl, and optionally substituted $C_{2-6}$ alkynyl, or independently two geminal $R^{10}$ together are oxo;
each $R^{11}$ is independently selected from the group consisting of halogen, —CN, optionally substituted $C_{1-6}$ alkyl, optionally substituted $C_{2-6}$ alkenyl, optionally substituted $C_{2-6}$ alkynyl, —O—(CH$_2)_n$—$C_{1-8}$ alkoxy, —C(O)$R^8$, and optionally substituted $C_{1-6}$ alkoxy;
each $R^{12}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;
each $R^{13}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

$R^{14}$ is selected from the group consisting of hydrogen, optionally substituted $C_{1-6}$ alkyl, optionally substituted $C_{6-10}$ aryl, and —C(O)$R^8$;

$R^{15}$ is selected from the group consisting of hydrogen, optionally substituted $C_{1-6}$ alkyl, optionally substituted $C_{6-10}$ aryl, and —C(O)$R^8$;

each $R^{16}$ is independently selected from the group consisting of optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —N$R^{12}R^{13}$, and —O$R^5$;

Z is selected from oxygen and sulfur;

each n is independently an integer from 0 to 4; and the bonds represented by a solid and dashed line are independently selected from the group consisting of a single bond and a double bond, provided that when $R^3$ is H, then $R^1$ is selected from $C_{6-10}$ aryl optionally substituted with one or more $R^4$, or 5-10 membered heteroaryl optionally substituted with one or more $R^4$;

when $R^2$ is —NH-(2-fluoro-4-bromo-phenyl) and $R^1$ is C(O)OH, then $R^3$ cannot be —CH$_2$-phenyl;

when $R^2$ is methoxy, $R^1$ is 4-methoxyphenyl, and Z is O, then $R^3$ is not —(CH$_2$)-2-fluro-4-chloro-phenyl;

when $R^3$ is a phenyl; $R^2$ is O$R^5$ or N$R^6R^7$; then $R^1$ is not triazolyl;

when $R^3$ is 4-methyl phenyl, $R^2$ is morpholinyl, and Z is O; then $R^1$ is not methyl; and when $R^3$ is 4-methyl phenyl, $R^2$ is —N(CH$_3$)$_2$, Z is O; then $R^1$ is not methyl.

Some embodiments of the present application provide a compound having the structure of formula (II):

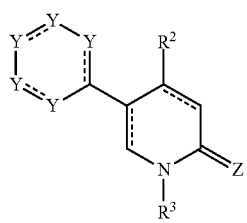

(II)

or a pharmaceutically acceptable salt thereof, wherein $R^2$ is selected from the group consisting of optionally substituted $C_{1-6}$ alkyl, optionally substituted $C_{2-6}$ alkenyl, and optionally substituted $C_{2-6}$ alkynyl;

$R^3$ is selected from the group consisting of hydrogen, —(CH$_2$)$_n$—($C_{6-10}$ aryl), —(CH$_2$)$_n$-(5-10 membered heteroaryl), —(CH$_2$)$_n$—($C_{3-10}$ carbocyclyl), and —(CH$_2$)$_n$-(3-10 membered heterocyclyl), each optionally substituted with one or more $R^9$;

Y is selected from N and C$R^4$;

each $R^4$ is independently selected from the group consisting of halogen, —CN, —OH, —C(O)$R^8$, —SO$_2R^{16}$, optionally substituted $C_{1-6}$ alkyl, optionally substituted $C_{2-6}$ alkenyl, optionally substituted $C_{2-6}$ alkynyl, optionally substituted $C_{1-6}$ alkoxy, $C_{6-10}$ aryl optionally substituted with one or more $R^{11}$, $C_{7-14}$ aralkyl optionally substituted with one or more $R^{11}$, 5-10 membered heteroaryl optionally substituted with one or more $R^{11}$, or independently two adjacent $R^4$ together with the carbon atoms to which they are attached form a fused ring selected from the group consisting of optionally substituted phenyl, optionally substituted 5-6 membered heteroaryl, optionally substituted $C_{3-7}$ carbocyclyl, and optionally substituted 3-7 membered heterocyclyl;

each $R^9$ is independently selected from the group consisting of hydroxy, halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, —O$R^5$, —N$R^{14}R^{15}$, —C(O)$R^8$, —CN, —SO$_2R^{16}$, and —NO$_2$;

$R^{14}$ is selected from the group consisting of hydrogen, optionally substituted $C_{1-6}$ alkyl, optionally substituted $C_{6-10}$ aryl, and —C(O)$R^8$;

$R^{15}$ is selected from the group consisting of hydrogen, optionally substituted $C_{1-6}$ alkyl, optionally substituted $C_{6-10}$ aryl, and —C(O)$R^8$;

each $R^8$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —N$R^{12}R^{13}$, and —O$R^5$;

each $R^{12}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

each $R^{13}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

each $R^5$ is independently selected from the group consisting of hydrogen, optionally substituted $C_{1-6}$ alkyl, optionally substituted $C_{2-6}$ alkenyl, optionally substituted $C_{2-6}$ alkynyl, optionally substituted $C_{2-8}$ alkoxyalkyl, $C_{6-10}$ aryl optionally substituted with one or more $R^{11}$, $C_{7-14}$ aralkyl optionally substituted with one or more $R^{11}$, and —(CH$_2$)$_n$-(3-10 membered heterocyclyl) optionally substituted with one or more $R^{10}$;

each $R^{10}$ is independently selected from the group consisting of optionally substituted $C_{1-6}$ alkyl, optionally substituted $C_{2-6}$ alkenyl, and optionally substituted $C_{2-6}$ alkynyl, or independently two geminal $R^{10}$ together are oxo;

each $R^{11}$ is independently selected from the group consisting of halogen, —CN, optionally substituted $C_{1-6}$ alkyl, optionally substituted $C_{2-6}$ alkenyl, optionally substituted $C_{2-6}$ alkynyl, and optionally substituted $C_{1-6}$ alkoxy;

each $R^{16}$ is independently selected from the group consisting of optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —N$R^{12}R^{13}$, and —O$R^5$;

Z is selected from oxygen and sulfur;

each n is independently an integer from 0 to 4; and the bonds represented by a solid and dashed line are independently selected from the group consisting of a single bond and a double bond.

In some embodiments, if R is hydrogen, then is

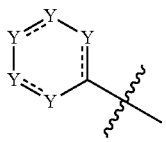

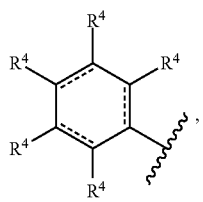

and the two adjacent $R^4$ together with the carbon atoms to which they are attached form a fused ring selected from optionally substituted 5 or 6 membered heteroaryl or optionally substituted 5 or 6 membered heterocyclyl.

Some embodiments of the present application provide a compound having the structure of formula (III):

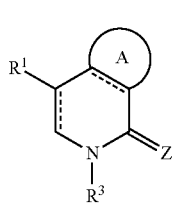

(III)

or a pharmaceutically acceptable salt thereof, wherein $R^1$ is selected from the group consisting of halogen, —CN, —C(O)$R^8$, —SO$_2$R$^{16}$, C$_{1-6}$ alkyl optionally substituted with one or more $R^4$, C$_{2-6}$ alkenyl optionally substituted with one or more $R^4$, C$_{2-6}$ alkynyl optionally substituted with one or more $R^4$, C$_{6-10}$ aryl optionally substituted with one or more $R^4$, 5-10 membered heteroaryl optionally substituted with one or more $R^4$, C$_{3-10}$ carbocyclyl optionally substituted with one or more $R^4$, and 3-10 membered heterocyclyl optionally substituted with one or more $R^4$;

$R^3$ is selected from the group consisting of hydrogen, —(CH$_2$)$_n$—(C$_{6-10}$ aryl), —(CH$_2$)$_n$-(5-10 membered heteroaryl), —(CH$_2$)$_n$—(C$_{3-10}$ carbocyclyl), and —(CH$_2$)$_n$-(3-10 membered heterocyclyl), each optionally substituted with one or more $R^9$;

ring A is selected from the group consisting of phenyl, 5-6 membered heteroaryl, C$_{3-7}$ carbocyclyl, and 3-7 membered heterocyclyl, each optionally substituted with one or more $R^4$;

each $R^4$ is independently selected from the group consisting of halogen, —CN, —OH, —C(O)$R^8$, —SO$_2$R$^{16}$, optionally substituted C$_{1-6}$ alkyl, optionally substituted C$_{2-6}$ alkenyl, optionally substituted C$_{2-6}$ alkynyl, optionally substituted C$_{1-6}$ alkoxy, optionally substituted C$_{6-10}$ aryl optionally substituted with one or more $R^{11}$, C$_{7-14}$ aralkyl optionally substituted with one or more $R^{11}$, 5-10 membered heteroaryl optionally substituted with one or more $R^{11}$, or independently two geminal $R^4$ together are oxo;

each $R^9$ is independently selected from the group consisting of hydroxy, halogen, optionally substituted C$_{1-6}$ alkyl, optionally substituted C$_{2-6}$ alkenyl, optionally substituted C$_{2-6}$ alkynyl, optionally substituted C$_{1-6}$ alkylthio, optionally substituted C$_{2-8}$ alkoxyalkyl, optionally substituted C$_{3-10}$ carbocyclyl, optionally substituted C$_{6-10}$ aryl, —OR$^5$, —NR$^{14}$R$^{15}$, —C(O)$R^8$, —SO$_2$R$^{16}$, —CN and —NO$_2$;

$R^{14}$ is selected from the group consisting of hydrogen, optionally substituted C$_{1-6}$ alkyl, optionally substituted C$_{6-10}$ aryl, and —C(O)$R^8$;

$R^{15}$ is selected from the group consisting of hydrogen, optionally substituted C$_{1-6}$ alkyl, optionally substituted C$_{6-10}$ aryl, and —C(O)$R^8$;

each $R^8$ is independently selected from the group consisting of hydrogen, optionally substituted C$_{1-6}$ alkyl, optionally substituted C$_{2-6}$ alkenyl, optionally substituted C$_{2-6}$ alkynyl, C$_{6-10}$ aryl optionally substituted with one or more $R^{11}$, C$_{7-14}$ aralkyl optionally substituted with one or more $R^{11}$, —NR$^{12}$R$^{13}$, and —OR$^5$;

each $R^{12}$ is independently selected from the group consisting of hydrogen, optionally substituted C$_{1-6}$ alkyl, optionally substituted C$_{2-6}$ alkenyl, optionally substituted C$_{2-6}$ alkynyl, C$_{6-10}$ aryl optionally substituted with one or more $R^{11}$, and C$_{7-14}$ aralkyl optionally substituted with one or more $R^{11}$;

each $R^{13}$ is independently selected from the group consisting of hydrogen, optionally substituted C$_{1-6}$ alkyl, optionally substituted C$_{2-6}$ alkenyl, optionally substituted C$_{2-6}$ alkynyl, C$_{6-10}$ aryl optionally substituted with one or more $R^{11}$, and C$_{7-14}$ aralkyl optionally substituted with one or more $R^{11}$;

each $R^5$ is independently selected from the group consisting of hydrogen, optionally substituted C$_{1-6}$ alkyl, optionally substituted C$_{2-6}$ alkenyl, optionally substituted C$_{2-6}$ alkynyl, optionally substituted C$_{2-8}$ alkoxyalkyl, C$_{6-10}$ aryl optionally substituted with one or more $R^{11}$, C$_{7-14}$ aralkyl optionally substituted with one or more $R^{11}$, and —(CH$_2$)$_n$-(3-10 membered heterocyclyl) optionally substituted with one or more $R^{10}$;

each $R^{10}$ is independently selected from the group consisting of optionally substituted C$_{1-6}$ alkyl, optionally substituted C$_{2-6}$ alkenyl, and optionally substituted C$_{2-6}$ alkynyl, or independently two geminal $R^{10}$ together are oxo;

each $R^{11}$ is independently selected from the group consisting of halogen, —CN, optionally substituted C$_{1-6}$ alkyl, optionally substituted C$_{2-6}$ alkenyl, optionally substituted C$_{2-6}$ alkynyl, and optionally substituted C$_{1-6}$ alkoxy;

each $R^{16}$ is independently selected from the group consisting of optionally substituted C$_{1-6}$ alkyl, optionally substituted C$_{2-6}$ alkenyl, optionally substituted C$_{2-6}$ alkynyl, C$_{6-10}$ aryl optionally substituted with one or more $R^{11}$, C$_{7-14}$ aralkyl optionally substituted with one or more $R^{11}$, —NR$^{12}$R$^{13}$, and —OR$^5$;

Z is selected from oxygen and sulfur;

each n is independently an integer from 0 to 4; and the bonds represented by a solid and dashed line are independently selected from the group consisting of a single bond and a double bond, provided that when $R^3$ is H, then $R^1$ is selected from C$_{6-10}$ aryl optionally substituted with one or more $R^4$, or 5-10 membered heteroaryl optionally substituted with one or more $R^4$;

when $R^3$ is phenyl optionally substituted with one or more $R^9$, and Z is O; then ring A cannot be optionally substituted phenyl;

when ring A is selected from cyclopentenyl, optionally substituted pyrrolyl or optionally substituted dihydropyrrolidinyl, R³ is phenyl optionally substituted with one or more R⁹, and Z is O; then R¹ is not halogen, 3-methoxy phenyl or 3,5-dimethoxy phenyl;

when ring A is pyridyl, R¹ is optionally substituted phenyl, and Z is O; then n in R³ is zero and R³ is not halogen substituted phenyl;

when ring A is optionally substituted pyrimidyl, R³ is phenyl or benzyl, and Z is O; then R¹ is not methyl or benzyl;

when ring A is optionally substituted furanyl, R³ is phenyl optionally substituted with one or more R⁹, and Z is O; then R¹ is not fluoro;

when ring A is optionally substituted pyrrolyl, R³ is phenyl optionally substituted with one or more R⁹, and Z is O; then R¹ is not methyl;

when ring A is tetrahydrofuranyl, R³ is phenyl, and Z is O; then R¹ is not methyl or phenyl; and when ring A is pyradizinyl, R³ is 4-NO₂-phenyl, and Z is O; then R¹ is not methyl.

Some embodiments of the present application provide a compound, having the structure of formula (IV):

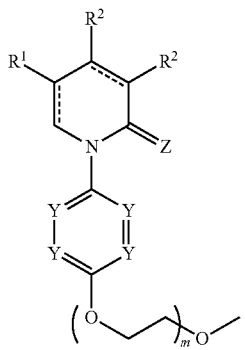

(IV)

or a pharmaceutically acceptable salt thereof, wherein

R¹ is selected from the group consisting of hydrogen, C₁₋₆ alkyl optionally substituted with one or more R⁴, C₂₋₆ alkenyl optionally substituted with one or more R⁴, C₂₋₆ alkynyl optionally substituted with one or more R⁴, C₆₋₁₀ aryl optionally substituted with one or more R⁴, 5-10 membered heteroaryl optionally substituted with one or more R⁴, C₃₋₁₀ carbocyclyl optionally substituted with one or more R⁴, and 3-10 membered heterocyclyl optionally substituted with one or more R⁴;

each R² is independently selected from the group consisting of hydrogen, halogen, optionally substituted C₁₋₆ alkyl, optionally substituted C₂₋₆ alkenyl, optionally substituted C₂₋₆ alkynyl, —CN, —OR⁵, —NR⁶R⁷, and —C(O)R⁸, or both R² together with the carbon atoms to which they are attached form a fused ring selected from the group consisting of phenyl, 5-6 membered heteroaryl, C₃₋₇ carbocyclyl, and 3-7 membered heterocyclyl, each optionally substituted with one or more R⁴;

each R⁴ is independently selected from the group consisting of halogen, —CN, optionally substituted C₁₋₆ alkyl, optionally substituted C₂₋₆ alkenyl, optionally substituted C₂₋₆ alkynyl, and optionally substituted C₁₋₆ alkoxy;

each R⁵ is independently selected from the group consisting of hydrogen, optionally substituted C₁₋₆ alkyl, optionally substituted C₂₋₆ alkenyl, optionally substituted C₂₋₆ alkynyl, optionally substituted C₂₋₈ alkoxyalkyl, C₆₋₁₀ aryl optionally substituted with one or more R¹¹, C₇₋₁₄ aralkyl optionally substituted with one or more R¹¹, —(CH₂)ₙ-(3-10 membered heterocyclyl) optionally substituted with one or more R¹⁰, and —(CH₂)ₙ—(C₆₋₁₀ aryl) optionally substituted with one or more R¹¹;

R⁶ is selected from the group consisting of hydrogen, optionally substituted C₁₋₆ alkyl, optionally substituted C₂₋₆ alkenyl, optionally substituted C₂₋₆ alkynyl, C₆₋₁₀ aryl optionally substituted with one or more R¹¹, C₇₋₁₄ aralkyl optionally substituted with one or more R¹¹, (5-10 membered heteroaryl)alkyl optionally substituted with one or more R¹¹, —C(O)R⁸, and —C(O)OR⁵;

R⁷ is selected from the group consisting of hydrogen, optionally substituted C₁₋₆ alkyl, optionally substituted C₂₋₆ alkenyl, optionally substituted C₂₋₆ alkynyl, C₆₋₁₀ aryl optionally substituted with one or more R¹¹, C₇₋₁₄ aralkyl optionally substituted with one or more R¹¹, (5-10 membered heteroaryl)alkyl optionally substituted with one or more R¹¹, —C(O)R⁸, and —C(O)OR⁵;

or R⁶ and R⁷ together with the nitrogen to which they are attached form an 3-10 membered heterocyclyl optionally substituted with one or more R¹⁰;

each R⁸ is independently selected from the group consisting of optionally substituted C₁₋₆ alkyl, optionally substituted C₂₋₆ alkenyl, optionally substituted C₂₋₆ alkynyl, —NR¹²R¹³, and —OR⁵;

each Y is independently N or CR⁹;

each R⁹ is independently selected from the group consisting of halogen, optionally substituted C₁₋₆ alkyl, optionally substituted C₂₋₆ alkenyl, optionally substituted C₂₋₆ alkynyl, optionally substituted C₁₋₆ alkoxy, and —NR¹⁴R¹⁵, or independently two adjacent R⁹ together with the ring atoms to which they are attached form a fused optionally substituted 3-10 membered heterocyclyl or a fused optionally substituted 5-10 membered heteroaryl;

each R¹⁰ is independently selected from the group consisting of oxo, optionally substituted C₁₋₆ alkyl, optionally substituted C₂₋₆ alkenyl, and optionally substituted C₂₋₆ alkynyl;

each R¹¹ is independently selected from the group consisting of halogen, —CN, optionally substituted C₁₋₆ alkyl, optionally substituted C₂₋₆ alkenyl, optionally substituted C₂₋₆ alkynyl, and optionally substituted C₁₋₆ alkoxy;

each R¹² is independently selected from the group consisting of hydrogen, optionally substituted C₁₋₆ alkyl, optionally substituted C₂₋₆ alkenyl, optionally substituted C₂₋₆ alkynyl, C₆₋₁₀ aryl optionally substituted with one or more R¹¹, and C₇₋₁₄ aralkyl optionally substituted with one or more R¹¹;

each R¹³ is independently selected from the group consisting of hydrogen, optionally substituted C₁₋₆ alkyl, optionally substituted C₂₋₆ alkenyl, optionally substituted C₂₋₆ alkynyl, C₆₋₁₀ aryl optionally substituted with one or more R¹¹, and C₇₋₁₄ aralkyl optionally substituted with one or more R¹¹;

R¹⁴ is selected from the group consisting of hydrogen, optionally substituted C₁₋₆ alkyl, optionally substituted C₆₋₁₀ aryl, and —C(O)R⁸;

R¹⁵ is selected from the group consisting of hydrogen, optionally substituted C₁₋₆ alkyl, optionally substituted C₆₋₁₀ aryl, and —C(O)R⁸;

Z is selected from oxygen and sulfur;

n is an integer from 0 to 4;

m is an integer from 1 to 4; and the bonds represented by a solid and dashed line are independently selected from the group consisting of a single bond and a double bond.

Some embodiments of the present application provide a compound having the structure of formula (V):

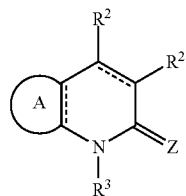

(V)

or a pharmaceutically acceptable salt thereof, wherein

A is a $C_{5-7}$ carbocyclyl optionally substituted with one or more $R^4$;

each $R^2$ is independently selected from the group consisting of hydrogen, halogen, optionally substituted $C_{1-6}$ alkyl, optionally substituted $C_{2-6}$ alkenyl, optionally substituted $C_{2-6}$ alkynyl, —CN, —OR$^5$, —NR$^6$R$^7$, and —C(O)R$^8$, or both $R^2$ together with the carbon atoms to which they are attached form a fused ring selected from the group consisting of phenyl, 5-6 membered heteroaryl, $C_{3-7}$ carbocyclyl, and 3-7 membered heterocyclyl, each optionally substituted with one or more $R^4$;

$R^3$ is selected from the group consisting of —(CH$_2$)$_n$—($C_{6-10}$ aryl), —(CH$_2$)$_n$-(5-10 membered hetero aryl), —(CH$_2$)$_n$—($C_{3-10}$ carbocyclyl), and —(CH$_2$)$_n$-(3-10 membered heterocyclyl), each optionally substituted with one or more $R^9$;

each $R^4$ is independently selected from the group consisting of halogen, —CN, —OH, —C(O)R$^8$, —SO$_2$R$^{16}$, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{6-10}$ aryl optionally substituted with one or more $R^{11}$, $C_{7-14}$ aralkyl optionally substituted with one or more $R^{11}$, 5-10 membered heteroaryl optionally substituted with one or more $R^{11}$, or independently two geminal $R^4$ together are oxo;

each $R^5$ is independently selected from the group consisting of hydrogen, optionally substituted $C_{1-6}$ alkyl, optionally substituted $C_{2-6}$ alkenyl, optionally substituted $C_{2-6}$ alkynyl, optionally substituted $C_{2-8}$ alkoxyalkyl, $C_{6-10}$ aryl optionally substituted with one or more $R^{11}$, $C_{7-14}$ aralkyl optionally substituted with one or more $R^{11}$, and —(CH$_2$)$_n$-(3-10 membered heterocyclyl) optionally substituted with one or more $R^{10}$;

$R^6$ is selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, (5-10 membered heteroaryl)alkyl optionally substituted with one or more $R^{11}$, —C(O)R$^8$, and —C(O)OR$^5$;

$R^7$ is selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, (5-10 membered heteroaryl)alkyl optionally substituted with one or more $R^{11}$, —C(O)R$^8$, and —C(O)OR$^5$;

or $R^6$ and $R^7$ together with the nitrogen to which they are attached form an 3-10 membered heterocyclyl optionally substituted with one or more $R^{10}$;

each $R^8$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —NR$^{12}$R$^{13}$, and —OR$^5$;

each $R^9$ is independently selected from the group consisting of halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, —OR$^5$, —NR$^{14}$R$^{15}$, —C(O)R$^8$, —SO$_2$R$^{16}$, and —NO$_2$;

each $R^{10}$ is independently selected from the group consisting of optionally substituted $C_{1-6}$ alkyl, optionally substituted $C_{2-6}$ alkenyl, and optionally substituted $C_{2-6}$ alkynyl, or independently two geminal $R^{10}$ together are oxo;

each $R^{11}$ is independently selected from the group consisting of halogen, —CN, optionally substituted $C_{1-6}$ alkyl, optionally substituted $C_{2-6}$ alkenyl, optionally substituted $C_{2-6}$ alkynyl, and optionally substituted $C_{1-6}$ alkoxy;

each $R^{12}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

each $R^{13}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

$R^{14}$ is selected from the group consisting of hydrogen, optionally substituted $C_{1-6}$ alkyl, optionally substituted $C_{6-10}$ aryl, and —C(O)R$^8$;

$R^{15}$ is selected from the group consisting of hydrogen, optionally substituted $C_{1-6}$ alkyl, optionally substituted $C_{6-10}$ aryl, and —C(O)R$^8$;

each $R^{16}$ is independently selected from the group consisting of optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —NR$^{12}$R$^{13}$, and —OR$^5$;

Z is selected from oxygen and sulfur;

each n is independently an integer from 0 to 4; and the bonds represented by a solid and dashed line are independently selected from the group consisting of a single bond and a double bond.

Some embodiments of the present application provide a compound having the structure of formula (VIa):

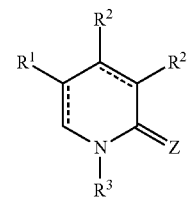

(VIa)

or a pharmaceutically acceptable salt thereof, wherein $R^1$ is a $C_{4-7}$ carbocyclyl optionally substituted with one or more $R^4$;

each $R^2$ is independently selected from the group consisting of hydrogen, halogen, optionally substituted $C_{1-6}$ alkyl, optionally substituted $C_{2-6}$ alkenyl, optionally substituted $C_{2-6}$ alkynyl, —CN, —OR$^5$, —NR$^6$R$^7$, and —C(O)R$^8$, or both R$^2$ together with the carbon atoms to which they are attached form a fused ring selected from the group consisting of phenyl, 5-6 membered heteroaryl, $C_{3-7}$ carbocyclyl, and 3-7 membered heterocyclyl, each optionally substituted with one or more R$^4$;

R$^3$ is selected from the group consisting of —(CH$_2$)$_n$—($C_{6-10}$ aryl), —(CH$_2$)$_n$-(5-10 membered heteroaryl), —(CH$_2$)$_n$—($C_{3-10}$ carbocyclyl), and —(CH$_2$)$_n$-(3-10 membered heterocyclyl), each optionally substituted with one or more R$^9$;

each R$^4$ is independently selected from the group consisting of halogen, —CN, —OH, —C(O)R$^8$, —SO$_2$R$^{16}$, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{6-10}$ aryl optionally substituted with one or more R$^{11}$, $C_{7-14}$ aralkyl optionally substituted with one or more R$^{11}$, 5-10 membered heteroaryl optionally substituted with one or more R$^{11}$, or independently two geminal R$^4$ together are oxo;

each R$^5$ is independently selected from the group consisting of hydrogen, optionally substituted $C_{1-6}$ alkyl, optionally substituted $C_{2-6}$ alkenyl, optionally substituted $C_{2-6}$ alkynyl, optionally substituted $C_{2-8}$ alkoxyalkyl, $C_{6-10}$ aryl optionally substituted with one or more R$^{11}$, $C_{7-14}$ aralkyl optionally substituted with one or more R$^{11}$, and —(CH$_2$)$_n$-(3-10 membered heterocyclyl) optionally substituted with one or more R$^{10}$;

R$^6$ is selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more R$^{11}$, $C_{7-14}$ aralkyl optionally substituted with one or more R$^{11}$, (5-10 membered heteroaryl)alkyl optionally substituted with one or more R$^{11}$, —C(O)R$^8$, and —C(O)OR$^5$;

R$^7$ is selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more R$^{11}$, $C_{7-14}$ aralkyl optionally substituted with one or more R$^{11}$, (5-10 membered heteroaryl)alkyl optionally substituted with one or more R$^{11}$, —C(O)R$^8$, and —C(O)OR$^5$;

or R$^6$ and R$^7$ together with the nitrogen to which they are attached form an 3-10 membered heterocyclyl optionally substituted with one or more R$^{10}$;

each R$^8$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more R$^{11}$, $C_{7-14}$ aralkyl optionally substituted with one or more R$^{11}$, —NR$^{12}$R$^{13}$, and —OR$^5$;

each R$^9$ is independently selected from the group consisting of halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, —OR$^5$, —NR$^{14}$R$^{15}$, —C(O)R$^8$, —SO$_2$R$^{16}$, and —NO$_2$;

each R$^{10}$ is independently selected from the group consisting of optionally substituted $C_{1-6}$ alkyl, optionally substituted $C_{2-6}$ alkenyl, and optionally substituted $C_{2-6}$ alkynyl, or independently two geminal R$^{10}$ together are oxo;

each R$^{11}$ is independently selected from the group consisting of halogen, —CN, optionally substituted $C_{1-6}$ alkyl, optionally substituted $C_{2-6}$ alkenyl, optionally substituted $C_{2-6}$ alkynyl, and optionally substituted $C_{1-6}$ alkoxy;

each R$^{12}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more R$^{11}$, and $C_{7-14}$ aralkyl optionally substituted with one or more R$^{11}$;

each R$^{13}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more R$^{11}$, and $C_{7-14}$ aralkyl optionally substituted with one or more R$^{11}$;

R$^{14}$ is selected from the group consisting of hydrogen, optionally substituted $C_{1-6}$ alkyl, optionally substituted $C_{6-10}$ aryl, and —C(O)R$^8$;

R$^{15}$ is selected from the group consisting of hydrogen, optionally substituted $C_{1-6}$ alkyl, optionally substituted $C_{6-10}$ aryl, and —C(O)R$^8$;

each R$^{16}$ is independently selected from the group consisting of optionally substituted $C_{1-6}$ alkyl, optionally substituted $C_{2-6}$ alkenyl, optionally substituted $C_{2-6}$ alkynyl, $C_{6-10}$ aryl optionally substituted with one or more R$^{11}$, $C_{7-14}$ aralkyl optionally substituted with one or more R$^{11}$, —NR$^{12}$R$^{13}$, and —OR$^5$;

Z is selected from oxygen and sulfur;

each n is independently an integer from 0 to 4; and the bonds represented by a solid and dashed line are independently selected from the group consisting of a single bond and a double bond.

Some embodiments of the present application provide a compound having the structure of formula (VII):

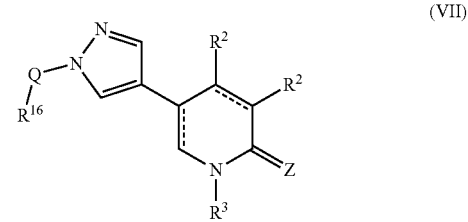

(VII)

or a pharmaceutically acceptable salt thereof, wherein each R$^2$ is independently selected from the group consisting of hydrogen, halogen, optionally substituted $C_{1-6}$ alkyl, optionally substituted $C_{2-6}$ alkenyl, optionally substituted $C_{2-6}$ alkynyl, —CN, —OR$^5$, —NR$^6$R$^7$, and —C(O)R$^8$, or both R$^2$ together with the carbon atoms to which they are attached form a fused ring selected from the group consisting of phenyl, 5-6 membered heteroaryl, $C_{3-7}$ carbocyclyl, and 3-7 membered heterocyclyl, each optionally substituted with one or more R$^4$;

R$^3$ is selected from the group consisting of —(CH$_2$)$_n$—($C_{6-10}$ aryl), —(CH$_2$)$_n$-(5-10 membered heteroaryl), —(CH$_2$)$_n$—($C_{3-10}$ carbocyclyl), and —(CH$_2$)$_n$-(3-10 membered heterocyclyl), each optionally substituted with one or more R$^9$;

each R$^4$ is independently selected from the group consisting of halogen, —CN, —OH, —C(O)R$^8$, —SO$_2$R$^{16}$, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{6-10}$ aryl optionally substituted with one or more R$^{11}$, $C_{7-14}$ aralkyl optionally substituted with one or more R$^{11}$, 5-10 membered heteroaryl optionally substituted with one or more R$^{11}$, or independently two geminal R$^4$ together are oxo;

each $R^5$ is independently selected from the group consisting of hydrogen, optionally substituted $C_{1-6}$ alkyl, optionally substituted $C_{2-6}$ alkenyl, optionally substituted $C_{2-6}$ alkynyl, optionally substituted $C_{2-8}$ alkoxyalkyl, $C_{6-10}$ aryl optionally substituted with one or more $R^{11}$, $C_{7-14}$ aralkyl optionally substituted with one or more $R^{11}$, and —$(CH_2)_n$-(3-10 membered heterocyclyl) optionally substituted with one or more $R^{10}$;

$R^6$ is selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, (5-10 membered heteroaryl)alkyl optionally substituted with one or more $R^{11}$, —$C(O)R^8$, and —$C(O)OR^5$;

$R^7$ is selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, (5-10 membered heteroaryl)alkyl optionally substituted with one or more $R^{11}$, —$C(O)R^8$, and —$C(O)OR^5$;

or $R^6$ and $R^7$ together with the nitrogen to which they are attached form an 3-10 membered heterocyclyl optionally substituted with one or more $R^{10}$;

each $R^8$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —$NR^{12}R^{13}$, and —$OR^5$;

each $R^9$ is independently selected from the group consisting of halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, —$OR^5$, —$NR^{14}R^{15}$, —$C(O)R^8$, —$SO_2R^{16}$, and —$NO_2$;

each $R^{10}$ is independently selected from the group consisting of optionally substituted $C_{1-6}$ alkyl, optionally substituted $C_{2-6}$ alkenyl, and optionally substituted $C_{2-6}$ alkynyl, or independently two geminal $R^{10}$ together are oxo;

each $R^{11}$ is independently selected from the group consisting of halogen, —CN, optionally substituted $C_{1-6}$ alkyl, optionally substituted $C_{2-6}$ alkenyl, optionally substituted $C_{2-6}$ alkynyl, and optionally substituted $C_{1-6}$ alkoxy;

each $R^{12}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

each $R^{13}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

$R^{14}$ is selected from the group consisting of hydrogen, optionally substituted $C_{1-6}$ alkyl, optionally substituted $C_{6-10}$ aryl, and —$C(O)R^8$;

$R^{15}$ is selected from the group consisting of hydrogen, optionally substituted $C_{1-6}$ alkyl, optionally substituted $C_{6-10}$ aryl, and —$C(O)R^8$;

Q is selected from $C(O)$ and $S(O)_t$;

each $R^{16}$ is independently selected from the group consisting of optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —$NR^{12}R^{13}$, and —$OR^5$;

Z is selected from oxygen and sulfur;

each n is independently an integer from 0 to 4;

t is 1 or 2; and the bonds represented by a solid and dashed line are independently selected from the group consisting of a single bond and a double bond.

Some embodiments of the present application provide a compound having the structure of formula (VIb):

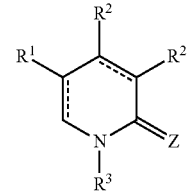

(VIb)

$R^1$ is selected from the group consisting of halogen, —CN, —$C(O)R^8$, —$SO_2R^{16}$, $C_{1-6}$ alkyl optionally substituted with one or more $R^4$, $C_{2-6}$ alkenyl optionally substituted with one or more $R^4$, $C_{2-6}$ alkynyl optionally substituted with one or more $R^4$, $C_{6-10}$ aryl optionally substituted with one or more $R^4$, 5-10 membered heteroaryl optionally substituted with one or more $R^4$, $C_{3-10}$ carbocyclyl optionally substituted with one or more $R^4$, and 3-10 membered heterocyclyl optionally substituted with one or more $R^4$;

each $R^2$ is independently selected from the group consisting of hydrogen, halogen, optionally substituted $C_{1-6}$ alkyl, optionally substituted $C_{2-6}$ alkenyl, optionally substituted $C_{2-6}$ alkynyl, —CN, —$OR^5$, —$NR^6R^7$, and —$C(O)R^8$, or both $R^2$ together with the carbon atoms to which they are attached form a fused ring selected from the group consisting of phenyl, 5-6 membered heteroaryl, $C_{3-7}$ carbocyclyl, and 3-7 membered heterocyclyl, each optionally substituted with one or more $R^4$;

$R^3$ is selected from the group consisting of —$(CH_2)_{1-4}$—$(C_{6-10}$ aryl), —$(CH_2)_{1-4}$-(5-10 membered heteroaryl), —$(CH_2)_{1-4}$—$(C_{3-10}$ carbocyclyl), and —$(CH_2)_{1-4}$-(3-10 membered heterocyclyl), each optionally substituted with one or more $R^9$;

each $R^4$ is independently selected from the group consisting of halogen, —CN, —OH, —$C(O)R^8$, —$SO_2R^{16}$, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{6-10}$ aryl optionally substituted with one or more $R^{11}$, $C_{7-14}$ aralkyl optionally substituted with one or more $R^{11}$, 5-10 membered heteroaryl optionally substituted with one or more $R^{11}$, or independently two geminal $R^4$ together are oxo;

each $R^5$ is independently selected from the group consisting of hydrogen, optionally substituted $C_{1-6}$ alkyl, optionally substituted $C_{2-6}$ alkenyl, optionally substituted $C_{2-6}$ alkynyl, optionally substituted $C_{2-8}$ alkoxyalkyl, $C_{6-10}$ aryl optionally substituted with one or more $R^{11}$, $C_{7-14}$ aralkyl optionally substituted with one or more $R^{11}$, and —$(CH_2)_n$-(3-10 membered heterocyclyl) optionally substituted with one or more $R^{10}$;

$R^6$ is selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, (5-10 membered heteroaryl)alkyl optionally substituted with one or more $R^{11}$, —C(O)$R^8$, and —C(O)O$R^5$;

$R^7$ is selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, (5-10 membered heteroaryl)alkyl optionally substituted with one or more $R^{11}$, —C(O)$R^8$, and —C(O)O$R^5$;

or $R^6$ and $R^7$ together with the nitrogen to which they are attached form an 3-10 membered heterocyclyl optionally substituted with one or more $R^{10}$;

each $R^8$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —N$R^{12}R^{13}$, and —O$R^5$;

each $R^9$ is independently selected from the group consisting of halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, —O$R^5$, —N$R^{14}R^{15}$, —C(O)$R^8$, —SO$_2R^{16}$, and —NO$_2$;

each $R^{10}$ is independently selected from the group consisting of optionally substituted $C_{1-6}$ alkyl, optionally substituted $C_{2-6}$ alkenyl, and optionally substituted $C_{2-6}$ alkynyl, or independently two geminal $R^{10}$ together are oxo;

each $R^{11}$ is independently selected from the group consisting of halogen, —CN, optionally substituted $C_{1-6}$ alkyl, optionally substituted $C_{2-6}$ alkenyl, optionally substituted $C_{2-6}$ alkynyl, and optionally substituted $C_{1-6}$ alkoxy;

each $R^{12}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

each $R^{13}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

$R^{14}$ is selected from the group consisting of hydrogen, optionally substituted $C_{1-6}$ alkyl, optionally substituted $C_{6-10}$ aryl, and —C(O)$R^8$;

$R^{15}$ is selected from the group consisting of hydrogen, optionally substituted $C_{1-6}$ alkyl, optionally substituted $C_{6-10}$ aryl, and —C(O)$R^8$;

each $R^{16}$ is independently selected from the group consisting of optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —N$R^{12}R^{13}$, and —O$R^5$;

Z is selected from oxygen and sulfur;

each n is independently an integer from 0 to 4; and the bonds represented by a solid and dashed line are independently selected from the group consisting of a single bond and a double bond; provided that when $R^1$ is selected from the group consisting of optionally substituted $C_{6-10}$ aryl, optionally substituted 5 to 10 membered heteroaryl, optionally substituted 6 to 10 membered heterocyclyl, optionally substituted hexyl, optionally substituted alkyl, optionally substituted alkenyl; each of $R^2$ is hydrogen or one of $R^2$ is hydrogen and the other $R^2$ is methyl; and Z is O; then $R^3$ is not —CH$_2$-phenyl substituted with one or more halogen atoms; and provided that $R^1$ is not 4-methoxy phenyl.

Some embodiments of the present application provide a compound having the structure of formula (VIII):

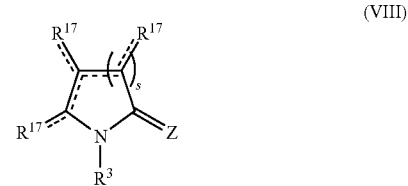

(VIII)

$R^3$ is selected from the group consisting of optionally substituted $C_{1-6}$ alkyl, optionally substituted $C_{2-6}$ alkenyl, optionally substituted $C_{2-6}$ alkynyl, —(CH$_2$)$_n$—(C$_{6-10}$ aryl) optionally substituted with one or more $R^9$, —(CH$_2$)$_n$-(5-10 membered heteroaryl) optionally substituted with one or more $R^9$, —(CH$_2$)$_n$—(C$_{3-10}$ carbocyclyl) optionally substituted with one or more $R^9$, and —(CH$_2$)$_n$-(3-10 membered heterocyclyl) optionally substituted with one or more $R^9$;

each $R^9$ is independently selected from the group consisting of halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, —O$R^5$, —N$R^{14}R^{15}$, —C(O)$R^8$, —SO$_2R^{16}$, and —NO$_2$;

$R^{14}$ is selected from the group consisting of hydrogen, optionally substituted $C_{1-6}$ alkyl, optionally substituted $C_{6-10}$ aryl, and —C(O)$R^8$;

$R^{15}$ is selected from the group consisting of hydrogen, optionally substituted $C_{1-6}$ alkyl, optionally substituted $C_{6-10}$ aryl, and —C(O)$R^8$;

each $R^8$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —N$R^{12}R^{13}$, and —O$R^5$;

each $R^{12}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

each $R^{13}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

each $R^5$ is independently selected from the group consisting of hydrogen, optionally substituted $C_{1-6}$ alkyl, optionally substituted $C_{2-6}$ alkenyl, optionally substituted $C_{2-6}$ alkynyl, optionally substituted $C_{2-8}$ alkoxyalkyl, $C_{6-10}$ aryl optionally substituted with one or more $R^{11}$, $C_{7-14}$ aralkyl optionally substituted with one or more $R^{11}$, and —(CH$_2$)$_n$-(3-10 membered heterocyclyl) optionally substituted with one or more $R^{10}$;

each $R^{10}$ is independently selected from the group consisting of optionally substituted $C_{1-6}$ alkyl, optionally substituted $C_{2-6}$ alkenyl, and optionally substituted $C_{2-6}$ alkynyl, or independently two geminal $R^{10}$ together are oxo;

each $R^{11}$ is independently selected from the group consisting of halogen, —CN, optionally substituted $C_{1-6}$ alkyl, optionally substituted $C_{2-6}$ alkenyl, optionally substituted $C_{2-6}$ alkynyl, and optionally substituted $C_{1-6}$ alkoxy;

each $R^{17}$ is independently selected from the group consisting of hydrogen, oxo, halogen, —CN, —C(O)R$^8$, —SO$_2$R$^{16}$, $C_{1-6}$ alkyl optionally substituted with one or more $R^4$, $C_{2-6}$ alkenyl optionally substituted with one or more $R^4$, $C_{2-6}$ alkynyl optionally substituted with one or more $R^4$, $C_{6-10}$ aryl optionally substituted with one or more $R^4$, 5-10 membered heteroaryl optionally substituted with one or more $R^4$, $C_{3-10}$ carbocyclyl optionally substituted with one or more $R^4$, and 3-10 membered heterocyclyl optionally substituted with one or more $R^4$, or independently two adjacent $R^{17}$ together with the carbon atoms to which they are attached form a fused phenyl or 5-6 membered heteroaryl, each optionally substituted with one or more $R^4$;

each $R^4$ is independently selected from the group consisting of halogen, —CN, —OH, —C(O)R$^8$, —SO$_2$R$^{16}$, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{6-10}$ aryl optionally substituted with one or more $R^{11}$, $C_{7-14}$ aralkyl optionally substituted with one or more $R^{11}$, 5-10 membered heteroaryl optionally substituted with one or more $R^{11}$, or independently two geminal $R^4$ together are oxo;

each $R^{16}$ is independently selected from the group consisting of optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —NR$^{12}$R$^{13}$, and —OR$^5$;

Z is selected from oxygen and sulfur;

each n is independently an integer from 0 to 4;

s is 0, 1, or 3; and the bonds represented by a solid and dashed line are independently selected from the group consisting of a single bond and a double bond.

Some embodiments of the present application provide a compound having the structure of formula (IX):

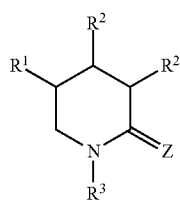

(IX)

$R^1$ is selected from the group consisting of hydrogen, halogen, —CN, —C(O)R$^8$, —SO$_2$R$^{16}$, $C_{1-6}$ alkyl optionally substituted with one or more $R^4$, $C_{2-6}$ alkenyl optionally substituted with one or more $R^4$, $C_{2-6}$ alkynyl optionally substituted with one or more $R^4$, $C_{6-10}$ aryl optionally substituted with one or more $R^4$, 5-10 membered heteroaryl optionally substituted with one or more $R^4$, $C_{3-10}$ carbocyclyl optionally substituted with one or more $R^4$, and 3-10 membered heterocyclyl optionally substituted with one or more $R^4$;

each $R^2$ is independently selected from the group consisting of hydrogen, halogen, optionally substituted $C_{1-6}$ alkyl, optionally substituted $C_{2-6}$ alkenyl, optionally substituted $C_{2-6}$ alkynyl, —CN, —OR$^5$, —NR$^6$R$^7$, and —C(O)R$^8$, or both $R^2$ together with the carbon atoms to which they are attached form a fused ring selected from the group consisting of $C_{3-7}$ carbocyclyl and 3-7 membered heterocyclyl, each optionally substituted with one or more $R^4$;

$R^3$ is selected from the group consisting of —(CH$_2$)$_n$—(C$_{6-10}$ aryl), —(CH$_2$)$_n$-(5-10 membered heteroaryl), —(CH$_2$)$_n$—(C$_{3-10}$ carbocyclyl), and —(CH$_2$)$_n$-(3-10 membered heterocyclyl), each optionally substituted with one or more $R^9$;

each $R^4$ is independently selected from the group consisting of halogen, —CN, —OH, —C(O)R$^8$, —SO$_2$R$^{16}$, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{6-10}$ aryl optionally substituted with one or more $R^{11}$, $C_{7-14}$ aralkyl optionally substituted with one or more $R^{11}$, 5-10 membered heteroaryl optionally substituted with one or more $R^{11}$, or independently two geminal $R^4$ together are oxo;

each $R^5$ is independently selected from the group consisting of hydrogen, optionally substituted $C_{1-6}$ alkyl, optionally substituted $C_{2-6}$ alkenyl, optionally substituted $C_{2-6}$ alkynyl, optionally substituted $C_{2-8}$ alkoxyalkyl, $C_{6-10}$ aryl optionally substituted with one or more $R^{11}$, $C_{7-14}$ aralkyl optionally substituted with one or more $R^{11}$, and —(CH$_2$)$_n$-(3-10 membered heterocyclyl) optionally substituted with one or more $R^{10}$;

$R^6$ is selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, (5-10 membered heteroaryl)alkyl optionally substituted with one or more $R^{11}$, —C(O)R$^8$, and —C(O)OR$^5$;

$R^7$ is selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, (5-10 membered heteroaryl)alkyl optionally substituted with one or more $R^{11}$, —C(O)R$^8$, and —C(O)OR$^5$;

or $R^6$ and $R^7$ together with the nitrogen to which they are attached form an 3-10 membered heterocyclyl optionally substituted with one or more $R^{10}$;

each $R^8$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —NR$^{12}$R$^{13}$, and —OR$^5$;

each $R^9$ is independently selected from the group consisting of halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, —OR$^5$, —NR$^{14}$R$^{15}$, —C(O)R$^8$, —SO$_2$R$^{16}$, and —NO$_2$;

each $R^{10}$ is independently selected from the group consisting of optionally substituted $C_{1-6}$ alkyl, optionally substituted $C_{2-6}$ alkenyl, and optionally substituted $C_{2-6}$ alkynyl, or independently two geminal $R^{10}$ together are oxo;

each $R^{11}$ is independently selected from the group consisting of halogen, —CN, optionally substituted $C_{1-6}$ alkyl, optionally substituted $C_{2-6}$ alkenyl, optionally substituted $C_{2-6}$ alkynyl, and optionally substituted $C_{1-6}$ alkoxy;

each $R^{12}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

each $R^{13}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

$R^{14}$ is selected from the group consisting of hydrogen, optionally substituted $C_{1-6}$ alkyl, optionally substituted $C_{6-10}$ aryl, and —C(O)$R^8$;

$R^{15}$ is selected from the group consisting of hydrogen, optionally substituted $C_{1-6}$ alkyl, optionally substituted $C_{6-10}$ aryl, and —C(O)$R^8$;

each $R^{16}$ is independently selected from the group consisting of optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —N$R^{12}R^{13}$, and —O$R^5$;

Z is selected from oxygen and sulfur; and each n is independently an integer from 0 to 4.

Some embodiments disclosed herein relate to methods of treating a fibrotic condition, comprising administering a therapeutically effective amount of a compound of any one of Formulae (I), (II), (III), (IV), (V), (VIa), (VIb), (VII), (VIII) and (IX), a compound selected from Table 1, a pharmaceutically acceptable salt thereof, or a pharmaceutical composition thereof to a subject in need thereof. In some such embodiments, the method further comprises identifying the subject as having or at risk of having said fibrotic condition. In some such embodiments, the fibrotic condition is selected from the group consisting of pulmonary fibrosis, dermal fibrosis, pancreatic fibrosis, liver fibrosis, and renal fibrosis. In some embodiment, the fibrotic condition is idiopathic pulmonary fibrosis. In some embodiments, the subject receiving such method of treatment is a human.

DETAILED DESCRIPTION OF THE PREFERRED EMBODIMENTS

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:

Ac Acetyl
$Ac_2O$ Acetic anhydride
aq. Aqueous
Bn Benzyl
Bz Benzoyl
BOC or Boc tert-Butoxycarbonyl
Bu n-Butyl
cat. Catalytic
Cbz Carbobenzyloxy
CDI 1,1'-carbonyldiimidazole
° C. Temperature in degrees Centigrade
DBU 1,8-Diazabicyclo[5.4.0]undec-7-ene
DCE 1,2-Dichloroethane
DCM Methylene chloride
DIEA Diisopropylethylamine
DMA Dimethylacetamide
DME Dimethoxyethane
DMF N,N'-Dimethylformamide
DMSO Dimethylsulfoxide
DPPA Diphenylphosphoryl azide
ee % Enantiomeric excess
Et Ethyl
EtOAc or EA Ethyl acetate
g Gram(s)
h or hr Hour(s)
HATU 2-(1H-7-azabenzotriazol-1-yl)-1,1,3,3-tetramethyl uronium hexafluorophosphate
HOBT N-Hydroxybenzotriazole
iPr Isopropyl
LCMS Liquid chromatography-mass spectrometry
LDA Lithium diisopropylamide
LiHMDS Lithium bis(trimethylsilyl)amide
m or min Minute(s)
mCPBA meta-Chloroperoxybenzoic Acid
MeOH Methanol
MeCN Acetonitrile
mL Milliliter(s)
MTBE Methyl tertiary-butyl ether
$NH_4OAc$ Ammonium acetate
PE Petroleum ether
PG Protecting group
Pd/C Palladium on activated carbon
Pd(dppf)$Cl_2$, 1,1'-Bis(diphenylphosphino)ferrocene-palladium(II)dichloride
Ph Phenyl
ppt Precipitate
PMBC 4-Methoxybenzyl chloride
RCM Ring closing metathesis
rt Room temperature
sBuLi sec-Butyllithium
SFC Supercritical fluid chromatography
TBAF Tetrabutylammonium fluoride TEA Triethylamine
TCDI 1,1'-Thiocarbonyl diimidazole
Tert, t tertiary
TFA Trifluoroacetic acid
TFAA Trifluoroacetic acid anhydride
THF Tetrahydrofuran
TLC Thin-layer chromatography
TMEDA Tetramethylethylenediamine
TMSNCO trimethylsilyl isocyanate
µL Microliter(s)

"Solvate" refers to the compound formed by the interaction of a solvent and a compound described herein or salt thereof. Suitable solvates are pharmaceutically acceptable solvates including hydrates.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

A "cyano" group refers to a "—CN" group.
A "cyanato" group refers to an "—OCN" group.
An "isocyanato" group refers to a "—NCO" group.
A "thiocyanato" group refers to a "—SCN" group.
An "isothiocyanato" group refers to an "—NCS" group.
A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)OC(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N(R$_A$)OC(=S)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

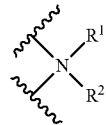

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

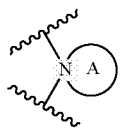

where ring A is a heteroaryl ring containing the depicted nitrogen.

Similarly, when two "adjacent" R groups are said to form a ring "together with the atom to which they are attached," it is meant that the collective unit of the atoms, intervening bonds, and the two R groups are the recited ring. For example, when the following substructure is present:

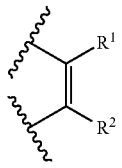

and $R^1$ and $R^2$ are defined as selected from the group consisting of hydrogen and alkyl, or $R^1$ and $R^2$ together with the atoms to which they are attached form an aryl or carbocylyl, it is meant that $R^1$ and $R^2$ can be selected from hydrogen or alkyl, or alternatively, the substructure has structure:

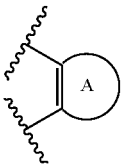

where A is an aryl ring or a carbocylyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

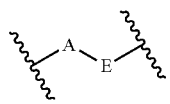

includes the substituent being oriented such that the A is attached at the leftmost attachment point of the molecule as well as the case in which A is attached at the rightmost attachment point of the molecule.

As used herein, "isosteres" of a chemical group are other chemical groups that exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated include —$SO_3H$, —$SO_2HNR$, —$PO_2(R)_2$, —$PO_3(R)_2$, —$CONHNHSO_2R$, —$COHNSO_2R$, and —CONRCN, where R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. In addition, carboxylic acid isosteres can include 5-7 membered carbocycles or heterocycles containing any combination of $CH_2$, O, S, or N in any chemically stable oxidation state, where any of the atoms of said ring structure are optionally substituted in one or more positions. The following structures are non-limiting examples of carbocyclic and heterocyclic isosteres contemplated. The atoms of said ring structure may be optionally substituted at one or more positions with R as defined above.

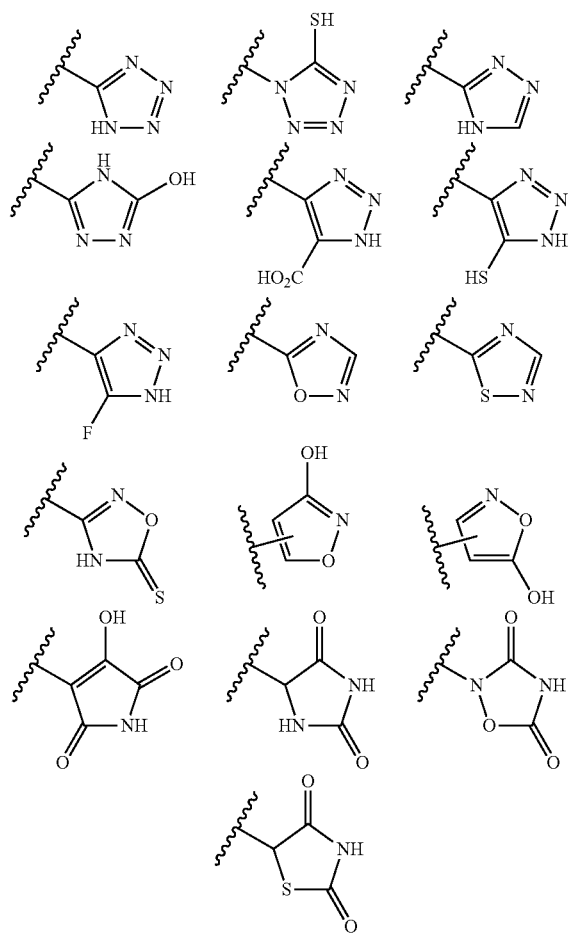

It is also contemplated that when chemical substituents are added to a carboxylic isostere, the compound retains the properties of a carboxylic isostere. It is contemplated that when a carboxylic isostere is optionally substituted with one or more moieties selected from R as defined above, then the substitution and substitution position is selected such that it does not eliminate the carboxylic acid isosteric properties of the compound. Similarly, it is also contemplated that the placement of one or more R substituents upon a carbocyclic or heterocyclic carboxylic acid isostere is not a substitution at one or more atom(s) that maintain(s) or is/are integral to the carboxylic acid isosteric properties of the compound, if such substituent(s) would destroy the carboxylic acid isosteric properties of the compound.

Other carboxylic acid isosteres not specifically exemplified in this specification are also contemplated.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

A therapeutic effect relieves, to some extent, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Compounds

Formula I

Some embodiments disclosed herein relate to a compound of formula (I) as described above or a pharmaceutically acceptable salt thereof.

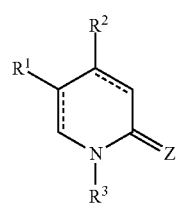

(I)

Some embodiments disclosed herein with respect to the compounds of formula (I), $R^2$ is selected from the group consisting of halogen, $-OR^5$, $-NR^6R^7$, and $-C(O)R^8$; $R^3$ is selected from the group consisting of $-(CH_2)_n-(C_{6-10}$ aryl), $-(CH_2)_n$-(5-10 membered heteroaryl), $-(CH_2)_n-(C_{3-10}$ carbocyclyl), and $-(CH_2)_n$-(3-10 membered heterocyclyl), each optionally substituted with one or more $R^9$; each $R^9$ is independently selected from the group consisting of halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, $-OR^5$, $-NR^{14}R^{15}$, $-C(O)R^8$, $-SO_2R^{16}$, and $-NO_2$; and each $R^{11}$ is independently selected from the group consisting of halogen, $-CN$, optionally substituted $C_{1-6}$ alkyl, optionally substituted $C_{2-6}$ alkenyl, optionally substituted $C_{2-6}$ alkynyl, and optionally substituted $C_{1-6}$ alkoxy.

In some embodiments, $R^1$ is a $C_{6-10}$ aryl optionally substituted with one or more $R^4$. In some further embodiments, $R^1$ is a phenyl optionally substituted with one or more $R^4$.

In some embodiments, $R^1$ is a 5-10 membered heteroaryl optionally substituted with one or more $R^4$. In some such embodiments, $R^1$ is a pyrazolyl or 1-methyl pyrazolyl optionally substituted with one or more $R^4$. In some such embodiments, $R^1$ is a pyridazinyl optionally substituted with one or more $R^4$. In some such embodiments, $R^1$ is a pyrimidinyl optionally substituted with one or more $R^4$.

In any of the embodiments of Formula (I) described herein, each $R^4$ is independently selected from halogen, or optionally substituted $C_{1-6}$ alkyl. In some embodiments, $R^4$ is halogen. In some embodiments, $R^4$ is substituted $C_{1-6}$ alkyl. In some other embodiments, $R^4$ is unsubstituted $C_{1-6}$ alkyl. In some embodiments, $R^4$ is fluoro. In some other embodiments, $R^4$ is methyl.

In some embodiments, $R^2$ is halogen. In some further embodiments, $R^2$ is selected from bromo or chloro.

In some embodiments, $R^2$ is $-CN$.

In some embodiments, $R^2$ is $-OR^5$. In some embodiments, $R^5$ is selected from hydrogen, optionally substituted $C_{1-6}$ alkyl, optionally substituted $C_{2-8}$ alkoxyalkyl, $C_{7-14}$ aralkyl optionally substituted with one or more $R^{11}$, $C_{6-10}$ aryl optionally substituted with one or more $R^{11}$, and $-(CH_2)_n$-(3-10 membered heterocyclyl) optionally substituted with one or more $R^{10}$. In some embodiments, $R^5$ is hydrogen. In some embodiments, $R^5$ is optionally substituted $C_{1-6}$ alkyl. In some such embodiments, $R^5$ is methyl. In some such embodiments, $R^5$ is halogen substituted ethyl. In some embodiments, $R^5$ is $C_{6-10}$ aryl optionally substituted with one or more $R^{11}$. In some such embodiments, $R^5$ is phenyl optionally substituted with one or more $R^{11}$. In some such embodiments, $R^5$ is unsubstituted phenyl. In some embodiments, $R^5$ is $C_{7-14}$ aralkyl optionally substituted with one or more $R^{11}$. In some such embodiments, $R^5$ is benzyl optionally substituted with one or more $R^{11}$. In some such embodiments, $R^5$ is unsubstituted benzy. In some such embodiments, $R^5$ is optionally substituted $C_{2-8}$ alkoxyalkyl. In some such embodiments, $R^5$ is selected from $-(CH_2)_2OCH_3$, $-(CH_2)_2OC_3H_7$ or $-(CH_2)_2O(CH_2)OCH_3$. In some such embodiments, $R^5$ is $-(CH_2)_n$-(5 or 6 membered heterocyclyl) optionally substituted with one or more $R^{10}$. In some such embodiments, $R^5$ is

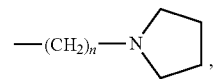

optionally substituted with one or more $R^{10}$. In some such embodiments, $R^5$ is selected from

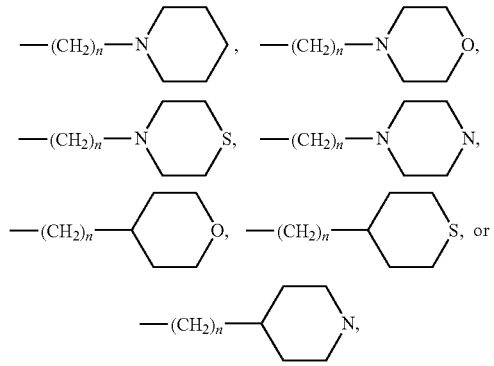

each optionally substituted with one or more $R^{10}$. In some embodiments, $R^5$ can be optionally substituted

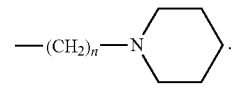

In some embodiments, $R^5$ can be optionally substituted

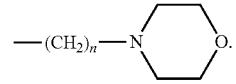

In some embodiments, $R^5$ can be optionally substituted

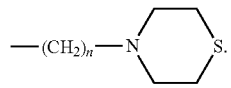

In some embodiments, $R^5$ can be optionally substituted

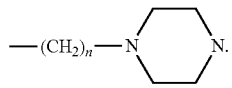

In some embodiments, $R^5$ can be optionally substituted

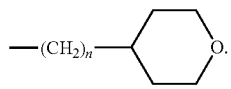

In some embodiments, $R^5$ can be optionally substituted

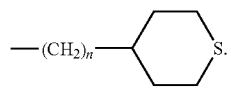

In some embodiments, $R^5$ can be optionally substituted

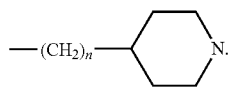

In some embodiments of this paragraph, n is 0. In some embodiments of this paragraph, n is 1. In some embodiments of this paragraph, $R^5$ is substituted with one or more substituents selected from $C_{1-6}$ alkyl, $C_{1-6}$ alkoxy, $C_{1-6}$ alkyl, —O(CH$_2$)$_2$OCH$_3$, halogen or —C(O)NH$_2$.

In some embodiments, $R^2$ is —NR$^6$R$^7$. In some embodiments, each $R^6$ and $R^7$ is independently selected from hydrogen, $C_{1-6}$ alkyl, $C_{6-10}$ aryl optionally substituted with one or more $R^{11}$, $C_{7-14}$ aralkyl optionally substituted with one or more $R^{11}$, (5-10 membered heteroaryl)alkyl optionally substituted with one or more $R^{11}$, —C(O)R$^8$, or —C(O)OR$^5$. In some embodiments, $R^6$ is hydrogen. In some other embodiments, $R^6$ is $C_{1-6}$ alkyl. In some embodiments, $R^7$ is hydrogen. In some embodiments, $R^7$ is $C_{1-6}$ alkyl. In some embodiments, $R^7$ is $C_{6-10}$ aryl optionally substituted with one or more $R^{11}$. In some embodiments, $R^7$ is phenyl optionally substituted with one or more $R^{11}$. In some other embodiments, $R^7$ is unsubstituted phenyl.

In some embodiments, $R^7$ is $C_{7-14}$ aralkyl optionally substituted with one or more $R^{11}$. In some embodiments, $R^7$ is benzyl or —(CH$_2$)$_2$Ph, each optionally substituted with one or more $R^{11}$. In some such embodiments, $R^7$ is substituted with one or more substituents selected from $C_{1-6}$ alkyl, $C_{1-6}$ alkoxy, $C_{1-6}$ alkyl, —O(CH$_2$)$_2$OCH$_3$, halogen or —CN. In some embodiments, $R^7$ is unsubstituted benzyl. In some other embodiments, $R^7$ is unsubstituted —(CH$_2$)$_2$Ph.

In some embodiments, $R^7$ is (6 membered heteroaryl) alkyl optionally substituted with one or more $R^{11}$. In some embodiments, $R^7$ is —CH$_2$-pyridyl, —CH$_2$-pyrimidinyl or —CH$_2$— pyrazinyl, each optionally substituted with one or more $R^{11}$. In some embodiments, $R^7$ is unsubstituted —CH$_2$-pyridyl. In some embodiments, $R^7$ is unsubstituted —CH$_2$-pyrazinyl. In some embodiments, $R^7$ is unsubstituted —CH$_2$-pyrimidinyl.

In some embodiments, $R^7$ is —C(O)R$^8$. In some embodiments, $R^8$ is selected from $C_{1-6}$ alkyl, $C_{6-10}$ aryl, or —NR$^{12}$R$^{13}$. In some embodiments, $R^8$ is selected from methyl, ethyl, propyl, isopropyl, butyl, pentyl or phenyl. In some embodiments, $R^8$ is methyl. In some other embodiments, $R^8$ is phenyl. In some embodiments, $R^8$ is —NR$^{12}$R$^{13}$. In some embodiments, each $R^{12}$ and $R^{13}$ is independently selected from hydrogen, $C_{1-6}$ alkyl, or benzyl.

In some embodiments, $R^7$ is —C(O)OR$^5$. In some embodiments, $R^5$ is selected from hydrogen, $C_{1-6}$ alkyl, $C_{6-10}$ aryl optionally substituted with one or more $R^{11}$, or $C_{7-14}$ aralkyl optionally substituted with one or more $R^{11}$. In some embodiments, $R^5$ is selected from methyl, ethyl, isopropyl, or butyl. In some embodiments, $R^5$ is selected from phenyl or benzyl, each optionally substituted with one or more $R^{11}$.

In some embodiments, $R^6$ and $R^7$ together with the nitrogen to which they are attached form a 6-10 membered heterocyclyl optionally substituted with one or more $R^{10}$. In some embodiments, the heterocyclyl formed by $R^6$ and $R^7$ together with the nitrogen to which they are attached is selected from

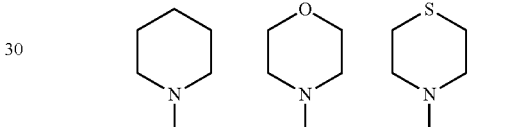

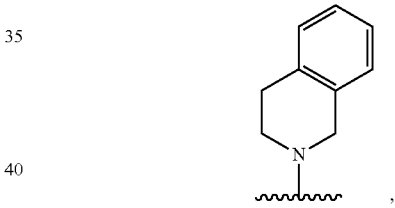

each optionally substituted with one or more $R^{10}$. In some such embodiments, the heterocyclyl formed by $R^6$ and $R^7$ together with the nitrogen to which they are attached can be optionally substituted

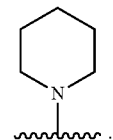

In some such embodiments, the heterocyclyl formed by $R^6$ and $R^7$ together with the nitrogen to which they are attached can be optionally substituted

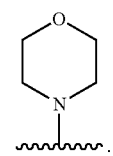

In some such embodiments, the heterocyclyl formed by $R^6$ and $R^7$ together with the nitrogen to which they are attached can be optionally substituted

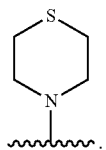

In some such embodiments, the heterocyclyl formed by $R^6$ and $R^7$ together with the nitrogen to which they are attached can be optionally substituted

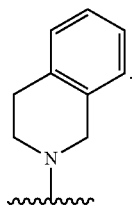

In some embodiments, $R^{10}$ is $C_{1-6}$ alkyl. In some embodiments, two geminal $R^{10}$ together are oxo. In some other embodiments, the heterocyclyl formed by $R^6$ and $R^7$ together with the nitrogen to which they are attached is unsubstituted.

In some embodiments, $R^2$ is —$SR^5$. In some such embodiments, $R^5$ is $C_{6-10}$ aryl optionally substituted with one or more $R^{11}$. In some further such embodiments, $R^5$ is optionally substituted phenyl.

In some embodiments, $R^2$ is —$C(O)R^8$. In some embodiments, $R^8$ is selected from —$NR^{12}R^{13}$. In some embodiments, each $R^{12}$ and $R^{13}$ is independently selected from hydrogen, optionally substituted $C_{1-6}$ alkyl, $C_{6-10}$ aryl optionally substituted with one or more $R^{11}$, or $C_{7-14}$ aralkyl optionally substituted with one or more $R^{11}$. In some embodiments, each $R^{12}$ and $R^{13}$ is independently selected from hydrogen, $C_{1-6}$ alkyl, phenyl optionally substituted with one or more $R^{11}$ or benzyl optionally substituted with one or more $R^{11}$. In some embodiments, the phenyl or benzyl is unsubstituted.

In some embodiments, $R^2$ is —$C(O)OR^5$. In some embodiments, $R^5$ is hydrogen or $C_{1-6}$ alkyl.

In any of the embodiments of formula (I) described herein, each $R^{11}$ is independently selected from —CN, halogen, optionally substituted $C_{1-6}$ alkyl, optionally substituted $C_{1-6}$ alkoxy, O—$(CH_2)_n$—$C_{2-8}$ alkoxy, or —$C(O)NR^{12}R^{13}$. In some such embodiments, $R^{11}$ is selected from —CN, —Cl, —F, —$CH_3$, —$OCH_3$, $OC_2H_5$, —$CF_3$ or —$OCF_3$. In some embodiments, $R^{11}$ is —F. In some embodiments, $R^{11}$ is —$OCF_3$. In yet some other embodiments, $R^{11}$ is —$OC_2H_5$. In yet some other embodiments, $R^{11}$ is methyl. In some embodiments, $R^{11}$ is —O—$(CH_2)_2$—$OCH_3$. In some other embodiments, $R^{11}$ is —$C(O)NH_2$ Some embodiments disclosed herein with respect to the compounds of formula (I), $R^3$ is selected from the group consisting of —$(CH_2)_n$—$(C_{6-10}$ aryl), —$(CH_2)_n$-(5-10 membered heteroaryl), —$(CH_2)_n$—$(C_{3-10}$ carbocyclyl), and —$(CH_2)_n$-(3-10 membered heterocyclyl), each optionally substituted with one or more $R^9$. In some embodiments, n is 0.

In some embodiments, $R^3$ is —$(CH_2)_n$—$(C_{6-10}$ aryl) optionally substituted with one or more $R^9$. In some embodiments, $R^3$ is —$(CH_2)_n$-phenyl, optionally substituted with one or more $R^9$. In some embodiments, n is 0. In some other embodiments, $R^3$ is unsubstituted —$(CH_2)_n$-phenyl. In some other embodiments, $R^3$ is unsubstituted phenyl.

In any of the embodiments of formula (I) described herein, $R^9$ is selected from halogen, optionally substituted $C_{1-6}$ alkyl, or —$OR^5$. In some further embodiments, $R^9$ is selected from fluoro, chloro. In some further embodiments, $R^9$ is selected from methyl, ethyl, or trifluoromethyl. In some embodiments, $R^9$ is —$OR^5$. In some embodiment, $R^5$ is selected from hydrogen, $C_{1-6}$ alkyl or halo substituted $C_{1-6}$ alkyl. In some further embodiments, $R^5$ is selected from trifluoromethyl or ethyl. In some further embodiments, $R^5$ is optionally substituted $C_{2-8}$ alkoxyalkyl. In some embodiment, $R^9$ is $NR^{14}R^{15}$. In some such embodiments, $R^9$ is —NH—$C(O)R^8$. In some further such embodiments, $R^9$ is selected from —NH—$C(O)$—$C_{1-6}$ alkyl, or —NH—$C(O)$—$NH_2$. In some embodiments, $R^9$ is hydroxy.

Some embodiments described herein with respect to compounds of formula (I), $R^3$ is unsubstituted. In some other embodiments, $R^3$ is hydrogen.

In some embodiments, Z is oxygen.

In some embodiments, the bonds represented by a solid and dashed line are double bonds. In some such embodiments, compounds of formula (I) are also represented by

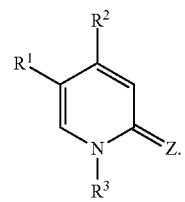

In some embodiments, the compound of formula (I) is selected from the group consisting of Compounds 85-162, 401-414, 523-545, 550, 551 and 664 in Table 1. In some further embodiments, the compound of formula (I) is selected from the group consisting of Compounds 85-162, 401-414, 523-538, 540, 541, 543, 545-, 664 and 696-707 of Table 1.

Some alternative embodiments provide compounds of formula (I) with the same variable definitions as provided above with the exception that $R^2$ is selected from 5-10 membered heteroaryl or 3-10 membered heterocyclyl, each optionally substituted with one or more $R^4$. One non-limiting example of these alternative embodiments is where the compound of formula (I) is Compound 708 of Table 1.

Formula II

Some embodiments disclosed herein relate to a compound of formula (II) as described above or a pharmaceutically acceptable salt thereof.

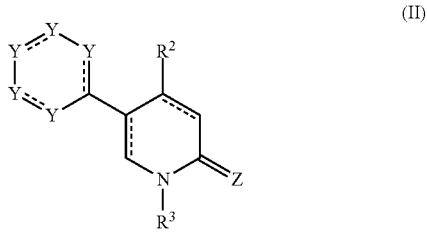

Some embodiments disclosed herein with respect to the compounds of formula (II), formula (II) is also represented by formula (IIa):

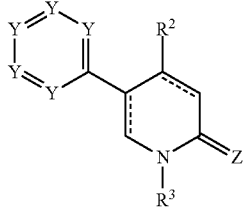

R³ is selected from the group consisting of —(CH₂)ₙ—(C₆₋₁₀ aryl), —(CH₂)ₙ-(5-10 membered heteroaryl), —(CH₂)ₙ—(C₃₋₁₀ carbocyclyl), and —(CH₂)ₙ-(3-10 membered heterocyclyl), each optionally substituted with one or more R⁹; and each R⁹ is independently selected from the group consisting of halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, —OR⁵, —NR¹⁴R¹⁵, —C(O)R⁸, —SO₂R¹⁶, and —NO₂.

In some embodiments, R² is selected from optionally substituted $C_{1-6}$ alkyl. In some embodiments, R² is selected from methyl, ethyl, isopropyl, or trifluoromethyl. In some embodiments, R² is methyl.

Some embodiments disclosed herein with respect to the compounds of formula (II), R³ is hydrogen. In some such embodiments, the compound of formula (II) is selected from the group consisting of compounds 562-565, 567, 662 and 663 of Table 1.

Some embodiments disclosed herein with respect to the compounds of formula (II), R³ is selected from the group consisting of —(CH₂)ₙ—(C₆₋₁₀ aryl), —(CH₂)ₙ-(5-10 membered heteroaryl), —(CH₂)ₙ—(C₃₋₁₀ carbocyclyl), and —(CH₂)ₙ-(3-10 membered heterocyclyl), each optionally substituted with one or more R⁹. In some embodiments, n is 0.

In some embodiments, R³ is selected from —(CH₂)ₙ—(C₆₋₁₀ aryl), optionally substituted with one or more R⁹. In some embodiments, R³ is —(CH₂)ₙ-phenyl optionally substituted with one or more R⁹. In some embodiments, R³ is phenyl, optionally substituted with one or more R⁹. In some embodiments, R³ is unsubstituted phenyl. In some embodiments, R³ is unsubstituted —(CH₂)ₙ—(C₆₋₁₀ aryl).

In some embodiments, R³ is selected from —(CH₂)ₙ-(9 membered heterocyclyl), optionally substituted with one or more R⁹. In some embodiments, R³ is selected from

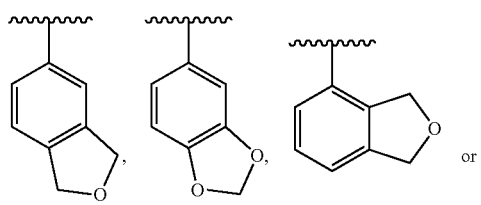

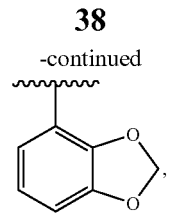

each optionally substituted with one or more R⁹. In some such embodiments, R³ is optionally substituted

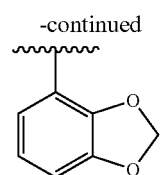

In some such embodiments, R³ is optionally substituted

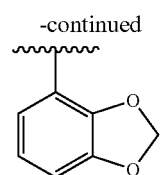

In some such embodiments, R³ is optionally substituted

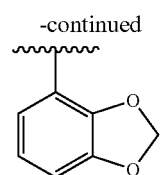

In some such embodiments, R³ is optionally substituted

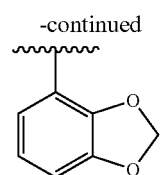

In some embodiments, R³ is unsubstituted.

In some embodiments, R³ is selected from —(CH₂)ₙ-(10 membered heterocyclyl), optionally substituted with one or more R⁹. In some embodiments, n is 0. In some embodiments, R³ is selected from

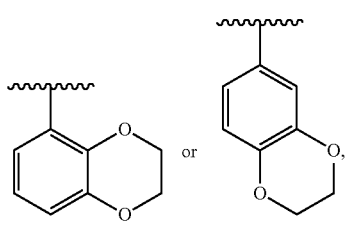

each optionally substituted with one or more $R^9$. In some embodiments, $R^3$ is unsubstituted.

In any of embodiments of formula (II) described herein, each $R^9$ is independently selected from halogen, optionally substituted $C_{1-6}$ alkyl, $-OR^5$, $-NR^{14}R^{15}$ or $-C(O)R^8$. In some embodiments, $R^9$ is selected from methyl, ethyl, propyl isopropyl, or trifluoromethyl. In some embodiments, $R^9$ is selected from fluoro or chloro.

In some embodiments, $R^9$ is $-OR^5$, and wherein $R^5$ is selected from optionally substituted $C_{1-6}$ alkyl. In some embodiments, $R^5$ is unsubstituted $C_{1-6}$ alkyl. In some embodiments, $R^5$ is selected from methyl, ethyl, propyl, isopropyl or trifluoromethyl. In some embodiments, $R^5$ is methyl. In some other embodiments, $R^5$ is trifluoromethyl.

In some embodiments, $R^9$ is $-NR^{14}R^{15}$, and wherein each $R^{14}$ and $R^{15}$ is independently selected from hydrogen, $C_{1-6}$ alkyl or $-C(O)R^8$. In some embodiments, $R^8$ is selected from optionally substituted $C_{1-6}$ alkyl, $-OR^5$ or $-NR^{12}R^{13}$. In some embodiments, each $R^{12}$ and $R^{13}$ is independently selected from hydrogen or $C_{1-6}$ alkyl. In some embodiments, each $R^{12}$ and $R^{13}$ is independently selected from hydrogen or methyl. In some embodiments, $R^5$ is selected from hydrogen or $C_{1-6}$ alkyl. In some embodiments, each $R^{14}$ and $R^{15}$ is independently selected from hydrogen, methyl, ethyl, $-C(O)NH_2$, $-C(O)NHCH_3$, $-C(O)N(CH_3)_2$, $-C(O)OH$ or $-C(O)OEt$.

In some embodiments, $R^9$ is $-C(O)R^8$. In some embodiments, $R^8$ is selected from optionally substituted $C_{1-6}$ alkyl or $-NR^{12}R^{13}$. In some embodiments, $R^8$ is selected from methyl, $-NH_2$ or $-NHCH_3$.

In some embodiments, all Y is $CR^4$.

In some embodiments, at least one Y in

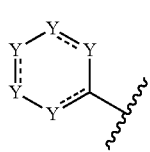

is N. In some embodiments,

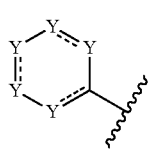

is selected from

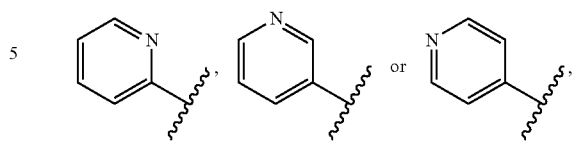

each optionally substituted with one to four $R^4$. In some such embodiments,

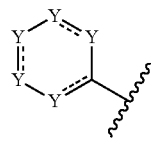

is optionally substituted

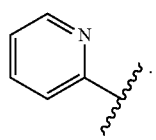

In some such embodiments,

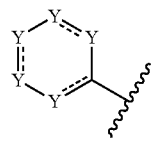

is optionally substituted

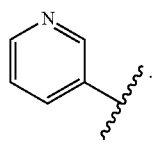

In some such embodiments,

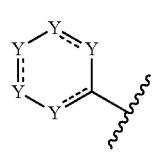

is optionally substituted

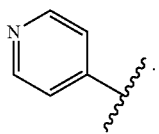

In some embodiments, at least one Y in

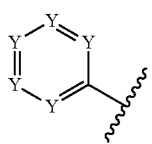

is N. In some embodiments,

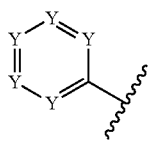

is selected from

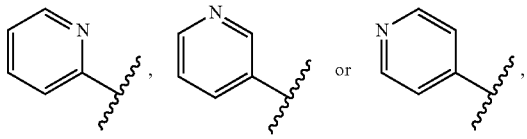

each optionally substituted with one to four R⁴. In some such embodiments,

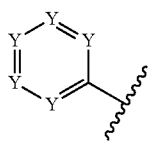

is optionally substituted

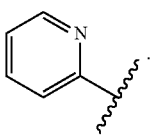

In some such embodiments,

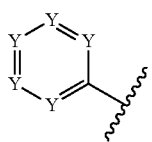

is optionally substituted

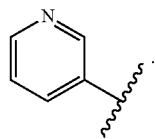

In some such embodiments,

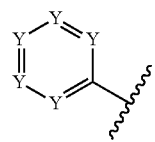

is optionally substituted

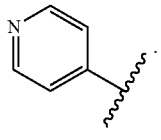

In some other embodiments, two of Y in

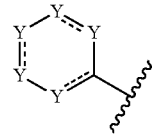

are N. In some embodiments,

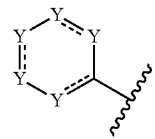

is selected from

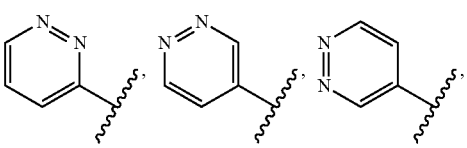

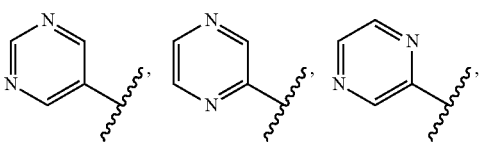

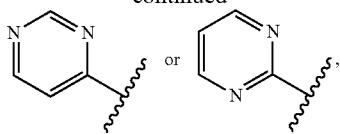

each optionally substituted with one to three R⁴. In some such embodiments,

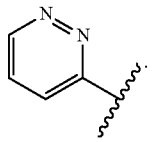

is optionally substituted

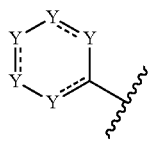

In some such embodiments,

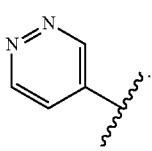

is optionally substituted

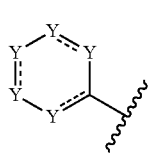

In some such embodiments,

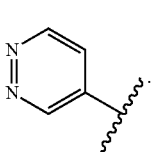

is optionally substituted

In some such embodiments,

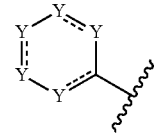

is optionally substituted

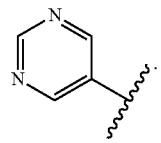

In some such embodiments,

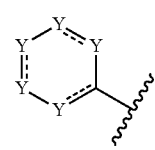

is optionally substituted

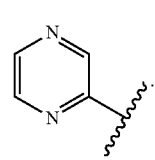

In some such embodiments,

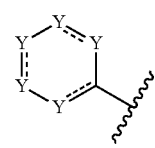

is optionally substituted

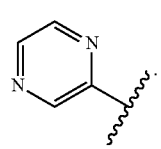

In some such embodiments,

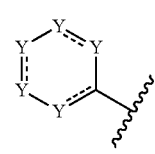

is optionally substituted

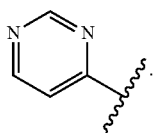

In some such embodiments,

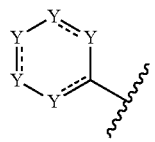

is optionally substituted

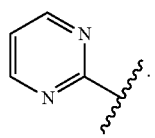

In some other embodiments, two of Y in

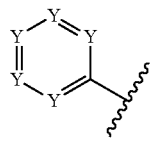

are N. In some such embodiments,

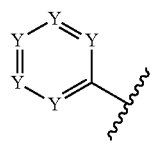

is selected from

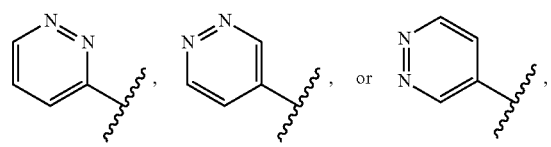

each optionally substituted with one to three R⁴. In some such further embodiments,

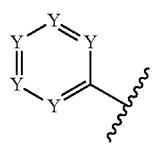

is selected from

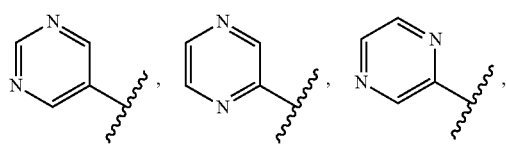

each optionally substituted with one to three R⁴. In some such embodiments,

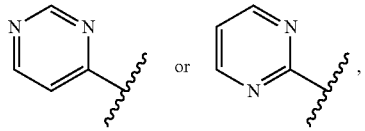

is optionally substituted

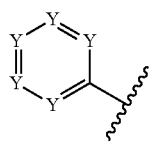

In some such embodiments,

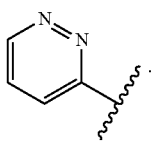

is optionally substituted

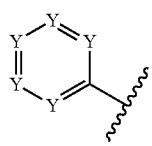

In some such embodiments,

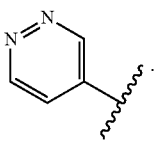

is optionally substituted

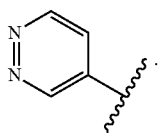

In some such embodiments,

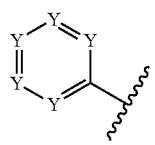

is optionally substituted

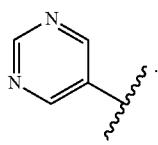

In some such embodiments,

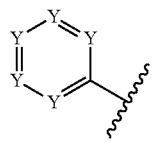

is optionally substituted

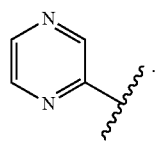

In some such embodiments,

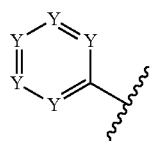

is optionally substituted

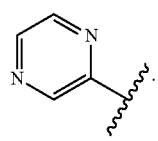

In some such embodiments,

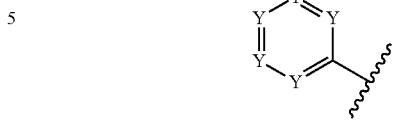

is optionally substituted

In some such embodiments,

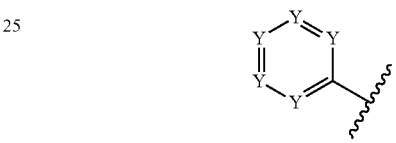

is optionally substituted

In any of the embodiments of

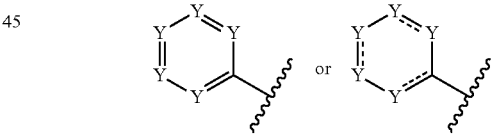

of formula (II) or (IIa) described herein, $R^4$ is selected from hydrogen, halogen, —CN, optionally substituted $C_{1-6}$ alkyl, optionally substituted $C_{1-6}$ alkoxy or 5 membered heteroaryl optionally substituted with one or more $R^{11}$. In some embodiments, $R^4$ is selected from hydrogen, fluoro, chloro, methyl, ethyl, methoxy, ethoxy or thiazolyl.

In some other embodiments, two adjacent $R^4$ together with the carbon atoms to which they are attached form a fused ring selected from optionally substituted 5 or 6 membered heteroaryl or optionally substituted 5 or 6 membered heterocyclyl.

In some embodiments, the optionally substituted 5 or 6 membered heterocyclyl formed by two adjacent $R^4$ together with the carbon atoms to which they are attached is selected from

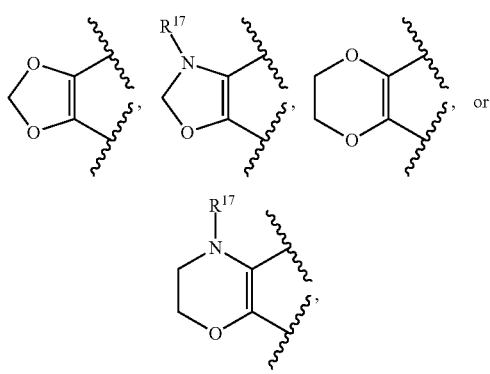

wherein each $R^{17}$ is independently selected from hydrogen, optionally substituted $C_{1-6}$ alkyl, optionally substituted $C_{3-6}$ cycloalkyl, $C_{6-10}$ aryl optionally substituted with one or more $R^{11}$, $C_{7-14}$ aralkyl optionally substituted with one or more $R^{11}$, or optionally substituted $C_{2-8}$ alkoxyalkyl. In some such embodiments, $R^{17}$ is selected from hydrogen, methyl, ethyl, —$(CH_2)_2OH$ or —$(CH_2)_2OCH_3$. In some further such embodiments, the optionally substituted 5 or 6 membered heterocyclyl is selected from In some further such embodiments, the optionally substituted 5 or 6 membered heterocyclyl is selected from

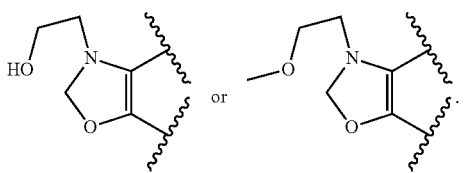

In some embodiments, the optionally substituted 5 or 6 membered heterocyclyl is substituted with one or more substituents selected from $C_{1-6}$ alkyl or halogen. In some other embodiments, the 5 or 6 membered heterocyclyl is unsubstituted.

In some embodiments, the optionally substituted 5 or 6 membered heteroaryl formed by two adjacent $R^4$ together with the carbon atoms to which they are attached is selected from wherein each $R^{18}$ is independently selected from hydrogen, optionally substituted $C_{1-6}$ alkyl, optionally substituted $C_{3-6}$ cycloalkyl, $C_{6-10}$ aryl optionally substituted with one or more $R^{11}$, $C_{7-14}$ aralkyl optionally substituted with one or more $R^{11}$, or optionally substituted $C_{2-8}$ alkoxyalkyl. In some such embodiments, $R^{18}$ is selected from hydrogen or methyl. In some further such embodiments, the optionally substituted 5 or 6 membered heteroaryl is selected from In some embodiments, the optionally substituted 5 or 6 membered heterocyclyl is substituted with one or more substituents selected from $C_{1-6}$ alkyl or halogen. In some other embodiments, the 5 or 6 membered heterocyclyl is unsubstituted.

In some embodiments, the substituent on the 5 or 6 membered heteroaryl or 5 or 6 membered heterocyclyl formed by two adjacent $R^4$ together with the carbon atoms to which they are attached is selected from $C_{1-6}$ alkyl, $C_{1-6}$ alkoxy, oxo or halogen. In some further embodiments, the substituent is selected from methyl, fluoro, or oxo. In some embodiments, the substituent is oxo. In some such embodiments, the 5 or 6 membered heteroaryl or 5 or 6 membered heterocyclyl are selected from

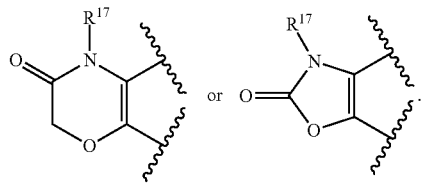

In some embodiments of

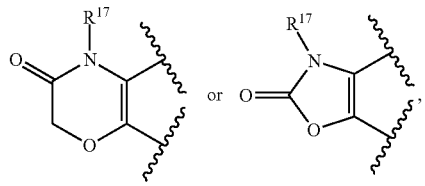

$R^{17}$ is alkyl.

In some embodiments, Z is oxygen.

In some embodiments, the bonds represented by a solid and dashed line are double bonds, provided that when the optionally substituted 5 or 6 membered heteroaryl formed by two adjacent $R^4$ together with the carbon atoms to which they are attached is selected from

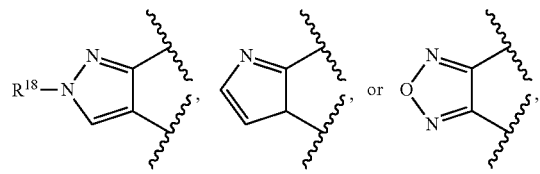

one of the bonds represented by a solid and dashed line in

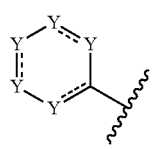

is a single bond. In some embodiments, the bonds represented by a solid and dashed line are double bonds in formula (IIa). In some such embodiments, compounds of formula (II) are also represented by

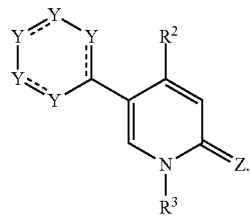

In some such embodiments, compounds of formula (IIa) are also represented by

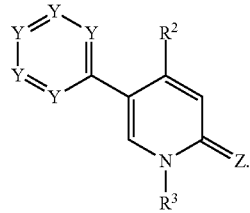

In some embodiments, the compound of formula (II) is selected from the group consisting of Compounds 163-216, 241-243, 245, 246, 248-252, 254, 255, 258-261, 263, 415-430, 432, 552-567, 629, 662 and 663 of Table 1. In some further embodiments, the compound of formula (II) is selected from the group consisting of Compounds 163-216, 241-243, 245, 246, 248-252, 254, 255, 258-261, 263, 415-430, 432, 552-561, 566 and 629 of Table 1.

Formula III

Some embodiments disclosed herein relate to a compound of formula (III) as described above or a pharmaceutically acceptable salt thereof.

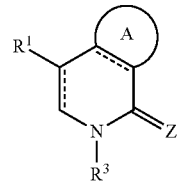

Some embodiments disclosed herein with respect to the compounds of formula (III), $R^3$ is selected from the group consisting of —$(CH_2)_n$—$(C_{6-10}$ aryl), —$(CH_2)_n$-(5-10 membered heteroaryl), —$(CH_2)_n$—$(C_{3-10}$ carbocyclyl), and —$(CH_2)_n$-(3-10 membered heterocyclyl), each optionally substituted with one or more $R^9$; and each $R^9$ is independently selected from the group consisting of halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, —$OR^5$, —$NR^{14}R^{15}$, —$(O)R^8$, —$SO_2R^{16}$, and —$NO_2$.

In some embodiments, $R^1$ is selected from halogen, $C_{1-6}$ alkyl optionally substituted with one or more $R^4$, $C_{6-10}$ aryl optionally substituted with one or more $R^4$, or 5 to 6-membered heteroaryl optionally substituted with one or more $R^4$. In some embodiments, $R^1$ is bromo or fluoro. In some embodiments, $R^1$ is methyl optionally substituted with one or more $R^4$. In some embodiments, $R^1$ is methyl. In some embodiments, $R^1$ is phenyl optionally substituted with one or more $R^4$. In some embodiments, $R^1$ is pyridazinyl optionally substituted with one or more $R^4$ In some embodiments, $R^1$ is unsubstituted phenyl. In some embodiments, $R^1$ is pyrazolyl or 1-methyl pyrazolyl optionally substituted with one or more $R^4$. In some embodiment, $R^4$ is selected from halogen.

Some embodiments disclosed herein with respect to the compounds of formula (III), $R^3$ is selected from the group consisting of —$(CH_2)_n$—$(C_{6-10}$ aryl), —$(CH_2)_n$-(5-10 membered heteroaryl), —$(CH_2)_n$—$(C_{3-10}$ carbocyclyl), and —$(CH_2)_n$-(3-10 membered heterocyclyl), each optionally substituted with one or more $R^9$. In some embodiments, n is 0.

In some embodiments, $R^3$ is selected from —$(CH_2)_n$—$(C_{6-10}$ aryl) optionally substituted with one or more $R^9$.

In some embodiments, $R^3$ is phenyl, optionally substituted with one or more $R^9$. In some other embodiments, $R^3$ is unsubstituted phenyl.

Some embodiments disclosed herein with respect to the compounds of formula (III), $R^3$ is hydrogen. In some such embodiments, the compound of formula (III) is selected from the group consisting of compounds 576, 578, 590, 595, 611-613, 616, 618, 621-623, 637 and 638 of Table 1.

In any of embodiments of formula (III) described herein, $R^9$ is selected from cyano, halogen, optionally substituted $C_{1-6}$ alkyl, or optionally substituted $C_{1-6}$ alkoxy. In some further embodiments, $R^9$ is selected from cyano, fluoro, chloro, methyl, ethyl, methoxy, ethoxy, trifluoromethyl or trifluoromethoxy. In some embodiments, $R^9$ is ethoxy. In some embodiments, $R^9$ is trifluoromethoxy. In still some other embodiment, $R^9$ is difluoromethoxy.

In any of the embodiments of formula (III) described herein, ring A is selected from 6-membered heteroaryl, 5-membered heterocyclyl or 6-membered heterocyclyl, each optionally substituted with one or more $R^4$.

In some such embodiments, ring A is selected from

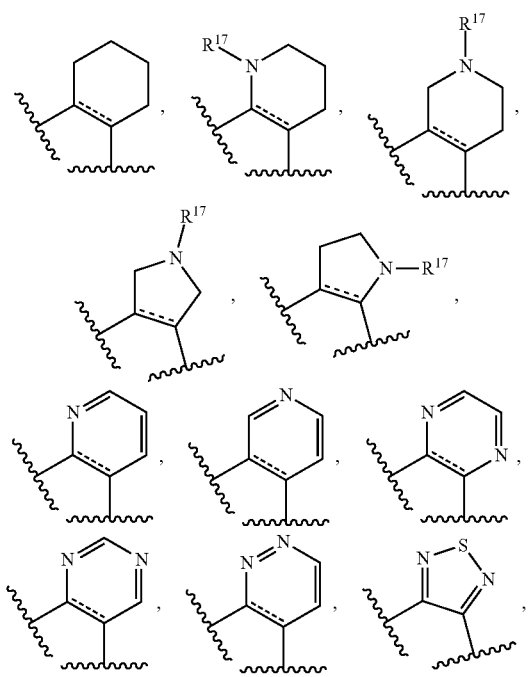

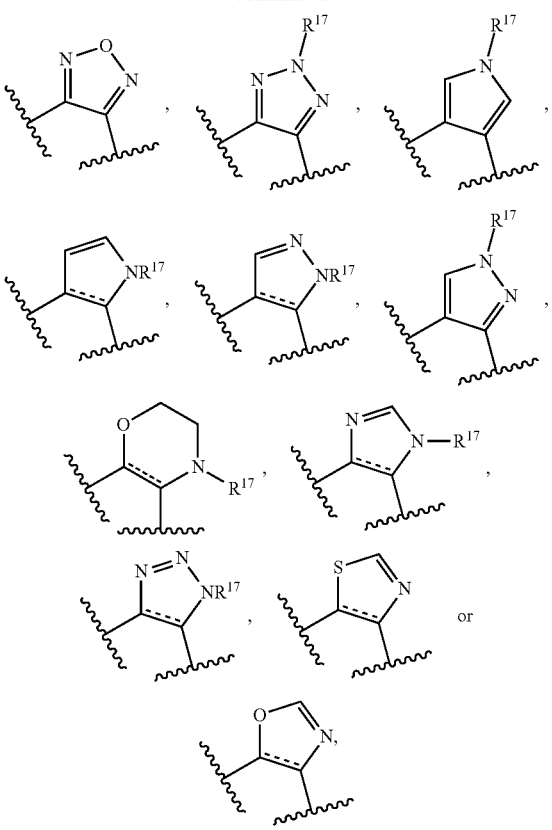

each optionally substituted with one or more $R^4$; and wherein each $R^{17}$ is independently selected from hydrogen, optionally substituted $C_{1-6}$ alkyl, optionally substituted $C_{3-6}$ cycloalkyl, optionally substituted $C_{2-8}$ alkoxyalkyl, optionally substituted C-carboxy, acyl, $C_{6-10}$ aryl optionally substituted with one or more $R^{11}$, or $C_{7-14}$ aralkyl optionally substituted with one or more $R^{11}$.

In some embodiments, ring A is selected from

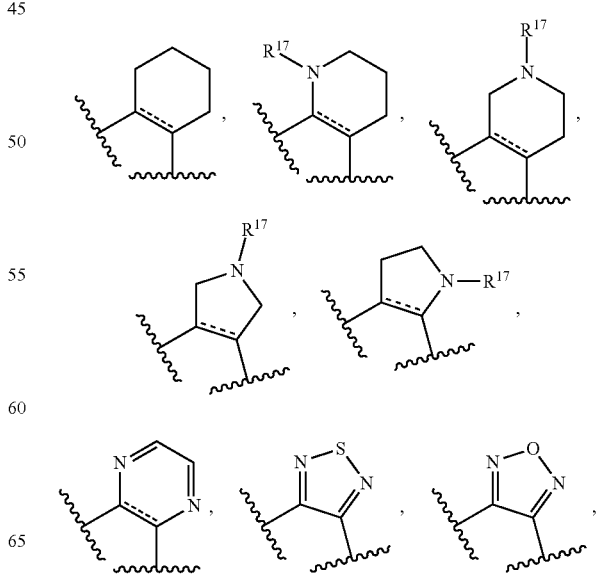

-continued

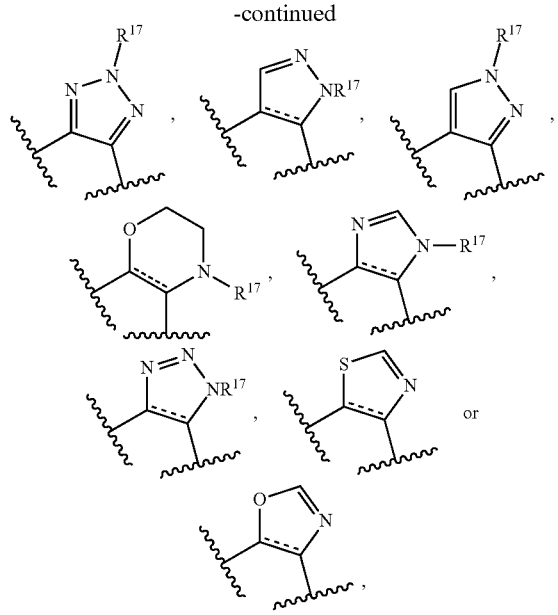

each optionally substituted with one or more R⁴.

In some embodiments, ring A is selected from

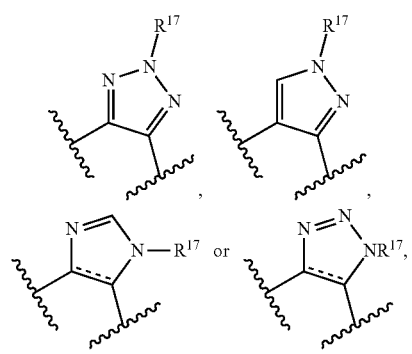

each optionally substituted with one or more R⁴.

In some embodiments, ring A is optionally substituted

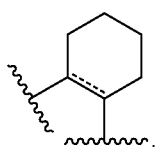

In some embodiments, ring A is optionally substituted

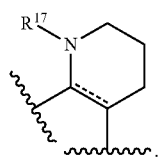

In some embodiments, ring A is optionally substituted

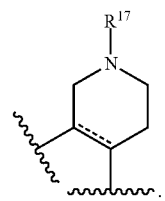

In some embodiments, ring A is optionally substituted

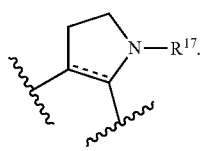

In some embodiments, ring A is optionally substituted

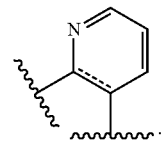

In some embodiments, ring A is optionally substituted

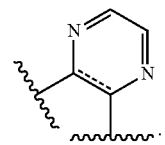

In some embodiments, ring A is optionally substituted

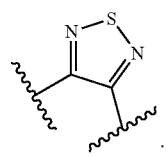

In some embodiments, ring A is optionally substituted

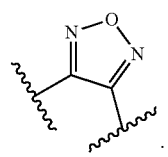

In some embodiments, ring A is optionally substituted

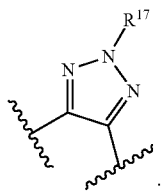

In some embodiments, ring A is optionally substituted

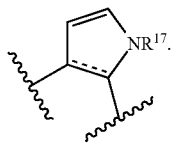

In some embodiments, ring A is optionally substituted

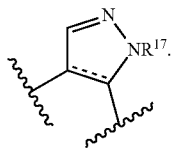

In some embodiments, ring A is optionally substituted

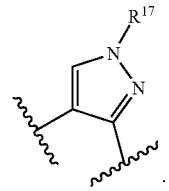

In some embodiments, ring A is optionally substituted

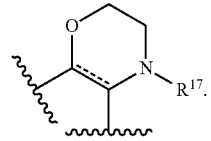

In some embodiments, ring A is optionally substituted

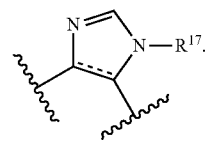

In some embodiments, ring A is optionally substituted

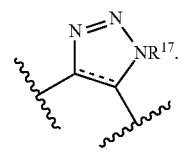

In some embodiments, ring A is optionally substituted

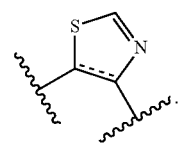

In some embodiments, ring A is optionally substituted

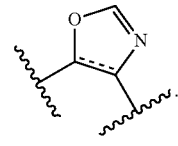

In any of embodiments of ring A as described herein in formula (III), $R^{17}$ is selected from hydrogen, methyl, ethyl, isopropyl, cyclopropyl, —$(CH_2)_2F$, —$(CH_2)_2OH$, —$(CH_2)_2OCH_3$, —$(CH_2)_2OC_2H_5$, —$(CH_2)_2OC_3H_7$, —$C(O)O^tBu$, —$C(O)CH_3$ or benzyl.

In some further such embodiments, ring A is selected from

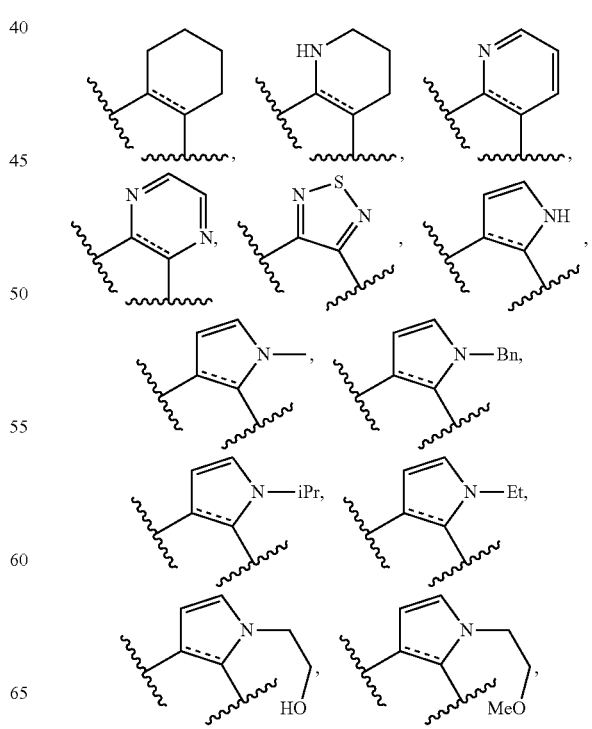

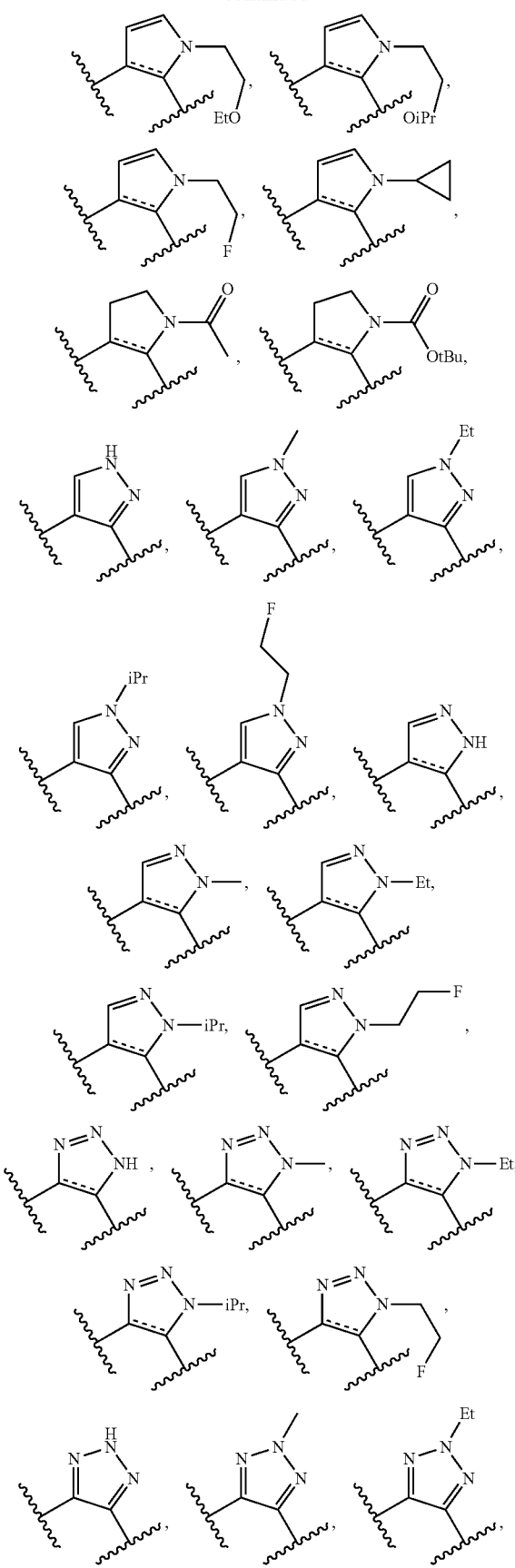

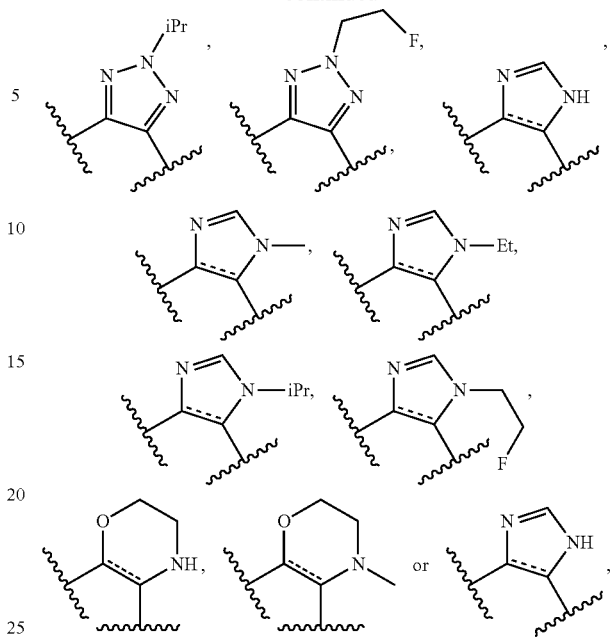

each optionally substituted with one or more $R^4$.

In some such further embodiments, ring A is selected from

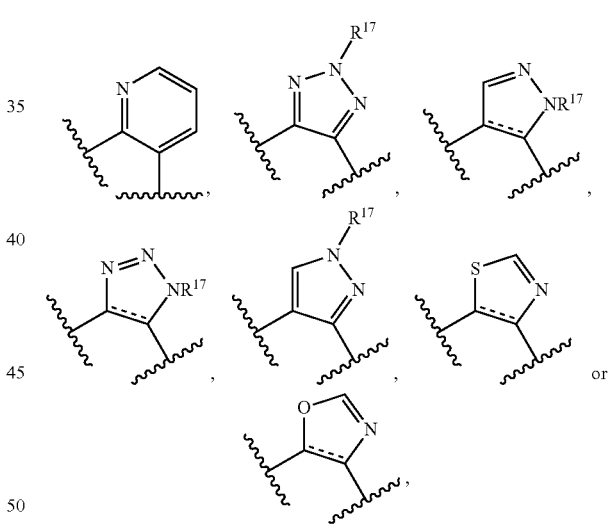

each optionally substituted with one or more $R^4$.

In any of the embodiments of formula (III) described herein, $R^4$ is selected from halogen, optionally substituted $C_{1-6}$ alkyl, or $C_{7-14}$ aralkyl optionally substituted with one or more $R^{11}$, or two geminal $R^4$ together are oxo. In some further embodiments, $R^4$ is selected from fluoro, methyl, trifluoromethyl, or benzyl. In some embodiments, two geminal $R^4$ together are oxo.

In some embodiments, ring A is unsubstituted.

In some embodiments, Z is oxygen.

In some embodiments, the bonds represented by a solid and dashed line are double bonds, provided that when ring A is

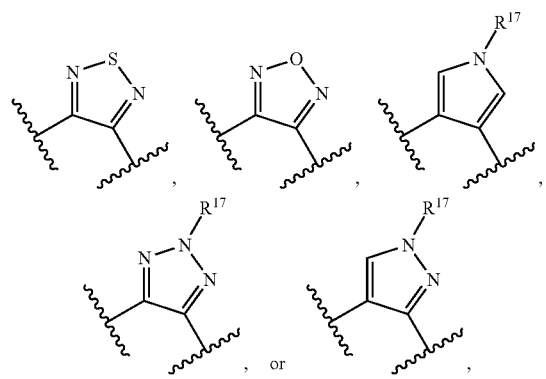

one of the bonds represented by a solid and dashed line is a single bond. In some such embodiments, compounds of formula (III) are also represented by

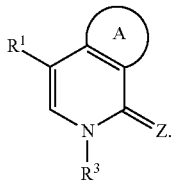

Formula IV

In some embodiments, the compound of formula (III) is selected from the group consisting of Compounds 29-63, 392-400, 568-628, 630-661, and 665 of Table 1. In some further embodiments, the compound of formula (III) is selected from the group consisting of Compounds 29-63, 392-400, 568-574, 577, 579-584, 586-589, 591-594, 596-608, 614, 615, 617, 619, 620, 624-626, 631, 634-636, 640, 642-655, 657-661, 665, and 669-695 of Table 1.

Formula IV

Some embodiments disclosed herein relate to a compound of formula (IV) as described above or a pharmaceutically acceptable salt thereof.

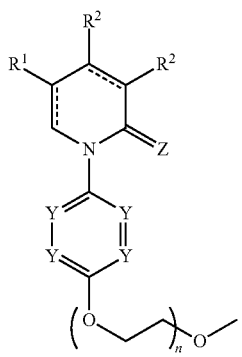

In some embodiments, $R^1$ is selected from the group consisting of hydrogen, $C_{1-6}$ alkyl optionally substituted with one or more $R^4$, or 5-membered heteroaryl optionally substituted with one or more $R^4$.

In some embodiments, $R^1$ is selected from methyl, phenyl, pyrazolyl, or 1-methyl pyrazolyl, each optionally substituted with one or more $R^4$. In some embodiments, $R^1$ is methyl. In some embodiments, $R^1$ is unsubstituted phenyl.

In some embodiments, $R^1$ is unsubstituted pyrazolyl. In yet some other embodiments, $R^1$ is unsubstituted 1-methyl pyrazolyl.

In some embodiments, $R^2$ is selected from hydrogen or optionally substituted $C_{1-6}$ alkyl.

In some embodiments, all Y are $CR^4$. In some other embodiment, at least one Y is nitrogen.

In some embodiments, $R^4$ is selected from halogen, $C_{1-6}$ alkyl or $C_{1-6}$ alkoxy. In some embodiments, $R^4$ is selected from fluoro or methyl.

In some embodiments, m is 1. In some embodiments, m is 2. In some embodiments, m is 3.

In some embodiments, Z is oxygen.

In some embodiments, the bonds represented by a solid and dashed line are double bonds.

In some embodiments, the compound of formula (IV) is selected from the group consisting of Compounds 21-26 of Table 1.

Formula V

Some embodiments disclosed herein relate to a compound of formula (V) as described above or a pharmaceutically acceptable salt thereof.

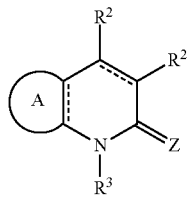

In some embodiments, each $R^2$ is independently selected from hydrogen, $C_{1-6}$ alkyl or $-OR^5$.

In some embodiments, each $R^2$ is hydrogen.

In some embodiments, $R^3$ is $-(CH_2)_n-(C_{6-10}$ aryl), optionally substituted with one or more $R^9$. In some embodiments, $R^3$ is phenyl, optionally substituted with one or more $R^9$. In some other embodiments, $R^3$ is unsubstituted phenyl.

In some embodiments, $R^9$ is selected from halogen, optionally substituted $C_{1-6}$ alkyl, optionally substituted $C_{2-8}$ alkoxyalkyl, $-OR^5$, or $-NR^{14}R^{15}$. In some embodiments, $R^9$ is selected from fluoro, chloro, methyl, ethyl, methoxy, ethoxy, trifluoromethyl, trifluoromethoxy, $-NHCH_3$, $-NH_2$, or $-NHC(O)CH_3$. In some embodiments, $R^9$ is trifluoromethoxy.

In some embodiments, ring A is a $C_5$ carbocyclyl optionally substituted with one or more $R^4$. In some embodiments, ring A is a $C_6$ carbocyclyl optionally substituted with one or more $R^4$. In some other embodiments, ring A is unsubstituted.

In some embodiments, wherein $R^4$ is selected from halogen, optionally substituted $C_{1-6}$ alkyl, optionally substituted $C_{1-6}$ alkoxy, or independently two geminal $R^4$ together are oxo.

In some embodiments, ring A is an unsubstituted $C_{5-7}$ carbocyclyl.

In some embodiments, Z is oxygen.

In some embodiments, the bonds represented by a solid and dashed line are double bonds.

In some embodiments, the compound of formula (V) is selected from the group consisting of Compounds 27 and 28 of Table 1.

Formula VIa

Some embodiments disclosed herein relate to a compound of formula (VIa) as described above or a pharmaceutically acceptable salt thereof.

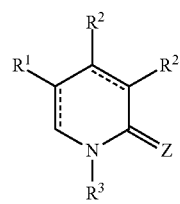

(VIa)

In some embodiments, R is a $C_4$ carbocyclyl optionally substituted with one or more $R^4$.

In some embodiments, $R^1$ is a $C_5$ carbocyclyl optionally substituted with one or more $R^4$.

In some embodiments, $R^1$ is a $C_6$ carbocyclyl optionally substituted with one or more $R^4$.

In some embodiments, $R^4$ is selected from halogen, optionally substituted $C_{1-6}$ alkyl, or optionally substituted $C_{1-6}$ alkoxy. In some embodiments, $R^4$ is selected from fluoro, chloro, methyl, methoxy, ethoxy, trifluoromethyl, or trifluoromethoxy.

In some other embodiments, $R^1$ is unsubstituted.

In some embodiments, each $R^2$ is independently selected from hydrogen, halogen, optionally substituted $C_{1-6}$ alkyl, —$OR^5$ or —$NR^6R^7$. In some embodiments, $R^2$ is hydrogen. In some embodiment, $R^2$ is halogen.

In some embodiments, $R^2$ is optionally substituted $C_{1-6}$ alkyl. In some embodiments, $R^2$ is methyl. In some other embodiments, $R^2$ is trifluoromethyl.

In some embodiments, $R^3$ is selected from —$(CH_2)_n$— ($C_{6-10}$ aryl), optionally substituted with one or more $R^9$. In some embodiments, $R^3$ is phenyl, optionally substituted with one or more $R^9$.

In some embodiments, $R^9$ is selected from halogen, optionally substituted $C_{1-6}$ alkyl, optionally substituted $C_{2-8}$ alkoxyalkyl, —$OR^5$, or —$NR^{14}R^{15}$. In some embodiments, $R^9$ is selected from fluoro, chloro, methyl, ethyl, methoxy, ethoxy, trifluoromethyl, trifluoromethoxy, —$NHCH_3$, —$NH_2$, or —$NHC(O)CH_3$.

In some embodiment, $R^3$ is unsubstituted phenyl.

In some embodiments, Z is oxygen.

In some embodiments, the bonds represented by a solid and dashed line are double bonds.

In some embodiments, the compound of formula (VIa) is selected from the group consisting of Compounds 64-66 of Table 1.

Formula VII

Some embodiments disclosed herein relate to a compound of formula (VII) as described above or a pharmaceutically acceptable salt thereof.

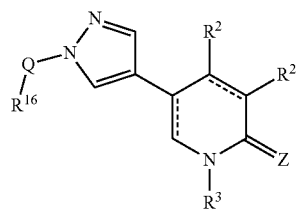

(VII)

In some embodiments, each $R^2$ is independently selected from hydrogen, halogen, optionally substituted $C_{1-6}$ alkyl, —$OR^5$ or —$NR^6R^7$. In some embodiments, $R^2$ is hydrogen. In some embodiments, $R^2$ is halogen. In some embodiments, $R^2$ is optionally substituted $C_{1-6}$ alkyl. In some further embodiments, $R^2$ is methyl or trifluoromethyl.

In some embodiments, $R^3$ is selected from —$(CH_2)_n$— ($C_{6-10}$ aryl), optionally substituted with one or more $R^9$. In some embodiments, $R^3$ is phenyl optionally substituted with one or more $R^9$.

In some embodiments, $R^9$ is selected from halogen, optionally substituted $C_{1-6}$ alkyl, optionally substituted $C_{2-8}$ alkoxyalkyl, —$OR^5$, or —$NR^{14}R^{15}$. In some embodiments, $R^9$ is selected from fluoro, chloro, methyl, ethyl, methoxy, ethoxy, trifluoromethyl, trifluoromethoxy, —$NHCH_3$, —$NH_2$, or —$NHC(O)CH_3$.

In some embodiments, $R^3$ is unsubstituted phenyl.

In some embodiments, Q is C(O). In some other embodiments, Q is $S(O)_t$. In some embodiments, t is 2.

In some embodiments, $R^{16}$ is selected from optionally substituted $C_{1-6}$ alkyl, $C_{6-10}$ aryl optionally substituted with one or more $R^{11}$, $C_{7-14}$ aralkyl optionally substituted with one or more $R^{11}$, —$NR^{12}R^{13}$, or —$OR^5$. In some embodiments, $R^{16}$ is optionally substituted $C_{1-6}$ alkyl. In some embodiments, $R^{16}$ is selected from methyl, ethyl, propyl, isopropyl, or butyl. In some embodiments, $R^{16}$ is phenyl optionally substituted with one or more $R^{11}$. In some other embodiments, $R^{16}$ is unsubstituted phenyl. In some embodiments, $R^{16}$ is benzyl optionally substituted with one or more $R^{11}$. In some other embodiments, $R^{16}$ is unsubstituted benzyl. In some embodiments, $R^{16}$ is —$NR^{12}R^{13}$. In some embodiments, each $R^{12}$ and $R^{13}$ is independently selected from hydrogen or optionally substituted $C_{1-6}$ alkyl. In some embodiments, $R^{16}$ is —$OR^5$. In some embodiments, $R^5$ is selected from hydrogen or optionally substituted $C_{1-6}$ alkyl. In some further embodiments, $R^5$ is selected from methyl, ethyl, propyl, isopropyl, or butyl.

In some embodiments, Z is oxygen.

In some embodiments, the bonds represented by a solid and dashed line are double bonds.

In some embodiments, the compound of formula (VII) is selected from the group consisting of Compounds 67-76 of Table 1.

Formula VIb

Some embodiments disclosed herein relate to a compound of formula (VIb) as described above or a pharmaceutically acceptable salt thereof.

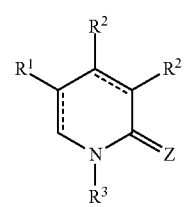

(VIb)

In some embodiments, $R^1$ is selected from $C_{1-6}$ alkyl optionally substituted with one or more $R^4$, $C_{6-10}$ aryl optionally substituted with one or more $R^4$, or 5-10 membered heteroaryl optionally substituted with one or more $R^4$. In some embodiments, $R^1$ is selected from $C_{1-6}$ alkyl optionally substituted with one or more $R^4$. In some further embodiments, $R^1$ is selected from methyl, ethyl, propyl, or isopropyl. In some further embodiments, $R^1$ is phenyl optionally substituted with one or more $R^4$. In some embodiments, $R^1$ is selected from 5 or 6 membered heteroaryl, each optionally substituted with one or more $R^4$. In some further embodiments, $R^1$ is selected from pyrazolyl or 1-methyl pyrazolyl, each optionally substituted with one or more $R^4$. In some other embodiment, $R^1$ is unsubstituted.

In some embodiments, $R^4$ is selected from halogen or optionally substituted $C_{1-6}$ alkyl. In some embodiments, $R^4$ is fluoro.

In some embodiments, each $R^2$ is independently selected from hydrogen, halogen, or optionally substituted $C_{1-6}$ alkyl. In some embodiments, $R^2$ is hydrogen.

In some embodiments, $R^3$ is —$(CH_2)_{1-4}$—$(C_{6-10}$ aryl), optionally substituted with one or more $R^9$. In some embodiments, $R^3$ is —$(CH_2)_{1-4}$-phenyl, optionally substituted with one or more $R^9$. In some other embodiments, $R^3$ is unsubstituted. In some embodiments, $R^3$ is —$(CH_2)$-phenyl, optionally substituted with one or more $R^9$. In some embodiments, $R^3$ is —$(CH_2)_2$-phenyl, optionally substituted with one or more $R^9$. In some other embodiments, $R^3$ is unsubstituted.

In some embodiments, $R^9$ is selected from halogen, optionally substituted $C_{1-6}$ alkyl, optionally substituted $C_{2-8}$ alkoxyalkyl, —$OR^5$, —$C(O)R^8$ or —$NR^{14}R^{15}$. In some further embodiments, $R^9$ is selected from fluoro, chloro, methyl, ethyl, methoxy, ethoxy, trifluoromethyl, trifluoromethoxy, —$C(O)CH_3$, —$NHCH_3$, —$NH_2$, or —$NHC(O)CH_3$.

In some embodiments, Z is oxygen.

In some embodiments, the bonds represented by a solid and dashed line are double bonds.

In some embodiments, the compound of formula (VIb) is selected from the group consisting of Compounds 77-80 of Table 1.

Formula VIII

Some embodiments disclosed herein relate to a compound of formula (VIII) as described above or a pharmaceutically acceptable salt thereof.

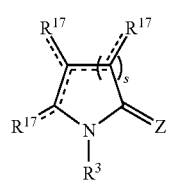

(VIII)

In some embodiments, $R^3$ is selected from optionally substituted $C_{1-6}$ alkyl or —$(CH_2)_n$—$(C_{6-10}$ aryl) optionally substituted with one or more $R^9$. In some embodiments, $R^3$ is —$(CH_2)_n$—$(C_{6-10}$ aryl) optionally substituted with one or more $R^9$. In some embodiments, $R^3$ is phenyl optionally substituted with one or more $R^9$.

In some embodiments, $R^9$ is selected from halogen, optionally substituted $C_{1-6}$ alkyl, optionally substituted $C_{2-8}$ alkoxyalkyl, —$OR^5$, —$C(O)R^8$ or —$NR^{14}R^{15}$. In some further embodiments, $R^9$ is selected from fluoro, chloro, methyl, ethyl, methoxy, ethoxy, trifluoromethyl, trifluoromethoxy, —$C(O)CH_3$, —$NHCH_3$, —$NH_2$, or —$NHC(O)CH_3$. In some embodiments, $R^9$ is trifluoromethoxy. In some other embodiments, $R^3$ is unsubstituted phenyl.

In some embodiments, $R^3$ is optionally substituted $C_{1-6}$ alkyl. In some further embodiments, $R^3$ is $C_{1-6}$ alkyl.

In some embodiments, each $R^{17}$ is independently selected from hydrogen, halogen, optionally substituted $C_{1-6}$ alkyl or oxo. In some embodiments, each $R^{17}$ is hydrogen.

In some embodiments, two adjacent $R^{17}$ together with the carbon atoms to which they are attached form a fused phenyl optionally substituted with one or more $R^4$. In some further embodiments, at least one $R^{17}$ is oxo. In some embodiments, at least one $R^{17}$ is optionally substituted $C_{1-6}$ alkyl. In some embodiments, the fused phenyl is unsubstituted.

In some embodiments, two adjacent $R^{17}$ together with the carbon atoms to which they are attached form a fused 5-6 membered heteroaryl, optionally substituted with one or more $R^4$. In some embodiments, at least one $R^{17}$ is oxo. In some embodiments, at least one $R^{17}$ is optionally substituted $C_{1-6}$ alkyl. In some embodiments, the fused 5-6 membered heteroaryl is unsubstituted.

In some embodiments, $R^4$ is selected from halogen or optionally substituted $C_{1-6}$ alkyl.

In some embodiments, n is 0. In some other embodiments, n is 1. In yet some other embodiments, n is 3.

In some embodiments, Z is oxygen.

In some embodiments, the compound of formula (VIII) is selected from the group consisting of Compounds 81, 82, and 513-519 of Table 1.

Formula IX

Some embodiments disclosed herein relate to a compound of formula (IX) as described above or a pharmaceutically acceptable salt thereof.

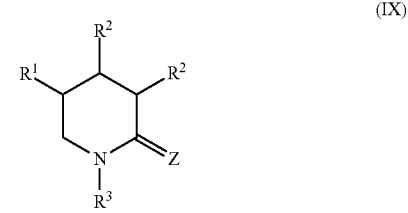

(IX)

In some embodiments, $R^1$ is selected from $C_{1-6}$ alkyl optionally substituted with one or more $R^4$, $C_{6-10}$ aryl optionally substituted with one or more $R^4$, or 5-10 membered heteroaryl optionally substituted with one or more $R^4$. In some embodiments, $R^1$ is $C_{1-6}$ alkyl optionally substituted with one or more $R^4$. In some embodiments, $R^1$ is $C_{6-10}$ aryl optionally substituted with one or more $R^4$.

In some further embodiments, $R^1$ is phenyl optionally substituted with one or more $R^4$. In some embodiments, $R^1$ is 5 or 6 membered heteroaryl optionally substituted with one or more $R^4$. In some further embodiments, $R^1$ is pyrazolyl or 1-methyl pyrazolyl optionally substituted with one or more $R^4$.

In some embodiments, $R^4$ is selected from halogen, optionally substituted $C_{1-6}$ alkyl, or optionally substituted $C_{1-6}$ alkoxy.

In some embodiments, $R^1$ is unsubstituted.

In some embodiments, each $R^2$ is independently selected from hydrogen, halogen or optionally substituted $C_{1-6}$ alkyl. In some embodiments, $R^2$ is hydrogen.

In some embodiments, $R^3$ is —$(CH_2)_n$—$(C_{6-10}$ aryl), optionally substituted with one or more $R^9$. In some further embodiments, $R^3$ is phenyl optionally substituted with one or more $R^9$. In some other embodiments, $R^3$ is unsubstituted.

In some embodiments, $R^9$ is selected from halogen, optionally substituted $C_{1-6}$ alkyl, optionally substituted $C_{2-8}$ alkoxyalkyl, —$OR^5$, —$C(O)R^8$ or —$NR^{14}R^{15}$. In some further embodiments, $R^9$ is selected from fluoro, chloro, methyl, ethyl, methoxy, ethoxy, trifluoromethyl, trifluoromethoxy, —C(O)CH$_3$, —NHCH$_3$, —NH$_2$, or —NHC(O)CH$_3$.

In some embodiments, Z is oxygen.

In some embodiments, the compound of formula (IX) is selected from the group consisting of Compounds 83, 84, 520-522 of Table 1.

Some embodiments described herein relate to one or more compounds selected from the group consisting of Compounds 1-20, 217-240, 244, 247, 253, 256, 257, 262, 264-283, 285, 287-339, 341-391, 431, 433, 434, 438-440, 442, 446-512, 546-549, 575, 585, 609, 610, 627, 628, 630, 632, 633, 639, 641, 656, 666-668, 708 and 709 of Table 1.

In some embodiments, compounds are selected from the following compounds as listed in Table 1.

TABLE 1

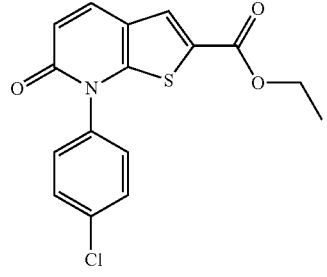

TABLE 1-continued

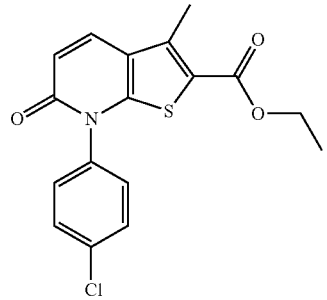

TABLE 1-continued
| Compd. # | Structure |
|---|---|
| 9 | 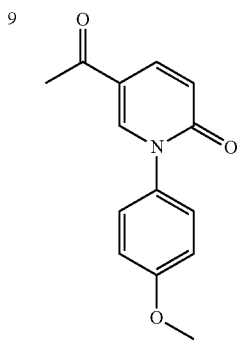 |
| 10 | 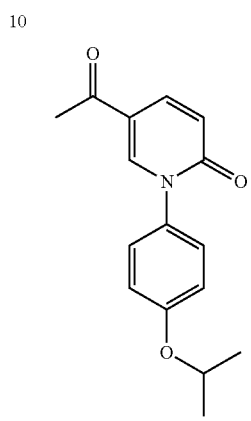 |
| 11 | 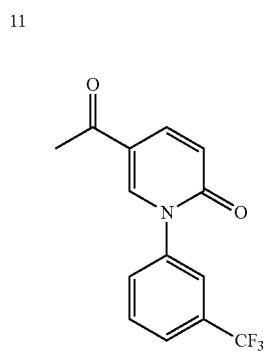 |
| 12 | 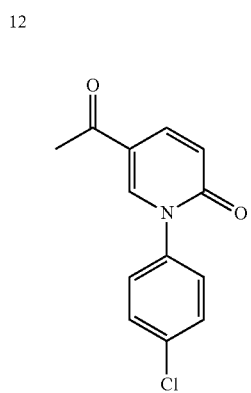 |
| 13 | 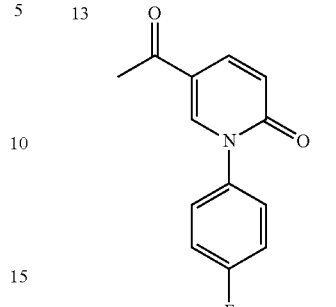 |
| 14 | 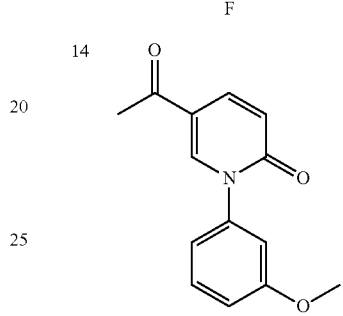 |
| 15 | 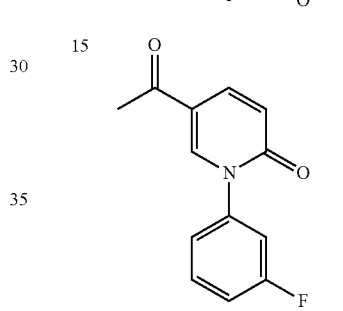 |
| 16 | 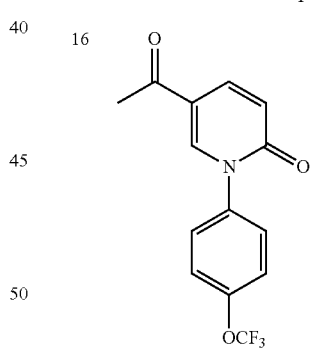 |
| 17 | 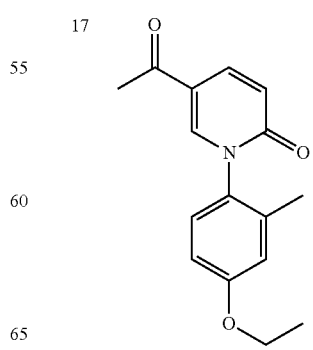 |

TABLE 1-continued
| Compd. # | Structure |
|---|---|
| 18 | 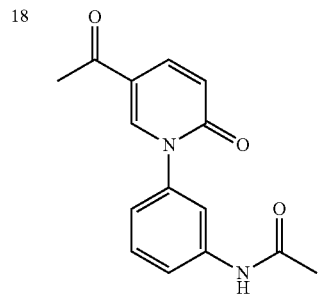 |
| 19 | 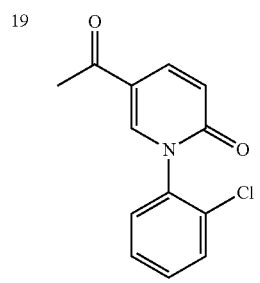 |
| 20 | 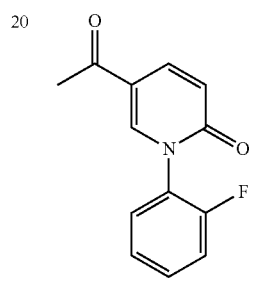 |
| 21 | 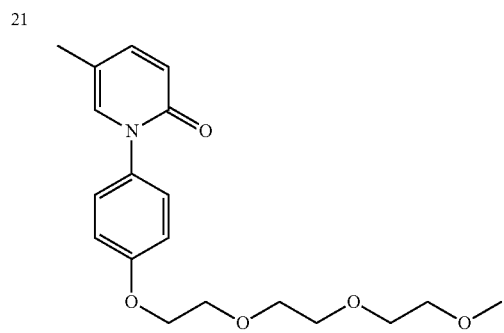 |
| 22 | 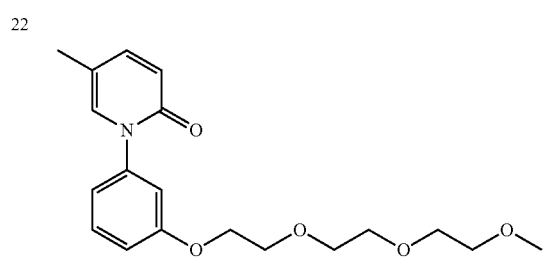 |
| 23 | 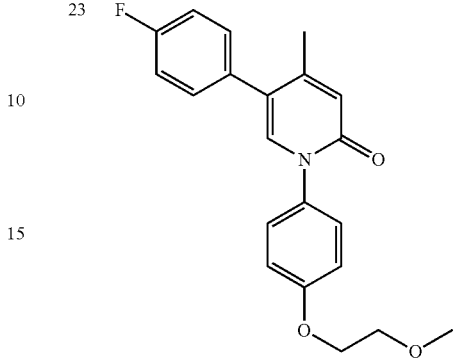 |
| 24 | 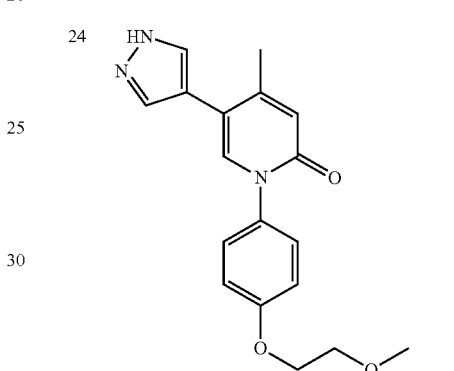 |
| 25 | 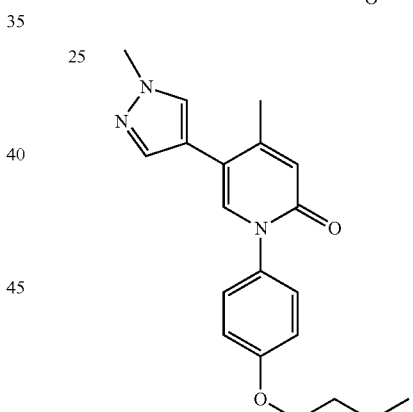 |
| 26 | 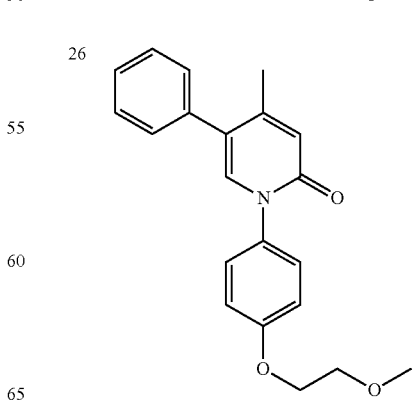 |

TABLE 1-continued
| Compd. # | Structure |
|---|---|
| 27 | 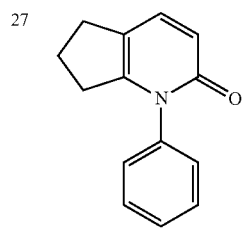 |
| 28 | 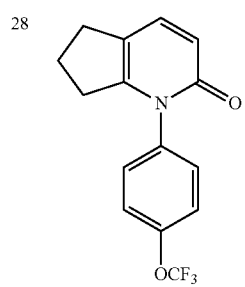 |
| 29 | 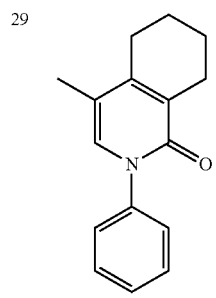 |
| 30 | 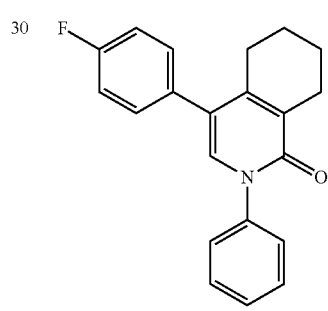 |
| 31 | 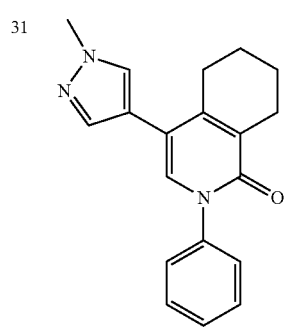 |
| 32 | 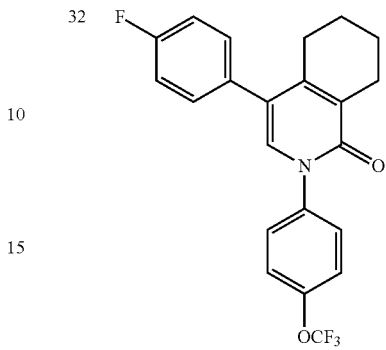 |
| 33 | 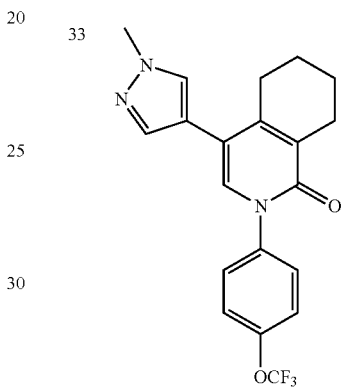 |
| 34 | 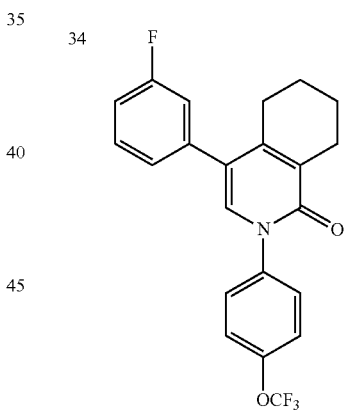 |
| 35 | 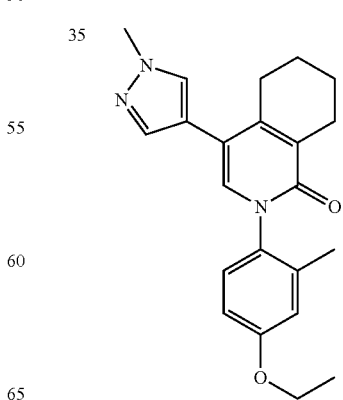 |

TABLE 1-continued
| Compd. # | Structure |
|---|---|
| 36 | 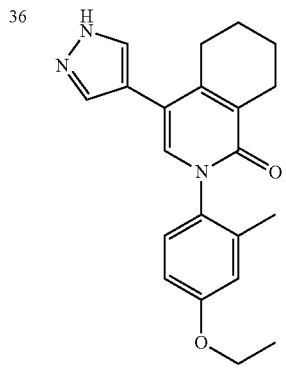 |
| 37 | 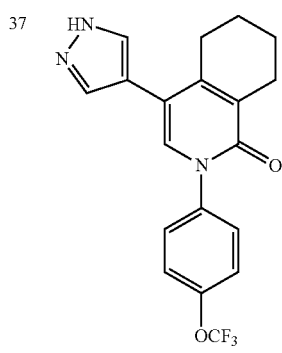 |
| 38 | 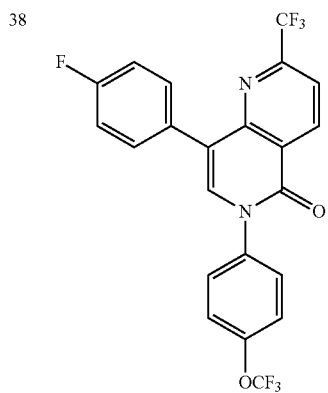 |
| 39 | 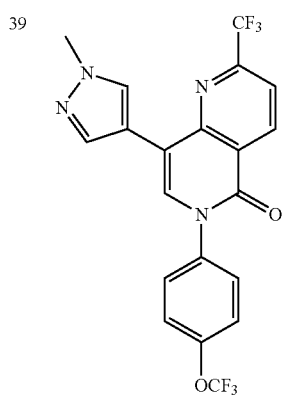 |
TABLE 1-continued
| Compd. # | Structure |
|---|---|
| 40 | 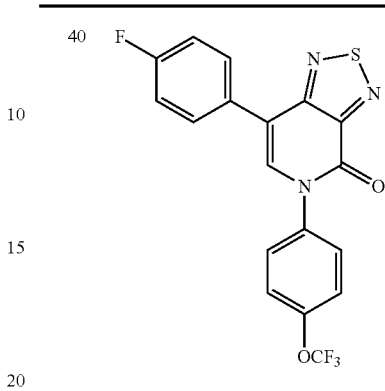 |
| 41 | 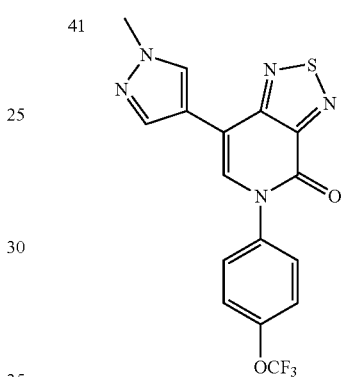 |
| 42 | 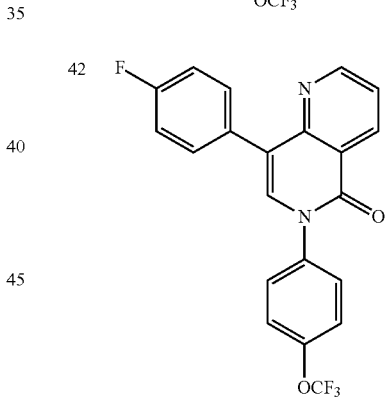 |
| 43 | 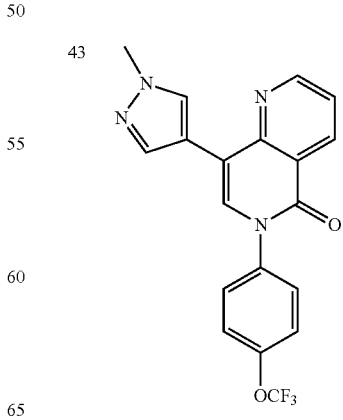 |

TABLE 1-continued
| Compd. # | Structure |
|---|---|
| 44 | 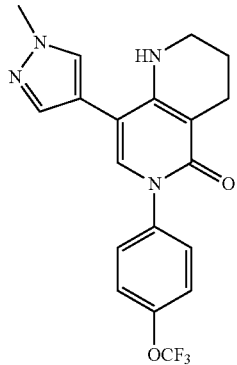 |
| 45 | 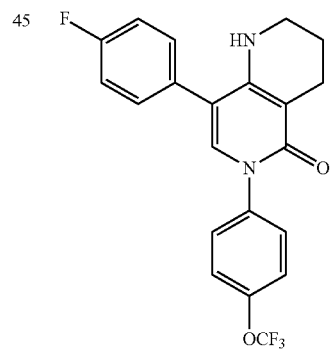 |
| 46 | 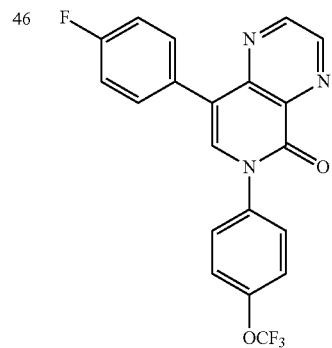 |
| 47 | 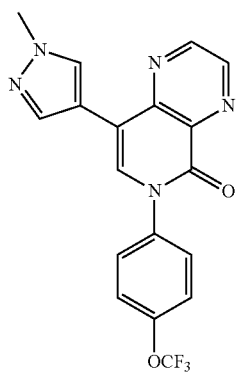 |
| 48 | 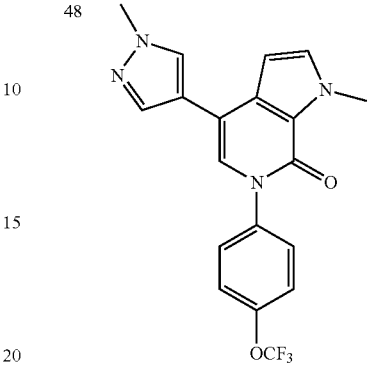 |
| 49 | 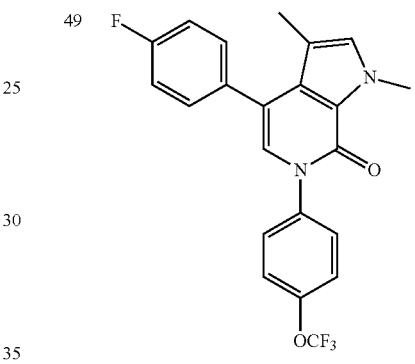 |
| 50 | 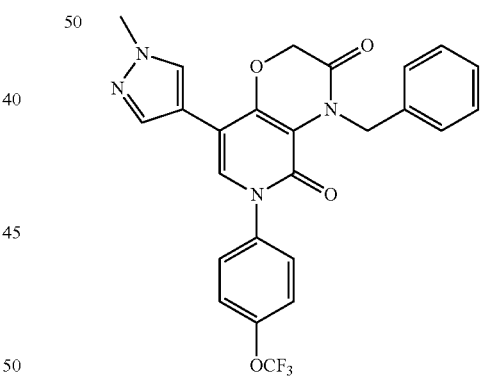 |
| 51 | 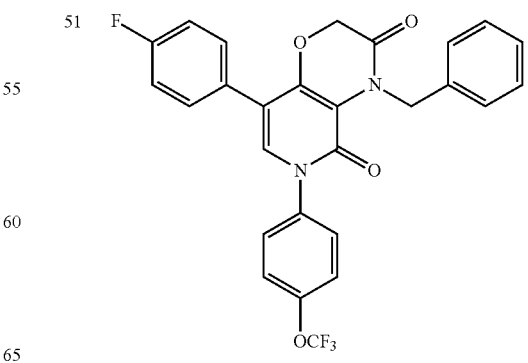 |

TABLE 1-continued
| Compd. # | Structure |
|---|---|
| 52 | 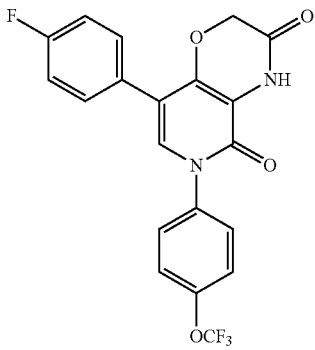 |
| 53 | 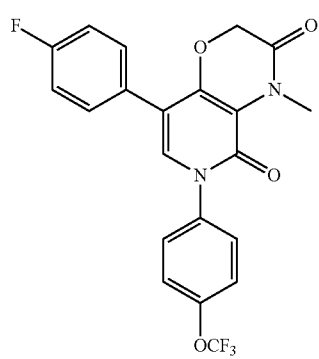 |
| 54 | 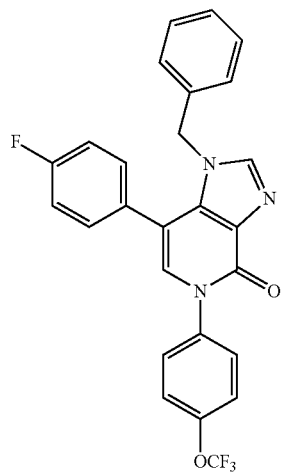 |
| 55 | 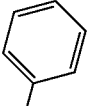 |
| 56 | 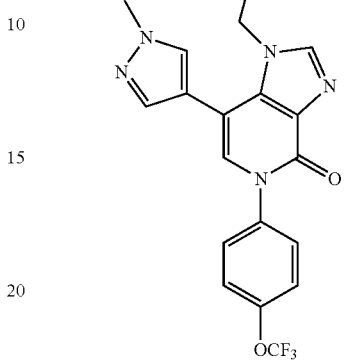 |
| 57 | 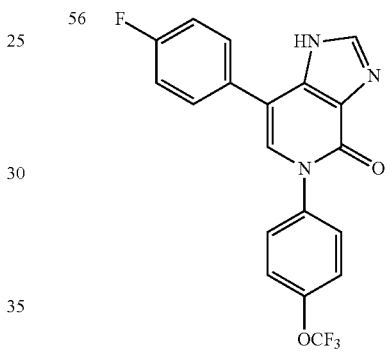 |
| 58 | 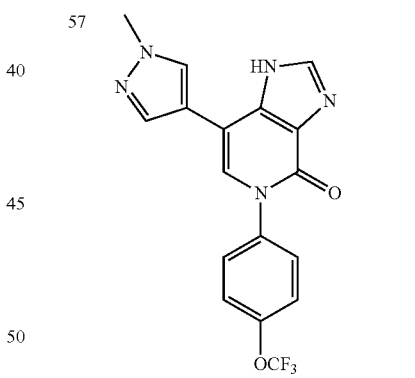 |

TABLE 1-continued
| Compd. # | Structure |
|---|---|
| 59 | 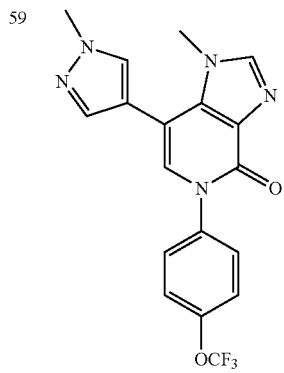 |
| 60 | 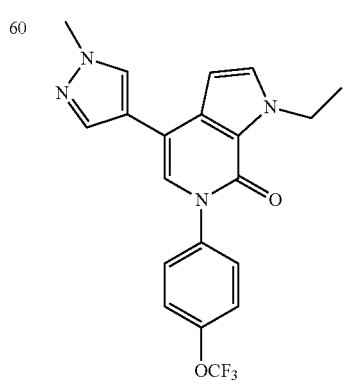 |
| 61 | 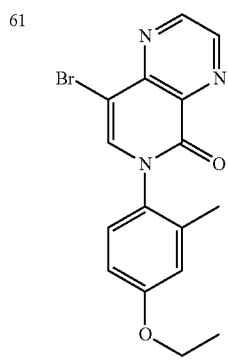 |
| 62 | 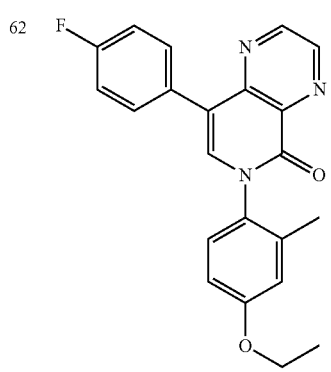 |
| 63 | 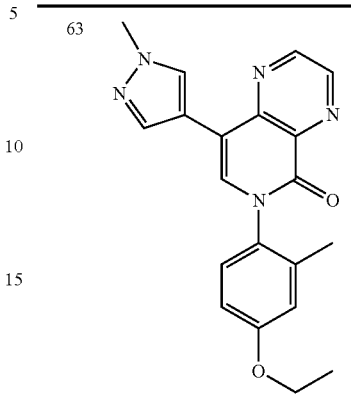 |
| 64 | 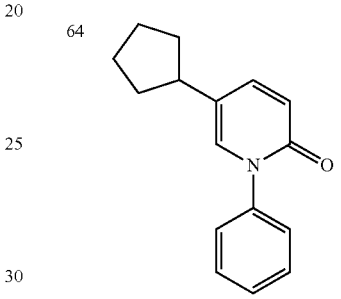 |
| 65 | 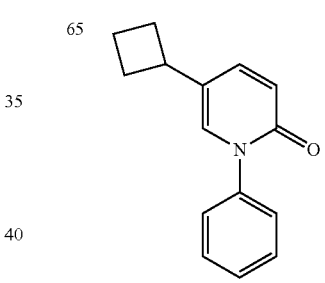 |
| 66 | 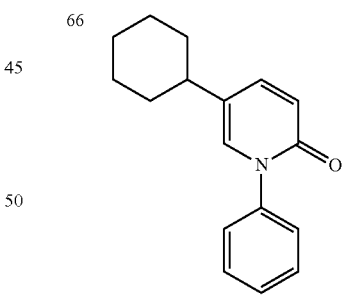 |
| 67 | 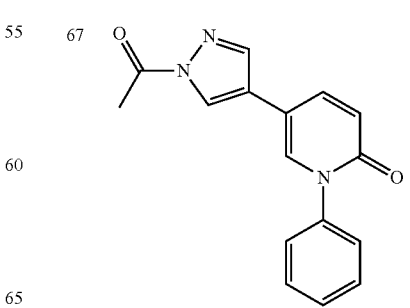 |

TABLE 1-continued
| Compd. # | Structure |
|---|---|
| 68 | 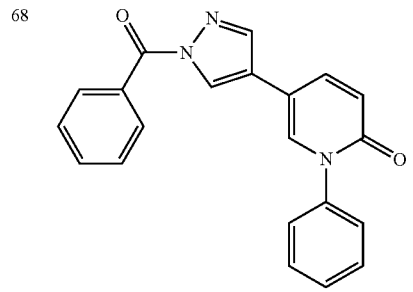 |
| 69 | 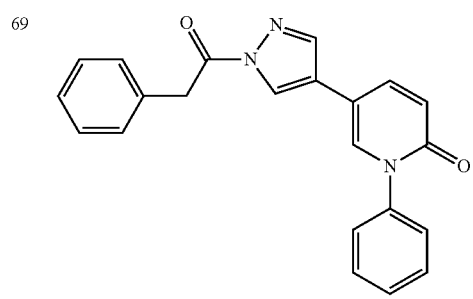 |
| 70 | 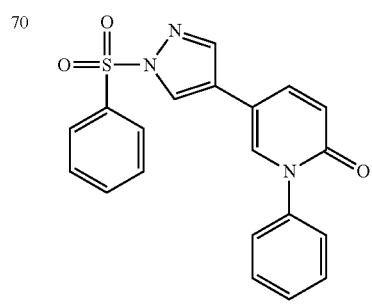 |
| 71 | 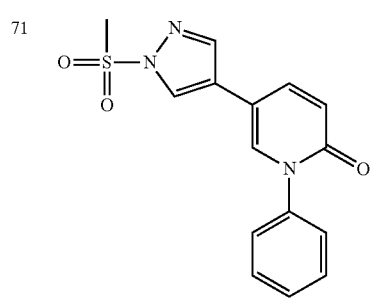 |
| 72 | 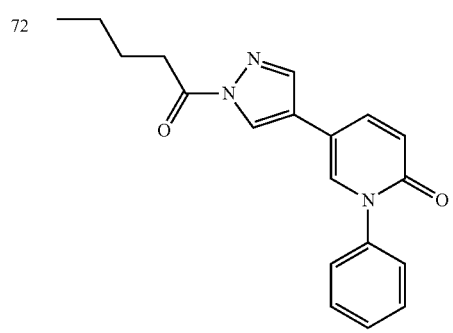 |
| 73 | 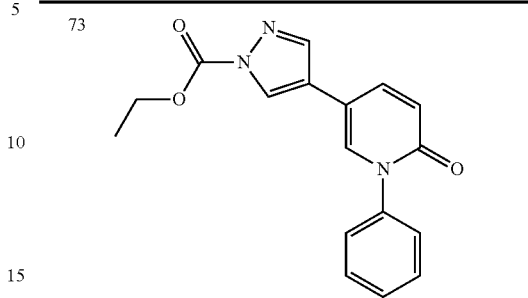 |
| 74 | 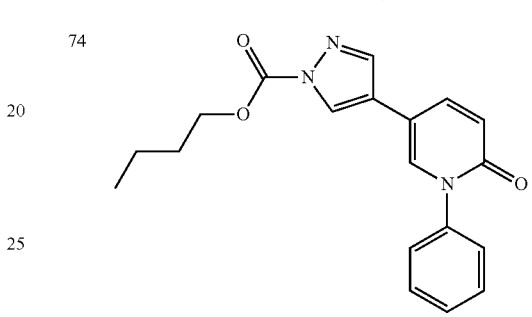 |
| 75 | 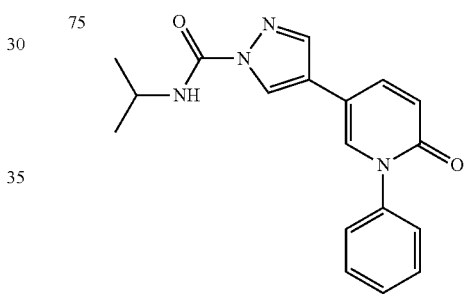 |
| 76 | 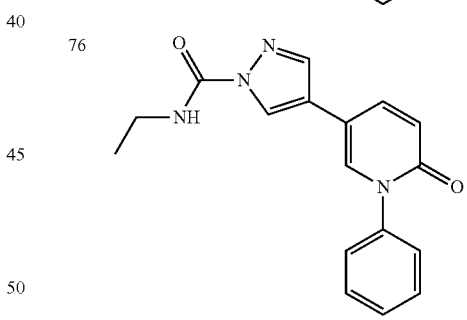 |
| 77 | 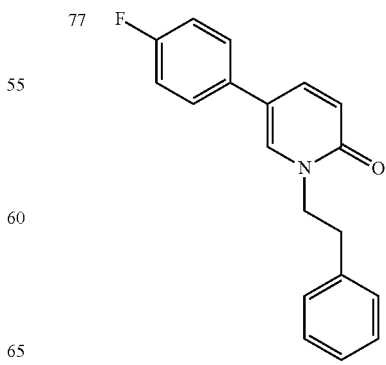 |

TABLE 1-continued
| Compd. # | Structure |
|---|---|
| 78 | 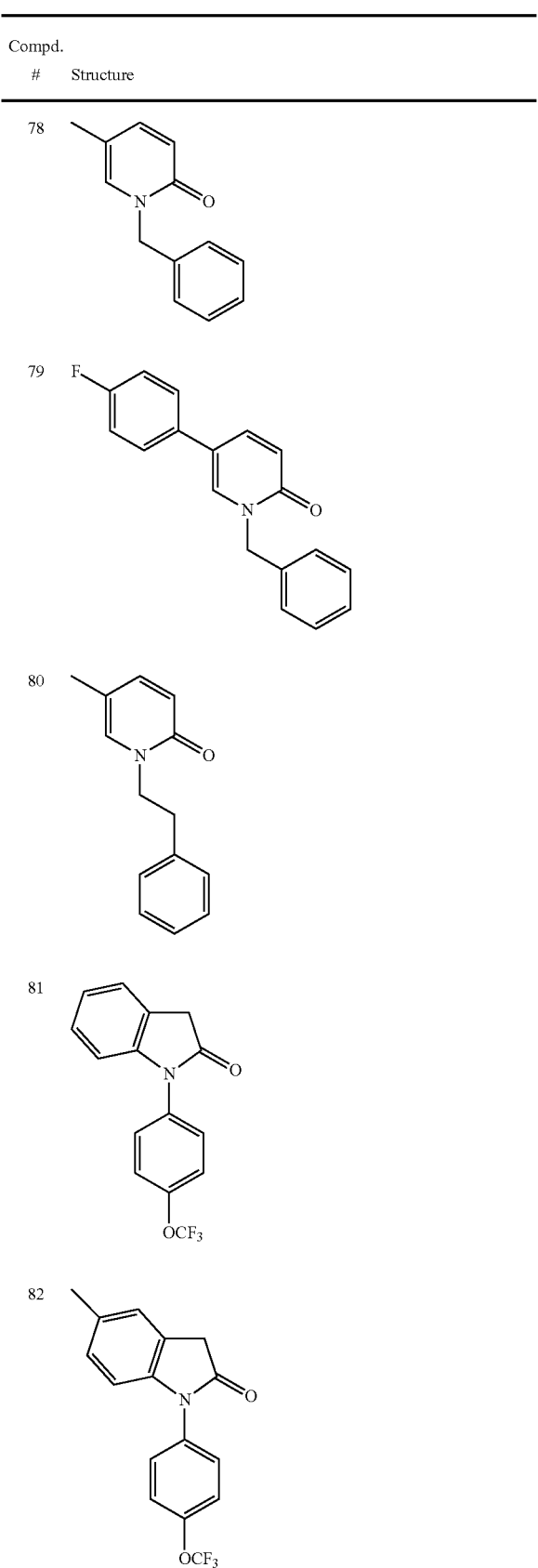 |
| 79 | 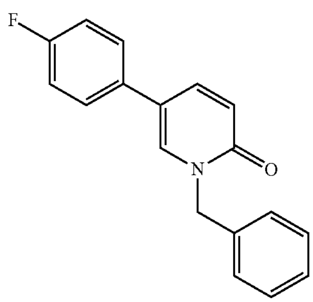 |
| 80 | 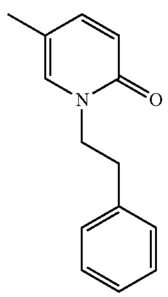 |
| 81 | 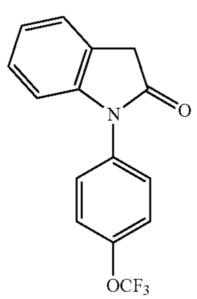 |
| 82 | 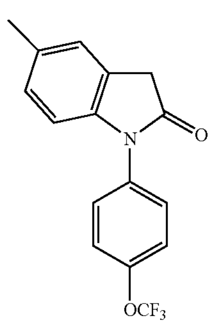 |
TABLE 1-continued
| Compd. # | Structure |
|---|---|
| 83 | 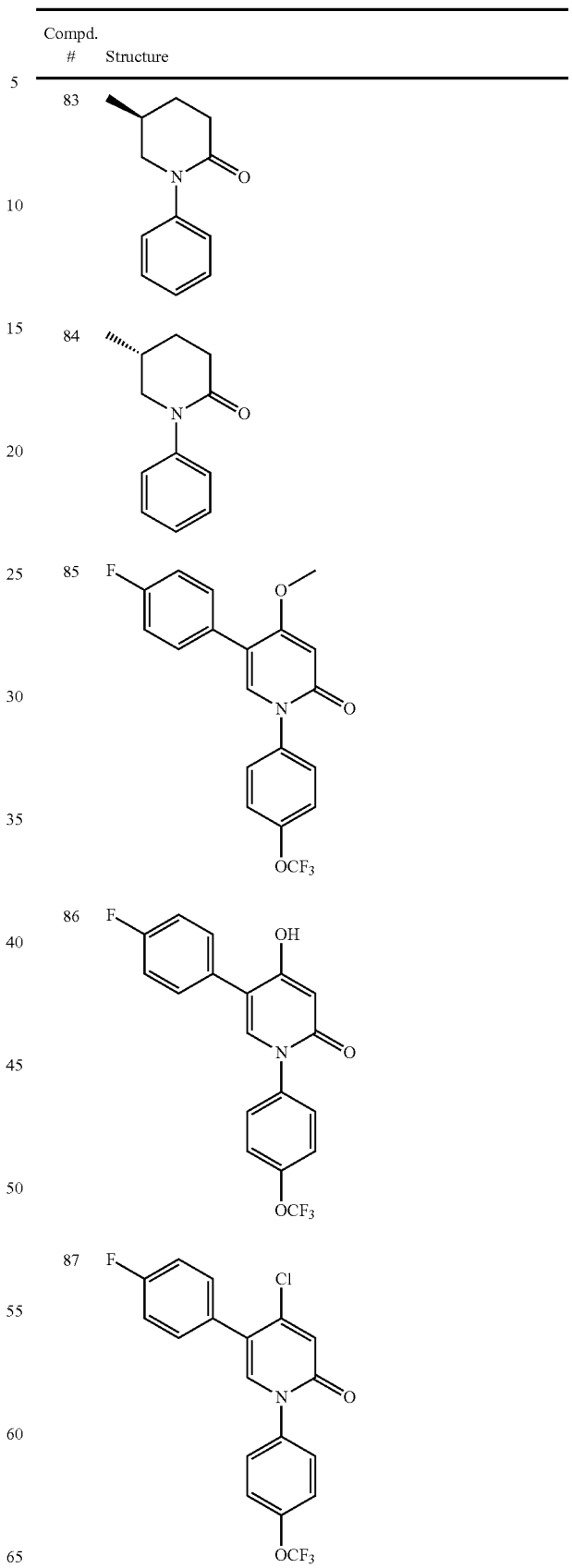 |
| 84 | |
| 85 | |
| 86 | |
| 87 | |

TABLE 1-continued
| Compd. # | Structure |
|---|---|
| 88 | 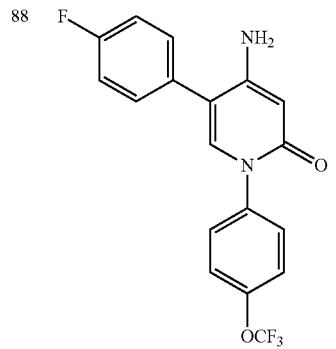 |
| 89 | 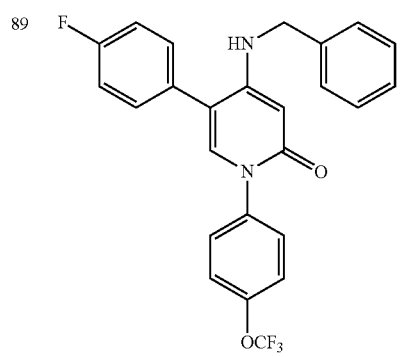 |
| 90 | 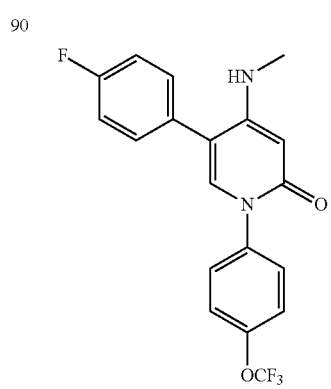 |
| 91 | 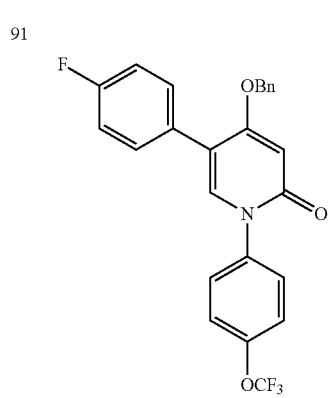 |
| 92 | 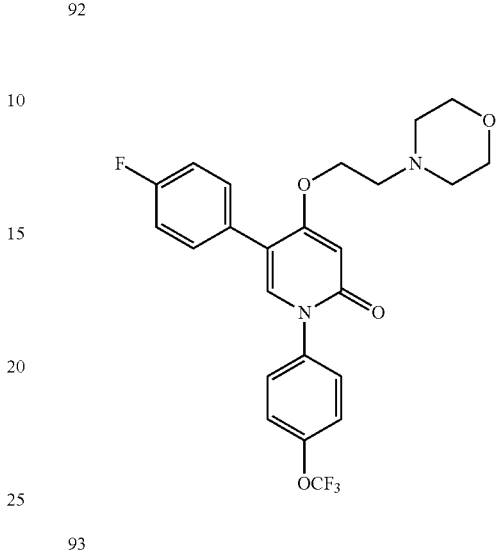 |
| 93 | 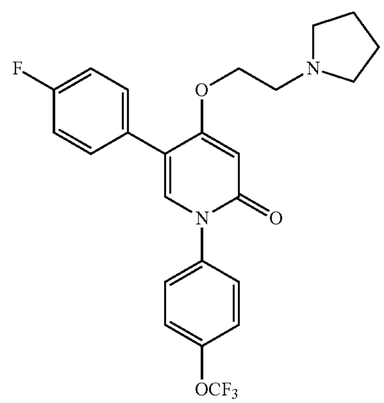 |
| 94 | 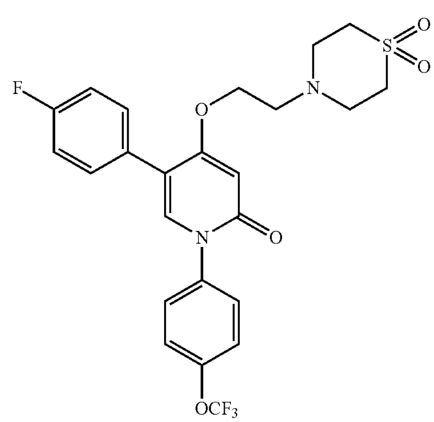 |

TABLE 1-continued
| Compd. # | Structure |
|---|---|
| 95 | 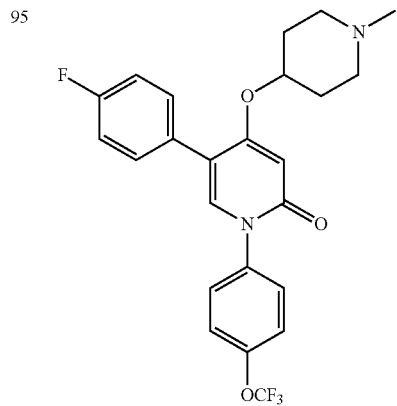 |
| 96 | 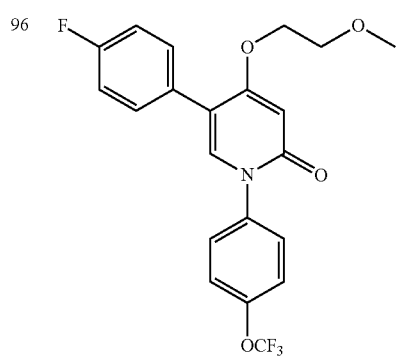 |
| 97 | 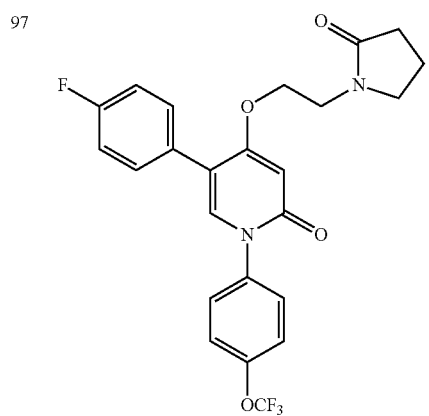 |
| 98 | 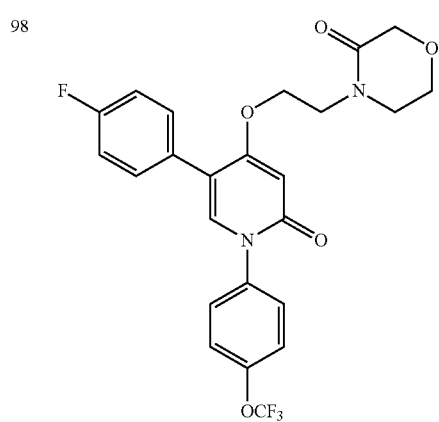 |
| 99 | 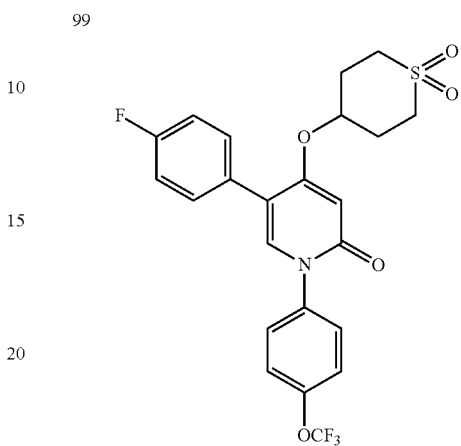 |
| 100 | 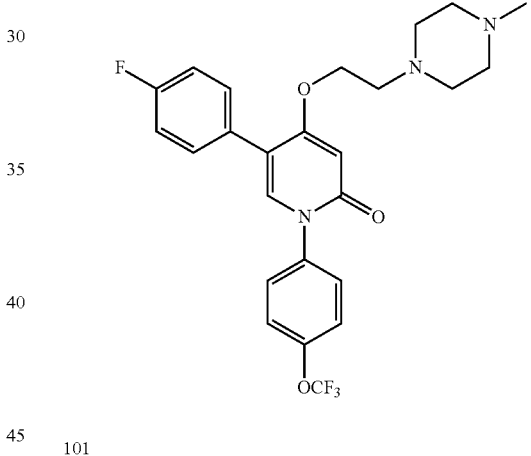 |
| 101 | 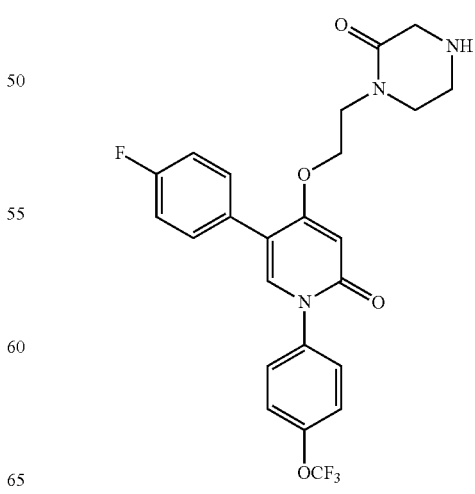 |

TABLE 1-continued
| Compd. # | Structure |
|---|---|
| 102 | 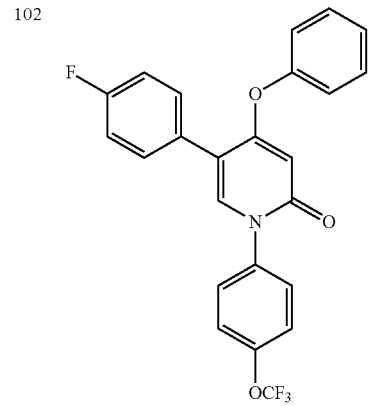 |
| 103 | 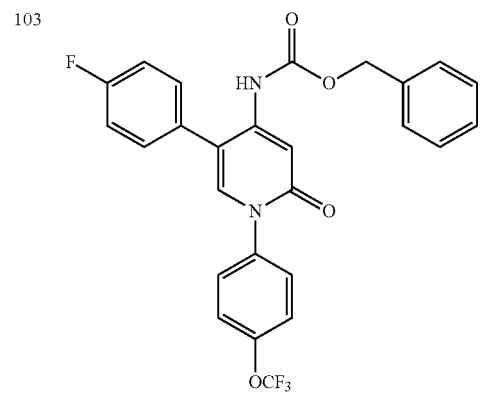 |
| 104 | 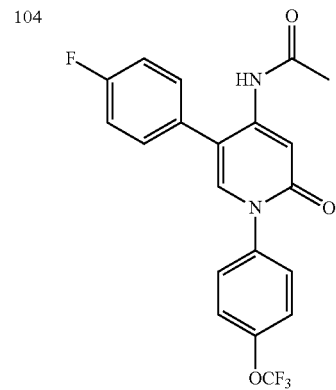 |
| 105 | 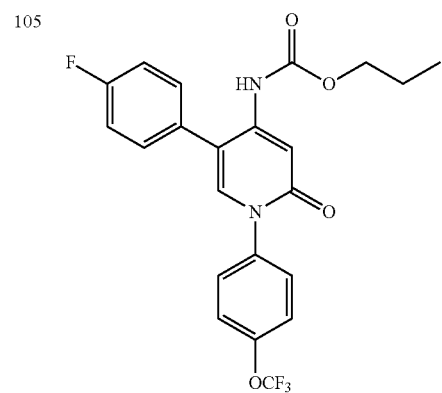 |
| 106 | 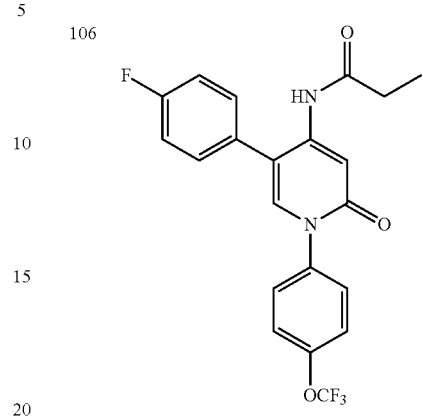 |
| 107 | 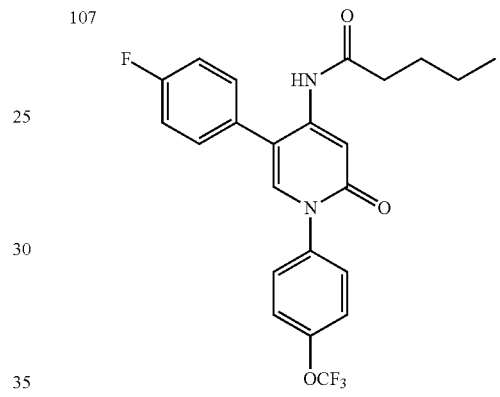 |
| 108 | 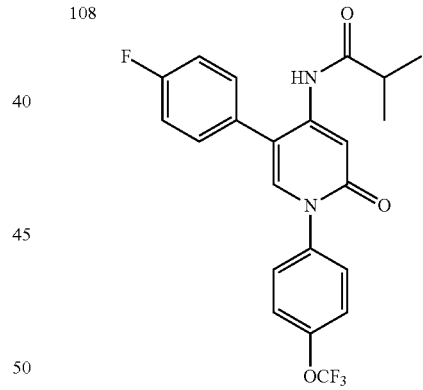 |
| 109 | 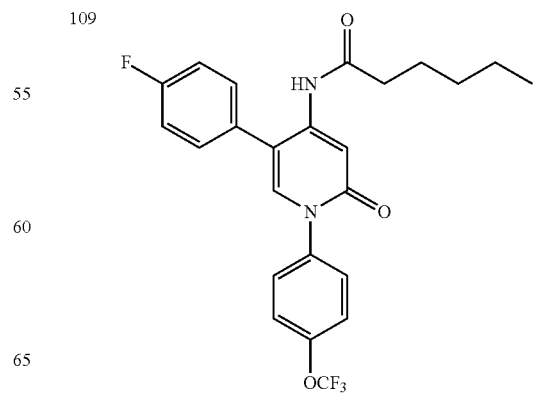 |

TABLE 1-continued
| Compd. # | Structure |
|---|---|
| 110 | 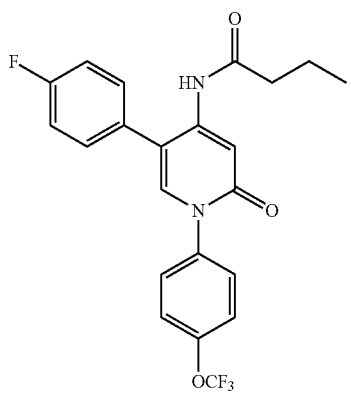 |
| 111 | 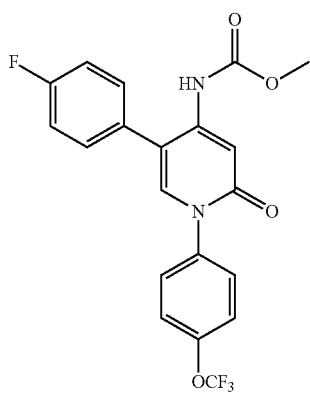 |
| 112 | 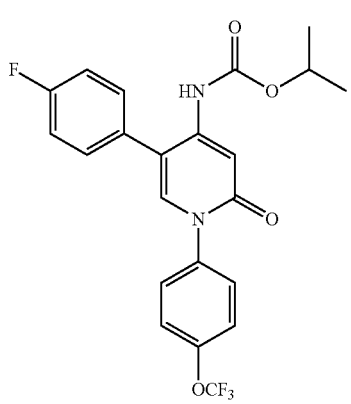 |
TABLE 1-continued
| Compd. # | Structure |
|---|---|
| 113 | 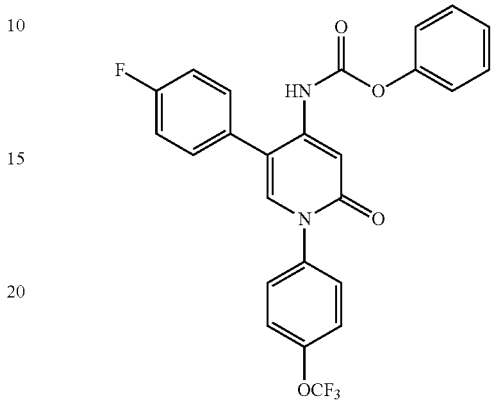 |
| 114 | 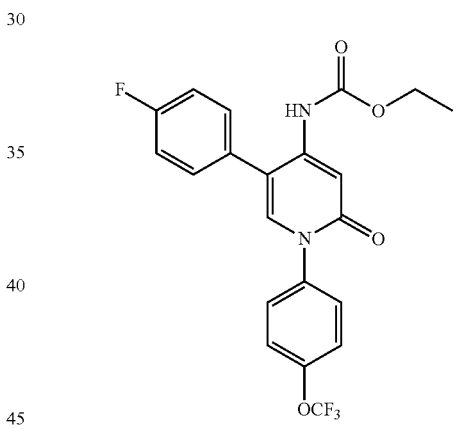 |
| 115 | 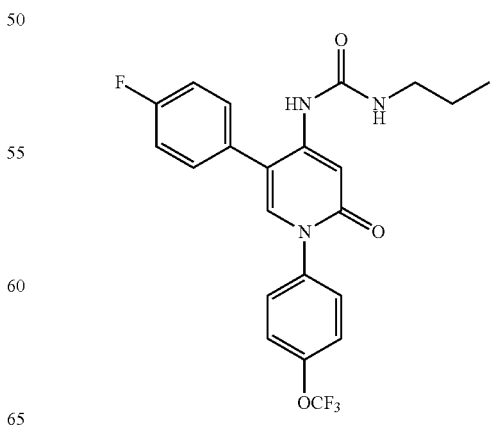 |

TABLE 1-continued
| Compd. # | Structure |
|---|---|
| 116 | 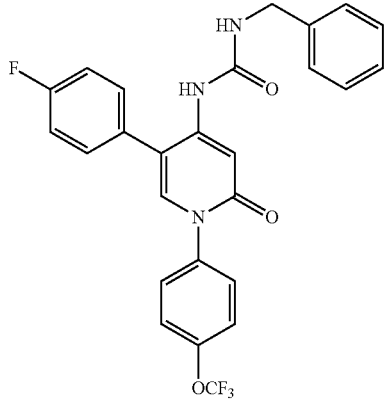 |
| 117 | 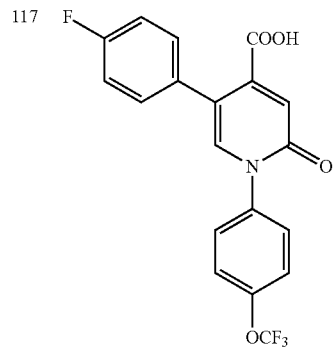 |
| 118 | 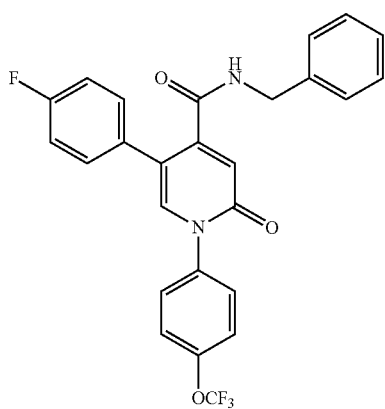 |
| 119 | 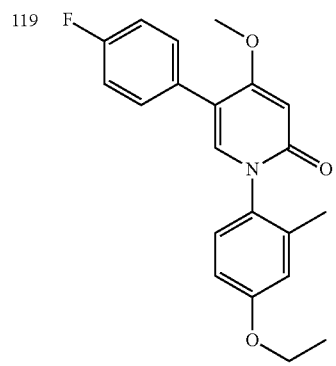 |
| 120 | 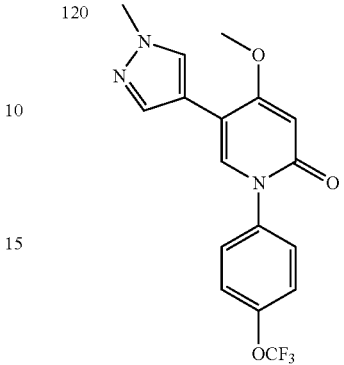 |
| 121 | 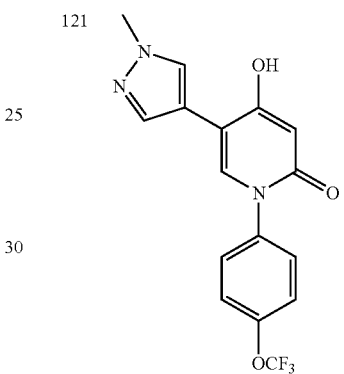 |
| 122 | 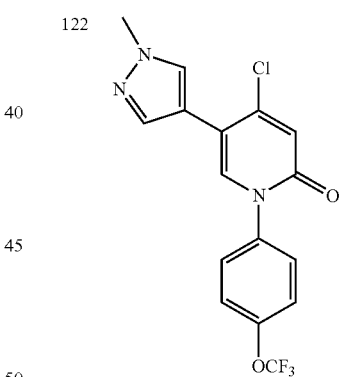 |
| 123 | 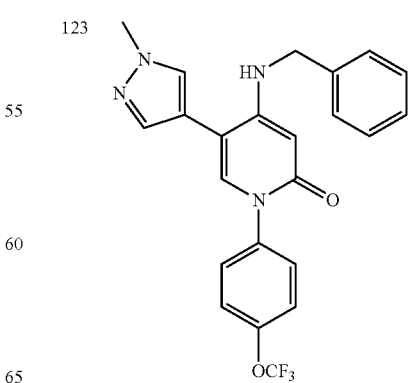 |

TABLE 1-continued
| Compd. # | Structure |
|---|---|
| 124 | 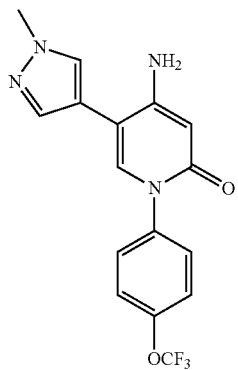 |
| 125 | 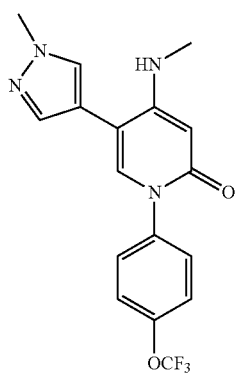 |
| 126 | 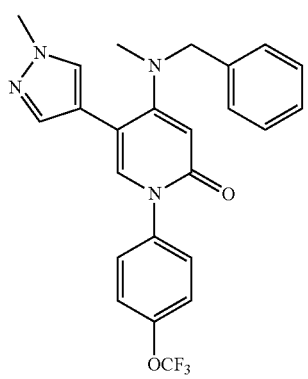 |
| 127 | 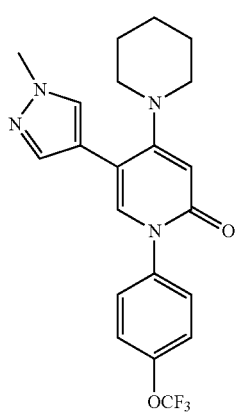 |
| 128 | 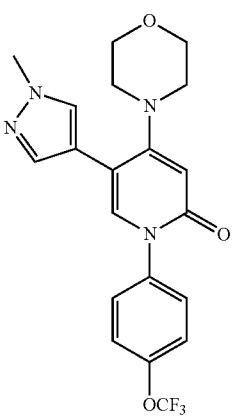 |
| 129 | 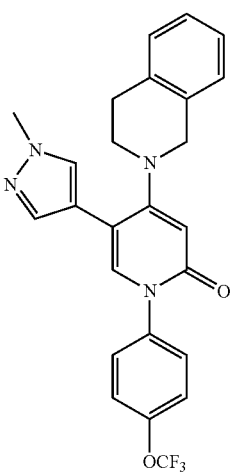 |
| 130 | 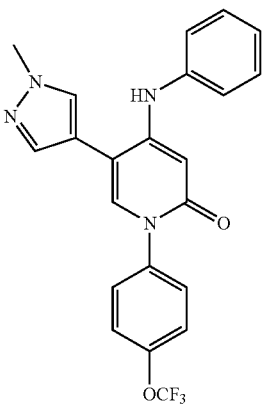 |

TABLE 1-continued
| Compd. # | Structure |
|---|---|
| 131 | 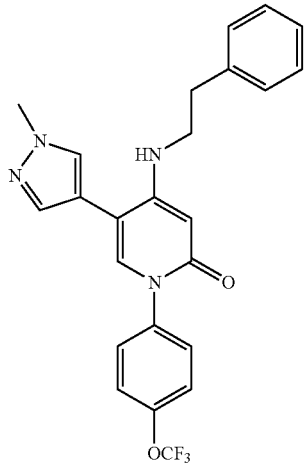 |
| 132 | 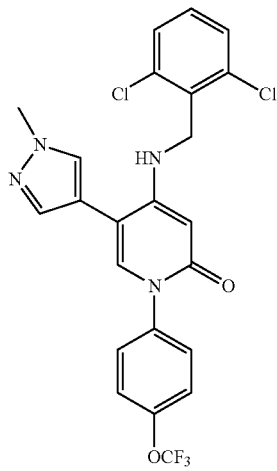 |
| 133 | 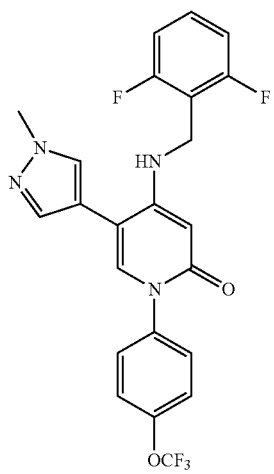 |
TABLE 1-continued
| Compd. # | Structure |
|---|---|
| 134 | 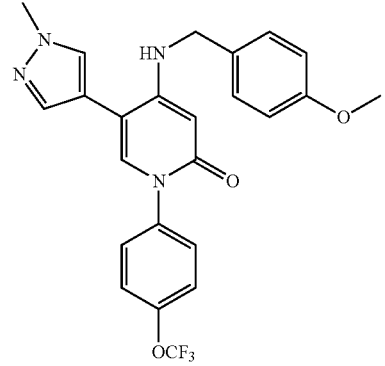 |
| 135 | 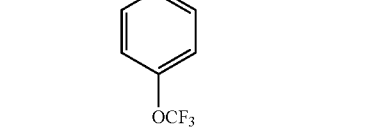 |
| 136 | 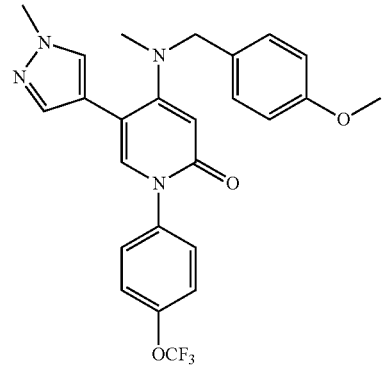 |
| 137 | 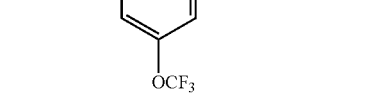 |

TABLE 1-continued
| Compd. # | Structure |
|---|---|
| 138 | 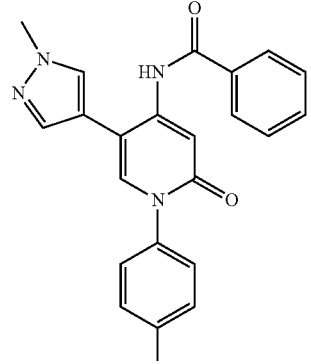 |
| 139 | 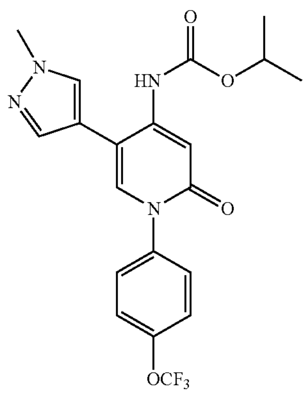 |
| 140 | 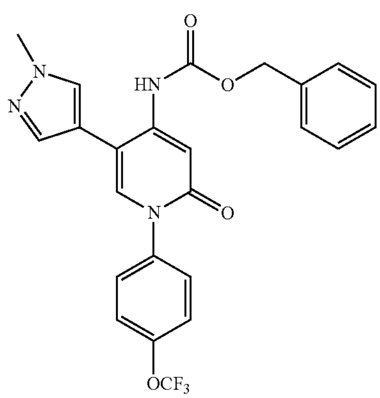 |
| 141 | 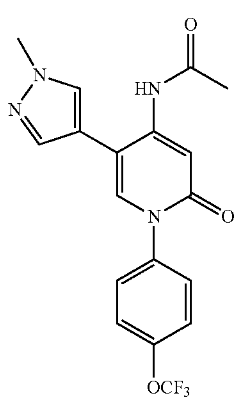 |
| 142 | 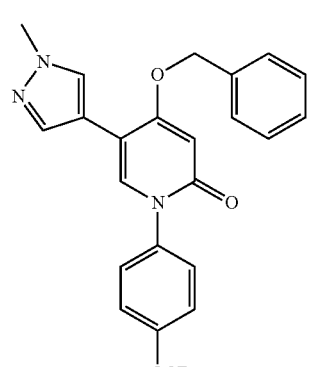 |
| 143 | |
| 144 | |
| 145 | |

TABLE 1-continued
| Compd. # | Structure |
|---|---|
| 146 | 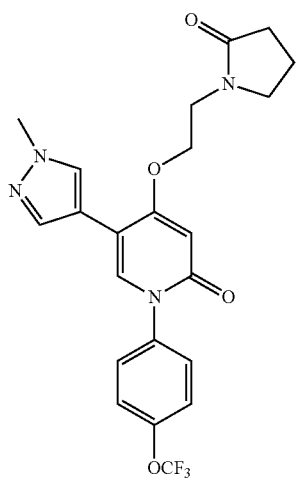 |
| 147 | 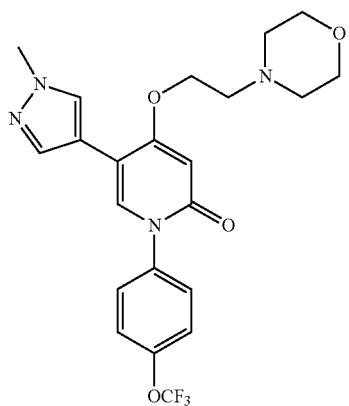 |
| 148 | 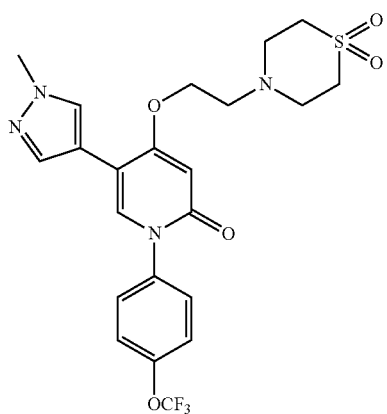 |
| 149 | 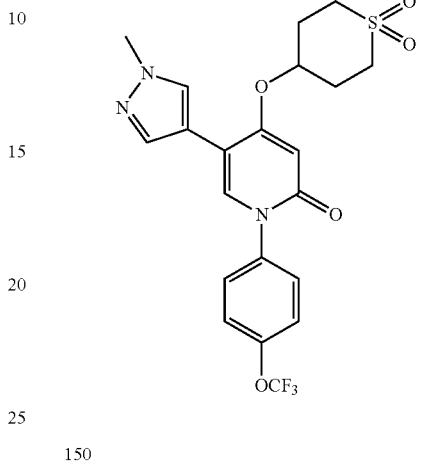 |
| 150 | 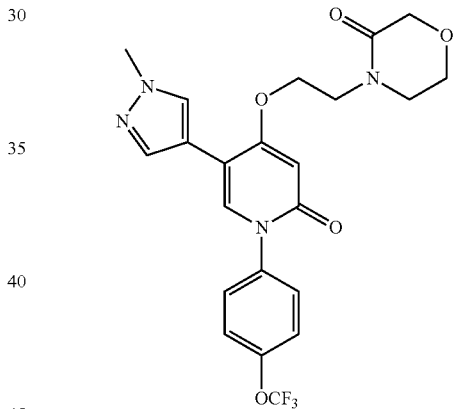 |
| 151 | 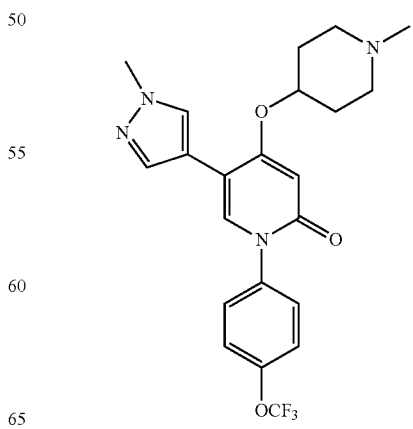 |

TABLE 1-continued
| Compd. # | Structure |
|---|---|
| 152 | 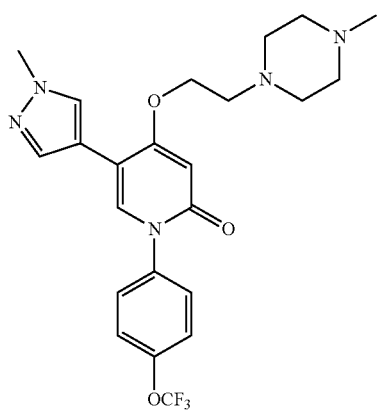 |
| 153 | 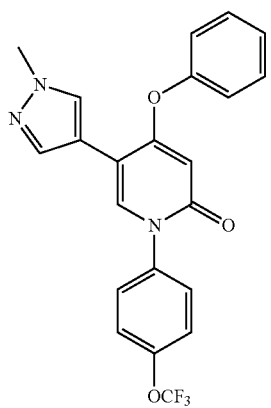 |
| 154 | 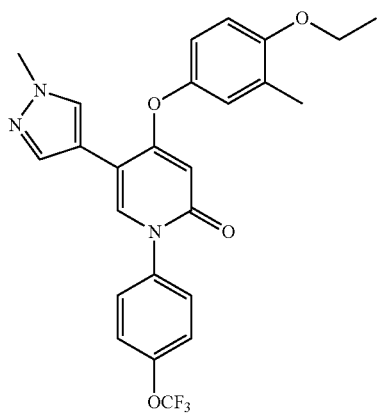 |
TABLE 1-continued
| Compd. # | Structure |
|---|---|
| 155 | 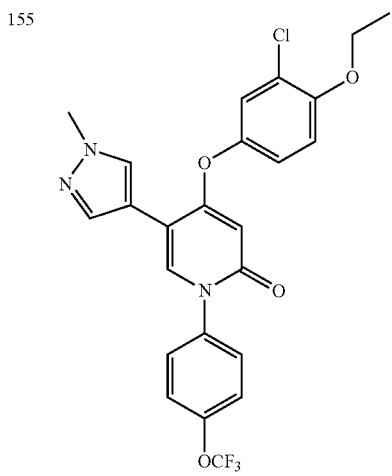 |
| 156 | 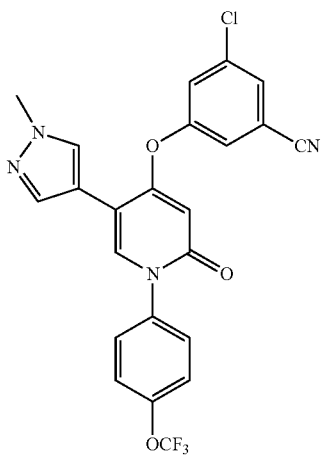 |
| 157 | 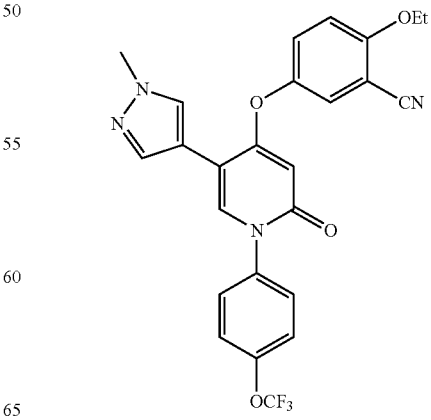 |

TABLE 1-continued
| Compd. # | Structure |
|---|---|
| 158 | 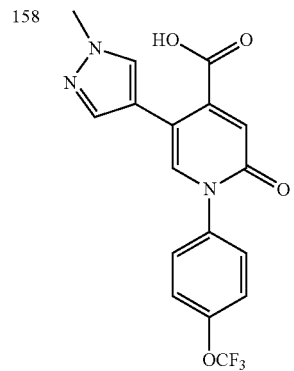 |
| 159 | 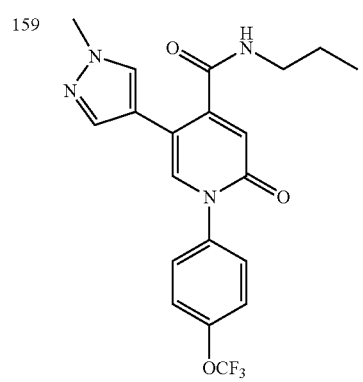 |
| 160 | 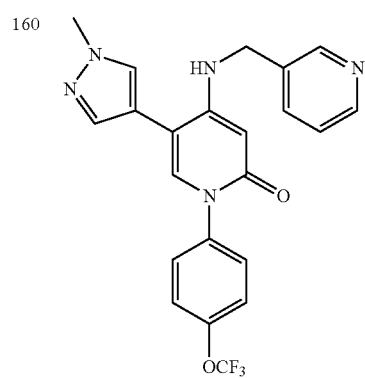 |
| 161 | 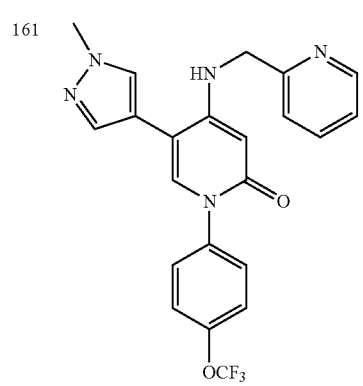 |
| 162 | 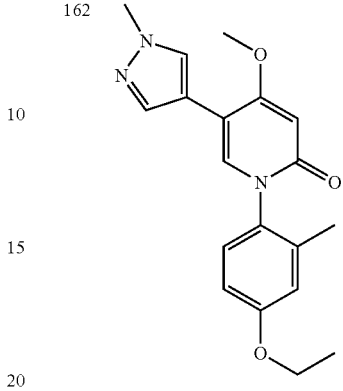 |
| 163 | 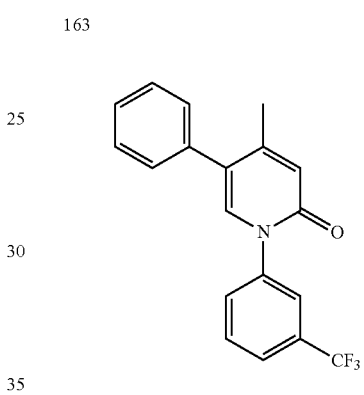 |
| 164 | 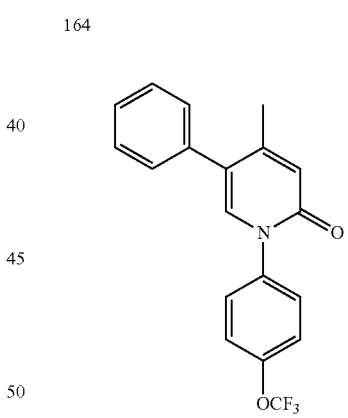 |
| 165 | 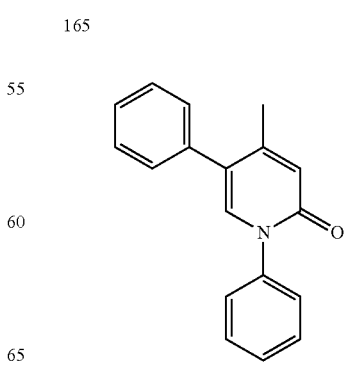 |

TABLE 1-continued
| Compd. # | Structure |
|---|---|
| 166 | 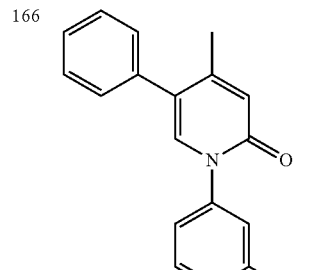 |
| 167 | 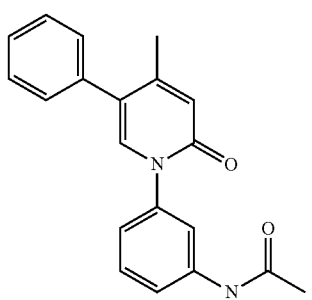 |
| 168 | 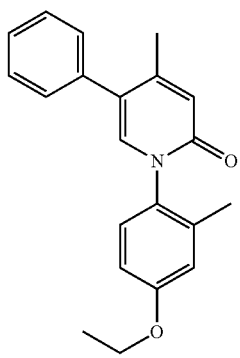 |
| 169 | 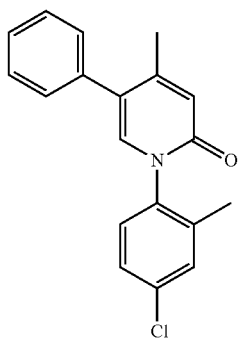 |
TABLE 1-continued
| Compd. # | Structure |
|---|---|
| 170 | 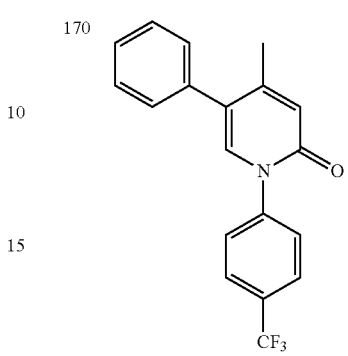 |
| 171 | 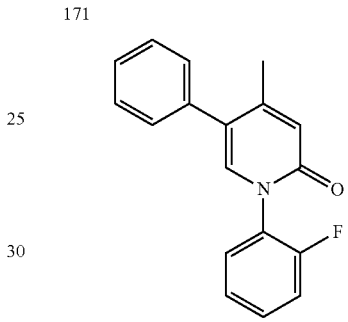 |
| 172 | 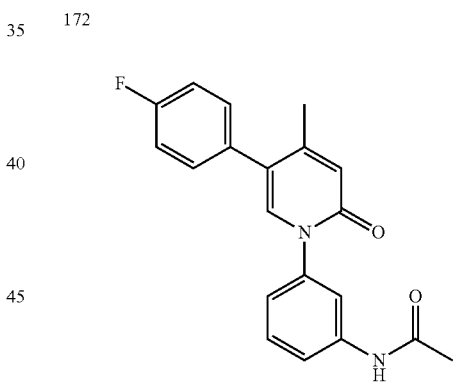 |
| 173 | 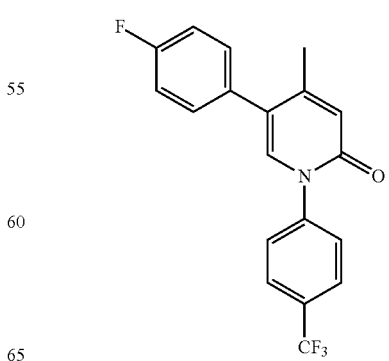 |

TABLE 1-continued
| Compd. # | Structure |
|---|---|
| 174 | 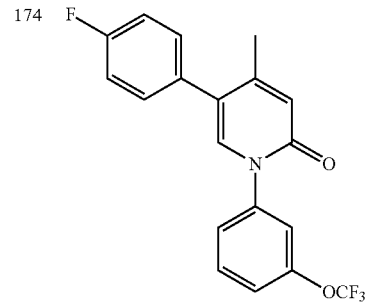 |
| 175 | 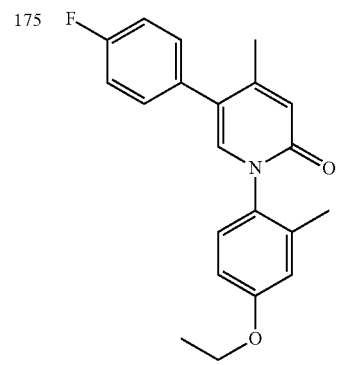 |
| 176 | 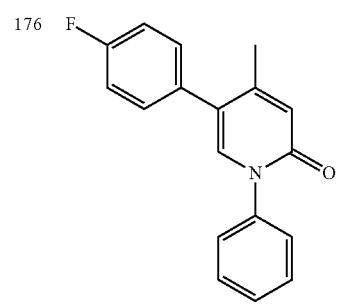 |
| 177 | 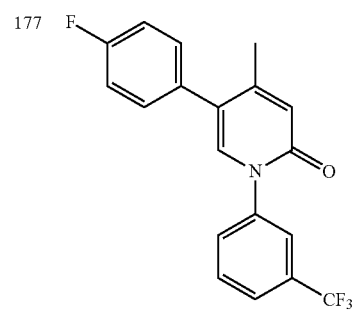 |
| 178 | 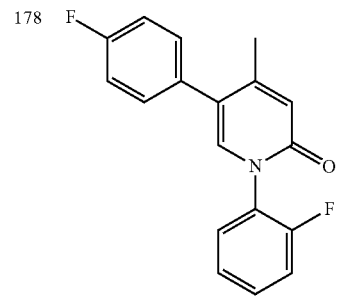 |
| 179 | 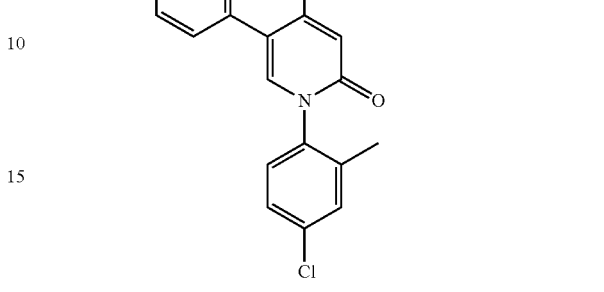 |
| 180 | 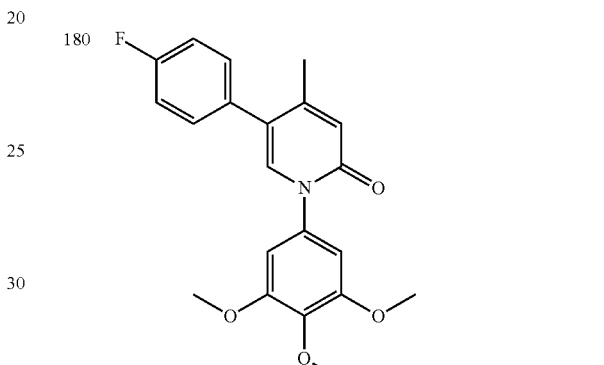 |
| 181 | 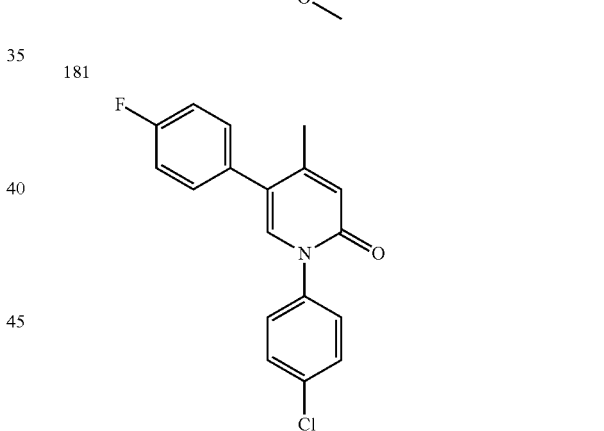 |
| 182 | 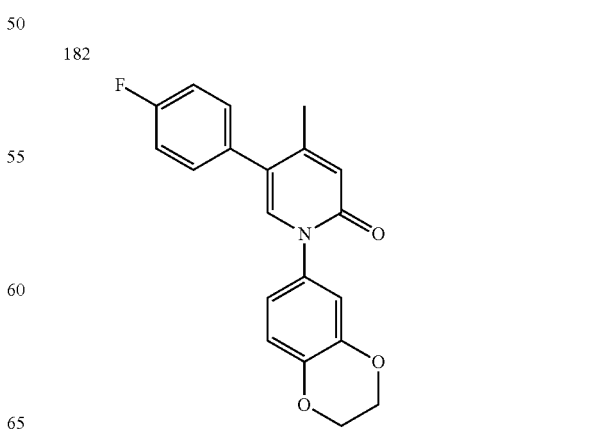 |

TABLE 1-continued
| Compd. # | Structure |
|---|---|
| 183 | 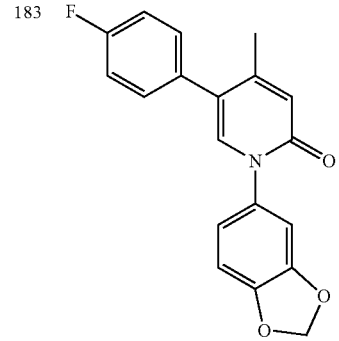 |
| 184 | 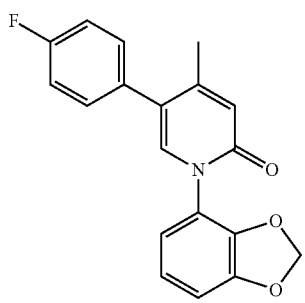 |
| 185 | 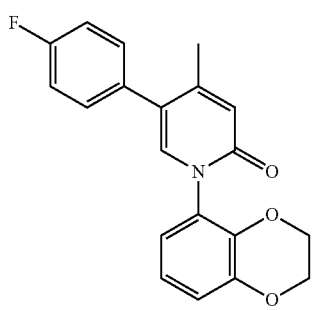 |
| 186 | 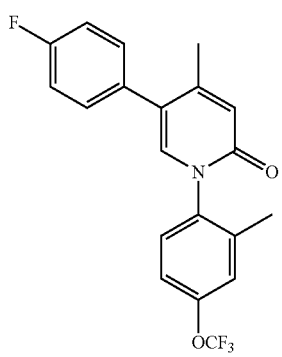 |
| 187 | 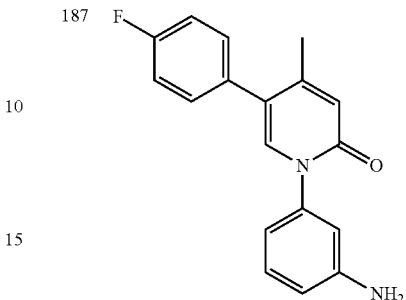 |
| 188 | 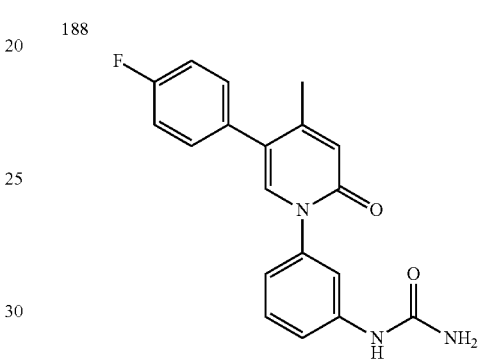 |
| 189 | 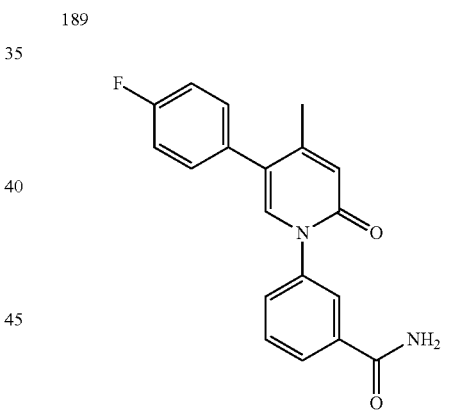 |
| 190 | 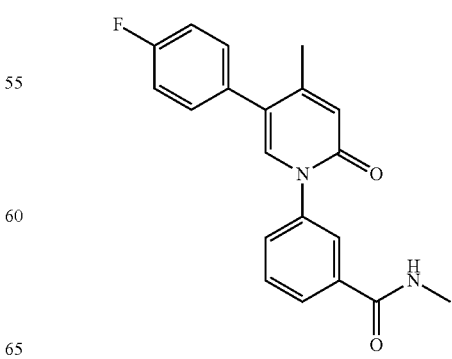 |

TABLE 1-continued
| Compd. # | Structure |
|---|---|
| 191 | 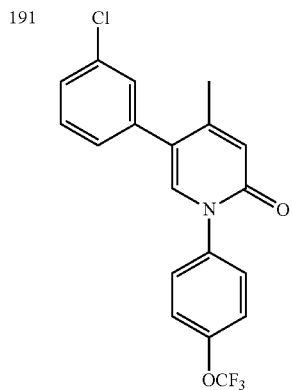 |
| 192 | 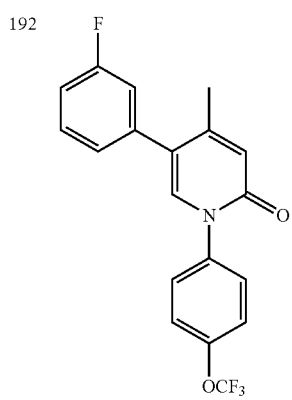 |
| 193 | 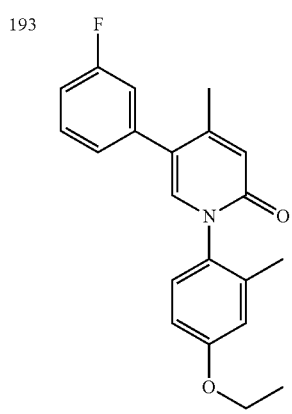 |
| 194 | 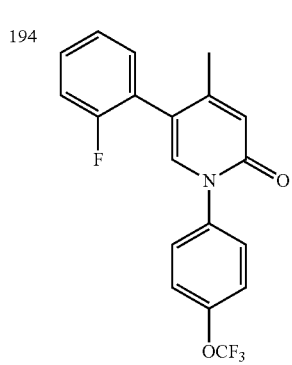 |
| 195 | 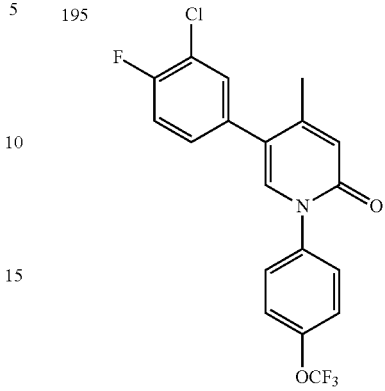 |
| 196 | 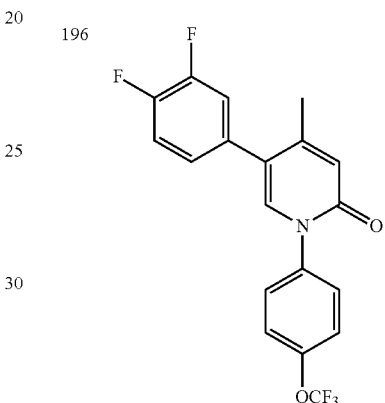 |
| 197 | 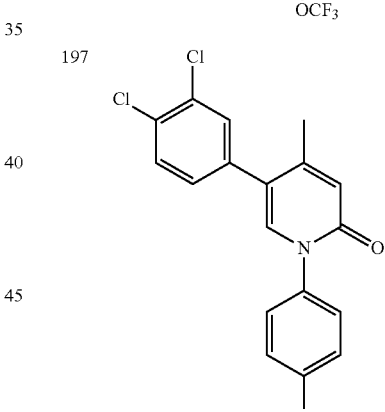 |
| 198 | 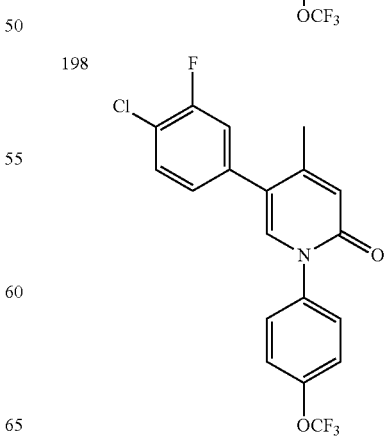 |

TABLE 1-continued
| Compd. # | Structure |
|---|---|
| 199 | 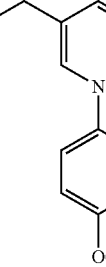 |
| 200 | 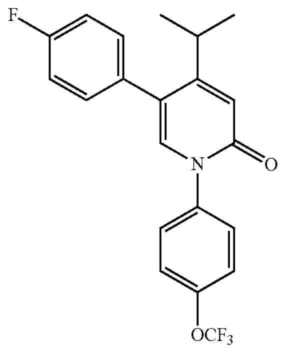 |
| 201 | 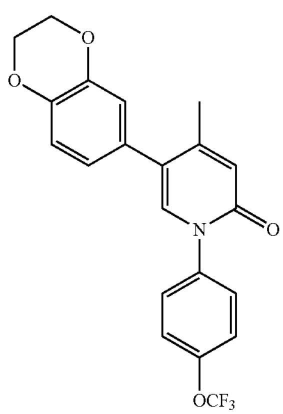 |
| 202 | 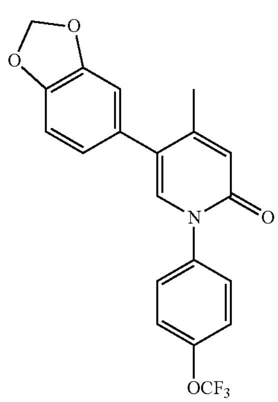 |
| 203 | 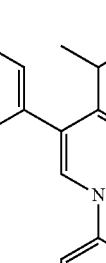 |
| 204 | |
| 205 | |
| 206 | |

TABLE 1-continued
| Compd. # | Structure |
|---|---|
| 207 | 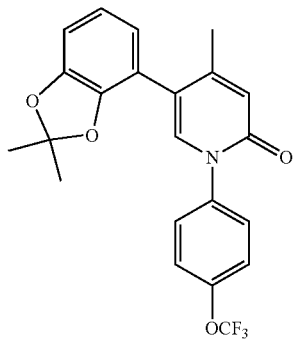 |
| 208 | 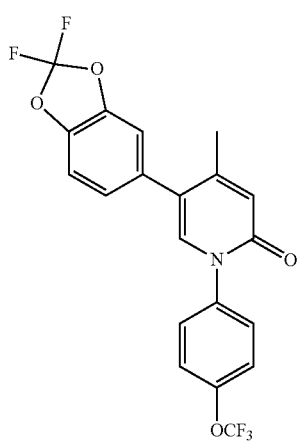 |
| 209 | 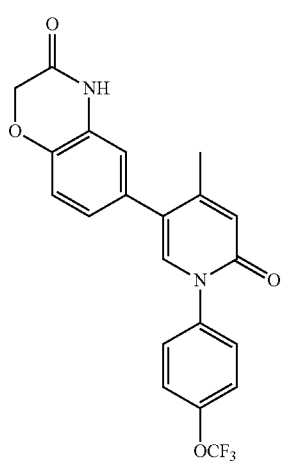 |
| 210 | 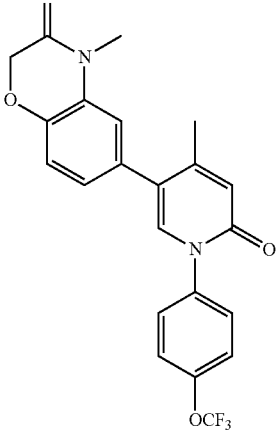 |
| 211 | 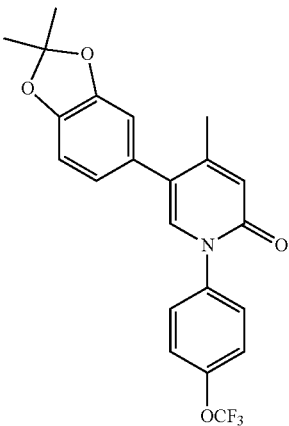 |
| 212 | 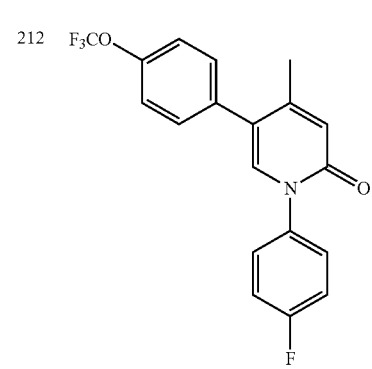 |
| 213 | 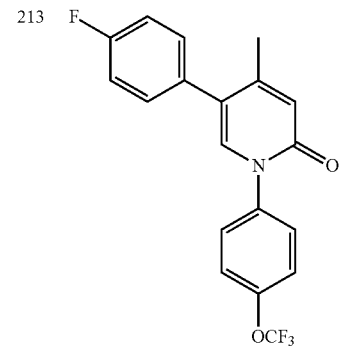 |

TABLE 1-continued
| Compd. # | Structure |
|---|---|
| 214 | 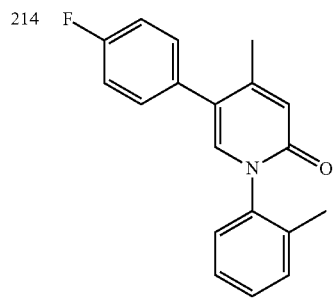 |
| 215 | 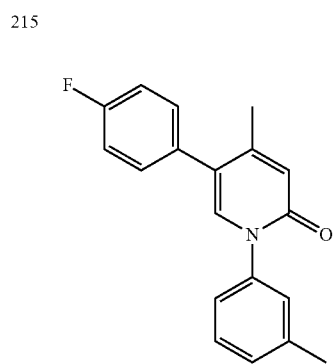 |
| 216 | 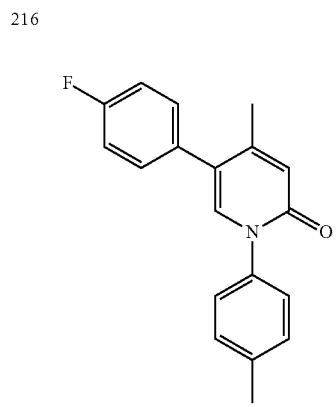 |
| 217 | 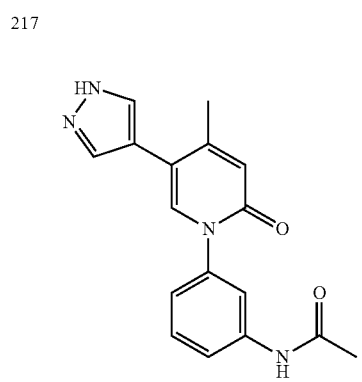 |
| 218 | 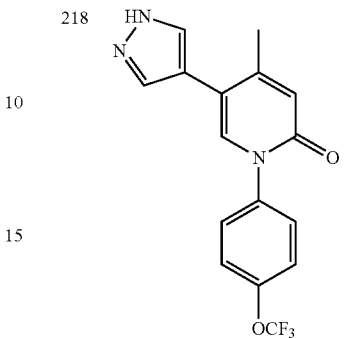 |
| 219 | 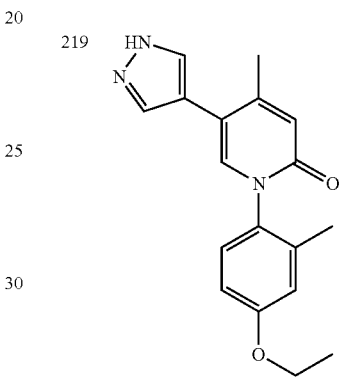 |
| 220 | 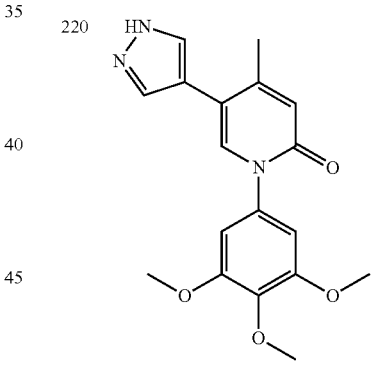 |
| 221 | 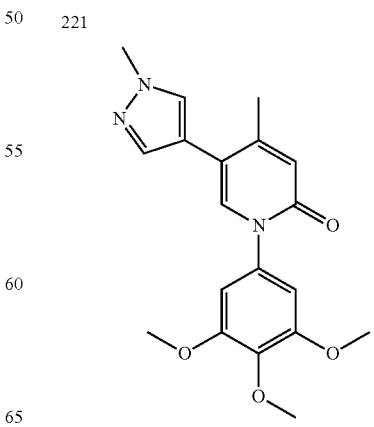 |

TABLE 1-continued

| Compd. # | Structure |
|---|---|
| 222 | 1-methylpyrazol-4-yl, 4-methylpyridin-2(1H)-one N-substituted with 2,3-dihydro-1,4-benzodioxin-6-yl |
| 223 | 1-methylpyrazol-4-yl, 4-methylpyridin-2(1H)-one N-substituted with 1,3-benzodioxol-5-yl |
| 224 | 1-methylpyrazol-4-yl, 4-methylpyridin-2(1H)-one N-substituted with benzoxazol-5-yl |
| 225 | 1-methylpyrazol-4-yl, 4-methylpyridin-2(1H)-one N-substituted with benzothiazol-5-yl |
| 226 | 1-methylpyrazol-4-yl, 4-methylpyridin-2(1H)-one N-substituted with 3-(trifluoromethyl)phenyl |
| 227 | 1-methylpyrazol-4-yl, 4-methylpyridin-2(1H)-one N-substituted with 3-(trifluoromethoxy)phenyl |
| 228 | 1-methylpyrazol-4-yl, 4-methylpyridin-2(1H)-one N-substituted with 4-(trifluoromethyl)phenyl |
| 229 | 1-methylpyrazol-4-yl, 4-methylpyridin-2(1H)-one N-substituted with 4-chloro-2-methylphenyl |

TABLE 1-continued
| Compd. # | Structure |
|---|---|
| 230 | 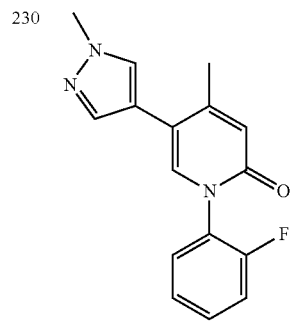 |
| 231 | 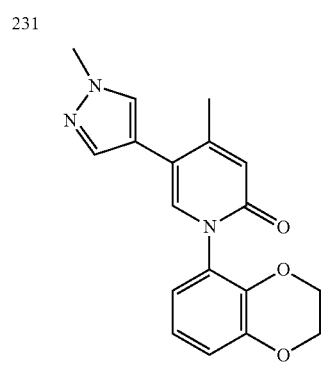 |
| 232 | 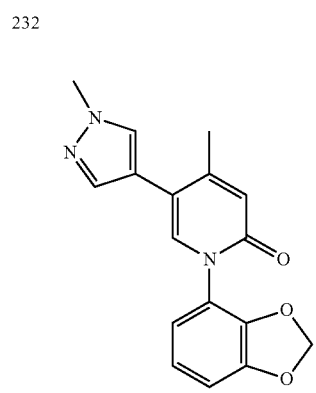 |
| 233 | 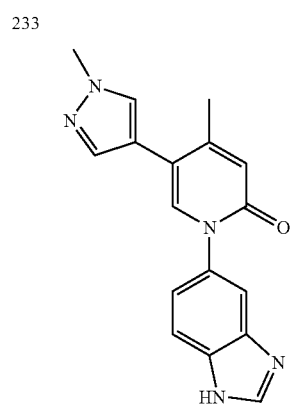 |
| 234 | 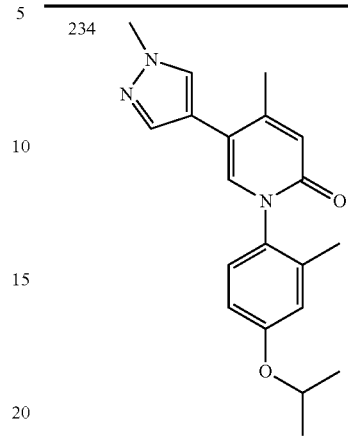 |
| 235 | 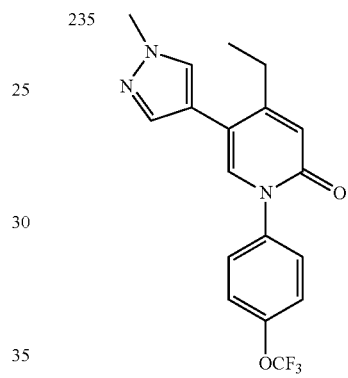 |
| 236 | 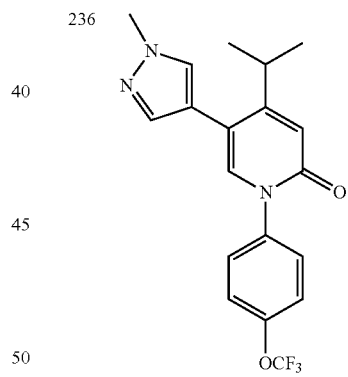 |
| 237 | 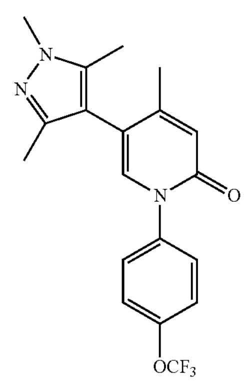 |

TABLE 1-continued

| Compd. # | Structure |
|---|---|
| 238 | 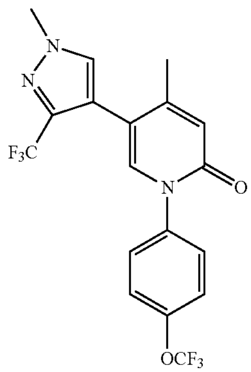 |
| 239 | 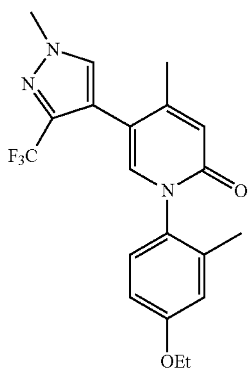 |
| 240 | 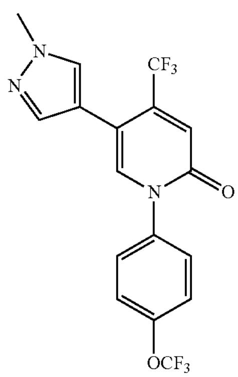 |
| 241 | 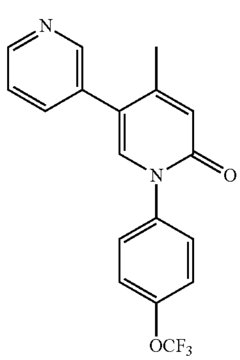 |
| 242 | |
| 243 | |
| 244 | |
| 245 | |

TABLE 1-continued
| Compd. # | Structure |
|---|---|
| 246 | 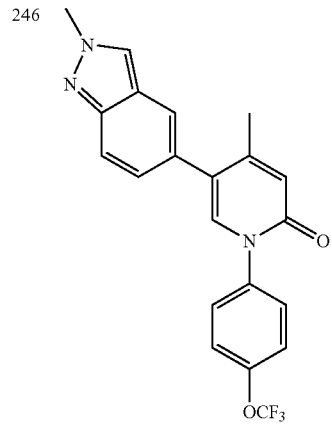 |
| 247 | 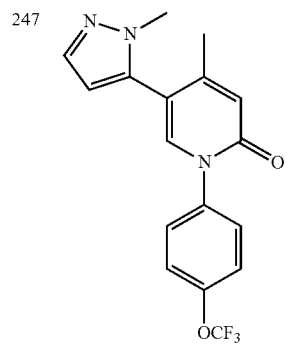 |
| 248 | 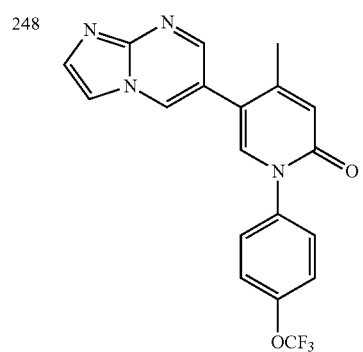 |
| 249 | 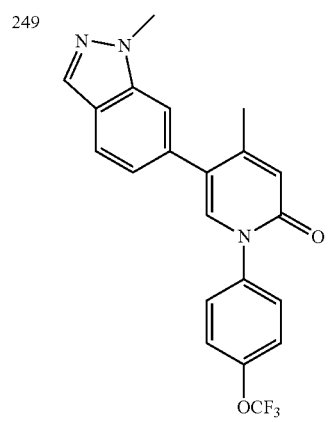 |
| 250 | 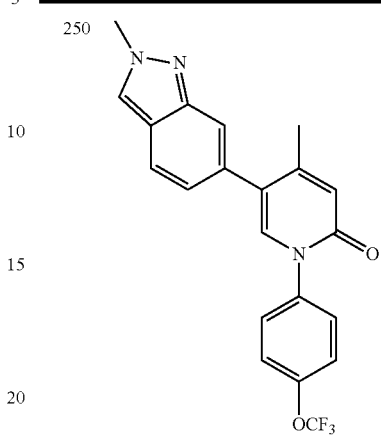 |
| 251 | 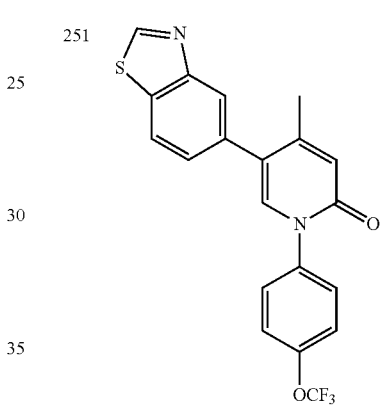 |
| 252 | 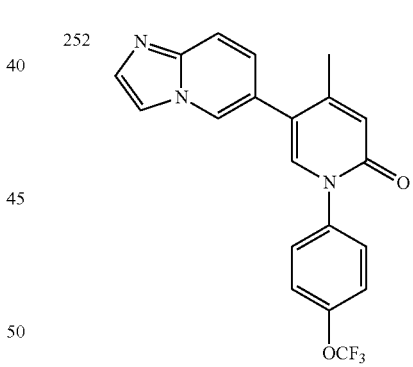 |
| 253 | 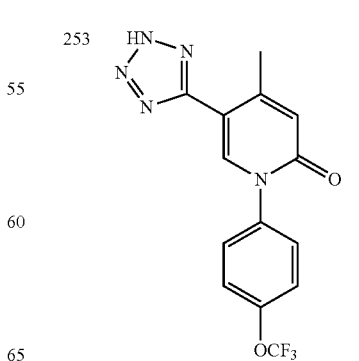 |

TABLE 1-continued
| Compd. # | Structure |
|---|---|
| 254 | 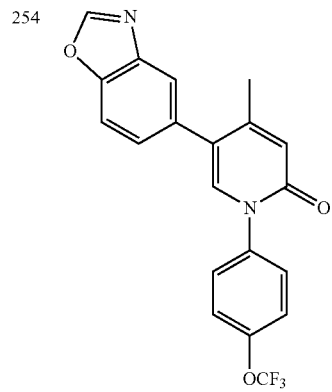 |
| 255 | 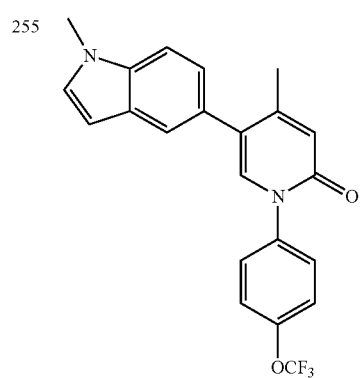 |
| 256 | 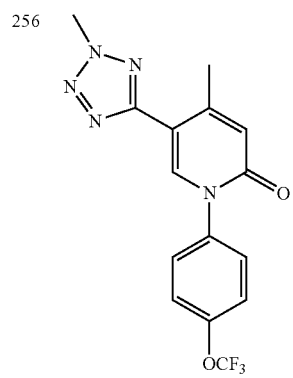 |
| 257 | 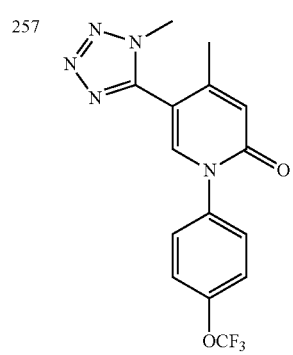 |
| 258 | 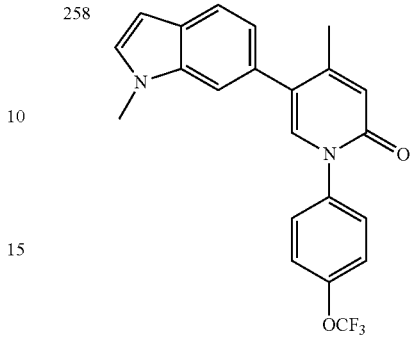 |
| 259 | 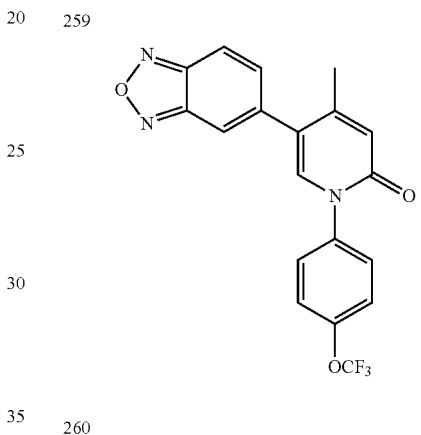 |
| 260 | 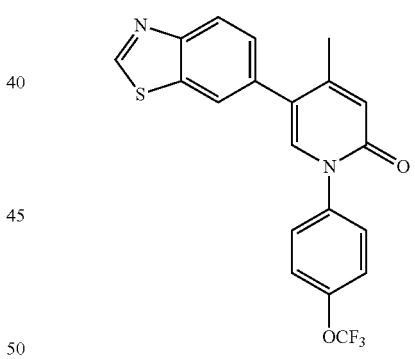 |
| 261 | 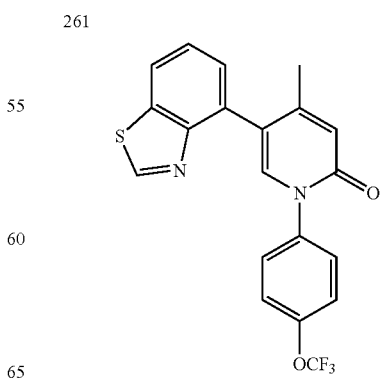 |

TABLE 1-continued
| Compd. # | Structure |
|---|---|
| 262 | 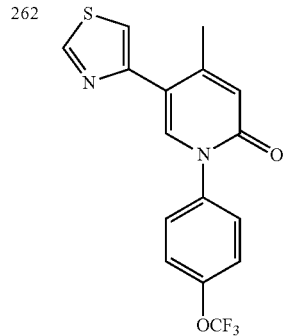 |
| 263 | 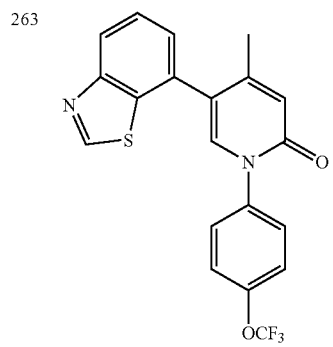 |
| 264 | 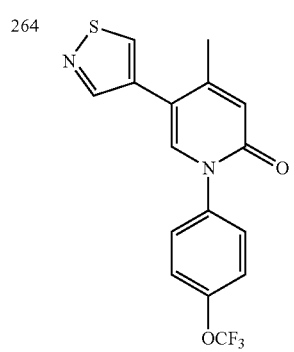 |
| 265 | 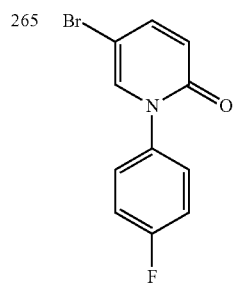 |
| 266 | 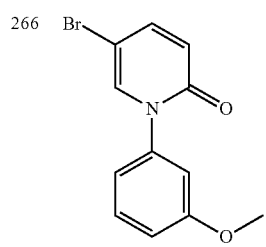 |
| 267 | 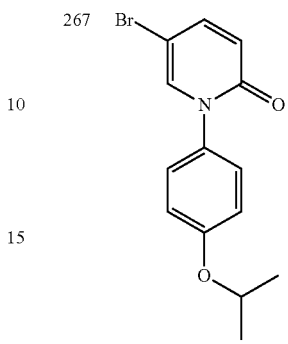 |
| 268 | 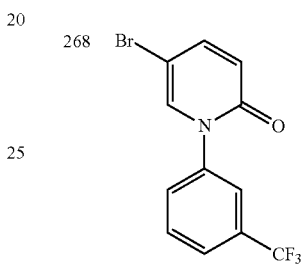 |
| 269 | 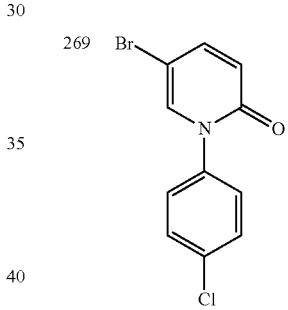 |
| 270 | 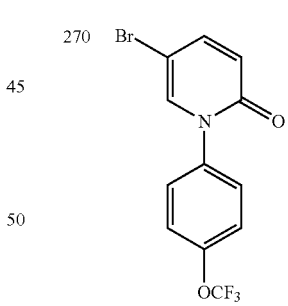 |
| 271 | 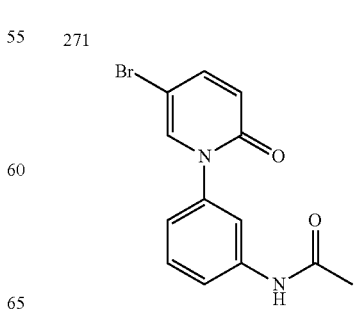 |

TABLE 1-continued
| Compd. # | Structure |
|---|---|
| 272 | 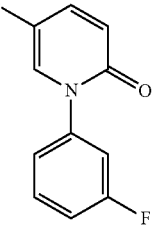 |
| 273 | 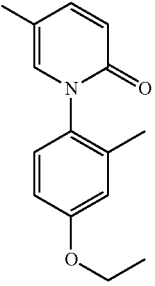 |
| 274 | 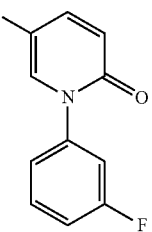 |
| 275 | 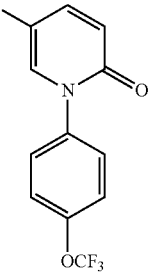 |
| 276 | 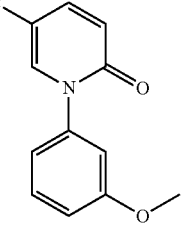 |
| 277 | 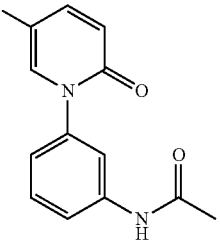 |
| 278 | 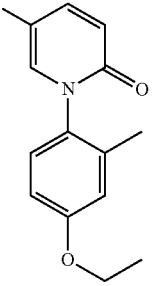 |
| 279 | 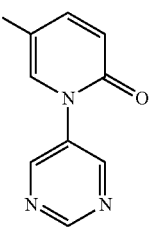 |
| 280 |  |
| 281 | 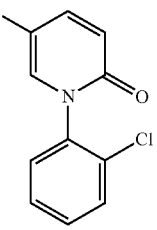 |
| 282 | 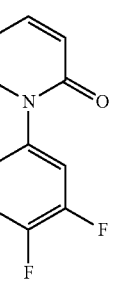 |
| 283 | 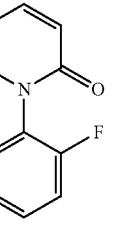 |

TABLE 1-continued
| Compd. # | Structure |
|---|---|
| 285 | 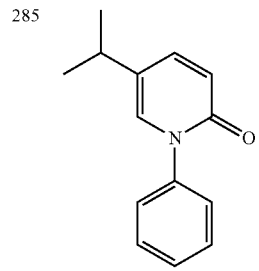 |
| 287 | 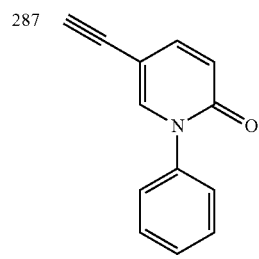 |
| 288 | 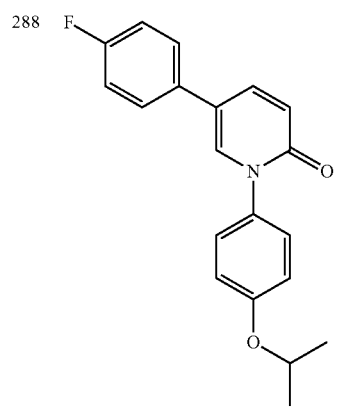 |
| 289 | 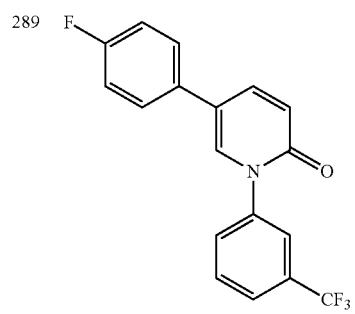 |
| 290 | 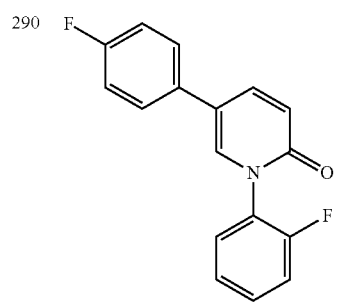 |
| 291 | 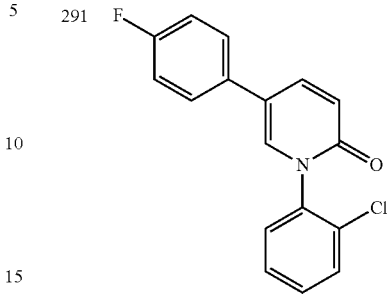 |
| 292 | 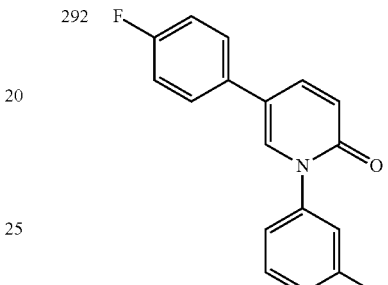 |
| 293 | 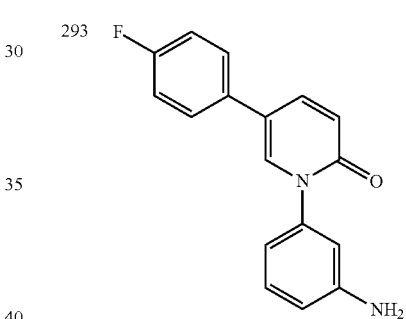 |
| 294 | 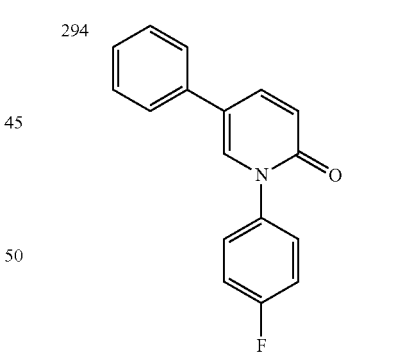 |
| 295 | 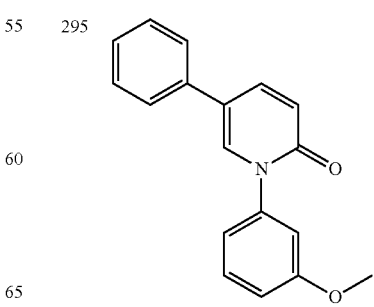 |

TABLE 1-continued

| Compd. # | Structure |
|---|---|
| 296 | 5-phenyl-1-(3-fluorophenyl)pyridin-2(1H)-one |
| 297 | 5-phenyl-1-(3-trifluoromethylphenyl)pyridin-2(1H)-one |
| 298 | 5-phenyl-1-(4-ethoxy-2-methylphenyl)pyridin-2(1H)-one |
| 299 | 5-phenyl-1-(pyridin-4-yl)pyridin-2(1H)-one |
| 300 | 5-phenyl-1-(pyrimidin-5-yl)pyridin-2(1H)-one |
| 301 | 5-phenyl-1-(2-fluorophenyl)pyridin-2(1H)-one |
| 302 | 5-phenyl-1-(2-chlorophenyl)pyridin-2(1H)-one |
| 303 | 5-(4-methoxyphenyl)-1-(4-chlorophenyl)pyridin-2(1H)-one |
| 304 | 5-(4-methoxyphenyl)-1-(3-trifluoromethylphenyl)pyridin-2(1H)-one |

TABLE 1-continued
| Compd. # | Structure |
|---|---|
| 305 | 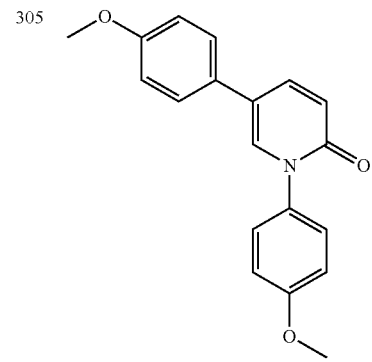 |
| 306 | 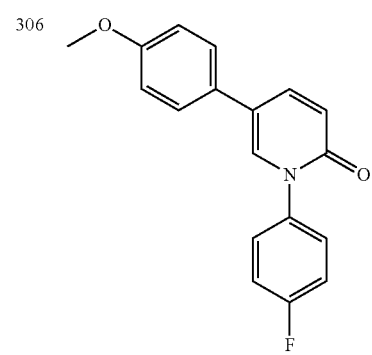 |
| 307 | 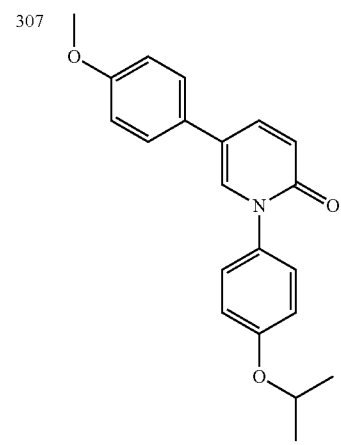 |
| 308 | 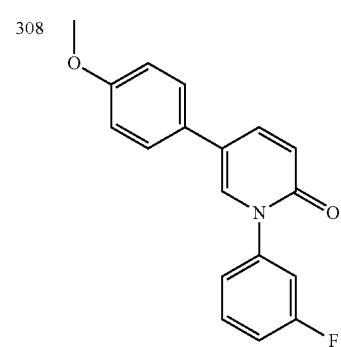 |
TABLE 1-continued
| Compd. # | Structure |
|---|---|
| 309 | 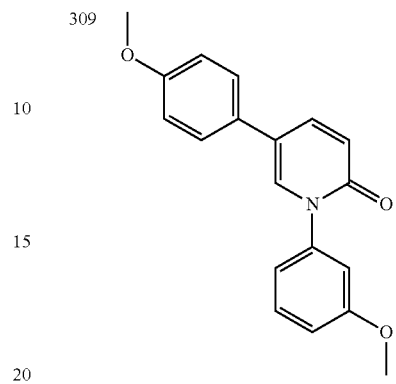 |
| 310 | 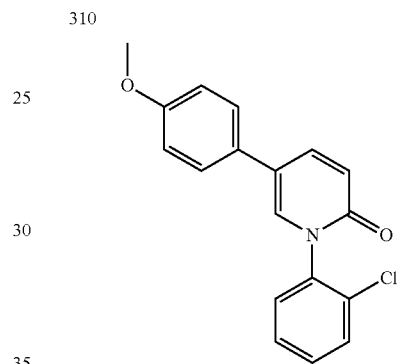 |
| 311 | 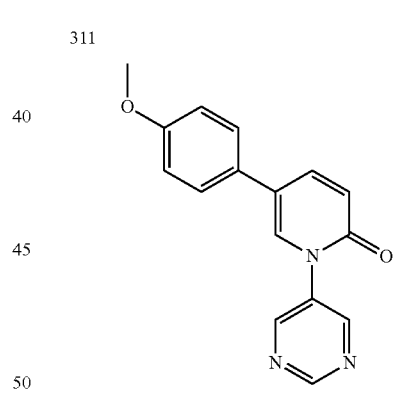 |
| 312 | 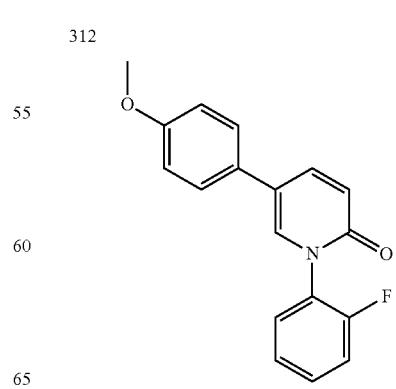 |

TABLE 1-continued
| Compd. # | Structure |
|---|---|
| 313 | 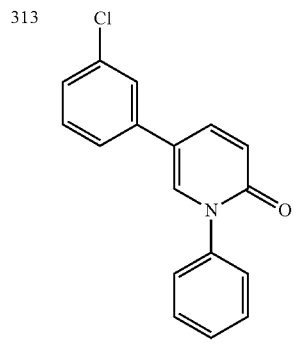 |
| 314 | 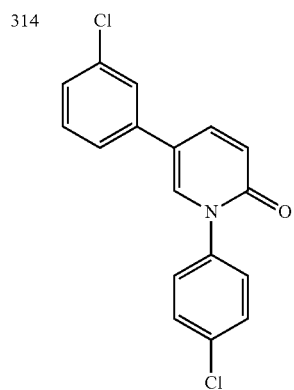 |
| 315 | 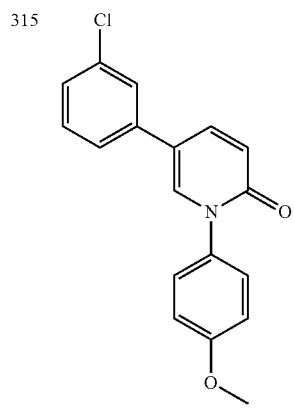 |
| 316 | 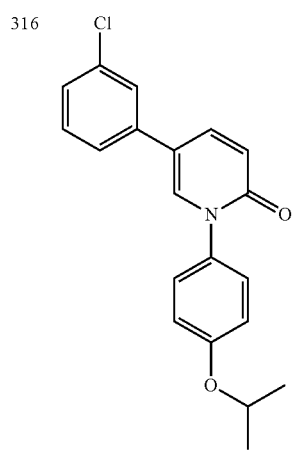 |
| 317 | 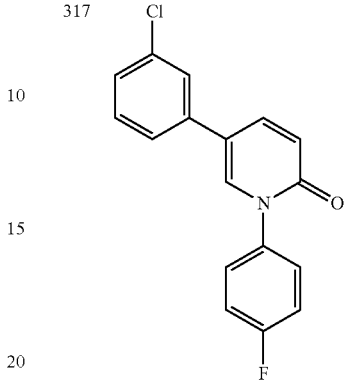 |
| 318 | 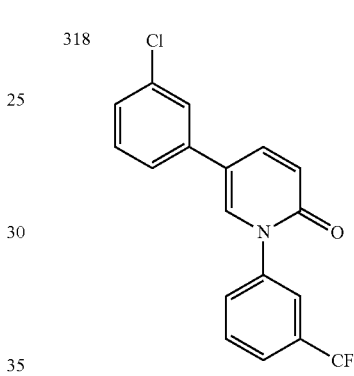 |
| 319 | 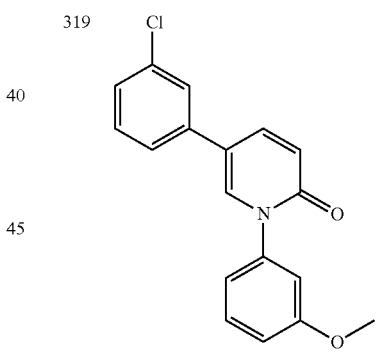 |
| 320 | 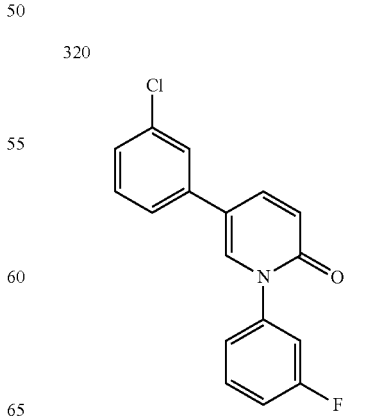 |

TABLE 1-continued
| Compd. # | Structure |
|---|---|
| 321 | 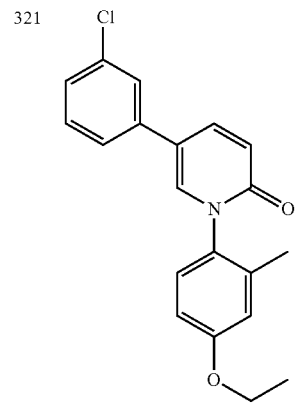 |
| 322 | 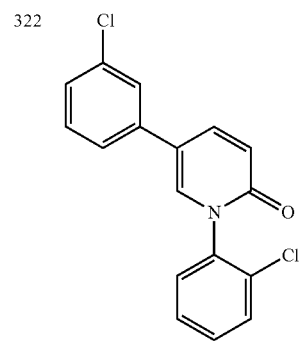 |
| 323 | 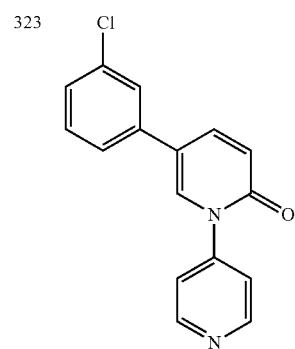 |
| 324 | 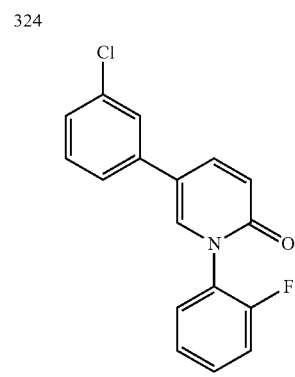 |
| 325 | 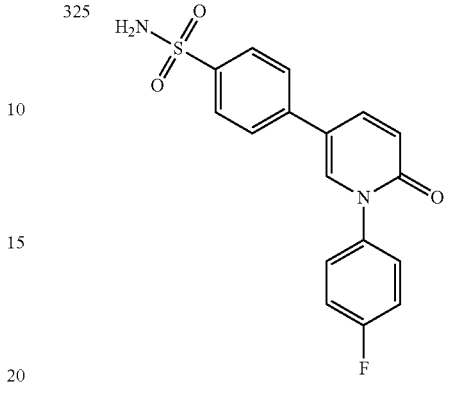 |
| 326 | 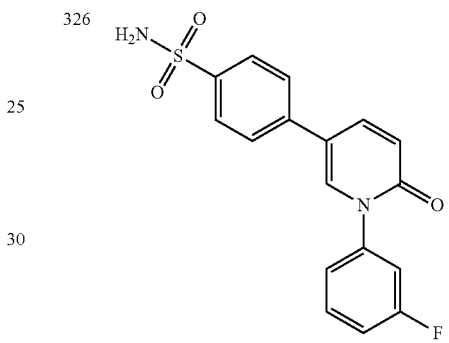 |
| 327 | 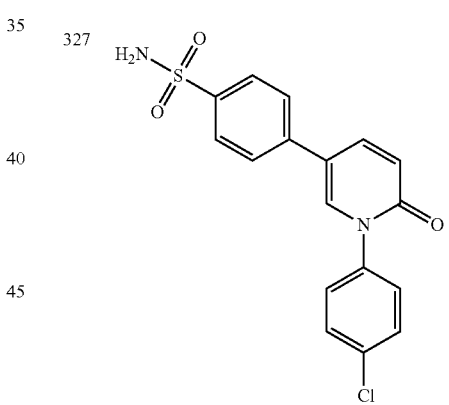 |
| 328 | 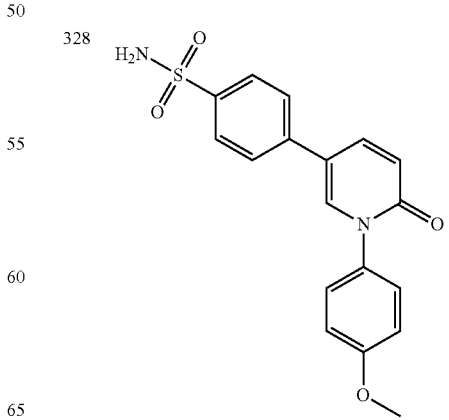 |

TABLE 1-continued
| Compd. # | Structure |
|---|---|
| 329 | 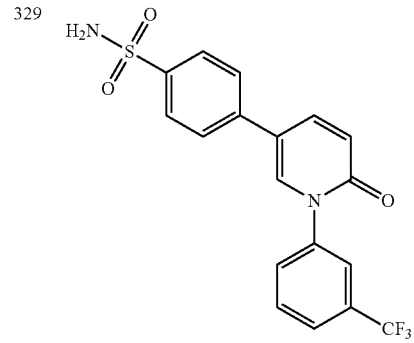 |
| 330 | 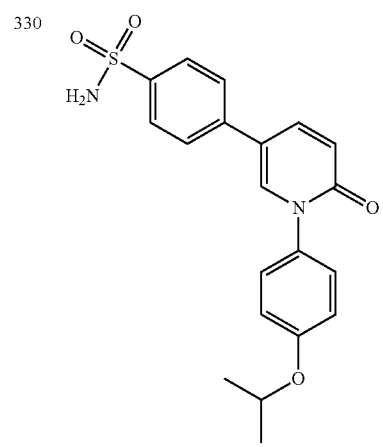 |
| 331 | 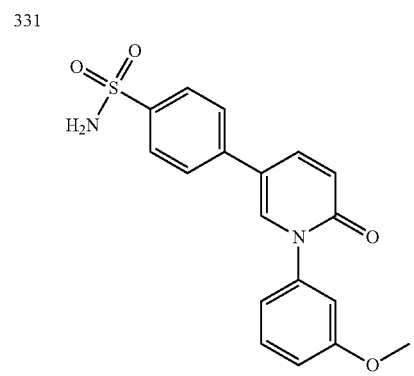 |
| 332 | 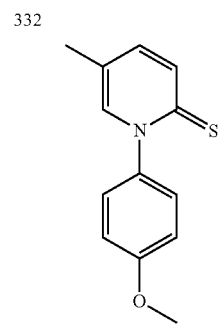 |
TABLE 1-continued
| Compd. # | Structure |
|---|---|
| 333 | 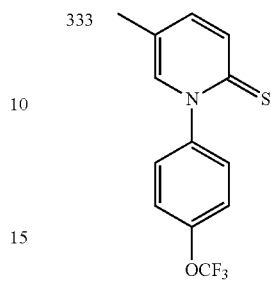 |
| 334 | 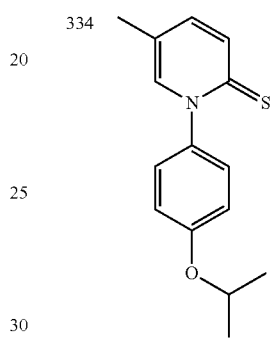 |
| 335 | 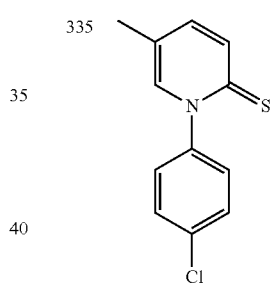 |
| 336 | 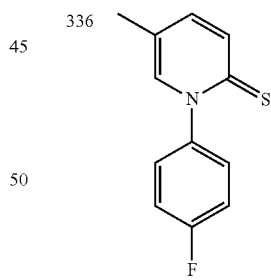 |
| 337 | 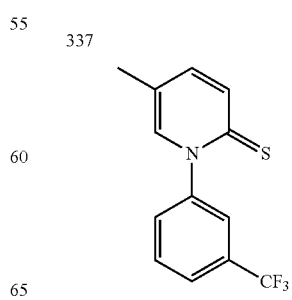 |

TABLE 1-continued
| Compd. # | Structure |
|---|---|
| 338 | 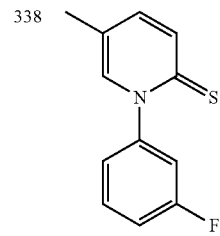 |
| 339 | 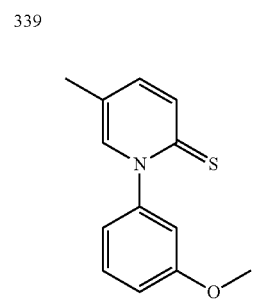 |
| 341 | 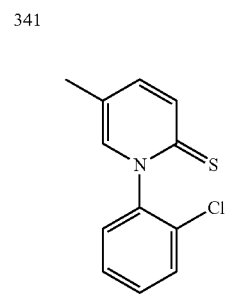 |
| 342 | 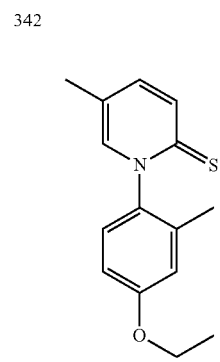 |
| 343 | 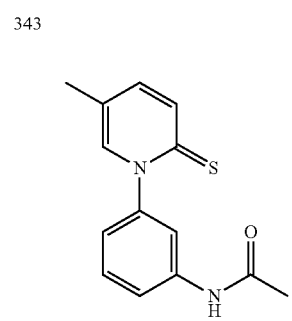 |
TABLE 1-continued
| Compd. # | Structure |
|---|---|
| 344 | 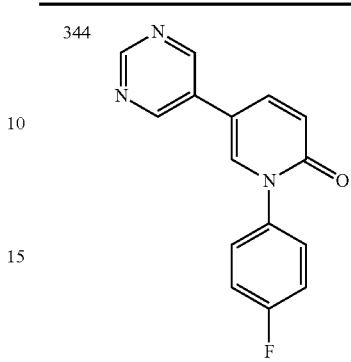 |
| 345 | 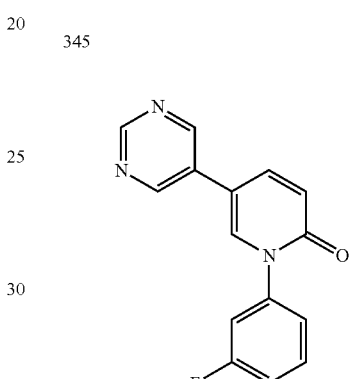 |
| 346 | 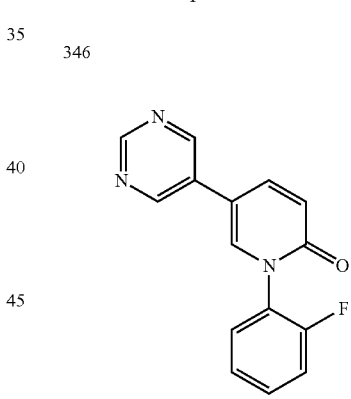 |
| 347 | 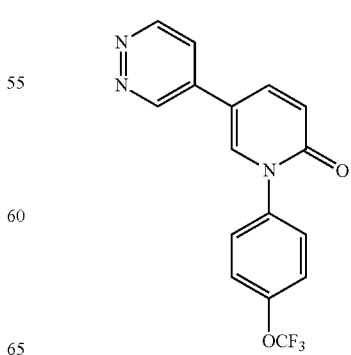 |

TABLE 1-continued
| Compd. # | Structure |
|---|---|
| 348 | 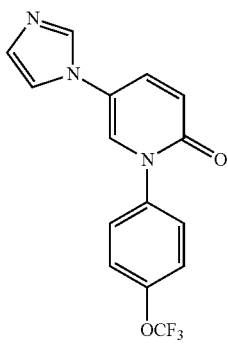 |
| 349 | 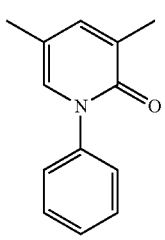 |
| 350 | 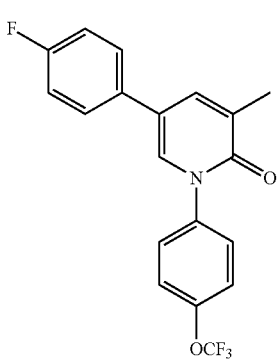 |
| 351 | 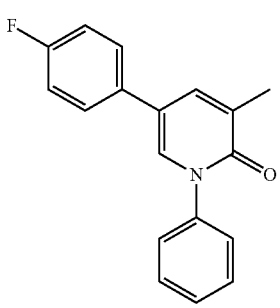 |
TABLE 1-continued
| Compd. # | Structure |
|---|---|
| 352 | 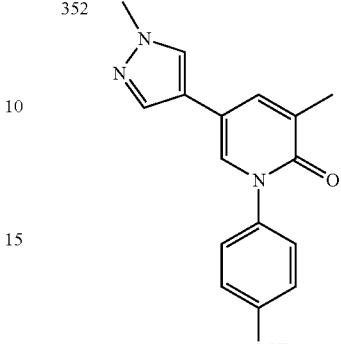 |
| 353 | 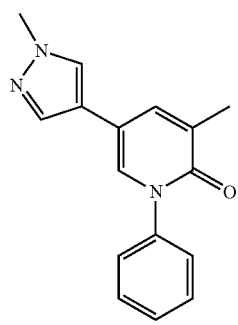 |
| 354 | 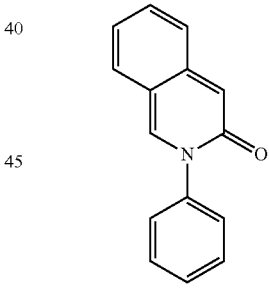 |
| 355 | 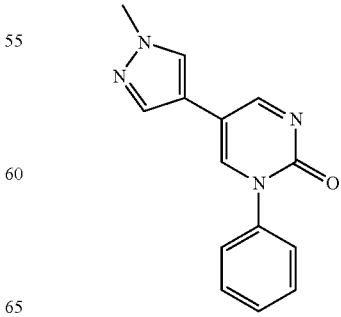 |

TABLE 1-continued
| Compd. # | Structure |
|---|---|
| 356 | 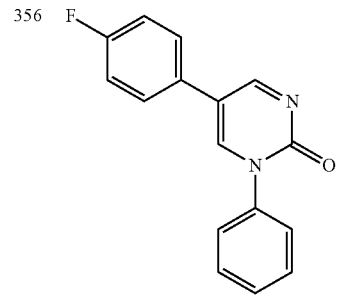 |
| 357 | 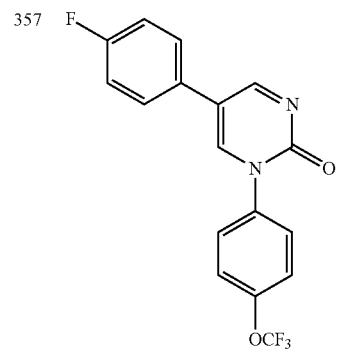 |
| 358 | 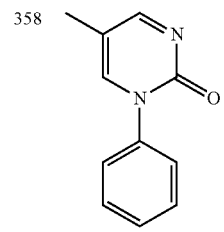 |
| 359 | 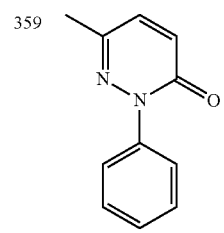 |
| 360 | 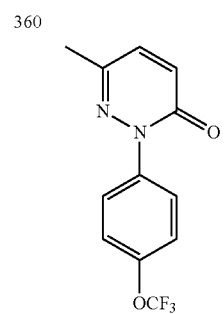 |
| 361 | 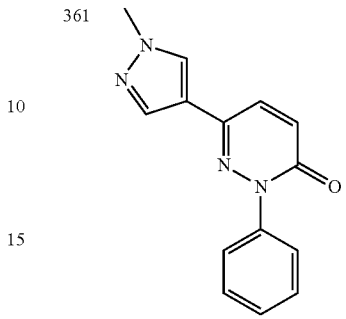 |
| 362 | 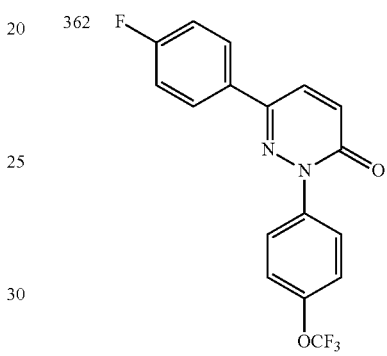 |
| 363 | 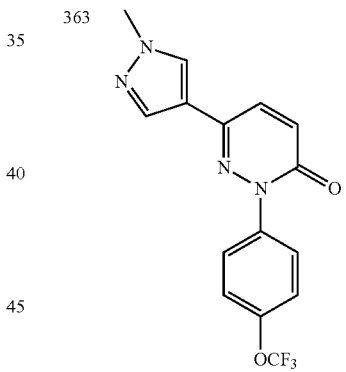 |
| 364 | 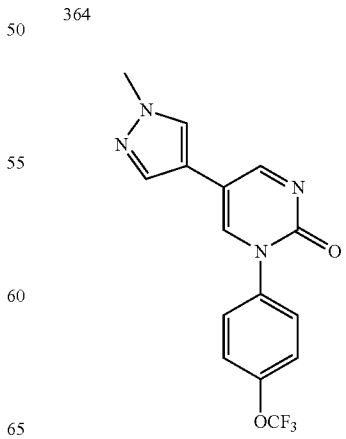 |

TABLE 1-continued

| Compd. # | Structure |
|---|---|
| 365 | 3,4-dihydro-1-phenylpyrimidin-2(1H)-one |
| 366 | 4,5-dimethyl-1-phenylpyridin-2(1H)-one |
| 367 | 4,5-dimethyl-1-(4-(trifluoromethoxy)phenyl)pyridin-2(1H)-one |
| 368 | 4-methyl-5-(trifluoromethyl)-1-(4-(trifluoromethoxy)phenyl)pyridin-2(1H)-one |
| 369 | 1-(4-isopropoxyphenyl)-5-(1H-pyrazol-4-yl)pyridin-2(1H)-one |
| 370 | 1-(4-methoxyphenyl)-5-(1H-pyrazol-4-yl)pyridin-2(1H)-one |
| 371 | 1-(4-chlorophenyl)-5-(1H-pyrazol-4-yl)pyridin-2(1H)-one |
| 372 | 1-(3-fluorophenyl)-5-(1H-pyrazol-4-yl)pyridin-2(1H)-one |
| 373 | 5-(1H-pyrazol-4-yl)-1-(3-(trifluoromethyl)phenyl)pyridin-2(1H)-one |

TABLE 1-continued
| Compd. # | Structure |
|---|---|
| 374 | 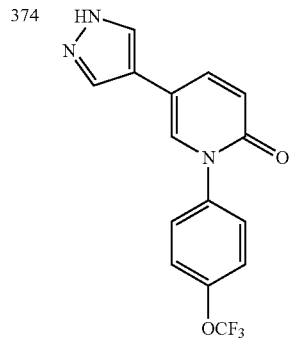 |
| 375 | 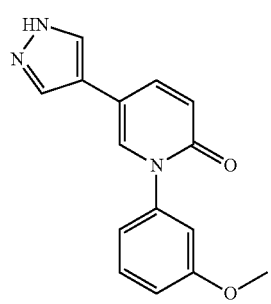 |
| 376 | 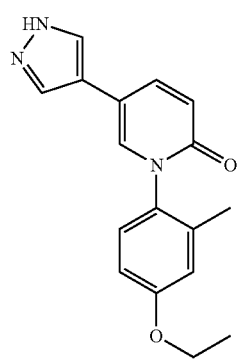 |
| 377 | 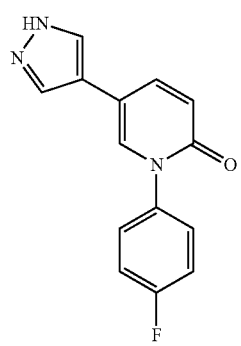 |
| 378 | 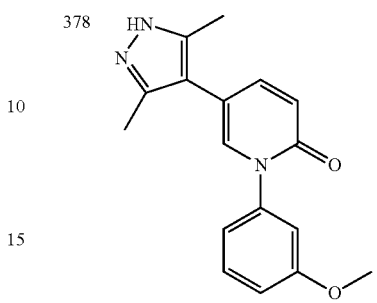 |
| 379 | 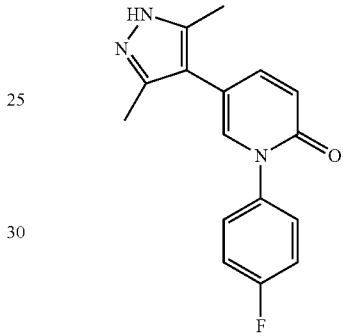 |
| 380 | 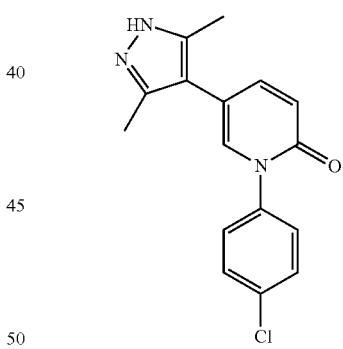 |
| 381 | 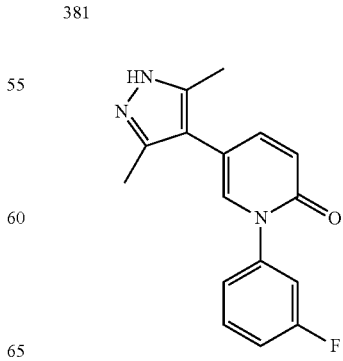 |

TABLE 1-continued

| Compd. # | Structure |
|---|---|
| 382 | (5-(3,5-dimethyl-1H-pyrazol-4-yl)-1-(4-isopropoxyphenyl)pyridin-2(1H)-one) |
| 383 | (5-(3,5-dimethyl-1H-pyrazol-4-yl)-1-(4-(trifluoromethoxy)phenyl)pyridin-2(1H)-one) |
| 384 | (5-(3,5-dimethyl-1H-pyrazol-4-yl)-1-(3-(trifluoromethyl)phenyl)pyridin-2(1H)-one) |
| 385 | (5-(1-benzyl-1H-pyrazol-4-yl)-1-phenylpyridin-2(1H)-one) |
| 386 | (5-(3,5-dimethyl-1H-pyrazol-4-yl)-1-(4-methoxyphenyl)pyridin-2(1H)-one) |
| 387 | (5-(3,5-dimethyl-1H-pyrazol-4-yl)-1-(4-ethoxy-2-methylphenyl)pyridin-2(1H)-one) |
| 388 | (5-(1-isopropyl-1H-pyrazol-4-yl)-1-phenylpyridin-2(1H)-one) |
| 389 | (1-phenyl-5-(1-phenyl-1H-pyrazol-4-yl)pyridin-2(1H)-one) |

TABLE 1-continued
| Compd. # | Structure |
|---|---|
| 390 | 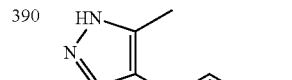 |
| 391 | 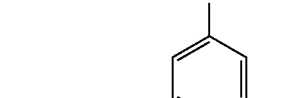 |
| 392 | 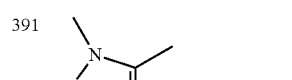 |
| 393 | 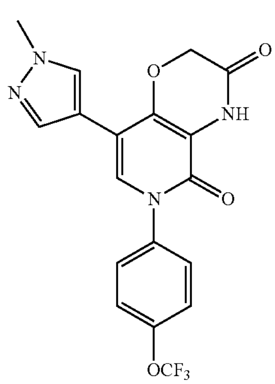 |
| 394 | 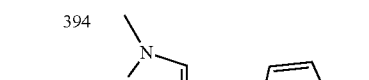 |
| 395 | 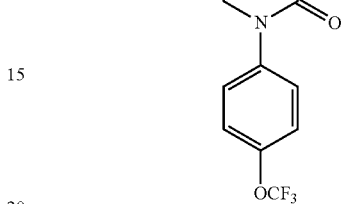 |
| 396 | 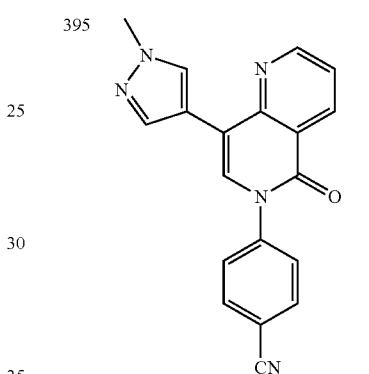 |
| 397 | 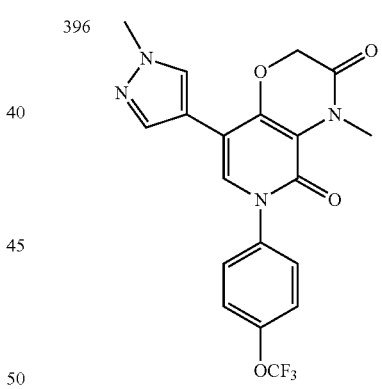 |

TABLE 1-continued
| Compd. # | Structure |
|---|---|
| 398 | 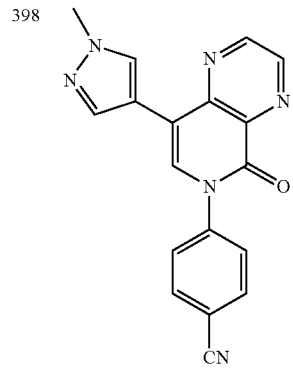 |
| 399 | 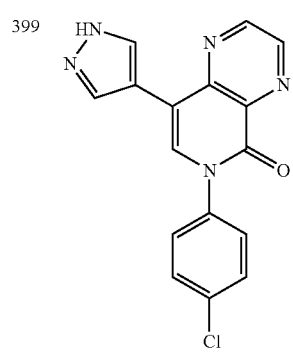 |
| 400 | 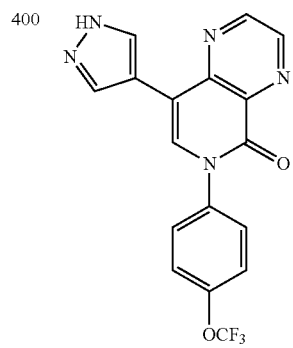 |
| 401 | 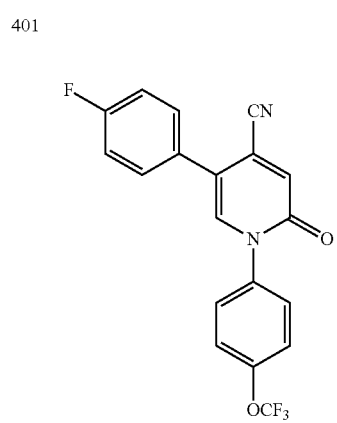 |
| 402 | 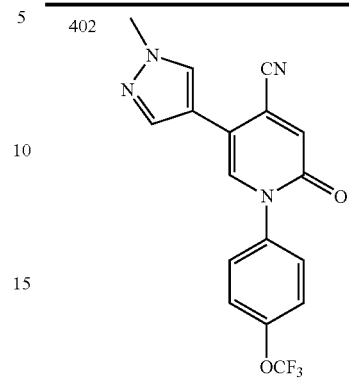 |
| 403 | 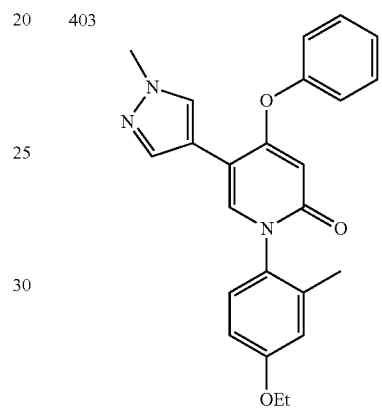 |
| 404 | 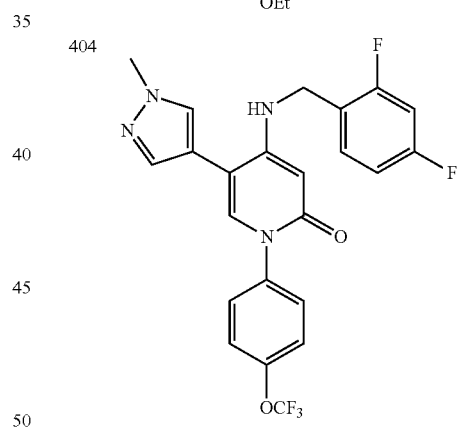 |
| 405 | 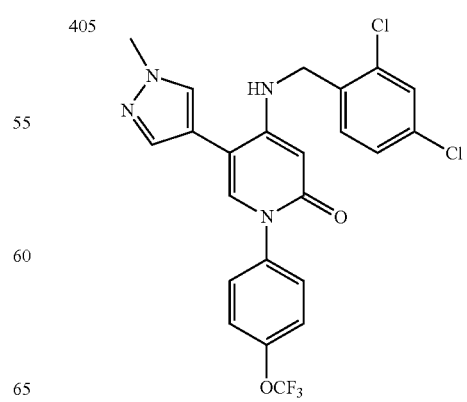 |

TABLE 1-continued
| Compd. # | Structure |
|---|---|
| 406 | 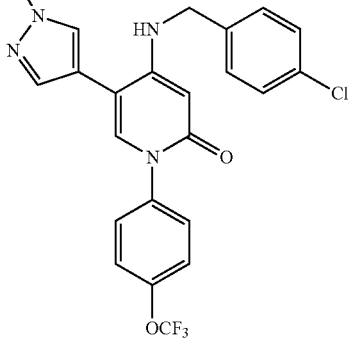 |
| 407 | 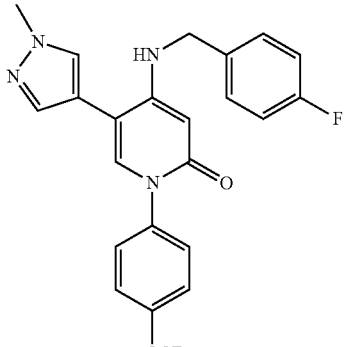 |
| 408 | 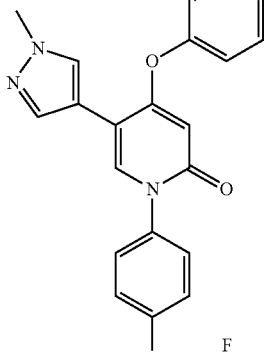 |
| 409 | 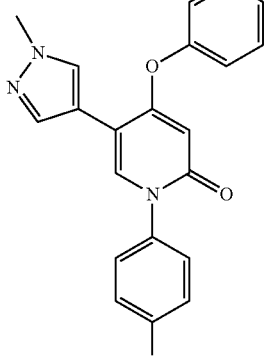 |
| 410 | 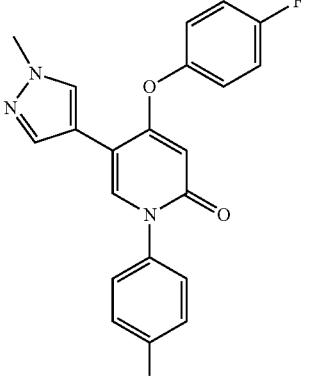 |
| 411 | 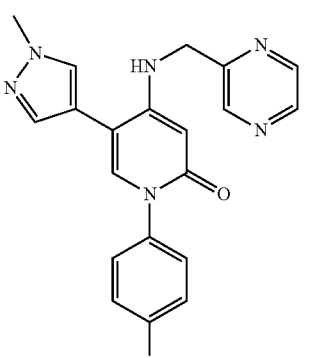 |
| 412 | 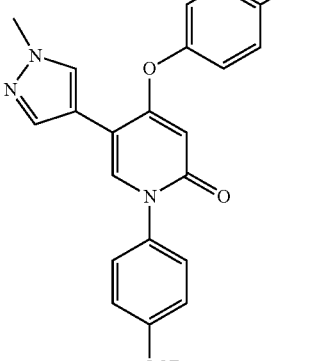 |
| 413 | 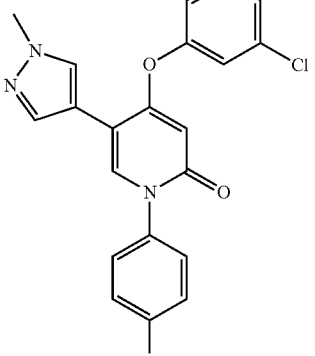 |

TABLE 1-continued
| Compd. # | Structure |
|---|---|
| 414 | 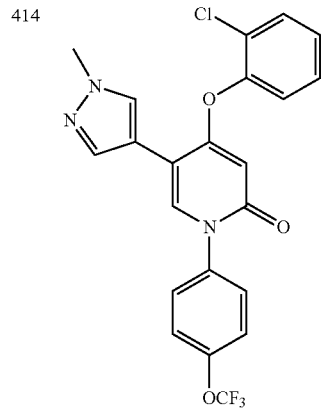 |
| 415 | 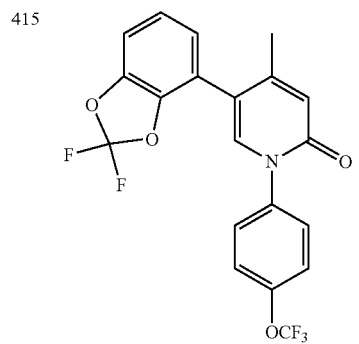 |
| 416 | 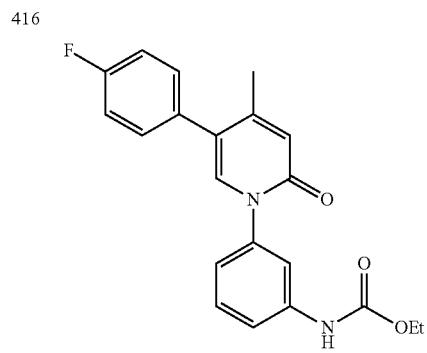 |
| 417 | 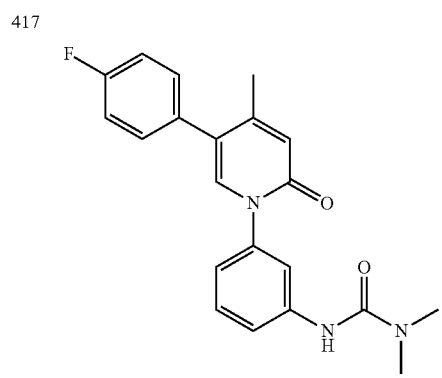 |
| 418 | 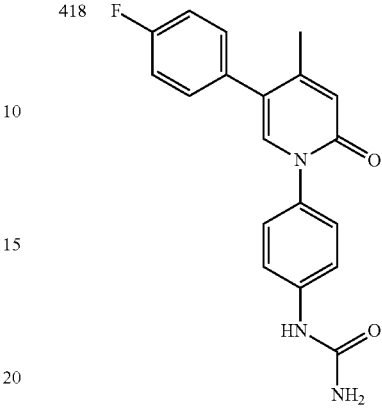 |
| 419 | 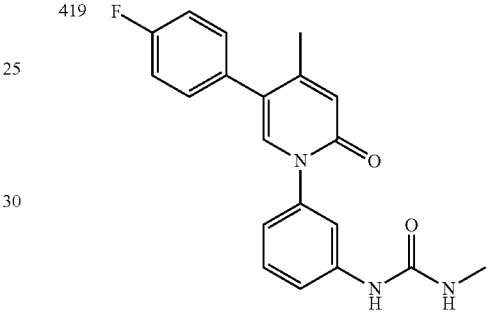 |
| 420 | 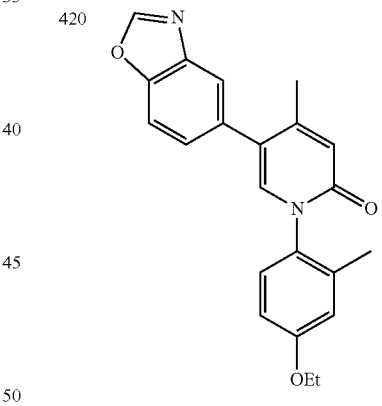 |
| 421 | 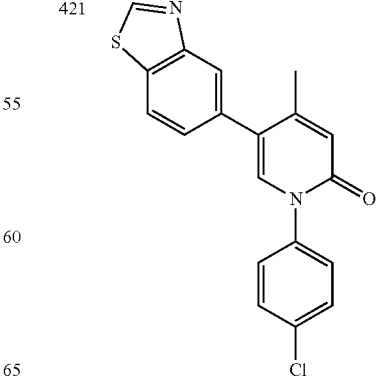 |

TABLE 1-continued
| Compd. # | Structure |
|---|---|
| 422 | 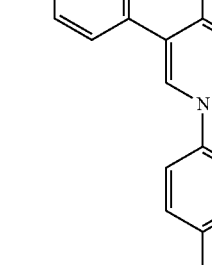 |
| 423 | 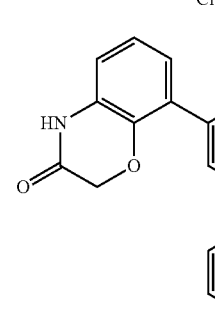 |
| 424 | 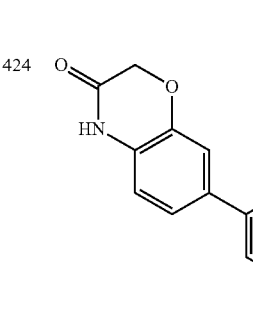 |
| 425 | 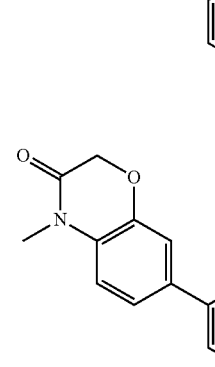 |“
TABLE 1-continued
| Compd. # | Structure |
|---|---|
| 426 | 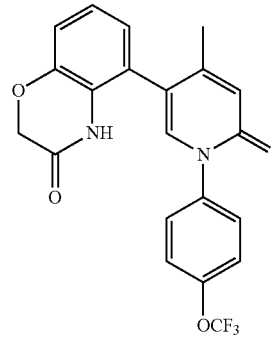 |
| 427 | 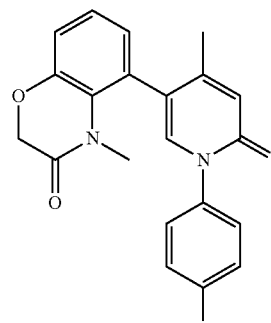 |
| 428 | 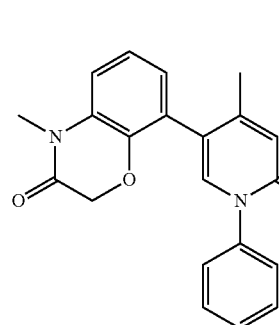 |
| 429 | 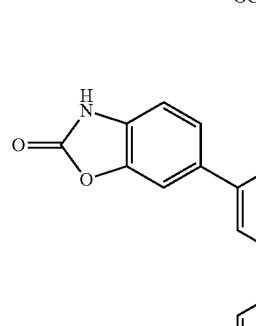 |

TABLE 1-continued
| Compd. # | Structure |
|---|---|
| 430 | 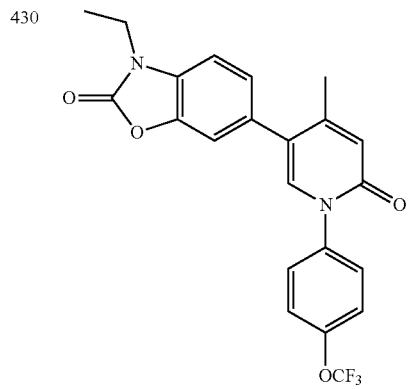 |
| 431 | 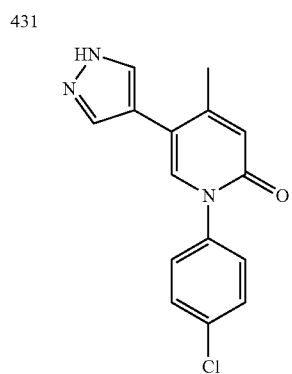 |
| 432 | 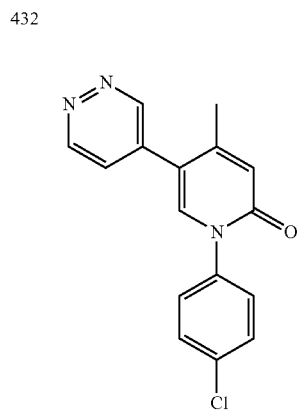 |
| 433 | 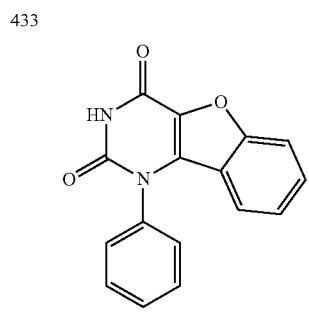 |
TABLE 1-continued
| Compd. # | Structure |
|---|---|
| 434 | 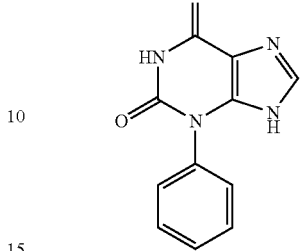 |
| 438 | 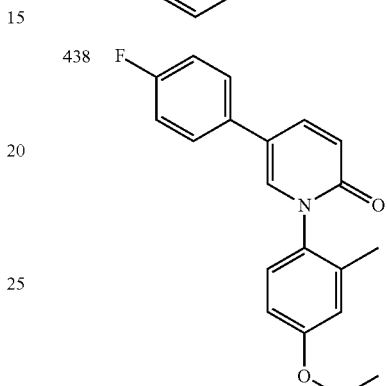 |
| 439 | 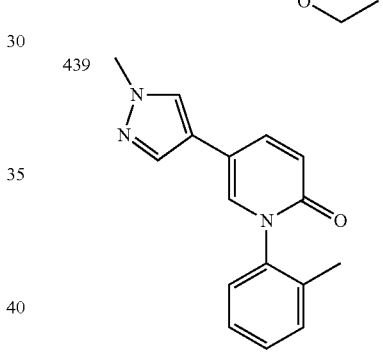 |
| 440 | 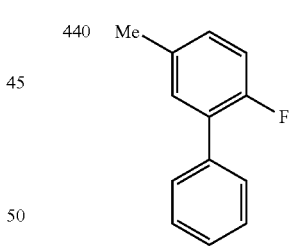 |
| 442 | 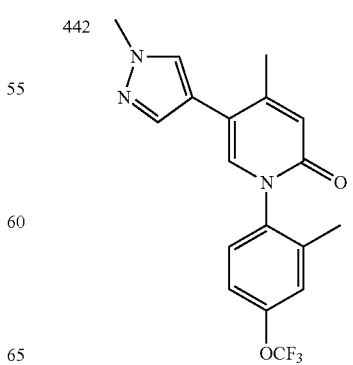 |

TABLE 1-continued

| Compd. # | Structure |
|---|---|
| 446 | 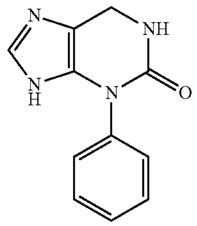 |
| 447 | 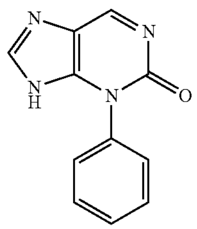 |
| 448 | 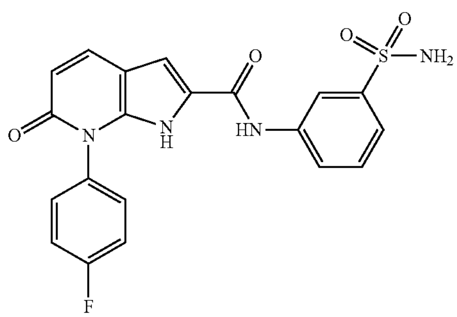 |
| 449 | 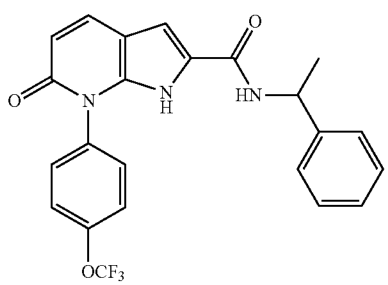 |
| 450 | 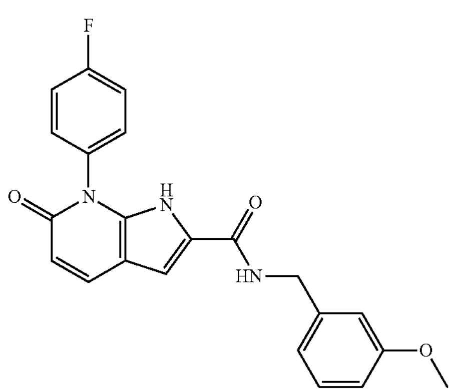 |
| 451 | |
| 452 | |
| 453 | |
| 454 | |

TABLE 1-continued
| Compd. # | Structure |
|---|---|
| 455 | 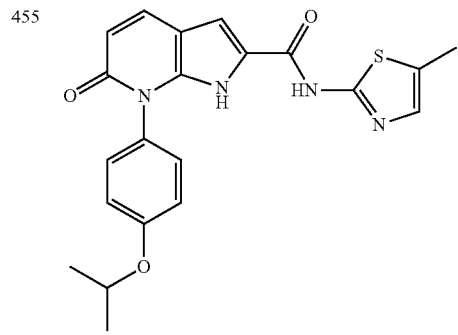 |
| 456 | 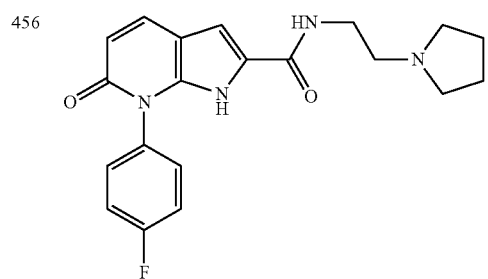 |
| 457 | 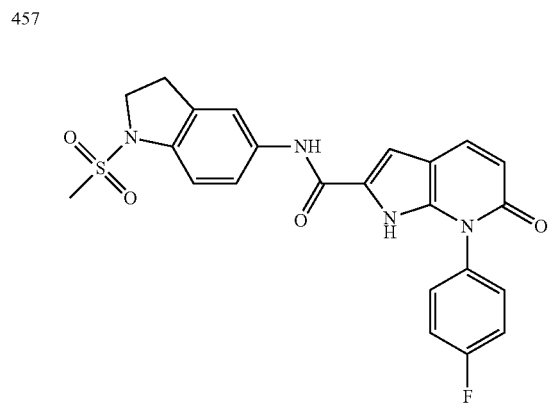 |
| 458 | 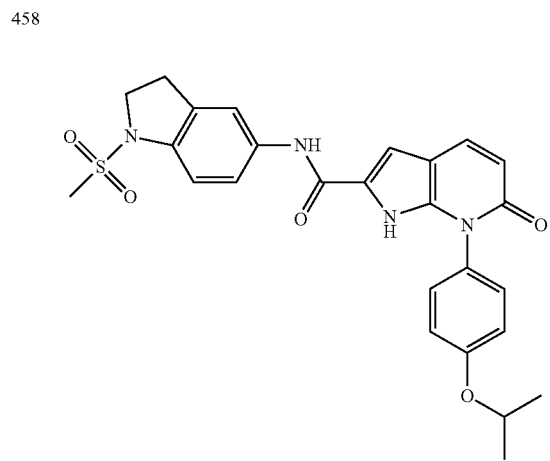 |
TABLE 1-continued
| Compd. # | Structure |
|---|---|
| 459 | 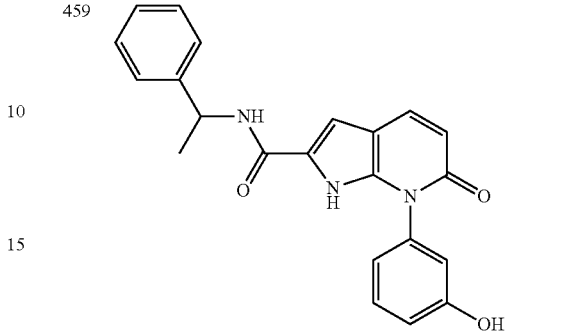 |
| 460 | 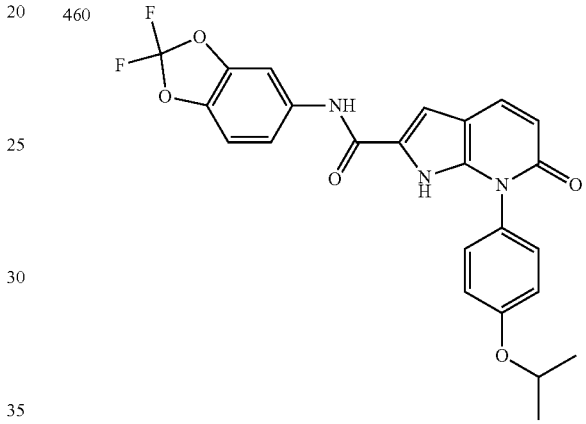 |
| 461 | 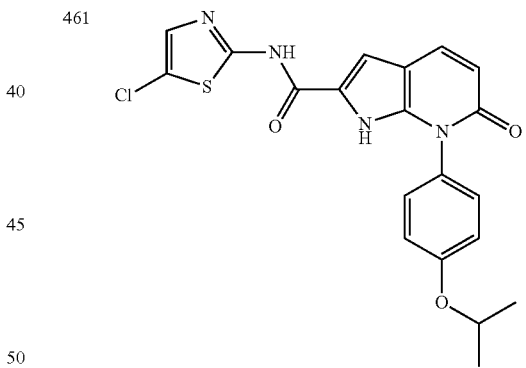 |
| 462 | 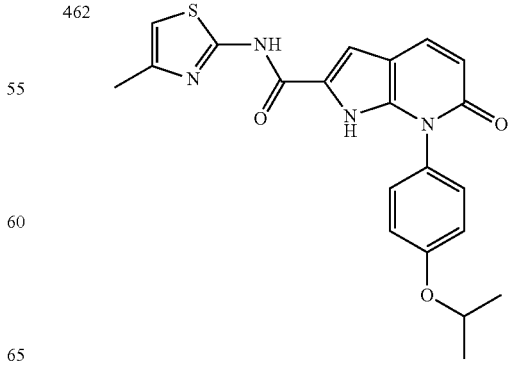 |

TABLE 1-continued

| Compd. # | Structure |
|---|---|
| 463 | (structure) |
| 464 | (structure) |
| 465 | (structure) |
| 466 | (structure) |
| 467 | (structure) |
| 468 | (structure) |
| 469 | (structure) |
| 470 | (structure) |
| 471 | (structure) |
| 472 | (structure) |

TABLE 1-continued
| Compd. # | Structure |
|---|---|
| 473 | 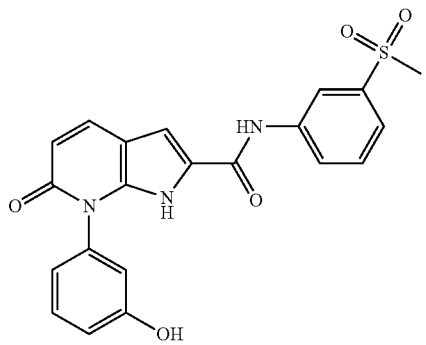 |
| 474 | 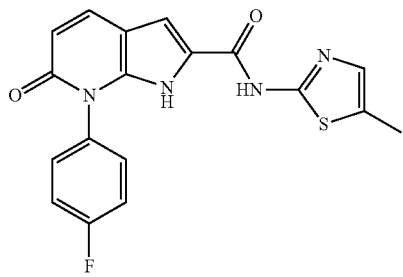 |
| 475 | 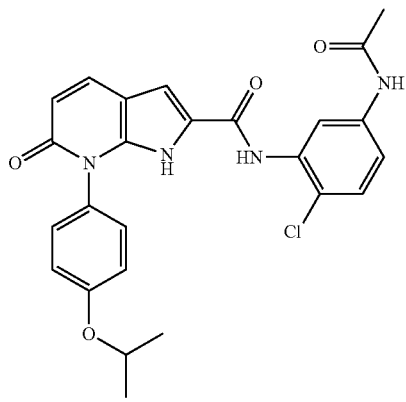 |
| 476 | 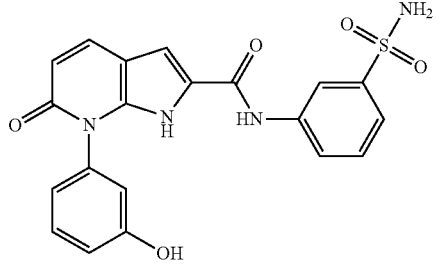 |
| 477 | 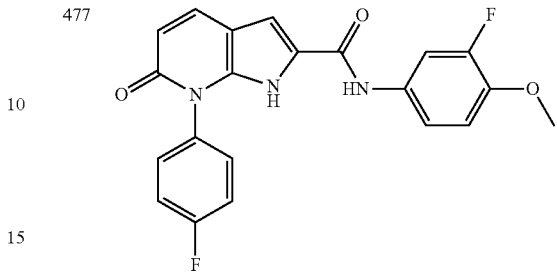 |
| 478 | 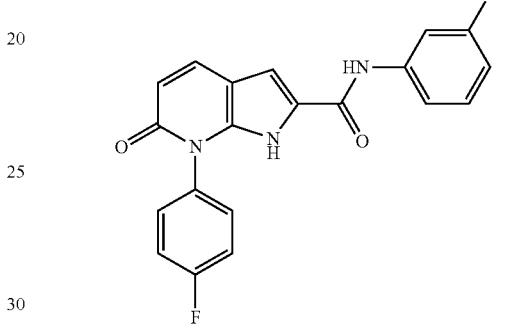 |
| 479 | 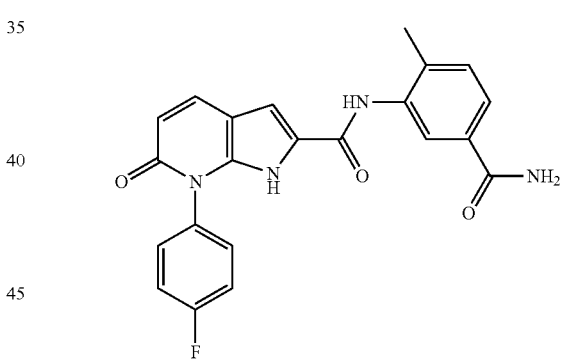 |
| 480 | 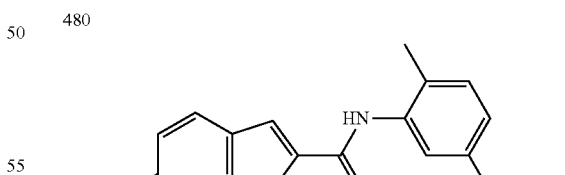 |

TABLE 1-continued
| Compd. # | Structure |
|---|---|
| 481 | 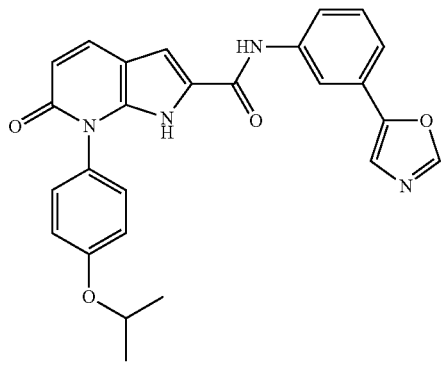 |
| 482 | 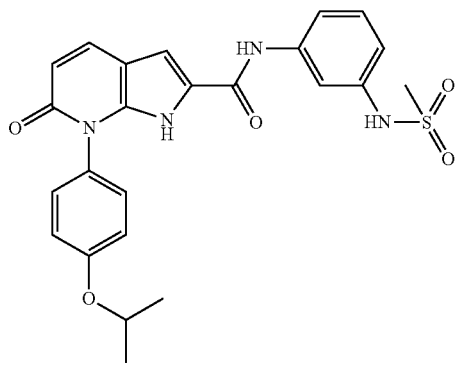 |
| 483 | 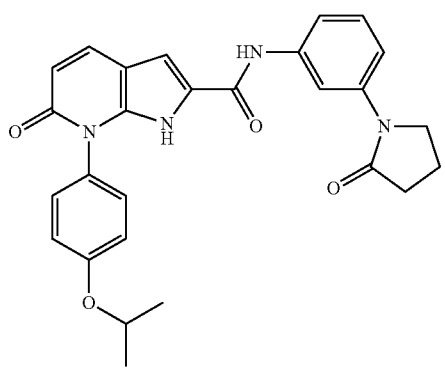 |
| 484 | 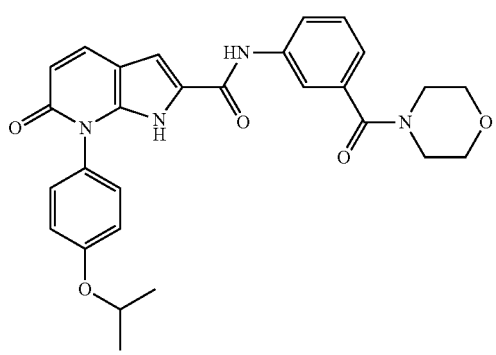 |
TABLE 1-continued
| Compd. # | Structure |
|---|---|
| 485 | 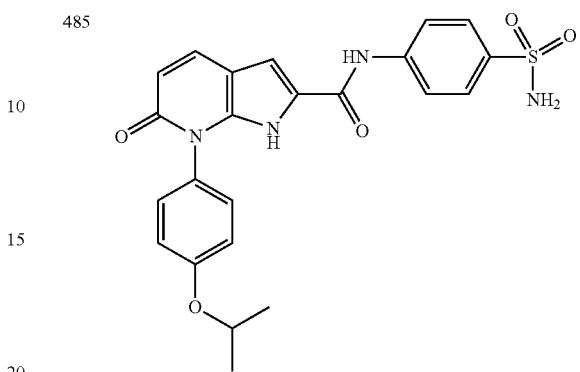 |
| 486 | 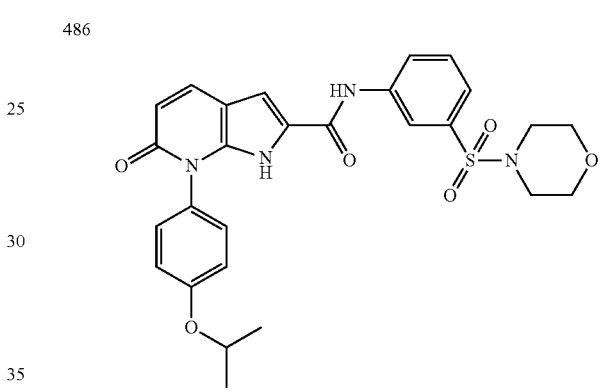 |
| 487 | 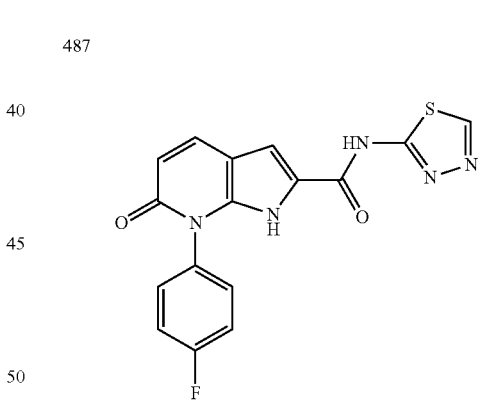 |
| 488 | 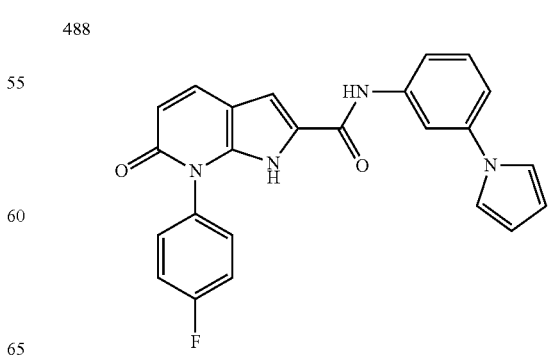 |

TABLE 1-continued

| Compd. # | Structure |
|---|---|
| 489 | (structure) |
| 490 | (structure) |
| 491 | (structure) |
| 492 | (structure) |
| 493 | (structure) |
| 494 | (structure) |
| 495 | (structure) |
| 496 | (structure) |

TABLE 1-continued

| Compd. # | Structure |
|---|---|
| 497 | 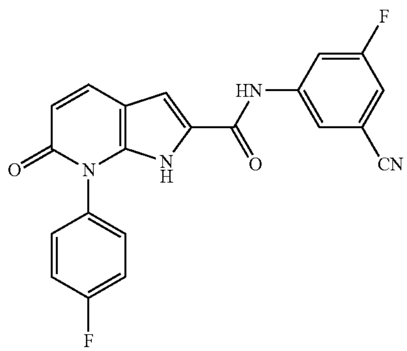 |
| 498 | 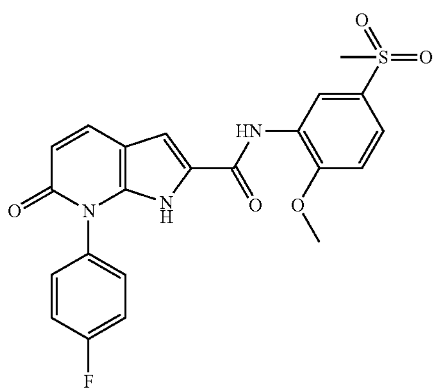 |
| 499 | 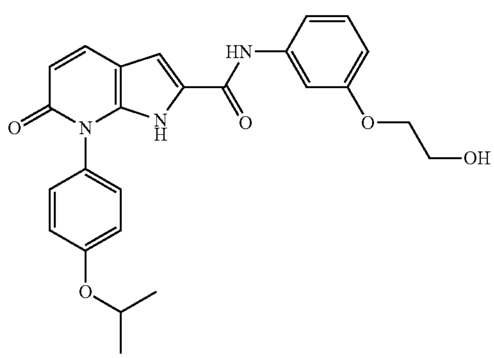 |
| 500 | 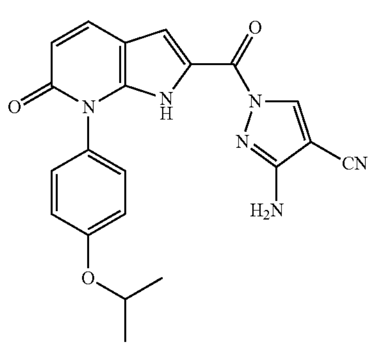 |
| 501 | |
| 502 | |
| 503 | |
| 504 | |

TABLE 1-continued

| Compd. # | Structure |
|---|---|
| 505 | (7-oxo-4-(4-isopropoxyphenyl)-pyrrolo[2,3-b]pyridine-2-carboxylic acid 3-methoxybenzyl ester) |
| 506 | (N-(1-methyl-1H-benzimidazol-5-yl)-7-(4-fluorophenyl)-6-oxo-6,7-dihydro-1H-pyrrolo[2,3-b]pyridine-2-carboxamide) |
| 507 | (7-(4-fluorophenyl)-6-oxo-N-(3-amino-5-methylthio-1,2,4-triazol-1-yl)-6,7-dihydro-1H-pyrrolo[2,3-b]pyridine-2-carboxamide) |
| 508 | (N-(3-(1-hydroxyethyl)phenyl)-7-(4-fluorophenyl)-6-oxo-6,7-dihydro-1H-pyrrolo[2,3-b]pyridine-2-carboxamide) |
| 509 | (7-(4-fluorophenyl)-6-oxo-(3-amino-1,2,4-triazol-1-yl)carbonyl-6,7-dihydro-1H-pyrrolo[2,3-b]pyridine) |
| 510 | (ethyl 6-oxo-6,7-dihydro-1H-pyrrolo[2,3-b]pyridine-2-carboxylate) |
| 511 | (N-(1-methyl-1H-benzimidazol-6-yl)-7-(4-fluorophenyl)-6-oxo-6,7-dihydro-1H-pyrrolo[2,3-b]pyridine-2-carboxamide) |
| 512 | (3-amino-6-(4-chlorophenyl)-cyclohexa-2,4-dienone) |
| 513 | (1-phenylazetidin-2-one) |
| 514 | (1-phenylindoline-2,3-dione) |
| 515 | (1-phenylazepan-2-one) |

TABLE 1-continued
| Compd. # | Structure |
|---|---|
| 516 | 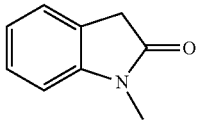 |
| 517 | 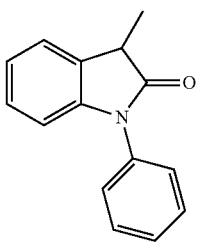 |
| 518 | 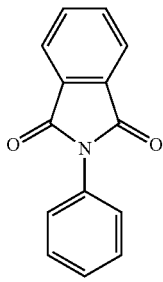 |
| 519 | 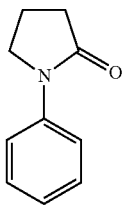 |
| 520 | 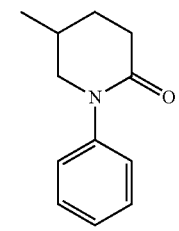<br>(racemic form of 83/84) |
| 521 | 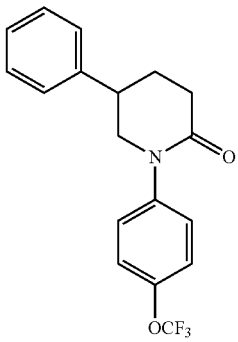 |
| 522 | 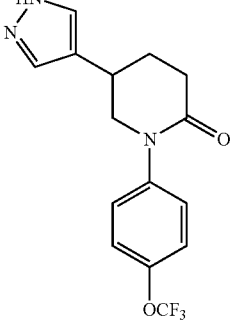 |
| 523 | 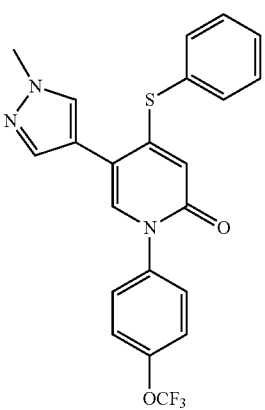 |
| 524 | 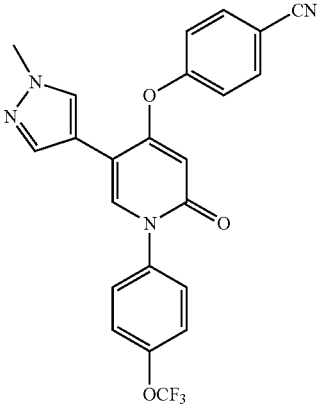 |
| 525 | 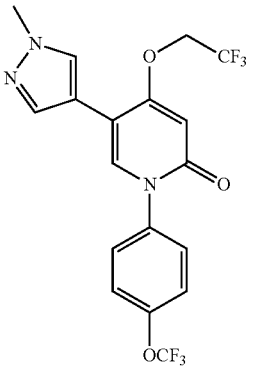 |

TABLE 1-continued
| Compd. # | Structure |
|---|---|
| 526 | 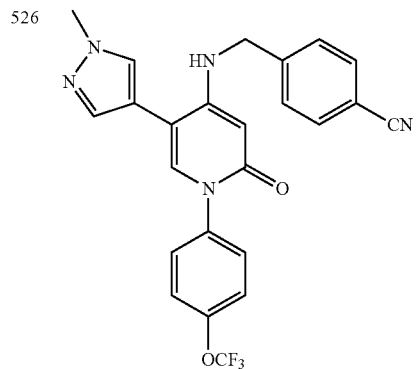 |
| 527 | 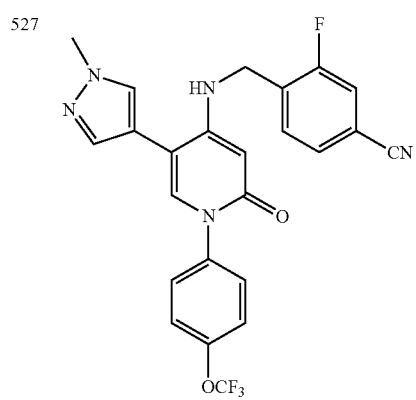 |
| 528 | 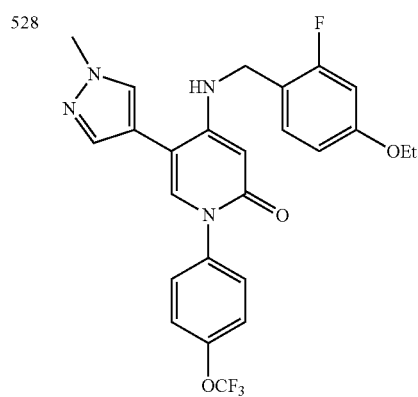 |
| 529 | 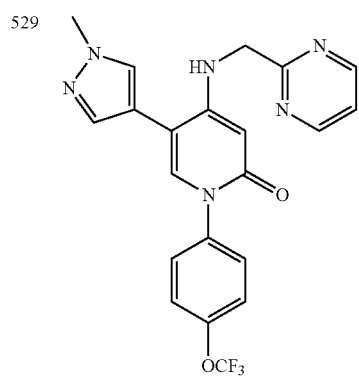 |
| 530 | 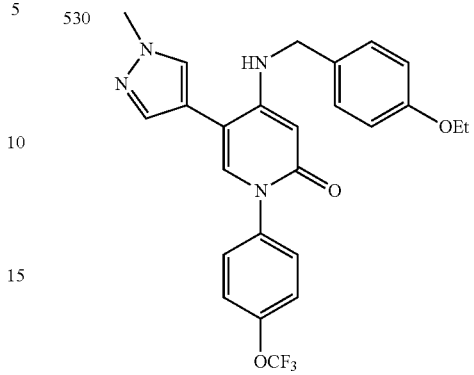 |
| 531 | 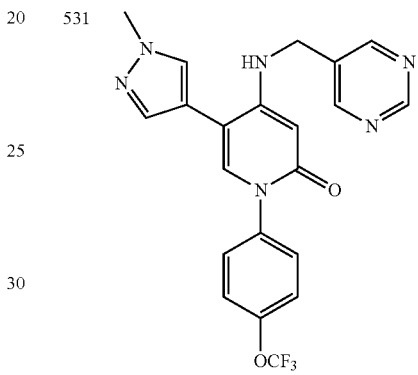 |
| 532 | 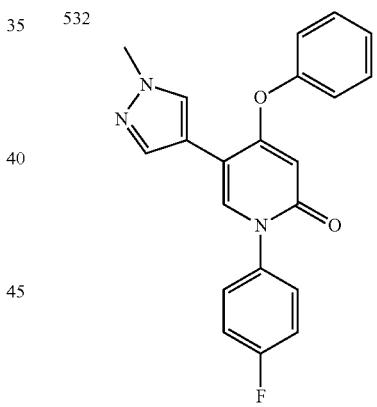 |
| 533 | 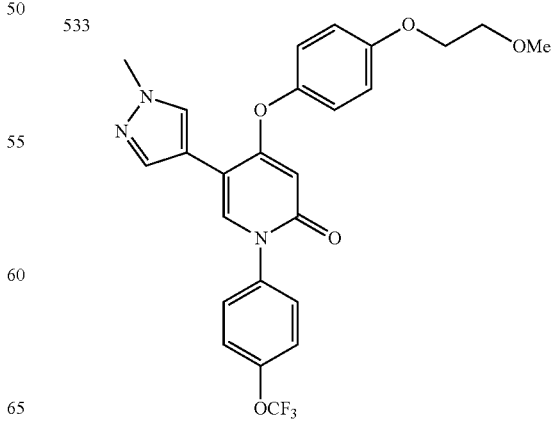 |

TABLE 1-continued
| Compd. # | Structure |
|---|---|
| 534 | 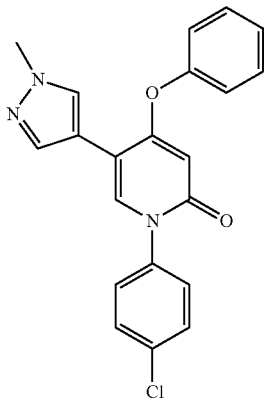 |
| 535 | 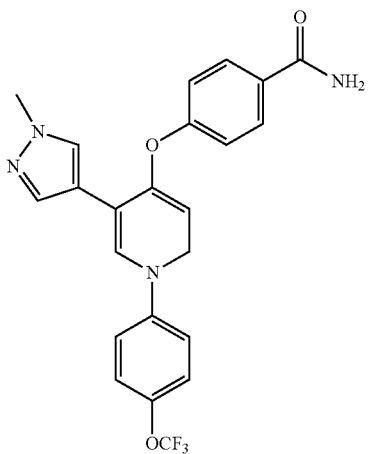 |
| 536 | 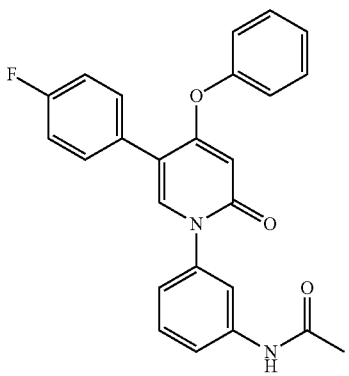 |
| 537 | 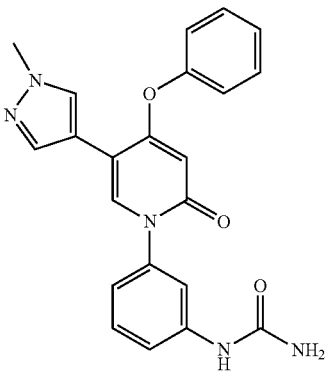 |
| 538 | 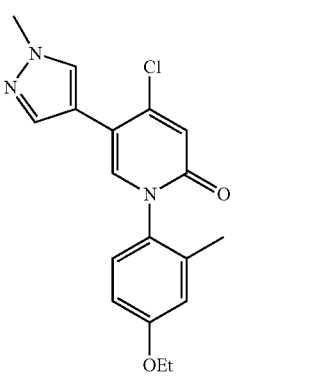 |
| 539 | 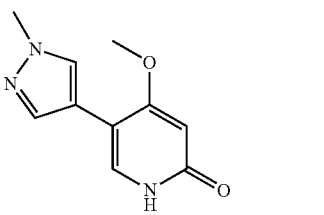 |
| 540 | 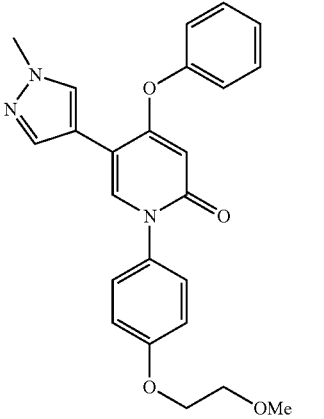 |

TABLE 1-continued

| Compd. # | Structure |
|---|---|
| 541 | [structure] |
| 542 | [structure] |
| 543 | [structure] |
| 544 | [structure] |
| 545 | [structure] |
| 546 | [structure] |
| 547 | [structure] |
| 548 | [structure] |
| 549 | [structure] |

TABLE 1-continued
| Compd. # | Structure |
|---|---|
| 550 | 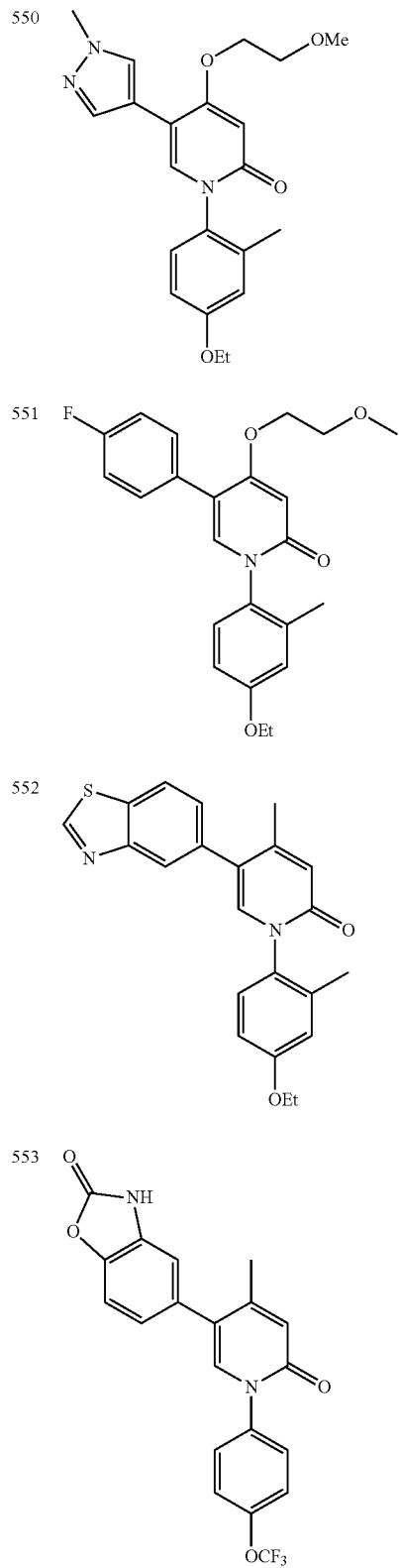 |
| 551 | 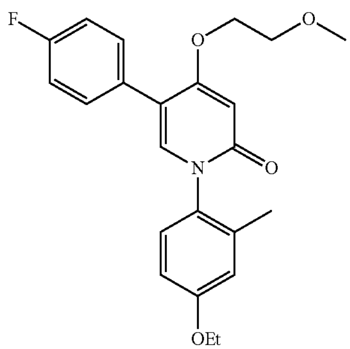 |
| 552 | 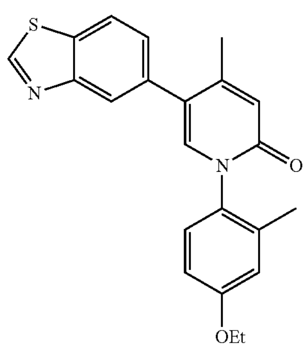 |
| 553 | 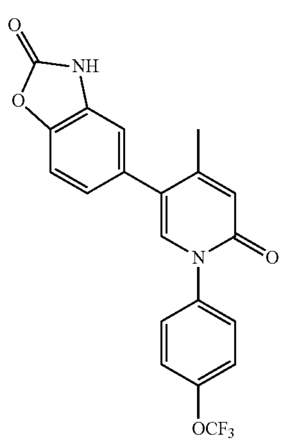 |
TABLE 1-continued
| Compd. # | Structure |
|---|---|
| 554 | 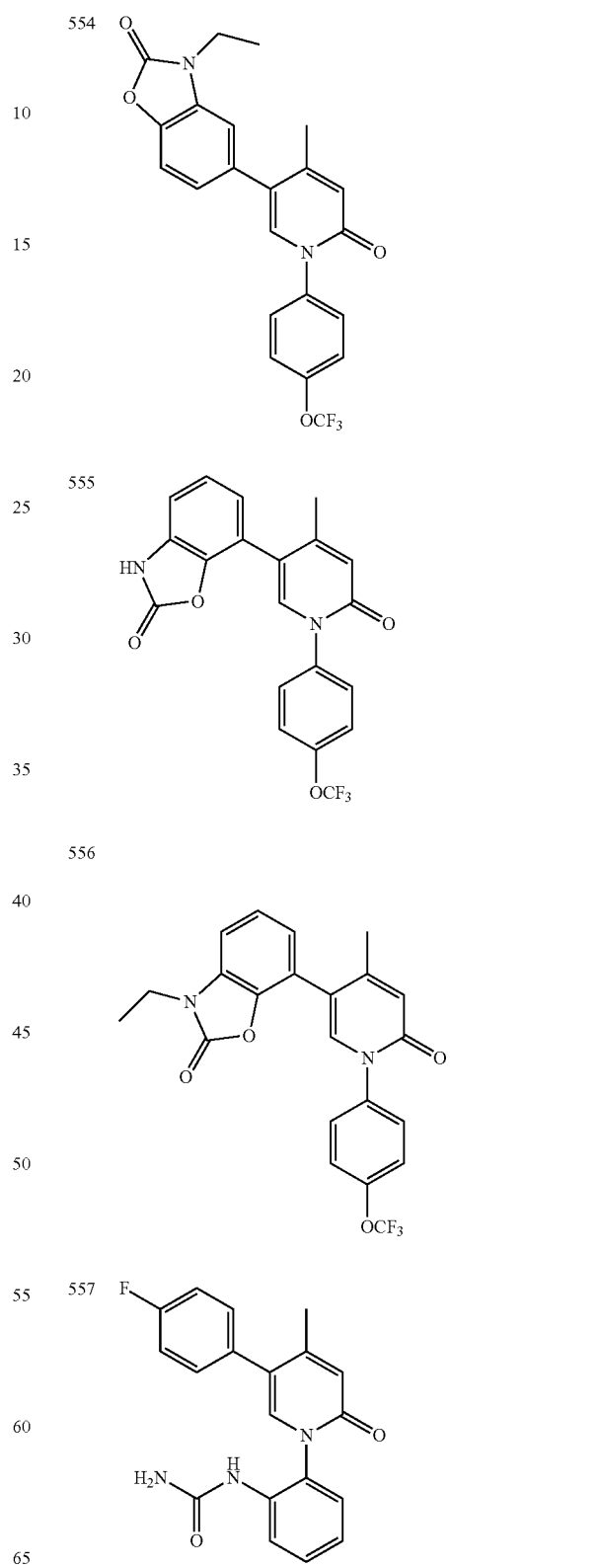 |
| 555 | |
| 556 | |
| 557 | |

TABLE 1-continued
| Compd. # | Structure |
|---|---|
| 558 | 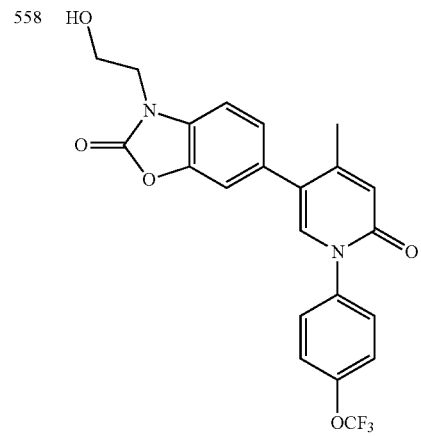 |
| 559 | 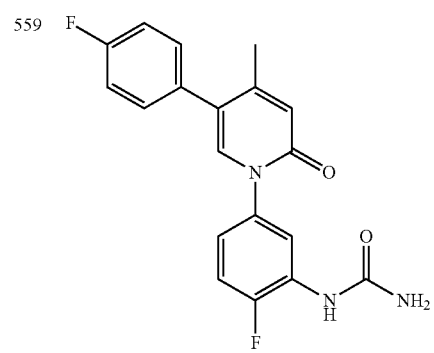 |
| 560 | 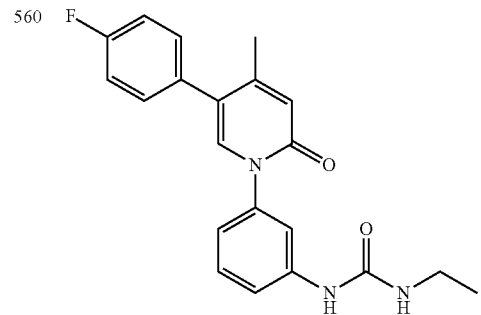 |
| 561 | 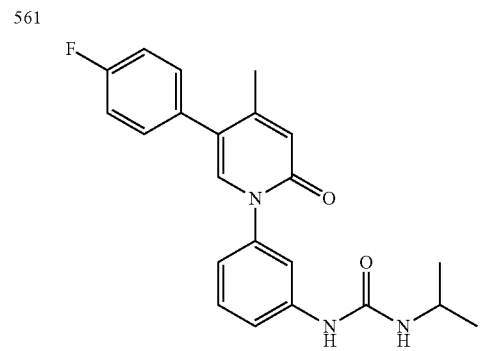 |
| 562 | 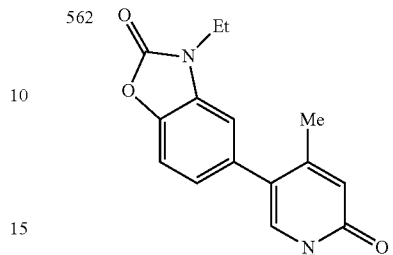 |
| 563 | 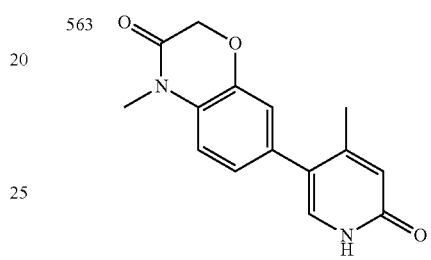 |
| 564 | 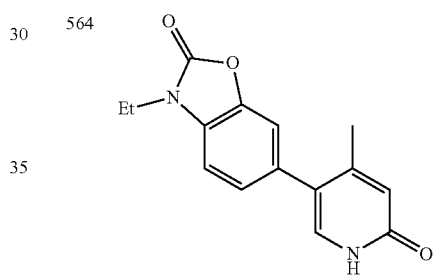 |
| 565 | 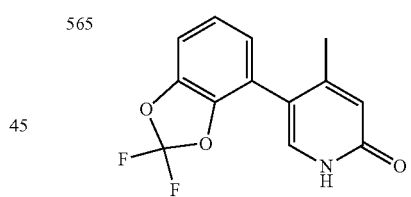 |
| 566 | 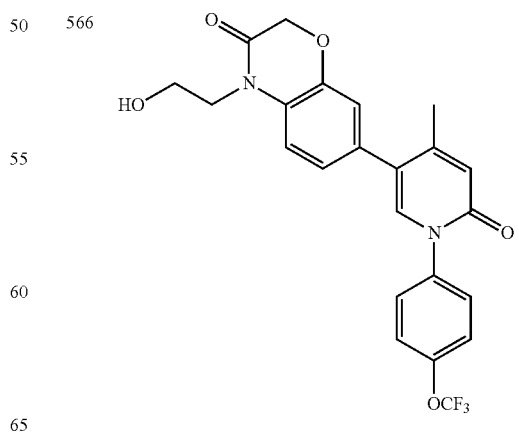 |

TABLE 1-continued

| Compd. # | Structure |
|---|---|
| 567 | 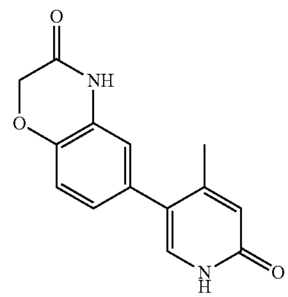 |
| 568 | 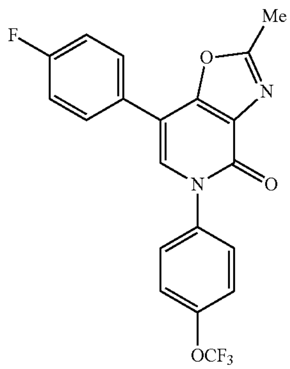 |
| 569 | 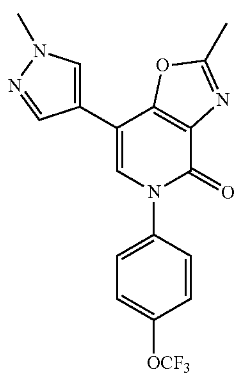 |
| 570 | 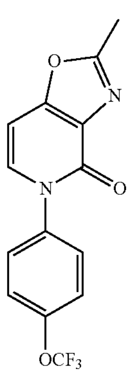 |
| 571 | |
| 572 | |
| 573 | |
| 574 | |

TABLE 1-continued
| Compd. # | Structure |
|---|---|
| 575 | 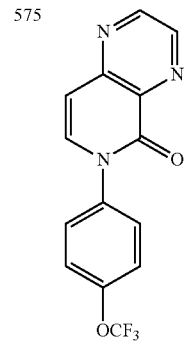 |
| 576 | 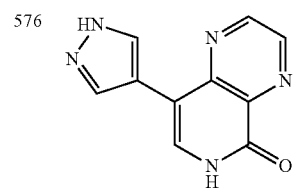 |
| 577 | 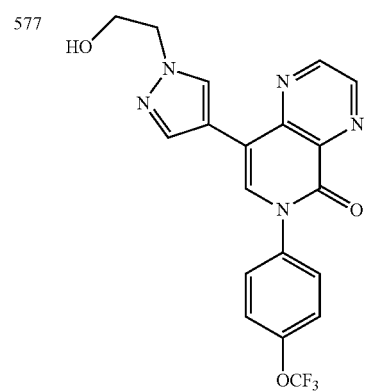 |
| 578 | 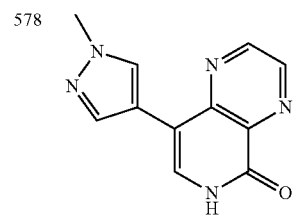 |
| 579 | 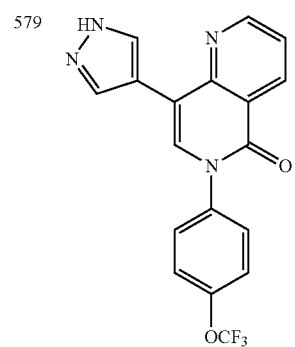 |
| 580 | 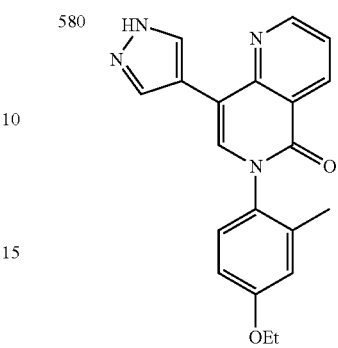 |
| 581 | 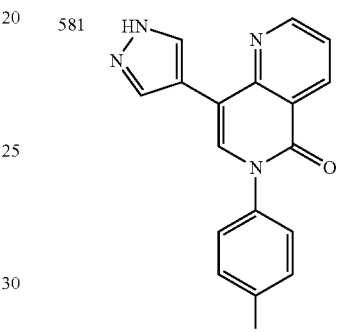 |
| 582 | 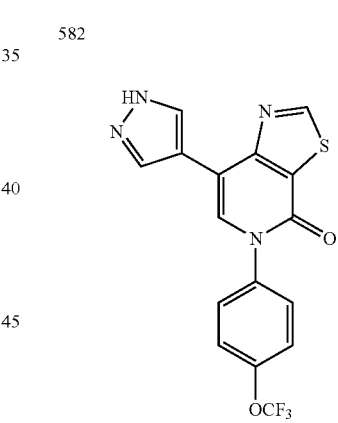 |
| 583 | 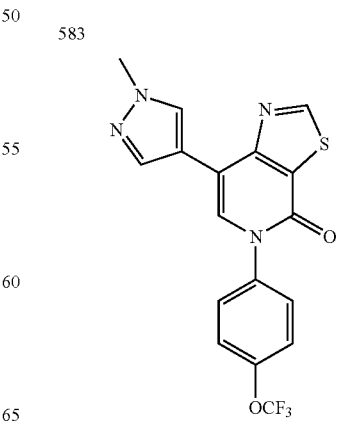 |

TABLE 1-continued
| Compd. # | Structure |
|---|---|
| 584 | 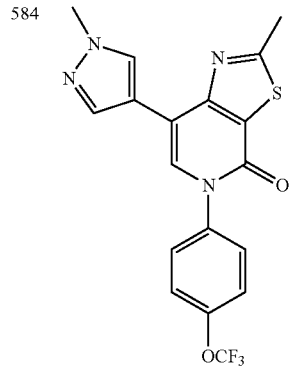 |
| 585 | 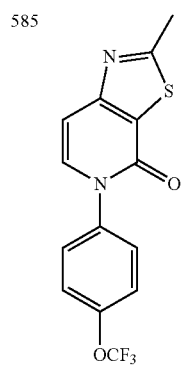 |
| 586 | 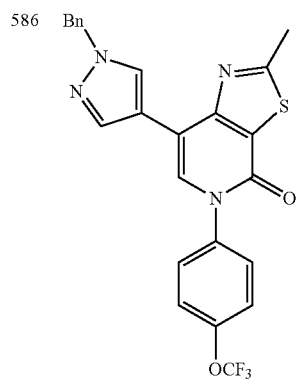 |
| 587 | 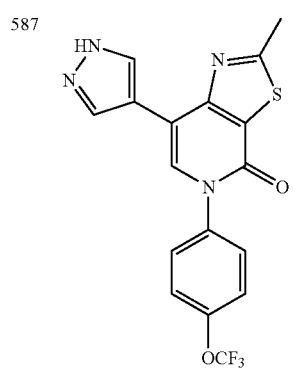 |
| 588 | 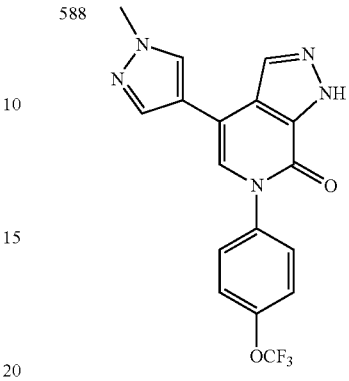 |
| 589 | 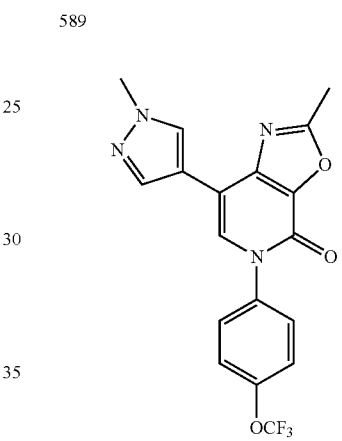 |
| 590 | 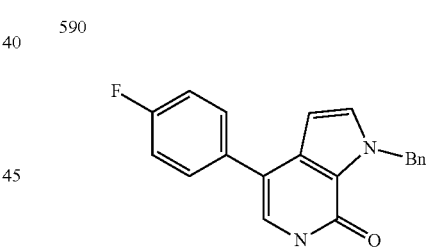 |
| 591 | 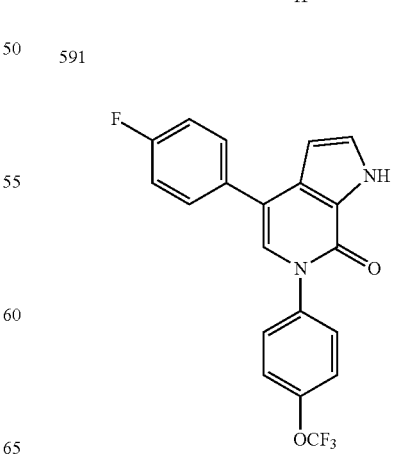 |

TABLE 1-continued
| Compd. # | Structure |
|---|---|
| 592 | 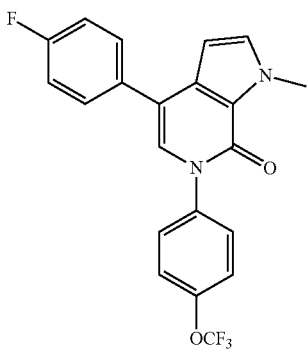 |
| 593 | 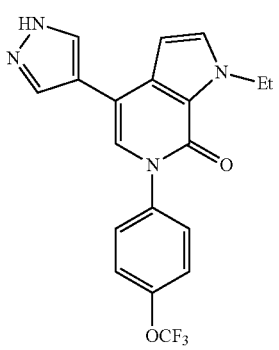 |
| 594 | 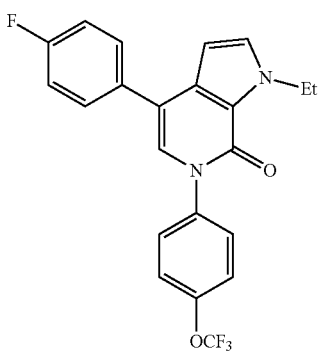 |
| 595 | 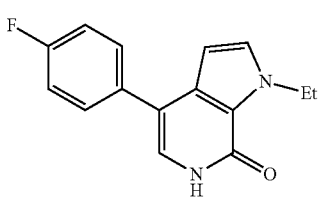 |
TABLE 1-continued
| Compd. # | Structure |
|---|---|
| 596 | 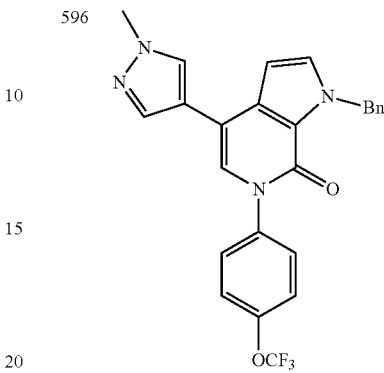 |
| 597 | 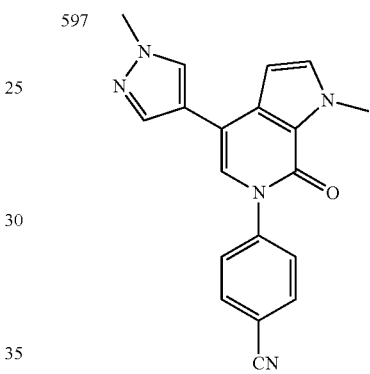 |
| 598 | 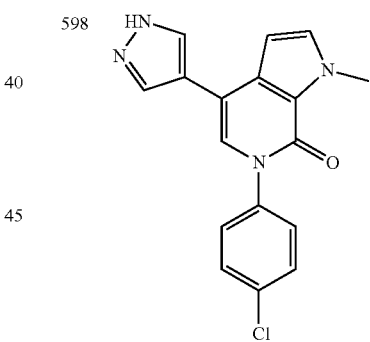 |
| 599 | 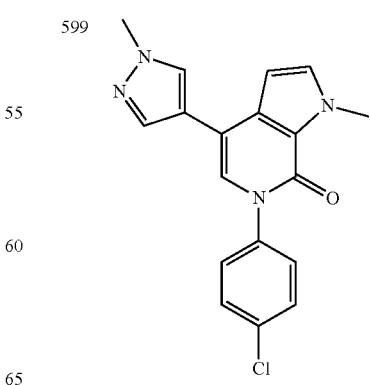 |

| Compd. # | Structure |
|---|---|
| 600 | 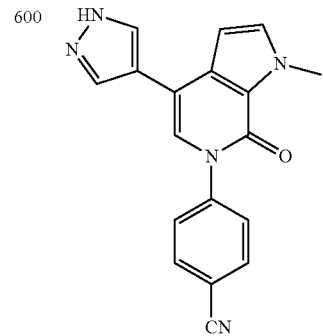 |
| 601 | 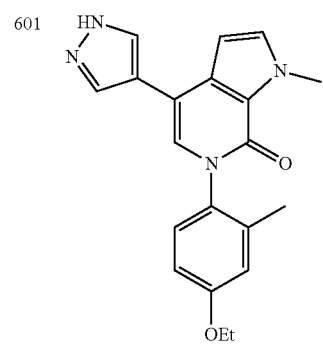 |
| 602 | 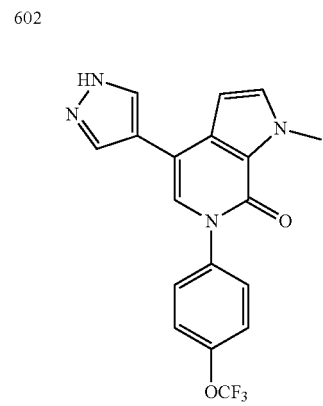 |
| 603 | 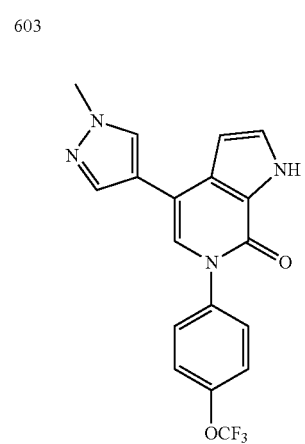 |
| Compd. # | Structure |
|---|---|
| 604 | 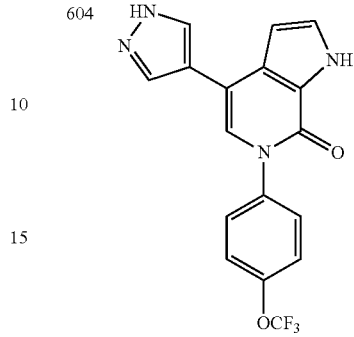 |
| 605 | 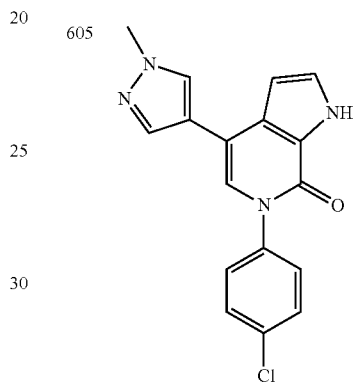 |
| 606 | 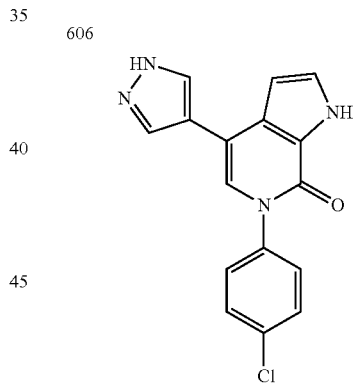 |
| 607 | 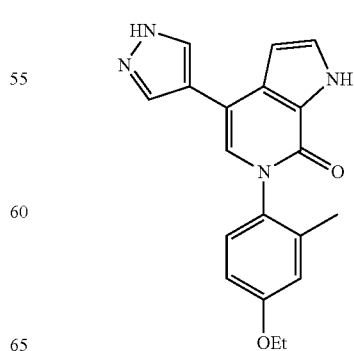 |

TABLE 1-continued

| Compd. # | Structure |
|---|---|
| 608 | (4-(1H-pyrazol-4-yl)-6-(4-cyanophenyl)-1H-pyrrolo[2,3-c]pyridin-7(6H)-one) |
| 609 | (6-(4-(trifluoromethoxy)phenyl)-1H-pyrrolo[2,3-c]pyridin-7(6H)-one) |
| 610 | (1-ethyl-6-(4-(trifluoromethoxy)phenyl)-1H-pyrrolo[2,3-c]pyridin-7(6H)-one) |
| 611 | (1-ethyl-4-(1-methyl-1H-pyrazol-4-yl)-1H-pyrrolo[2,3-c]pyridin-7(6H)-one) |
| 612 | (4-(1-methyl-1H-pyrazol-4-yl)-1H-pyrrolo[2,3-c]pyridin-7(6H)-one) |
| 613 | (1-ethyl-4-(1H-pyrazol-4-yl)-1H-pyrrolo[2,3-c]pyridin-7(6H)-one) |
| 614 | (1-(2-hydroxyethyl)-4-(1-methyl-1H-pyrazol-4-yl)-6-(4-(trifluoromethoxy)phenyl)-1H-pyrrolo[2,3-c]pyridin-7(6H)-one) |
| 615 | (1-ethyl-4-(1-(2-hydroxyethyl)-1H-pyrazol-4-yl)-6-(4-(trifluoromethoxy)phenyl)-1H-pyrrolo[2,3-c]pyridin-7(6H)-one) |
| 616 | (4-(1H-pyrazol-4-yl)-1H-pyrrolo[2,3-c]pyridin-7(6H)-one) |
| 617 | (3-ethyl-7-(1-methyl-1H-pyrazol-4-yl)-5-(4-(trifluoromethoxy)phenyl)-3H-imidazo[4,5-c]pyridin-4(5H)-one) |

TABLE 1-continued

| Compd. # | Structure |
|---|---|
| 618 | (structure) |
| 619 | (structure) |
| 620 | (structure) |
| 621 | (structure) |
| 622 | (structure) |
| 623 | (structure) |
| 624 | (structure) |
| 625 | (structure) |
| 626 | (structure) |

TABLE 1-continued
| Compd. # | Structure |
|---|---|
| 627 | 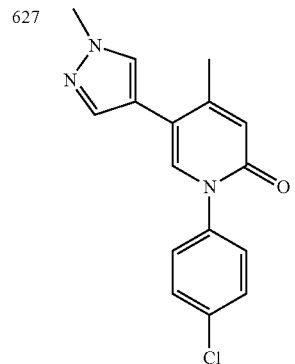 |
| 628 | 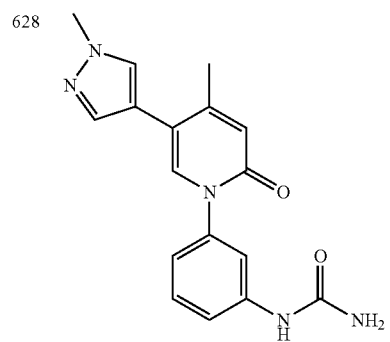 |
| 629 | 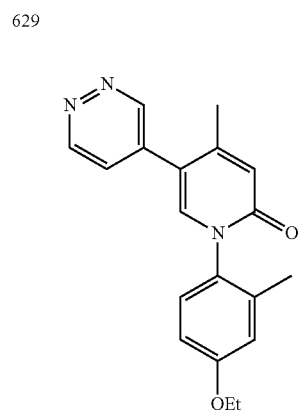 |
| 630 | 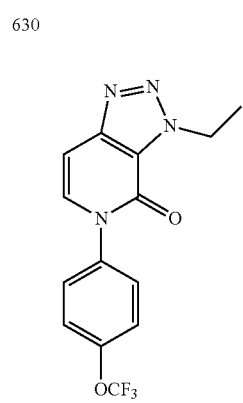 |
| 631 | 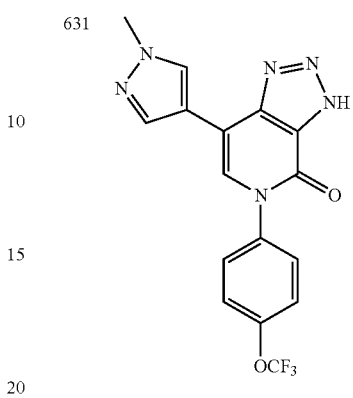 |
| 632 | 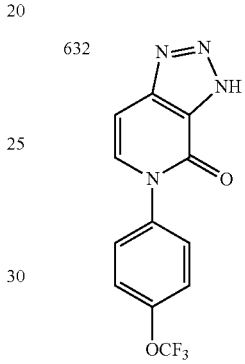 |
| 633 | 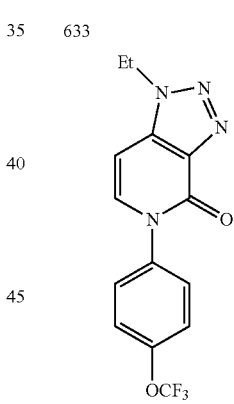 |
| 634 | 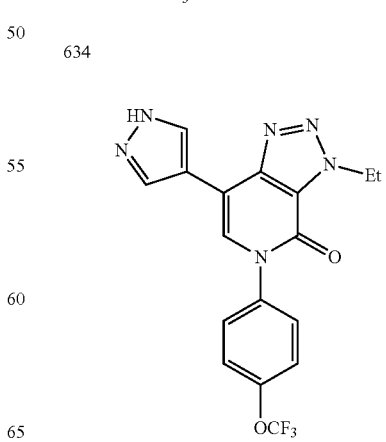 |

TABLE 1-continued

| Compd. # | Structure |
|---|---|
| 635 | (1-methylpyrazol-4-yl, 3-isopropyl-triazolo-pyridinone with 4-OCF3-phenyl) |
| 636 | (1-methylpyrazol-4-yl, 1-Et-imidazo-pyridinone with 4-OCF3-phenyl) |
| 637 | (1-methylpyrazol-4-yl, 1-Et-imidazo-pyridinone NH with 4-OCF3-phenyl absent; N-H) |
| 638 | (1H-pyrazol-4-yl, 1-Et-imidazo-pyridinone, N-H) |
| 639 | (1-Et-imidazo-pyridinone with 4-OCF3-phenyl) |
| 640 | (1H-pyrazol-4-yl, 1-Et-imidazo-pyridinone with 4-OCF3-phenyl) |
| 641 | (1H-imidazo-pyridinone with 4-OCF3-phenyl) |
| 642 | (1-Et-pyrazol-4-yl, 1H-imidazo-pyridinone with 4-OCF3-phenyl) |
| 643 | (1-iPr-pyrazol-4-yl, 1H-imidazo-pyridinone with 4-OCF3-phenyl) |

TABLE 1-continued
| Compd. # | Structure |
|---|---|
| 644 | 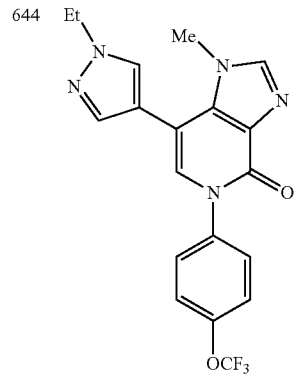 |
| 645 | 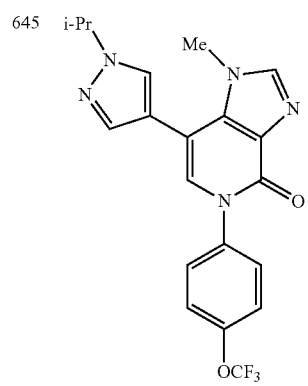 |
| 646 | 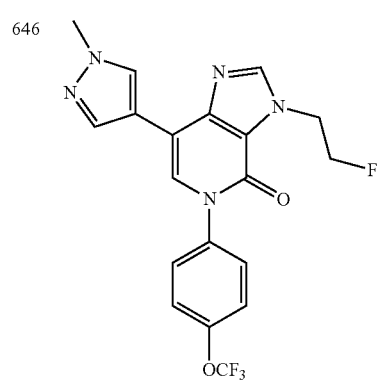 |
| 647 | 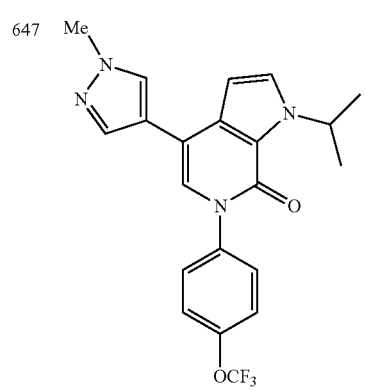 |
| 648 | 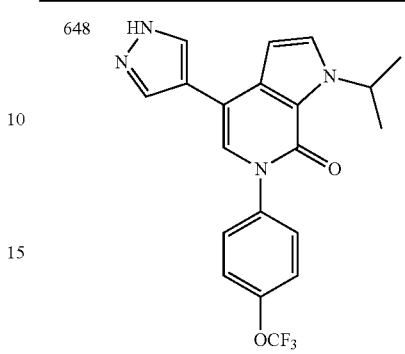 |
| 649 | 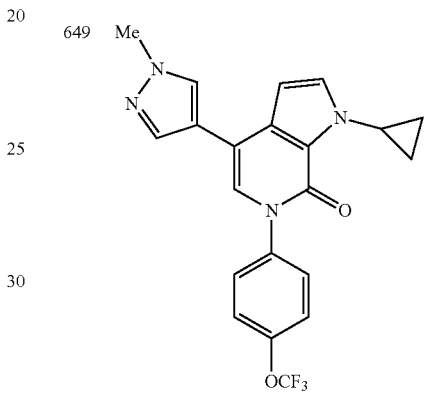 |
| 650 | 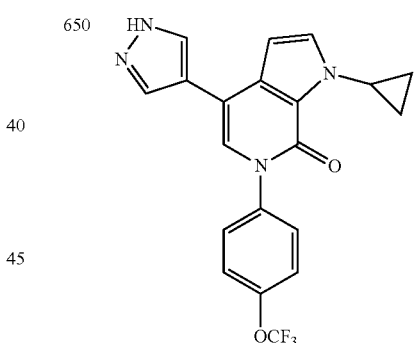 |
| 651 | 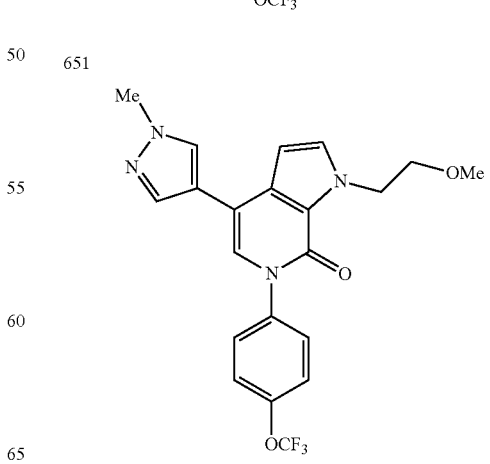 |

TABLE 1-continued
| Compd. # | Structure |
|---|---|
| 652 | 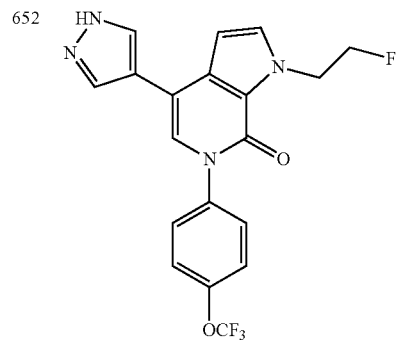 |
| 653 | 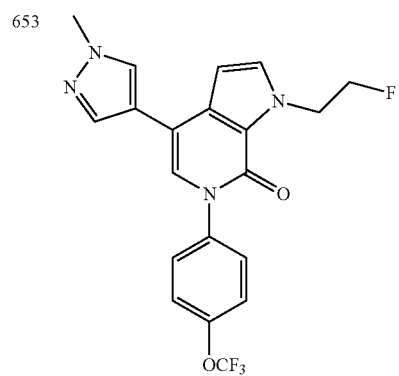 |
| 654 | 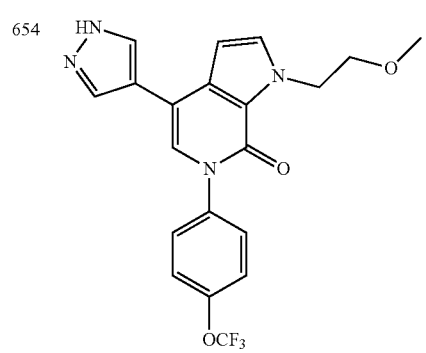 |
| 655 | 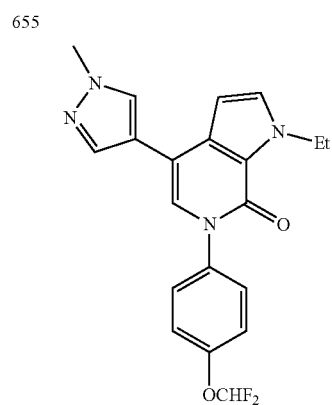 |
TABLE 1-continued
| Compd. # | Structure |
|---|---|
| 656 | 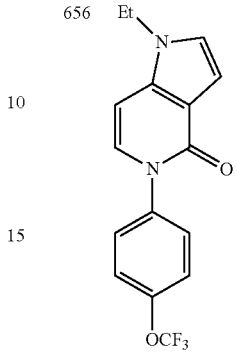 |
| 657 | 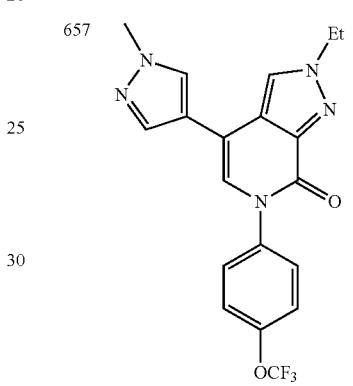 |
| 658 | 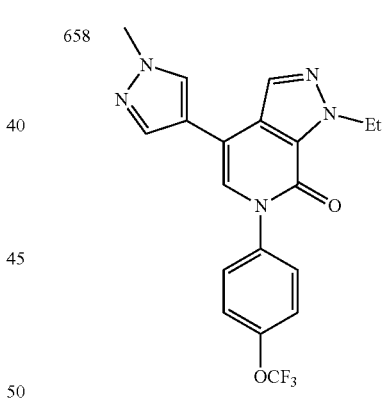 |
| 659 | 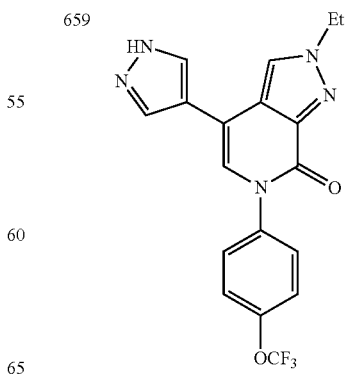 |

TABLE 1-continued

| Compd. # | Structure |
|---|---|
| 660 | |
| 661 | |
| 662 | |
| 663 | |
| 664 | 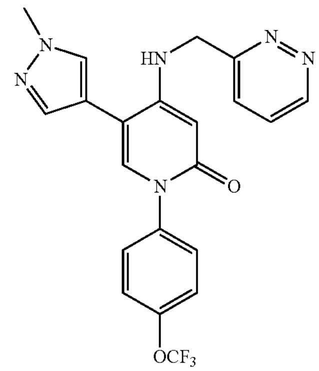 |
| 665 | 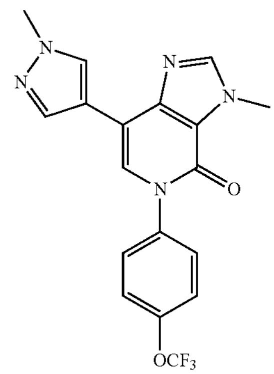 |
| 666 | 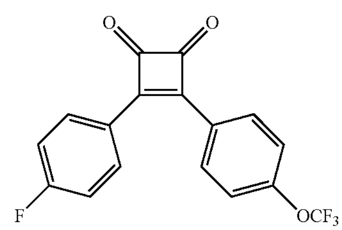 |
| 667 | 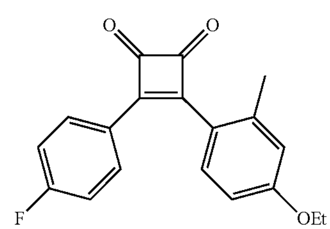 |
| 668 | 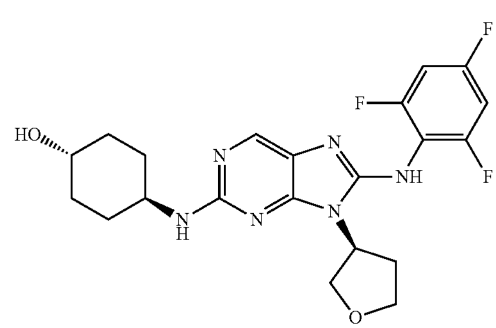 |

TABLE 1-continued

| Compd. # | Structure |
|---|---|
| 669 | (structure) |
| 670 | (structure) |
| 671 | (structure) |
| 672 | (structure) |
| 673 | (structure) |
| 674 | (structure) |
| 675 | (structure) |
| 676 | (structure) |

TABLE 1-continued
| Compd. # | Structure |
|---|---|
| 677 | 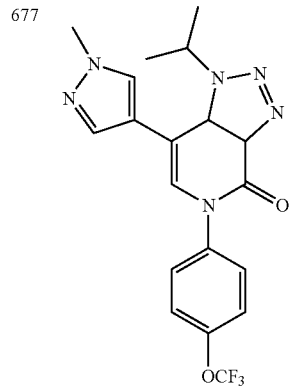 |
| 678 | 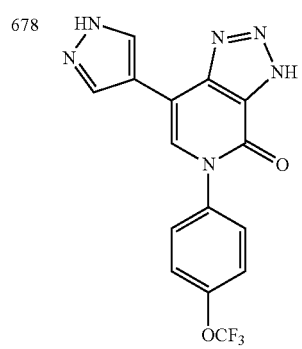 |
| 679 | 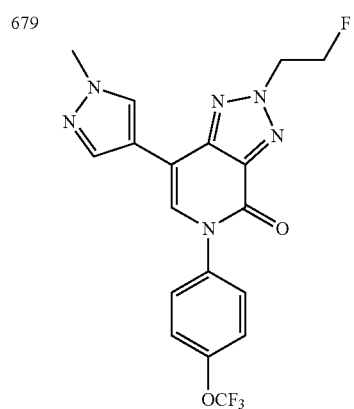 |
| 680 | 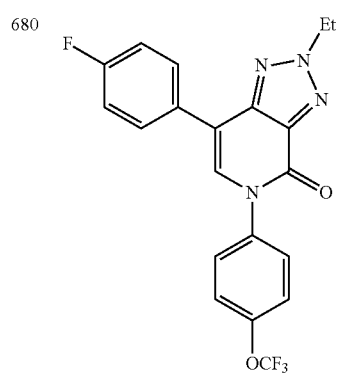 |
| 681 | 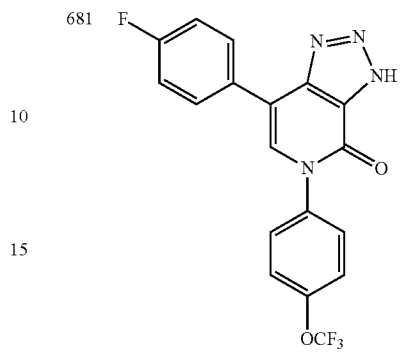 |
| 682 | 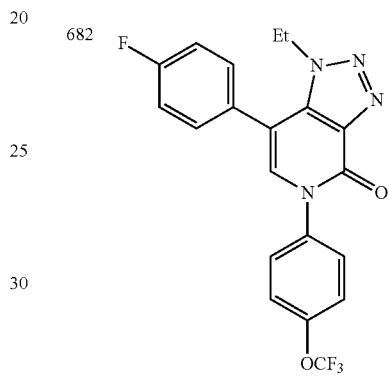 |
| 683 | 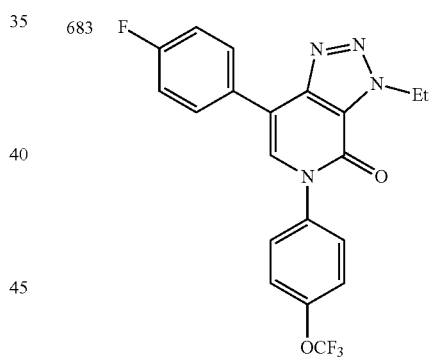 |
| 684 | 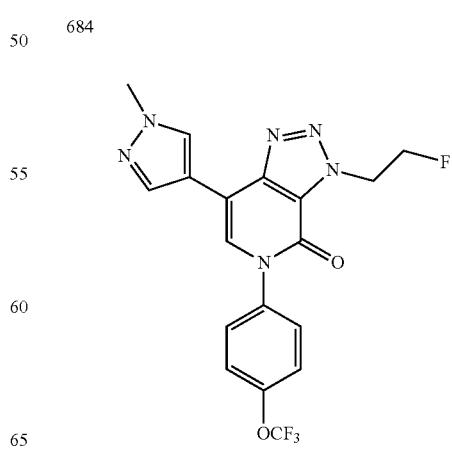 |

TABLE 1-continued
| Compd. # | Structure |
|---|---|
| 685 | 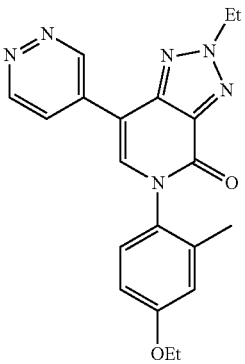 |
| 686 | 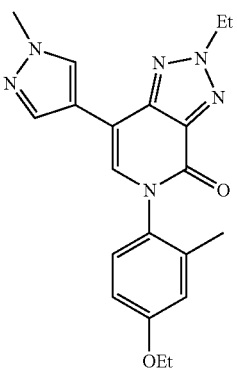 |
| 687 | 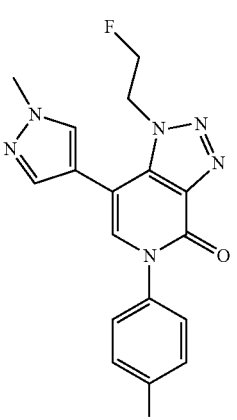 |
| 688 | 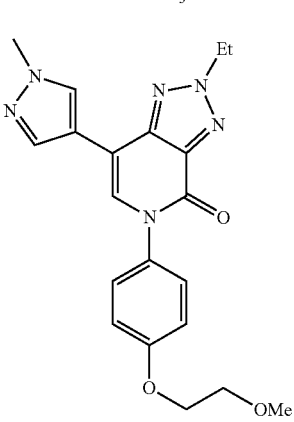 |
| 689 | 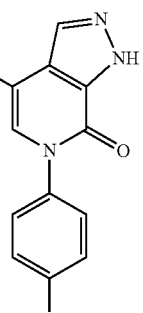 |
| 690 | 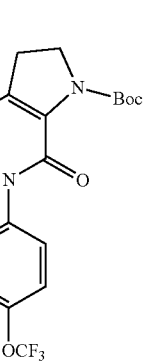 |
| 691 | 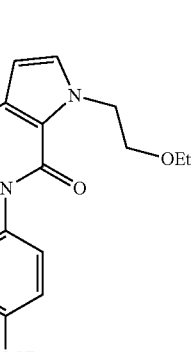 |
| 692 | 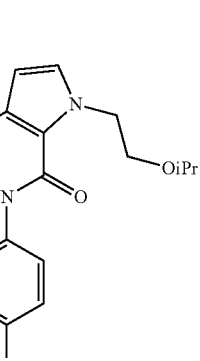 |

TABLE 1-continued
| Compd. # | Structure |
|---|---|
| 693 | 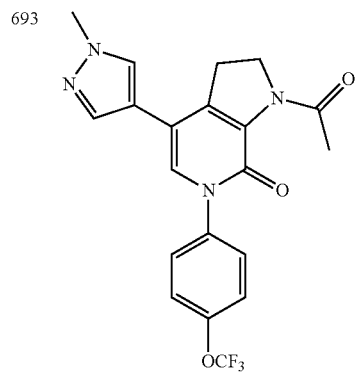 |
| 694 | 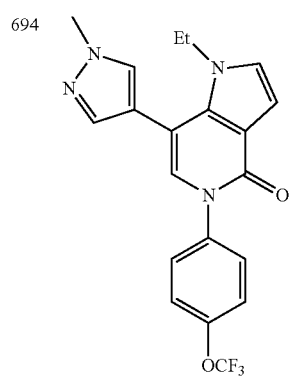 |
| 695 | 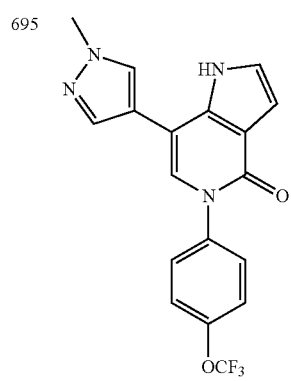 |
| 696 | 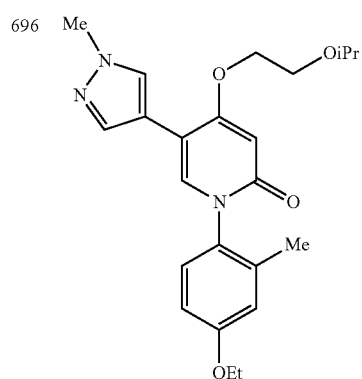 |
TABLE 1-continued
| Compd. # | Structure |
|---|---|
| 697 | 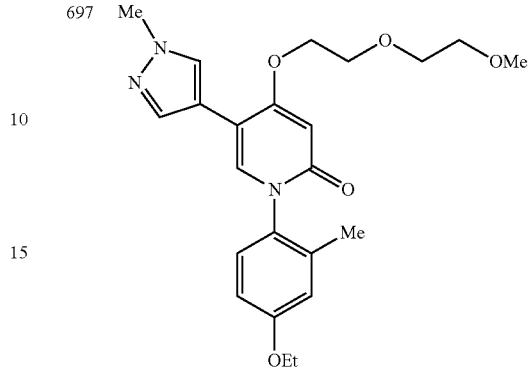 |
| 698 | 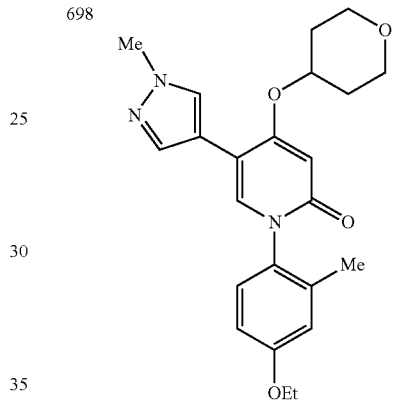 |
| 699 | 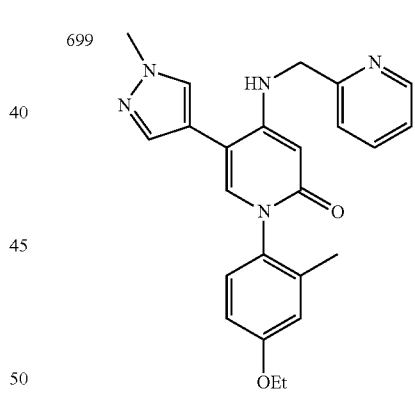 |
| 700 | 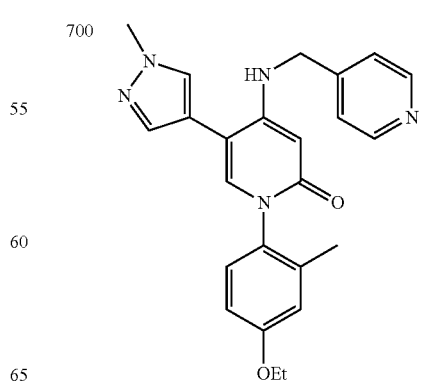 |

TABLE 1-continued

| Compd. # | Structure |
|---|---|
| 701 | 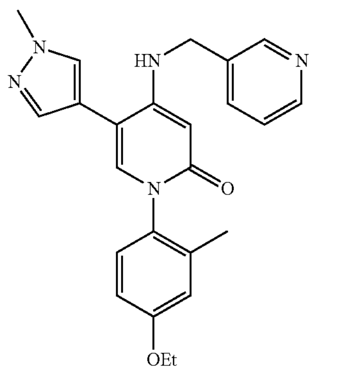 |
| 702 | 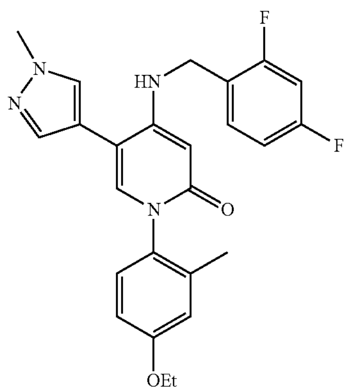 |
| 703 | 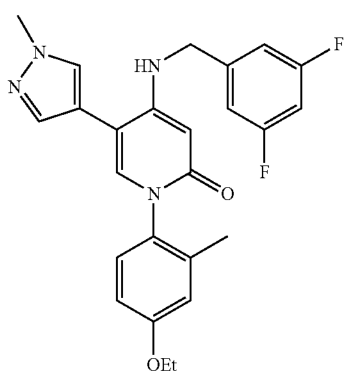 |
| 704 | 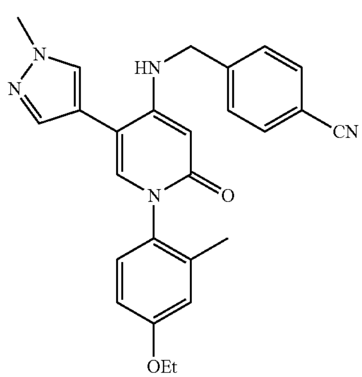 |
| 705 | 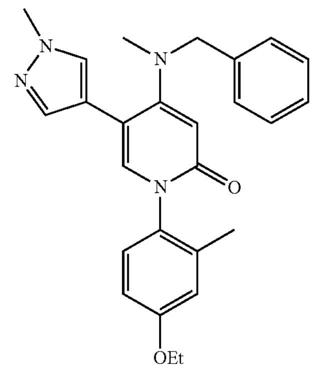 |
| 706 | 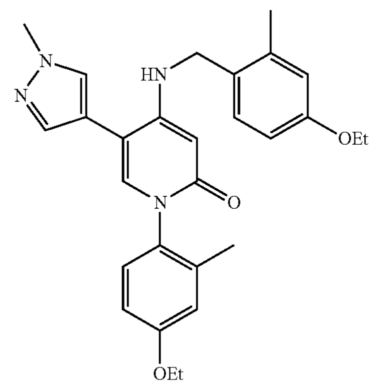 |
| 707 | 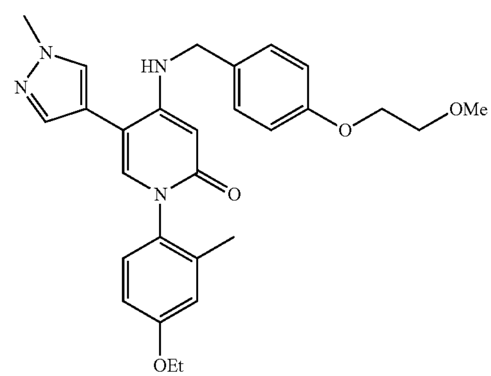 |
| 708 | 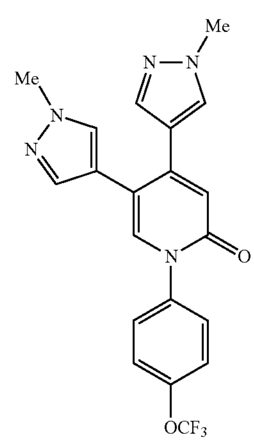 |

TABLE 1-continued

| Compd. # | Structure |
|---|---|
| 709 | (structure: 5-(trifluoromethyl)-1-(2-chloro-4-((2-(4-(2-hydroxyethyl)piperazin-1-yl)ethyl)amino)phenyl)pyridin-2(1H)-one) |

Administration and Pharmaceutical Compositions

Some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

The compounds are administered at a therapeutically effective dosage, e.g., a dosage sufficient to provide treatment for the disease states previously described. While human dosage levels have yet to be optimized for the compounds of the preferred embodiments, generally, a daily dose for most of the compounds described herein is from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg per day to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety.

In addition to the selected compound useful as described above, come embodiments include compositions containing a pharmaceutically-acceptable carrier. The term "pharmaceutically-acceptable carrier", as used herein, means one or more compatible solid or liquid filler diluents or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Method of Treatment

Some embodiments described herein relate to a method of treating a fibrotic condition, which can include administering a therapeutically effective amount of a compound disclosed herein, or a pharmaceutically acceptable salt thereof, to a subject. The methods include identifying a subject at risk for or having a fibrotic condition and administering a compound to the subject in an effective amount for therapeutic treatment or prophylactic treatment of the fibrotic condition.

A "fibrotic condition," "fibroproliferative condition," "fibrotic disease," "fibroproliferative disease," "fibrotic disorder," and "fibroproliferative disorder" are used interchangeably to refer to a condition, disease or disorder that is characterized by dysregulated proliferation or activity of fibroblasts and/or abnormal accumulation of fibronectin and/or pathologic or excessive accumulation of collagenous tissue. Typically, any such disease, disorder or condition is amenable to treatment by administration of a compound having anti-fibrotic activity. Fibrotic disorders include, but are not limited to, pulmonary fibrosis, including idiopathic pulmonary fibrosis (IPF) and pulmonary fibrosis from a known etiology, dermal fibrosis, pancreatic fibrosis, liver fibrosis (e.g., hepatic fibrosis associated with chronic active hepatitis), and renal fibrosis.

In some embodiments, the subject is a human.

The terms "therapeutically effective amount," as used herein, refer to an amount of a compound sufficient to cure, ameliorate, slow progression of, prevent, or reduce the likelihood of onset of the identified disease or condition, or to exhibit a detectable therapeutic, prophylactic, or inhibitory effect. The effect can be detected by, for example, the assays disclosed in the following examples. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

For any compound, the therapeutically or prophylactically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans.

Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. However, pharmaceutical compositions that exhibit narrow therapeutic indices are also within the scope of the invention. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

In one aspect, treating a condition described herein results in an increase in average survival time of a population of treated subjects in comparison to a population of untreated subjects. Preferably, the average survival time is increased by more than about 30 days; more preferably, by more than about 60 days; more preferably, by more than about 90 days; and even more preferably by more than about 120 days. An increase in survival time of a population may be measured by any reproducible means. In a preferred aspect, an increase in average survival time of a population may be measured, for example, by calculating for a population the average length of survival following initiation of treatment with an active compound. In an another preferred aspect, an increase in average survival time of a population may also be measured, for example, by calculating for a population the average length of survival following completion of a first round of treatment with an active compound.

In another aspect, treating a condition described herein results in a decrease in the mortality rate of a population of treated subjects in comparison to a population of subjects receiving carrier alone. In another aspect, treating a condition described herein results in a decrease in the mortality rate of a population of treated subjects in comparison to an untreated population. In a further aspect, treating a condition described herein results a decrease in the mortality rate of a population of treated subjects in comparison to a population receiving monotherapy with a drug that is not a compound of the embodiments, or a pharmaceutically acceptable salt, metabolite, analog or derivative thereof. Preferably, the mortality rate is decreased by more than about 2%; more preferably, by more than about 5%; more preferably, by more than about 10%; and most preferably, by more than about 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease related deaths per unit time following completion of a first round of treatment with an active compound.

In another aspect, treating a condition described herein results in a reduction in the rate of cellular proliferation. Preferably, after treatment, the rate of cellular proliferation is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating a condition described herein results in a reduction in the proportion of proliferating cells. Preferably, after treatment, the proportion of proliferating cells is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating a condition described herein results in a decrease in size of an area or zone of cellular proliferation. Preferably, after treatment, size of an area or zone of cellular proliferation is reduced by at least 5% relative to its size prior to treatment; more preferably, reduced by at least about 10%; more preferably, reduced by at least about 20%; more preferably, reduced by at least about 30%; more preferably, reduced by at least about 40%; more preferably, reduced by at least about 50%; even more preferably, reduced by at least about 60%; and most preferably, reduced by at least about 75%. Size of an area or zone of cellular proliferation may be measured by any reproducible means of measurement. In a preferred aspect, size of an area or zone of cellular proliferation may be measured as a diameter or width of an area or zone of cellular proliferation.

The methods described herein may include identifying a subject in need of treatment. In a preferred embodiment, the methods include identifying a mammal in need of treatment. In a highly preferred embodiment, the methods include identifying a human in need of treatment. Identifying a subject in need of treatment may be accomplished by any means that indicates a subject who may benefit from treatment. For example, identifying a subject in need of treatment may occur by clinical diagnosis, laboratory testing, or any other means known to one of skill in the art, including any combination of means for identification.

As described elsewhere herein, the compounds described herein may be formulated in pharmaceutical compositions, if desired, and can be administered by any route that permits treatment of the disease or condition. A preferred route of administration is oral administration. Administration may take the form of single dose administration, or the compound of the embodiments can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In some embodiments, the agents are administered simultaneously. In some such embodiments, administration in combination is accomplished by combining the agents in a single dosage form. In some embodiments, the agents are administered sequentially. In some embodiments the agents are administered through the same route, such as orally. In some other embodiments, the agents are administered through different routes, such as one being administered orally and another being administered i.v. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Pulmonary Fibrosis

Pulmonary fibrosis also called idiopathic pulmonary fibrosis (IPF), interstitial diffuse pulmonary fibrosis, inflammatory pulmonary fibrosis, or fibrosing alveolitis, is a lung disorder and a heterogeneous group of conditions characterized by abnormal formation of fibrous tissue between alveoli caused by alveolitis comprising cellular infiltration into the alveolar septae with resulting fibrosis. The effects of IPF are chronic, progressive, and often fatal. The compounds and methods described herein are useful in the treatment of pulmonary fibrosis, such as IPF.

Renal Fibrosis

Irrespective of the nature of the initial insult, renal fibrosis is considered to be the common final pathway by which kidney disease progresses to end-stage renal failure. The compounds and methods described herein are useful in the treatment of renal fibrosis.

Synthesis

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, Protecting Groups in Organic Synthesis (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

EXAMPLES

Additional embodiments are disclosed in further detail in the following examples, which are not in any way intended to limit the scope of the claims.

Example 1-A

Synthesis of Compound 1 (Scheme I)

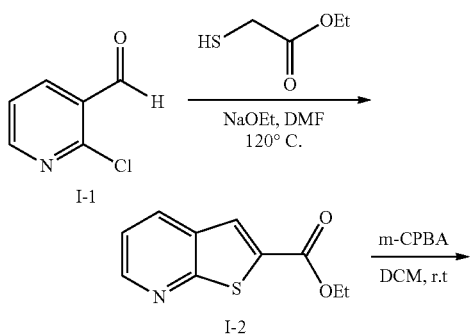

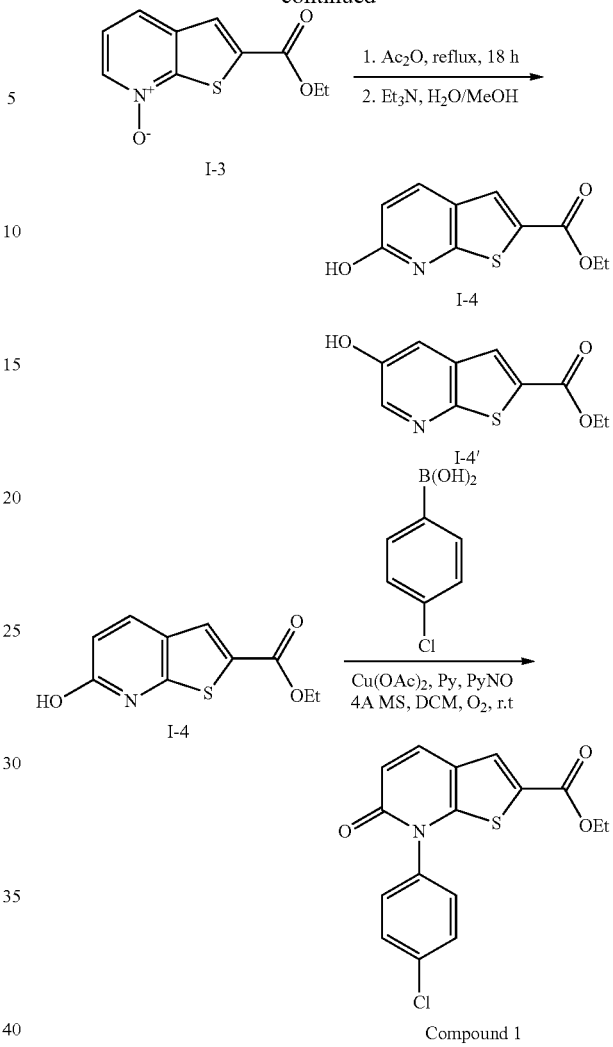

Compound 1

To a solution of ethyl thioglycolate (11.14 g, 92.8 mmol) in 400 mL of DMF was added NaOEt (14.5 g, 185.7 mmol) by portion wise. The resulting mixture was stirred for 30 min at 0° C. And then I-1 (10 g, 71.4 mmol) was added to the solution by portion wise. The mixture was stirred at 120° C. overnight. The reaction mixture was cooled to it, diluted with water (300 mL), extracted with EtOAc (300 mL×3), the combined organic layers were washed with brine, dried over anhydrous $Na_2SO_4$ and concentrated. The residue was washed with petroleum ether to afford I-2 (8.7 g, 59% yield) as a pale brown solid. $^1$H NMR (CDCl$_3$, 400 MHz) δ 8.68 (dd, J=1.6, 4.4 Hz, 1H), 8.16 (dd, J=1.6, 8.0 Hz, 1H), 8.00 (s, 1H), 7.36 (m, 1H), 4.43 (q, J=7.2 Hz, 2H), 1.42 (t, J=7.2 Hz, 3H). MS (ESI) m/z [M+H]$^+$ 208.0.

To a solution of I-2 (7.5 g, 36.2 mmol) in 300 mL of DCM was added m-CPBA (12.4 g, 72.4 mmol) by portion wise at 0° C. The resulting solution was stirred at rt overnight, followed by quench with saturated aq.$Na_2S_2O_3$. The organic layer was separated, the aqueous layer was extracted with EtOAc (200 mL×3). The combined organic layers were washed with saturated aq. NaHCO$_3$ and brine, dried over anhydrous $Na_2SO_4$ and concentrated. The crude product was washed with petroleum ether to produce I-3 (7.5 g, 93% yield) as a white solid. MS (ESI) m/z [M+H]$^+$ 224.0.

I-3 (7.0 g, 31.4 mmol) was added into 60 mL of Ac$_2$O, the solution was heated to reflux overnight. The reaction mixture was concentrated, the residue was dissolved with 100 mL of MeOH, and 6 mL of TEA was added thereto, the mixture was stirred at rt for 4 hours, and then it was concentrated, diluted with EtOAc (500 mL), washed with water and brine, dried over anhydrous Na$_2$SO$_4$ and concentrated. The residue was purified by flash chromatography on silica gel with petroleum ether/EtOAc (20:1→10:1→5:1→1:1→1:2→1:10) to afford I-4 (2.8 g, 40% yield) as a brown solid. MS (ESI) m/z [M+H]$^+$ 223.8.

A flask was charged with I-4 (1.0 g, 4.48 mmol), 4-chlorophenyl boronic acid (2.11 g, 13.45 mmol), Cu(OAc)$_2$ (4.05 g, 22.4 mmol), pyridine N-oxide (4.26 g, 44.8 mmol), pyridine (2.69 g, 35.8 mmol), 4 Å molecular sieve (1.0 g) and 300 mL of anhydrous DCM. The mixture was stirred under oxygen atmosphere at rt. overnight. The reaction was monitored by TLC, when the starting material was consumed, the mixture was concentrated, diluted with water (100 mL), extracted with EtOAc (300 mL×3). The combined organic layer was washed with brine, dried over anhydrous Na$_2$SO$_4$ and concentrated. The residue was purified by flash chromatography on silica gel with petroleum ether/EtOAc (50:1→30:1→10:1→5:1→2:1) to afford Compound 1 (900 mg, 60% yield) as a pale yellow solid. $^1$H NMR (DMSO-d$_6$, 400 MHz) δ 8.04-8.00 (m, 2H), 7.71 (d, J=8.4 Hz, 2H), 7.60 (d, J=8.4 Hz, 2H), 6.60 (d, J=9.6 Hz, 1H), 4.24 (q, J=7.2 Hz, 2H), 1.24 (t, J=7.2 Hz, 3H). MS (ESI) m/z [M+H]$^+$ 333.9.

Compound 2 was prepared following the procedure for obtaining Compound 1 using 1-(2-chloropyridin-3-yl)ethanone in place of I-1 as a white solid. $^1$H NMR (CD$_3$OD, 400 MHz) δ 8.06 (d, J=9.2 Hz, 1H), 7.70-7.67 (m, 2H), 7.50-7.48 (m, 2H), 6.68 (d, J=9.6 Hz, 1H), 4.29 (q, J=7.2 Hz, 2H), 2.69 (s, 3H), 1.35 (t, J=7.2 Hz, 3H). MS (ESI) m/z (M+H)$^+$ 347.9.

Example 1-B

Synthesis of Compound 3 (Scheme II)

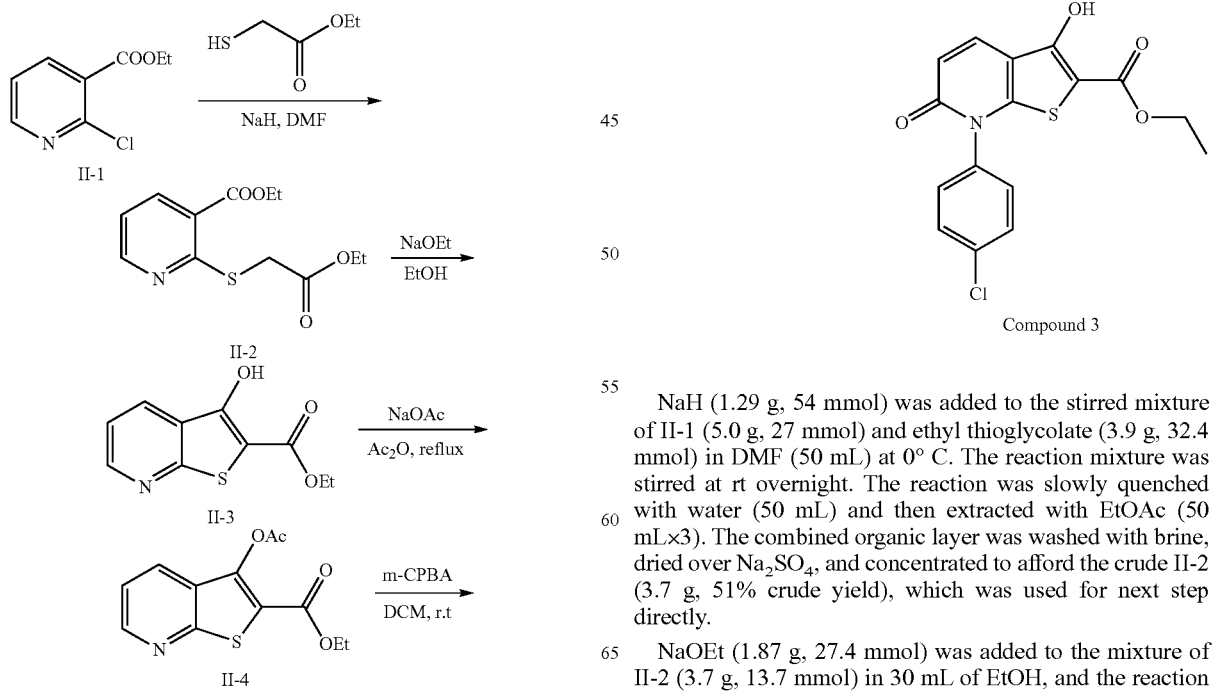

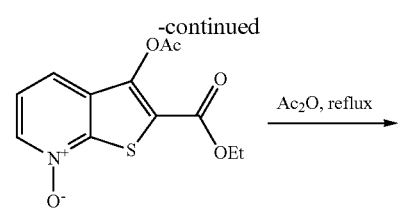

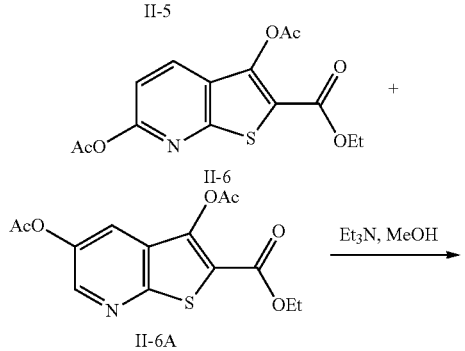

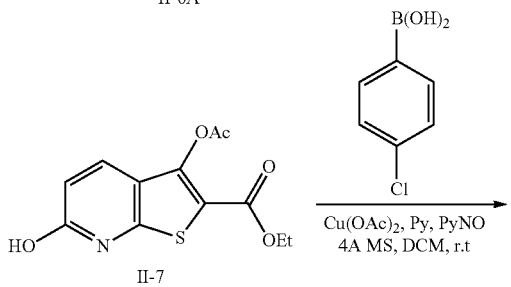

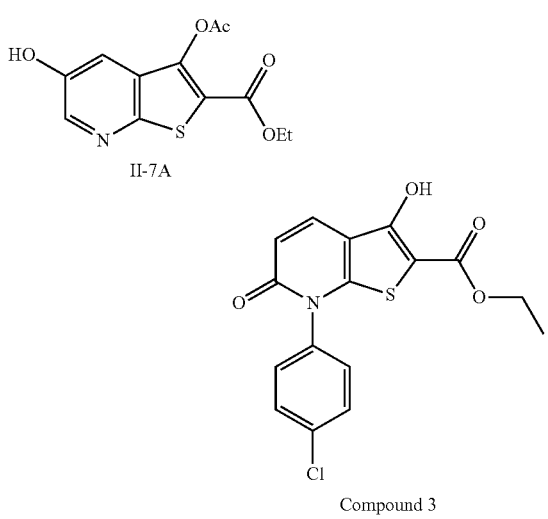

Compound 3

NaH (1.29 g, 54 mmol) was added to the stirred mixture of II-1 (5.0 g, 27 mmol) and ethyl thioglycolate (3.9 g, 32.4 mmol) in DMF (50 mL) at 0° C. The reaction mixture was stirred at rt overnight. The reaction was slowly quenched with water (50 mL) and then extracted with EtOAc (50 mL×3). The combined organic layer was washed with brine, dried over Na$_2$SO$_4$, and concentrated to afford the crude II-2 (3.7 g, 51% crude yield), which was used for next step directly.

NaOEt (1.87 g, 27.4 mmol) was added to the mixture of II-2 (3.7 g, 13.7 mmol) in 30 mL of EtOH, and the reaction mixture was stirred at rt for 2 hours. Then the mixture was adjusted to pH=2 with aq. HCl (2 M), the precipitated solid was collect to afford II-3 (2.4 g, 79% yield), which was used for next step directly.

A mixture of II-3 (3 g, 13.4 mmol) and NaOAc (2.2 g, 26.8 mmol) in Ac$_2$O (50 ml) was stirred at reflux for 2 hours. The mixture was cooled to rt., concentrated in vacuo, the mixture was dissolved in EtOAc (100 mL), washed with saturated aq. Na$_2$CO$_3$ and water. The organic phase was dried over Na$_2$SO$_4$, concentrated under reduced pressure to give II-4 (3 g, 84% yield).

To a stirring solution of II-4 (3 g, 11.3 mmol) in anhydrous DCM (60 mL) at 0° C. was added m-CPBA (5.85 g, 34 mmol). Then the mixture was stirred overnight at rt. After that the mixture was washed with saturated aq. Na$_2$SO$_3$ solution, dried over Na$_2$SO$_4$ and concentrated under reduced pressure. The residue was re-crystallized from EtOAc to produce II-5 (2.5 g, 79% yield) as white solid.

II-5 (2.5 g, 8.9 mmol) was dissolved in Ac$_2$O (30 mL) and the mixture was refluxed at 140° C. for 18 hrs. After being cooled to rt, the mixture was concentrated under reduced pressure. The residue was purified by column chromatography on silica gel with petroleum ether/EtOAc (20:1) to give a mixture of II-6 and II-6A (1.5 g, 52% yield) as yellow solid.

To a stirring solution of mixture II-6 and II-6A (1.3 g, 4 mmol) in MeOH (65 mL) was added TEA (10 mL) at rt. Then the mixture was stirred for 1 h at ambient temperature. The mixture was concentrated under reduced pressure to afford a mixture of II-7 and II-7A (1.0 g, 88% crude yield) as yellow solid, which was used directly without further purification.

A mixture of II-7 and II-7A (500 mg, 1.8 mmol), 4-chlorophenyl boronic acid (842 mg, 5.4 mmol), Cu(OAc)$_2$ (1.63 g, 9 mmol), pyridine-N-oxide (1.71 g, 18 mmol) and pyridine (1.42 g, 18 mmol) in anhydrous DCM (50 mL) was stirred for 80 hours at rt under air. Then the mixture was washed with water and the organic phase was dried over Na$_2$SO$_4$, concentrated under reduced pressure. The residue was purified by Prep-HPLC to give Compound 3 (100 mg, 16% yield). $^1$H NMR (CD$_3$OD, 400 MHz) δ 7.96 (d, J=9.2 Hz, 1H), 7.62 (d, J=8.4 Hz, 2H), 7.41 (d, J=8.4 Hz, 2H), 6.43 (d, J=9.2 Hz, 1H), 4.15 (q, J=7.2 Hz, 2H), 1.24 (t, J=7.2 Hz, 3H). MS (ESI) m/z (M+H)$^+$ : 349.9.

Compound 4 was prepared following the similar procedure for obtaining Compound 3 using 1-(2-chloropyridin-3-yl)propan-1-one in place of II-1. $^1$H NMR (DMSO-d$_6$, 400 MHz) δ 12.3 (brs, 1H), 8.03 (d, J=9.6 Hz, 1H), 6.53 (d, J=9.2 Hz, 1H), 4.29 (q, J=7.2 Hz, 2H), 3.12 (q, J=7.2 Hz, 2H), 1.33 (t, J=7.2 Hz, 3H), 1.15 (t, J=7.2 Hz, 3H).

Example 2

Synthesis of 5-Acyl Pirfenidone Analogs (Scheme III)

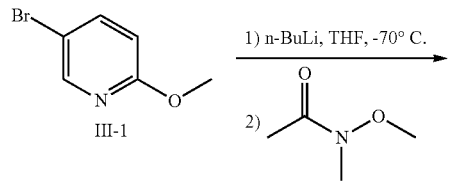

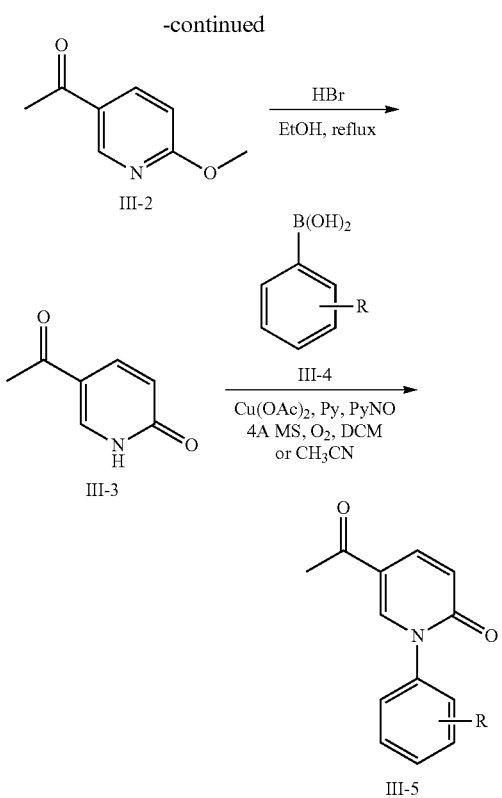

To a solution of III-1 (30 g, 0.162 mol, 1 eq.) in 300 mL of anhydrous THF was added dropwise a solution of n-BuLi (2.5M in hexane, 77.5 mL, 0.19 mol, 1.2 eq.) at −70° C. After completion of addition, the mixture was stirred at −70° C. for 20 min, followed by addition of a solution of N-methoxy-N-methylacetamide (33 g, 0.322 mol, 2 eq.) in 100 mL of anhydrous THF by drop wise, the solution was allowed to warm to rt and stirred for 2 hrs. The reaction was quenched with saturated aq. NH$_4$Cl (100 mL), extracted with EtOAc (300 mL×3), the organic layer was washed with brine, dried over anhydrous Na$_2$SO$_4$, and concentrated in vacuo. The residue was purified by flash chromatography on silica gel with petroleum ether/EtOAc (100:1) to yield III-2 (14.8 g, 62% yield) as a white solid. $^1$H NMR (DMSO-d$_6$, 400 MHz) δ 8.81 (d, J=2.0 Hz, 1H), 8.16 (dd, J=2.4, 8.4 Hz, 1H), 6.90 (d, J=8.8 Hz, 1H), 3.93 (s, 3H), 2.55 (s, 3H). MS (ESI) m/z [M+H]$^+$ 151.6.

To a solution of III-2 (5 g, 33 mmol) in 20 mL of EtOH was added aq. HBr (48%, 60 mL), the reaction mixture was heated to reflux overnight. After being cooled to rt., the mixture was neutralized by addition of saturated aq. NaHCO$_3$, extracted with EtOAc (100 mL×3). The combined organic layer was washed with brine, dried over anhydrous Na$_2$SO$_4$ and concentrated to supply crude III-3 (3 g, 65% yield) as white solid.

To a solution of III-3 (1 eq.) in DCM (0.1 mmol/mL) was added boronic acid III-4 (2 eq.), Cu(OAc)$_2$ (1 eq), Pyridine (10 eq.) and Pyridine-N-Oxide (2 eq.), followed by addition of 4 Å molecular sieve (quantity approx. equal to III-3). The reaction mixture was stirred at rt under oxygen atmosphere overnight. After completion of the reaction indicated by TLC, the resulting mixture was filtered and washed with, the filtrate was washed with brine, dried over Na$_2$SO$_4$ and concentrated. The residue was purified by column chromatography on silica gel to give III-5.

Compound 10 (61% yield): $^1$H NMR (DMSO-$d_6$, 400 MHz) δ 8.43 (d, J=2.4 Hz, 1H), 7.90 (dd, J=9.6, 2.4 Hz, 1H), 7.39 (d, J=8.8 Hz, 2H), 7.06 (d, J=8.8 Hz, 2H), 6.51 (d, J=9.6 Hz, 1H), 3.81 (s, 3H), 2.41 (s, 3H).

Compound 11 (67% yield): $^1$H NMR (DMSO-$d_6$, 300 MHz) δ 8.42 (d, J=2.4 Hz, 1H), 7.88 (dd, J=9.6, 2.4 Hz, 1H), 7.34 (d, J=8.7 Hz, 2H), 7.02 (d, J=9.0 Hz, 2H), 6.49 (d, J=9.6 Hz, 1H), 4.68-4.64 (m, 1H), 3.40 (s, 3H), 1.28 (s, 3H), 1.26 (s, 3H).

Compound 12 (50% yield): $^1$H NMR (DMSO-$d_6$, 400 MHz) δ 8.57 (d, J=2.4 Hz, 1H), 7.95-7.92 (m, 2H), 7.87 (d, J=7.6 Hz, 1H), 7.82-7.79 (m, 2H), 6.56 (d, J=9.6 Hz, 1H), 2.43 (s, 3H).

Compound 13 (78% yield): $^1$H NMR (DMSO-$d_6$, 400 MHz) δ 8.52 (d, J=2.4 Hz, 1H), 7.95-7.91 (m, 1H), 7.64 (d, J=8.8 Hz, 2H), 7.56 (d, J=8.8 Hz, 2H), 6.56 (d, J=9.6 Hz, 1H), 2.44 (s, 3H).

Compound 14 (74% yield): $^1$H NMR (DMSO-$d_6$, 400 MHz) δ 8.49 (d, J=2.4 Hz, 1H), 7.91 (dd, J=9.6, 2.4 Hz, 1H), 7.56-7.52 (m, 2H), 7.40-7.35 (m, 2H), 6.53 (d, J=9.6 Hz, 1H), 2.42 (s, 3H).

Compound 15 (67% yield): $^1$H NMR (DMSO-$d_6$, 400 MHz) δ 8.45 (d, J=2.4 Hz, 1H), 7.90 (dd, J=9.6, 2.8 Hz, 1H), 7.46-7.41 (m, 1H), 7.03 (t, 3H), 6.52 (d, J=9.6 Hz, 1H), 3.79 (s, 3H), 2.42 (s, 3H).

Compound 16 (74% yield): $^1$H NMR (DMSO-$d_6$, 400 MHz) δ 8.53 (d, J=2.8 Hz, 1H), 7.90 (dd, J=9.6, 2.4 Hz, 1H), 7.64-7.58 (m, 1H), 7.52-7.48 (m, 1H), 7.41-7.35 (m, 2H), 6.57 (d, J=9.6 Hz, 2H), 2.45 (s, 3H).

Compound 17 (64% yield): $^1$H NMR (DMSO-$d_6$, 400 MHz) δ 8.55 (d, J=2.4 Hz, 1H), 7.92 (dd, J=9.6, 2.4 Hz, 1H), 7.67-7.63 (m, 2H), 7.55 (d, J=8.4 Hz, 2H), 6.56 (d, J=9.6 Hz, 1H), 2.42 (s, 3H).

Compound 18 (23% yield): $^1$H NMR (DMSO-$d_6$, 400 MHz) δ 8.37 (d, J=2.4 Hz, 1H), 7.92 (dd, J=9.6, 2.4 Hz, 1H), 7.20 (d, J=8.4 Hz, 1H), 6.95 (d, J=2.8 Hz, 1H), 6.52 (d, J=9.6 Hz, 1H), 4.06 (q, J=6.8 Hz, 2H), 2.40 (s, 3H), 2.00 (s, 3H), 1.34 (t, J=6.8 Hz, 3H).

Compound 19 (40% yield): $^1$H NMR (DMSO-$d_6$, 400 MHz) δ 10.18 (s, 1H), 8.46 (d, J=2.4 Hz, 1H), 7.91 (dd, J=9.6, 2.4 Hz, 1H), 7.73 (s, 1H), 7.60 (d, J=8.4 Hz, 1H), 7.46 (t, J=8.0 Hz, 1H), 7.12 (dd, J=7.6, 0.8 Hz, 1H), 6.53 (d, J=9.6 Hz, 1H), 2.41 (s, 3H), 2.05 (s, 3H).

Compound 20 was prepared following the general procedure, except the solvent was changed to acetonitrile (10% yield). $^1$H NMR (CDCl$_3$, 400 MHz) δ 8.06 (d, J=2.4 Hz, 1H), 7.97 (dd, J=10, 2.4 Hz, 1H), 7.53-7.45 (m, 1H), 7.43-7.36 (m, 1H), 7.34-7.25 (m, 2H), 6.67 (d, J=10 Hz, 1H), 2.45 (s, 3H). MS (ESI) m/z (M+H)$^+$ 232.0.

Example 3-A

Synthesis of Compound 21 (Scheme IV)

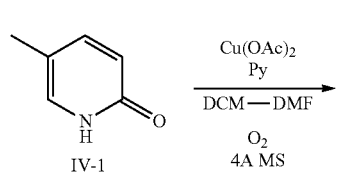

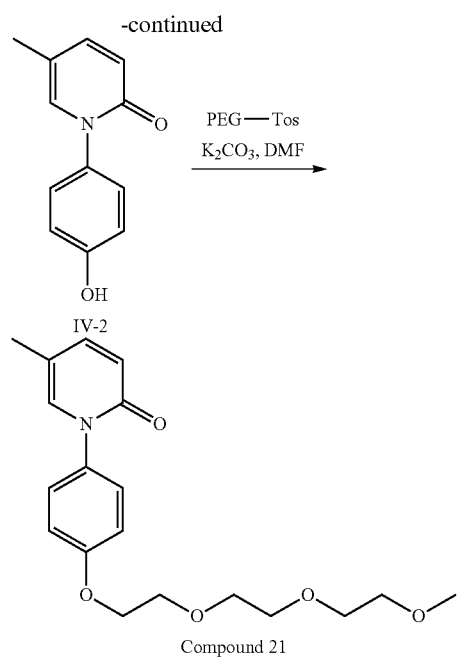

Compound 21

To a solution of 5-methyl-2-pyridone IV-1 (643 mg, 5.9 mmol) in DCM (71 mL) and DMF (23.5 mL), Cu(OAc)$_2$ (2.14 g, 11.784 mmol), 4-hydroxy phenyl boronic acid (0.975 g, 7.07 mmol), pyridine (0.95 mL, 11.784 mmol) and activated 4 Å molecular sieves (7.1 g) were added. The mixture was stirred at rt for 24 hours. A concentrated solution of NH$_4$OH was added, filtered through celite. Filtrate was evaporated under vacuum, and the resulting crude was purified by flash chromatography (SiO$_2$, DCM/MeOH) to afford IV-2, 600 mg (51% yield) of pure product as pale yellow solid. MS: m/z 202.2 (M+H).

To a suspension of IV-2 (250 mg, 1.24 mmol) in DMF (9 mL) was added PEG-Tos (395 mg, 1.24 mmol), K$_2$CO$_3$ (343 mg, 2.48 mmol) and heated at 50° C. for 24 hours. Reaction mixture was filtered through a celite pad, washed with MeOH and solvents were removed under vacuum. The crude material was purified by flash chromatography (SiO$_2$, DCM/MeOH) to afford Compound 21 (400 mg, 93% yield) of pure product as colorless oil. MS: m/z 348.4 (M+H).

Compound 22 was prepared following the similar procedure for obtaining Compound 21 using 1-(3-hydroxyphenyl)-5-methylpyridin-2(1H)-one in place of IV-2. MS: m/z=348.6 (M+H).

Example 3-B

Synthesis of Compound 23 (Scheme V)

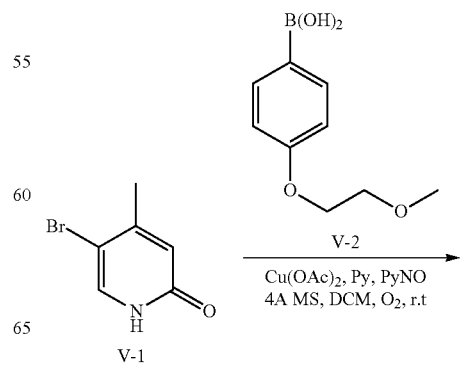

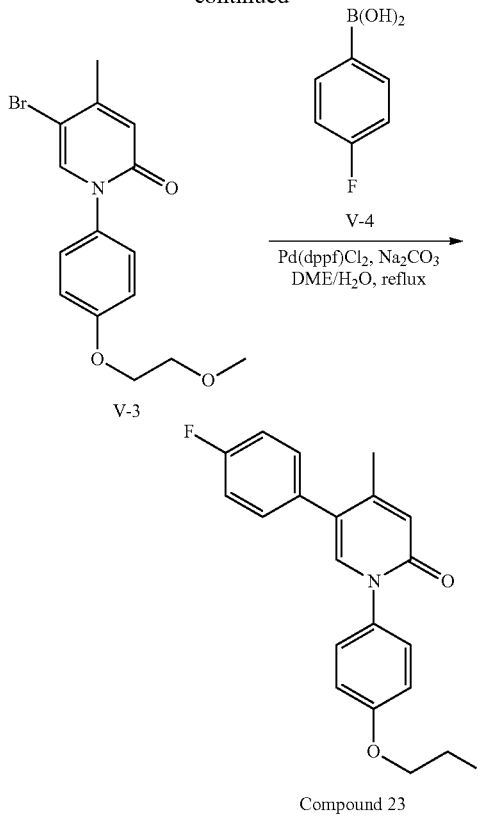

Compound 23

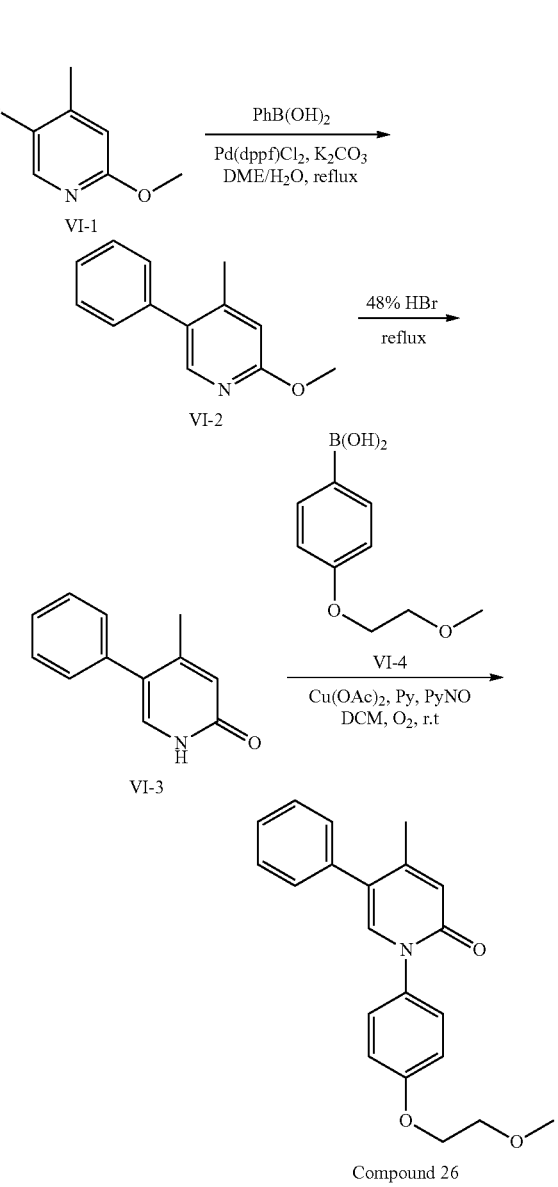

Compound 26

1H), 7.01 (d, J=8.8 Hz, 2H), 6.58 (s, 1H), 4.15 (t, J=4.8 Hz, 2H), 3.76 (t, J=4.8 Hz, 2H), 3.46 (s, 3H), 2.21 (s, 3H).

Compound 25 was prepared following the similar procedure for obtaining Compound 23 using 1-methyl-4-(4,4,5,5-tetramethyl-1,3,2-dioxaborolan-2-yl)-1H-pyrazole in place of V-4 as a yellow oil. $^1$H NMR (CDCl$_3$, 400 MHz) δ 7.47 (s, 1H), 7.36 (s, 1H), 7.31-7.22 (m, 3H), 7.03-6.98 (m, 2H), 6.55 (s, 1H), 4.14 (t, J=4.8 Hz, 2H), 3.93 (s, 3H), 3.76 (t, J=4.8 Hz, 2H), 3.46 (s, 3H), 2.21 (s, 3H).

Example 3-C

Synthesis of Compound 26 (Scheme VI)

A mixture of V-1 (4.3 g, 22 mmol), boronic acid V-2 (2.75 g, 14 mmol), pyridine (3.58 mL, 43.9 mmol), pyridine N-oxide (4.2 g, 43.9 mmol), 4 Å molecular sieve (300 mg) and Cu(OAc)$_2$ (7.95 g, 43.9 mmol) in anhydrous DCM (200 mL) was degassed by purging with O$_2$. The reaction mixture was stirred at r.t. for 12 hours. The suspension was filtered and filtrate was washed with brine, dried over anhydrous Na$_2$SO$_4$, and concentrated in vacuo. The residue was purified by flash chromatography on silica gel with PE/EtOAc (10:1→2:1) to give V-3 (1.76 g, 36% yield). $^1$H NMR (CDCl$_3$, 300 MHz) δ 7.48 (s, 1H), 7.26-7.23 (m, 2H), 7.01-6.98 (m, 2H), 6.54 (s, 1H), 4.14 (t, J=4.8 Hz, 2H), 3.76 (t, J=4.8 Hz, 2H), 3.45 (s, 3H), 2.27 (s, 3H).

To a solution of V-3 (510 mg, 1.51 mmol) in 12 mL of DME/H$_2$O (v/v=5/1) was added Na$_2$CO$_3$ (320 mg, 3.02 mmol), V-4 (317 mg, 2.26 mmol), Pd(dppf)Cl$_2$ (110 mg, 0.15 mmol). The mixture was purged with nitrogen and then heated at reflux overnight. The mixture was cooled to r.t., diluted with water (30 mL), extracted with EtOAc (100 mL×3). The combined organic layer was washed with brine, dried over anhydrous Na$_2$SO$_4$, and concentrated in vacuo. The residue was purified by flash chromatography on silica gel with PE/EtOAc (10:1→1:1) to produce Compound 23 (300 mg, 56% yield) as a yellow oil. $^1$H NMR (CDCl$_3$, 400 MHz) δ 7.33-7.30 (m, 2H), 7.25-7.23 (m, 2H), 7.17 (s, 1H), 7.11-7.07 (m, 2H), 7.02-7.00 (m, 2H), 6.56 (s, 1H), 4.15 (t, J=4.8 Hz, 2H), 3.76 (t, J=4.8 Hz, 2H), 3.45 (s, 3H), 2.12 (s, 3H).

Compound 24 was prepared following the similar procedure for obtaining Compound 23 using tert-butyl 4-(4,4,5,5-tetramethyl-1,3,2-dioxaborolan-2-yl)-1H-pyrazole-1-carboxylate in place of V-4 as a yellow oil. $^1$H NMR (CDCl$_3$, 400 MHz) δ 7.58 (s, 2H), 7.30 (d, J=8.8 Hz 2H), 7.26 (s, To a stirred mixture of VI-1 (600 mg, 2.97 mmol), phenyl boronic acid (435 mg, 3.56 mmol), and K$_3$CO$_3$ (409 mg, 8.91 mmol) in DME/H$_2$O (22 mL, v/v=10/1) was added Pd(dppf)Cl$_2$ (436 mg, 0.594 mmol). The mixture was purged with nitrogen for three times and then heated at 100° C. overnight. The mixture was concentrated to remove DME, diluted with H$_2$O (50 mL), extracted with EtOAc (100 mL×3). The combined organic layer was washed with water and brine, dried over anhydrous Na$_2$SO$_4$, and concentrated in vacuo. The crude product was purified by prep-TLC (PE/EA=5/1) to give VI-2 (226 mg, 38% yield).

A mixture of VI-2 (226 mg, 1.13 mmol) with aq. HBr (48%, 10 mL) was heated to reflux under nitrogen overnight. After being cooled to r.t., the mixture was neutralized by adding saturated aq. NaHCO$_3$, and then extracted with EtOAc (80 mL×3). The combined organic layer was washed with water and brine, dried over anhydrous Na$_2$SO$_4$, and concentrated in vacuo to afford VI-3 (180 mg, 85% yield).

To a stirred mixture of VI-3 (180 mg, 0.972 mmol), boronic acid VI-4 (285 mg, 1.46 mmol), copper (II) acetate (528 mg, 2.92 mmol) and pyridine (231 mg, 2.92 mmol) in DCM (10 mL) was added pyridine-N-oxide (277 mg, 2.92 mmol) in one portion. The solution was stirred at r.t. under oxygen atmosphere overnight. After completion of the reaction indicated by TLC, the resulting mixture was concentrated in vacuo. Dissolved the residue in ethyl acetate (100 mL), filtered, and washed the filtrate with brine. The organic phase was dried over anhydrous sodium sulfate, filtered, concentrated in vacuo to afford a yellowish solid. The crude product was purified by prep-HPLC to give Compound 26 (48.8 mg, 15% yield) as a yellow solid. $^1$H NMR (CDCl$_3$, 400 MHz) δ 7.42-7.28 (m, 7H), 7.20 (s, 1H), 7.00 (d, J=8.8 Hz, 2H), 6.57 (s, 1H), 4.14 (t, J=4.8 Hz, 2H), 3.76 (t, J=4.8 Hz, 2H), 3.46 (s, 3H), 2.15 (s, 3H).

Example 4

Synthesis of Compound 27 (Scheme VII)

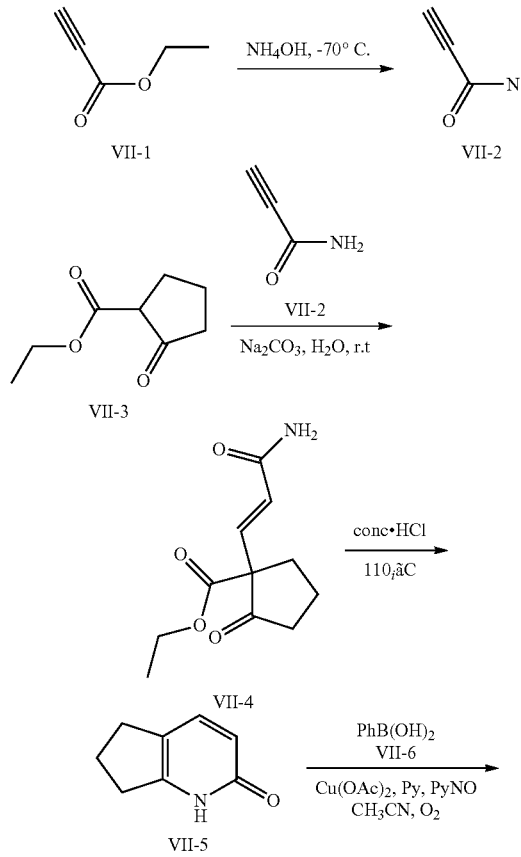

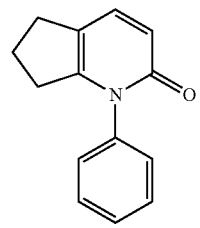

Compound 27

VII-1 (2 g, 20 mmol) was added dropwise to ammonia (7 mL) at −70° C. The reaction mixture was stirred at −70° C. for 1 hour, and then the reaction mixture was warmed to rt for one additional hour. The organic layer was separated and evaporated to produce VII-2, which was used directly for next step.

A mixture of VII-2 (0.69 g, 10 mmol), VII-3 (1.56 g, 10 mmol), and Na$_2$CO$_3$ (1.06 g, 10 mmol) in water (25 ml) was stirred at rt overnight. And then the mixture was extracted with EtOAc (50 mL×3). The combined organic layer was washed with brine, dried over anhydrous Na$_2$SO$_4$ and concentrated. The residue was purified by flash chromatography on silica gel with PE/EtOAc (4/1) to yield VII-4 (0.55 g, 24% yield). $^1$H NMR (CDCl$_3$, 400 MHz) δ 7.13 (s, 1H), 6.63 (d, J=10 Hz, 1H), 5.88 (d, J=10 Hz, 1H), 5.39 (brs, 1H), 4.24-4.15 (m, 2H), 2.50-2.42 (m, 1H), 2.33-2.25 (m, 1H), 2.02-1.95 (m, 1H), 1.92-1.80 (m, 2H), 1.76-1.66 (m, 1H), 1.27-1.18 (m, 3H).

A solution of VII-4 (1.13 g, 5 mmol) in conc. HCl (30 mL) was stirred in a sealed tube at 110° C. overnight. The solvent was evaporated under vacuum to yield crude VII-5 (0.95 g, 111% crude yield). $^1$H NMR (DMSO-d$_6$, 400 MHz) δ 7.85 (d, J=8.8 Hz, 1H), 6.82 (d, J=8.8 Hz, 1H), 2.93-2.80 (m, 2H), 2.78-2.72 (m, 2H), 2.13-2.02 (m, 2H).

To a mixture of VII-5 (0.513 g, 3 mmol) and phenyl boronic acid VII-6 (0.732 g, 6 mmol) in acetonitrile (30 mL) was added Cu(OAc)$_2$ (1.64 g, 9 mmol), pyridine (1.42 g, 18 mmol) and pyridine-N-oxide (0.86 g, 9 mmol). The mixture was stirred under oxygen atmosphere at rt overnight. The mixture was diluted with water (50 mL) and extracted with CH$_2$Cl$_2$ (50 mL×3). The combined organic layer was washed with brine, dried over Na$_2$SO$_4$, and concentrated under reduced pressure. The residue was purified by column chromatography on silica gel with petroleum ether/EtOAc (8:1~1:1) to afford Compound 27 (0.38 g, 60% yield). $^1$H NMR (CDCl$_3$, 400 MHz) δ 7.51-7.41 (m, 3H), 7.33-7.31 (m, 1H), 7.25-7.22 (m, 2H), 6.51 (d, J=9.2 Hz, 1H), 2.81-2.77 (m, 2H), 2.50-2.46 (m, 2H), 2.07-2.00 (m, 2H). MS (ESI) m/z (M+H)$^+$ 212.0.

Compound 28 was prepared following the similar procedure for obtaining Compound 27 using (4-(trifluoromethoxy)phenyl)boronic acid in place of phenyl boronic acid (VII-6). $^1$H NMR: (CDCl$_3$, 400 MHz) δ 7.37-7.26 (m, 5H), 6.50 (d, J=9.2 Hz, 1H), 2.81-2.77 (m, 2H), 2.51-2.47 (m, 2H), 2.09-2.02 (m, 2H). MS (ESI) m/z (M+H)$^+$ 295.9.

Example 5-A

Synthesis of Compound 29 (Scheme VIII)

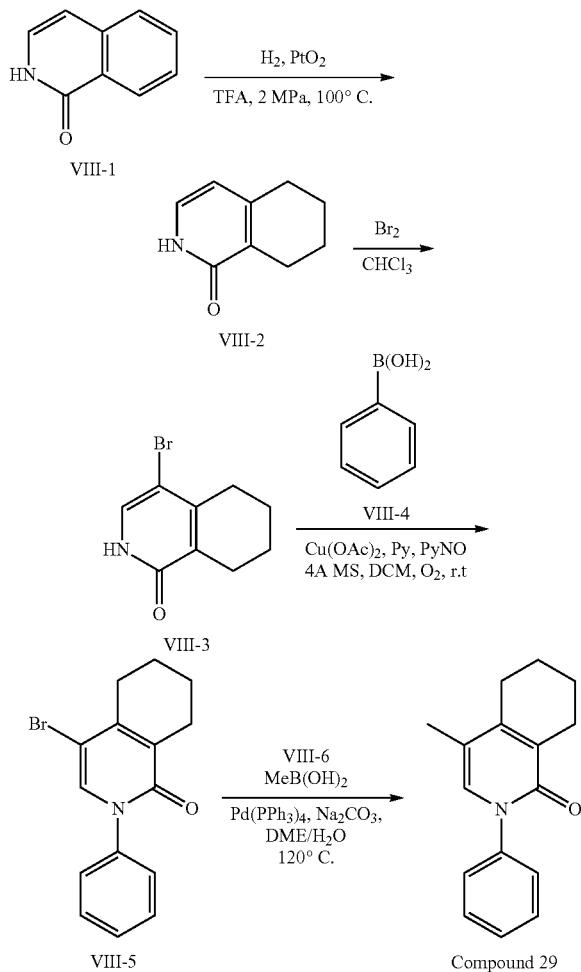

An autoclave was charged with VIII-1 (4.0 g, 27.6 mmol), $PtO_2$ (400 mg) and 50 mL of TFA. The mixture was stirred at 110° C. under hydrogen (pressure 2.0 MPa) for 1 day, then the solution was filtered, and the solid was washed with MeOH. The filtrate was concentrated under reduced pressure. The resulting residue was purified by column chromatography on silica gel with petroleum ether/EtOAc (10:1→5:1→1:1→1:5→EtOAc) to give VIII-2 (2.1 g, 51% yield) as white solid. $^1$H NMR (CDCl$_3$, 400 MHz) δ 12.85 (brs, 1H), 7.16 (d, J=6.4 Hz, 1H), 6.02 (d, J=6.4 Hz, 1H), 2.60-2.50 (m, 4H), 1.81-1.71 (m, 4H). MS (ESI) m/z [M+H]$^+$ 149.8.

To a solution of VIII-2 (1.04 g, 7 mmol) in CHCl$_3$ (20 mL) was added Br$_2$ (1.12 g, 7 mmol) dropwise at 0° C. The reaction mixture was stirred at rt for 2 hrs. And then the reaction mixture was poured into ice-water, and the solid formed was collected by filtration, the filtrate was extracted with EtOAc (50 mL×3), the solid was re-dissolved in EtOAc (40 mL). The combined organic layer was washed with brine, dried over Na$_2$SO$_4$ and concentrated under reduced pressure to afford crude VIII-3 (1.3 g, 61% yield). $^1$H NMR (CDCl$_3$, 300 MHz) δ 7.44 (s, 1H), 2.62-2.52 (m, 4H), 1.81-1.72 (m, 4H). MS (ESI) m/z [M+H]$^+$ 227.

VIII-3 (500 mg, 2.2 mmol, 1.0 eq.), VIII-4 (405 mg, 3.3 mmol, 1.5 eq.), Cu(OAc)$_2$ (1.2 g, 6.6 mmol, 3 eq.), pyridine-N-oxide (630 mg, 6.6 mmol, 3 eq.) and pyridine (520 mg, 6.6 mmol, 3 eq.) and 4 Å molecular sieve (500 mg) was added into 150 mL of anhydrous DCM. The mixture was stirred under oxygen atmosphere at r.t. overnight. The reaction mixture was filtered; the combined organic layer was washed with brine, dried over Na$_2$SO$_4$, and concentrated. The resulting residue was re-crystallized from EtOAc to yield VIII-5 (550 mg, 83% yield). $^1$H NMR (CDCl$_3$, 300 MHz) δ 7.49-7.30 (m, 6H), 2.64-2.58 (m, 4H), 1.81-1.72 (m, 4H). MS (ESI) m/z (M+H)$^+$ 303.9.

A flask was charged with VIII-5 (300 mg, 1 mmol, 1 eq.), MeB(OH)$_2$ (240 mg, 4.0 mmol, 4 eq.), and Na$_2$CO$_3$ (418 mg, 3.0 mmol, 3 eq.) in DME/H$_2$O (24 mL, V/V=5/1). It was purged with N$_2$, and then Pd(PPh$_3$)$_4$ (115 mg, 0.1 mmol, 0.1 eq.) was added. The reaction mixture was purged with N$_2$ again and then stirred at 110° C. overnight. The mixture was concentrated under reduced pressure to remove the solvent, and then it was diluted with H$_2$O (30 mL), extracted with EtOAc (30 mL×3), the combined organic layer was washed with brine, dried over Na$_2$SO$_4$, and concentrated in vacuo. The residue was purified by prep-TLC (PE: EA=2.5:1) to give Compound 29 (190 mg, 79% yield) as white solid. $^1$H NMR (CDCl$_3$, 400 MHz) δ 7.47-7.42 (m, 2H), 7.39-7.35 (m, 3H), 6.99 (s, 1H), 2.61-2.58 (m, 2H), 2.52-2.50 (m, 2H), 2.00 (s, 3H), 1.81-1.75 (m, 4H). MS (ESI) m/z [M+H]$^+$ 240.1.

Compound 30 was prepared following the similar procedure for obtaining Compound 29 using (4-fluorophenyl) boronic acid in place of methyl boronic acid (VIII-6) as a white solid. $^1$H NMR (CDCl$_3$, 400 MHz) δ 7.48-7.37 (m, 5H), 7.26-7.23 (m, 2H), 7.10-7.06 (m, 3H), 2.68-2.64 (m, 2H), 2.40-2.37 (m, 2H), 1.81-1.77 (m, 2H), 1.72-1.68 (m, 2H). MS (ESI) m/z [M+H]$^+$ 320.0.

Compound 31 was prepared following the similar procedure for obtaining Compound 29 using 1-methyl-4-(4,4,5,5-tetramethyl-1,3,2-dioxaborolan-2-yl)-1H-pyrazole in place of methyl boronic acid (VIII-6). $^1$H NMR (CDCl$_3$, 400 MHz) δ 7.49-7.45 (m, 3H), 7.41-7.39 (m, 3H), 7.34 (s, 1H), 7.15 (s, 1H), 3.93 (s, 3H), 2.65-2.62 (m, 2H), 2.55-2.52 (m, 2H), 1.80-1.72 (m, 4H). MS (ESI) m/z [M+H]$^+$ 306.2.

Compound 32 was prepared following the similar procedure for obtaining Compound 30 using (4-(trifluoromethoxy)phenyl)boronic acid in place of phenyl boronic acid (VIII-4). $^1$H NMR (CDCl$_3$, 400 MHz) δ 7.49-7.45 (m, 2H), 7.31 (d, J=8.4 Hz, 2H), 7.26-7.22 (m, 2H), 7.11-7.06 (m, 3H), 2.66-2.63 (m, 2H), 2.40-2.37 (m, 2H), 1.81-1.74 (m, 2H), 1.72-1.67 (m, 2H). MS (ESI) m/z [M+H]$^+$ 404.2.

Compound 33 was prepared following the similar procedure for obtaining Compound 31 using (4-(trifluoromethoxy)phenyl)boronic acid in place of phenyl boronic acid (VIII-4). $^1$H NMR (CDCl$_3$, 400 MHz) δ 7.46-7.43 (m, 3H), 7.34-7.30 (m, 3H), 7.17 (s, 1H), 3.94 (s, 3H), 2.64-2.61 (m, 2H), 2.54-2.51 (m, 2H), 1.81-1.72 (m, 4H). MS (ESI) m/z [M+H]$^+$ 390.2.

Compound 34 was prepared following the similar procedure for obtaining Compound 30 using (4-(trifluoromethoxy)phenyl)boronic acid in place of phenyl boronic acid (VIII-4) and (4-fluorophenyl)boronic acid in place of methyl boronic acid (VIII-6). $^1$H NMR (CDCl$_3$, 400 MHz) δ 7.48-7.45 (m, 2H), 7.44-7.30 (m, 3H), 7.10-6.97 (m, 4H), 2.64 (t, J=6.0 Hz, 2H), 2.41 (t, J=6.0 Hz, 2H), 1.82-1.76 (m, 2H), 1.72-1.66 (m, 2H). MS (ESI) m/z [M+H]$^+$ 404.0.

Compound 35 was prepared following the similar procedure for obtaining Compound 29 using (4-ethoxy-2-methylphenyl)boronic acid in place of phenyl boronic acid (VIII- 4) and 1-methyl-4-(4,4,5,5-tetramethyl-1,3,2-dioxaborolan-2-yl)-1H-pyrazole in place of methyl boronic acid (VIII-6). $^1$H NMR (CDCl$_3$, 400 MHz) δ 7.45 (s, 1H), 7.33 (s, 1H), 7.08 (d, J=8.4 Hz, 1H), 7.00 (s, 1H), 6.85-6.77 (m, 2H), 4.04 (q, J=6.8 Hz, 2H), 3.92 (s, 3H), 2.65-2.61 (m, 2H), 2.57-2.52 (m, 2H), 3.13 (s, 3H), 1.82-1.70 (m, 4H), 1.42 (t, J=6.8 Hz, 3H). MS (ESI) m/z [M+H]$^+$ 364.1

Compound 36 was prepared following the similar procedure for obtaining Compound 29 using (4-ethoxy-2-methylphenyl)boronic acid in place of phenyl boronic acid (VIII-4) and tert-butyl 4-(4,4,5,5-tetramethyl-1,3,2-dioxaborolan-2-yl)-1H-pyrazole-1-carboxylate in place of methyl boronic acid (VIII-6). $^1$H NMR (CDCl$_3$, 400 MHz) δ 7.72 (s, 2H), 7.19 (s, 1H), 7.10 (d, J=8.4 Hz, 1H), 6.92 (s, 1H), 6.85-6.82 (m, 2H), 4.05 (q, J=6.8 Hz, 2H), 2.65-2.61 (m, 2H), 2.57-2.52 (m, 2H), 2.01 (s, 3H), 1.80-1.70 (m, 4H), 1.35 (t, J=6.8 Hz, 3H). MS (ESI) m/z [M+H]$^+$ 350.1.

Compound 37 was prepared following the similar procedure for obtaining Compound 29 using (4-(trifluoromethoxy)phenyl)boronic acid in place of phenyl boronic acid (VIII-4) and tert-butyl 4-(4,4,5,5-tetramethyl-1,3,2-dioxaborolan-2-yl)-1H-pyrazole-1-carboxylate in place of methyl boronic acid (VIII-6) as white solid. Na$_2$CO$_3$ was replaced with K$_3$PO$_4$. $^1$H NMR (CDCl$_3$, 400 MHz) δ 7.60-7.52 (m, 2H), 7.46 (d, J=8.4 Hz, 2H), 7.31 (d, J=8.4 Hz, 2H), 7.14 (s, 1H), 2.65-2.62 (m, 2H), 2.52-2.49 (m, 2H), 1.82-1.70 (m, 4H). MS (ESI) m/z [M+H]$^+$ 376.0.

Example 5-B

Synthesis of Compound 38 (Scheme IX)

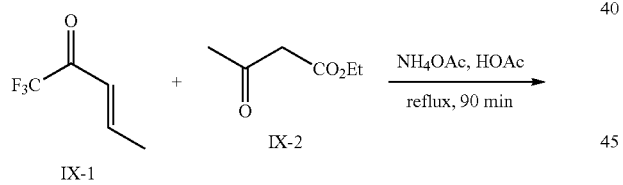

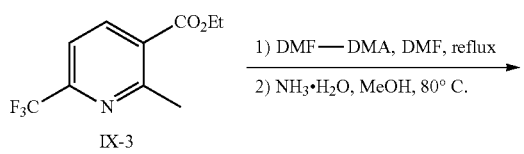

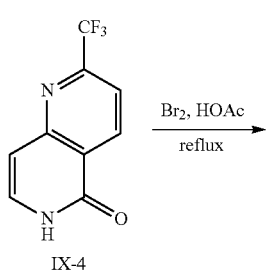

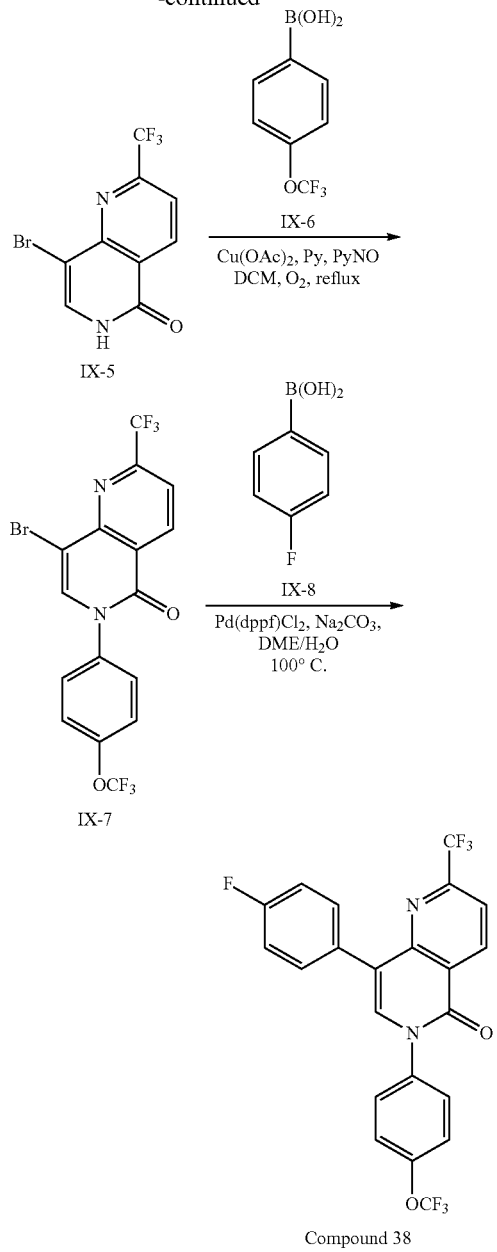

A mixture of IX-1 (14.2 g, 84.6 mmol), IX-2 (10.0 g, 76.9 mmol), NH$_4$OAc (12.0 g 153.8 mmol) in HOAc (18.6 g, 307.6 mmol) was heated at reflux for 90 min. The mixture was allowed to cool to rt. Water (30 mL) was added and the reaction mixture was extracted with DCM (100 mL×3). The combined organic layer was washed with brine, dried over anhydrous Na$_2$SO$_4$ and concentrated in vacuo. The crude product was purified by column chromatography with petroleum ether/EtOAc (5:1→1:1) to afford IX-3 (12 g, 67% yield) as yellow solid. MS (ESI) m/z [M+H]$^+$ 234.1.

A mixture of IX-3 (12 g, 52 mmol) and DMF-dimethylacetal (6.2 g, 52 mmol) in DMF (30 mL) was heated to reflux overnight. And then it was allowed to cool to rt. The solvent was removed under reduced pressure and the residue was treated with 18% ammonia in methanol (50 mL) at 80° C. for 2 hrs. The solvent was removed under reduced pressure and the resulting residue was purified by column chromatography with petroleum ether/EtOAc (2:1→1:2) yield IX-4 (2.3 g, 21% yield) as a yellow solid. MS (ESI) m/z [M+H]+ 214.9.

A solution of $Br_2$ (747 mg, 4.67 mmol) in HOAc (5 mL) was added dropwise to a stirred solution of IX-4 (1 g, 4.67 mmol) in HOAc (10 mL). Upon complete addition, the reaction mixture was allowed to stir at rt for 30 min before being heated at reflux for 2 hrs. Once the reaction mixture was cooled to rt, water (20 mL) was added, the resultant precipitate was filtered off and air-dried. The product was then taken up in EtOAc (100 mL), the organic layer was washed with water, saturated aqueous sodium hydrogen carbonate, brine, dried over anhydrous $Na_2SO_4$, and concentrated in vacuo. The crude product was purified by column chromatography with petroleum ether/EtOAc (2:1→1:2) to afford IX-5 (1.3 g, 95% yield) as solid. MS (ESI) m/z [M+H]+ 293.

To a stirred solution of IX-5 (500 mg, 1.7 mmol), IX-6 (380 mg, 1.88 mmol), $Cu(OAc)_2$ (923 mg, 5.1 mmol) and pyridine (408 mg, 5.1 mmol) in DCM (10 mL) was added pyridine-N-oxide (484 mg, 5.1 mmol) in one portion. The solution was refluxed under oxygen atmosphere overnight. After completion of the reaction indicated by TLC, the reaction mixture was concentrated in vacuo. Dissolved the residue in ethyl acetate (100 mL), filtered, and washed the filtrate with brine. The organic phase was dried over anhydrous sodium sulfate, filtered, concentrated in vacuo to afford a yellowish solid. The crude product was purified by flash column chromatography with petroleum ether/EtOAc (5:1→1:1) to afford IX-7 (600 mg, 78% yield) as a yellow solid. MS (ESI) m/z [M+H]+ 453.

To a stirred mixture of IX-7 (250 mg, 0.55 mmol), IX-8 (116 mg, 0.83 mmol), and $Na_2CO_3$ (117 mg, 1.1 mmol) in $DME/H_2O$ (5 mL, v:v=5:1) was added $Pd(dppf)Cl_2$ (41 mg, 0.055 mmol). The mixture was purged with nitrogen for three times and then heated at 100° C. overnight. The mixture was concentrated to remove diluted with water (30 mL), extracted with EtOAc (30 mL×3). The combined organic layer was washed with brine, dried over anhydrous $Na_2SO_4$ and concentrated in vacuo. The crude product was purified by flash column chromatography with PE/EA (5:1→1:1) to give Compound 38 (176.5 mg, 68% yield) as a yellow solid. $^1$H NMR (DMSO-$d_6$, 400 MHz) δ 8.94 (d, J=8.0 Hz, 1H), 8.08 (d, J=8.0 Hz, 1H), 7.99 (s, 1H), 7.78-7.72 (m, 4H), 7.59-7.55 (m, 2H), 7.31-7.27 (m, 2H). MS (ESI) m/z [M+H]+ 469.1.

Compound 39 was prepared following the similar procedure for obtaining Compound 38 using 1-methyl-4-(4,4,5,5-tetramethyl-1,3,2-dioxaborolan-2-yl)-1H-pyrazole in replace of IX-8. $^1$H NMR (DMSO-$d_6$, 400 MHz) δ 8.91 (d, J=8.4 Hz, 1H), 8.33 (s, 1H), 8.19 (s, 1H), 8.09-8.06 (m, 2H), 7.74-7.70 (m, 2H), 7.60-7.57 (m, 2H), 3.87 (s, 3H). MS (ESI) m/z [M+H]+ 455.0.

Example 5-C

Synthesis of Compound 40 (Scheme X)

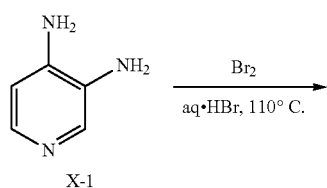

To the mixture of X-1 (10.0 g, 10 mmol) dissolved in HBr 48% (200 mL), $Br_2$ (12.5 mL, 13.4 mmol) was added dropwise under ice-water cooling bath, maintaining the temperature below 40° C. After that, the mixture was heated at 110° C. for 5 hrs. The reaction mixture was cooled to rt, filtered and washed with little water. The filter cake is basified to pH 7-8 with saturated aq. $NaHCO_3$ and extracted with EtOAc (200 mL×3). The combined organic layer was

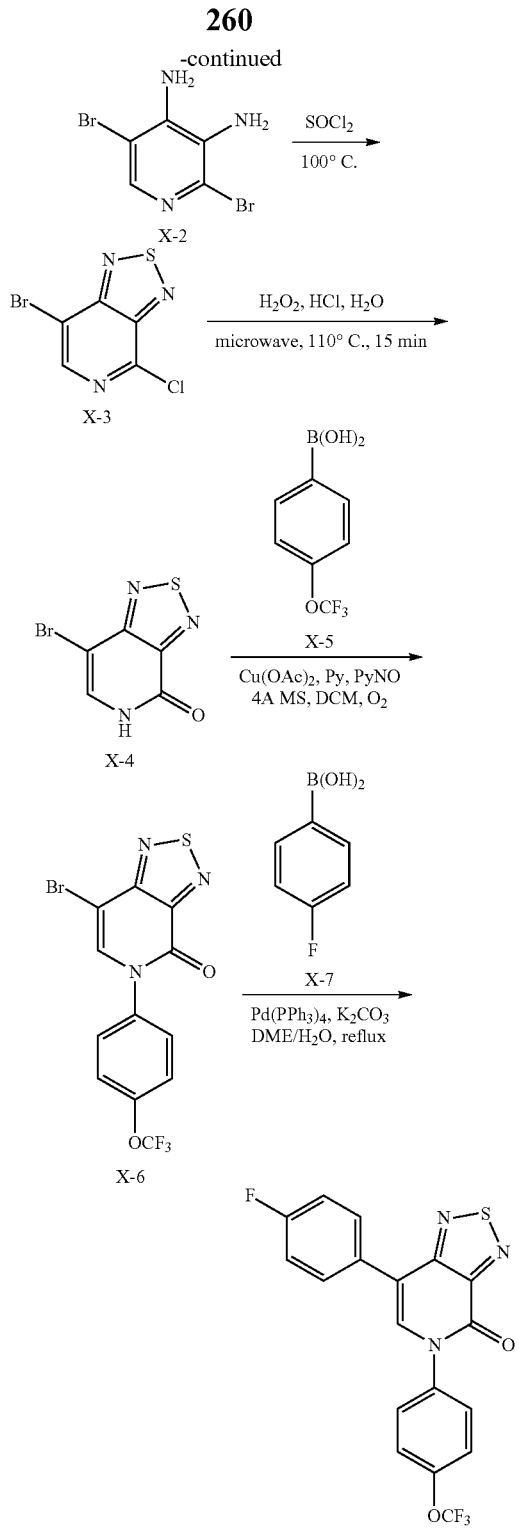

Compound 40 washed with brine, dried over anhydrous Na₂SO₄ and concentrated to yield X-2 (17.2 g, 71% yield). ¹H NMR (DMSO-d₆, 400 MHz) δ 7.95 (s, 1H), 5.20 (brs, 4H).

X-2 (5.0 g, 18.9 mmol) was dissolved in SOCl₂ (50 mL). The mixture was stirred at 100° C. for 5 hrs. Removed the excessive solvent, the residue was diluted with EtOAc (200 mL), washed with brine, dried over Na₂SO₄. Filtration, concentration and the residue was X-3 (4.64 g, 100% yield). Compound 3 was used in next step without further purification. ¹H NMR (DMSO-d₆, 400 MHz) δ 8.55 (s, 1H).

X-3 (1.0 g, 4 mmol) was dissolved in water (10 mL), and then two drops H₂O₂ (30%) and 2 drops conc. HCl was added. The mixture was stirred at 100° C. for 15 min under microwave. After being cooled to rt, the reaction mixture was extracted with EtOAc (50 mL×3). The combined organic layer was washed with brine, dried over anhydrous Na₂SO₄ and concentrated in vacuo to afford X-4 (700 mg, 75% yield). X-4 was used in next step without further purification. ¹H NMR (DMSO-d₆, 400 MHz) δ 11.97 (s, 1H), 7.81 (s, 1H).

To a solution of X-4 (330 mg, 1.4 mmol) in DCM (30 mL), Cu(OAc)₂ (800 mg, 4.4 mmol), X-5 (500 mg, 2 mmol), pyridine (1 mL), pyridine-N-oxide (400 mg, 4 mmol) and finely ground, activated 4 Å molecular sieves (300 mg) were added. The mixture was stirred at rt for 12 hrs under O₂ atmosphere. The mixture was diluted with EtOAc (100 mL) and filtered, the filtrate was washed with brine, dried over Na₂SO₄, and concentrated. The residue was purified by flash column chromatography (PE/EtOAc=5/1) to give X-6 (280 mg, 50% yield) as a yellow solid. ¹H NMR (CDCl₃, 400 MHz) δ 7.67 (s, 1H), 7.50-7.48 (m, 2H), 7.41-7.39 (m, 2H).

X-6 (230 mg, 0.58 mmol), X-7 (100 mg, 0.71 mmol) and K₂CO₃ (300 mg, 2.17 mmol) were charged into 22 mL of DME/H₂O (v/v=10/1). The reaction mixture was degassed by N₂ for three times and then Pd(PPh₃)₄ (60 mg, 0.052 mmol) was added. The reaction mixture was refluxed for 3 hrs. After being cooled to rt, the mixture was diluted with EtOAc (60 mL) and filtered. The filtrate was washed with brine, dried over Na₂SO₄, concentrated. The residue was purified by flash column chromatography (PE/EtOAc=5/1) to give Compound 40 (150 mg, 63% yield) as a yellow solid. ¹H NMR (CDCl₃, 400 MHz) δ 7.77-7.73 (m, 2H), 7.56-7.51 (m, 3H), 7.41 (d, J=8.0 Hz, 2H), 7.22-7.17 (m, 2H). MS (ESI) m/z (M+H)⁺ 407.8.

Compound 41 was prepared following the similar procedure for obtaining Compound 40 using 1-methyl-4-(4,4,5,5-tetramethyl-1,3,2-dioxaborolan-2-yl)-1H-pyrazole in replace of X-7. ¹H NMR (CDCl₃, 400 MHz) δ 8.23 (s, 1H), 7.85 (s, 1H), 7.58 (s, 1H), 7.53 (d, J=8.8 Hz, 2H), 7.41 (d, J=8.8 Hz, 2H), 4.00 (s, 3H). MS (ESI) m/z (M+H)⁺ 393.8.

Example 5-D

Synthesis of Compound 42 (Scheme XI)

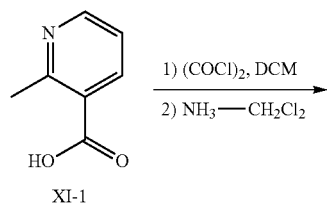

XI-1

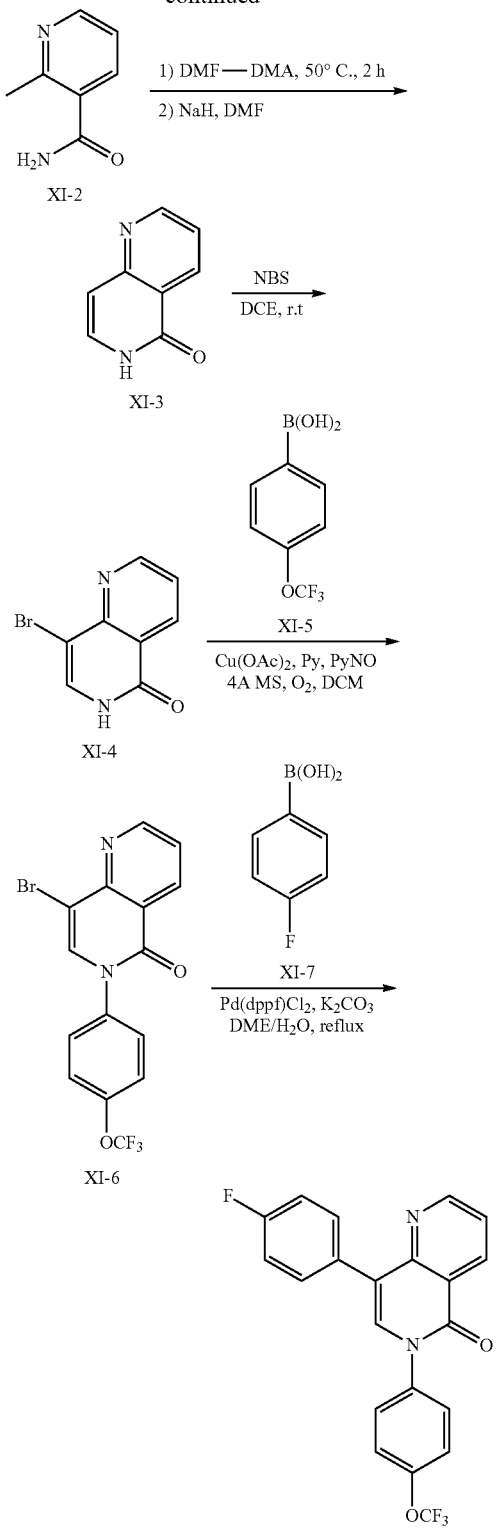

To the solution of XI-1 (10 g, 73 mmol, 1 eq) in 50 mL of DCM was added 15 mL of oxalyl chloride (adding a drop of DMF). The mixture was stirred for 18 hrs at rt. All the volatiles were removed under reduced pressure. The residue was dried and used directly for the next step (11.3 g, 100% yield). The solid was dissolved in 30 mL of DCM and added into 200 mL of $CH_2Cl_2$—$NH_3$ at −30° C. The mixture was stirred for 18 hrs. LCMS analysis showed the reaction completed. All the volatiles were removed under reduced pressure to afford XI-2 (7 g, 71% yield), which was used directly for the next step. $^1H$ NMR (DMSO-$d_6$, 400 MHz): δ 8.45 (m, 1H), 7.93 (s, 1H), 7.71 (d, J=7.6 Hz, 1H), 7.54 (s, 1H), 7.23 (m, 1H), 2.48 (s, 3H).

A mixture of XI-2 (13 g, 95.6 mmol, 1 eq) and 18.2 mL of N,N-dimethylformamide dimethyl acetal was heated at 50° C. for 2 hrs. During the second hour, all the volatiles was removed. The residue was cooled to rt., diluted with 100 mL of anhydrous N,N-dimethylformamide, and then treated carefully with batch wise portions of sodium hydride (5 g, 124.3 mmol, 1.3 eq, 60% oil dispersion; caution: vigorous evolution of hydrogen). The mixture was heated at 80° C. for 2.5 hrs, and then ice-cooled, treated cautiously with 25 mL of 2-propanol, and then maintained at 0-5° C. overnight. The solid were collected, and then dissolved in 10 mL of hot water. The solution was filtered, the filtrate was ice-cooled and then treated dropwise with concentrated hydrochloric acid to pH=~7.0. After storage at 0-5° C. for 3 hrs, the precipitated solids were collected, washed with ice-cold water, and dried in vacuum to give XI-3 (3 g, 32% yield). $^1H$ NMR (DMSO-$d_6$, 300 MHz): δ 8.90 (s, 1H), 8.49 (d, J=7.6 Hz, 1H), 7.51-7.43 (m, 2H), 6.61 (d, J=7.6 Hz, 1H).

A suspension of XI-3 (2.36 g, 15.7 mmol, 1 eq), N-bromosuccinimide (3.1 g, 17.3 mmol, 1 eq), and 50 mL of 1,2-dichloroethane was stirred at rt for 3.5 hrs. The mixture was filtered; the solids were washed successively with small amounts of chloroform, water, and diethyl ether, and then dried to leave XI-4 (0.8 g, 23% yield). MS (ESI) m/z $(M+H)^+$ 226.8.

A flask was charged with XI-4 (0.6 g, 2.67 mmol, 1 eq.), XI-5 (1.1 g, 5.33 mmol, 2 eq.), $Cu(OAc)_2$ (1.45 g, 8 mmol, 3 eq.), pyridine (2.1 g, 26.7 mmol, 10 eq.), pyridine-N-oxide (0.76 g mg, 8.01 mmol, 3 eq.), 200 mg of 4 Å molecular sieves and 45 mL of $CH_2Cl_2$. The mixture was stirred under oxygen atmosphere at rt for 18 hrs. LCMS analysis showed the reaction completed. All the volatiles were removed under reduced pressure. The residue was diluted with water, extracted with ethyl acetate (100 mL×3). The combined organic layer was washed with brine, dried over anhydrous sodium sulfate, filtered and concentrated to give a brown oil. Purification by column chromatography on silica gel with petroleum ether/EtOAc (3:1→1:1) to provide XI-6 (0.5 g, 50% yield). MS (ESI) m/z $(M+H)^+$ 386.8.

A flak was charged with XI-6 (140 mg, 0.36 mmol, 1 eq), XI-7 (76 mg, 0.54 mmol, 1.5 eq), $K_2CO_3$ (100 mg, 0.72 mmol, 2 eq), $Pd(dppf)Cl_2$ (13 mg, 0.018 mmol, 0.05 eq), 10 mL of DME and 2 mL of $H_2O$, and then it was flushed with nitrogen for three times. The mixture was heated at 100° C. for 18 hrs. LCMS analysis showed the reaction completed. All the volatiles were removed under reduced pressure. The residue was diluted with water, extracted with ethyl acetate (50 mL×3). The combined organic layer was washed with brine, dried over anhydrous sodium sulfate, filtered and concentrated to give brown oil. Purification by prep-TLC (PE/EA=2/1) gave Compound 42 (102.4 mg, 71% yield). $^1H$ NMR (CDCl$_3$, 300 MHz): δ 8.93 (m, 1H), 8.74 (d, J=7.8 Hz, 2H), 7.54-7.42 (m, 5H), 7.39-7.31 (m, 3H), 7.09 (t, J=9.0 Hz, 2H). MS (ESI) m/z $(M+H)^+$ 400.9.

Compound 43 was prepared following the similar procedure for obtaining Compound 42 using 1-methyl-4-(4,4,5,5-tetramethyl-1,3,2-dioxaborolan-2-yl)-1H-pyrazole in replace of XI-7. $^1H$ NMR (CDCl$_3$, 400 MHz): δ 9.04 (m, 1H), 8.80 (d, J=8.4 Hz, 1H), 8.22 (s, 1H), 7.80 (s, 1H), 7.58 (s, 1H), 7.56-7.51 (m, 3H), 7.40 (d, J=8.4 Hz, 2H), 4.00 (s, 3H). MS (ESI) m/z $(M+H)^+$ 386.9.

Compound 45: A flask was charged with Compound 42 (500 mg, 1.25 mmol, 1 eq) and Pd/C (50 mg), 30 mL of MeOH and 3 mL of $H_2O$. The mixture was stirred for 18 hrs under hydrogen (45 Psi). LCMS analysis showed the reaction completed. The mixture was filtered. The filtrate was concentrated and purified by prep-TLC (PE/EA=2/1) to give Compound 45 as a white solid (300 mg, 59% yield). $^1H$ NMR (CDCl$_3$, 400 MHz): δ 7.45 (d, J=8.8 Hz, 2H), 7.36-7.26 (m, 4H), 7.14 (t, J=8.8 Hz, 2H), 6.99 (s, 1H), 4.30 (s, 1H), 3.29 (m, 2H), 2.67 (t, J=6.4 Hz, 2H), 1.93 (m, 2H). MS (ESI) m/z $(M+H)^+$ 404.9.

Compound 44 was prepared following the similar procedure for obtaining Compound 45. $^1H$ NMR (CDCl$_3$, 300 MHz): δ 7.41 (s, 1H), 7.36-7.32 (m, 3H), 7.20-7.15 (m, 2H), 6.90 (s, 1H), 4.41 (brs, 1H), 3.85 (s, 3H), 3.20 (m, 2H), 2.54 (m, 2H), 1.82 (m, 2H). MS (ESI) m/z $(M+H)^+$ 390.9.

Compound 395 was prepared following the similar procedure for obtaining Compound 43 using (4-cyanophenyl) boronic acid in place of XI-5. $^1H$ NMR (CDCl$_3$, 400 MHz) δ 9.10 (dd, J=1.6 Hz, 4.4 Hz, 1H), 8.79 (dd, J=2.0, 8.0 Hz, 1H), 8.21 (s, 1H), 7.85 (d, J=8.4 Hz, 2H), 7.79 (s, 1H), 7.65 (d, J=8.4 Hz, 2H), 7.56-7.52 (m, 2H), 3.99 (s, 3H). MS (ESI) m/z $(M+H)^+$ 328.0.

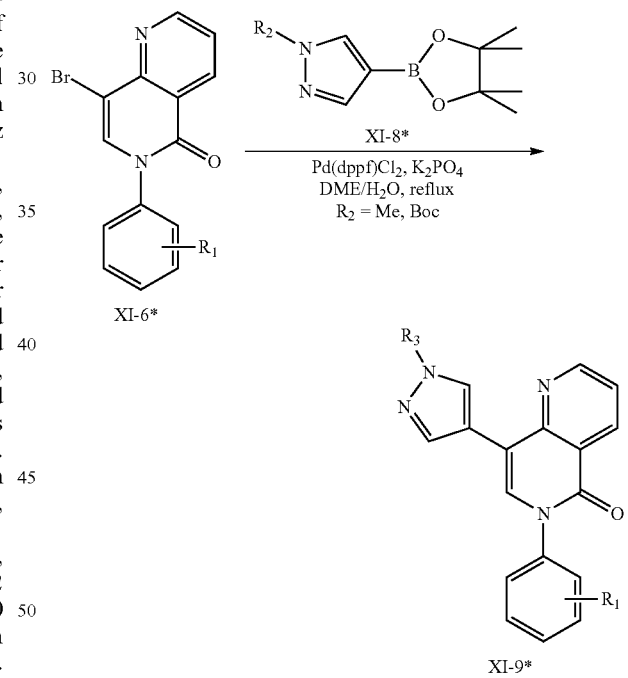

$R_1$ = 4-CN, 4-Cl, 4-OCF$_3$, 2-Me-4 OEt $R_3$ = Me, H

XI-6*with various $R^1$ groups can be prepared following the similar procedure described in the synthesis of XI-6. The last Suzuki-Coupling step was conducted either using Method 1 or Method 2 as described herein. Compounds 571, 572 and 579-581 were prepared by Suzuki-Coupling of XI-6* with the corresponding XI-8* using standard procedure described Method A using $K_3PO_4$ in place of $K_2CO_3$. The HCl salts were prepared by reacting the compounds with aq. HCl (1.0M, 1.1 eq) at 0° C. in dioxne for 20 mins then concentrated and dried in vacuo.

Compound 571: $^1H$ NMR (CDCl$_3$, 400 MHz) δ 9.03 (dd, J=2.0, 5.2 Hz, 1H), 8.79 (dd, J=1.6, 8.0 Hz, 1H), 8.20 (s, 1H), 7.79 (s, 1H), 7.56 (s, 1H), 7.53-7.50 (m, 3H), 7.43 (d, J=6.8 Hz, 2H), 3.99 (s, 3H). MS (ESI) m/z (M+H)+ 385.0.

Compound 572: $^1$H NMR (DMSO-d$_6$, 400 MHz) δ 12.90 (s, 1H), 9.09 (dd, J=2.0, 4.8 Hz, 1H), 8.65 (dd, J=1.6, 8.0 Hz, 1H), 8.43 (s, 1H), 8.11 (s, 1H), 8.01 (s, 1H), 7.66-7.63 (m, 5H). MS (ESI) m/z (M+H)+ 322.9.

Compound 579: $^1$H NMR (DMSO-d$_6$, 400 MHz) δ 12.88 (s, 1H), 9.09 (dd, J=1.6, 4.4 Hz, 1H), 8.64 (dd, J=1.6, 8.0 Hz, 1H), 8.44 (s, 1H), 8.13 (s, 1H), 8.05 (s, 1H), 7.73 (d, J=8.8 Hz, 2H), 7.66-7.62 (m, 1H), 7.58 (d, J=8.4 Hz, 2H). MS (ESI) m/z (M+H)+ 373.1.

Compound 580: $^1$H NMR (DMSO-d$_6$, 300 MHz) δ 12.86 (s, 1H), 9.09 (dd, J=1.8, 4.5 Hz, 1H), 8.65 (dd, J=1.8, 8.1 Hz, 1H), 8.43 (s, 1H), 8.10 (s, 1H), 7.86 (s, 1H), 7.65-7.62 (m, 1H), 7.30-7.23 (m, 1H), 6.99 (d, J=2.4 Hz, 1H), 6.93-6.89 (m, 1H), 4.09 (q, J=7.2 Hz, 2H), 2.07 (s, 3H), 1.37 (t, J=7.2 Hz, 3H). MS (ESI) m/z (M+H)+ 347.1.

Compound 581: $^1$H NMR (DMSO-d$_6$, 300 MHz) δ 12.90 (s, 1H), 9.09 (d, J=3.0 Hz, 1H), 8.66 (d, J=7.2 Hz, 1H), 8.34 (s, 1H), 8.08-8.04 (m, 4H), 7.85 (d, J=8.1 Hz, 2H), 7.67-7.64 (m, 2H). MS (ESI) m/z (M+H)+ 314.1.

Example 5-E

Synthesis of Compound 46 (Scheme XII)

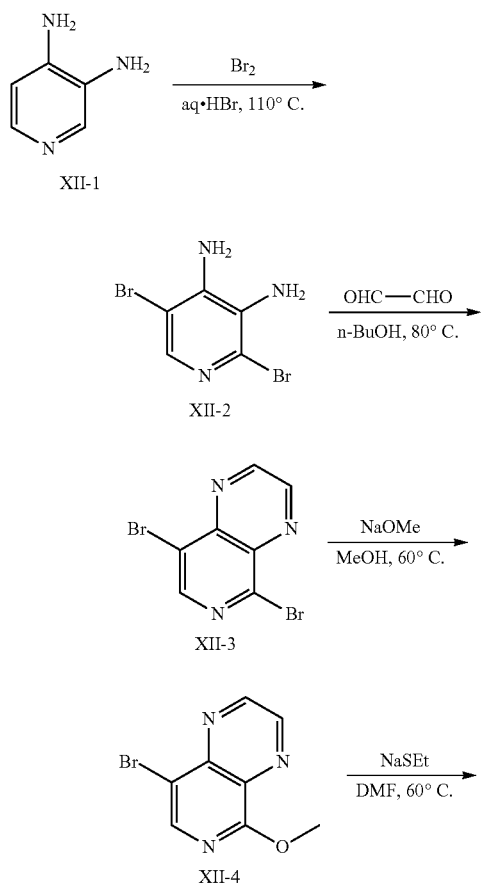

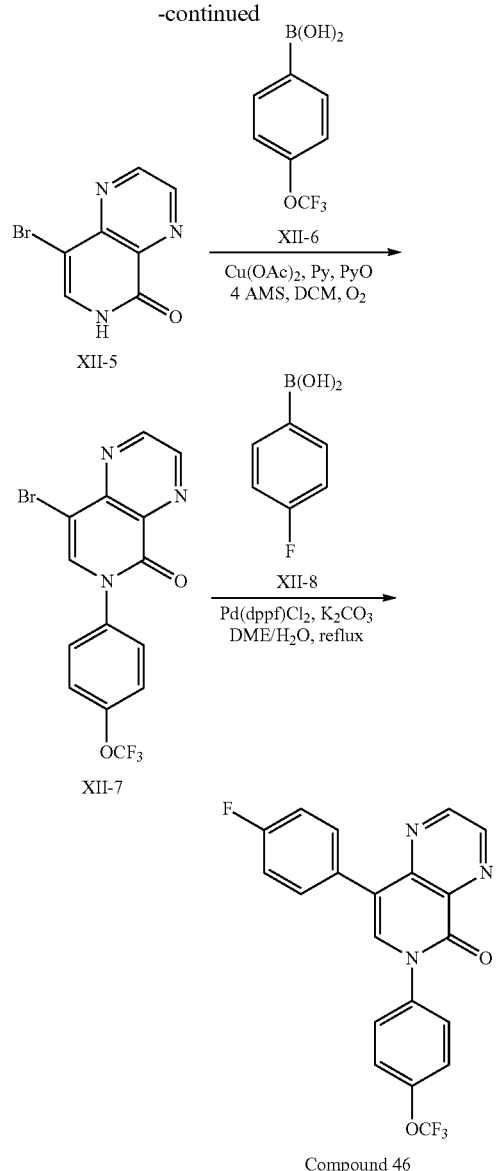

Compound 46

To the mixture of XII-1 (10.0 g, 10 mmol) dissolved in HBr 48% (200 mL), Br$_2$ (12.5 mL, 13.4 mmol) was added dropwise under ice-water cooling bath, maintaining the temperature below 40° C. After that, the mixture was heated at 110° C. for 5 hrs. The reaction mixture was cooled to rt, filtered and washed with little water. The filter cake is basified to pH 7-8 with saturated aq. NaHCO$_3$ and extracted with EtOAc (200 mL×3). The combined organic layer was washed with brine, dried over anhydrous Na$_2$SO$_4$ and concentrated to yield XII-2 (17.2 g, 71% yield). $^1$H NMR (DMSO-d$_6$, 400 MHz) δ 7.95 (s, 1H), 5.20 (brs, 4H).

XII-2 (5.0 g, 18.9 mmol) and aqueous glyoxal (40%, 5 mL) was dissolved in n-BuOH (15 mL), the mixture was stirred at 80° C. for 2 hrs. The reaction mixture was cooled to rt, a solid was precipitated out, filtered, washed with PE and dried in vacuum to afford XII-3 (5.0 g, 92% yield) as a yellow solid, which was used in next step without further purification. $^1$H NMR (CDCl$_3$, 400 MHz) δ 9.18 (d, J=2.0 Hz, 1H), 9.11 (d, J=2.0 Hz, 1H), 8.84 (s, 1H).

XII-3 (5.0 g, 17.3 mmol) and NaOMe (1.4 g, 26 mmol) were dissolved in MeOH (60 mL), and then the mixture was stirred at 60° C. for 0.5 h. Removed the solvent, diluted with EtOAc (100 mL), washed with brine, dried over Na₂SO₄ and concentrated to give XII-4 (3.7 g, 89% yield) as a light yellow solid, which was used in next step without further purification. ¹H NMR (CDCl₃, 300 MHz) δ 9.05 (d, J=1.8 Hz, 1H), 8.88 (d, J=1.8 Hz, 1H), 8.46 (s, 1H), 4.17 (s, 3H).

XII-4 (2.0 g, 8.4 mmol) and NaSEt (3.2 g, 38 mmol) was dissolved in DMF (30 mL), the mixture was stirred at 60° C. for 1.5 hrs. The reaction mixture was cooled to rt, diluted with water (30 mL) and acidified to pH=6-7 with conc. HCl. The precipitate was collected by filtration, washed with water and dried in vacuum to afford XII-5 (1.9 g, 100% yield) as a brown solid. ¹H NMR (DMSO-d₆, 400 MHz) δ 8.84 (d, J=2.0 Hz, 1H), 8.57 (d, J=1.6 Hz, 1H), 7.95 (s, 1H).

To a solution of XII-5 (2.0 g, 10 mmol) in DCM (100 mL), copper (II) acetate (3.6 g, 20 mmol), XII-6 (2.0 g, 12 mmol), pyridine (3 mL), pyridine-N-oxide (1.9 g, 20 mmol) and finely ground, activated 4 Å molecular sieves (3.0 g) were added. The mixture was stirred at rt. for 18 hrs under O₂ atmosphere. The solvent was evaporated and the residue was diluted with AcOEt (150 mL) and filtered. The filtrate was washed with brine, dried over Na₂SO₄ and concentrated. The residue was purified by flash chromatography on silica gel with petroleum ether/EtOAc (1:1~1:2) to yield XII-7 (400 mg, 12% yield) as a yellow solid. MS (ESI) m/z (M+H)⁺ 386.

Compound 46 was prepared following the similar procedure for obtaining Compound 42 (75 mg, 72% yield). ¹H NMR (CD₃OD, 400 MHz) δ 9.01 (d, J=2.0 Hz, 1H), 8.89 (d, J=2.0 Hz, 1H), 7.83 (s, 1H), 7.73-7.70 (m, 2H), 7.68-7.65 (m, 2H), 7.51 (d, J=8.0 Hz, 2H), 7.21-7.16 (m, 2H). MS (ESI) m/z (M+H)⁺ 401.9.

Compound 47 was prepared following the similar procedure for obtaining Compound 46 using 1-methyl-4-(4,4,5,5-tetramethyl-1,3,2-dioxaborolan-2-yl)-1H-pyrazole in replace of XII-8. ¹H NMR (CD₃OD, 400 MHz) δ 9.01 (d, J=2.0 Hz, 1H), 8.89 (d, J=2.0 Hz, 1H), 8.35 (s, 1H), 8.04 (m, 2H), 7.73-7.70 (m, 2H), 7.55-7.50 (m, 2H), 3.97 (s, 3H). MS (ESI) m/z (M+H)⁺ 387.9.

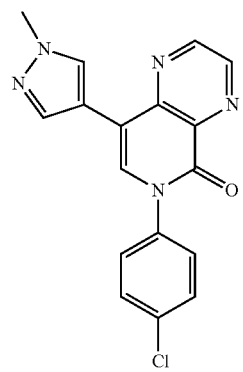

Compound 397

Compound 397 was prepared following the similar procedure for obtaining Compound 47 using XII-6a in place of XII-6. ¹H NMR (CDCl₃, 400 MHz) δ 8.98 (d, J=2.0 Hz, 1H), 8.90 (d, J=2.0 Hz, 1H), 8.13 (s, 1H), 7.80 (s, 1H), 7.64 (s, 1H), 7.55-7.52 (m, 2H), 7.47-7.45 (m, 2H), 4.00 (s, 3H). MS (ESI) m/z [M+H]⁺ 337.9.

Compound 398 was prepared following the similar procedure for obtaining Compound 397 using (4-cyanophenyl) boronic acid in place of XII-6a. ¹H NMR (CDCl₃, 400 MHz) δ 9.00 (d, J=2.0 Hz, 1H), 8.93 (d, J=2.0 Hz, 1H), 8.14 (s, 1H), 7.89-7.87 (m, 2H), 7.81 (s, 1H), 7.71-7.67 (m, 2H), 7.64 (s, 1H), 4.00 (s, 3H). MS (ESI) m/z [M+H]⁺ 328.9.

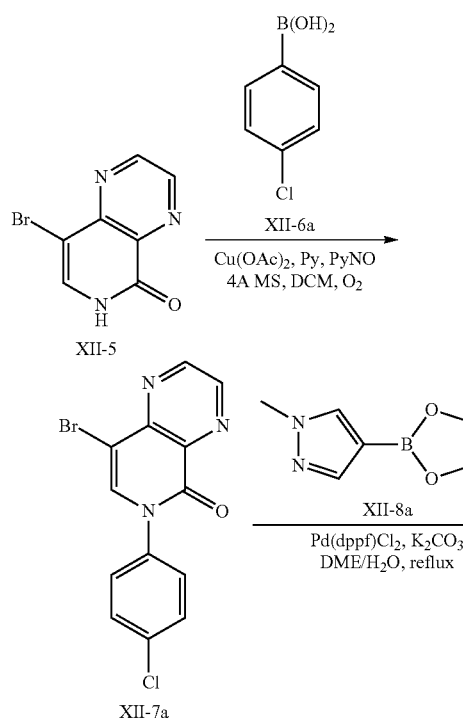

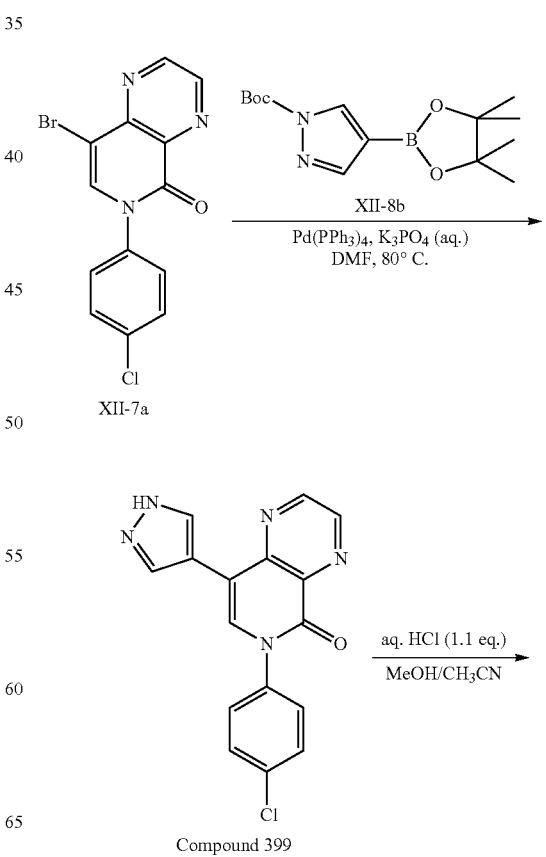

-continued

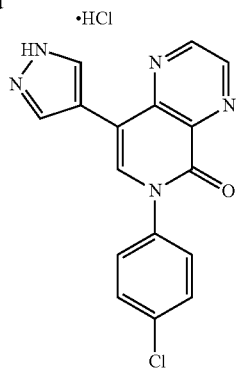

Compound 399a

To a solution of XII-7a (400 mg, 1.2 mmol, 1 eq.) in DMF (4 mL) was added aq. K$_3$PO$_4$ (2 M, 1.2 mL, 2.4 mmol, 2 eq.), XII-8b (425 mg, 1.44 mmol, 1.2 eq.), Pd(PPh$_3$)$_4$ (67 mg, 0.06 mmol, 0.05 eq.). The mixture was purged with nitrogen and then heated at 80° C. for 5 hrs. The mixture was cooled to rt, diluted with water (20 mL), extracted with EtOAc (30 mL×3). The combined organic layer was washed with brine, dried over anhydrous Na$_2$SO$_4$, and concentrated in vacuo. The residue was purified by flash chromatography (PE/EA=1/3) to give Compound 399 (90 mg, 24% yield). $^1$H NMR (CDCl$_3$, 400 MHz) δ 8.99 (d, J=2.0 Hz, 1H), 8.93 (d, J=2.0 Hz, 1H), 8.15 (s, 2H), 7.68 (s, 1H), 7.56-7.52 (m, 2H), 7.48-7.46 (m, 2H). MS (ESI) m/z [M+H]$^+$ 323.9.

To the mixture of Compound 399 (85 mg, 0.365 mmol) in MeOH (5 mL) and CH$_3$CN (5 mL) was added aq.HCl (0.2 M, 2 mL, 0.4 mmol, 1.1 eq.). After stirring for 0.5 h, removed the solvent under reduced pressure, and the residue was dried in vacuum to afford the hydrochloride salt Compound 399a as a yellow solid (120 mg, 91% yield). $^1$H NMR (DMSO-d$_6$, 400 MHz) δ 9.12 (d, J=2.0 Hz, 1H), 8.95 (d, J=2.0 Hz, 1H), 8.28 (s, 2H), 8.11 (s, 1H), 7.68-7.62 (m, 4H). MS (ESI) m/z [M+H]$^+$ 323.9.

Compound 400 was prepared following the similar procedure for obtaining Compound 399 by reacting XII-7 with XII-8b. $^1$H NMR (CD$_3$OD, 400 MHz) δ 9.09 (d, J=1.6 Hz, 1H), 8.88 (d, J=1.6 Hz, 1H), 8.35-8.20 (m, 2H), 8.05 (s, 1H), 7.71-7.68 (m, 2H), 7.52-7.50 (m, 2H). MS (ESI) m/z [M+H]$^+$ 374.2.

The hydrochloride salt of Compound 400 was prepared following the similar procedure for obtaining Compound 399a as a yellow solid. $^1$H NMR (DMSO-d$_6$, 400 MHz) δ 9.12 (d, J=2.0 Hz, 1H), 8.95 (d, J=2.0 Hz, 1H), 8.29 (s, 2H), 8.16 (s, 1H), 7.76-7.73 (m, 2H), 7.62-7.59 (m, 2H). MS (ESI) m/z [M+H]$^+$ 374.0.

Compounds 573 and 574 were prepared by following the similar procedure described in the synthesis of Compound 399. The corresponding HCl salts were also prepared following the similar procedure described in the synthesis of Compound 399a.

Compounds 573: $^1$H NMR (DMSO-d$_6$, 400 MHz) δ 12.93 (s, 1H), 9.11 (d, J=1.6 Hz, 1H), 8.93 (d, J=1.6 Hz, 1H), 8.37 (s, 1H), 8.12-8.06 (m, 4H), 7.84-7.82 (m, 2H). MS (ESI) m/z (M+H)$^+$ 315.0.

Compound 574: $^1$H NMR (DMSO-d$_6$, 400 MHz) δ 12.93 (s, 1H), 9.12 (s, 1H), 8.94 (s, 1H), 8.40 (s, 1H), 8.11 (s, 1H), 7.98 (s, 1H), 7.32 (m, 1H), 7.00 (m, 1H), 6.91 (m, 1H), 4.10 (q, J=6.8 Hz, 2H), 2.09 (s, 3H), 1.37 (t, J=6.8 Hz, 3H). MS (ESI) m/z (M+H)$^+$ 348.1.

Compound 575: To a solution of XII-7 (300 mg, 0.78 mmol) in DMF (5 mL) was added Pd(OAc)$_2$ (9 mg, 0.039 mmol), Et$_3$N (240 mg, 2.4 mmol), HCOOH (72 mg, 1.5 mmol) and PPh$_3$ (20.4 mg, 0.078 mmol). The mixture was purged with nitrogen for three times and then heated at 60° C. under nitrogen for 12 hrs. After cooling to rt, the mixture was concentrated, the residue was partitioned between H$_2$O and EtOAc. The organic layer was washed with brine, dried over Na$_2$SO$_4$, concentrated in vacuo. The crude residue was purified by column chromatography on silica gel using EA as eluent to afford Compound 575 (146 mg, 61% yield). $^1$H NMR (DMSO-d$_6$, 300 MHz) δ 9.02 (d, J=1.5 Hz, 1H), 8.88 (d, J=1.8 Hz, 1H), 7.89 (d, J=7.5 Hz, 1H), 7.70 (d, J=8.7 Hz, 2H), 7.60 (d, J=8.4 Hz, 2H), 6.82 (d, J=7.5 Hz, 1H).

Compound 577 was prepared by Suzuki-coupling of XII-7 with XII-8b in DMF/H$_2$O at 100° C. for 12 h followed by reacting with 1,3-dioxolan-2-one in the presence of NaOH. $^1$H NMR (DMSO-d$_6$, 300 MHz) δ 9.12 (s, 1H), 8.95 (s, 1H), 8.42 (s, 1H), 8.15 (s, 1H), 8.07 (s, 1H), 7.75 (d, J=8.7 Hz, 2H), 7.61 (d, J=8.7 Hz, 2H), 4.18 (d, J=5.7 Hz, 2H), 3.77 (d, J=6.9 Hz, 2H).

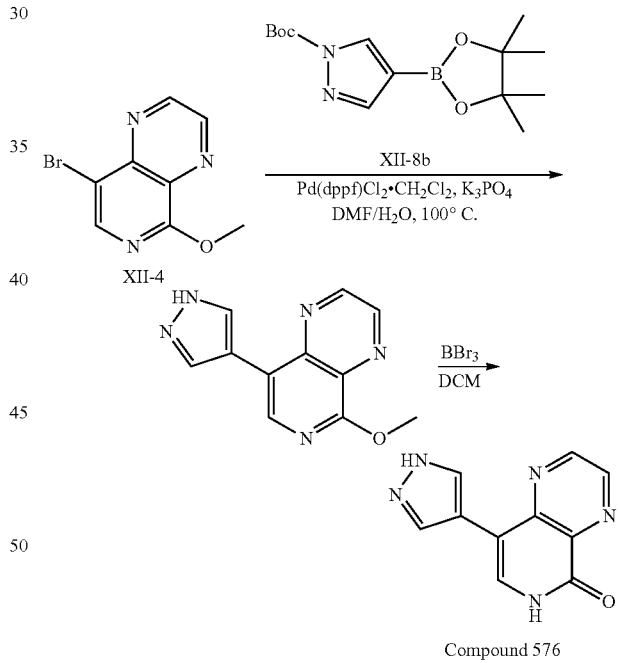

Compound 576

Compound 576 was prepared by Suzuki-Coupling of XII-4 and XII-8b using the standard procedure described herein followed by reaction with BBr$_3$ in DCM. $^1$H NMR (DMSO-d$_6$, 300 MHz) δ 12.83 (s, 1H), 9.04 (s, 1H), 8.84 (s, 1H), 8.17 (s, 1H), 7.82 (s, 1H).

Compound 578 was prepared following the similar procedure described in the synthesis of Compound 576 using 1-methyl-4-(4,4,5,5-tetramethyl-1,3,2-dioxaborolan-2-yl)-1H-pyrazole in place of XII-8b. $^1$H NMR (DMSO-d$_6$, 300 MHz) δ 8.99 (s, 1H), 8.80 (s, 1H), 8.27 (s, 1H), 7.93 (s, 1H), 7.84 (s, 1H), 3.88 (s, 3H).

Example 5-F

Synthesis of Compound 48 (Scheme XIII)

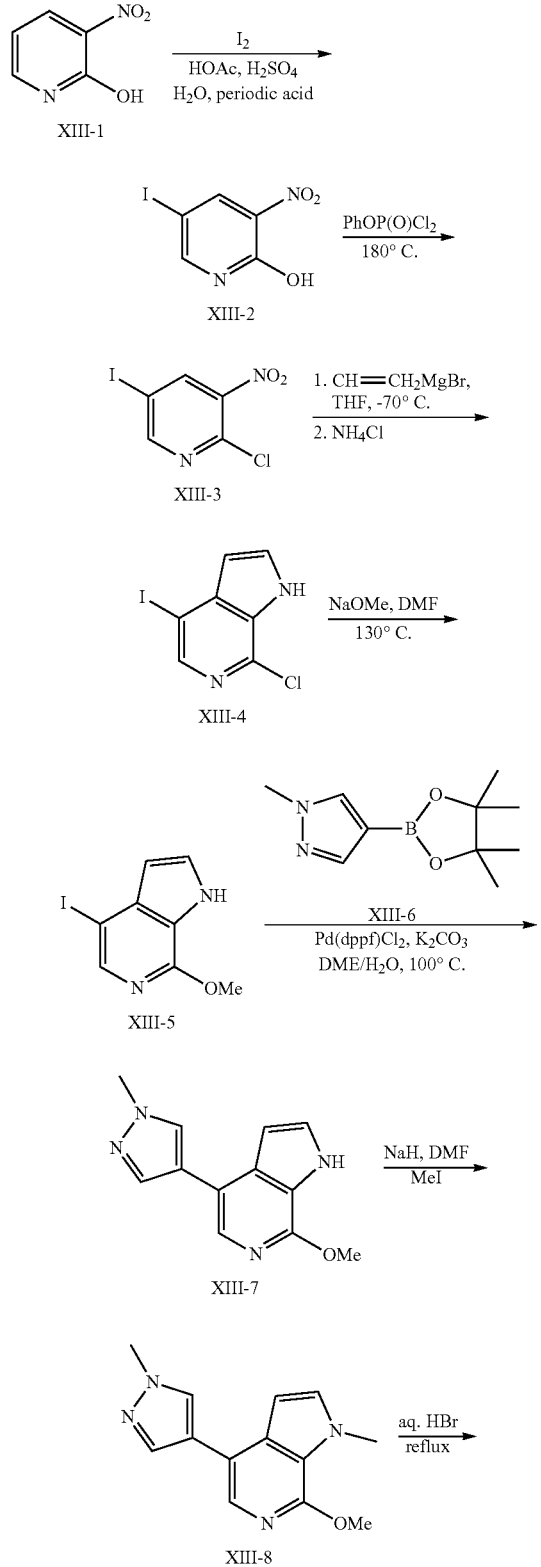

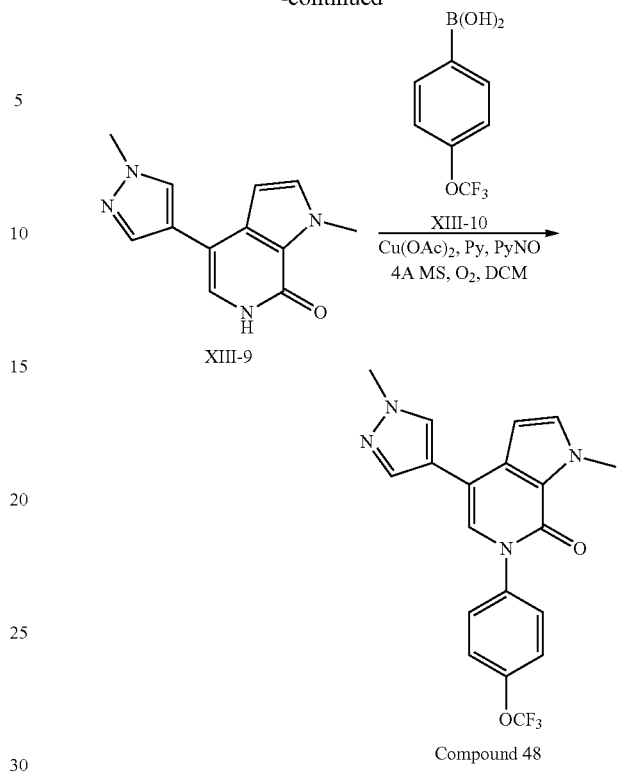

A suspension of XIII-1 (10.3 g, 73.4 mmol, 1 eq) in 46 mL of acetic acid, 20 mL of water, 1.4 mL of concentrated sulfuric acid and periodic acid (3.5 g, 18 mmol, 0.25 eq) was stirred at 90° C. for 15 minutes whereby a solution was obtained. Iodine crystals (7.7 g, 30.1 mmol, 0.4 eq) were added portionwise and after 20 minutes a dense yellow precipitate had formed. The mixture was cooled and saturated sodium thiosulphate (50 mL) was added. The solid was filtered and washed with saturated sodium thiosulphate (50 mL) followed by water. The solid was dried under vacuum to afford XIII-2 (14 g, 72% yield).

A suspension of XIII-2 (15 g, 56.4 mmol, 1 eq.) in 35 mL of phenyl dichlorophosphate was heated at 180° C. for 30 minutes whereby a brown solution was obtained. TLC analysis (PE:EA=10:1) showed the reaction completed. The solution was allowed to cool then poured onto ice/water, neutralized by a portionwise addition of solid NaHCO$_3$ and extracted with ethyl acetate (150 mL×3), and then washed with aq. NaHCO$_3$ (5%, 50 mL). The organic layer was dried over anhydrous sodium sulfate, filtered and concentrated to give brown solid. The crude product was purified by flash chromatography on silica gel with petroleum ether/EtOAc (5:1→2:1) to give XIII-3 as yellow solid (14 g, 87% yield). MS (ESI) m/z (M+H)$^+$ 284.7.

To a solution of vinyl magnesium bromide (66 mL, 66 mmol, 3.4 eq, 1.0 M solution in 2-methyl tetrahydrofuran) at −70° C. under nitrogen was added a solution of XIII-3 (5.5 g, 19.3 mmol, 1 eq.) in 120 mL of dry tetrahydrofuran, dropwise over 45 min. After 30 min at −70° C. TLC analysis (PE:EA=3:1) showed the starting material was consumed completely. The reaction was quenched with saturated ammonium chloride (50 mL). The mixture was extracted with ethyl acetate (150 mL×3). The combined organic layers was washed with brine, dried over anhydrous sodium sulfate, filtered and concentrated to give a brown oil. It was purified by flash chromatography on silica gel with petroleum ether/EtOAc (5:1→2:1) to give XIII-4 (0.5 g, 9% yield). MS (ESI) m/z (M+H)$^+$ 278.8.

A flask was charged with XIII-4 (450 mg, 1.6 mmol, 1 eq), NaOMe (864 mg, 16 mmol, 10 eq.) and 8 mL of DMF. The mixture was heated at 130° C. for 18 hrs. LCMS analysis showed the reaction completed. The reaction mixture was cooled down to rt, diluted with water, extracted with ethyl acetated (50 mL×3). The combined organic layer was washed with brine, dried over anhydrous sodium sulfate, filtered and concentrated to yield XIII-5 (0.2 g, 46% yield). MS (ESI) m/z (M+H)$^+$ 274.8.

XIII-7 was prepared following the similar procedure for obtaining Compound 42 using 1-methyl-4-(4,4,5,5-tetramethyl-1,3,2-dioxaborolan-2-yl)-1H-pyrazole (XIII-6) in replace of XI-7. (150 mg, 51% yield). MS (ESI) m/z (M+H)$^+$ 228.9.

To a solution of XIII-7 (100 mg, 0.44 mmol, 1 eq.) in DMF (5 mL) was added NaH (60% in mineral oil, 35 mg, 0.88 mmol, 2 eq.). After stirring for 30 min, MeI (75 mg, 0.53 mmol, 1.2 eq.) was added. The mixture was stirred at rt. for 2 hrs. And then it was slowly quenched with water, extracted with EtOAc (30 mL×3). The combined organic layer was washed with brine, dried over anhydrous Na$_2$SO$_4$ and concentrated. The residue was purified by prep-TLC (PE/EA=1:2) to afford XIII-8 (90 mg, 85% yield). MS (ESI) m/z (M+H)$^+$ 243.0.

A mixture of XIII-8 (90 mg, 0.374 mmol) in 10 mL aq.HBr (48%) was heated to reflux overnight. After being cooled to rt, the mixture was neutralized by addition of saturated aq. NaHCO$_3$, extracted with DCM/i-PrOH (30 mL×3, v/v=9/1). The combined organic layer was washed with brine, dried over anhydrous Na$_2$SO$_4$ and concentrated to afford crude XIII-9 (70 mg, 82% yield). MS (ESI) m/z (M+H)$^+$ 229.0.

Compound 48 was prepared following the similar procedure for obtaining XII-7. (51.9 mg, 43% yield). $^1$H NMR (CDCl$_3$, 300 MHz): δ 7.63 (s, 1H), 7.53 (s, 1H), 7.42 (d, J=8.7 Hz, 2H), 7.27 (d, J=8.7 Hz, 2H), 7.03 (d, J=3.0 Hz, 1H), 6.95 (s, 1H), 6.39 (d, J=3 Hz, 1H), 4.10 (s, 3H), 3.90 (s, 3H). MS (ESI) m/z (M+H)$^+$ 388.9.

Compound 49 was prepared following the similar procedure for obtaining Compound 48 using 1-propenylmagnesium bromide in place of vinyl magnesium bromide and (4-fluorophenyl)boronic acid in place of XIII-6. $^1$H NMR (CDCl$_3$, 300 MHz) δ 7.43 (d, J=8.7 Hz, 2H), 7.32-7.29 (m, 4H), 7.02 (t, J=8.4 Hz, 2H), 6.77 (s, 1H), 6.71 (s, 1H), 4.08 (s, 3H), 1.69 (s, 3H). MS (ESI) m/z (M+H)$^+$ 416.9.

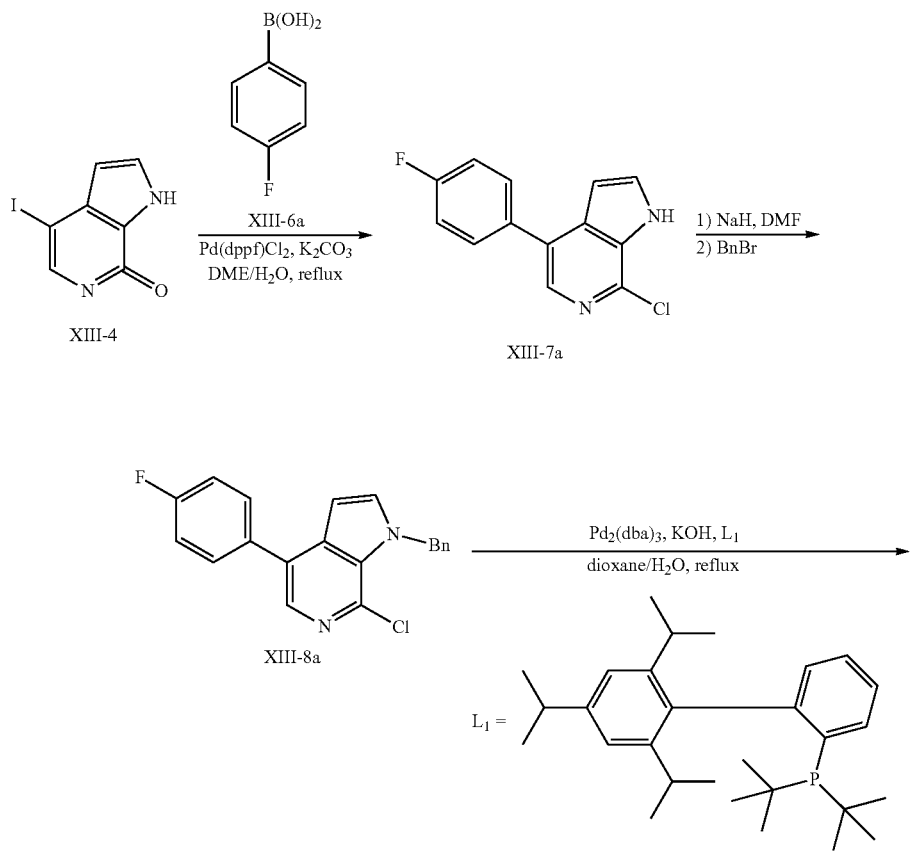

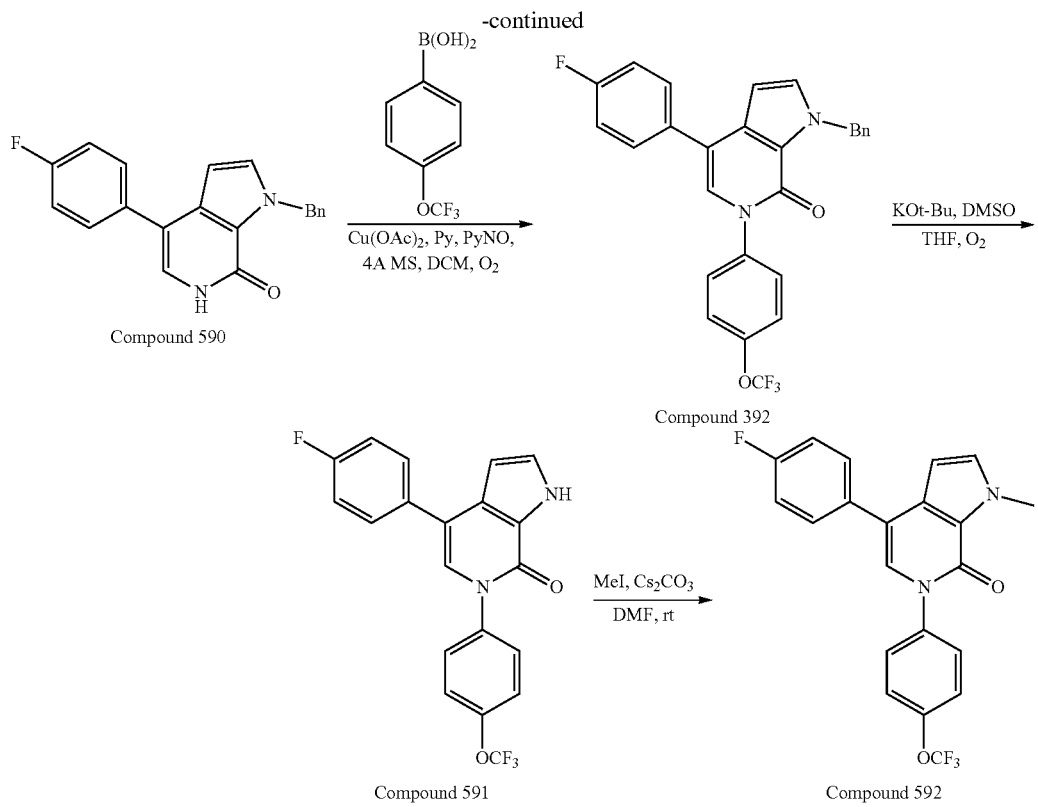

Compound 590

Compound 392

Compound 591

Compound 592

XIII-7a was prepared following the similar procedure for obtaining Compound 42. MS (ESI) m/z (M+H)⁺ 246.9.

To a solution of XIII-7a (400 mg, 1.63 mmol, 1 eq.) in 10 mL of DMF was added NaH (60% dispersion in mineral oil, 98 mg, 2.44 mmol, 1.5 eq.) at 0° C. The mixture was stirred at 0° C. for 30 min. After that, BnBr (417 mg, 2.44 mmol, 1.5 eq.) was added into the flask. The resulting mixture was stirred for 16 hrs at rt. TLC (PE/EA=5/1) analysis showed the reaction completed. The mixture was diluted with water, extracted with EtOA (50 mL×3). The combined organic layer was washed with brine, dried over Na$_2$SO$_4$, filtered and concentrated to give a yellow oil. Purification by column chromatography on silica gel (PE/EA=5/1) afford XIII-8a (250 mg, 46% yield). MS (ESI) m/z (M+H)⁺ 336.9.

A flask was charged with XIII-8a (250 mg, 0.74 mmol, 1 eq.), KOH (499 mg, 8.9 mmol, 12 eq.), L$_1$ (97 mg, 0.23 mmol, 0.3 eq.), 10 mL of dioxane and 10 mL of H$_2$O. The flask was flushed with nitrogen, and then Pd$_2$(dba)$_3$ (37 mg, 0.04 mmol, 0.05 eq.) was added. The mixture was flushed with nitrogen again, and heated to reflux for 10 hrs. LCMS analysis showed the reaction completed. The mixture was cooled down to rt, diluted with water (20 mL), extracted with ethyl acetate (50 mL×3). The combined organic layer was washed with brine, dried over anhydrous sodium sulfate, filtered and concentrated. Purification by prep-TLC (PE/EA=1/1) gave Compound 590 (200 mg, 85% yield). MS (ESI) m/z (M+H)⁺ 318.9.

Compound 392 was prepared by Suzuki Coupling of Compound 590 with XIII-10 following the similar procedure for obtaining Compound 48 (19% yield). ¹H NMR (CDCl$_3$, 400 MHz) δ 7.53-7.50 (m, 4H), 7.36-7.27 (m, 7H), 7.19 (d, J=2.8 Hz, 1H), 7.14 (t, J=8.4 Hz, 2H), 7.01 (s, 1H), 6.46 (d, J=2.8 Hz, 1H), 5.86 (s, 2H). MS (ESI) m/z (M+H)⁺ 479.1.

To a solution of Compound 392 (220 mg, 0.51 mmol, 1 eq) and DMSO (400 mg, 5.14 mmol, 10 eq) in 20 mL of THF was added KOt-Bu (1.15 g, 10.28 mmol, 20 eq) at 0° C. The mixture was stirred for 18 h at rt under oxygen. The reaction was quenched with water, extracted with EtOAc. The combined organic layer was washed with brine, dried over anhydrous sodium sulfate, filtrated and concentrated. Purification by prep-TLC (PE: EA=1:1) gave Compound 591 as a white solid (140 mg, 70% yield). ¹H NMR (DMSO-d$_6$, 400 MHz) δ 12.37 (s, 1H), 7.69-7.65 (m, 4H), 7.51 (d, J=8.4 Hz, 2H), 7.44 (t, J=2.8 Hz, 1H), 7.29-7.25 (m, 3H), 6.48 (t, J=2.4 Hz, 1H). MS (ESI) m/z (M+H)⁺ 388.9.

To a solution of Compound 591 (200 mg, 0.52 mmol, 1 eq) in 5 mL of DMF was added Cs$_2$CO$_3$ (336 mg, 1.03 mmol, 2 eq) at rt. The mixture was stirred for 30 min. MeI (146 mg, 1.03 mmol, 2 eq) was added into the flask. The mixture was stirred for 18 h at rt. The mixture was diluted with water, extracted with EtOAc. The combined organic layer was washed with brine, dried over Na$_2$SO$_4$, filtered and concentrated to give yellow solid. Purification by prep-TLC (PE:EA=1:1) gave Compound 592 as a light yellow solid (90 mg, 43% yield). ¹HNMR (DMSO-d$_6$, 400 MHz) δ 7.68-7.64 (m, 4H), 7.52 (d, J=8.0 Hz, 2H), 7.48 (d, J=2.8 Hz, 1H), 7.31-7.26 (m, 3H), 6.42 (d, J=2.8 Hz, 1H), 4.11 (s, 3H). MS (ESI) m/z (M+H)⁺ 403.1.

Compound 394 was prepared following the similar procedure for obtaining Compound 392 and using 4-bromo-7-chloro-1H-pyrrolo[2,3-c]pyridine in place of XIII-4, XIII-6 in place of XIII-6a, and methyl iodide in place of BnBr. ¹H NMR (CDCl$_3$, 400 MHz) δ 7.70 (s, 1H), 7.60 (s, 1H), 7.49 (d, J=8.4 Hz, 2H), 7.34 (d, J=8.4 Hz, 2H), 7.10 (d, J=2.8 Hz, 1H), 7.02 (s, 1H), 6.46 (d, J=2.8 Hz, 1H), 4.20 (s, 3H), 3.97 (s, 3H). MS (ESI) m/z (M+H)⁺ 389.0.

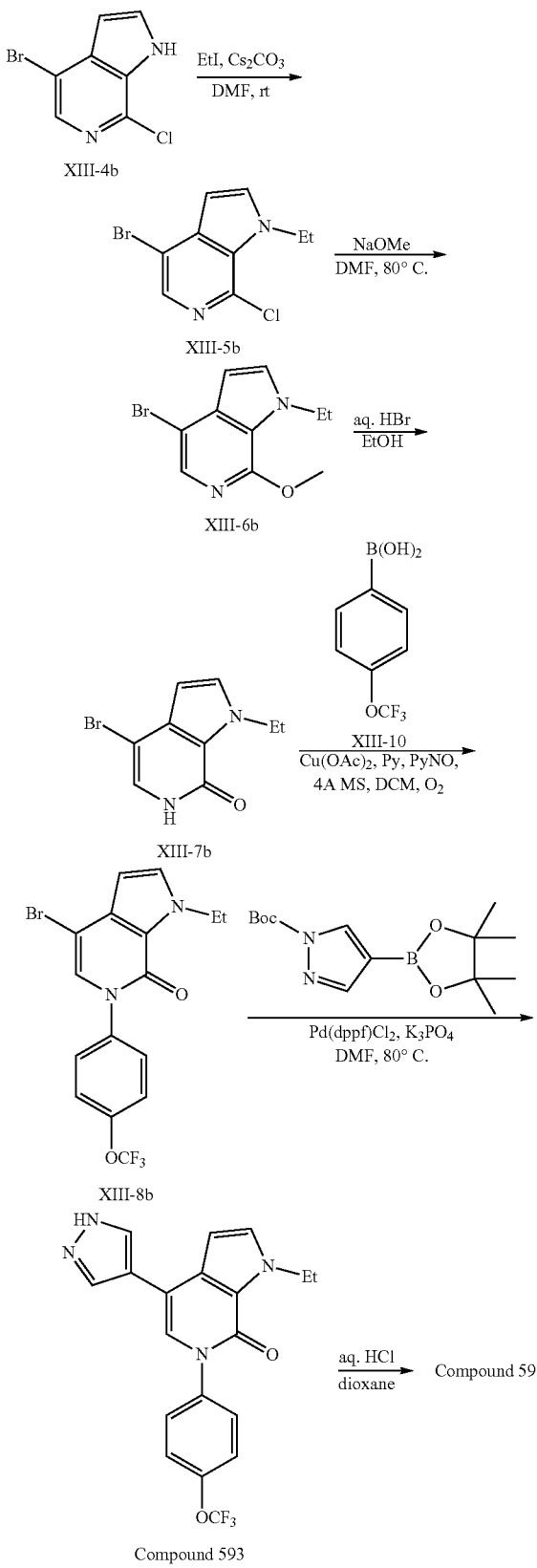

Compound 593 was prepared following the similar procedure for obtaining Compound 48 using XIII-4b in place of XIII-4. The ethylation by EtI and treatment with NaOMe were conducted following the similar procedure described in the synthesis of Compound 592 and XIII-5. After HBr hydrolysis, XIII-7b was subject to two Suzuki-Coupling reactions to afford Compound 593 as a white solid. $^1$H NMR (DMSO-d$_6$, 400 MHz) δ 12.94 (s, 1H), 8.05-7.98 (m, 2H), 7.63-7.61 (m, 2H), 7.52-7.49 (m, 3H), 7.38 (s, 1H), 6.61 (d, J=2.4 Hz, 1H), 4.51 (q, J=7.2 Hz, 2H), 1.33 (t, J=7.2 Hz, 3H). MS (ESI) m/z (M+H)$^+$ 389.1.

HCl salt compound 593a: $^1$H NMR (DMSO-d$_6$, 400 MHz) δ 8.01 (s, 2H), 7.62 (d, J=8.8 Hz, 2H), 7.98 (s, 1H), 7.53-7.50 (m, 3H), 7.38 (s, 1H), 6.61 (d, J=8.8 Hz, 1H), 4.51 (q, J=7.2 Hz, 2H), 1.33 (t, J=7.2 Hz, 3H). MS (ESI) m/z [M+H]$^+$ 389.1.

Compound 595 was obtained by Suzuki-Coupling of XIII-4b with XIII-6a, followed by dechlorination following the same procedure described above in the dechlorination of XIII-8a. $^1$H NMR (CDCl$_3$, 400 MHz) δ 11.18 (s, 1H), 7.52-7.49 (m, 2H), 7.16-7.11 (m, 3H), 6.97 (s, 1H), 6.41 (d, J=3.2 Hz, 1H), 4.66 (q, J=7.2 Hz, 2H), 1.52 (t, J=7.2 Hz, 3H). MS (ESI) m/z (M+H)$^+$ 257.1.

Compound 594 was obtained by Suzuki Coupling of Compound 595 with XIII-10 following the same procedure for obtaining Compound 48. $^1$H NMR (CDCl$_3$, 400 MHz) δ 7.54-7.51 (m, 2H), 7.35 (d, J=8.4 Hz, 1H), 7.18-7.12 (m, 3H), 7.00 (s, 1H), 6.42 (d, J=2.4 Hz, 1H), 4.62 (q, J=7.2 Hz, 2H), 1.51 (t, J=7.2 Hz, 3H). MS (ESI) m/z (M+H)$^+$ 417.2.

Compound 615 was obtained as a white solid by reacting Compound 593 with 2-(2-bromoethoxy)tetrahydro-2H-pyran in the presence of Cs$_2$CO$_3$ in DMF at 50° C., followed by hydroxy deprotection using TsOH in MeOH at 60° C. $^1$H NMR (DMSO-d$_6$, 400 MHz) δ 8.12 (s, 1H), 7.83 (s, 1H), 7.64 (d, J=8.8 Hz, 2H), 7.55-7.51 (m, 3H), 7.38 (s, 1H), 4.92 (t, J=5.2 Hz, 1H), 4.57 (q, J=7.2 Hz, 2H), 4.16 (t, J=5.6 Hz, 2H), 3.76 (q, J=4.6 Hz, 2H), 1.35 (t, J=7.2 Hz, 3H). MS (ESI) m/z (M+H)$^+$ 433.0.

Compound 596 was prepared by following the similar procedure for the preparation of Compound 48. $^1$H NMR (DMSO-d$_6$, 400 MHz) δ 8.13 (s, 1H), 7.82 (s, 1H), 7.66-7.62 (m, 3H), 7.53-7.51 (m, 2H), 7.40 (s, 1H), 7.31-7.25 (m, 5H), 6.68 (d, J=2.8 Hz, 1H), 5.77 (s, 2H), 3.87 (s, 3H). MS (ESI) m/z (M+H)$^+$ 465.1.

HCl salt compound 596a: $^1$H NMR (DMSO-d$_6$, 400 MHz) δ 8.11 (s, 1H), 7.80 (s, 1H), 7.64-7.60 (m, 3H), 7.51-7.49 (m, 3H), 7.39 (s, 1H), 7.31-7.22 (m, 5H), 6.66 (d, J=2.8 Hz, 1H), 5.76 (s, 2H), 3.85 (s, 3H). MS (ESI) m/z (M+H)$^+$ 465.1.

Compound 614 was obtained by amino deprotection of Compound 596 using KO$^t$Bu, followed by reaction with 2-(2-bromoethoxy)tetrahydro-2H-pyran in the presence of Cs$_2$CO$_3$ in DMF, then hydroxy deprotection using TsOH in MeOH. $^1$H NMR (DMSO-d$_6$, 400 MHz) δ 8.12 (s, 1H), 7.82 (s, 1H), 7.63 (d, J=6.8 Hz, 2H), 7.52 (d, J=8.4 Hz, 2H), 7.47 (s, 1H), 7.38 (s, 1H), 6.60 (d, J=2.8 Hz, 1H), 4.54 (t, J=6.0 Hz, 2H), 3.87 (s, 3H), 3.70 (t, J=5.6 Hz, 2H). MS (ESI) m/z (M+H)$^+$ 419.1.

Compound 597 was prepared by following the similar procedure for the preparation of Compound 48 using (4-cyanophenyl)boronic acid in place of XIII-10. $^1$H NMR (DMSO-d$_6$, 400 MHz) δ 8.11 (s, 1H), 7.99 (d, J=8.5 Hz, 2H), 7.80 (s, 1H), 7.72 (d, J=8.5 Hz, 2H), 7.46 (d, J=2.8 Hz, 1H), 7.35 (s, 1H), 6.60 (d, J=2.8 Hz, 1H), 4.07 (s, 3H), 3.85 (s, 3H).

HCl salt compound 597a: $^1$H NMR (DMSO-d$_6$, 400 MHz) δ 8.13 (s, 1H), 8.01 (d, J=7.5 Hz, 2H), 7.78 (m, 3H), 7.48 (s, 1H), 7.37 (s, 1H), 6.62 (s, 1H), 4.09 (s, 3H), 3.86 (s, 3H).

Compound 600 was prepared by following the similar procedure for the preparation of Compound 597 using the Boc-protected boronic ester in place of XIII-6. $^1$H NMR (DMSO-d$_6$, 400 MHz) δ 12.95 (s, 1H), 8.13 (s, 1H), 7.99 (d, J=8.4 Hz, 2H), 7.87 (s, 1H), 7.73 (d, J=8.4 Hz, 2H), 7.45 (d, J=2.8 Hz, 1H), 7.37 (s, 1H), 6.61 (d, J=2.8 Hz, 1H), 4.08 (s, 3H).

HCl salt compound 600a: $^1$H NMR (DMSO-d$_6$, 400 MHz) δ 8.00 (m, 4H), 7.74 (d, J=8.0 Hz, 2H), 7.46 (m, 1H), 7.37 (s, 1H), 6.61 (d, J=2.4 Hz, 1H), 4.08 (s, 3H).

Compound 599 was obtained by Suzuki-Coupling of 4-bromo-1-methyl-1H-pyrrolo[2,3-c]pyridin-7(6H)-one with (4-chlorophenyl)boronic acid then Suzuki-Coupling with XIII-6, following the similar procedure described in the synthesis of XIII-8b and Compound 593. $^1$H NMR (DMSO-d$_6$, 400 MHz) δ 8.10 (s, 1H), 7.78 (s, 1H), 7.57 (m, 2H), 7.50 (m, 2H), 7.44 (d, J=2.8 Hz, 1H), 7.30 (s, 1H), 6.58 (d, J=2.8 Hz, 1H), 4.07 (s, 3H), 3.85 (s, 3H).

Compound 598 was prepared by following the similar procedure for the preparation of Compound 599 using the Boc-protected boronic ester in place of XIII-6. $^1$H NMR (DMSO-d$_6$, 400 MHz) δ 12.95 (s, 1H), 8.13 (s, 1H), 7.88 (s, 1H), 7.59 (m, 2H), 7.52 (m, 2H), 7.45 (d, J=2.8 Hz, 1H), 7.34 (s, 1H), 6.62 (d, J=2.8 Hz, 1H), 4.10 (s, 3H).

HCl salt compound 598a: $^1$H NMR (DMSO-d$_6$, 400 MHz) δ 8.05 (d, J=2 Hz, 2H), 7.56 (m, 2H), 7.50 (m, 2H), 7.44 (d, J=2.8 Hz, 1H), 7.34 (s, 1H), 6.6 (d, J=2.8 Hz, 1H), 4.07 (s, 3H).

Compounds 601 and 602 was prepared following the similar procedure described in the synthesis of Compound 598 using the corresponding aromatic boronic acids. Their respective HCl salts compounds 601a and 602a were also obtained by reacting with aq. HCl in acetonitrile.

Compound 601: $^1$H NMR (DMSO-d$_6$, 400 MHz) δ 12.90 (s, 1H), 8.09 (s, 1H), 7.84 (s, 1H), 7.40 (d, J=2.4 Hz, 1H), 7.14 (d, J=8.0 Hz, 2H), 6.92 (d, J=2.0 Hz, 1H), 6.85 (d, J=8.0 Hz, 1H), 6.59 (d, J=2.8 Hz, 1H), 4.07 (m, 5H), 2.02 (s, 3H), 1.34 (t, J=6.8 Hz, 3H). MS (ESI) m/z (M+H)$^+$ 349.0.

Compound 601a: $^1$H NMR (DMSO-d$_6$, 400 MHz) δ 8.04 (s, 2H), 7.42 (d, J=2.8 Hz, 1H), 7.15 (d, J=8.4 Hz, 2H), 6.93 (d, J=2.4 Hz, 1H), 6.85 (d, J=8.4 Hz, 1H), 6.61 (d, J=2.8 Hz, 1H), 4.09-4.05 (m, 5H), 2.04 (s, 3H), 1.35 (t, J=6.8 Hz, 3H). MS (ESI) m/z (M+H)$^+$ 348.9.

Compound 602: $^1$H NMR (DMSO-d$_6$, 400 MHz) δ 12.94 (s, 1H), 8.13 (s, 1H), 7.89 (s, 1H), 7.62 (d, J=8.4 Hz, 2H), 7.51 (d, J=8.4 Hz, 2H), 7.45 (d, J=2.4 Hz, 1H), 7.38 (s, 1H), 6.62 (d, J=3.2 Hz, 1H), 4.09 (s, 3H).

Compound 602a: $^1$H NMR (DMSO-d$_6$, 400 MHz) δ 8.06 (s, 2H), 7.62 (d, J=8.0 Hz, 2H), 7.51 (d, J=8.0 Hz, 2H), 7.46 (d, J=2.8 Hz, 1H), 7.40 (s, 1H), 6.62 (d, J=2.8 Hz, 1H), 4.09 (s, 3H). MS (ESI) m/z (M+H)$^+$ 374.9.

Compound 603 was prepared by benzyl deprotection of 1-benzyl-4-bromo-6-(4-(trifluoromethoxy)phenyl)-1H-pyrrolo[2,3-c]pyridin-7(6H)-one to form an intermediate 4-bromo-6-(4-(trifluoromethoxy)phenyl)-1H-pyrrolo[2,3-c]pyridin-7(6H)-one, followed by Suzuki-Coupling with XIII-6 to afford the final product. $^1$H NMR (DMSO-d$_6$, 400 MHz) δ 12.29 (s, 1H), 8.14 (s, 1H), 7.83 (s, 1H), 7.64 (d, J=8.8 Hz, 2H), 7.52 (d, J=8.8 Hz, 2H), 7.43 (m, 1H), 7.38 (s, 1H), 6.66 (m, 1H), 3.86 (s, 3H). MS (ESI) m/z (M+H)$^+$ 375.0.

Compound 604 was prepared by Suzuki-Coupling of 4-bromo-6-(4-(trifluoromethoxy)phenyl)-1H-pyrrolo[2,3-c]pyridin-7(6H)-one with XII-8b. $^1$H NMR (DMSO-d$_6$, 400 MHz) δ 12.93 (s, 1H), 12.27 (s, 1H), 8.15 (s, 1H), 7.90 (s, 1H), 7.64 (d, J=8.4 Hz, 2H), 7.52 (d, J=8.4 Hz, 2H), 7.41 (d, J=8.4 Hz, 2H), 6.67 (d, J=2.4 Hz, 1H). HCl salt compound 604a: $^1$H NMR (DMSO-d$_6$, 400 MHz) δ 12.28 (s, 1H), 8.06 (s, 2H), 7.64 (d, J=8.4 Hz, 2H), 7.52 (d, J=8.4 Hz, 2H), 7.42 (m, 2H), 6.67 (d, J=2.4 Hz, 1H). MS (ESI) m/z (M+H)$^+$ 361.0.

Compound 609 was obtained by Pd/C hydrogenation of 4-bromo-6-(4-(trifluoromethoxy)phenyl)-1H-pyrrolo[2,3-c]pyridin-7(6H)-one as a white solid. $^1$H NMR (DMSO-d$_6$, 400 MHz) δ 12.15 (s, 1H), 7.59-7.57 (m, 2H), 7.51-7.49 (m, 2H), 7.35 (t, J=2.6 Hz, 1H), 7.17 (d, J=7.2 Hz, 1H), 6.62 (d, J=7.2 Hz, 1H), 6.37 (d, J=2.0 Hz, 1H). MS (ESI) m/z (M+H)$^+$ 295.0.

Compound 610 was obtained by ethylation of Compound 609 using EtI in the presence of Cs$_2$CO$_3$ in DMF. $^1$H NMR (DMSO-d$_6$, 400 MHz) δ 7.57-7.55 (m, 2H), 7.50-7.48 (m, 2H), 7.44 (d, J=2.4 Hz, 1H), 7.16 (d, J=7.2 Hz, 1H), 6.56 (d, J=7.2 Hz, 1H), 6.33 (d, J=2.8 Hz, 1H), 4.46 (q, J=7.2 Hz, 2H), 1.31 (t, J=7.2 Hz, 3H). MS (ESI) m/z (M+H)$^+$ 322.9.

Other compounds were also prepared using the various procedures described in Example 5-F.

Compound 605: $^1$H NMR (CDCl$_3$, 400 MHz) δ 10.73 (s, 1H), 7.73 (s, 1H), 7.63 (s, 1H), 7.50 (d, J=8.4 Hz, 2H), 7.44 (d, J=8.4 Hz, 2H), 7.32 (s, 1H), 7.08 (s, 1H), 6.57 (d, J=2.4 Hz, 1H), 3.98 (s, 3H). MS (ESI) m/z (M+H)$^+$ 324.9.

Compound 606: $^1$H NMR (DMSO-d$_6$, 400 MHz) δ 12.95 (s, 1H), 12.28 (s, 1H), 8.15 (s, 1H), 7.90 (s, 1H), 7.61-7.54 (m, 4H), 7.43 (s, 1H), 7.37 (s, 1H), 6.68 (d, J=2.0 Hz, 1H). HCl salt: MS (ESI) m/z (M+H)$^+$ 310.9.

Compound 607: $^1$H NMR (DMSO-d$_6$, 400 MHz) δ 12.93 (s, 1H), 12.21 (s, 1H), 8.13-7.89 (m, 2H), 7.42-7.41 (m, 1H), 7.20-7.18 (m, 2H), 6.96-6.86 (m, 2H), 6.68 (d, J=2.4 Hz, 1H), 4.08 (q, J=6.8 Hz, 2H), 2.04 (s, 3H), 1.36 (t, J=6.8 Hz, 3H). MS (ESI) m/z (M+H)$^+$ 334.9.

Compound 608: $^1$H NMR (DMSO-d$_6$, 400 MHz) δ 12.37 (s, 1H), 8.07-8.02 (m, 4H), 7.78 (d, J=8.8 Hz, 2H), 7.45 (d, J=8.8 Hz, 2H), 6.70 (d, J=2.4 Hz, 1H). MS (ESI) m/z (M+H)$^+$ 301.9.

Compound 611: $^1$H NMR (DMSO-d$_6$, 400 MHz) δ 10.97 (s, 1H), 8.01 (s, 1H), 7.71 (s, 1H), 7.41 (s, 1H), 6.98 (s, 1H), 6.50 (d, J=2.8 Hz, 1H), 4.51 (q, J=6.8 Hz, 2H), 3.85 (s, 3H), 1.33 (t, J=6.8 Hz, 3H). MS (ESI) m/z (M+H)$^+$ 242.9.

Compound 612: $^1$H NMR (DMSO-d$_6$, 400 MHz) δ 12.08 (s, 1H), 11.03 (s, 1H), 8.06 (s, 1H), 7.76 (s, 1H), 7.35 (s, 1H), 7.05 (d, J=5.6 Hz, 1H), 6.58 (d, J=2.8 Hz, 1H), 3.87 (s, 3H). MS (ESI) m/z [M+H]$^+$ 215.0.

Compound 613: $^1$H NMR (DMSO-d$_6$, 400 MHz) δ 12.91 (s, 1H), 11.00 (d, J=3.6 Hz, 1H), 8.05 (s, 1H), 7.81 (s, 1H), 7.43 (d, J=2.8 Hz, 1H), 7.03 (d, J=5.2 Hz, 1H), 6.53 (d, J=2.8 Hz, 1H), 4.54 (q, J=7.2 Hz, 2H), 1.36 (t, J=7.2 Hz, 3H). MS (ESI) m/z [M+H]$^+$ 229.1.

Compound 616: $^1$H NMR (DMSO-d$_6$, 400 MHz) δ 12.93 (s, 1H), 12.08 (s, 1H), 11.05 (s, 1H), 7.96 (brs, 2H), 7.35 (d, J=2.8 Hz, 1H), 7.07 (s, 1H), 6.60 (d, J=2.8 Hz, 1H). MS (ESI) m/z [M+H]$^+$ 201.1.

Compound 647 was prepared following the similar procedure described in the synthesis of compound 593 using benzyl bromide in place of ethyl bromide in the reaction with XIII-4b. After Suzuki-Coupling with XIII-10, benzyl was replaced by isopropyl by reaction with KOtBu followed by isopropyl iodide. A second Suzuki-Coupling with 1-methyl-4-(4,4,5,5-tetramethyl-1,3,2-dioxaborolan-2-yl)-1H-pyrazole afforded the final product. $^1$H NMR (DMSO-d$_6$, 400 MHz) δ 8.13 (s, 1H), 7.81 (s, 1H), 7.72 (d, J=3.2 Hz, 1H), 7.63 (d, J=8.8 Hz, 2H), 7.52 (d, J=8.8 Hz, 2H), 7.38 (s, 1H), 6.67 (d, J=3.2 Hz, 1H), 5.77-5.70 (m, 1H), 3.88 (s, 3H), 1.44 (d, J=6.8 Hz, 6H). MS (ESI) m/z (M+H)$^+$ 417.1.

Compound 648 was prepared following the similar procedure described in the synthesis of Compound 647 using the Boc-protected boronic ester in the last coupling reaction. $^1$H NMR (DMSO-d$_6$, 400 MHz) δ 12.96 (s, 1H), 8.14 (s, 1H), 7.89 (s, 1H), 7.71 (d, J=3.2 Hz, 1H), 7.64 (d, J=8.8 Hz, 2H), 7.52 (d, J=8.8 Hz, 2H), 7.39 (s, 1H), 6.67 (d, J=3.2 Hz, 1H), 5.77-5.71 (m, 1H), 1.44 (d, J=6.8 Hz, 6H). MS (ESI) m/z (M+H)$^+$ 403.1.

Compounds 649 and 650 were prepared by Suzuki-Coupling of 4-bromo-6-(4-(trifluoromethoxy)phenyl)-1H-pyrrolo[2,3-c]pyridin-7(6H)-one with cyclopropylboronic acid then a second Suzuki Coupling with the corresponding boronic esters. Compound 649: $^1$H NMR (DMSO-d$_6$, 400 MHz) δ 8.12 (s, 1H), 7.81 (s, 1H), 7.64 (d, J=8.8 Hz, 2H), 7.53 (d, J=8.8 Hz, 2H), 7.46 (d, J=2.8 Hz, 1H), 7.38 (s, 1H), 6.57 (d, J=2.8 Hz, 1H), 4.20-4.15 (m, 1H), 3.86 (s, 3H), 1.07-0.96 (m, 4H). MS (ESI) m/z (M+H)$^+$ 415.0. Compound 650: $^1$H NMR (DMSO-d$_6$, 400 MHz) δ 12.95 (brs, 1H), 8.13 (s, 1H), 7.88 (s, 1H), 7.64 (d, J=8.8 Hz, 2H), 7.52 (d, J=8.8 Hz, 2H), 7.38 (d, J=3.6 Hz, 1H), 7.40 (s, 1H), 6.58 (d, J=3.6 Hz, 1H), 4.19-4.14 (m, 1H), 1.03-0.97 (m, 4H). MS (ESI) m/z (M+H)$^+$ 401.1.

Compounds 651 and 654 were prepared by reacting 4-bromo-6-(4-(trifluoromethoxy)phenyl)-1H-pyrrolo[2,3-c]pyridin-7(6H)-one with 1-chloro-2-methoxyethane in the presence of Cs$_2$CO$_3$ in DMF, followed by Suzuki-Coupling with the corresponding boronic esters. Compound 651: $^1$H NMR (DMSO-d$_6$, 400 MHz) δ 8.13 (s, 1H), 7.82 (s, 1H), 7.64 (d, J=8.8 Hz, 2H), 7.53 (d, J=8.8 Hz, 2H), 7.50 (d, J=3.2 Hz, 1H), 7.39 (s, 1H), 6.61 (d, J=3.2 Hz, 1H), 4.66 (t, J=5.6 Hz, 2H), 3.88 (s, 3H), 3.66 (t, J=5.6 Hz, 2H), 3.23 (s, 3H). MS (ESI) m/z (M+H)$^+$ 433.1. Compound 654: $^1$H NMR (DMSO-d$_6$, 300 MHz) δ 12.96 (brs, 1H), 8.03 (brs, 2H), 7.63 (d, J=9.0 Hz, 2H), 7.51 (d, J=3.0 Hz, 1H), 7.49 (d, J=9.0 Hz, 2H), 7.41 (s, 1H), 6.61 (d, J=3.0 Hz, 1H), 4.66 (t, J=5.4 Hz, 2H), 3.65 (t, J=5.4 Hz, 2H), 3.23 (s, 3H). MS (ESI) m/z (M+H)$^+$ 419.1.

Compounds 652 and 653 were prepared by reacting 4-bromo-6-(4-(trifluoromethoxy)phenyl)-1H-pyrrolo[2,3-c]pyridin-7(6H)-one with 1-bromo-2-fluoroethane in the presence of Cs$_2$CO$_3$ in DMF, followed by Suzuki-Coupling with the corresponding boronic esters. Compound 652: $^1$H NMR (DMSO-d$_6$, 400 MHz) δ 12.96 (brs, 1H), 8.03 (brs, 2H), 7.64 (d, J=8.4 Hz, 2H), 7.53 (d, J=2.8 Hz, 1H), 7.52 (d, J=8.8 Hz, 2H), 7.44 (s, 1H), 6.66 (d, J=2.8 Hz, 1H), 4.85-4.75 (m, 3H), 4.69 (m, 1H). MS (ESI) m/z (M+H)$^+$ 407.1. Compound 653: $^1$H NMR (DMSO-d$_6$, 400 MHz) δ 8.14 (s, 1H), 7.83 (s, 1H), 7.64 (d, J=8.8 Hz, 2H), 7.53 (d, J=2.8 Hz, 1H), 7.52 (d, J=8.8 Hz, 2H), 7.42 (s, 1H), 6.65 (d, J=2.8 Hz, 1H), 4.84-4.77 (m, 3H), 4.69 (m, 1H), 3.87 (s, 3H). MS (ESI) m/z (M+H)$^+$ 421.1.

Compound 655 was prepared following the similar procedure described in the synthesis of compound 593 where 1-(difluoromethoxy)-4-iodobenzene was used in place of XIII-10, and CuI, Cs$_2$CO$_3$, and 8-hydroxyquinoline in DMSO/dioxane used as the reaction catalysts. The reaction mixture was purged with N$_2$ and stirred at 110° C. overnight. In the last step coupling reaction, Pd-118 and K$_3$PO$_4$ were used in place of Pd(dppf)Cl$_2$ and K$_2$CO$_3$. $^1$H NMR (DMSO-d$_6$, 400 MHz) δ 8.10 (s, 1H), 7.79 (s, 1H), 7.54-7.51 (m, 3H), 7.32-7.14 (m, 4H), 6.59 (d, J=2.8 Hz, 1H), 4.51 (q, J=7.2 Hz, 2H), 3.85 (s, 3H), 1.33 (t, J=7.2 Hz, 3H).

Compound 691 was prepared following the similar procedure described in the synthesis of Compound 593 using 4-bromo-1-(2-ethoxyethyl)-6-(4-(trifluoromethoxy)phenyl)-1H-pyrrolo[2,3-c]pyridin-7(6H)-one in place of XIII-8b. $^1$H NMR (CDCl$_3$, 400 MHz) δ 7.83 (br. s., 2H), 7.51 (d, J=8.5 Hz, 2H), 7.36 (d, J=8.5 Hz, 2H), 7.29 (d, J=2.5 Hz, 1H), 7.08 (s, 1H), 6.47 (d, J=2.3 Hz, 1H), 4.76 (t, J=4.9 Hz, 2H), 3.81 (t, J=4.9 Hz, 2H), 3.45 (q, J=6.9 Hz, 2H), 1.15 (t, J=6.9 Hz, 3H). MS (ESI) m/z (M+H)$^+$ 433.1.

Compound 692 was prepared following the similar procedure described in the synthesis of Compound 593 using 4-bromo-1-(2-isopropoxyethyl)-6-(4-(trifluoromethoxy)phenyl)-1H-pyrrolo[2,3-c]pyridin-7(6H)-one in place of XIII-8b. $^1$H NMR (CDCl$_3$, 400 MHz) δ 7.85 (br.s., 2H), 7.52 (d, J=8.4 Hz, 2H), 7.36 (d, J=8.4 Hz, 2H), 7.31 (d, J=2.4 Hz, 1H), 7.08 (s, 1H), 6.46 (d, J=2.4 Hz, 1H), 4.74 (t, J=4.8 Hz, 2H), 3.79 (t, J=4.8 Hz, 2H), 3.52-3.45 (m, 1H), 1.09 (d, J=6.0 Hz, 6H).

Compound 693 was prepared by the Suzuki-coupling of 4-bromo-6-(4-(trifluoromethoxy)phenyl)-2,3-dihydro-1H-pyrrolo[2,3-c]pyridin-7 (6H)-one with 1-methyl-4-(4,4,5,5-tetramethyl-1,3,2-dioxaborolan-2-yl)-1H-pyrazole catalyzed by Pd-118/K$_3$PO$_4$ in dioxane/H$_2$O mixture; followed by reaction with acetyl chloride to afford the final product. $^1$H NMR (CDCl$_3$, 400 MHz) δ 7.53 (s, 1H), 7.49-7.45 (m, 2H), 7.42 (s, 1H), 7.40-7.34 (m, 2H), 7.28 (s, 1H), 4.28 (t, J=8.2 Hz, 2H), 3.95 (s, 3H), 3.04 (t, J=8.2 Hz, 2H), 2.36 (s, 3H).

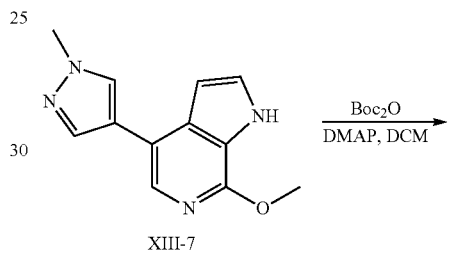

XIII-7

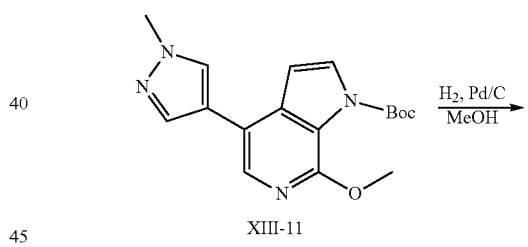

XIII-11

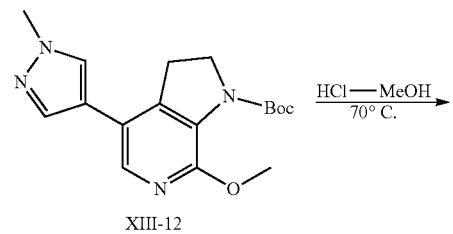

XIII-12

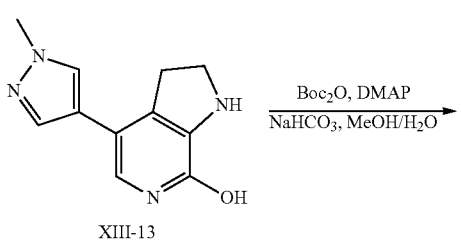

XIII-13

283
-continued

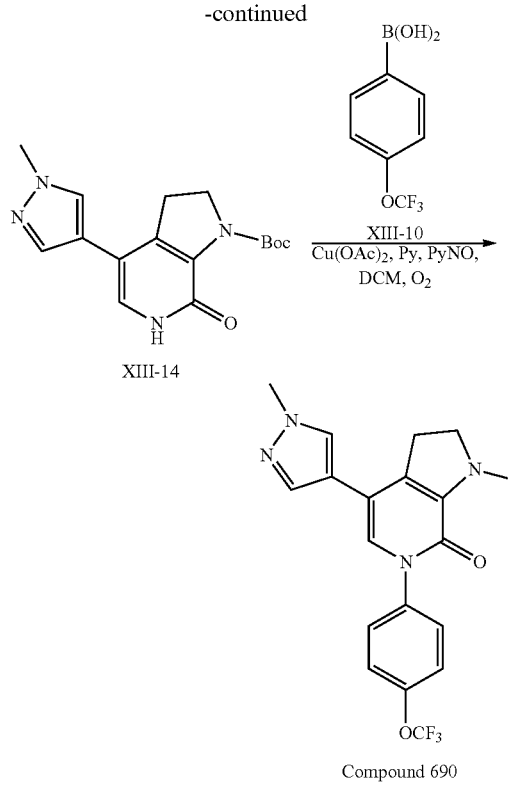

Compound 690

XIII-7 (2.5 g, 11 mmol) was dissolved in DCM (20 mL), then DMAP (98 mg, 0.66 mmol) and Boc$_2$O (2.87 g, 13 mmol) was added. The mixture was stirred at 25° C. for 1 h, then the solvent was removed in vacuo to give XIII-11 (3.3 g, yield 91.6%).

XIII-11 (4 g, 12.2 mmol) was dissolved in MeOH (40 mL), then Pd/C (400 mg, 10%) was added. The mixture was purged with hydrogen for three times and then stirred at 70° C. for 40 h. Then the solvent was removed in vacuo to give XIII-12 (3.1 g, yield 77%) as a white solid.

XIII-12 (3.3 g, 10.3 mmol) was dissolved in HCl-MeOH (4 M, 30 mL). The mixture was stirred at 70° C. for 2 h. Then the solvent was removed in vacuo to give XIII-13 (2.1 g, yield 97%) as a white solid.

XIII-13 (1.5 g, 6.9 mmol) was dissolved in sat. aq. NaHCO$_3$ (20 mL) and MeOH/H$_2$O (v/v=1/1, 20 mL), then DMAP (102 mg, 0.69 mmol) and Boc$_2$O (2.27 g, 1.0 mmol) was added. The mixture was stirred at 25° C. for 48 h. Then the mixture was extracted with EA, the combined organic phase was dried over anhydrous Na$_2$SO$_4$, filtered, concentrated in vacuo to afford a yellowish solid. The crude product was purified to give XIII-14 (380 mg, 16.8%) as a white solid.

XIII-14 was reacted with XIII-10 following the standard procedure described herein to give Compound 690 (230 mg, 41.7%) as a white solid. $^1$HNMR (CDCl$_3$, 400 MHz) δ 7.51 (s, 1H), 7.44 (d, J=8.5 Hz, 2H), 7.39 (s, 1H), 7.32 (d, J=8.5 Hz, 2H), 7.20 (s, 1H), 4.11 (t, J=8.3 Hz, 2H), 3.93 (s, 3H), 3.05 (t, J=8.3 Hz, 2H), 1.52 (s, 9H). MS (ESI) m/z (M+H)$^+$ 477.2.

284

Example 5-G

Synthesis of Compounds 50-53 (Scheme XIV)

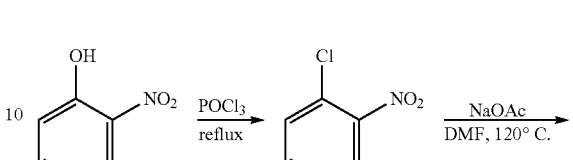

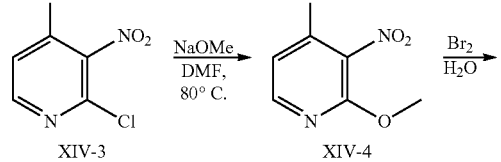

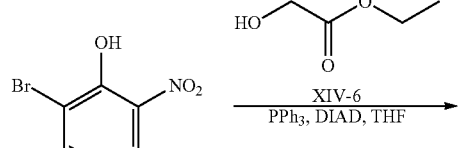

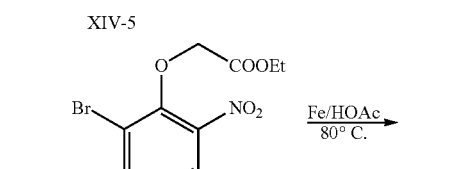

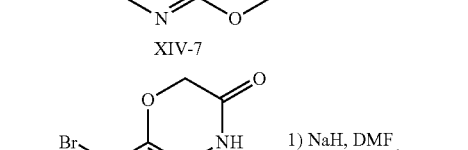

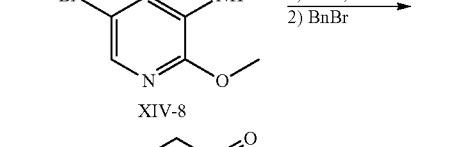

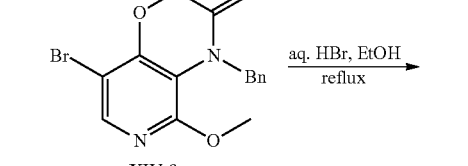

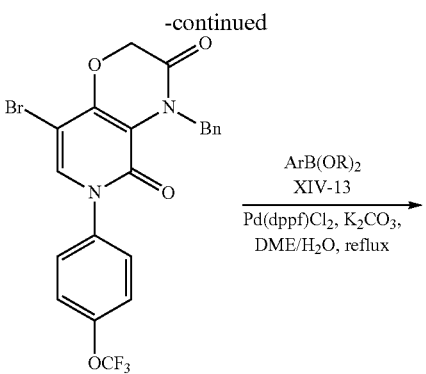

XIV-12

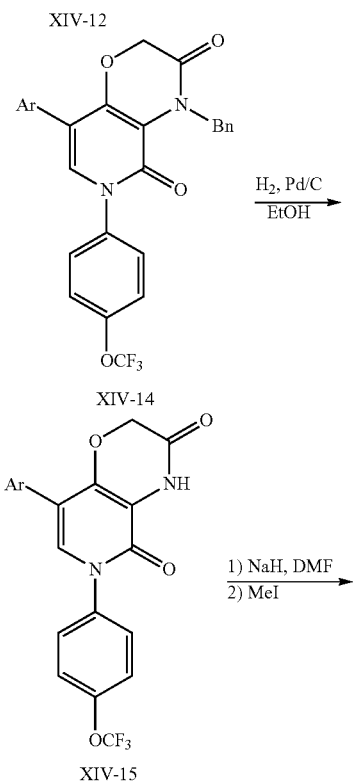

XIV-14

XIV-15

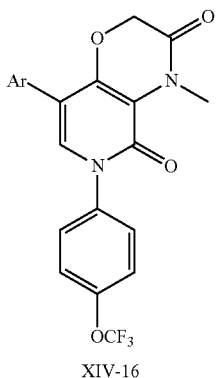

XIV-16

XIV-1 (10 g, 64.1 mmol) was added into POCl$_3$ (20 mL), the reaction mixture was heated at reflux for 2 hrs. The mixture was cooled to rt and poured into saturated aqueous Na$_2$CO$_3$, the mixture was extracted with EtOAc. The combined organic phase was dried over Na$_2$SO$_4$, and concentrated under reduced pressure. The residue was purified by column chromatography (PE:EA=10:1) to afford XIV-2 as a pale yellow solid (10 g, 83% yield). $^1$HNMR (CDCl$_3$, 300 MHz) δ 8.45 (d, J=5.4 Hz, 1H), 7.48 (d, J=5.4 Hz, 1H).

To a solution of XIV-2 (10 g, 52.1 mmol) in DMF (60 mL) was added NaOAc (10.3 g, 125 mmol), the reaction mixture was stirred at 120° C. for 3 hrs. The mixture was cooled to rt and poured into water, extracted with EtOAc. Combined organic phase was washed with brine and concentrated under vacuum to afford the crude product. The residue was purified by column chromatography (PE:EA=1:1) to afford XIV-3 as a pale yellow solid (5.4 g, 60% yield). $^1$HNMR (CD$_3$OD, 300 MHz) δ 8.14 (d, J=6.0 Hz, 1H), 6.98 (d, J=6.0 Hz, 1H).

To a solution of XIV-3 (5.4 g, 31.03 mmol) in DMF (30 mL) was added NaOMe (8.4 g, 155.17 mmol), the reaction mixture was stirred at 80° C. for 10 hrs. The mixture was cooled to rt and poured into water, extracted with EtOAc. Combined organic phase was washed with brine and concentrated under vacuum to afford the crude product. The residue was purified by column chromatography (PE:EA=1:1) to afford XIV-4 as a pale yellow solid (4.5 g, 85% yield). $^1$HNMR (CDCl$_3$, 300 MHz) δ 11.48 (brs, 1H), 8.10 (d, J=5.7 Hz, 1H), 6.71 (d, J=5.7 Hz, 1H), 4.11 (s, 3H).

To a suspension of XIV-4 (4.5 g, 26.47 mmol) in water (30 mL) were added drop wise Br$_2$ (5.3 g, 33.35 mmol) at rt, the reaction mixture was stirred for 30 min then heated at 50° C. for 1 h. After cooling to rt, the mixture was filtered, washed with water and dried under vacuum to yield XIV-5 as a pale yellow solid. (3.0 g, 46% yield). $^1$HNMR (CDCl$_3$, 400 MHz) δ 8.29 (s, 1H), 4.08 (s, 3H).

A flask was charged with XIV-5 (2.49 g, 10 mmol, 1 eq.), XIV-6 (1.25 g, 12 mmol, 1.2 eq.), PPh$_3$ (3.14 g, 12 mmol, 1.2 eq.) and 30 mL of anhydrous THF, flushed with nitrogen for three times. DIAD (2.42 g, 12 mmol, 1.2 eq.) was added drop wise into the mixture at 0° C. After that, the mixture was warmed to rt and stirred for another 16 hrs. TLC (PE:EA=5:1) analysis showed the reaction completed. The mixture was diluted with water, extracted with EtOAc (100 mL×3). The combined organic layer was washed with brine, dried over Na$_2$SO$_4$, filtered and concentrated to give a yellow oil. Purification by column chromatography gave XIV-7 (3 g, yield 89%). $^1$H NMR (CDCl$_3$, 300 MHz): δ 8.33 (s, 1H), 4.82 (s, 2H), 4.27 (q, J=7.2 Hz, 2H), 4.02 (s, 3H), 1.30 (t, J=7.2 Hz, 3H).

A flask was charged with XIV-7 (3 g, 8.96 mmol, 1 eq.), Fe powder (2 g, 35.82 mmol, 4 eq.) and 40 mL of AcOH. The mixture was heated at 80° C. for 3 hrs. TLC (PE:EA=3:1) analysis showed the reaction completed. The mixture was cooled down to rt, adjusted pH=7-8 with saturated aq. K$_3$PO$_4$, extracted with EtOA (100 mL×3). The combined organic layer was washed with brine, dried over Na$_2$SO$_4$, filtered and concentrated to give a yellow oil. Purification by column chromatography gave XIV-8 (1.5 g, 65% yield). MS (ESI) m/z (M+H)$^+$ 260.8

To a solution of XIV-8 (1 g, 3.86 mmol, 1 eq.) in 15 mL of DMF was added NaH (60%, 185 mg, 4.63 mmol, 1.2 eq.) at 0° C. The mixture was stirred at 0° C. for 30 min. After that, BnBr (792 mg, 4.63 mmol, 1.2 eq.) was added. The resulting mixture was stirred for 16 hrs at rt. TLC (PE:EA=3:1) analysis showed the reaction completed. The mixture was diluted with water, extracted with EtOA (80 mL×3). The combined organic layer was washed with brine, dried over Na$_2$SO$_4$, filtered and concentrated to give yellow oil. Purification by column chromatography gave XIV-9 (1.2 g, 89% yield). MS (ESI) m/z (M+H)$^+$ 350.9.

To a solution of XIV-9 (50 mg, 0.14 mmol, 1 eq.) in 6 mL of EtOH was added 1 mL of aq. HBr (40%). The mixture was heated at 100° C. for 1 h. TLC (EA) analysis showed the reaction completed. The mixture was cooled down to rt, adjusted pH=7-8 with saturated aq. NaHCO₃, extracted with EtOA (50 mL×3). The combined organic layer was washed with brine, dried over Na₂SO₄, filtered and concentrated to give XIV-10 (45 mg, 95% yield). ¹H NMR (CDCl₃, 400 MHz): δ 12.49 (brs, 1H), 7.26-7.22 (m, 6H), 5.64 (s, 2H), 4.73 (s, 2H).

The preparation of XIV-12 was followed the general procedure as described in the synthesis of X-6.

Compound 50 was prepared following the similar procedure for obtaining Compound 40 using 1-methyl-4-(4,4,5,5-tetramethyl-1,3,2-dioxaborolan-2-yl)-1H-pyrazole in replace of X-7. ¹H NMR (CDCl₃, 300 MHz) δ 7.56 (s, 1H), 7.51 (s, 1H), 7.30-7.17 (m, 11H), 5.58 (s, 2H), 4.65 (s, 2H), 3.86 (s, 3H). MS (ESI) m/z [M+H]⁺ 496.9.

Compound 51 was prepared following the similar procedure for obtaining Compound 40. ¹H NMR (CDCl₃, 300 MHz) δ 7.29-7.19 (m, 11H), 7.05-7.02 (m, 3H), 5.59 (s, 2H), 4.60 (s, 2H). MS (ESI) m/z [M+H]⁺ 511.2.

Compound 52: A flask was charged with Compound 51 (340 mg, 0.67 mmol), Pd/C (34 mg, 10% mol) and 10 mL of EtOH. The mixture was stirred for 30 hrs under hydrogen (50 psi). TLC (PE: EA=1:1) analysis showed the reaction completed. The mixture was filtered; the filtrate was concentrated to give yellow solid. Purification by prep-TLC gave Compound 52 (190 mg, 68% yield). ¹H NMR (CDCl₃, 400 MHz) δ 8.07 (s, 1H), 7.49 (d, J=8.8 Hz, 2H), 7.40-7.38 (m, 4H), 7.12-7.10 (m, 3H), 4.74 (s, 2H). MS (ESI) m/z [M+H]⁺ 421.2.

Compound 53: To a solution of Compound 52 (100 mg, 0.24 mmol, 1 eq.) in 5 mL of DMF was added NaH (14 mg, 0.54 mmol, 1.5 eq.) at 0° C. The mixture was stirred at 0° C. for 30 min. After that, MeI (50.7 mg, 0.54 mmol, 1.5 eq.) was added into the flask. The resulting mixture was stirred for 16 hrs at rt. TLC (PE: EA=1:1) analysis showed the reaction completed. The mixture was diluted with water, extracted with EtOAc (50 mL×3). The combined organic layer was washed with brine, dried over Na₂SO₄, filtered and concentrated to give yellow oil. Purification by prep-TLC gave Compound 53 (55.5 mg, 54% yield). ¹H NMR (CDCl₃, 300 MHz) δ 7.51-7.48 (m, 2H), 7.42-7.37 (m, 4H), 7.22 (s, 1H), 7.16-7.13 (m, 2H), 4.63 (s, 2H), 3.61 (s, 3H).

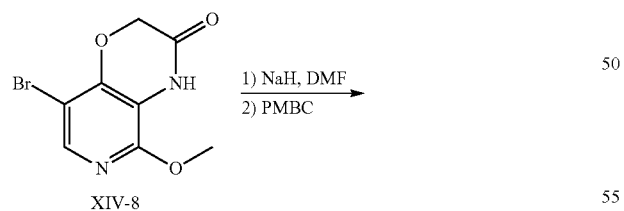

XIV-8

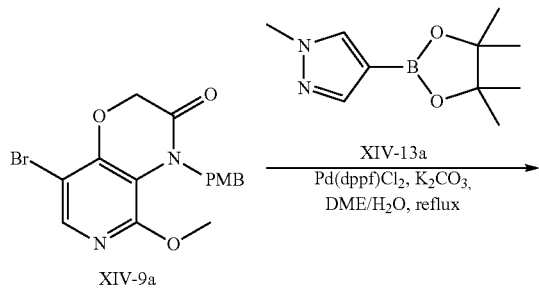

XIV-9a

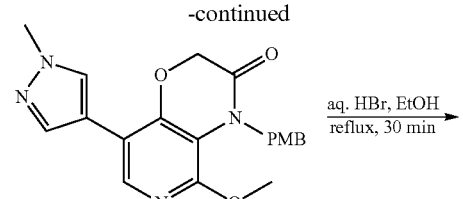

XIV-10a

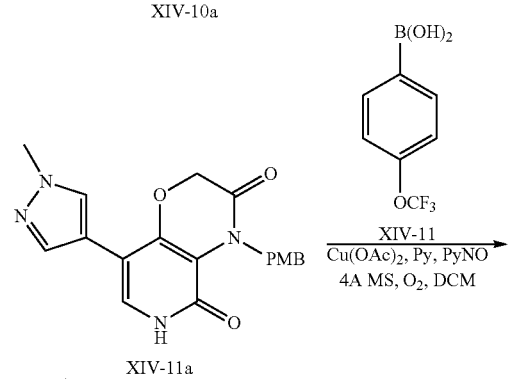

XIV-11a

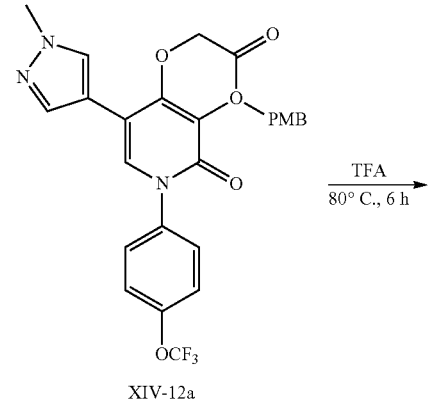

XIV-12a

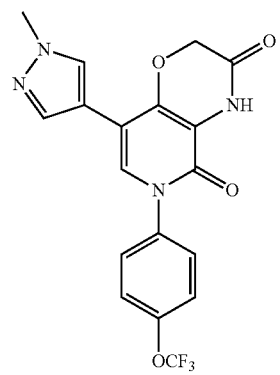

Compound 393

To a solution of XIV-8 (200 mg, 0.77 mmol, 1 eq.) in 10 mL of DMF was added NaH (60% dispersion in mineral oil, 60 mg, 1.16 mmol, 1.5 eq.) at 0° C. The mixture was stirred at 0° C. for 30 min. After that, PMBC (181 mg, 1.16 mmol, 1.5 eq.) was added into the flask. The resulting mixture was stirred for another 16 hrs at rt. TLC (PE/EA=3/1) analysis showed the reaction completed. The mixture was diluted with water (20 mL), extracted with EtOA (30 mL×3). The combined organic layer was washed with brine, dried over Na₂SO₄, filtered and concentrated to give yellow oil. Purification by prep-TLC (PE/EA=3/1) yield XIV-9a (245 mg, 85% yield). MS (ESI) m/z (M+H)⁺ 379.0.

XIV-12a was prepared following the scheme illustrated above. MS (ESI) m/z (M+H)⁺ 526.9.

The mixture of XIV-12a (100 mg, 0.19 mmol) and 5 mL of TFA was heated at 80° C. for 6 hrs. TLC (EA) analysis showed the reaction completed. The mixture was cooled down to rt, most of TFA was evaporated, the residue was neutralized with saturated aq.NaHCO$_3$, extracted with EtOAc (50 mL×3). The combined organic layer was washed with brine, dried over Na$_2$SO$_4$, filtered, concentrated to give a yellow solid. Purification by prep-TLC (EA) gave Compound 393 (72.3 mg, 93% yield). $^1$H NMR (CDCl$_3$, 400 MHz) δ 8.06 (brs, 1H), 7.67 (s, 1H), 7.63 (s, 1H), 7.48-7.45 (m, 2H), 7.38-7.35 (m, 2H), 7.22 (s, 1H), 4.81 (s, 2H), 3.95 (s, 3H). MS (ESI) m/z (M+H)⁺406.9.

Compound 396 was prepared following the similar procedure for obtaining XIV-12a using methyl iodide in place of PMBC. $^1$H NMR (CDCl$_3$, 400 MHz) δ 7.64-7.61 (m, 2H), 7.47-7.45 (m, 2H), 7.39-7.37 (m, 2H), 7.31 (s, 1H), 4.67 (s, 2H), 3.95 (s, 3H), 3.58 (s, 3H). MS (ESI) m/z [M+H]⁺ 420.9.

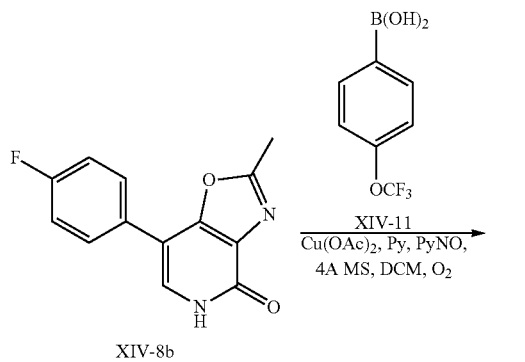

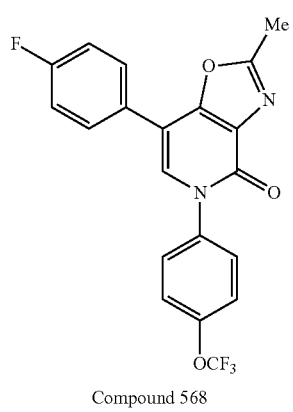

Compound 568

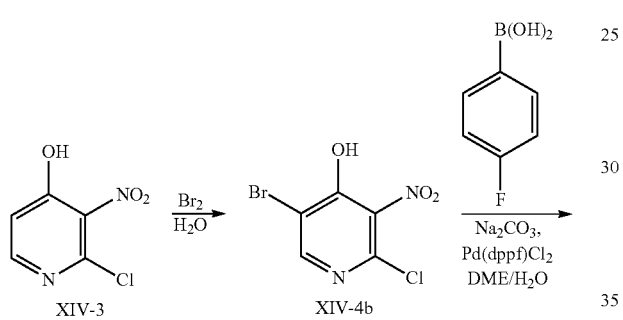

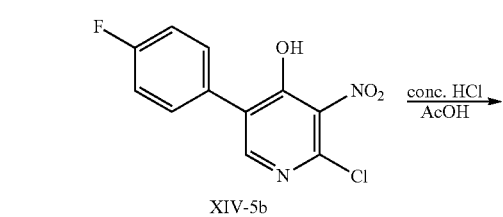

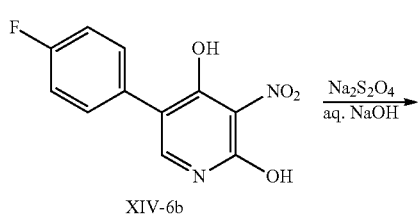

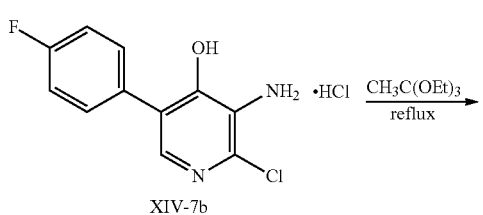

XIV-5b was obtained from XIV-3 in two steps by bromination and Suzuki-Coupling with (4-fluorophenyl)boronic acid using the standard procedure described herein.

A solution of XIV-5b (1.5 g, 5.6 mmol) in conc.HCl/AcOH (14 mL, v/v=1/1) was heated at reflux overnight. After cooling to r.t, the mixture was concentrated under reduced pressure to give XIV-6b without further purification (1.1 g, 78% yield).

XIV-6b (1.1 g, 4.4 mmol) was added into aq.NaOH (15 mL, 1M). Then Na$_2$S$_2$O$_4$ (1.5 g, 8.8 mmol) was added. The mixture was stirred at rt. under dark for 1 h. After completion of the reaction indicated by TLC (PE/EA=1:2), the mixture was acidified to pH=5-6, then extracted with EA. The organic layer was washed with brine, dried over Na$_2$SO$_4$, concentrated in vacuo to give XIV-7b without further purification (0.8 g, 83% yield).

A mixture of XIV-7b (0.8 g, 3.6 mmol) in CH$_3$C(OEt)$_3$ (10 mL) was heated at reflux overnight. After cooling to rt, the mixture was filtered, the filtrate cake was washed with EA/PE (1:1) to give crude XIV-8b (340 mg, 39% yield).

Compound 568 was obtained by Suzuki-Coupling of XIV-8b with XIV-11 using standard procedure described herein. $^1$H NMR (Methanol-d$_4$, 300 MHz) δ 7.78 (s, 1H), 7.72-7.67 (m, 2H), 7.55-7.51 (m, 2H), 7.41 (d, J=8.4 Hz, 2H), 7.16-7.10 (m, 2H), 2.59 (s, 3H).

Example 5-H

Synthesis of Compounds 54-59 (Scheme XV)

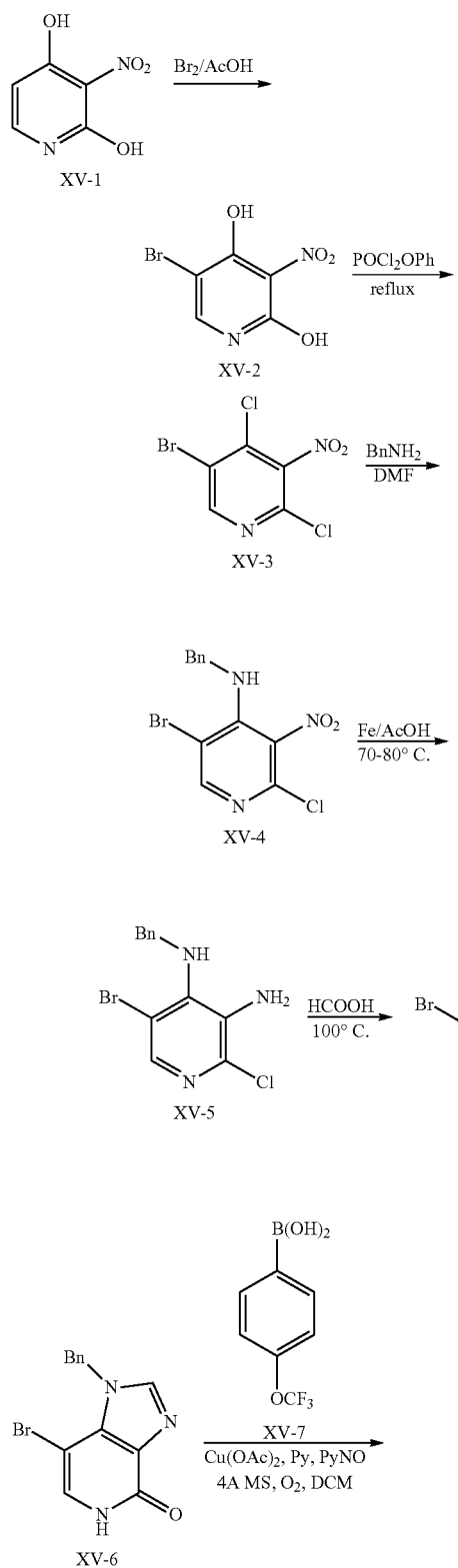

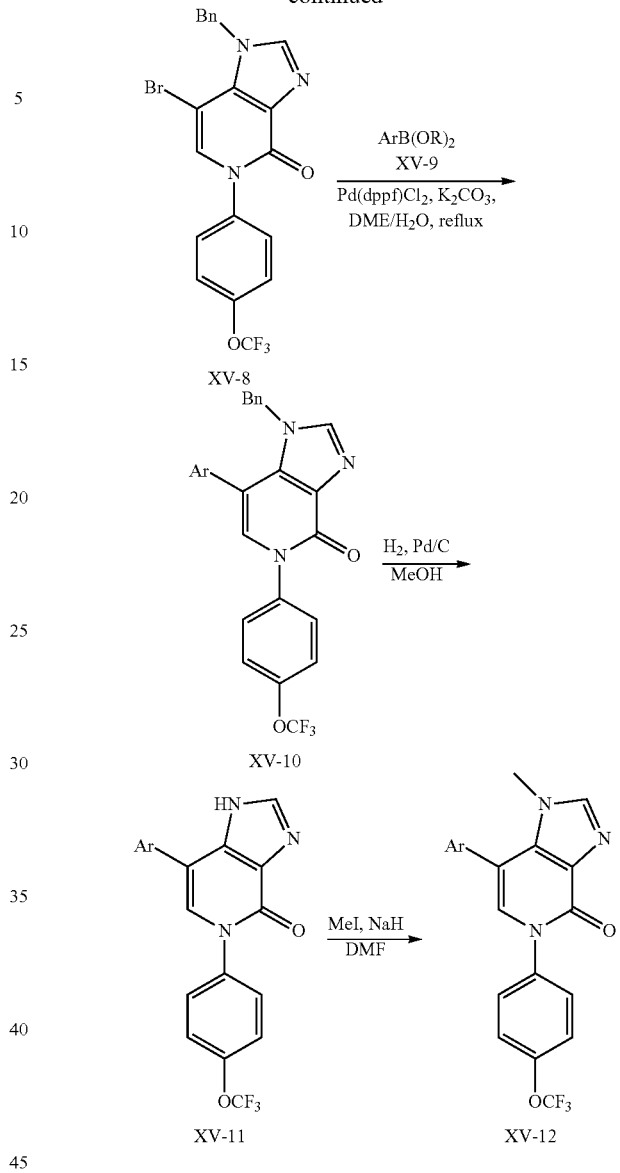

To a solution of XV-1 (15 g, 96.2 mmol) in AcOH (120 mL) were added Br$_2$ (16.7 g, 105.8 mmol). After addition, the reaction mixture was stirred at 70° C. for 30 min. Then the reaction mixture was poured into ice-water, the resulting precipitate was collected by filtration, washed with water and dried in reduced pressure to afford XV-2 as a yellow solid (14 g, 60% yield). $^1$H NMR (DMSO-d$_6$, 400 MHz) δ 7.85 (s, 1H).

XV-2 (2 g, 8.5 mmol) was added into POCl$_2$OPh (10 mL), and then the reaction mixture was heated at refluxed for 2 hrs. The mixture was cooled to rt and neutralize with saturated aq. Na$_2$CO$_3$, the mixture was extracted with EtOAc. The combined organic phase was dried over Na$_2$SO$_4$, and concentrated under reduced pressure. The residue was purified by column chromatography (PE: EA=10:1) to afford XV-3 as a pale yellow solid. (1.5 g, 65% yield). $^1$HNMR (CDCl$_3$, 300 MHz) δ 8.71 (s, 1H).

To a solution of XV-3 (544 mg, 2 mmol) in 10 mL of DMF was added BnNH$_2$ (268 mg, 2 mmol) at 0° C. The mixture was stirred for 18 h at rt. TLC (PE: EA=5:1) analysis showed the reaction completed. The mixture was diluted with water, extracted with EtOAc (30 mL×3). The combined organic layer was washed with brine, dried over Na₂SO₄, filtered, concentrated to give yellow oil. Purification by column chromatography gave XV-4 as a white solid (400 mg, 58% yield). MS (ESI) m/z [M+H]⁺ 342.2.

To a solution of XV-4 (200 mg, 0.58 mmol, 1 eq.) in 6 mL of AcOH was added Fe powder (131 mg, 2.34 mmol, 4 eq.). The mixture was heated at 70-80° C. and stirred for 3 hrs. TLC (PE: EA=5:1) analysis showed the reaction completed. The mixture was cooled down to rt, neutralized with saturated aq. K₃PO₄, extracted with EtOAc (50 mL×3). The combined organic layer was washed with brine, dried over Na₂SO₄, filtered, concentrated to give yellow oil. Purification by prep-TLC gave crude XV-5 (182 mg, 100% crude yield). MS (ESI) m/z (M+H)⁺ 313.9.

The mixture of XV-5 (1.5 g, 4.8 mmol, 1 eq) and 20 mL of formic acid was heated at 100° C. for 18 hrs. The reaction mixture was cooled down to rt, neutralized with saturated aq. K₃PO₄, extracted with EtOAc (100 mL×3). The combined organic layer was washed with brine, dried over Na₂SO₄, filtered, concentrated to give XV-6 (1.2 g, 82% yield). MS (ESI) m/z (M+H)⁺304.0.

The preparation of XV-8 followed the similar procedure for obtaining X-6 (1.1 g, 61% yield). MS (ESI) m/z (M+H)⁺ 465.9.

Compound 54 was prepared following the similar procedure for obtaining Compound 40. ¹H NMR (CDCl₃, 300 MHz) δ 7.75 (s, 1H), 7.44 (d, J=8.1 Hz, 2H), 7.26-6.90 (m, 10H), 6.55-6.50 (m, 2H), 4.92 (s, 2H). MS (ESI) m/z (M+H)⁺ 480.2.

Compound 55 was prepared following the similar procedure for obtaining Compound 40 using 1-methyl-4-(4,4,5,5-tetramethyl-1,3,2-dioxaborolan-2-yl)-1H-pyrazole in replace of X-7. ¹H NMR (CDCl₃, 300 MHz) δ 7.73 (s, 1H), 7.44-7.41 (m, 2H), 7.32-7.19 (m, 6H), 6.92 (s, 1H), 6.73-6.63 (m, 3H), 5.05 (s, 2H), 3.70 (s, 3H). MS (ESI) m/z (M+H)⁺ 466.0.

XV-11: A flask was charged with XV-10, Pd/C (10% mol) and EtOH. The mixture was stirred for 24 hrs under hydrogen (50 psi). TLC (PE: EA=1:1) analysis showed the reaction completed. The mixture was filtered; the filtrate was concentrated to give a yellow solid. Purification by prep-TLC gave XV-11.

Compound 56 was prepared from the Pd/C catalytic hydrogenation of Compound 54. ¹H NMR (DMSO-d₆, 400 MHz): δ 13.74 (s, 1H), 8.32 (s, 1H), 8.12-8.09 (m, 2H), 7.73-7.67 (m, 3H), 7.57-7.54 (m, 2H), 7.28-7.23 (m, 2H). MS (ESI) m/z (M+H)⁺ 390.0.

Compound 57 was prepared from the catalytic hydrogenation of Compound 55. ¹H NMR (CDCl₃, 400 MHz): δ 12.39 (s, 1H), 8.33 (s, 1H), 8.09 (s, 2H), 7.82 (s, 1H), 7.55 (d, J=8.8 Hz, 2H), 7.45-7.41 (m, 2H), 3.99 (s, 3H). MS (ESI) m/z (M+H)⁺ 376.0.

XV-12: To a solution of XV-11 (1 eq.) in DMF was added NaH (1.5 eq.) at 0° C. The mixture was stirred at 0° C. for 30 min. After that, MeI (1.5 eq.) was added. The resulting mixture was stirred for 16 hrs at rt. TLC (PE: EA=1:1) analysis showed the reaction completed. The mixture was diluted with water, extracted with EtOAc. The combined organic layer was washed with brine, dried over Na₂SO₄, filtered and concentrated. The residue was purified by prep-HPLC to yield XV-12.

Compound 58 was prepared by reacting Compound 56 with NaH in DMF followed by MeI. ¹H NMR (CDCl₃, 400 MHz): δ 7.90-7.75 (m, 3H), 7.56-7.13 (m, 7H), 4.19 (s, 3H). MS (ESI) m/z (M+H)⁺ 404.0.

Compound 59 was prepared from Compound 57. ¹H NMR (CDCl₃, 400 MHz): δ 8.26 (s, 1H), 7.86 (s, 1H), 7.79 (s, 1H), 7.50 (d, J=8.8 Hz, 2H), 7.40-7.33 (m, 3H), 4.17 (s, 3H), 3.97 (s, 3H). MS (ESI) m/z (M+H)⁺ 390.1.

Alternative Synthesis of Compound 59

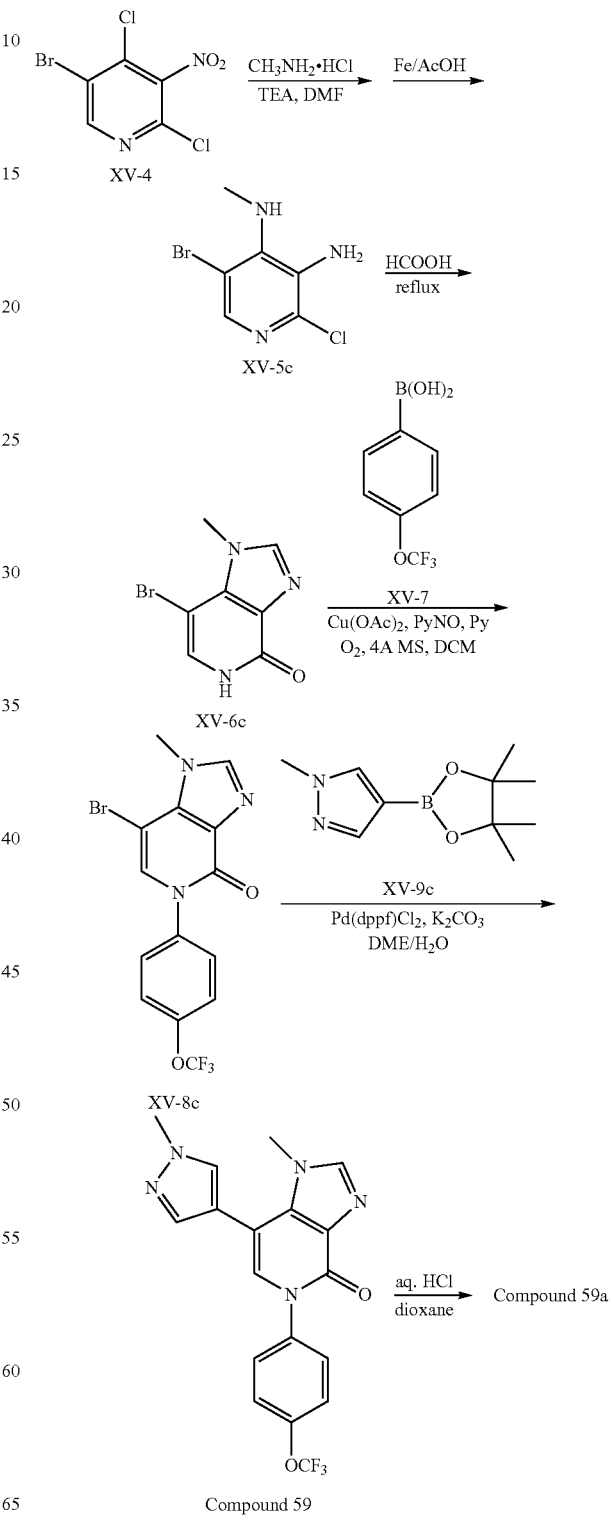

Compound 59

The alternative synthesis of Compound 59 was performed according to the standard procedure as described herein. HCl salt compound 59a: $^1$H NMR (DMSO-$d_6$, 400 MHz) δ 8.43 (s, 1H), 7.97 (s, 1H), 7.67 (s, 1H), 7.63 (d, J=8.8 Hz, 2H), 7.54 (d, J=8.8 Hz, 2H), 7.38 (s, 1H), 3.89 (s, 3H), 3.61 (s, 3H). MS (ESI) m/z (M+H)$^+$ 390.1.

Compound 636 was prepared following a modified synthetic route where XV-3 was reacted with ethylamine instead of benzy amine, followed by two-step Suzuki-Coupling reactions. Pd-118, $K_3PO_4$ were used in place of Pd(dppf)Cl$_2$ and $K_2CO_3$. $^1$H NMR (DMSO-$d_6$, 400 MHz): δ 8.14 (s, 1H), 7.96 (s, 1H), 7.66 (s, 1H), 7.61 (d, J=8.4 Hz, 2H), 7.51 (d, J=8.4 Hz, 2H), 7.26 (s, 1H), 4.01 (q, J=7.2 Hz, 2H), 3.88 (s, 3H), 1.06 (t, J=7.2 Hz, 3H).

Compound 637 was prepared by Suzuki-Coupling of a modified XV-5 (where benzyl is replaced by ethyl) with 1-methyl-4-(4,4,5,5-tetramethyl-1,3,2-dioxaborolan-2-yl)-1H-pyrazole, followed by reaction with HCOOH. $^1$H NMR (DMSO-$d_6$, 400 MHz) δ 12.2 (s, 1H), 9.17 (s, 1H), 7.96 (s, 1H), 7.63 (s, 1H), 7.19 (s, 1H), 4.04 (q, J=7.2 Hz, 2H), 3.91 (s, 3H), 1.11 (t, J=7.2 Hz, 3H).

Compound 638 was prepared following the same procedure for the synthesis of Compound 637 using the Boc-protected bononic ester. $^1$H NMR (DMSO-$d_6$, 400 MHz) δ 9.41 (s, 1H), 7.94 (s, 2H), 7.38 (s, 1H), 4.16 (q, J=7.2 Hz, 2H), 1.28 (t, J=7.2 Hz, 3H).

Compound 640 was prepared following the same procedure for the synthesis of Compound 636 with a Boc-protected boronic ester in place in the last Suzuki-Coupling reaction. $^1$H NMR (DMSO-$d_6$, 400 MHz): δ 13.07 (brs, 1H), 8.14 (s, 1H), 8.02 (s, 1H), 7.72 (s, 1H), 7.61 (d, J=8.8 Hz, 2H), 7.51 (d, J=8.8 Hz, 2H), 7.26 (s, 1H), 3.97 (q, J=7.2 Hz, 2H), 1.02 (t, J=7.2 Hz, 3H). HCl salt Compound 640a: $^1$H NMR (DMSO-$d_6$, 400 MHz): δ 8.76 (s, 1H), 7.91 (s, 2H), 7.65 (d, J=8.8 Hz, 2H), 7.55 (d, J=8.8 Hz, 2H), 7.46 (s, 1H), 4.05 (q, J=6.8 Hz, 2H), 1.08 (t, J=6.8 Hz, 3H).

Compound 641 was prepared by Pd/C hydrogenation (50 psi) of XV-8 in ethanol at 40° C. overnight. $^1$H NMR (DMSO-$d_6$, 400 MHz) δ 8.58 (s, 1H), 7.62-7.54 (m, 6H), 6.78 (d, J=7.2 Hz, 1H). HCl salt compound 641a: $^1$H NMR (DMSO-$d_6$, 400 MHz) δ 8.01 (s, 1H), 7.68-7.54 (m, 6H), 6.83 (d, J=6.4 Hz, 1H).

Compound 639 was prepared by Pd/C hydrogenation of a modified XV-8 (wherein benzyl is replaced by ethyl). $^1$H NMR (DMSO-$d_6$, 400 MHz): δ 8.14 (s, 1H), 7.55 (m, 5H), 6.83 (d, J=7.6 Hz, 1H), 4.23 (q, J=6.8 Hz, 2H), 1.40 (t, J=6.8 Hz, 3H). HCl salt compound 639a: $^1$H NMR (DMSO-$d_6$, 400 MHz): δ 8.69 (s, 1H), 7.69 (d, J=7.6 Hz, 1H), 7.61-7.54 (m, 4H), 6.96 (d, J=7.6 Hz, 1H), 4.31 (q, J=7.2 Hz, 2H), 1.43 (t, J=7.2 Hz, 3H).

Alternatively, Compound 639 can be prepared from reacting Compound 641 with NaH followed by reacting with ethyl iodide.

Compound 642 was prepared by Suzuki-Coupling of XV-8 with 1-ethyl-4-(4,4,5,5-tetramethyl-1,3,2-dioxaborolan-2-yl)-1H-pyrazole followed by deprotection of the benzyl group using KOt-Bu in DMSO. $^1$H NMR (DMSO-d6, 300 MHz): δ 8.46 (s, 1H), 8.32 (s, 1H), 8.11 (s, 1H), 7.78 (s, 1H), 7.69 (d, J=8.7 Hz, 2H), 7.58 (d, J=8.7 Hz, 2H), 4.17 (t, J=7.2 Hz, 2H), 1.41 (t, J=7.2 Hz, 3H).

Compound 643 was prepared by Suzuki-Coupling of XV-8 with 1-isopropyl-4-(4,4,5,5-tetramethyl-1,3,2-dioxaborolan-2-yl)-1H-pyrazole followed by deprotection of the benzyl group using KOt-Bu in DMSO. $^1$H NMR (DMSO-$d_6$, 400 MHz): δ 13.63 (brs, 1H), 8.46 (s, 1H), 8.30 (s, 1H), 8.12 (s, 1H), 7.77 (s, 1H), 7.67 (d, J=8.4 Hz, 2H), 7.57 (d, J=8.4 Hz, 2H), 4.52 (m, 2H), 1.44 (d, J=6.4 Hz, 6H).

Compound 644 was prepared by Suzuki-Coupling of a modified XV-8 (wherein benzyl is replaced by methyl) with 1-ethyl-4-(4,4,5,5-tetramethyl-1,3,2-dioxaborolan-2-yl)-1H-pyrazole using Pd-118 and $K_3PO_4$ in dioxane/$H_2O$ refluxing for 8 h. $^1$H NMR (DMSO-$d_6$, 400 MHz): δ 8.06 (s, 1H), 8.00 (s, 1H), 7.66 (s, 1H), 7.60 (d, J=8.8 Hz, 2H), 7.51 (d, J=8.8 Hz, 2H), 7.28 (s, 1H), 4.16 (q, J=7.2 Hz, 2H), 3.55 (s, 3H), 1.40 (t, J=8.8 Hz, 3H).

Compound 645 was prepared by Suzuki-Coupling of a modified XV-8 (wherein benzyl is replaced by methyl) with 1-isopropyl-4-(4,4,5,5-tetramethyl-1,3,2-dioxaborolan-2-yl)-1H-pyrazole using Pd-118 and $K_3PO_4$ in dioxane/$H_2O$ refluxing for 8 h. $^1$H NMR (DMSO-$d_6$, 400 MHz): δ 8.04 (d, J=7.2 Hz, 2H), 7.65 (s, 1H), 7.61 (d, J=8.8 Hz, 2H), 7.53 (d, J=8.8 Hz, 2H), 7.29 (s, 1H), 4.52 (m, 1H), 3.55 (s, 3H), 1.44 (d, J=6.8 Hz, 6H).

Compound 646 was prepared by Suzuki-Coupling of XV-8 with 1-methyl-4-(4,4,5,5-tetramethyl-1,3,2-dioxaborolan-2-yl)-1H-pyrazole, then KOt-Bu deprotecting of the benzyl group, followed by deprotonation with NaH in DMF, then reaction with 1-bromo-2-fluoroethane. $^1$H NMR (DMSO-d6, 300 MHz) δ 8.44 (s, 1H), 8.39 (s, 1H), 8.09 (s, 1H), 7.84 (s, 1H), 7.68 (d, J=8.7 Hz, 2H), 7.57 (d, J=8.7 Hz, 2H), 4.90 (m, 1H), 4.82 (m, 1H), 4.74 (s, 2H), 3.89 (s, 3H).

Compound 665 was prepared by Suzuki-Coupling of XV-8 with 1-methyl-4-(4,4,5,5-tetramethyl-1,3,2-dioxaborolan-2-yl)-1H-pyrazole, then KOt-Bu deprotecting of the benzyl group, followed by deprotonation with NaH in DMF, then reacting with Md. $^1$H NMR (DMSO-$d_6$, 400 MHz) δ 8.43 (s, 1H), 8.30 (s, 1H), 8.08 (s, 1H), 7.78 (s, 1H), 7.64 (d, J=8.8 Hz, 2H), 7.55 (d, J=8.8 Hz, 2H), 4.05 (s, 3H), 3.88 (s, 3H). MS (ESI) m/z (M+H)$^+$ 390.1.

Compound 669 was prepared by reacting 7-bromo-3-ethyl-3H-imidazo[4,5-c]pyridin-4(5H)-one with XV-7 following the standard copper acetate/pyridine/pyridine-N-oxide catalyzed reaction in DMF at 100° C. to form 7-bromo-3-ethyl-5-(4-(trifluoromethoxy)phenyl)-3H-imidazo[4,5-c]pyridin-4(5H)-one, followed by Suzuki-couling with tert-butyl 4-(4,4,5,5-tetramethyl-1,3,2-dioxaborolan-2-yl)-1H-pyrazole-1-carboxylate, catalyzed by Pd-118/$K_3PO_4$ in dioxane/$H_2O$ mixture under reflux condition to provide the final product. $^1$H NMR (DMSO-$d_6$, 400 MHz) δ 12.86 (brs, 1H), 8.43 (brs, 1H), 8.36 (s, 1H), 8.17 (brs, 1H), 7.80 (s, 1H), 7.65 (d, J=8.4 Hz, 2H), 7.54 (d, J=8.4 Hz, 2H), 4.45 (q, J=7.2 Hz, 2H), 1.40 (t, J=7.2 Hz, 3H). MS (ESI) m/z [M+H]$^+$ 390.1.

Compound 670 was prepared by reacting Compound 642 with ethyl iodide with the presence of NaH in DMF solution at rt for 2 hrs. $^1$H NMR (CDCl$_3$, 400 MHz) δ 8.29 (s, 1H), 7.92 (s, 1H), 7.82 (s, 1H), 7.51 (d, J=8.8 Hz, 2H), 7.38 (d, J=8.8 Hz, 2H), 7.37 (s, 1H), 4.56 (q, J=7.2 Hz, 2H), 4.24 (q, J=7.2 Hz, 2H), 1.59-1.51 (m, 6H). MS (ESI) m/z [M+H]$^+$ 418.1.

Compound 671 was prepared by reacting Compound 643 with ethyl iodide in the presence of NaH in DMF solution at rt for 2 hrs. $^1$H NMR (CDCl$_3$, 300 MHz) δ 8.33 (s, 1H), 7.95 (s, 1H), 7.86 (s, 1H), 7.53 (d, J=8.4 Hz, 2H), 7.41 (d, J=8.4 Hz, 2H), 7.39 (s, 1H), 4.62-4.55 (m, 3H), 1.60-1.55 (m, 9H). MS (ESI) m/z [M+H]$^+$ 431.9.

Compound 673 was prepared by reacting Compound 643 with methyl iodide in the presence of NaH in DMF solution at rt for 2 hrs. $^1$H NMR (CDCl$_3$, 300 MHz): δ 8.29 (s, 1H), 7.84 (d, J=10.0 Hz, 2H), 7.41 (d, J=8.4 Hz, 2H), 7.49 (d, J=9.2 Hz, 2H), 7.38-7.34 (m, 3H), 4.57-4.52 (m, 1H), 4.16 (s, 3H), 1.47 (s, 3H), 1.45 (s, 3H). MS (ESI) m/z [M+H]$^+$ 418.1.

Compound 672 was prepared by reacting XV-8 with tert-butyl 4-(4,4,5,5-tetramethyl-1,3,2-dioxaborolan-2-yl)-1H-pyrazole-1-carboxylate catalyzed by Pd-118/K$_3$PO$_4$ in dioxane/H$_2$O mixture under reflux condition overnight, followed by removal of the benzyl protecting group using t-BuOK in DMSO/THF at rt for 1 h under oxygen atmosphere. MS (ESI) m/z [M+H]$^+$ 361.9. $^1$H NMR (DMSO-d$_6$, 400 MHz) δ 13.66 (brs, 1H), 12.87 (brs, 1H), 8.45 (brs, 1H), 8.31 (brs, 1H), 8.19 (brs., 1H), 7.79 (brs, 1H), 7.66 (d, J=8.5 Hz, 2H), 7.54 (d, J=8.5 Hz, 2H).

Compound 674 was prepared by reacting 7-bromo-1,2-dimethyl-1H-imidazo[4,5-c]pyridin-4(5H)-one with XV-7 following the standard copper acetate/pyridine/pyridine-N-oxide catalyzed reaction in DMF at 100° C. to form 7-bromo-1,2-dimethyl-5-(4-(trifluoromethoxy)phenyl)-1H-imidazo[4,5-c]pyridin-4(5H)-one; followed by Suzuki-couling with 1-methyl-4-(4,4,5,5-tetramethyl-1,3,2-dioxaborolan-2-yl)-1H-pyrazole, catalyzed by Pd-118/K$_3$PO$_4$ in dioxane/H$_2$O mixture under reflux condition to provide the final product. $^1$H NMR (DMSO-d$_6$, 300 MHz): δ 7.56 (s, 1H), 7.51-7.45 (m, 3H), 7.31 (d, J=8.3 Hz, 2H), 6.99 (s, 1H), 3.99 (s, 3H), 3.44 (s, 3H), 2.55 (s, 3H). MS (ESI) m/z (M+H)$^+$ 404.1.

Compound 675 was prepared following the similar procedure for the synthesis of Compound 674 using tert-butyl 4-(4,4,5,5-tetramethyl-1,3,2-dioxaborolan-2-yl)-1H-pyrazole-1-carboxylate in place of 1-methyl-4-(4,4,5,5-tetramethyl-1,3,2-dioxaborolan-2-yl)-1H-pyrazole. $^1$H NMR (DMSO-d$_6$, 400 MHz) δ 13.07 (brs, 1H), 7.98 (brs, 1H), 7.69 (brs, 1H), 7.59 (d, J=8.0 Hz, 2H), 7.50 (d, J=8.0 Hz, 2H), 7.21 (s, 1H), 3.40 (s, 3H), 2.45 (s, 3H). MS (ESI) m/z (M+H)$^+$ 390.0.

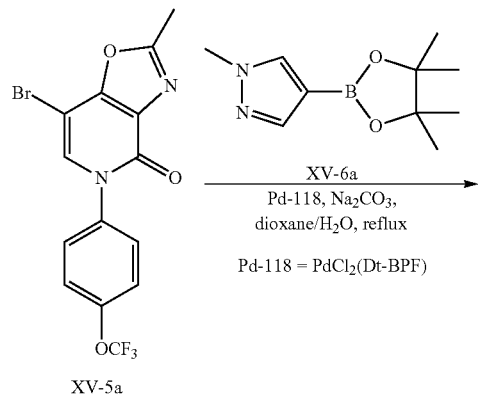

XV-5a

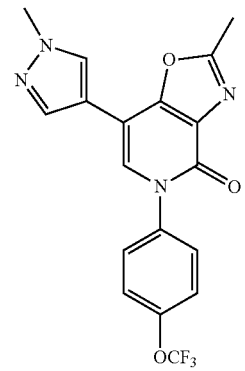

Compound 569

XV-4a was obtained in two steps from XV-2 following the similar procedure described in the synthesis of XIV-7b and XIV-8b. XV-5a was obtained by Suzuki-Coupling of XV-4a and XV-7 using the standard procedure described herein.

Compound 569 was obtained by Suzuki-Coupling of XV-5a and XV-6a following the similar procedure described in the synthesis of Compound 209. $^1$H NMR (CDCl$_3$, 300 MHz) δ 7.83 (s, 1H), 7.79 (s, 1H), 7.52-7.47 (m, 3H), 7.40 (d, J=8.7 Hz, 2H), 4.01 (s, 3H), 2.73 (s, 3H).

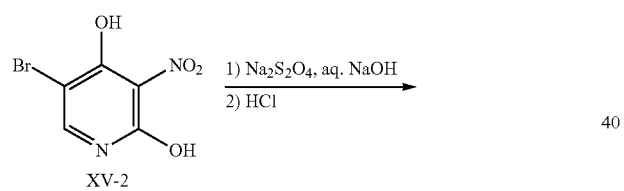

XV-2

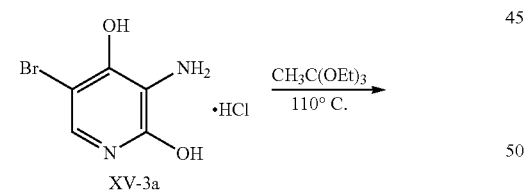

XV-3a

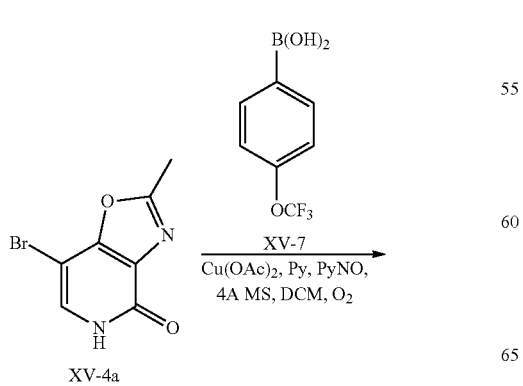

XV-4a

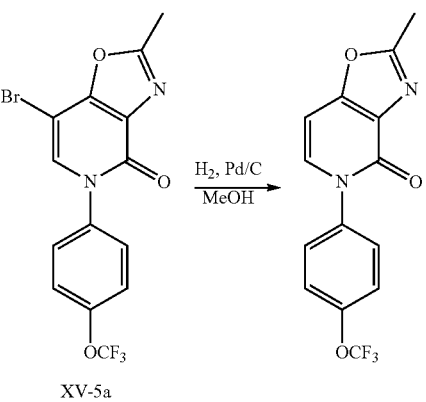

XV-5a

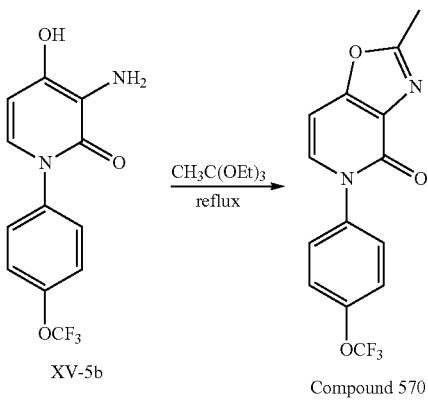

To a solution of XV-5a (150 mg, 0.39 mol) in MeOH (10 mL) was added Pd/C (20 mg), the mixture was stirred at rt under $H_2$ overnight. After completion of the reaction indicated by TLC (EA:PE=1:1), the mixture was filtered, the filtrate was concentrated in vacuo to afford a mixture of Compound 570 and XV-5b. The mixture were added into $CH_3C(OEt)_3$ (10 mL). The mixture was heated at reflux overnight. After cooling to rt, the mixture was filtered, the cake was collected and purified by prep-TLC (EA:PE=1:1) to give Compound 570 (50 mg, 41% yield). $^1H$ NMR (DMSO-$d_6$, 300 MHz) δ 7.77 (d, J=7.5 Hz, 1H), 7.60-7.52 (m, 4H), 6.94 (d, J=7.2 Hz, 1H), 2.59 (s, 3H).

Example 5-I

Synthesis of Compounds 60-63 (Scheme XVI)

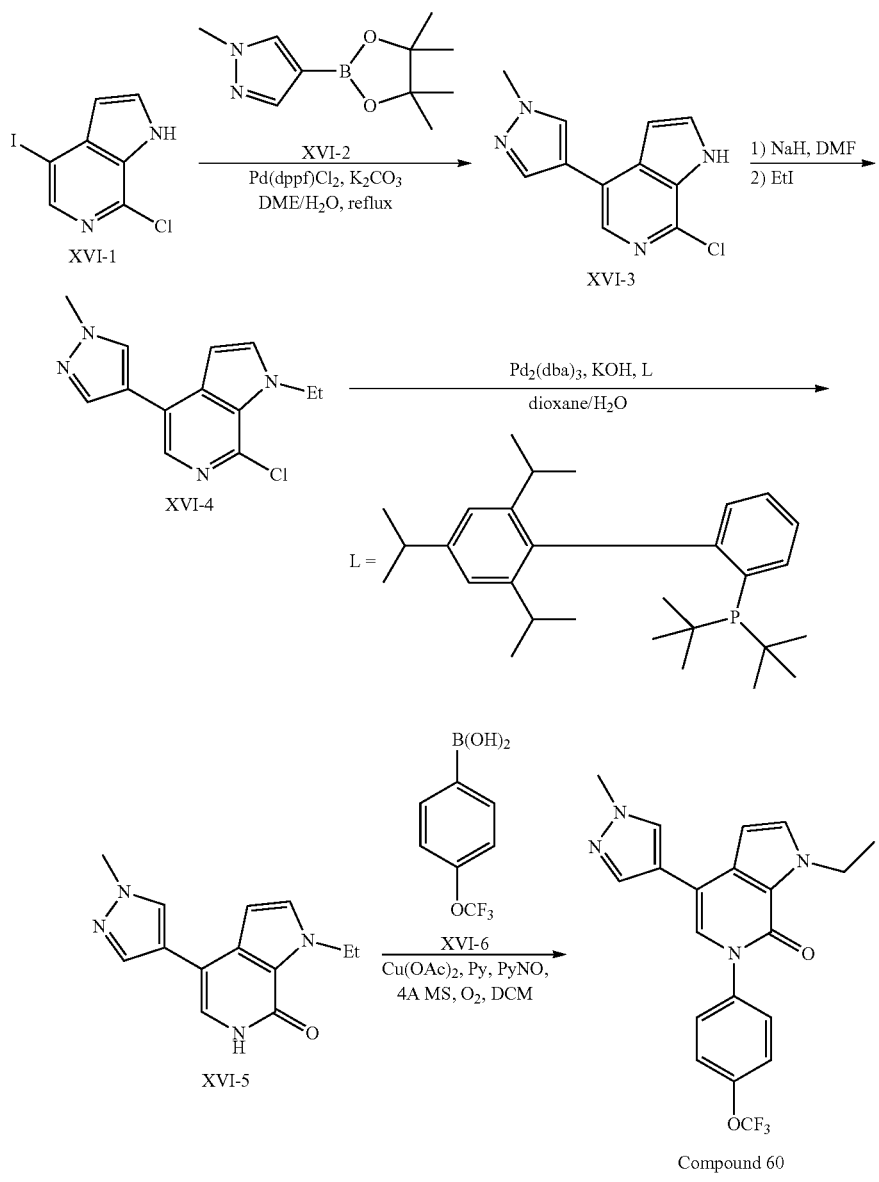

XVI-3 was prepared following the similar procedure for obtaining XIII-7. MS (ESI) m/z (M+H)⁺ 233.0.

XVI-4 was prepared following the similar procedure for obtaining XV-12, using ethyl iodide in place of methyl iodide. MS (ESI) m/z (M+H)⁺ 261.1.

XVI-5: A flask was charged with XVI-4 (150 mg, 0.57 mmol, 1 eq.), Pd₂(dba)₃ (285 mg, 0.46 mmol, 0.8 eq.), KOH (383 mg, 6.84 mmol, 12 eq.), Ligand (252 mg, 0.57 mmol, 1 eq.), 10 mL of dioxane and 10 mL of H₂O, flushed with nitrogen for three times. The mixture was heated at 100° C. for 10 hrs. LCMS analysis showed the reaction completed. The mixture was cooled down to rt, diluted with water, extracted with ethyl acetate (50 mL×3). The combined organic layer was washed with brine, dried over anhydrous sodium sulfate, filtrated and concentrated. Purification by prep-TLC gave XVI-5 (130 mg, yield 72%). MS (ESI) m/z (M+H)⁺ 243.1.

Compound 60 was prepared following the similar procedure for obtaining X-6. ¹H NMR (CDCl₃, 400 MHz) δ 7.71 (s, 1H), 7.60 (s, 1H), 7.50 (d, J=8.4 Hz, 2H), 7.34 (d, J=8.4 Hz, 2H), 7.18 (d, J=2.8 Hz, 1H), 7.04 (s, 1H), 6.47 (d, J=2.8 Hz, 1H), 4.61 (q, J=7.2 Hz, 2H), 3.97 (s, 3H), 1.48 (t, J=7.2 Hz, 3H). MS (ESI) m/z (M+H)⁺ 403.1.

Compound 61 was prepared following the similar procedure for obtaining XII-7 using (4-ethoxy-2-methylphenyl) boronic acid in place of XII-6. ¹H NMR (CDCl₃, 300 MHz) δ 9.03 (d, J=2.0 Hz, 1H), 8.86 (d, J=2.0 Hz, 1H), 7.73 (s, 1H), 7.16 (d, J=8.0 Hz, 1H), 6.89-6.84 (m, 2H), 4.07 (q, J=7.2 Hz, 2H), 2.18 (s, 3H), 1.44 (t, J=7.2 Hz, 3H). MS (ESI) m/z (M+H)⁺ 359.9.

Compound 62 was prepared from Compound 61 following the similar procedure for obtaining Compound 46. ¹H NMR (CDCl₃, 400 MHz) δ 8.93 (d, J=2.0 Hz, 1H), 8.90 (d, J=2.0 Hz, 1H), 7.57-7.54 (m, 2H), 7.43 (s, 1H), 7.22-7.14 (m, 3H), 6.90-6.84 (m, 2H), 4.07 (q, J=7.2 Hz, 2H), 2.22 (s, 3H), 1.44 (t, J=7.2 Hz, 3H). MS (ESI) m/z (M+H)⁺ 376.0.

Compound 63 was prepared from Compound 61 following the similar procedure for obtaining Compound 47. ¹H NMR (CDCl₃, 400 MHz) δ 8.93 (d, J=2.0 Hz, 1H), 8.90 (d, J=2.0 Hz, 1H), 8.14 (s, 1H), 7.79 (s, 1H), 7.56 (s, 1H), 7.20 (d, J=8.8 Hz, 1H), 6.90-6.85 (m, 2H), 4.08 (q, J=7.2 Hz, 2H), 3.99 (s, 3H), 2.19 (s, 3H), 1.45 (t, J=7.2 Hz, 3H). MS (ESI) m/z (M+H)⁺362.0.

Example 5-J

Synthesis of Compounds 582-584 and 586-587

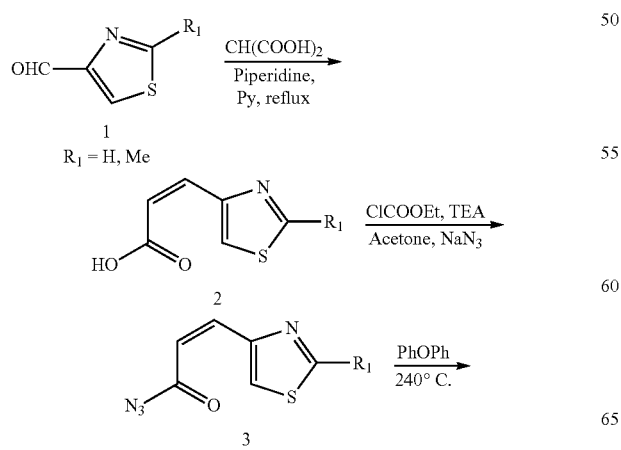

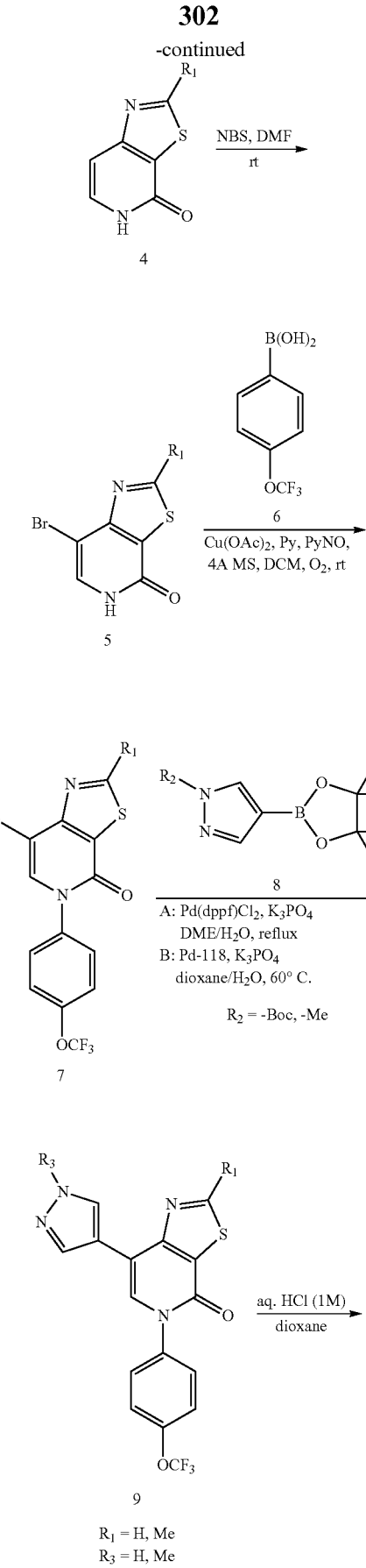

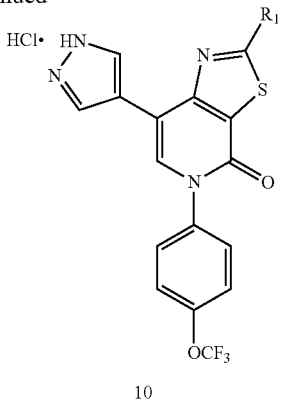

R₁ = H, Me
R₃ = H, Me

A flask was charged with compound 1 (3.0 g, 1 eq.), malonic acid (1.2 eq.), pyridine (20 mL), peperidine (1.56 mL). The mixture was stirred under nitrogen atmosphere at 90° C. for 2 h, cooled, concentrated under reduced pressure, the residue was diluted with water and adjusted pH=~5 by adding aq. HCl, the resulting solid was filtered and washed with water, the solid was dried in vacuo to give compound 2.

ClCOOEt (1.2 eq) was added into the solution of compound 2 (1.0 g, 1.0 eq.) and TEA (1.3 eq) in 20 mL of acetone by dropwise at 0° C. The mixture was stirred at 0° C. for 1 h. The resulting mixture was added into the solution of sodium azide (4 eq.) in 30 mL of acetone and water (v/v=1:1) at 0° C. and stirred for 30 mins. The mixture was diluted with water, extracted with EtOAc. The combined organic layer was washed with brine, dried over anhydrous sodium sulfate, filtered and concentrated to afford compound 3.

Compound 3 was added into 10 mL of oxydibenzene. The mixture was stirred at 240° C. for 2 h, cooled the mixture to rt and stirred overnight, filtered the resulting brown solid and washed with EtOAc to give compound 4 as a pale-brown solid.

A suspension of 4 (1 eq.), N-bromosuccinimide (1.1 eq.) and 50 mL of DMF was stirred at rt for 4 h. The mixture was filtered; the solids were washed successively with small amounts of DCM and dried to give compound 5 as a brown solid.

Compound 7 was prepared from reacting compound 5 with compound 6 using Method 1 as described herein.

Compound 9 was prepared by Suzuki-coupling of Compound 7 with the corresponding boronic ester 8 using the standard procedure A or B described herein.

Compound 582 was prepared following procedure A. ¹H NMR (DMSO-d₆, 300 MHz) δ 12.96 (s, 1H), 9.73 (s, 1H), 8.42 (s, 1H), 8.18 (s, 1H), 8.13 (s, 1H), 7.73 (d, J=8.7 Hz, 2H), 7.58 (d, J=8.7 Hz, 2H). MS (ESI) m/z (M+H)⁺ 378.9.

Compound 583 was prepared following procedure A. ¹H NMR (DMSO-d₆, 400 MHz) δ 9.72 (s, 1H), 8.40 (s, 1H), 8.10 (d, J=9.6 Hz, 2H), 7.72 (d, J=8.8 Hz, 2H), 7.58 (d, J=8.4 Hz, 2H), 3.89 (s, 3H). MS (ESI) m/z (M+H)⁺ 393.0.

Compound 584 was prepared following procedure B. ¹H NMR (CDCl₃, 400 MHz) δ 8.18 (s, 1H), 7.80 (s, 1H), 7.52 (d, J=9.2 Hz, 3H), 7.38 (d, J=8.4 Hz, 2H), 3.98 (s, 3H), 2.91 (s, 3H). MS (ESI) m/z (M+H)⁺ 407.0.

Compound 586 was prepared following procedure A. ¹H NMR (DMSO-d₆, 400 MHz) δ 8.51 (s, 1H), 8.15 (s, 1H), 8.10 (s, 1H), 7.70 (d, J=8.8 Hz, 2H), 7.57 (d, J=8.4 Hz, 2H), 7.35-7.24 (m, 5H), 5.39 (s, 2H), 2.90 (s, 3H). MS (ESI) m/z (M+H)⁺ 483.0.

Compound 587 was prepared following procedure B. ¹H NMR (DMSO-d₆, 300 MHz) δ 12.94 (s, 1H), 8.41 (s, 1H), 8.16 (s, 1H), 8.08 (s, 1H), 7.71 (d, J=8.7 Hz, 2H), 7.58 (d, J=8.7 Hz, 2H), 2.91 (s, 3H). MS (ESI) m/z (M+H)⁺ 392.7.

Compound 585 was prepared by Suzuki-Coupling of 2-methylthiazolo[5,4-c]pyridin-4(5H)-one with (4-(trifluoromethoxy)phenyl)boronic acid using the same method described in the synthesis of Compound 7. ¹H NMR (DMSO-d₆, 400 MHz) δ 7.76 (d, J=7.2 Hz, 1H), 7.65 (d, J=9.2 Hz, 2H), 7.55 (d, J=8.8 Hz, 2H), 6.96 (d, J=7.2 Hz, 1H), 2.84 (s, 3H). MS (ESI) m/z (M+H)⁺ 326.8.

Example 5-K

Synthesis of Compound 589

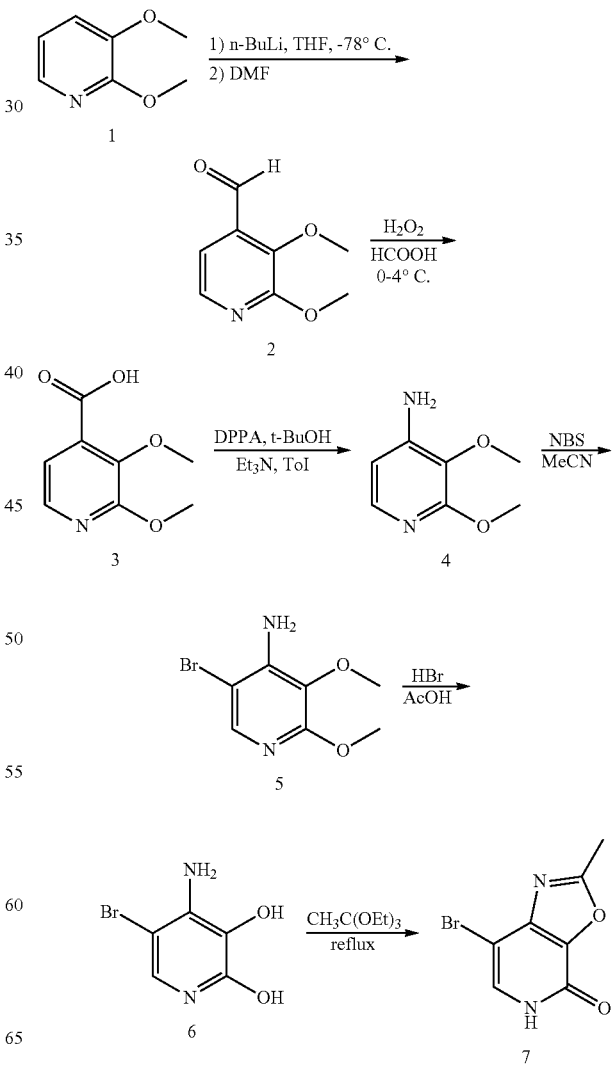

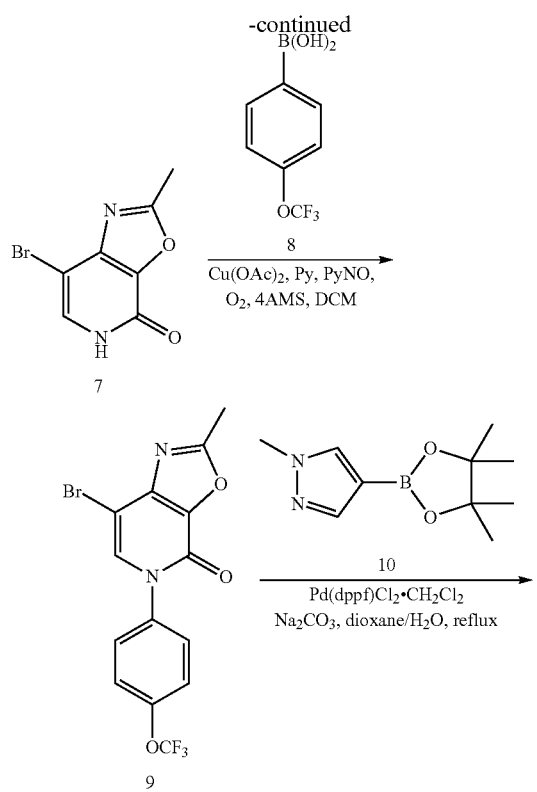

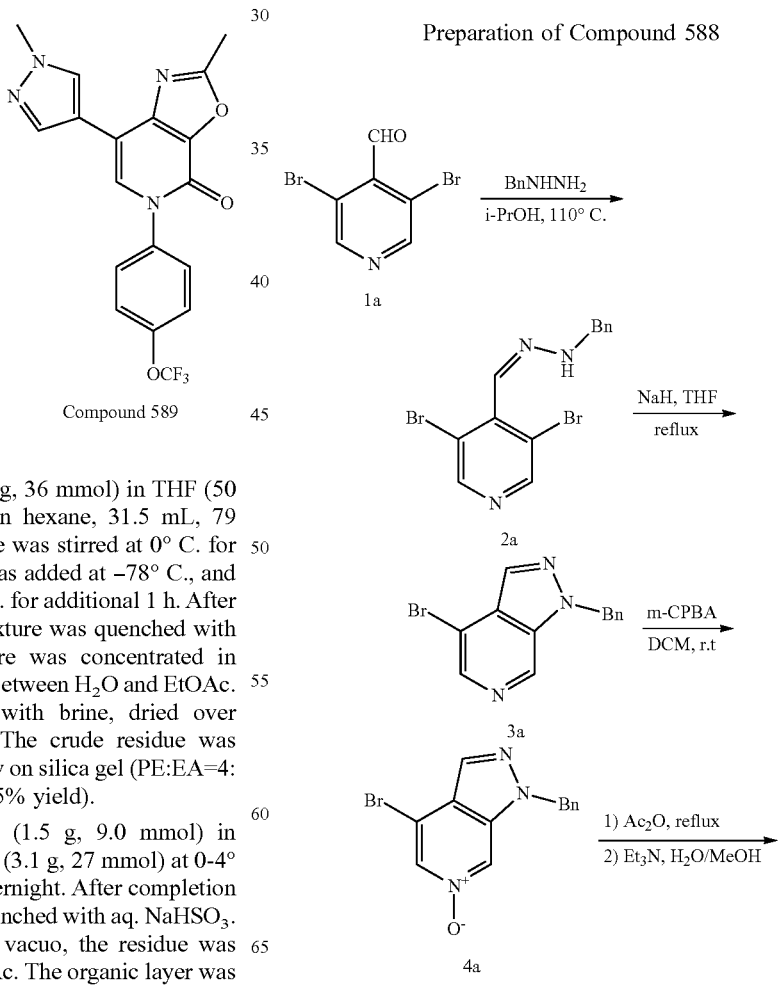

vacuo. The crude residue was purified by column chromatography on silica gel (PE:EA=1:1) to afford compound 3 (1.5 g, 94% yield).

To a solution of compound 3 (1.5 g, 8.2 mmol) in toluene (20 mL) was added Et$_3$N (2.1 g, 20.5 mmol), 4 Å molecular sieve (3.0 g). The mixture was purged with nitrogen for three times and then heated to reflux under nitrogen for 0.5 h. Then t-BuOH (0.73 g, 9.8 mmol), DPPA (2.4 g, 8.6 mmol) were added in turn. The mixture was stirred at reflux overnight. After cooling to rt, the mixture was filtered, the filtrate was partitioned between H$_2$O and EtOAc. The organic layer was washed with brine, dried over Na$_2$SO$_4$, concentrated in vacuo. The crude residue was purified by column chromatography on silica gel (PE:EA=3:1) to afford compound 4 (500 mg, 42% yield).

Compound 6 was prepared by bromination of compound 4 using NBS followed by HBr hydrolysis. A mixture of compound 6 (300 g, 1.5 mmol) in CH$_3$C(OEt)$_3$ (10 mL) was refluxed overnight. After cooling to rt, the mixture was filtered, the cake was washed with EA/PE (v/v=1/1) to give compound 7 (150 mg, 44% yield). MS (ESI) m/z (M+H)$^+$ 230.8.

Compound 589 was prepared from compound 7 by two Suzuki coupling steps as indicated in the scheme above. $^1$H NMR (DMSO-d$_6$, 300 MHz) δ 8.32 (s, 1H), 8.05 (d, J=4.5 Hz, 2H), 7.68 (d, J=8.7 Hz, 2H), 7.59 (d, J=8.7 Hz, 2H), 3.88 (s, 3H), 2.71 (s, 3H).

Preparation of Compound 588

To a solution of compound 1 (5 g, 36 mmol) in THF (50 mL) was added n-BuLi (2.5 M in hexane, 31.5 mL, 79 mmol) at −78° C., then the mixture was stirred at 0° C. for 1 h. DMF (12 mL, 157.5 mmol) was added at −78° C., and then the mixture was stirred at 0° C. for additional 1 h. After completion of the reaction, the mixture was quenched with saturated aq. NH$_4$Cl. The mixture was concentrated in vacuo, the residue was partitioned between H$_2$O and EtOAc. The organic layer was washed with brine, dried over Na$_2$SO$_4$, concentrated in vacuo. The crude residue was purified by column chromatography on silica gel (PE:EA=4:1) to afford compound 2 (1.5 g, 25% yield).

To a solution of compound 2 (1.5 g, 9.0 mmol) in HCOOH (20 mL) was added H$_2$O$_2$ (3.1 g, 27 mmol) at 0-4° C. The mixture was stirred at rt overnight. After completion of the reaction, the mixture was quenched with aq. NaHSO$_3$. The mixture was concentrated in vacuo, the residue was partitioned between H$_2$O and EtOAc. The organic layer was washed with brine, dried over Na$_2$SO$_4$, concentrated in

307

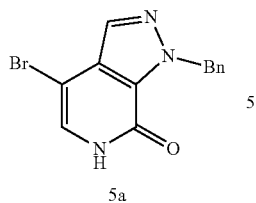

5a

The mixture of compound 1a (16 g, 60.4 mmol, 1 eq.), BnNHNH$_2$ (15 g, 129.3 mmol, 2 eq.) in 100 mL of i-PrOH was sealed and heated by microwave at 110° C. for 20 min. TLC analysis (PE/EA=5/1) showed the reaction completed. The mixture was cooled to rt. The precipitate was filtered and washed with cool i-PrOH to give a light yellow solid Compound 2a. (16.5 g, 74% yield).

Compound 2a (12 g, 32.5 mmol, 1 eq.) was dissolved in 1200 mL of THF, treated with NaH (60% dispersion in mineral oil, 1.56 g, 39.02 mmol, 1.2 eq.). The mixture was heated to reflux for 2 h. The mixture was cooled down to rt. The reaction was quenched with water slowly, extracted with EtOAc. The combined organic layer was washed with brine, dried over anhydrous sodium sulfate, filtered and concentrated to give brown oil. Purification by column (PE/EA=20/1-5/1) gave compound 3a (5.5 g, yield 59%).

To a solution of compound 3a (5.5 g, 19.1 mmol, 1 eq.) in 100 mL of DCM was added m-CPBA (6.5 g, 38.2 mmol, 2 eq.). The mixture was stirred for 18 h at rt. The reaction was diluted with water, extracted with DCM. The combined organic layer was washed with brine, dried over anhydrous sodium sulfate, filtered and concentrated to give brown oil. Purification by column (PE/EA=5/1-1/1) gave compound 4a (5.2 g, yield 89%).

The solution of compound 4a (4 g, 13.1 mmol, 1 eq.) in 70 mL of Ac$_2$O was heated to reflux for 18 h. All the volatiles were removed under vacuo. The residue was diluted with MeOH and adjusted pH=7-8 with Et$_3$N. The mixture was stirred for 4 h at rt. The reaction was diluted with water, extracted with EtOAc (150 mL×3). The combined organic layer was washed with brine, dried over anhydrous sodium sulfate, filtered and concentrated to give brown oil. Purification by column chrom (PE/EA=5/1-1/1) gave compound 5a (0.6 g, yield 15%). MS (ESI) m/z (M+H)$^+$305.9.

Compound 588 was prepared from compound 5a in three steps by Suzuki coupling with compound 8 followed by Suzuki coupling with compound 10, then deprotection of the benzyl group using KOt-Bu in DMSO. $^1$H NMR (DMSO-d$_6$, 400 MHz) δ 14.37 (s, 1H), 8.33 (s, 1H), 8.28 (s, 1H), 7.94 (s, 1H), 7.68 (d, J=8.4 Hz, 2H), 7.57-7.51 (m, 3H), 3.88 (s, 3H).

HCl salt Compound 588a: $^1$H NMR (DMSO-d$_6$, 400 MHz) δ 8.38 (s, 1H), 8.28 (s, 1H), 7.94 (s, 1H), 7.69 (d, J=8.8 Hz, 2H), 7.57 (d, J=8.8 Hz, 2H), 7.50 (s, 1H), 3.88 (s, 3H). MS (ESI) m/z (M+H)$^+$ 376.0.

Compounds 657 and 658 were prepared by reacting Compound 588 with ethyl iodide and NaH in DMF. Compound 657: $^1$H NMR (DMSO-d$_6$, 400 MHz): δ 8.62 (s, 1H), 8.18 (s, 1H), 7.90 (s, 1H), 7.64 (d, J=8.8 Hz, 2H), 7.55 (d, J=8.8 Hz, 2H), 7.42 (s, 1H), 4.44 (q, J=7.2 Hz, 2H), 3.88 (s, 3H), 1.53 (t, J=7.2 Hz, 3H). Compound 658: $^1$H NMR (DMSO-d$_6$, 400 MHz): δ 8.27 (s, 1H), 8.26 (s, 1H), 7.92 (s, 1H), 7.68 (d, J=8.8 Hz, 2H), 7.55 (d, J=8.8 Hz, 2H), 7.51 (s, 1H), 4.72 (q, J=6.8 Hz, 2H), 3.88 (s, 3H), 1.40 (t, J=6.8 Hz, 3H).

308

Preparation of Compound 660

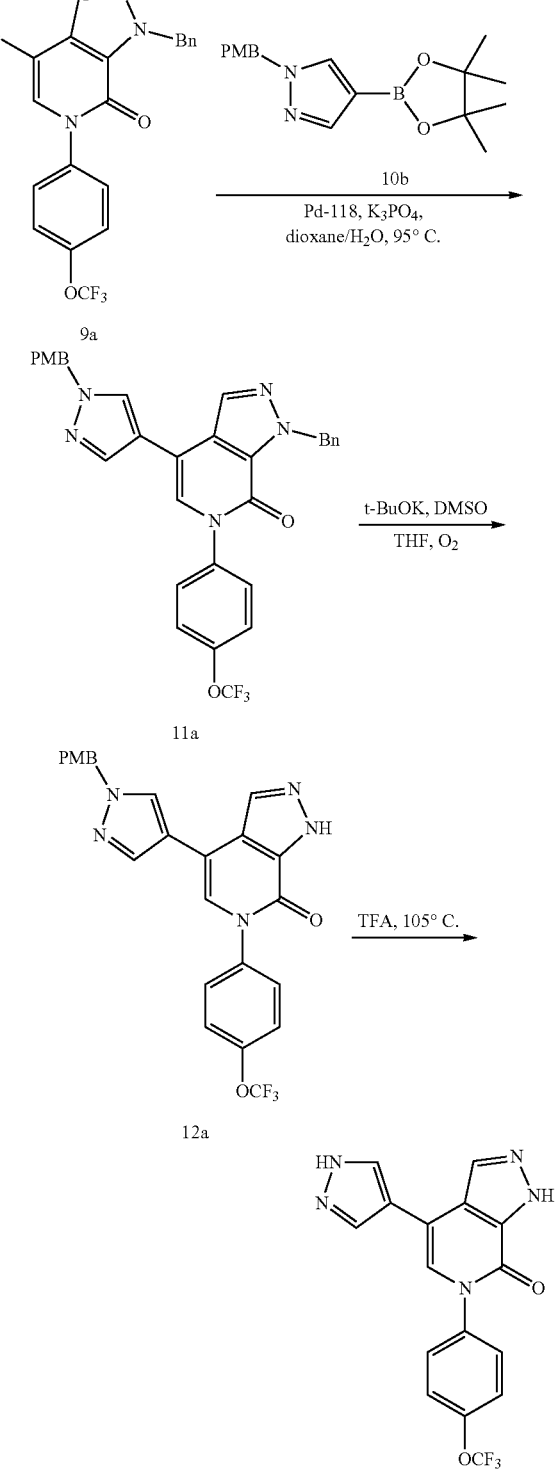

To a solution of compound 9a (1.8 g, 3.88 mmol, 1 eq.) in dioxane/H$_2$O (72 mL, v/v=5/1) was added K$_3$PO$_4$ (1.6 g, 7.76 mmol, 2 eq.), compound 10b (1.47 g, 4.66 mmol, 1.2 eq.), Pd-118 (125 mg, 0.19 mmol, 0.05 eq.). The mixture was purged with nitrogen and then heated at 95° C. for 8 hrs. The mixture was cooled to rt, diluted with water, extracted with EtOAc. The combined organic layer was washed with brine, dried over anhydrous Na$_2$SO$_4$, and concentrated in vacuo. The residue was purified by column chromatography (PE/EA=1/1) to give 11a as white solid (1.3 g, 59% yield).

To a solution of compound 11a (1.3 g, 2.27 mmol, 1 eq.), DMSO (1.77 g, 22.76 mmol, 10 eq.) in THF (75 mL) was added t-BuOK (5.1 g, 45.4 mmol, 20 eq.) at 0° C. The mixture was stirred under oxygen atmosphere at rt for 3 h. The reaction was quenched with water, extracted with EtOAc. The combined organic layer was washed with brine, dried over anhydrous Na$_2$SO$_4$, and concentrated in vacuo. The residue was purified by column chromatography (PE/EA=1/3) to give crude compound 12a (1.1 g, 100% yield).

The solution of compound 12a (320 mg, 0.66 mmol, 1 eq.) in TFA (5 mL) was heated at 105° C. for 3 hrs. The mixture was cooled to rt. All the volatiles were removed under reduced pressure. The residue was neutralized with saturated aq. NaHCO$_3$, extracted with EtOAc. The combined organic layer was washed with brine, dried over anhydrous Na$_2$SO$_4$, and concentrated to give brown oil. Purification by column chromatography gave Compound 660 (180 mg, 75% yield). $^1$H NMR (DMSO-d$_6$, 400 MHz): δ 14.27 (brs, 1H), 13.00 (brs, 1H), 8.38 (brs, 1H), 8.25 (brs, 1H), 8.01 (brs, 1H), 7.67 (d, J=8.4 Hz, 2H), 7.55 (d, J=8.4 Hz, 2H), 7.50 (s, 1H). MS (ESI) m/z (M+Na)$^+$ 383.9.

Compounds 659 and 661 were prepared by reacting compound 12a with ethyl iodide and NaH in DMF, separating the two intermediates and then treating each with TFA to afforded the final products. Compound 659: $^1$H NMR (DMSO-d$_6$, 400 MHz): δ 13.01 (brs, 1H), 8.65 (s, 1H), 8.09 (brs, 2H), 7.63 (d, J=8.0 Hz, 2H), 7.53 (d, J=8.0 Hz, 2H), 7.43 (s, 1H), 4.43 (q, J=7.2 Hz, 2H), 1.51 (t, J=7.2 Hz, 3H). MS (ESI) m/z (M+H)$^+$ 389.9. Compound 661: $^1$H NMR (DMSO-d$_6$, 400 MHz): δ 13.04 (br, 1H), 8.30 (s, 1H), 8.27-8.14 (br, 2H), 7.68 (d, J=8.4 Hz, 2H), 7.55 (d, J=8.4 Hz, 2H), 7.53 (s, 1H), 4.72 (q, J=7.2 Hz, 2H), 1.40 (t, J=7.2 Hz, 3H). MS (ESI) m/z (M+H)$^+$ 389.9.

Compound 689 was prepared by reacting compound 9a with (4-fluorophenyl)boronic acid catalyzed by Pd-118/K$_3$PO$_4$ in dioxane/H$_2$O at 90° C., followed by t-BuOK deprotecting benzyl group to afford the final product. $^1$H NMR (CDCl$_3$, 400 MHz) δ 8.08 (s, 1H), 7.59-7.52 (m, 4H), 7.39 (d, J=8.4 Hz, 2H), 7.19 (t, J=8.4 Hz, 2H), 7.08 (s, 1H). MS (ESI) m/z [M+H]$^+$ 390.0.

Example 5-L

Synthesis of Compound 617

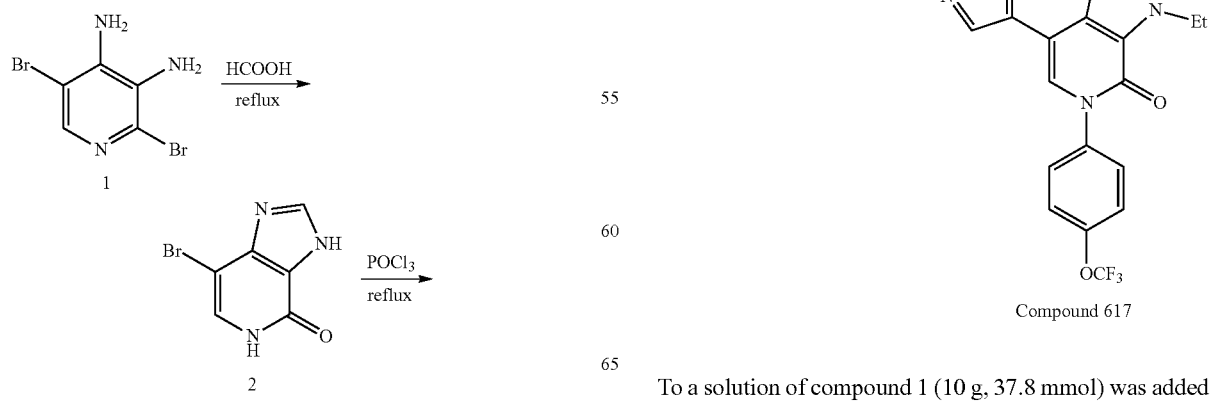

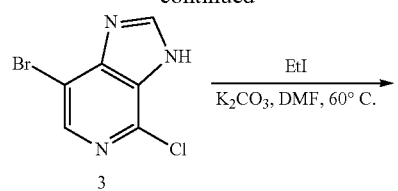

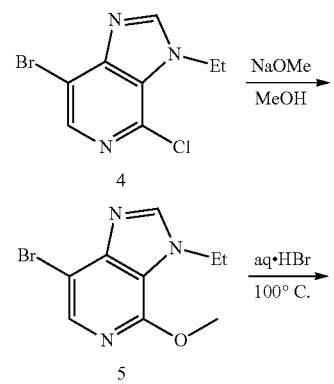

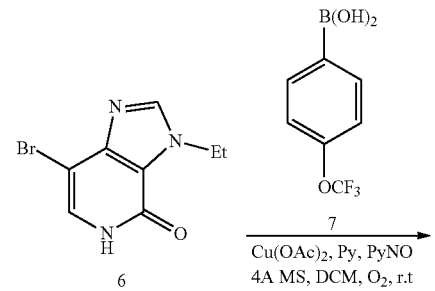

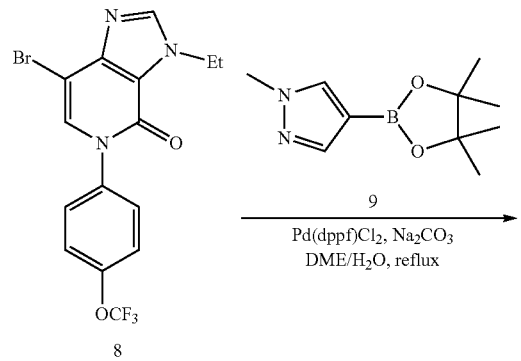

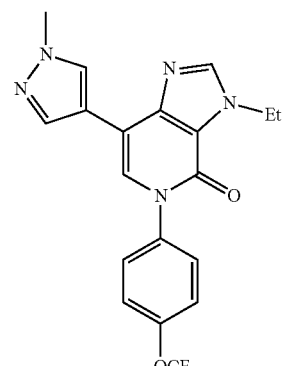

Compound 617

To a solution of compound 1 (10 g, 37.8 mmol) was added 20 mL of HCOOH. The mixture was refluxed overnight. The mixture was concentrated, purified by column chromatography on silica gel (DCM: MeOH=5:1) to give compound 2 (8 g, yield 99%).

A mixture of compound 2 (8.0 g, 37.4 mmol) in POCl₃ (10 mL) was refluxed for 3 h. Cooled down to rt. Then poured into water slowly, adjusted pH=7-8 with saturated aq. NaHCO₃, extracted with EtOAc. The combined organic layer was washed with brine, dried over anhydrous Na₂SO₄ and concentrated. The residue was purified by column chromatography on silica gel (PE:EA=2:1 to 1:1) to give compound 3 (4.57 g, 53% yield).

Compounds 4-8 were prepared following the similar procedures described in Example 5-F.

Compound 617 was prepared by Suzuki-Coupling of compound 8 with compound 9 following the standard procedure described herein as a white solid.

Alternative Synthesis of Compound 617

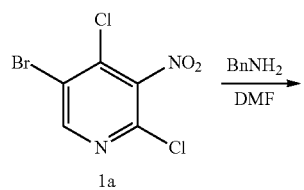
1a

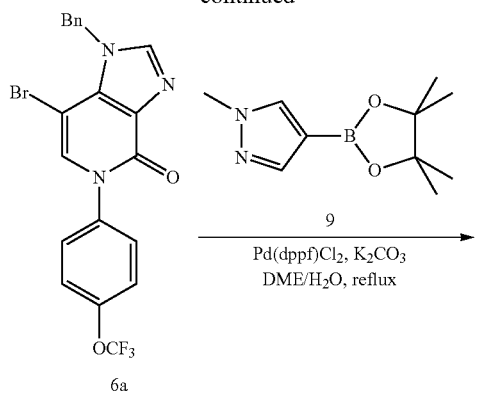
6a

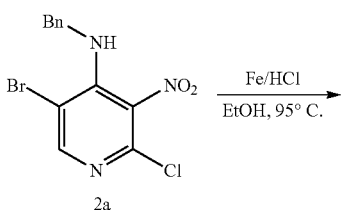
2a

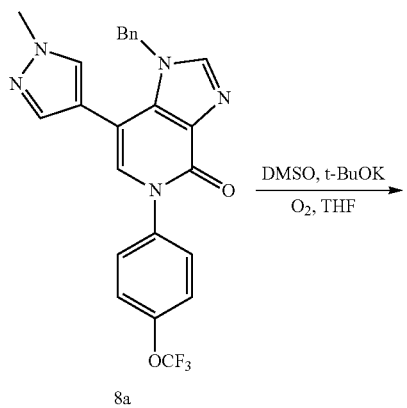
8a

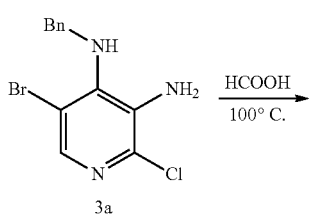
3a

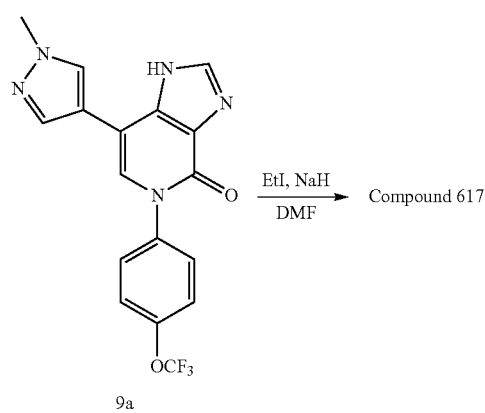
9a

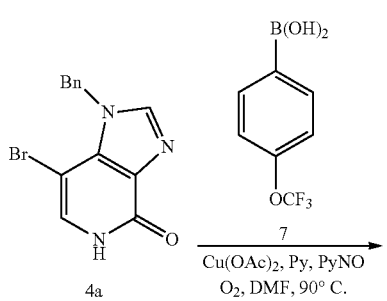
4a

The detailed synthetic procedure for the alternative synthesis of Compound 617 has been described herein. ¹H NMR (DMSO-d₆, 400 MHz) δ 8.41 (s, 1H), 8.36 (s, 1H), 8.06 (s, 1H), 7.78 (s, 1H), 7.65 (d, J=8.8 Hz, 2H), 7.54 (d, J=8.8 Hz, 2H), 4.45 (q, J=7.2 Hz, 2H), 3.86 (s, 3H), 1.40 (t, J=7.2 Hz, 3H).

Compound 618 was prepared by Suzuki-Coupling of compound 6 with compound 9, followed by HBr acid hydrolysis. ¹H NMR (CDCl₃, 400 MHz) δ 8.20 (d, J.=6.4 Hz, 1H), 7.93 (s, 1H), 7.38 (s, 1H), 4.56 (d, J.=7.2 Hz, 2H), 3.95 (s, 3H), 1.53 (t, J.=7.2 Hz, 3H). MS (ESI) m/z (M+H)⁺ 244.1.

Example 5-M

Synthesis of Compound 619

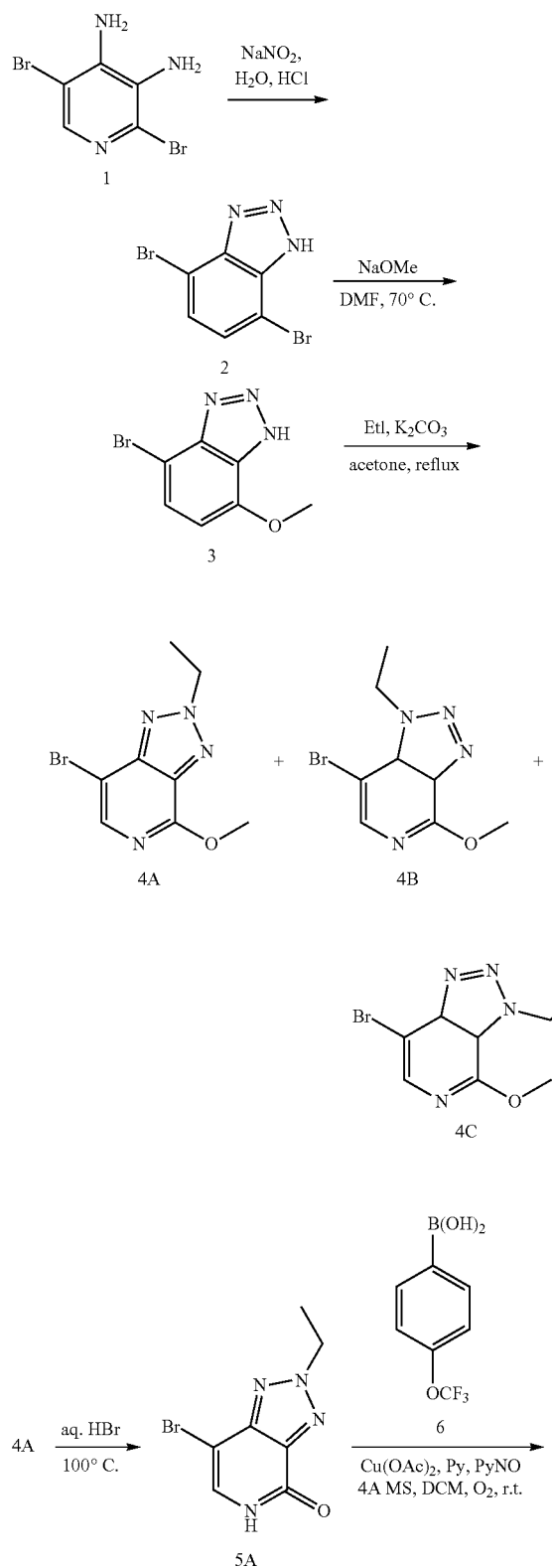

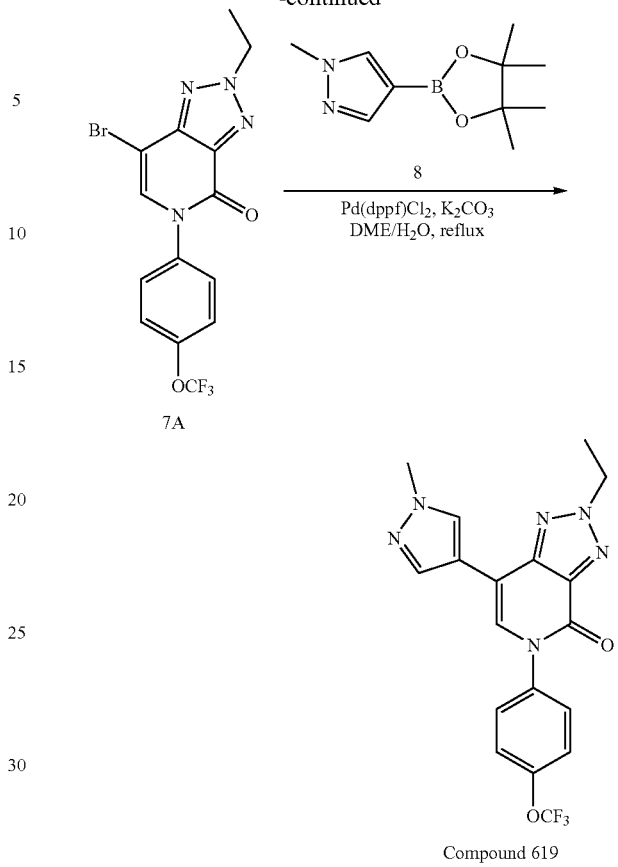

A solution of NaNO₂ (7.8 g, 113.3 mmol) in water (30 mL) was added dropwise into a solution of compound 1 (20 g, 75.5 mmol) in 2N hydrochloric acid (100 mL) at 0° C., and stirred for 1 h at 0° C. The precipitate was filtered and wash with ice-water and dried in vacuum to afford compound 2 (17 g, 82% yield) as a yellow brown solid.

Compounds 3, 4A-4C, 5A, and 7A were prepared following the similar procedures described in Example 5-F.

Compound 619 was prepared by Suzuki-Coupling of compound 7a with compound 8 following the standard procedure described herein. $^1$H NMR (CDCl$_3$, 400 MHz) δ 8.08 (s, 1H), 7.84 (s, 1H), 7.52 (d, J=8.0 Hz, 2H), 7.38 (d, J=8.4 Hz, 3H), 4.78 (q, J=6.8 Hz, 2H), 3.99 (s, 3H), 1.74 (t, J=6.8 Hz, 3H).

Compound 620 was prepared following the similar procedure described in the synthesis of Compound 619 using the Boc-protected boronic ester in place of compound 8. $^1$H NMR (CDCl$_3$, 400 MHz) δ 12.99 (s, 1H), 8.34 (s, 1H), 8.15 (s, 1H), 7.96 (s, 1H), 7.65-7.69 (m, 2H), 7.57 (d, J=8.4 Hz, 2H), 4.79 (q, J=7.2 Hz, 2H), 1.63 (t, J=7.2 Hz, 3H).

Compound 624 was prepared from compound 4B following the general procedure described above. $^1$HNMR (DMSO-d$_6$, 400 MHz) δ 8.01 (s, 1H), 7.71 (s, 1H), 7.67-7.65 (m, 2H), 7.55-7.53 (m, 3H), 4.42 (q, J=7.2 Hz, 2H), 3.90 (s, 3H), 1.20 (t, J=7.2 Hz, 3H). MS (ESI) m/z [M+H]⁺ 405.1.

Compound 633 was prepared from compound 4B following the general procedure described above to form an intermediate compound 7B followed by Pd/C hydrogenation to afforded the final product. $^1$HNMR (CDCl$_3$, 400 MHz) δ 7.46 (d, J=8.8 Hz, 2H), 7.37-7.33 (m, 3H), 6.50 (d, J=7.2 Hz, 1H), 4.60 (q, J=7.2 Hz, 2H), 1.64 (t, J=7.2 Hz, 3H). MS (ESI) m/z [M+H]⁺ 324.9.

Compound 625 was prepared from compound 4C following the general procedure described above. $^1$H NMR (DMSO-d$_6$, 400 MHz) δ 8.47 (s, 1H), 8.13 (s, 1H), 7.90 (s, 1H), 7.71-7.69 (m, 2H), 7.59 (d, J=8.4 Hz, 2H), 4.86 (q, J=7.2 Hz, 2H), 3.91 (s, 3H), 1.52 (t, J=7.2 Hz, 3H). MS (ESI) m/z [M+H]$^+$ 405.1.

Compound 630 was prepared from compound 4C following the general procedure described above to form an intermediate compound 7C followed by Pd/C hydrogenation to afforded the final product. $^1$HNMR (CDCl$_3$, 400 MHz) δ 7.46 (d, J=8.8 Hz, 2H), 7.38 (d, J=8.8 Hz, 2H), 7.19 (d, J=7.2 Hz, 1H), 6.93 (d, J=7.2 Hz, 1H), 4.92 (q, J=7.2 Hz, 2H), 1.63 (t, J=7.2 Hz, 3H). MS (ESI) m/z [M+H]$^+$ 325.1.

Compound 634 was prepared by Suzuki-Coupling of compound 7C with tert-butyl 4-(4,4,5,5-tetramethyl-1,3,2-dioxaborolan-2-yl)-1H-pyrazole-1-carboxylate using Pd-118, K$_3$PO$_4$ in dioxane/H$_2$O. $^1$HNMR (DMSO-d$_6$, 400 MHz) δ 13.1 (s, 1H), 8.47 (s, 1H), 8.23 (s, 1H), 7.93 (s, 1H), 7.71 (d, J=8.8 Hz, 2H), 7.59 (d, J=8.8 Hz, 2H), 4.86 (q, J=7.2 Hz, 2H), 1.53 (t, J=7.2 Hz, 3H). MS (ESI) m/z [M+H]$^+$ 391.1.

HCl salt compound 634a: $^1$HNMR (DMSO-d$_6$, 400 MHz) δ 8.36 (s, 2H), 7.93 (s, 1H), 7.70 (d, J=8.4 Hz, 2H), 7.59 (d, J=8.4 Hz, 2H), 4.86 (q, J=7.2 Hz, 2H), 1.53 (t, J=7.2 Hz, 3H). MS (ESI) m/z [M+H]$_+$391.0.

Compound 621 was prepared by Suzuki-Coupling of compound 4C with compound 8 followed by HBr hydrolysis. $^1$H NMR (DMSO-d$_6$, 400 MHz) δ 11.8 (s, 1H), 8.39 (s, 1H), 8.08 (s, 1H), 7.50 (s, 1H), 4.85 (q, J=7.2 Hz, 2H), 3.91 (s, 3H), 1.52 (t, J=7.2 Hz, 3H).

Compound 622 was prepared by Suzuki-Coupling of compound 4B with compound 8 followed by HBr hydrolysis. $^1$H NMR (DMSO-d$_6$, 400 MHz) δ 11.66 (s, 1H), 7.96 (s, 1H), 7.64 (s, 1H), 7.13 (s, 1H), 4.31 (q, J=7.2 Hz, 2H), 3.90 (s, 3H), 1.15 (t, J=7.2 Hz, 3H).

Compound 623 was prepared by amino protection of compound 3 using SEMCl and NaH in DMF, followed by Suzuki-Coupling with compound 8 then HCl hydrolysis in MeOH as a white solid. $^1$H NMR (DMSO-d$_6$, 400 MHz) δ 11.61 (s, 1H), 8.28 (s, 1H), 7.99 (s, 1H), 7.47 (s, 1H), 3.89 (s, 3H). MS (ESI) m/z (M+H)$^+$ 216.9.

Compound 631 was prepared from Compound 623 by first protecting the triazole hydrogen with Trt-Cl, then Suzuki-Coupling with (4-(trifluoromethoxy)phenyl)boronic acid using standard procedure described herein, followed by deprotecting in HCl/MeOH solution. $^1$HNMR (DMSO-d$_6$, 400 MHz) δ 8.38 (s, 1H), 8.07 (s, 1H), 7.89 (s, 1H), 7.69 (d, J=8.4 Hz, 2H), 7.58 (d, J=8.4 Hz, 2H), 3.90 (s, 3H). MS (ESI) m/z [M+H]$^+$ 376.9.

Compound 632 was prepared by reacting 3-benzyl-7-bromo-3H-[1,2,3]triazolo[4,5-c]pyridin-4(5H)-one with compound 6, followed by deprotection of the Bz group using Pd/C in hydrogen atmosphere (45 Psi) at rt overnight. $^1$H NMR (CDCl$_3$, 400 MHz) δ 7.67-7.60 (m, 3H), 7.55 (d, J=8.8 Hz, 2H), 6.82 (brs, 1H). MS (ESI) m/z (M+H)$^+$ 296.9.

Compound 635 was prepared following the similar synthetic scheme described in the synthesis of Compound 619 using isopropyl iodide in place of ethyl iodide in the reaction with compound 3. $^1$H NMR (CDCl$_3$, 400 MHz) δ 8.08 (s, 1H), 7.85 (s, 1H), 7.51 (d, J=8.8 Hz, 2H), 7.37 (d, J=8.8 Hz, 2H), 7.36 (s, 1H), 5.19-5.12 (m, 1H), 4.00 (s, 3H), 1.75 (d, J=6.8 Hz, 6H).

Compound 676 was prepared following the similar procedure described in the synthesis of Compound 619. First, 7-bromo-3-isopropyl-4-methoxy-3H-[1,2,3]triazolo[4,5-c] pyridine was formed by reacting compound 3 with isopropyl iodide; followed by Pd(dppf)Cl$_2$ catalyzed Suzuki-coupling with compound 8, subsequent acid hydrolysis to form 1-isopropyl-7-(1-methyl-1H-pyrazol-4-yl)-1H-[1,2,3]triazolo[4,5-c]pyridin-4(5H)-one. Finally, copper acetate catalyzed coupling with compound 6 provided the final product. $^1$H NMR (CDCl$_3$, 400 MHz) δ 8.41 (s, 1H), 7.85 (s, 1H), 7.52 (d, J=8.4 Hz, 2H), 7.41 (d, J=8.4 Hz, 2H), 7.37 (s, 1H), 5.73-5.66 (m, 1H), 4.00 (s, 3H), 1.75 (d, J=6.8 Hz, 6H). MS (ESI) m/z (M+H)$^+$ 418.9.

Compound 677 was prepared similarly as Compound 676 using 7-bromo-1-isopropyl-4-methoxy-3H-[1,2,3]triazolo [4,5-c]pyridine as starting material. $^1$H NMR (CDCl3, 400 MHz) δ 7.59 (s, 1H), 7.54 (s, 1H), 7.48 (d, J=8.4 Hz, 2H), 7.34 (d, J=8.4 Hz, 2H), 7.13 (s, 1H), 4.67-4.57 (m, 1H), 4.01 (s, 3H), 1.55 (d, J=6.8 Hz, 6H). MS (ESI) m/z (M+H)$^+$ 418.8.

Compound 679 was prepared following the similar procedure described in the synthesis of Compound 676 using 7-bromo-2-(2-fluoroethyl)-4-methoxy-2H-[1,2,3]triazolo[4,5-c]pyridine as starting material as a white solid. $^1$H NMR (DMSO-d$_6$, 400 MHz) δ 8.31 (s, 1H), 8.07 (s, 1H), 7.93 (s, 1H), 7.68 (d, J=8.8 Hz, 2H), 7.58 (d, J=8.8 Hz, 2H), 5.14 (s, 2H), 5.09-5.06 (m, 1H), 5.03-5.01 (m, 1H), 3.89 (s, 3H).

Compound 684 was prepared following the similar procedure described in the synthesis of Compound 676 using 7-bromo-3-(2-fluoroethyl)-4-methoxy-2H-[1,2,3]triazolo[4,5-c]pyridine as starting material. $^1$H NMR (CDCl$_3$, 400 MHz) δ 8.47 (s, 1H), 7.87 (s, 1H), 7.52 (d, J=8.8 Hz, 2H), 7.43-7.39 (m, 3H), 5.27 (t, J=4.8 Hz, 1H), 5.22 (t, J=4.8 Hz, 1H), 5.04 (t, J=4.8 Hz, 1H), 4.92 (t, J=4.8 Hz, 1H), 4.01 (s, 3H).

Compound 687 was prepared following the similar procedure described in the synthesis of Compound 676 using 7-bromo-1-(2-fluoroethyl)-4-methoxy-2H-[1,2,3]triazolo[4,5-c]pyridine as starting material. $^1$H NMR (CDCl$_3$, 400 MHz) δ 7.60 (s, 1H), 7.54 (s, 1H), 7.50 (d, J=8.8 Hz, 2H), 7.36 (d, J=8.8 Hz, 2H), 7.18 (s, 1H), 4.85 (t, J=4.8 Hz, 1H), 4.73 (t, J=4.8 Hz, 1H), 4.65 (t, J=4.8 Hz, 1H), 4.60 (t, J=4.8 Hz, 1H), 4.01 (s, 3H).

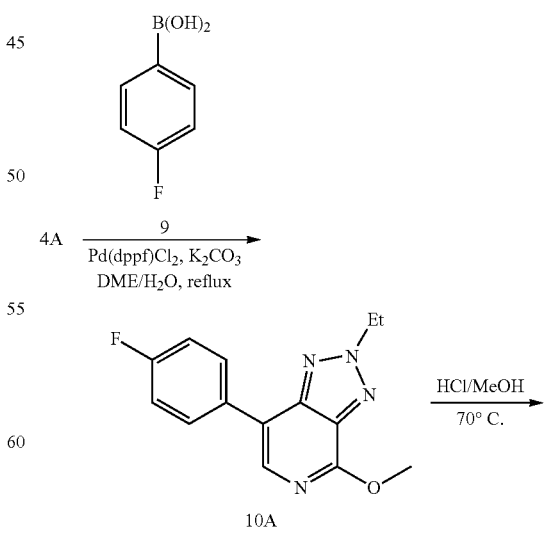

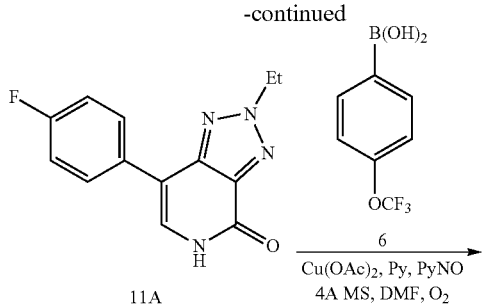

A mixture of compound 4A (1.0 g, 3.906 mmol, 1 eq), compound 9 (820 mg, 5.859 mmol, 1.5 eq), Pd(dppf)Cl$_2$ (287 mg, 0.391 mmol, 0.1 eq) and K$_2$CO$_3$ (1.08 g, 7.812 mmol, 2 eq) in DME/H$_2$O (20 mL, v/v=5/1) was flushed with N$_2$. And then the mixture was stirred at 80° C. under N$_2$ for 1 h. 30 mL of water was added and extracted with EtOAc. The combined organic layer was washed with brine, dried over Na$_2$SO$_4$ and concentrated. The residue was purified to afford compound 10A (750 mg, 71% yield).

A mixture of compound 10A (650 mg, 2.39 mmol) in HCl/MeOH (4M, 50 mL) was stirred at 70° C. overnight. The mixture was concentrated and adjusted to pH=7-8 with saturated aq. NaHCO$_3$. The mixture was filtered and the filter cake was dried in vacuum to afford compound 11A (570 mg, 92% yield).

A flask was charged with compound 11A (250 mg, 0.97 mmol, 1 eq), compound 6 (260 mg, 1.26 mmol, 1.3 eq), Cu(OAc)$_2$ (351 mg, 1.94 mmol, 2 eq), Py (230 mg, 2.91 mmol, 3 eq), pyridine N-Oxide (184 mg, 1.94 mmol, 2 eq) and 4 Å molecular sieves (150 mg) in DMF. The mixture was stirred under O$_2$ at rt overnight. The mixture was concentrated and 50 mL of water was added. The mixture was extracted with EtOAc. The combined organic layer was washed with brine, dried over Na$_2$SO$_4$ and concentrated. The residue was purified to afford Compound 680 (300 mg, 74% yield) as a white solid. $^1$H NMR (DMSO-d$_6$, 400 MHz) δ 8.02 (dd, J=5.6, 8.8 Hz, 2H), 7.89 (s, 1H), 7.71 (d, J=8.8 Hz, 2H), 7.57 (d, J=8.4 Hz, 2H), 7.31 (t, J=8.8 Hz, 2H), 4.78 (q, J=7.2 Hz, 2H), 1.59 (t, J=7.2 Hz, 3H). MS (ESI) m/z [M+H]$^+$ 419.0.

Compound 682 was prepared following the similar procedure described in the synthesis of Compound 680 using 4B as starting material. $^1$H NMR (CDCl$_3$, 400 MHz) δ 7.53 (d, J=8.8 Hz, 2H), 7.43 (dd, J=3.2, 8.4 Hz, 2H), 7.36 (d, J=8.4 Hz, 2H), 7.25-7.19 (m, 3H), 4.23 (q, J=7.2 Hz, 2H), 1.24 (t, J=7.2 Hz, 3H).

Compound 683 was prepared following the similar procedure described in the synthesis of Compound 680 using 4C as starting material. $^1$H NMR (CDCl$_3$, 400 MHz) δ 7.93-7.90 (m, 2H), 7.53 (d, J=8.8 Hz, 2H), 7.42 (d, J=8.4 Hz, 2H), 7.34 (s, 1H), 7.19 (t, J=8.8 Hz, 2H), 4.99 (q, J=7.2 Hz, 2H), 1.67 (t, J=7.2 Hz, 3H).

Compound 685 was prepared following the similar procedure described in the synthesis of Compound 680 using 4-(tributylstannyl)pyridazine in place of compound 9 catalyzed by Pd(PPh$_3$)$_2$Cl$_2$ in dioxane refluxed overnight. After HCl hydrolysis, (4-ethoxy-2-methylphenyl)boronic acid was used in place of compound 6 to afford the final product. $^1$H NMR (CDCl$_3$, 400 MHz) δ 9.70 (s, 1H), 9.22 (d, J=5.2 Hz, 1H), 8.12 (dd, J=2.4, 5.4 Hz, 1H), 7.68 (s, 1H), 7.18 (d, J=8.4 Hz, 1H), 6.91-6.83 (m, 2H), 4.80 (q, J=7.4 Hz, 2H), 4.08 (q, J=6.8 Hz, 2H), 2.17 (s, 3H), 1.76 (t, J=7.4 Hz, 3H), 1.45 (t, J=7.0 Hz, 3H).

Compound 686 was prepared following the similar procedure described in the synthesis of Compound 619 using (4-ethoxy-2-methylphenyl)boronic acid in place of compound 6 to afford the final product. $^1$H NMR (CDCl$_3$, 400 MHz) δ 8.07 (s, 1H), 7.83 (s, 1H), 7.26 (s, 1H), 7.18 (d, J=8.8 Hz, 1H), 6.88 (d, J=2.4 Hz, 1H), 6.85 (dd, J=2.4, 8.8 Hz, 1H), 4.77 (q, J=7.2 Hz, 2H), 4.08 (q, J=7.2 Hz, 2H), 3.99 (s, 3H), 2.16 (s, 3H), 1.75 (t, J=7.2 Hz, 3H), 1.45 (t, J=7.2 Hz, 3H).

Compound 688 was prepared following the similar procedure described in the synthesis of Compound 619 using (4-(2-methoxyethoxy)phenyl)boronic acid in place of compound 6 to afford the final product. $^1$H NMR (CDCl$_3$, 400 MHz) δ 8.07 (s, 1H), 7.84 (s, 1H), 7.39-7.34 (m, 3H), 7.06 (dd, J=2.0, 6.8 Hz, 2H), 4.77 (q, J=7.2 Hz, 2H), 4.19 (t, J=4.8 Hz, 2H), 3.99 (s, 3H), 3.79 (t, J=4.8 Hz, 2H), 3.48 (s, 3H), 1.74 (t, J=7.2 Hz, 3H).

Example 5-N

Synthesis of Compound 626

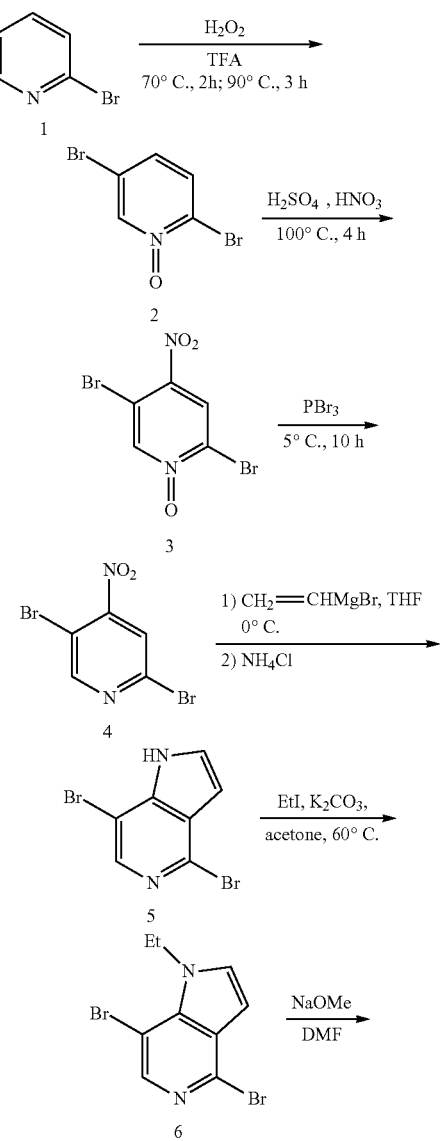

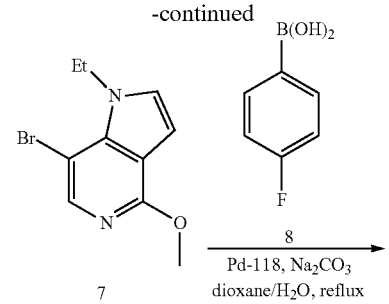

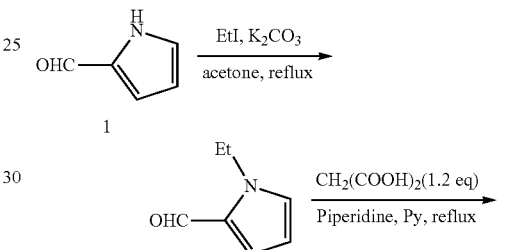

Compound 3 (18 g, 60.84 mmol) was added into the stirring PBr₃ (46 mL) in portions at 0-5° C. The mixture was stirred at 5° C. for about 7 h, and then it was poured over crushed ice and extracted with EA. The combined organic layers were washed with brine, dried over anhydrous Na₂SO₄, and concentrated in vacuo to afford the crude product, which was purified by flash column chromatography (PE:EA=10:1) to give compound 4 (10 g, 59% yield).

Compounds 5-10 were prepared following the general procedure described in the synthesis of Compound 48.

Compound 626 was prepared by Suzuki-Coupling of compounds 10 and 11. ¹H NMR (CDCl₃, 400 MHz) δ 7.51 (d, J=8.4 Hz, 2H), 7.44-7.41 (m, 2H), 7.32 (d, J=8.4 Hz, 2H), 7.14 (t, J=8.4 Hz, 2H), 6.94 (d, J=2.8 Hz, 1H), 6.91-6.89 (m, 2H), 3.67 (q, J=7.2 Hz, 2H), 1.10 (t, J=7.2 Hz, 3H). MS (ESI) m/z (M+H)⁺ 417.1.

Example 5-O

Synthesis of Compound 656

Hydrogen peroxide (30%, 35 mL) was added slowly to the solution of compound 1 (40 g, 186.8 mmol) in TFA (200 mL). The resulting mixture was stirred at 70° C. for 2 h and at 90° C. for another 3 h. After the mixture was cooled to rt, the mixture was poured over crushed ice. The mixture was extracted with DCM. The combined organic layers were washed with aq. Na₂S₂O₃ and brine, dried over anhydrous Na₂SO₄, and concentrated in vacuo to afford compound 2 (45 g, 96% crude yield), which was used directly for the next step.

Compound 2 (45 g, 180 mmol) was added to the mixture of conc. sulfuric acid (200 mL) and fuming nitric acid (150 mL) at rt during stirring. The mixture was heated to 100° C. and then stirred for 2 h. The reaction mixture was allowed to cool to rt and then poured over crushed ice. The mixture was neutralized with NH₃·H₂O in the ice bath. The precipitate was filtered and washed with PE to give compound 3 (29.6 g, 56% yield).

Cs₂CO₃ (124 g, 0.38 mol) was added to a solution of the compound 1 (60 g, 0.63 mol) in acetone (500 mL). And then iodoethane (118 g, 0.76 mol, 61 mL) was added to the stirring mixture. The mixture was stirred at reflux overnight.

The mixture was cooled to rt, filtered and the solvent was evaporated. The residue was purified by column chromatography (PE:EA=200:1 to 100:1) to afford compound 2 (30 g, 39% yield).

A flask was charged with compound 2 (23 g, 187 mmol), malonic acid (23.3 g, 224 mmol), pyridine (100 mL) and piperidine (22 mL). The mixture was reflux under nitrogen atmosphere overnight. Then the mixture was cooled to rt and concentrated under reduced pressure. The residue was diluted with water and adjusted to pH=~5 by aq. HCl (2 N), the resulting solid was filtered and washed with amount water, the solid was dried in vacuo to give compound 3 (26.3 g, 85% yield).

Ethyl chloroformate (10 g, 87.6 mmol) was added dropwise into the solution of compound 3 (10 g, 73 mmol) and TEA (11.1 g, 109.5 mmol) in 100 mL of acetone at 0° C. The mixture was stirred at 0° C. for 1.5 h. The resulting mixture was added into the solution of sodium azide (14.3 g, 219 mmol) in 30 mL of acetone and water (V/V=1/1) at 0° C. and stirred for 30 min. Then the mixture was warmed to rt and stirred for another 2 h. The mixture was poured onto ice-water and the precipitate was collect by filtration. The solid was washed with amount water, dried in vacuo to give compound 4 (2.87 g, 21% yield).

Compound 4 (2.8 g, 15 mmol) was added into 20 mL of diphenyl ether and the mixture was stirred at 240° C. for 3 h. Then the mixture was cooled to rt and the residue was purified by column chromatography (PE:EA=1:1 to EA:MeOH=100:1) to afford compound 5 (1.1 g, 46% yield).

To a solution of compound 5 (200 mg, 1.24 mmol) in DCM (10 mL) was added compound 6 (306.5 mg, 1.49 mmol), Cu(OAc)$_2$ (743 mg, 2.48 mmol), Pyridine (1.17 g, 12.4 mmol, 1.2 mL) and Pyridine-N-Oxide (295 mg, 3.1 mmol), followed by addition of 4 Å molecular sieve (100 mg). The reaction mixture was stirred at 30° C. under oxygen atmosphere overnight. The resulting mixture was filtered and washed with EtOAc; the filtrate was washed with brine, dried over Na$_2$SO$_4$ and concentrated in vacuo. The residue was purified by column chromatography on silica gel (PE/EA=1:1) to give Compound 656 (80 mg, 20% yield). $^1$H NMR (CDCl$_3$, 400 MHz) δ 7.46 (d, J=9.2 Hz, 2H), 7.32 (d, J=8.0 Hz, 2H), 7.10 (d, J=7.6 Hz, 1H), 6.93 (d, J=3.2 Hz, 1H), 6.84 (d, J=3.2 Hz, 1H), 6.45 (d, J=7.2 Hz, 1H), 4.10 (q, J=7.2 Hz, 2H), 1.48 (t, J=7.2 Hz, 3H). MS (ESI) m/z (M+H)$^+$ 323.0.

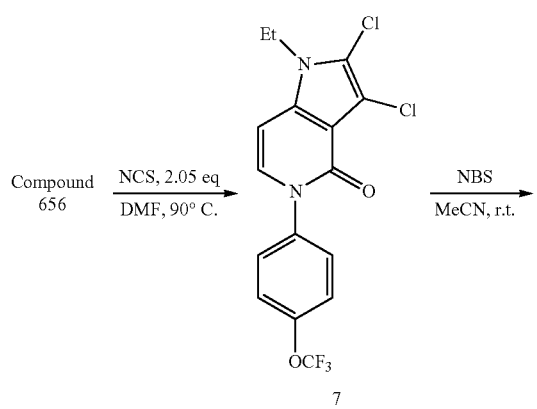

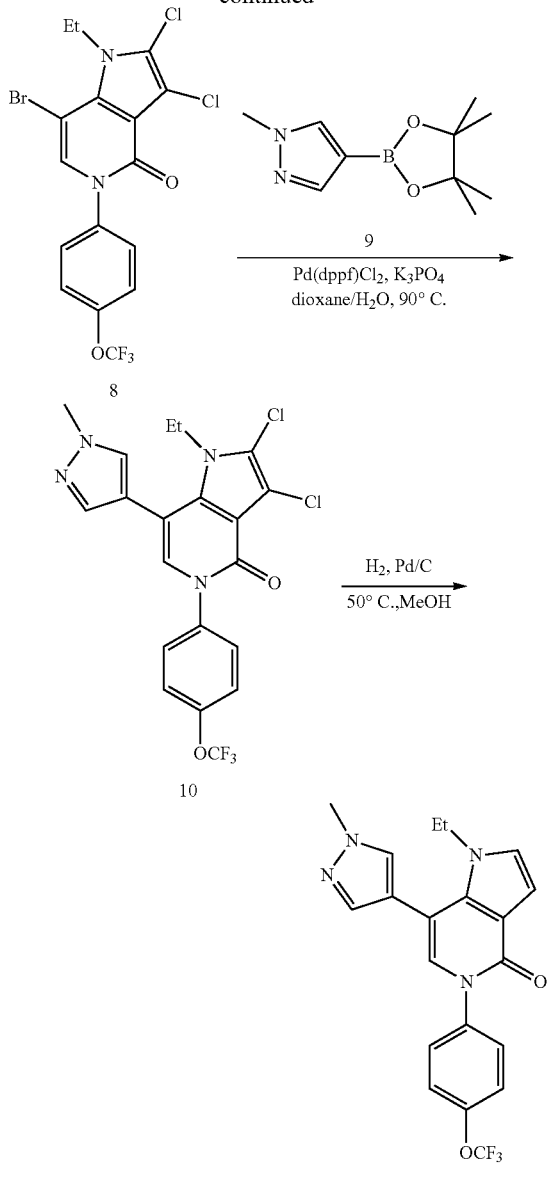

To a solution of compound 656 (1.8 g, 5.6 mmol) in DMF (20 mL) was added NCS (1.53 g, 11.5 mmol). The mixture was heated at 90° C. for 2 hrs. Then the mixture was washed with water, extracted with EA. The organic layer was washed with brine, dried under Na$_2$SO$_4$, concentrated in vacuo. The crude residue was purified to afford compound 7 (1.6 g, 73% yield).

To a solution of compound 7 (1.0 g, 2.56 mmol) in MeCN (20 mL) was added NBS (543 mg, 3.07 mmol) at 0-5° C. The mixture was stirred at rt overnight. Then the mixture was concentrated in vacuo. The crude residue was purified to afford compound 8 (0.5 g, 42% yield).

To a stirred mixture of compound 8 (800 mg, 1.7 mmol), and 9 (530 mg, 2.55 mmol) in dioxane/H$_2$O (30 mL, V:V=5:1) was added K$_3$PO$_4$ (720 mg, 3.4 mmol), Pd(dppf)Cl$_2$ (125 mg, 0.17 mmol) under N$_2$ protection. The reaction mixture was heated at 90° C. overnight. The mixture was poured into water, extracted with EtOAc, the organic layer was washed with brine, dried over anhydrous Na$_2$SO$_4$, and concentrated in vacuo, the residue was purified to afford compound 10 (310 mg, yield: 38.8%).

Compound 10 (250 mg, 0.53 mmol) was dissolved in MeOH (20 mL), Pd/C (30 mg) was added under N$_2$ protect, the reaction was stirred overnight at H$_2$ balloon at 50° C. The suspension was filtered through a pad of celite. The filter cake was washed with MeOH, the combined filtrate was concentrated in vacuo, the crude product was purified to afford Compound 694 (95 mg, 45% yield). $^1$H NMR (400 MHz, CDCl$_3$) δ 7.57 (s, 1H), 7.49-7.42 (m, 3H), 7.29 (d, J=8.4 Hz, 2H), 6.93-6.90 (m, 1H), 6.89-6.84 (m, 2H), 3.96 (s, 3H), 3.86 (q, J=7.2 Hz, 2H), 1.18 (t, J=7.2 Hz, 3H). MS (ESI) m/z [M+H]$^+$ 403.1.

Compound 695 was prepared following the similar procedure described in the synthesis of Compound 694 using 1-benzyl-5-(4-(trifluoromethoxy)phenyl)-1H-pyrrolo[3,2-c]pyridin-4(5H)-one as starting material. $^1$H NMR (DMSO-d$_6$, 400 MHz) δ 11.5 (s, 1H), 8.16 (s, 1H), 7.83 (s, 1H), 7.61 (d, J=8.8 Hz, 2H), 7.51 (d, J=8.8 Hz, 2H), 7.42 (s, 1H), 7.19 (s, 1H), 6.66 (s, 1H), 3.89 (s, 3H).

Example 5-P

Synthesis of Compound 678

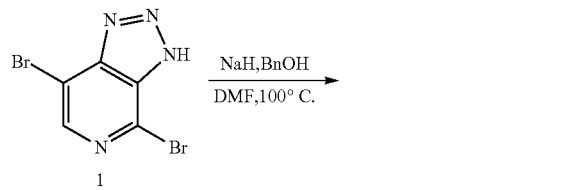

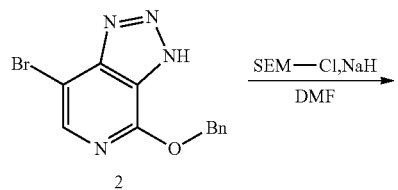

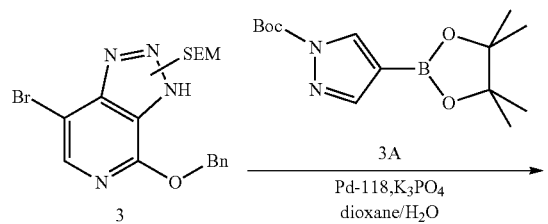

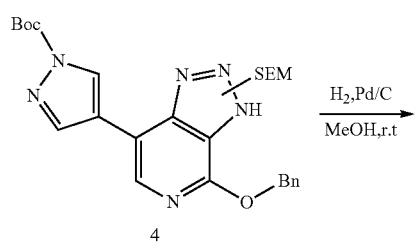

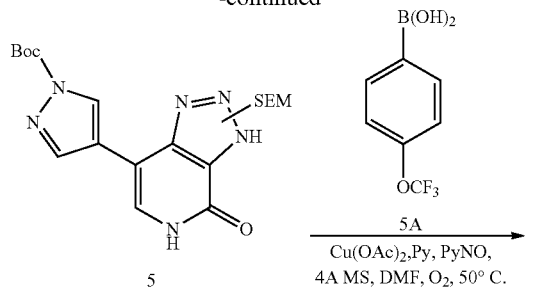

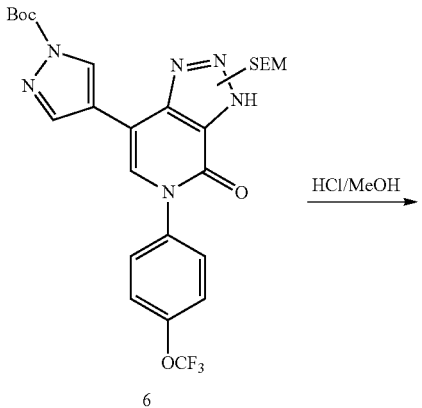

Compound 678

To a solution of BnOH (2.3 g, 21.7 mmol) in DMF (50 mL) was added NaH (60% dispersion in mineral oil, 1.5 g, 36.2 mmol) at 0° C., the mixture was stirred for 30 mins at rt, compound 1 (5 g, 18.1 mmol) was added, the solution was heated to 100° C. for 3-4 hours, then quenched with aq. HCl (1N), extracted with EA, the combined organic layer was washed with brine and concentrated to give crude product, which was purified to afford compound 2 (4 g, yield 72%).

To a solution of compound 2 (4 g, 13.2 mmol) in DMF (50 mL) was added NaH (60% dispersion in mineral oil, 1 g, 26.4 mmol) at 0° C., the mixture was stirred for 30 minutes at rt, and then SEM-Cl (3.3 g, 19.8 mmol) was added, the reaction was stirred for 12 hours at rt. The mixture was quenched with water, extracted with EA, the combined organic layer was washed with brine and concentrated to give crude product, the residue was purified to afford compound 3 (3.7 g, yield 65%).

To a stirred mixture of compound 3 (4 g, 9.2 mmol), and 3A (4.2 g, 18.4 mmol) in dioxane/H$_2$O (100 mL, V/V=5/1) was added K$_3$PO$_4$ (3.9 g, 18.4 mmol), Pd-118 (600 mg, 0.92 mmol) under N$_2$ protection. The reaction mixture was heated to 60-70° C. overnight. The mixture was poured into water, extracted with EtOAc, the organic layer was washed with brine, dried over anhydrous Na$_2$SO$_4$, and concentrated in vacuo, the residue was purified by column chromatography on silica gel (PE/EA=5:1) to afford compound 4 (3 g, yield 62.5%).

To a solution of compound 4 (3 g, 5.7 mmol) in MeOH (50 mL) was added Pd/C (600 mg) under $N_2$ protection, the reaction was stirred overnight under $H_2$ balloon at rt, then the mixture was filtered through a pad of celite. The filter cake was washed with MeOH (50 mL), the combined filtrates was concentrated in vacuo, the crude product was purified to afford compound 5 (1.2 g, 48% yield).

To a solution of compound 5 (400 mg, 0.93 mmol) in DMF (20 mL) was added compound 5A (288 mg, 1.4 mmol), and Cu(OAc)$_2$ (336.7 mg, 1.86 mmol), Py (367.4 mg, 4.65 mmol), pyridine N-Oxide (176.7 mg, 1.86 mmol). The reaction mixture was stirred at 50° C. overnight, and then it was poured into water, extracted with EA, the combined organic layer was washed with brine and concentrated to give crude product. The residue was purified to afford compound 6 (300 mg, yield 54%).

Compound 6 (700 mg, 1.18 mmol) was dissolved in HCl/MeOH (4M, 20 mL), the reaction was stirred for 1-2 hours at rt, and then the solvents were evaporated. The residue was neutralized with saturated aq. NaHCO$_3$, and extracted with EA. The combined organic layer was concentrated in vacuo, and the crude product was washed with EA to afford Compound 678 (260 mg, 61% yield). $^1$H NMR (DMSO-d$_6$, 400 MHz) δ 8.28 (brs, 2H), 7.92 (s, 1H), 7.69 (d, J=8.4 Hz, 2H), 7.57 (d, J=8.0 Hz, 2H). MS (ESI) m/z [M+H]$^+$ 362.9.

Compound 681 was prepared following the similar procedure described in the synthesis of Compound 678 using (4-fluorophenyl)boronic acid in place of compound 3A. $^1$H NMR (CD$_3$OD, 400 MHz) δ 7.84-7.80 (m, 2H), 7.70-7.64 (m, 3H), 7.49 (d, J=8.4 Hz, 2H), 7.25-7.20 (m, 2H). MS (ESI) m/z [M+H]+ 391.0.

Example 6-A

Synthesis of Compound 64 (Scheme XVII)

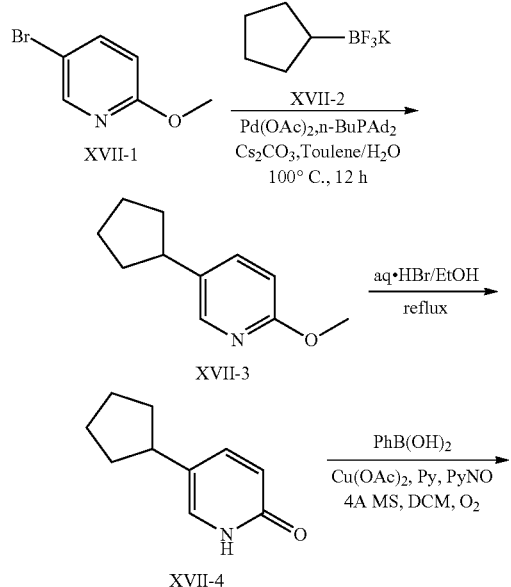

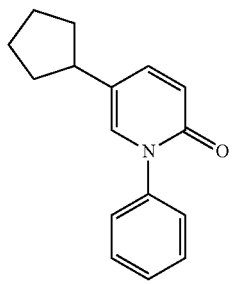

Compound 64

A mixture of XVII-1 (1.57 g, 8.35 mmol), XVII-2 (1.61 g, 9.19 mmol), Pd(OAc)$_2$ (0.187 g, 0.835 mmol), n-BuPAd$_2$ (0.298 g, 0.835 mmol) and Cs$_2$CO$_3$ (8.17 g, 25.05 mmol) in toluene/H$_2$O (50 mL/10 mL) was degassed by purging with nitrogen. The mixture was heated at 100° C. for 12 hrs. After being cooled to rt, the mixture was diluted with water (30 mL), extracted with EtOAc (100 mL×3). The combined organic layer was washed with brine, dried over anhydrous Na$_2$SO$_4$, and concentrated in vacuo. The residue was purified by flash chromatography on silica gel (PE/EA=100: 1→40:1) to produce XVII-3 as a yellow oil (0.8 g, 54% yield).

Compound 64: $^1$H NMR (CDCl$_3$, 300 MHz) δ 7.50-7.47 (m, 2H), 7.42-7.34 (m, 4H), 7.12 (d, J=2.1 Hz, 1H), 6.64 (d, J=6.9 Hz, 1H), 2.72-2.80 (m, 1H), 2.05-1.96 (m, 2H), 1.80-1.63 (m, 4H), 1.52-1.47 (m, 2H). MS (ESI) m/z [M+H]$^+$ 240.1.

Example 6-B

Synthesis of Compound 65 (Scheme XVIII)

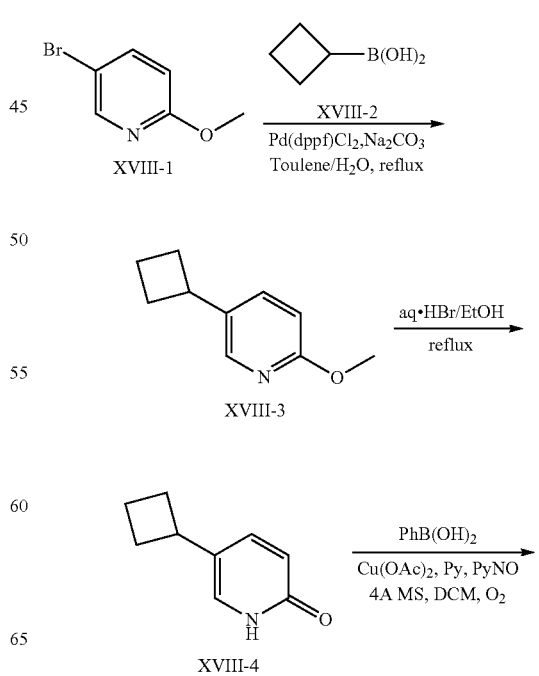

-continued

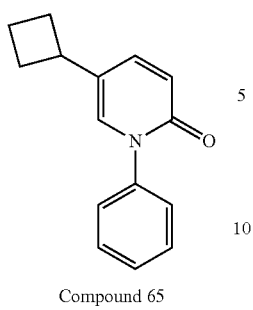

Compound 65

To a solution of XVIII-1 (2.1 g, 10.9 mmol) in toluene/H$_2$O (60 mL, v/v=5/1) was added Na$_2$CO$_3$ (1.4 g, 14.71 mmol), XVIII-2 (1.2 g, 11.99 mmol), followed by Pd(dppf)Cl$_2$ (812 mg, 1.11 mmol). The mixture was purged with nitrogen and then heated at reflux overnight. The mixture was cooled to rt., diluted with water (50 mL), extracted with EtOAc (100 mL×3). The combined organic layer was washed with brine, dried over anhydrous Na$_2$SO$_4$, and concentrated in vacuo. The residue was purified by flash chromatography on silica gel (PE/EA 100:1→40:1) to give XVIII-3 as a yellow oil (0.4 g, 24% yield). $^1$H NMR (CDCl$_3$, 300 MHz) δ 7.97 (d, J=2.4 Hz, 1H), 7.46 (dd, J=8.4, 2.4 Hz, 1H), 6.68 (d, J=8.4 Hz, 1H), 3.90 (s, 3H), 3.51-3.40 (m, 1H), 2.37-2.30 (m, 2H), 2.28-1.99 (m, 3H), 1.96-1.82 (m, 1H).

Compound 65: $^1$H NMR (CDCl$_3$, 400 MHz) δ 7.51-7.47 (m, 2H), 7.46-7.36 (m, 4H), 7.08 (d, J=2.8 Hz, 1H), 6.65 (d, J=9.2 Hz, 1H), 3.35-3.26 (m, 1H), 2.31-2.23 (m, 2H), 2.09-1.96 (m, 3H), 1.87-1.83 (m, 1H). MS (ESI) m/z [M+H]$^+$ 226.0.

Compound 66 was prepared following the similar procedure for obtaining Compound 64. $^1$H NMR (CDCl$_3$, 400 MHz) δ 7.51-7.46 (m, 2H), 7.43-7.33 (m, 4H), 7.09 (d, J=2.4 Hz, 1H), 6.63 (d, J=9.6 Hz, 1H), 2.32-2.25 (m, 1H), 1.87-1.82 (m, 4H), 1.76-1.72 (m, 1H), 1.41-1.18 (m, 5H). MS (ESI) m/z [M+H]$^+$ 254.1.

Example 7

Synthesis of Compounds 67-76 (Scheme XIX)

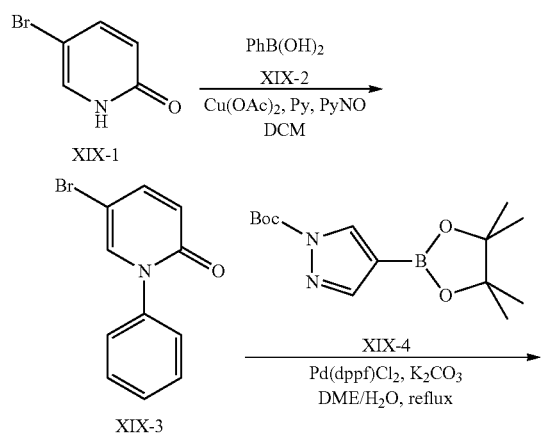

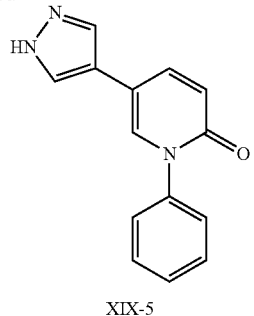

XIX-5

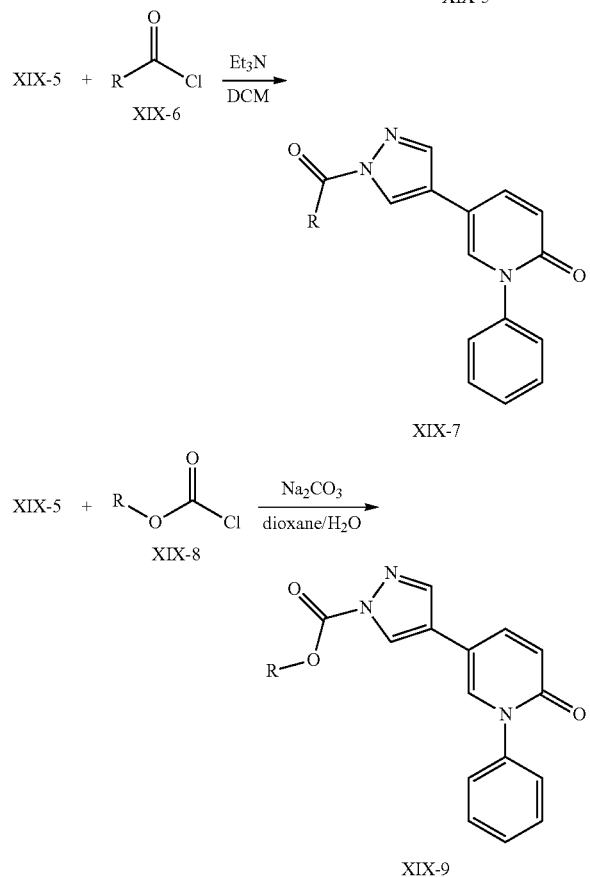

-continued

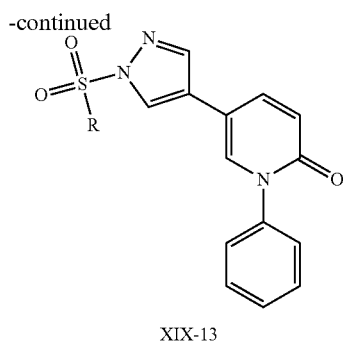

XIX-13

XIX-3 was prepared following the similar procedure for obtaining V-3 using XIX-2 in place of V-2 as a yellow solid.

XIX-5 was prepared following the similar procedure for obtaining Compound 23 using XIX-4 in place of V-4.

XIX-7: To a stirring solution of XIX-5 (1.0 eq) and TEA (3 eq.) in DCM was added acyl chloride (2.0 eq) dropwise at 0° C. The mixture was stirred for 1 h at rt. then it was washed with water and brine, dried over $Na_2SO_4$, and concentrated under reduced pressure. The residue was purified by prep-TLC (EtOAc) to afford XIX-7.

Compound 67: $^1$H NMR (CDCl$_3$, 400 MHz) δ 8.34 (s, 1H), 7.82 (s, 1H), 7.59-7.41 (m, 7H), 6.77-6.74 (m, 1H), 2.72 (s, 3H).

Compound 68: $^1$H NMR (CDCl$_3$, 400 MHz) δ 8.54 (s, 1H), 8.13 (d, J=7.2 Hz, 2H), 7.91 (s, 1H), 7.66-7.43 (m, 10H), 6.78 (d, J=9.6 Hz, 1H).

Compound 69: $^1$H NMR (CDCl$_3$, 400 MHz) δ 8.34 (s, 1H), 7.86 (s, 1H), 7.59-7.28 (m, 12H), 6.75 (d, J=8.8 Hz, 1H), 4.45 (s, 2H).

Compound 72: $^1$H NMR (CDCl$_3$, 400 MHz) δ 8.34 (s, 1H), 7.80 (s, 1H), 7.60-7.40 (m, 7H), 6.74 (d, J=8.8 Hz, 1H), 3.15-3.10 (m, 2H), 1.81-1.72 (m, 2H), 1.481-1.40 (m, 2H), 0.98-0.93 (m, 3H).

XIX-9: To a solution of XIX-5 (1.0 eq) in dioxane/H$_2$O (v/v=10:1) was added Na$_2$CO$_3$ (1.5 eq) with stirring at 0° C. for 10 min. Then XIX-8 (1.2 eq) was added dropwise. The mixture was stirred at rt for 5 hours. The reaction was concentrated. The residue was partitioned between EtOAc and H$_2$O. The organic layer was separated, washed with brine, dried over Na$_2$SO$_4$, concentrated. The crude product was purified by prep-TLC (EtOAc) to give XIX-9.

Compound 73: $^1$H NMR (DMSO-d$_6$, 400 MHz) δ 8.80 (s, 1H), 8.33 (s, 1H), 8.22 (d, J=2.4 Hz, 1H), 8.01 (dd, J=2.4, 9.6 Hz, 1H), 7.57-7.52 (m, 2H), 7.49-7.45 (m, 3H), 6.58 (d, J=9.6 Hz, 1H), 4.44 (q, J=7.2 Hz, 2H), 1.36 (t, J=7.2 Hz, 3H).

Compound 74: $^1$H NMR (DMSO-d$_6$, 400 MHz) δ 8.78 (s, 1H), 8.33 (s, 1H), 8.22 (d, J=2.4 Hz, 1H), 8.00 (dd, J=2.8, 9.6 Hz, 1H), 7.57-7.53 (m, 2H), 7.49-7.46 (m, 3H), 6.58 (d, J=9.6 Hz, 1H), 4.40 (t, J=6.4 Hz, 2H), 1.74-1.70 (m, 2H), 1.46-1.39 (m, 2H), 0.94 (t, J=7.2 Hz, 3H).

XIX-11: A mixture of XIX-5 (1 eq.) and XIX-10 (0.5 mmol/mL) was stirred at 90-100° C. under N$_2$ overnight. The mixture was concentrated. The residue was purified by prep-TLC (PE: EtOAc=1:1) to give XIX-11.

Compound 75: $^1$H NMR (DMSO-d$_6$, 300 MHz) δ 8.70 (s, 1H), 8.24-8.21 (m, 2H), 8.14 (d, J=2.4 Hz, 1H), 7.95 (dd, J=9.3, 2.4 Hz, 1H), 7.53-7.42 (m, 5H), 6.53 (d, J=9.3 Hz, 1H), 3.99-3.92 (m, 1H), 1.18 (s, 3H), 1.15 (s, 3H).

Compound 76: $^1$H NMR (DMSO-d$_6$, 300 MHz) δ 8.70 (s, 1H), 8.51 (t, J=6.0 Hz, 1H), 8.20 (d, J=0.6 Hz, 1H), 8.13 (d, J=2.1 Hz, 1H), 7.95 (dd, J=9.6, 2.7 Hz, 1H), 7.51-7.42 (m, 5H), 6.53 (d, J=9.3 Hz, 1H), 3.31-3.24 (m, 2H), 1.12-1.07 (m, 3H).

XIX-13: To a solution of XIX-5 (1 eq.) in DCM (0.16 mmol/mL) was added XIX-12 (1.25 eq.) and TEA (3 eq.) at 0° C. Then the mixture was stirred at rt. overnight. The mixture was concentrated, diluted with water, extracted with EtOAc. The combined organic layer was washed with brine, dried over anhydrous Na$_2$SO$_4$, and concentrated in vacuo. The residue was purified by prep-TLC (PE: EA=1:2) to give XIX-13.

Compound 70: $^1$H NMR (CDCl$_3$, 400 MHz) δ 8.19 (s, 1H), 8.04-8.02 (m, 2H), 7.82 (s, 1H), 7.69-7.65 (m, 1H), 7.58-7.49 (m, 6H), 7.47-7.45 (m, 1H), 7.39-7.37 (m, 2H), 6.72 (d, J=9.2 Hz, 1H). MS (ESI) m/z (M+H)$^+$ 378.1.

Compound 71: $^1$H NMR (CDCl$_3$, 400 MHz) δ 8.11 (s, 1H), 7.91 (s, 1H), 7.55-7.39 (m, 7H), 6.75 (d, J=9.6 Hz, 1H), 3.35 (s, 3H). MS (ESI) m/z (M+Na)$^+$ 338.0.

Example 8

Synthesis of Compounds 77-80 (Scheme XX)

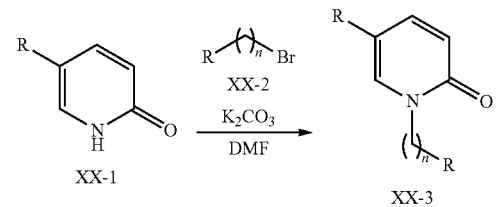

XX-3: XX-1 (1 eq.), XX-2 (1.2 eq.) and K$_2$CO$_3$ (1.5 eq.) were dissolved in DMF. The solution was stirred at 50° C. for 6 hrs under N$_2$ atmosphere. The reaction mixture was diluted with water and extracted with EtOAc. The combined organic phase was washed with brine, dried over Na$_2$SO$_4$ and concentrated to give crude product, it was purified by prep-TLC (PE:EA=1:1) to yield XX-3.

Compound 77 was prepared by reacting 5-(4-fluorophenyl)pyridin-2(1H)-one with (2-bromoethyl)benzene following the general procedure described above. $^1$H NMR (CDCl$_3$, 400 MHz) δ 7.53 (m, 1H), 7.33-7.24 (m, 3H), 7.18-7.16 (d, J=6.8 Hz, 2H), 7.09-7.00 (m, 4H), 6.92 (d, J=2.4 Hz, 1H), 6.68-6.66 (d, J=9.6 Hz, 1H), 4.23-4.20 (m, 2H), 3.12-3.09 (m, 2H). MS (ESI) m/z (M+H)$^+$ 293.9.

Compound 79 was prepared by reacting 5-(4-fluorophenyl)pyridin-2(1H)-one with (bromomethyl)benzene following the general procedure described above. $^1$H NMR (CDCl$_3$, 400 MHz) δ 7.57-7.55 (m, 1H), 7.42-7.41 (d, J=2.8 Hz, 1H), 7.38-7.28 (m, 7H), 7.10-7.05 (m, 2H), 6.72-6.70 (d, J=9.2 Hz, 1H), 5.22 (s, 2H). MS (ESI) m/z (M+H)$^+$ 280.1.

Compound 78 was prepared by reacting 5-methylpyridin-2(1H)-one with (bromomethyl)benzene following the general procedure described above. $^1$H NMR (CDCl$_3$, 400 MHz) δ 7.36-7.27 (m, 5H), 7.19-7.16 (m, 1H), 7.02 (s, 1H), 6.58-6.56 (d, J=7.2 Hz, 1H), 5.12 (s, 2H), 2.03 (s, 3H). MS (ESI) m/z (M+H)$^+$ 199.8.

Compound 80 was prepared by reacting 5-methylpyridin-2(1H)-one with (2-bromoethyl)benzene following the general procedure described above. $^1$H NMR (CDCl$_3$, 400 MHz) δ 7.31-7.21 (m, 3H), 7.18-7.15 (m, 3H), 6.70 (s, 1H), 6.54-6.52 (d, J=9.2 Hz, 1H), 4.16-4.08 (m, 2H), 3.06-3.02 (m, 2H), 1.96 (s, 3H). MS (ESI) m/z (M+H)$^+$ 213.9.

Example 9

Synthesis of Compound 82 (Scheme XXI)

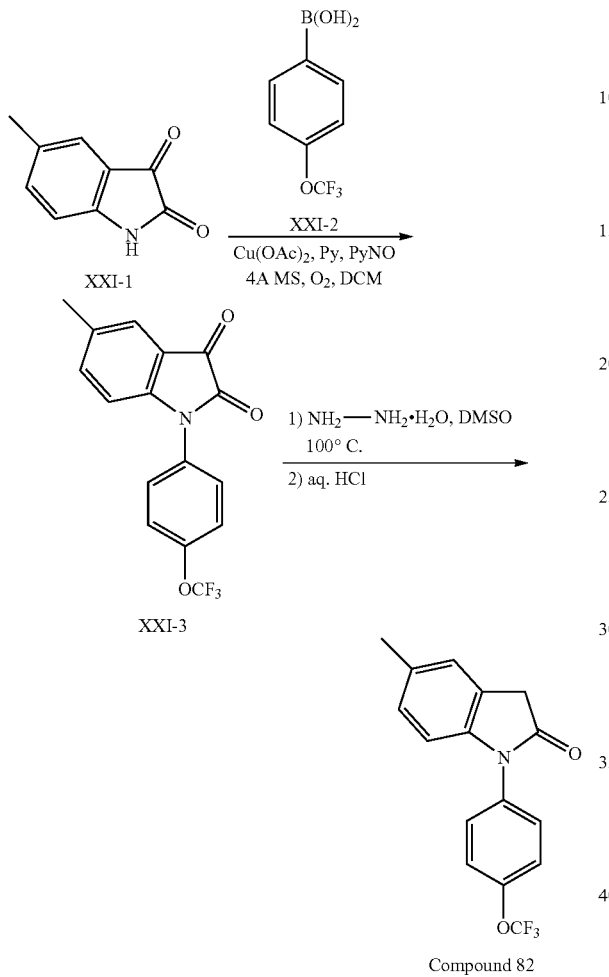

XXI-3 was obtained following the similar procedure for obtaining X-6 as a red solid. $^1$H NMR (CDCl$_3$, 300 MHz) δ 7.52-7.35 (m, 5H), 7.26 (s, 1H), 6.82 (d, J=8.1 Hz, 1H), 2.37 (s, 3H).

To the solution of XXI-3 (500 mg, 1.56 mmol) in 10 mL of DMSO was added hydrazine hydrate (1 mL) at 0° C., The mixture was stirred at 100° C. for 2 hrs. After being cooled, the mixture was quenched with aq. HCl (1M) and stirred for 1 h, extracted with EA (50 mL×3). The combined organic layers were washed with brine, dried over anhydrous Na$_2$SO$_4$ and concentrated. The residue was purified by column chromatography on silica gel (PE/EA=20/1) to afford Compound 82 (50 mg, 11% yield) as a white solid. $^1$H NMR (CDCl$_3$, 400 MHz) δ 7.48 (d, J=8.8 Hz, 2H), 7.37 (d, J=8.4 Hz, 2H), 7.15 (s, 1H), 7.03 (d, J=8.0 Hz, 1H), 6.70 (d, J=8.0 Hz, 1H), 3.69 (s, 2H), 2.35 (s, 3H). MS (ESI) m/z [M+H]$^+$ 308.1.

Compound 81 was obtained by reacting indolin-2-one with (4-(trifluoromethoxy)phenyl)boronic acid refluxing in anhydrous DCM under oxygen atmosphere overnight in the presence of Cu(OAc)$_2$ and 4 Å molecular sieve as a white solid. $^1$H NMR (CDCl$_3$, 400 MHz) δ 7.47 (d, J=8.0 Hz, 2H), 7.38-7.32 (m, 3H), 7.23 (t, J=7.6 Hz, 1H), 7.11 (t, J=7.6 Hz, 1H), 6.80 (d, J=7.6 Hz, 1H), 3.73 (s, 2H). MS (ESI) m/z [M+H]$^+$ 294.0.

Example 10

Synthesis of Compounds 83 and 84 (Scheme XXII)

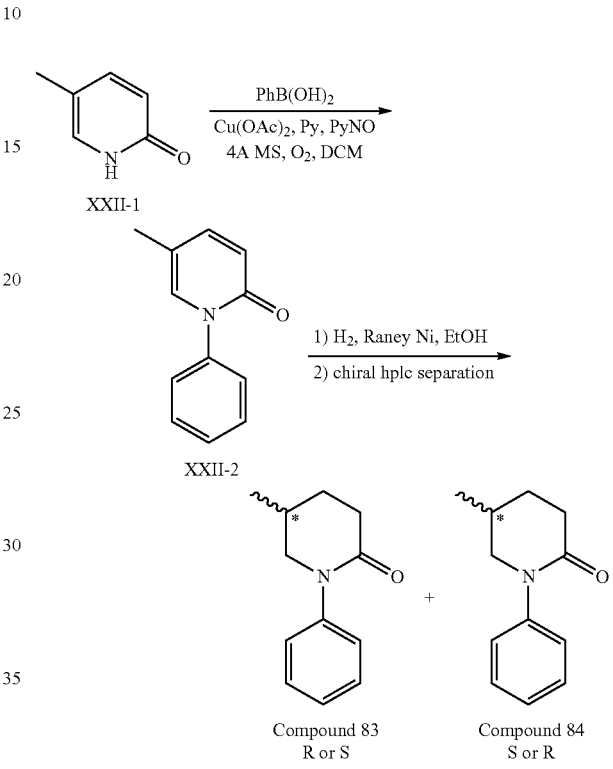

XXII-2 was prepared following the similar procedure for obtaining XIX-3 as a white solid.

XXII-2 (500 mg, 2.7 mmol) was dissolved in EtOH, the solution was degassed with Ar for three times and then Raney Ni was added. The mixture was degassed by Ar and H$_2$ in turn for three times. The mixture was stirred at rt for 24 hrs under H$_2$ (15-20 psi). The reaction was detected by LCMS and TLC. The reaction mixture was filtrated and washed with EA, the filtrate was concentrated and the residue was purified by column chromatography (PE/EA=3/1) and then separated by chiral prep-HPLC to give the two pure optical enantiomer: Compound 83 (149 mg, 30% yield) and Compound 84 (30.3 mg, 6% yield). The absolute chirality of the two compounds was not identified.

Compound 83: $^1$H NMR (CDCl$_3$, 400 MHz) δ 7.41-7.37 (m, 2H), 7.27-7.23 (m, 3H), 3.59-3.54 (m, 1H), 3.36-3.30 (m, 1H), 2.66-2.50 (m, 2H), 2.19-2.10 (m, 1H), 2.00-1.94 (m, 1H), 1.67-1.57 (m, 1H), 1.07 (d, J=6.8 Hz, 3H). MS (ESI) m/z (M+H)$^+$ 190.0. RT (SFC)=3.99.

Compound 84: $^1$H NMR (CDCl$_3$, 400 MHz) δ 7.41-7.37 (m, 2H), 7.27-7.23 (m, 3H), 3.59-3.55 (m, 1H), 3.36-3.31 (m, 1H), 2.66-2.50 (m, 2H), 2.19-2.10 (m, 1H), 2.00-1.94 (m, 1H), 1.67-1.57 (m, 1H), 1.07 (d, J=6.8 Hz, 3H). MS (ESI) m/z (M+H)$^+$ 190.0. RT (SFC)=4.18.

Example 11-A

Synthesis of Compounds 85-87 (Scheme XXIII)

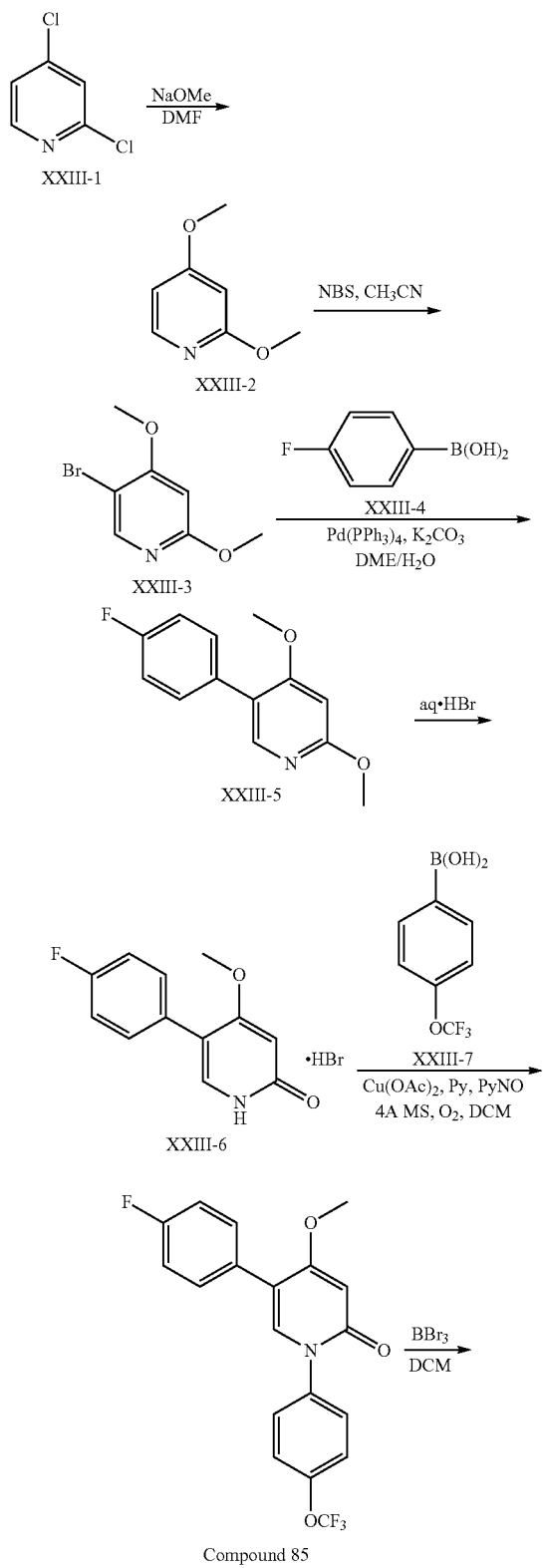

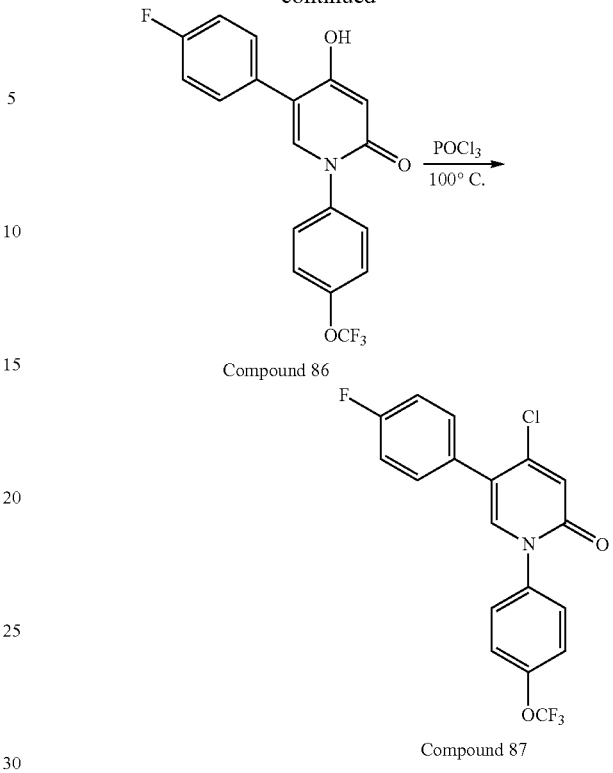

XXIII-1 (15 g, 0.1 mol) was dissolved in anhydrous DMF (80 mL), and then freshly prepared sodium methoxide (24 g, 0.44 mol) was added. The resulting mixture was stirred at 110-120° C. for 12 hrs under $N_2$. Cooled to rt, diluted with EA (800 mL) and washed with water and brine, dried over $Na_2SO_4$, concentrated. The residue was purified by flash column chromatography (PE/EA=10:1) to give XXIII-2 (7.5 g, 54% yield) as a colorless oil.

The mixture of XXIII-2 (7.4 g, 53 mmol) and N-bromosuccinimide (9.3 g, 52 mmol) in anhydrous $CH_3CN$ (250 mg) was stirred at 70-85° C. for 12 hrs in dark. Cooled to rt, the mixture was concentrated and the residue was purified by flash column chromatography (PE/EA=50/1) to give XXIII-3 (8.3 g, 72% yield) as a white solid.

XXIII-3 (16.0 g, 38.2 mmol), XXIII-4 (13.4 g, 95.9 mmol) and $K_2CO_3$ (36.6 g, 265.3 mmol) were dissolved in a mixture of $DME/H_2O$ (250 mL/25 mL). The solution was degassed by $N_2$ for three times and then $Pd(PPh_3)_4$ (8.5 g, 7.37 mmol) was added. The reaction mixture was stirred at 90-100° C. for 10 h under $N_2$ and then cooled to rt, diluted with AcOEt and filtered, the filtrate was washed with brine. The separated organic phase was dried over $Na_2SO_4$, concentrated. The residue was purified by flash column chromatography (PE/EA=20:1~5:1) to give XXIII-5 (16.0 g, 93% yield).

A solution of XXIII-5 (15.0 g, 64.4 mmol) in aq.HBr (48%, 250 mL) was stirred at 100° C. for 7 h. Then the mixture was cooled to rt, the formed precipitate was filtrated, washed with water to give XXIII-6 (17.6 g, yield 91%) as a white solid, which would be utilized in next step without any further purification.

To a solution of XXIII-6 (4.6 g, 21 mmol) in DCM (180 mL), copper (II) acetate (7.42 g, 41 mmol), XXIII-7 (8.65 g, 42 mmol), pyridine (10 mL), pyridine-N-oxide (7.8 g, 82 mmol) and 4 Å molecular sieves (3.0 g) were added. The mixture was stirred at rt for 38 hrs under $O_2$ atmosphere. The mixture was filtered; the filtrate was washed with brine, dried over $Na_2SO_4$, concentrated. The residue was purified by flash column chromatography (PE/EA=1/1) to give Compound 85 (3.7 g, 46% yield) as a white solid. $^1$H NMR (CD$_3$OD, 400 MHz) δ 7.57-7.55 (m, 3H), 7.47-7.44 (m, 4H), 7.13-7.09 (m, 2H), 6.12 (s, 1H), 3.90 (s, 3H). MS (ESI) m/z (M+H)$^+$ 380.0.

To a solution of Compound 85 (2.0 g, 5.26 mmol) in dry DCM (25 mL) was added BBr$_3$ (2.63 g, 10.52 mmol) dropwise at −65° C.~−70° C. After addition, the mixture was stirred at 5-8° C. for 12 h, but the starting material still remained. More BBr$_3$ (5.26 g, 21 mmol) was added dropwise at −65° C.~−70° C., after that, the mixture was stirred at 25-30° C. for 24 hrs. And then the mixture was cooled to 0° C. under ice-water bath, quenched with methanol by dropwise addition until no smoke appeared. Then the mixture was concentrated, the residue was basified to pH 8-9 with saturated aq.NaHCO$_3$, extracted with EA (50 mL×3), washed with brine, dried over $Na_2SO_4$, concentrated. The residue was purified by flash column chromatography (PE/EtOAc=1/2) to give Compound 86 (1.2 g, 52% yield) as a white solid. $^1$H NMR (CD$_3$OD, 400 MHz) δ 7.58-7.49 (m, 5H), 7.45-7.43 (m, 2H), 7.13-7.09 (m, 2H), 6.01 (s, 1H). MS (ESI) m/z (M+H)$^+$ 366.0.

To a solution of Compound 86 (3.3 g, 9.0 mmol) in POCl$_3$ (60 mL) was added N, N-Dimethylaniline (1.5 g, 12.4 mmol). The resulting mixture was stirred at 100° C. for 2 hrs, cooled to rt, distilled most of POCl$_3$, quenched with ice-water, and then basified to pH 7-8 with saturated aq. NaHCO$_3$, and extracted with EA (50 mL×3). The combined organic phase was washed with brine, dried over $Na_2SO_4$ and concentrated. The residue was purified by flash chromatography (PE:EA=5:1) to give Compound 87 (2.0 g, 58% yield) as a light yellow solid. $^1$H NMR (CD$_3$OD, 400 MHz) δ 7.72 (s, 1H), 7.61-7.58 (m, 2H), 7.48-7.44 (m, 4H), 7.19-7.15 (m, 2H), 6.85 (s, 1H). MS (ESI) m/z (M+H)$^+$ 384.0.

Compound 88: Compound 87 was dissolved in 4-methoxybenzylamine (2 mL), the mixture was stirred at 180° C. for 2.5 h under $N_2$. After being cooled to rt, the mixture was diluted with EA (60 mL), washed with aq.HCl (2 M) with brine, dried over $Na_2SO_4$ and concentrated. The residue was purified by prep-TLC (PE:EA=1:2) to give an intermediate (47 mg, 50% yield) which was further dissolved in TFA (2 mL) and stirred at rt for 3 h. Then it was diluted with water and basified to pH 8-9 with saturated aq. NaHCO$_3$, extracted with EA (30 mL×3). The combined organic layer was washed with brine, dried over anhydrous $Na_2SO_4$ and concentrated. The residue was purified by prep-TLC (PE:EA=1/3) to give Compound 88 (30 mg, 79% yield). $^1$H NMR (CD$_3$OD, 400 MHz) δ 7.53-7.51 (m, 2H), 7.45-7.40 (m, 4H), 7.32 (s, 1H), 7.19 (t, J=8.8 Hz, 2H), 5.78 (s, 1H).

Compound 89: A mixture of Compound 87 (75 mg, 0.2 mmol) in benzylamine (1 mL) was stirred at 180° C. for 4 hrs, then it was cooled to rt and purified by flash column chromatography (PE:AE=1:1) to give Compound 89 (80 mg, 90% yield). $^1$H NMR (CDCl$_3$, 400 MHz) δ 7.47-7.44 (m, 2H), 7.38-7.34 (m, 4H), 7.31-7.27 (m, 5H), 7.16-7.12 (m, 2H), 7.06 (s, 1H), 5.70 (s, 1H), 4.59 (t, J=5.2 Hz, 1H), 4.34 (d, J=5.2 Hz, 2H). MS (ESI) m/z (M+H)$^+$ 455.3.

Compound 90 was prepared following the similar procedure for obtaining Compound 88 using 1-(4-methoxyphenyl)-N-methylmethanamine in place of 4-methoxybenzylamine. $^1$H NMR (CDCl$_3$, 400 MHz) δ 7.47-7.45 (m, 2H), 7.34-7.28 (m, 4H), 7.17-7.12 (m, 2H), 7.03 (s, 1H), 5.65 (s, 1H), 4.28 (m, 1H), 2.83 (d, J=4.8 Hz, 3H). MS (ESI) m/z (M+H)$^+$ 379.0.

Compounds 104 and 107-110 were prepared by the reaction of Compound 88 (1 eq.) with the relevant acyl chloride (1.1 eq.) in DCM and pyridine (5 eq.). The mixture was stirred at rt overnight.

Compound 104: $^1$H NMR (CDCl$_3$, 400 MHz) δ 7.76 (s, 1H), 7.47 (d, J=8.8 Hz, 2H), 7.36-7.30 (m, 4H), 7.23-7.19 (m, 3H), 6.96 (s, 1H), 2.06 (s, 3H).

Compound 107: $^1$H NMR (CDCl$_3$, 400 MHz) δ 7.78 (s, 1H), 7.47 (d, J=8.8 Hz, 2H), 7.35-7.31 (m, 4H), 7.24-7.19 (m, 3H), 6.95 (s, 1H), 2.22 (t, J=7.6 Hz, 2H), 1.59-1.51 (m, 2H), 1.36-1.26 (m, 2H), 0.89 (t, J=7.2 Hz, 3H).

Compound 108: $^1$H NMR (CDCl$_3$, 400 MHz) δ 7.79 (s, 1H), 7.47 (d, J=8.8 Hz, 2H), 7.36-7.31 (m, 4H), 7.25-7.20 (m, 3H), 7.02 (s, 1H), 2.39-2.32 (m, 1H), 1.12 (d, J=6.8 Hz, 2H).

Compound 109: $^1$H NMR (CDCl$_3$, 300 MHz) δ 7.81 (s, 1H), 7.50-7.46 (m, 2H), 7.38-7.33 (m, 4H), 7.25-7.21 (m, 3H), 6.97 (s, 1H), 2.24 (t, J=7.5 Hz, 2H), 1.59 (t, J=6.9 Hz, 2H), 1.32-1.26 (m, 4H), 0.89 (t, J=6.9 Hz, 3H).

Compound 110: $^1$H NMR (CDCl$_3$, 400 MHz) δ 7.78 (s, 1H), 7.47 (d, J=8.8 Hz, 2H), 7.35-7.31 (m, 4H), 7.24-7.20 (m, 3H), 6.94 (s, 1H), 2.20 (t, J=7.6 Hz, 2H), 0.93 (t, J=7.6 Hz, 3H).

Compound 106: To a solution of Compound 88 (120 mg, 0.33 mmol) in toluene (3 mL) was added propionic anhydride (50 mg, 0.38 mmol). The mixture was heated to reflux overnight. The reaction was concentrated to remove toluene. The residue was purified by prep-HPLC to give Compound 106 (38.2 mg, 28% yield). $^1$H NMR (CDCl$_3$, 400 MHz) δ 7.78 (s, 1H), 7.46 (d, J=8.8 Hz, 2H), 7.36-7.31 (m, 4H), 7.24-7.20 (m, 3H), 6.96 (s, 1H), 2.27 (q, J=7.6 Hz, 2H), 1.11 (t, J=7.6 Hz, 3H).

Compounds 105, 112 and 113 were prepared by reacting Compound 88 with the relevant chloroformate in LiHMDS and THF.

Compound 105: $^1$H NMR (CDCl$_3$, 400 MHz) δ 7.48-7.45 (m, 3H), 7.34-7.30 (m, 4H), 7.23-7.17 (m, 3H), 6.46 (s, 1H), 4.12 (d, J=6.8 Hz, 2H), 1.70-1.63 (m, 2H), 0.93 (t, J=7.6 Hz, 3H).

Compound 112: $^1$H NMR (CDCl$_3$, 400 MHz) δ 7.49-7.41 (m, 3H), 7.34-7.30 (m, 4H), 7.23-7.16 (m, 3H), 6.41 (s, 1H), 5.05-4.98 (m, 1H), 1.26 (d, J=6.4 Hz, 6H).

Compound 113: $^1$H NMR (CDCl$_3$, 400 MHz) δ 7.53 (s, 1H), 7.49 (d, J=9.2 Hz, 4H), 7.41-7.37 (m, 4H), 7.34 (d, J=8.4 Hz, 2H), 7.28-7.14 (m, 3H), 7.15-7.12 (m, 2H), 6.81 (s, 1H).

Compound 91: To a solution of Compound 86 (250 mg, 0.7 mmol) in dry DMF (5 mL) was added BnBr (128 mg, 0.77 mmol) and $Na_2CO_3$ (112 mg, 1.1 mmol), the reaction mixture was stirred at rt overnight. And then it was diluted with water (10 mL), extracted by ethyl acetate (30 mL×3). The combined extract was washed with brine and water, dried over Na$_2$SO4, concentrated to give crude product. The crude product was purified by flash chromatography (PE/EA=5/1) to give Compound 91 (60 mg, 19% yield). $^1$H NMR (CD$_3$OD, 400 MHz) δ 7.59-7.56 (m, 3H), 7.53-7.49 (m, 2H), 7.46 (d, J=8.4 Hz, 2H), 7.40-7.33 (m, 5H), 7.14-7.09 (m, 2H), 6.23 (s, 1H), 5.23 (s, 2H). MS (ESI) m/z (M+H)$^+$ 456.1.

Compounds 92-100 were prepared by reacting Compound 87 with the relevant alcohol (1 eq.) in DMF and NAH (1.5 eq.) at rt for 2 hrs. After the reaction mixture was quenched with water and extract with EA, the organic phase was washed with brine, dried over Na₂SO₄ and concentrated in vacuo. The residue was purification by prep-TLC to give the final product.

Compound 92: ¹H NMR (CDCl₃, 400 MHz) δ 7.47-7.45 (m, 2H), 7.41-7.37 (m, 2H), 7.35-7.33 (m, 2H), 7.24 (m, 1H), 7.08-7.04 (m, 2H), 6.06 (s, 1H), 4.15-4.12 (m, 2H), 3.69-3.66 (m, 4H), 2.76-2.74 (m, 2H), 2.47-2.45 (m, 4H). MS (ESI) m/z (M+H)⁺ 479.2.

Compound 93: ¹H NMR (CDCl₃, 400 MHz) δ 7.47-7.45 (m, 2H), 7.38-7.32 (m, 4H), 7.23 (s, 1H), 7.09-7.05 (m, 2H), 6.06 (s, 1H), 4.30 (m, 2H), 3.06 (m, 2H), 2.70 (m, 4H), 1.84 (m, 4H). MS (ESI) m/z (M+H)⁺ 463.1.

Compound 94: ¹H NMR (CDCl₃, 400 MHz) δ 7.47-7.45 (m, 2H), 7.36-7.32 (m, 4H), 7.24 (m, 1H), 7.09-7.05 (m, 2H), 6.04 (s, 1H), 4.11-4.09 (m, 2H), 2.98-2.93 (m, 10H). MS (ESI) m/z (M+H)⁺ 527.0.

Compound 95: ¹H NMR (CDCl₃, 400 MHz) δ 7.47-7.45 (m, 2H), 7.37-7.32 (m, 4H), 7.26 (s, 1H), 7.11-7.07 (m, 2H), 6.06 (s, 1H), 4.58 (m, 1H), 2.62 (m, 4H), 2.42 (s, 3H), 2.27 (m, 2H), 2.02 (m, 2H). MS (ESI) m/z (M+H)⁺ 463.1.

Compound 96: ¹H NMR (CDCl₃, 400 MHz) δ 7.47-7.45 (m, 2H), 7.42-7.39 (m, 2H), 7.35-7.33 (m, 2H), 7.25 (s, 1H), 7.09-7.05 (m, 2H), 6.06 (s, 1H), 4.15 (t, J=4.4 Hz, 2H), 3.72 (t, J=4.4 Hz, 2H), 3.37 (s, 3H). MS (ESI) m/z (M+H)⁺ 424.1.

Compound 97: ¹H NMR (CDCl₃, 400 MHz) δ 7.47-7.45 (m, 2H), 7.36-7.32 (m, 4H), 7.23 (s, 1H), 7.10-7.06 (m, 2H), 6.04 (s, 1H), 4.15-4.12 (m, 2H), 3.65-3.62 (m, 2H), 3.17-3.13 (m, 2H), 2.32-2.28 (m, 2H), 2.91-1.84 (m, 2H). MS (ESI) m/z (M+H)⁺ 477.1.

Compound 98: ¹H NMR (CDCl₃, 400 MHz) δ 7.47-7.44 (m, 2H), 7.35-7.32 (m, 4H), 7.23 (s, 1H), 7.10-7.06 (m, 2H), 6.04 (s, 1H), 4.22-4.19 (m, 2H), 4.10 (s, 2H), 3.73-3.71 (m, 2H), 3.62-3.59 (m, 2H), 3.11-3.08 (m, 2H). MS (ESI) m/z (M+H)⁺ 492.9.

Compound 99: ¹H NMR (CDCl₃, 400 MHz) δ 7.47-7.44 (m, 2H), 7.36-7.29 (m, 5H), 7.14-7.10 (m, 2H), 6.06 (s, 1H), 4.72 (s, 1H), 3.05-2.91 (m, 4H), 2.53-2.39 (m, 4H). MS (ESI) m/z (M+H)⁺ 498.0.

Compound 100: ¹H NMR (CDCl₃, 400 MHz) δ 7.47-7.45 (m, 2H), 7.39-7.32 (m, 4H), 7.24 (s, 1H), 7.09-7.04 (m, 2H), 6.05 (s, 1H), 4.14-4.11 (m, 2H), 2.83-2.80 (m, 2H), 2.69 (brm, 4H), 2.49 (s, 3H). MS (ESI) m/z (M+H)⁺ 492.1.

Compound 102: To a stirred mixture of Compound 87 (200 mg, 0.521 mmol), phenol (59 mg, 0.625 mmol), and K₃PO₄ (331 mg, 1.56 mmol) in THF (5 mL) was added Pd₂(dba)₃ (96 mg, 0.104 mmol). The mixture was purged with nitrogen for three times and then heated to reflux overnight. The mixture was concentrated to remove THF, diluted with H₂O, extracted with EtOAc (30 mL×3), the organic layer was washed with brine, dried over anhydrous Na₂SO₄, and concentrated in vacuo, the crude product was purified by prep-HPLC to give Compound 102 (158 mg, 69% yield) as a yellow solid. ¹H NMR: (CDCl₃, 400 MHz) δ 7.53-7.42 (m, 6H), 7.35-7.33 (m, 3H), 7.30-7.26 (m, 1H), 7.14-7.09 (m, 4H), 5.82 (s, 1H).

Compound 541 was prepared following the similar procedure described in the synthesis of Compound 85 by reacting 4-chloro-5-(4-fluorophenyl)pyridin-2(1H)-one with 2-methyl-4-ethoxy boronic acid. ¹H NMR (DMSO-d₆, 400 MHz) δ 7.66 (s, 1H), 7.49 (m, 2H), 7.28-7.20 (m, 3H), 6.93 (s, 1H), 6.93-6.87 (m, 1H), 6.81 (s, 1H), 4.05 (q, J=6.8 Hz, 2H), 2.06 (s, 3H), 1.33 (t, J=6.8 Hz, 3H). MS (ESI) m/z (M+H)⁺ 358.0.

Compound 551 was prepared by reacting Compound 541 with 2-methoxyethanol in DMF and KOH at 150° C. overnight. ¹H NMR (CDCl₃, 400 MHz) δ 7.45-7.39 (m, 2H), 7.14-7.02 (m, 4H), 6.85-6.80 (m, 2H), 6.07 (s, 1H), 4.14 (t, J=4.4 Hz, 2H), 4.04 (q, J=7.2 Hz, 2H), 3.72 (t, J=4.4 Hz, 2H), 3.38 (s, 3H), 2.16 (s, 3H), 1.42 (t, J=7.2 Hz, 3H). MS (ESI) m/z (M+H)⁺ 398.2.

Compound 550 was prepared following the similar procedure for the synthesis of Compound 551 using 4-chloro-2-methoxy-5-(1-methyl-1H-pyrazol-4-yl)pyridine in place of XXIII-5. ¹H NMR (CDCl₃, 400 MHz) δ 7.69 (s, 1H), 7.63 (s, 1H), 7.29 (s, 1H), 7.11 (d, J=8.4 Hz, 1H), 6.85-7.96 (m, 2H), 6.05 (s, 1H), 4.18 (t, J=4.4 Hz, 2H), 4.06 (q, J=6.8 Hz, 2H), 3.91 (s, 3H), 3.82 (t, J=4.4 Hz, 2H), 3.48 (s, 3H), 2.14 (s, 3H), 1.42 (t, J=6.8 Hz, 3H). MS (ESI) m/z (M+H)⁺ 384.1.

Example 11-B

Synthesis of Compound 101 (Scheme XXIV)

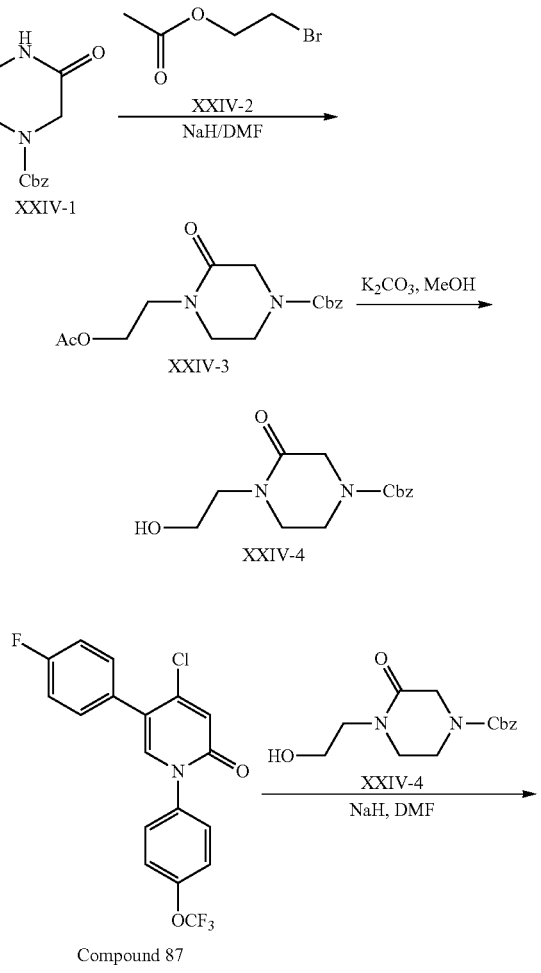

-continued

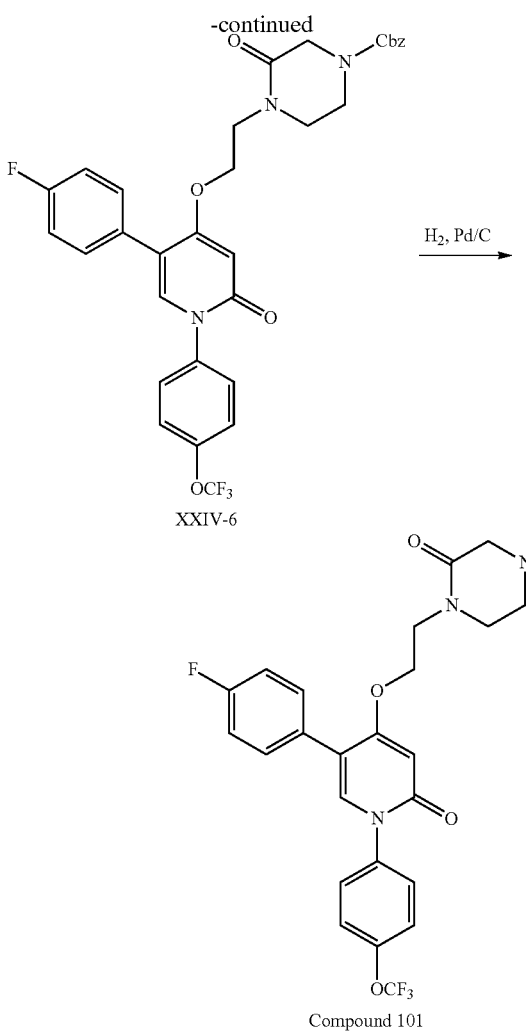

XXIV-6

Compound 101

To the solution of XXIV-1 (20 g, 85.5 mmol) in DMF (100 mL) was added NaH (60%, 4.1 g, 103 mmol) in portions. The mixture was stirred at rt for 30 min. Then XXIV-2 (14.3 g, 85.5 mmol) was added. The reaction was stirred at rt overnight. The reaction was quenched with ice-water carefully, and then extracted with EtOAc (100 mL×2). The combined organic layer was washed with brine, dried over anhydrous Na$_2$SO$_4$ and concentrated. The residue was used for next step directly (40 g, 140% crude yield).

To the solution of XXIV-3 (6.8 g, 21.25 mmol) in MeOH (50 mL) was added K$_2$CO$_3$ (8.8 g, 64 mmol). The mixture was stirred at rt for 2 hrs. Then concentrated, diluted with H$_2$O, extracted with EtOAc (100 mL×2). The combined organic layer was washed with brine, dried over anhydrous Na$_2$SO$_4$ and concentrated. The crude product was used directly (3.0 g, 51% yield).

To the solution of XXIV-4 (900 mg, 3.24 mmol) in DMF (10 mL) was added NaH (60%, 160 mg, 3.9 mmol). The mixture was stirred at rt for 30 min. Then Compound 87 (1.25 g, 3.24 mmol) was added. The reaction was stirred at rt overnight. LCMS showed the reaction was completed. The reaction was quenched with ice-water carefully, and then extracted with EtOAc (30 mL×3). The combined organic layer was washed with brine, dried over anhydrous Na$_2$SO$_4$ and concentrated to give XXIV-6 (140 mg, 22% yield).

A mixture of XXIV-6 (140 mg, 0.224 mmol) and Pd/C in ethanol (5 mL) was stirred under H$_2$ at rt for 4 hours. Filtered the reaction, and concentrated. The residue was purified by prep-HPLC to afford Compound 101 (30.9 mg, 28% yield). $^1$H NMR (CDCl$_3$, 400 MHz) δ 7.45-7.40 (m, 2H), 7.36-7.31 (m, 4H), 7.26 (m, 1H), 7.11-7.07 (m, 2H), 6.14 (s, 1H), 4.18 (m, 2H), 3.75-3.70 (m, 4H), 3.30 (m, 2H), 3.07 (m, 2H).

Example 11-C

Synthesis of Compounds 117 and 118 (Scheme XXV)

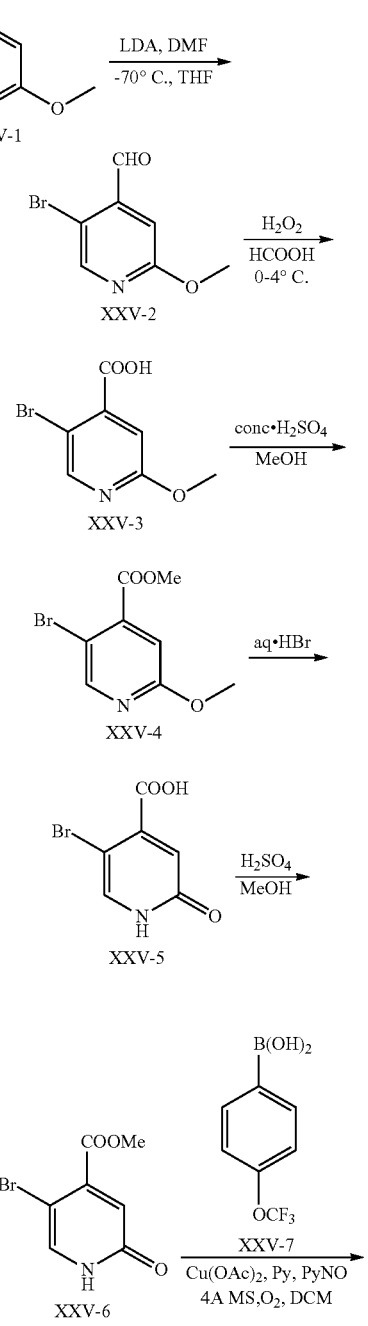

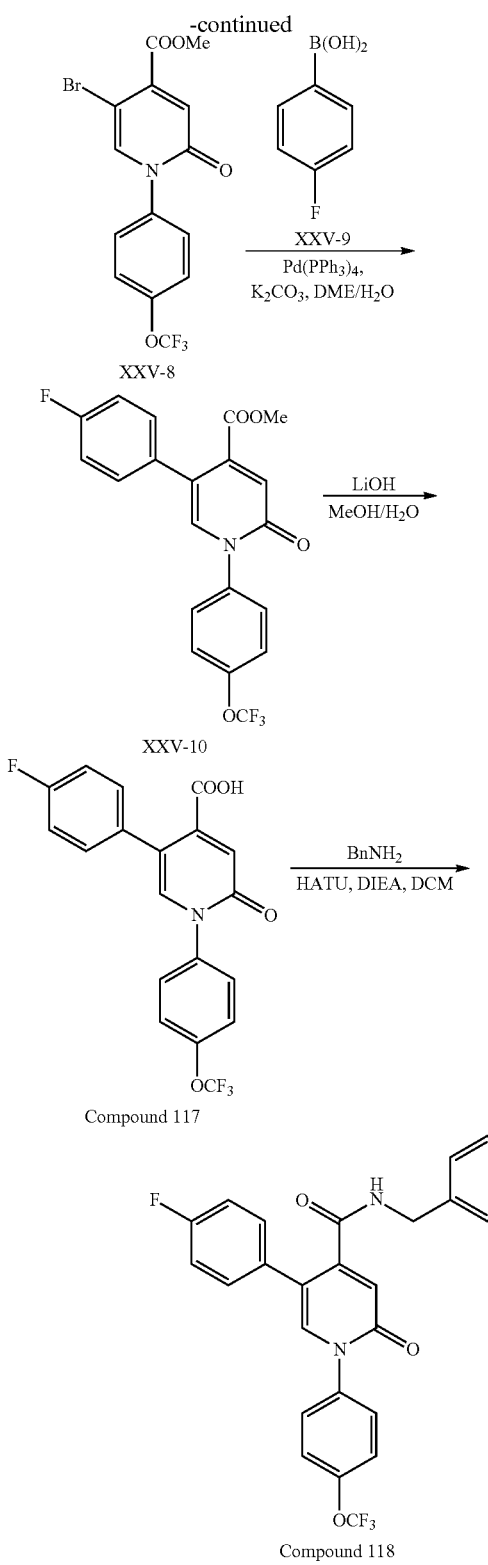

Compound 117: The mixture of XXV-10 (1.0 g, 2.5 mmol), LiOH.H$_2$O (1.0 g, 24 mmol) in MeOH/H$_2$O (15 mL/3 mL) was stirred at rt overnight. The mixture was evaporated and then acidified with aq. HCl (2 M) to pH=4-5, extracted with EtOAc (30 mL×3). The combined organic layer was washed with brine, dried over anhydrous Na$_2$SO$_4$ and concentrated. The residue was purified by prep-HPLC to give Compound 117 (806 mg, 83% yield) as a white solid. $^1$H NMR (DMSO-d$_6$, 400 MHz) δ 7.80 (s, 1H), 7.72-7.67 (m, 2H), 7.57-7.53 (m, 2H), 7.43-7.38 (m, 2H), 7.25-7.20 (m, 2H), 6.75 (s, 1H). MS (ESI) m/z [M+H]$^+$ 394.0.

Compound 118: To a solution of Compound 117 (98.2 mg, 0.25 mmol) in dry DCM (40 mL) was added benzyl amine (29 mg, 0.28 mmol), followed by adding HATU (105 mg, 0.28 mmol) and DIEA (65 mg, 0.5 mmol). The reaction mixture was stirred at rt overnight. The resulting mixture was concentrated to remove solvent, diluted with EtOAc (50 mL), washed with 5% citric acid, sat. aq. NaHCO$_3$ and brine, dried over Na$_2$SO$_4$, concentrated to give crude product. The crude product was purified by prep-TLC (PE: EA=5:1) to yield Compound 118 (10 mg, 8.3% yield) as a yellow solid. $^1$HNMR (CD$_3$OD, 400 MHz) δ 7.69 (s, 1H), 7.60 (d, J=8.8 Hz, 2H), 7.48 (d, J=8.4 Hz, 2H), 7.34-7.26 (m, 5H), 7.12-7.10 (m, 2H), 7.02-6.98 (m, 2H), 6.69 (s, 1H), 4.38 (s, 2H). MS (ESI) m/z (M+H)$^+$ 483.1.

General procedure for preparing Compounds 103, 111, and 114: To a mixture of Compound 117 (1 eq.) in toluene was added TEA (2.6 eq.) and 4 Å molecular sieve. The mixture was stirred at 100° C. for 1 h, then DPPA (1.05 eq.) and the relevant alcohol (1.2 eq.) was added under N$_2$ protection. The reaction mixture was stirred at 110° C. overnight. The mixture was concentrated, diluted with H$_2$O, extracted with EtOAc. The combined organic layer was washed with water and brine, dried over anhydrous Na$_2$SO$_4$, and concentrated in vacuo, the residue was purified by prep-TLC (PE:EA=2:1) to give the final product.

Compound 103: $^1$H NMR (CDCl$_3$, 400 MHz) δ 7.52 (s, 1H), 7.49-7.45 (m, 2H), 7.44-7.26 (m, 9H), 7.22-7.15 (m, 3H), 6.53 (s, 1H), 5.18 (s, 2H). MS (ESI) m/z [M+H]$^+$ 499.0.

Compound 111: $^1$H NMR (CDCl$_3$, 400 MHz) δ 7.47-7.45 (m, 3H), 7.33-7.30 (m, 4H), 7.21-7.17 (m, 3H), 6.50 (s, 1H), 3.76 (s, 3H). MS (ESI) m/z [M+H]$^+$ 422.0.

Compound 114: $^1$H NMR (CDCl$_3$, 400 MHz) δ 7.50-7.45 (m, 3H), 7.35-7.30 (m, 4H), 7.22-7.17 (m, 3H), 6.46 (s, 1H), 4.21 (q, J=6.8 Hz, 2H), 1.28 (t, J=6.8 Hz, 3H). MS (ESI) m/z [M+H]$^+$ 436.1.

General procedure for preparing Compounds 115 and 116: To the solution of Compound 117 (1 eq.) in toluene was added TEA (2.5 eq) and 4 Å molecular sieve (100 mg). The mixture was heated to 100° C. for 30 minutes. Then cooled to 80° C., the relevant amine (1.2 eq.) and DPPA (1.2 eq) were added. The mixture was heated to 110° C. for 3 hrs. The mixture was filtered, diluted with water, extracted with EtOAc. The combined organic layer was washed with brine, dried over anhydrous Na$_2$SO$_4$ and concentrated. The residue was purified by Prep-HPLC to give the final product.

Compound 115: $^1$H NMR (400 MHz, CDCl$_3$) δ 7.46-7.44 (m, 2H), 7.35-7.30 (m, 5H), 7.20-7.15 (m, 3H), 6.09 (s, 1H), 4.77 (s, 1H), 3.13 (d, J=6.0 Hz, 2H), 1.51 (m, 2H), 0.90 (t, J=7.2 Hz, 3H).

Compound 116: $^1$H NMR (CDCl$_3$, 400 MHz) δ 7.33 (s, 2H), 7.26-7.22 (m, 5H), 7.21-7.17 (m, 6H), 7.03-6.97 (m, 3H), 6.90 (brs, 1H), 4.24 (d, J=5.2 Hz, 2H).

Compound 119 was prepared following the similar procedure for obtaining Compound 85 using (4-ethoxy-2-methylphenyl)boronic acid in place of XXIII-7. $^1$H NMR (CDCl$_3$, 400 MHz) δ 7.38-7.34 (m, 2H), 7.13-7.11 (m, 2H), XXV-6 was obtained following the synthetic scheme as described above. MS (ESI) m/z (M+H)$^+$ 231.95.

XXV-10 was prepared following the similar procedure for obtaining Compound 40. $^1$HNMR (CDCl$_3$, 400 MHz) δ 7.50-7.42 (m, 2H), 7.40-7.31 (m, 4H), 7.26-7.20 (m, 1H), 7.10-7.03 (m, 3H), 3.73 (s, 3H).

7.08-7.04 (m, 2H), 6.84-6.78 (m, 2H), 6.10 (s, 1H), 4.04 (q, J=7.2 Hz, 2H), 3.85 (s, 3H), 2.17 (s, 3H), 1.42 (t, J=7.2 Hz, 3H). MS (ESI) m/z (M+H)+ 353.9.

Compound 120 was prepared following the similar procedure for obtaining Compound 85 using 1-methyl-4-(4,4,5,5-tetramethyl-1,3,2-dioxaborolan-2-yl)-1H-pyrazole in place of XXIII-4 as a white solid. $^1$H NMR (CD$_3$OD, 400 MHz) δ 7.61 (m, 2H), 7.47-7.43 (m, 2H), 7.38-7.33 (m, 3H), 6.07 (s, 1H), 3.93 (s, 3H), 3.91 (s, 3H). MS (ESI) m/z (M+H)+ 365.9.

Compound 121 was prepared following the similar procedure for obtaining Compound 86. $^1$H NMR (DMSO-d$_6$, 400 MHz) δ 7.97 (s, 1H), 7.82 (s, 1H), 7.76 (s, 1H), 7.55-7.53 (m, 2H), 7.48-7.46 (m, 2H), 6.00 (s, 1H), 3.89 (s, 3H). MS (ESI) m/z (M+H)+ 352.0.

Compound 122 was prepared following the similar procedure for obtaining Compound 87. $^1$H NMR (CD$_3$OD, 400 MHz) δ 7.88 (s, 1H), 7.81 (s, 1H), 7.68 (s, 1H), 7.59-7.57 (m, 2H), 7.48-7.46 (m, 2H), 6.84 (s, 1H), 4.90 (s, 3H). MS (ESI) m/z (M+H)+ 370.1.

General procedure for preparing Compounds 123, 126-129, 131-135, 160 and 161: A mixture of Compound 122 (200 mg, 0.542 mmol) in the relevant amine (1 mL) was stirred at 130-160° C. for 4 hrs. After being cooled to rt, the mixture was diluted with H$_2$O, extracted with EtOAc, the organic layer was washed with water and brine, dried over anhydrous Na$_2$SO$_4$, and concentrated in vacuo, the crude product was purified by flash column chromatography (PE:AE=1:3) to give the final product.

Compound 123: $^1$H NMR (CD$_3$OD, 400 MHz) δ 7.82 (s, 1H), 7.64 (s, 1H), 7.51-7.47 (m, 2H), 7.42-7.38 (m, 2H), 7.36-7.35 (m, 5H), 7.28-7.25 (m, 1H), 5.53 (s, 1H), 4.45 (d, J=4.4 Hz, 2H), 3.97 (s, 3H). MS (ESI) m/z (M+H)+ 441.1.

Compound 126: $^1$H NMR (CDCl$_3$, 400 MHz) δ 7.55 (s, 1H), 7.50-7.45 (m, 2H), 7.40 (s, 1H), 7.33-7.28 (m, 4H), 7.25 (m, 1H), 7.13-7.09 (m, 3H), 6.00 (s, 1H), 4.16 (s, 2H), 3.81 (s, 3H), 2.65 (s, 3H). MS (ESI) m/z (M+H)+ 455.

Compound 127: $^1$H NMR (CDCl$_3$, 400 MHz) δ 7.61 (s, 1H), 7.55 (s, 1H), 7.46-7.42 (m, 2H), 7.32-7.28 (m, 2H), 7.12 (s, 1H), 6.05 (s, 1H), 3.93 (s, 3H), 2.91 (m, 4H), 1.56 (m, 6H). MS (ESI) m/z (M+H)+ 419.

Compound 128: $^1$H NMR (CDCl$_3$, 400 MHz) δ 7.63 (s, 1H), 7.52 (s, 1H), 7.45-7.41 (m, 2H), 7.32-7.28 (m, 2H), 7.12 (s, 1H), 6.06 (s, 1H), 3.92 (s, 3H), 3.70 (m, 4H), 2.96 (m, 4H). MS (ESI) m/z (M+H)+ 421.1.

Compound 129: $^1$H NMR (CDCl$_3$, 400 MHz) δ 7.60 (s, 1H), 7.51 (s, 1H), 7.48-7.45 (m, 2H), 7.33-7.30 (m, 2H), 7.20-7.17 (m, 3H), 7.13-7.11 (m, 1H), 7.08-7.05 (m, 1H), 6.23 (s, 1H), 4.23 (s, 2H), 3.89 (s, 3H), 3.28 (t, J=6.0 Hz, 2H), 2.77 (t, J=6.0 Hz, 2H). MS (ESI) m/z (M+H)+ 467.1.

Compound 131: $^1$H NMR (CDCl$_3$, 400 MHz) δ 7.45-7.41 (m, 2H), 7.37-7.26 (m, 6H), 7.18-7.16 (m, 2H), 7.08 (s, 1H), 7.02 (s, 1H), 5.70 (s, 1H), 4.43 (t, J=6.4 Hz, 1H), 3.88 (s, 3H), 3.42 (q, J=6.4 Hz, 2H), 2.93 (t, J=6.4 Hz, 3H). MS (ESI) m/z (M+H)+ 454.0.

Compound 132: $^1$H NMR (CDCl$_3$, 400 MHz) δ 7.49 (s, 1H), 7.45-7.42 (m, 2H), 7.39-7.33 (m, 3H), 7.31-7.24 (m, 3H), 7.05 (s, 1H), 5.90 (s, 1H), 4.61-4.55 (m, 3H), 3.91 (s, 3H). MS (ESI) m/z (M+H)+ 508.0.

Compound 133: $^1$H NMR (CDCl$_3$, 400 MHz) δ 7.49 (s, 1H), 7.44-7.39 (m, 3H), 7.30-7.26 (m, 3H), 7.04 (s, 1H), 6.95-6.90 (m, 2H), 5.81 (s, 1H), 4.79 (t, J=6.0 Hz, 1H), 4.41 (d, J=6.0 Hz, 2H), 3.94 (s, 3H). MS (ESI) m/z (M+H)+ 477.1.

Compound 134: $^1$H NMR (CDCl$_3$, 400 MHz) δ 7.51 (s, 1H), 7.45-7.39 (m, 3H), 7.30-7.25 (m, 3H), 7.22-7.20 (m, 2H), 7.06 (s, 1H), 6.90-6.87 (m, 2H), 5.70 (s, 1H), 4.70 (t, J=5.2 Hz, 1H), 4.25 (d, J=5.2 Hz, 2H), 3.93 (s, 3H), 3.81 (s, 3H). MS (ESI) m/z (M+H)+ 471.2.

Compound 135: $^1$H NMR (CDCl$_3$, 400 MHz) δ 7.56 (s, 1H), 7.48-7.42 (m, 3H), 7.32-7.30 (m, 2H), 7.13 (s, 1H), 7.03-7.00 (m, 2H), 6.85-6.81 (m, 2H), 5.98 (s, 1H), 4.08 (s, 2H), 3.85 (s, 3H), 3.79 (s, 3H), 2.59 (s, 3H). MS (ESI) m/z (M+H)+ 485.0.

Compound 160: $^1$H NMR (CDCl$_3$, 400 MHz) δ 8.56-8.55 (m, 2H), 7.61 (d, J=8.0 Hz, 1H), 7.52 (s, 1H), 7.43-7.41 (m, 3H), 7.31-7.28 (m, 3H), 7.08 (s, 1H), 5.64 (s, 1H), 4.82 (t, J=5.6 Hz, 1H), 4.37 (d, J=5.6 Hz, 2H), 3.94 (s, 3H). MS (ESI) m/z (M+H)+ 442.0.

Compound 161: $^1$H NMR (CDCl$_3$, 400 MHz) δ 8.53 (d, J=4.4 Hz, 1H), 7.71-7.67 (m, 1H), 7.61 (s, 1H), 7.54 (s, 1H), 7.46-7.44 (m, 2H), 7.30-7.27 (m, 3H), 7.23-7.20 (m, 1H), 7.11 (s, 1H), 6.10 (t, J=4.4 Hz, 1H), 5.67 (s, 1H), 4.44 (d, J=4.4 Hz, 2H), 3.98 (s, 3H). MS (ESI) m/z (M+H)+ 442.0.

Compound 124: Compound 134 (200 mg, 0.42 mmol) was dissolved in TFA (3 mL). The solution was stirred at rt for 3 days under N$_2$. After the material was consumed, most of TFA was evaporated, the remaining mixture was diluted with water and neutralized with saturated aq. NaHCO$_3$, extracted with EA (30 mL×3), the organic phase was washed with brine, dried over Na$_2$SO$_4$, concentrated. The residue was purified by prep-TLC (PE/EA=1/3) to give Compound 124 (50 mg, 34% yield). $^1$H NMR (CDCl$_3$, 400 MHz) δ 7.54 (s, 1H), 7.45-7.43 (m, 3H), 7.31-7.29 (m, 2H), 7.12 (s, 1H), 5.80 (s, 1H), 4.39 (brs, 2H), 3.96 (s, 3H). MS (ESI) m/z (M+H)+ 350.9.

Compound 125 was prepared from Compound 135 following the similar procedure for obtaining Compound 124. $^1$H NMR (CDCl$_3$, 400 MHz) δ 7.50 (s, 1H), 7.45-7.41 (m, 3H), 7.30-7.28 (m, 2H), 7.04 (s, 1H), 5.63 (s, 1H), 4.50 (t, J=4.8 Hz, 1H), 3.95 (s, 3H), 2.83 (d, J=4.8 Hz, 3H). MS (ESI) m/z (M+H)+ 364.9.

Compound 130: To a stirred mixture of Compound 122 (100 mg, 0.271 mmol, 1 eq.), aniline (76 mg, 0.81 mmol, 3.0 eq), Xantphos (8 mg, 0.0135 mmol, 0.05 eq.), and K$_3$PO$_4$ (57 mg, 0.271 mmol, 1.0 eq.) in DMF (2 mL) was added Pd$_2$(dba)$_3$ (12 mg, 0.0135 mmol, 0.05 eq.). The mixture was purged with nitrogen for three times and then heated at 100° C. under nitrogen overnight. After being cooled to rt, the mixture was diluted with H$_2$O (10 mL), extracted with EtOAc (20 mL×3). The combined organic layer was washed with brine, dried over anhydrous Na$_2$SO$_4$, and concentrated in vacuo. The crude product was purified by Prep-HPLC to afford Compound 130 (20 mg, 18% yield). $^1$H NMR (CDCl$_3$, 400 MHz) δ 7.62 (s, 1H), 7.53 (s, 1H), 7.47-7.44 (m, 2H), 7.38 (t, J=7.6 Hz, 2H), 7.32 (d, J=8.4 Hz, 2H), 7.22-7.18 (m, 4H), 6.20 (s, 1H), 6.12 (s, 1H), 3.99 (s, 3H).

Compound 158 was prepared following the similar procedure for obtaining Compound 117 using 1-methyl-4-(4,4,5,5-tetramethyl-1,3,2-dioxaborolan-2-yl)-1H-pyrazole in place of XXV-9 as a white solid. $^1$H NMR (CD$_3$OD, 400 MHz) δ 7.71 (m, 2H), 7.61-7.58 (m, 2H), 7.55 (s, 1H), 7.48-7.46 (m, 2H), 6.83 (s, 1H), 3.88 (s, 3H). MS (ESI) m/z [M+H]+ 380.1.

Compound 159 was prepared following the similar procedure for obtaining Compound 118 using propan-1-amine in place of benzyl amine as a white solid. $^1$H NMR (400 MHz, CDCl$_3$) δ 7.52 (s, 1H), 7.46 (s, 1H), 7.35-7.32 (m, 3H), 7.29-7.26 (m, 2H), 6.85 (t, J=4.8 Hz, 1H), 6.59 (s, 1H), 3.86 (s, 3H), 3.22 (q, J=6.4 Hz, 2H), 1.45 (q, J=7.2 Hz, 2H), 0.82 (t, J=7.2 Hz, 3H). MS (ESI) m/z [M+H]+ 420.1.

Compounds 136-140 were prepared from Compound 158 following the similar procedure for obtaining Compound 103.

Compound 136: ¹H NMR (400 MHz, CDCl₃) δ 7.52 (s, 1H), 7.45-7.41 (m, 4H), 7.32-7.29 (m, 2H), 7.17 (s, 1H), 6.71 (s, 1H), 4.18-4.14 (m, 2H), 3.98 (s, 3H), 1.67-1.59 (m, 2H), 1.42-1.23 (m, 2H), 0.94 (t, J=7.2 Hz, 3H). MS (ESI) m/z [M+H]⁺ 450.1.

Compound 137: ¹H NMR (400 MHz, CDCl₃) δ 7.50 (s, 1H), 7.45 (s, 1H), 7.43-7.41 (m, 3H), 7.29-7.27 (m, 2H), 7.16 (s, 1H), 6.72 (s, 1H), 4.22-4.17 (m, 2H), 3.96 (s, 3H), 1.28-1.25 (m, 3H). MS (ESI) m/z [M+H]⁺ 422.1.

Compound 138: ¹H NMR (400 MHz, CDCl₃) δ 7.51 (s, 1H), 7.45-7.43 (m, 4H), 7.33-7.30 (m, 2H), 7.18 (s, 1H), 6.75 (s, 1H), 3.98 (s, 3H), 3.77 (s, 3H). MS (ESI) m/z [M+H]⁺ 408.1

Compound 139: ¹H NMR (400 MHz, CDCl₃) δ 7.52 (s, 1H), 7.47-7.43 (m, 4H), 7.33-7.30 (m, 2H), 7.17 (s, 1H), 6.65 (s, 1H), 5.05-5.00 (m, 1H), 3.98 (s, 3H), 1.28 (d, J=6.0 Hz, 3H). MS (ESI) m/z [M+H]⁺ 436.1.

Compound 140: ¹H NMR (CDCl₃, 400 MHz) δ 7.49 (s, 2H), 7.44-7.40 (m, 3H), 7.38 (m, 5H), 7.33-7.30 (m, 2H), 7.29 (s, 1H), 7.16 (s, 1H), 6.77 (s, 1H), 5.18 (s, 2H), 3.95 (s, 3H). MS (ESI) m/z [M+H]⁺ 484.14.

Compound 141: Compound 124 (150 mg, 0.43 mmol) was dissolved in 6 mL of DCM/pyridine (v/v=1/1), and then acetyl chloride (36 mg, 0.46 mmol) was added. The mixture was stirred at rt overnight. Then the mixture was diluted with DCM (50 mL), washed with water and brine, dried over Na₂SO₄, concentrated in vacuo to give the crude product. The crude product was purification by prep-TLC (PE/EA=1/1) to afford Compound 141 (70 mg, 42% yield). ¹H NMR (CDCl₃, 400 MHz) δ 7.73 (s, 1H), 7.54 (s, 1H), 7.45-7.43 (m, 3H), 7.32-7.30 (m, 2H), 7.22-7.19 (m, 2H), 3.99 (s, 3H), 2.12 (s, 3H). MS (ESI) m/z (M+H)⁺ 392.9.

Compound 142 was prepared following the similar procedure for obtaining Compound 141 using bezoyl chloride in place of acetyl chloride. ¹H NMR (CDCl₃, 400 MHz) δ 8.07 (s, 1H), 7.94 (s, 1H), 7.68-7.64 (m, 3H), 7.58-7.55 (m, 1H), 7.49-7.44 (m, 5H), 7.34-7.32 (m, 2H), 7.25 (s, 1H), 4.00 (s, 3H). MS (ESI) m/z (M+H)⁺ 455.

Compound 143 was prepared from Compound 121 following the similar procedure for obtaining Compound 91. ¹H NMR (CD₃OD, 400 MHz) δ 7.83 (s, 2H), 7.73 (s, 1H), 7.56 (d, J=6.4 Hz, 2H), 7.54-7.37 (m, 7H), 6.20 (s, 1H), 5.27 (s, 2H), 3.84 (s, 3H). MS (ESI) m/z (M+H)⁺ 442.1.

Compounds 144-152 were prepared by reacting Compound 121 with the relevant alcohol (1 eq.) in DMF and NAH (1.5 eq.) at rt for 2 hrs. After the reaction mixture was quenched with water and extract with EA, the organic phase was washed with brine, dried over Na₂SO₄ and concentrated in vacuo. The residue was purification by prep-TLC to give the final product.

Compound 144: ¹H NMR (DMSO-d₆, 400 MHz) δ 7.94 (s, 1H), 7.87 (s, 1H), 7.78 (s, 1H), 7.58 (d, J=8.8 Hz, 2H), 7.50 (d, J=8.8 Hz, 2H), 5.99 (s, 1H), 4.20-4.18 (m, 2H), 3.80 (s, 3H), 3.75-3.73 (m, 2H), 3.35 (s, 3H).

Compound 145: ¹H NMR (DMSO-d₆, 400 MHz) δ 7.80 (s, 1H), 7.63 (s, 1H), 7.46-7.44 (m, 2H), 7.38 (s, 1H), 7.33-7.26 (m, 2H), 6.05 (s, 1H), 4.18 (m, 2H), 3.91 (s, 3H), 2.97-3.00 (m, 2H), 2.62 (m, 4H), 1.82 (m, 4H).

Compound 146: ¹H NMR (DMSO-d₆, 400 MHz) δ 7.80 (s, 1H), 7.55 (s, 1H), 7.42-7.46 (m, 3H), 7.33-7.35 (m, 2H), 6.04 (s, 1H), 4.15 (t, J=5.2 Hz, 2H), 3.95 (s, 3H), 3.83 (t, J=5.2 Hz, 2H), 3.39 (t, J=6.8 Hz, 2H), 2.36 (t, J=8.0 Hz, 2H), 2.05-1.98 (m, 2H).

Compound 147: ¹H NMR (CDCl₃, 400 MHz) δ 7.80 (s, 1H), 7.67 (s, 1H), 7.45-7.43 (m, 2H), 7.39 (s, 1H), 7.33-7.26 (m, 2H), 6.05 (s, 1H), 4.16 (t, J=5.2 Hz, 2H), 3.92 (s, 3H), 3.74 (m, 4H), 2.85 (t, J=5.2 Hz, 2H), 2.56 (m, 4H).

Compound 148: ¹H NMR (CDCl₃, 400 MHz) δ 7.65 (s, 1H), 7.56 (s, 1H), 7.46-7.44 (m, 2H), 7.36-7.34 (m, 3H), 6.05 (s, 1H), 4.17-4.14 (m, 2H), 3.93 (s, 3H), 3.11-3.03 (m, 10H). MS (ESI) m/z (M+H)⁺ 513.1.

Compound 149: ¹H NMR (CDCl₃, 400 MHz) δ 7.55 (s, 1H), 7.43 (m, 3H), 7.35 (m, 3H), 6.06 (s, 1H), 4.73 (m, 1H), 3.95 (s, 3H), 3.21-3.14 (m, 2H), 3.03-2.09 (m, 2H), 2.59-2.45 (m, 4H).

Compound 150: ¹H NMR (CDCl₃, 400 MHz) δ 7.69 (s, 1H), 7.56 (s, 1H), 7.46-7.44 (m, 2H), 7.38-7.33 (m, 3H), 6.05 (s, 1H), 4.24-4.21 (m, 2H), 4.16 (s, 2H), 3.93-3.91 (m, 5H), 3.84-3.81 (m, 2H), 3.39-3.37 (m, 2H). MS (ESI) m/z (M+H)⁺ 479.1.

Compound 151: ¹H NMR (CDCl₃, 400 MHz) δ 7.59 (s, 1H), 7.54 (s, 1H), 7.46-7.43 (m, 2H), 7.37-7.34 (m, 3H), 6.06 (s, 1H), 4.61-4.58 (m, 1H), 3.94 (s, 3H), 2.90 (m, 2H), 2.55 (m, 3H), 2.18-2.08 (m, 2H), 1.80-1.67 (m, 2H). MS (ESI) m/z (M+H)⁺ 449.0.

Compound 152: ¹H NMR (CDCl₃, 400 MHz) δ 7.82 (s, 1H), 7.65 (s, 1H), 7.46-7.44 (m, 2H), 7.40 (s, 1H), 7.39-7.32 (m, 2H), 6.04 (s, 1H), 4.16 (t, J=5.6 Hz, 2H), 3.95 (s, 3H), 2.87 (t, J=5.6 Hz, 2H), 2.61-2.49 (m, 8H), 2.31 (s, 3H).

Compound 153: Compound 122 (1.5 g, 4.06 mmol), phenol (763 mg, 8.12 mmol) and K₃PO₄ (2.6 g, 12.2 mmol) were added into DMF (15 mL). The solution was degassed by N₂ for three times and then Pd₂(dba)₃ (570 mg, 0.81 mmol) was added. The reaction mixture was stirred at 110° C. for 14 hrs under N₂. After being cooled to rt, the mixture was diluted with EA (80 mL) and filtered; the filterate was washed with brine. The separated organic phase was dried over Na₂SO₄, concentrated under reduced pressure. The residue was purified by flash column chromatography (PE/EA=1/1) to give Compound 153 (848 mg, 49% yield). ¹H NMR (CDCl₃, 400 MHz) δ 7.76 (s, 1H), 7.69 (s, 1H), 7.50-7.44 (m, 5H), 7.36-7.26 (m, 3H), 7.16 (m, 2H), 5.79 (s, 1H), 3.94 (s, 3H). MS (ESI) m/z (M+H)⁺ 428.

Compound 156 was prepared following the similar procedure for obtaining Compound 153 using 3-chloro-5-hydroxybenzonitrile in place of phenol. ¹H NMR (CDCl₃, 400 MHz) δ 7.64-7.59 (m, 3H), 7.52 (s, 1H), 7.48-7.44 (m, 3H), 7.39-7.36 (m, 3H), 5.82 (s, 1H), 3.94 (s, 3H). MS (ESI) m/z (M+H)⁺ 486.9.

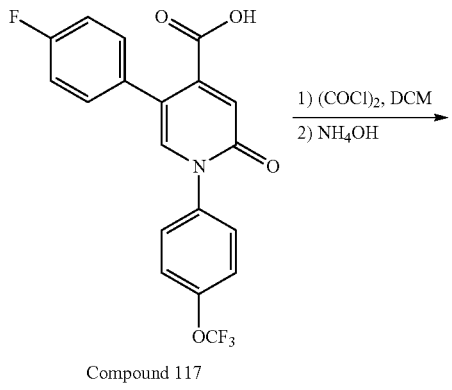

Compound 117

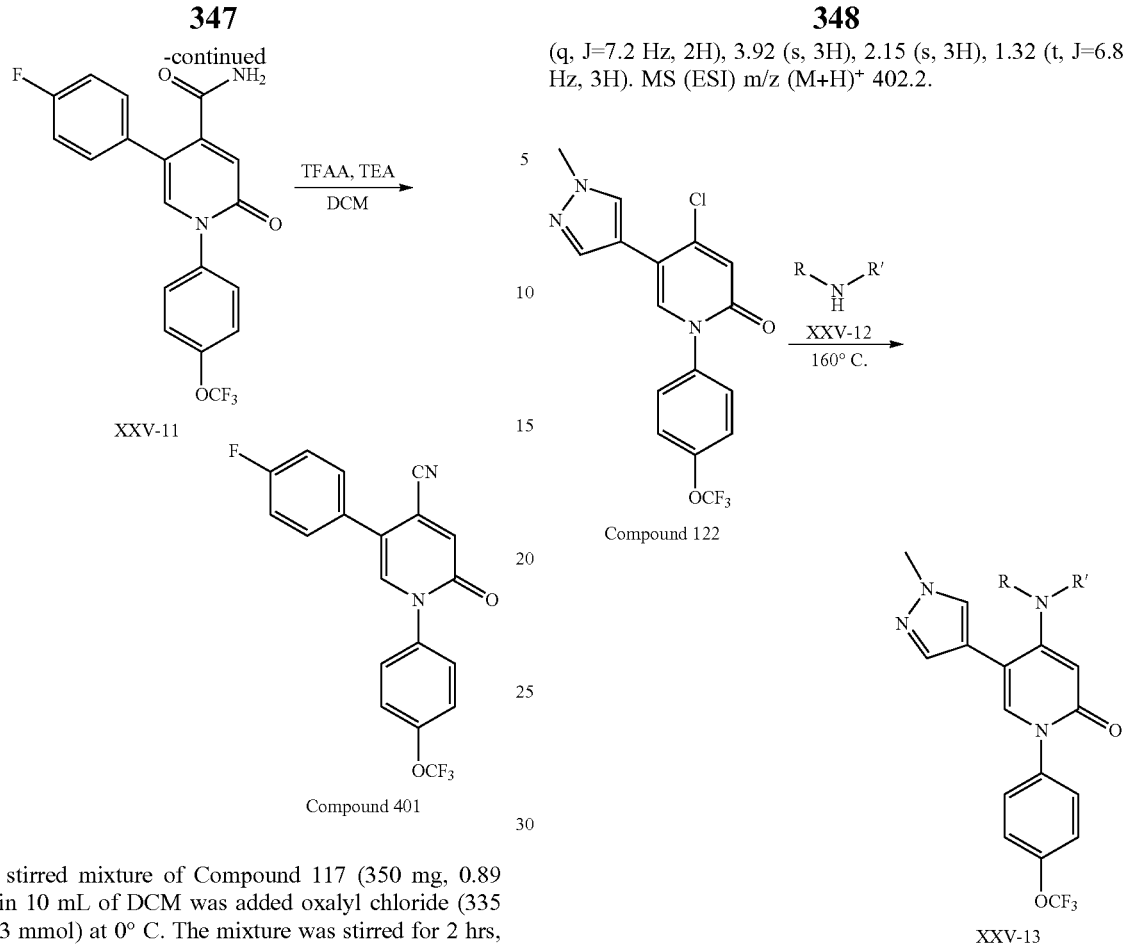

Compound 401

Compound 122

XXV-13

To a stirred mixture of Compound 117 (350 mg, 0.89 mmol) in 10 mL of DCM was added oxalyl chloride (335 mg, 2.63 mmol) at 0° C. The mixture was stirred for 2 hrs, and then the mixture was concentrated under reduced pressure. The residue was re-dissolved in DCM (10 mL) and the mixture was added to the well-stirred ammonia (5 mL) at 0° C. After the mixture was stirred at 0° C. for 30 min, the reaction mixture was extracted with EA (20 mL×3). The combined organic layer was washed with brine, dried over anhydrous $Na_2SO_4$ and concentrated. The residue was purified by column chromatography ($CH_2Cl_2$/MeOH=20/1) to give XXV-11 (220 mg, 63% yield). MS (ESI) m/z $(M+H)^+$ 393.1.

To a solution of XXV-11 (220 mg, 0.56 mmol) in 10 mL of DCM was added TEA (85.3 mg, 0.84 mmol) and TFAA (81.6 mg, 0.84 mmol). The reaction mixture was stirred at rt under $N_2$ for 3 hrs and then diluted with DCM (30 mL) and filtered. The filtrate was washed with brine, dried over $Na_2SO_4$, the residue was purified by prep-HPLC to give Compound 401 (180 mg, 86% yield). $^1$H NMR ($CDCl_3$, 400 MHz) δ 7.48-7.37 (m, 7H), 7.19-7.14 (m, 3H). MS (ESI) m/z $(M+H)^+$ 375.1.

Compound 402 was prepared following the similar procedure for obtaining Compound 401 using Compound 158 in place of Compound 117. $^1$H NMR ($CDCl_3$, 400 MHz) δ 7.83 (s, 1H), 7.76 (d, J=9.6 Hz, 1H), 7.61 (s, 3H), 7.39 (m, 2H), 7.12 (d, J=9.6 Hz, 1H), 3.97 (s, 3H). MS (ESI) m/z $(M+H)^+$ 361.1.

Compound 403 was prepared following the similar procedure for obtaining Compound 153 using 4-chloro-1-(4-ethoxy-2-methylphenyl)-5-(1-methyl-1H-pyrazol-4-yl)pyridin-2(1H)-one in place of Compound 122. $^1$H NMR ($CDCl_3$, 400 MHz) δ 7.74 (s, 1H), 7.67 (s, 1H), 7.47-7.43 (m, 2H), 7.39 (s, 1H), 7.30 (d, J=3.6 Hz, 1H), 7.17 (d, J=3.6 Hz, 2H), 7.12 (d, J=3.6 Hz, 2H), 6.85-6.80 (m, 2H), 5.80 (s, 1H), 4.04 (q, J=7.2 Hz, 2H), 3.92 (s, 3H), 2.15 (s, 3H), 1.32 (t, J=6.8 Hz, 3H). MS (ESI) m/z $(M+H)^+$ 402.2.

A mixture of Compound 122 in the relevant amine (1 mmol/1 mL) was stirred at 160° C. for 4 hrs. After being cooled to rt, the mixture was diluted with $H_2O$, extracted with EtOAc, the organic layer was washed with water and brine, dried over anhydrous $Na_2SO_4$, and concentrated in vacuo, the crude product was purified by column chromatography (PE/EtOAc=1/1) to give the final products.

Alternatively, a solution of Compound 122 (1.355 mmol) in toluene (20 mL) were added the relevant amine (2.71 mmol), NaOtBu (520 mg, 5.42 mmol), Xphos (64.9 mg, 0.136 mmol), Pd(OAc)$_2$ (30.5 mg, 0.136 mmol). The mixture was degassed under in vacuum and purged with $N_2$ three times. The reaction mixture was heated to 100° C. or to reflux overnight. The mixture was cooled to rt, diluted with water, extracted with EA. The combined organic layer was dried over $Na_2SO_4$, concentrated in vacuum. The residual was purified by silica gel chromatography eluted with DCM: MeOH (50:1-10:1) to give the final product.

Compounds 404-407, 411, 526-531, and 546-549 were prepared following the general scheme as illustrated above.

Compound 404: $^1$H NMR ($CDCl_3$, 400 MHz) δ 7.50 (s, 1H), 7.43-7.39 (m, 3H), 7.30-7.25 (m, 3H), 7.06 (s, 1H), 6.88-6.80 (m, 2H), 5.64 (s, 1H), 4.85 (t, J=6.0 Hz, 1H), 4.34 (d, J=6.0 Hz, 2H), 3.93 (s, 3H). MS (ESI) m/z $(M+H)^+$ 477.1.

Compound 405: $^1$H NMR ($CDCl_3$, 400 MHz) δ 7.54 (s, 1H), 7.45-7.40 (m, 4H), 7.30-7.24 (m, 4H), 7.08 (s, 1H), 5.59 (s, 1H), 4.92 (t, J=6.0 Hz, 1H), 4.38 (d, J=6.0 Hz, 2H), 3.95 (s, 3H). MS (ESI) m/z $(M+H)^+$ 510.1.

Compound 406: $^1$H NMR ($CDCl_3$, 400 MHz) δ 7.52 (s, 1H), 7.47-7.40 (m, 3H), 7.35-7.20 (m, 5H), 7.11 (s, 1H), 5.91 (s, 1H), 4.97 (t, J=6.0 Hz, 1H), 4.34 (d, J=6.0 Hz, 2H), 3.95 (s, 3H). MS (ESI) m/z (M+H)+ 475.1.

Compound 407: ¹H NMR (CDCl₃, 400 MHz) δ 7.52 (s, 1H), 7.46-7.41 (m, 3H), 7.32-7.25 (m, 4H), 7.08-7.03 (m, 3H), 5.65 (s, 1H), 4.77 (t, J=5.6 Hz, 1H), 4.30 (d, J=5.6 Hz, 2H), 3.94 (s, 3H). MS (ESI) m/z (M+H)+ 458.9.

Compound 411: ¹H NMR (CDCl₃, 400 MHz) δ 8.62 (s, 1H), 8.53 (s, 2H), 7.60 (s, 1H), 7.50 (s, 1H), 7.45-7.43 (m, 2H), 7.31-7.29 (m, 2H), 7.12 (s, 1H), 5.74 (t, J=5.2 Hz, 1H), 5.68 (s, 1H), 4.52 (d, J=5.2 Hz, 2H), 3.98 (s, 3H). MS (ESI) m/z (M+H)+ 443.0.

Compound 526: ¹H NMR (CDCl₃, 300 MHz) δ 7.58 (d, J=8.1 Hz, 2H), 7.48 (s, 1H), 7.33-7.38 (m, 5H), 6.59 (s, 1H), 7.21 (d, J=8.1 Hz, 2H), 7.03 (s, 1H), 5.48 (s, 1H), 4.87 (t, J=5.7 Hz, 1H), 4.36 (d, J=5.7 Hz, 2H), 3.89 (s, 3H).

Compound 527: ¹H NMR (Methanol-d₄, 300 MHz) δ 7.75 (s, 1H), 7.55 (d, J=5.7 Hz, 2H), 7.50-7.41 (m, 5H), 7.34 (d, J=8.7 Hz, 2H), 5.52 (s, 1H), 4.51 (s, 2H), 3.86 (s, 3H).

Compound 528: ¹H NMR (DMSO-d₆, 400 MHz) δ 7.89 (s, 1H), 7.57 (s, 1H), 7.52 (d, J=8.4 Hz, 2H), 7.44 (d, J=8.4 Hz, 2H), 7.40 (s, 1H), 7.25 (t, J=8.8 Hz, 1H), 6.80-6.83 (dd, J₁=2.4 Hz, J₂=12.4 Hz), 6.74-6.77 (dd, J₁=2.4 Hz, J₂=8.8 Hz), 6.63 (t, J=5.6 Hz, 1H), 5.35 (s, 1H), 4.32 (d, J=5.6 Hz, 2H), 4.00 (q, J=6.8 Hz, 2H), 3.86 (s, 3H), 1.29 (t, J=6.8 Hz, 3H).

Compound 529: ¹H NMR (CDCl₃, 300 MHz) δ 8.65 (d, J=5.1 Hz, 2H), 7.58 (s, 1H), 7.47 (s, 1H), 7.35-7.40 (m, 3H), 7.16-7.24 (m, 2H), 7.05 (s, 1H), 6.10 (t, J=4.5 Hz, 1H), 5.65 (s, 1H), 4.50 (d, J=4.5 Hz, 2H), 3.92 (s, 3H).

Compound 530: MS (ESI) m/z [M+H]+ 485.0. Hydrogen chloride salt: ¹H NMR (CDCl₃, 400 MHz) δ 7.91 (s, H), 7.58 (s, H), 7.54-7.50 (m, 2H), 7.48-7.43 (m, 2H), 7.33 (m, 1H), 7.26 (d, J.=8.4 Hz, 2H), 6.89 (d, J.=8.4 Hz, 2H), 6.51 (m, 1H), 5.27 (s, 1H), 4.28 (d, J.=6.0 Hz, 2H), 3.99 (q, J.=6.8 Hz, 2H), 3.88 (s, 3H), 1.31 (t, J.=7.2 Hz, 3H)

Compound 531: ¹H NMR (CDCl₃, 300 MHz) δ 9.11 (s, 1H), 8.62 (s, 2H), 7.46 (s, 1H), 7.35 (d, J=9.3 Hz, 3H), 7.24 (s, 1H), 7.20 (d, J=4.2 Hz, 1H), 7.03 (s, 1H), 5.53 (s, 1H), 4.80 (t, J=5.7 Hz, 1H), 4.34 (d, J=5.7 Hz, 2H), 3.88 (s, 3H). MS (ESI) m/z [M+H]+ 443.0.

Preparation of various salts of Compound 531: Compound 531 was dissolved in MeOH, followed by addition of aqueous salt solution. The mixture was stirred at rt for 1 h. The reaction mixture was concentrated to dryness. The residual aqueous solution was lyophilized to give the final corresponding salt of Compound 531.

Hydrogen chloride salt: ¹H NMR (DMSO-d₆, 400 MHz) δ 9.10 (s, 1H), 8.82 (s, 2H), 7.95 (s, 1H), 7.60 (s, 1H), 7.52 (d, J=9.2 Hz, 2H), 7.43 (d, J=8.4 Hz, 2H), 7.40 (s, 1H), 6.80 (t, J=5.6 Hz, 1H), 5.43 (s, 1H), 4.45 (d, J=5.6 Hz, 2H), 3.87 (s, 3H).

Citrate salt: ¹H NMR (DMSO-d₆, 400 MHz) δ 12.22 (brs, 1H), 9.08 (s, 1H), 9.08 (s, 1H), 8.80 (s, 1H), 7.91 (s, 1H), 7.58 (s, 1H), 7.49 (d, J=8.8 Hz, 2H), 7.41 (d, J=8.8 Hz, 2H), 7.31 (s, 1H), 6.56 (t, J=6 Hz, 1H), 5.28 (s, 1H), 4.41 (d, J=6 Hz, 2H), 3.86 (s, 3H), 2.74 (d, J=15.6 Hz, 2H), 2.65 (d, J=15.6 Hz, 2H).

p-TsOH salt: ¹H NMR (DMSO-d₆, 400 MHz) δ 9.11 (s, 1H), 8.82 (s, 2H), 7.97 (s, 1H), 7.61 (s, 1H), 7.45-7.56 (m, 7H), 7.10 (d, J=8 Hz, 2H), 6.94 (s, 1H), 5.48 (s, 1H), 4.47 (d, J=5.2 Hz, 2H), 3.87 (s, 3H), 2.27 (s, 3H).

Acetic acid salt: ¹H NMR (DMSO-d₆, 400 MHz) δ 9.18 (s, 1H), 8.70 (s, 2H), 7.53 (s, 1H), 7.44 (s, 1H), 7.42 (d, J=8.8 Hz, 2H), 7.29 (d, J=8.8 Hz, 2H), 7.10 (s, 1H), 4.87 (t, J=5.6 Hz, 1H), 4.41 (d, J=5.6 Hz, 2H), 3.95 (s, 3H), 2.06 (s, 1H).

Compounds 546-549 were prepared by reacting 4-bromo-1-(4-(trifluoromethoxy)phenyl)pyridin-2(1H)-one with the corresponding amines.

Compound 546: ¹H NMR (DMSO-d₆, 300 MHz) δ 8.83 (d, J=5.1 Hz, 2H), 7.49-7.44 (m, 6H), 7.37 (d, J=7.5 Hz, 1H), 6.01 (dd, J=1.8, 7.5 Hz, 1H), 5.17 (s, 1H), 4.49 (d, J=5.7 Hz, 2H).

Compound 547: ¹H NMR (DMSO-d₆, 300 MHz) δ 8.55 (d, J=4.2 Hz, 1H), 7.82 (d, J=7.5 Hz, 1H), 7.66 (d, J=5.1 Hz, 1H), 7.44-7.43 (m, 7H), 6.02 (t, J=7.5 Hz, 1H), 5.14 (s, 1H), 4.38 (d, J=5.7 Hz, 2H).

Compound 548: ¹H NMR (DMSO-d₆, 300 MHz) δ 9.12 (s, 1H), 8.80 (s, 2H), 7.45-7.37 (m, 6H), 6.90 (t, J=7.5 Hz, 1H), 5.30 (s, 1H), 4.39 (d, J=5.7 Hz, 2H).

Compound 549: ¹H NMR (DMSO-d₆, 300 MHz) δ 8.68-8.63 (m, 2H), 8.58 (s, 1H), 7.51-7.36 (m, 6H), 5.98 (d, J=7.5 Hz, 1H), 5.23 (s, 1H), 4.48 (d, J=5.1 Hz, 2H).

Compound 538 was prepared from Compound 403 in three steps: first, Compound 403 (3.6 g, 11 mmol) was stirred in HBr aqueous solution (40%, 30 mL) at 90° C. for 12 hrs. After standard workup, the resulting intermediate was redissolved in POCl₃ (20 mL) and refluxed for 2 h to afford the corresponding chloride (520 mg, 18% yield). Subsequently, acetone (10 mL), K₂CO₃ (342 mg, 2.48 mmol) and iodomethane (387 mg, 2.48 mmol) were added in portions. The mixture was stirred at 60° C. overnight. The mixture was cooled to rt and filtered. The filtrate was concentrated and purified by flash column chromatography (PE:EA=2:1) to give Compound 538 (252 mg, 43%). ¹H NMR (DMSO-d₆, 400 MHz) δ 7.96 (s, 1H), 7.69 (s, 1H), 7.64 (s, 1H), 7.18-7.16 (d, J=8 Hz, 1H), 6.92 (s, 1H), 6.85-6.83 (m, 1H), 6.76 (s, 1H), 4.05 (q, J=6.8 Hz, 2H), 3.82 (s, 3H), 2.01 (s, 3H), 1.33 (t, J=6.8 Hz, 3H). MS (ESI) m/z (M+H)+ 344.1.

Compound 543: Compound 538 (100 mg, 0.29 mmol) was dissolved in BnNH₂ (5 mL), the mixture was stirred at 160° C. for 3 h under N₂. After cooled to rt, the mixture was diluted with water and extracted with EtOAc. Following standard workup and purification, Compound 543 was obtained (53 mg, yield 44%). MS (ESI) m/z (M+H)+ 414.9.

Alternative way to prepare Compound 543: first, 5-bromo-4-chloro-2-methoxypyridine was reacted with 1-methyl-4-(4,4,5,5-tetramethyl-1,3,2-dioxaborolan-2-yl)-1H-pyrazole under the standard Suzuki-Coupling condition to form 4-chloro-2-methoxy-5-(1-methyl-1H-pyrazol-4-yl)pyridine; then it was subject to HBr hydrolysis, followed by a second Suzuki-Coupling with (4-ethoxy-2-methylphenyl)boronic acid, then reaction with BnNH₂ as described herein. Hydrogen chloride salt: ¹H NMR (DMSO-d₆, 400 MHz)¹H NMR (DMSO-d₆, 400 MHz) δ 8.01 (s, 1H), 7.64 (s, 1H), 7.46 (s, 1H), 7.41-7.35 (m, 5H), 7.28 (m, 1H), 7.18 (d, J=8.8 Hz, 1H), 6.93 (s, 1H), 6.83 (d, J=8.8 Hz, 1H), 5.87 (s, 1H), 4.45 (s, 2H), 4.04 (q, J=6.8 Hz, 2H), 3.89 (s, 3H), 2.00 (s, 3H), 1.32 (t, J=6.8 Hz, 3H).

Compounds 699-704 and 706 were prepared by reacting 4-chloro-1-(4-ethoxy-2-methylphenyl)-5-(1-methyl-1H-pyrazol-4-yl)pyridin-2(1H)-one with the corresponding amines following the similar procedure described above. The HCl salts thereof were also prepared following the similar procedure above.

Compound 699: ¹H NMR (DMSO-d₆, 400 MHz) δ 8.54 (d, J=4.0 Hz, 1H), 7.90 (s, 1H), 7.80 (dt, J=1.8, 7.7 Hz, 1H), 7.58 (s, 1H), 7.40 (d, J=7.8 Hz, 1H), 7.29 (dd, J₁=5.3, J₂=6.8 Hz, 1H), 7.08 (s, 1H), 7.04 (d, J=8.5 Hz, 1H), 6.86 (d, J=2.8 Hz, 1H), 6.78 (dd, J₁=2.9, J₂=8.7 Hz, 1H), 6.49 (t, J=5.5 Hz, 1H), 5.75 (s, 1H), 5.22 (s, 1H), 4.42 (d, J=5.5 Hz, 2H), 4.03

(q, J=6.9 Hz, 2H), 3.87 (s, 3H), 2.00 (s, 3H), 1.32 (t, J=7.0 Hz, 3H). MS (ESI) m/z (M+H)⁺ 416.2.

HCl salt of Compound 699: ¹H NMR (DMSO-d₆, 400 MHz) δ 8.74 (d, J=4.5 Hz, 1H), 8.23 (t, J=7.2 Hz, 1H), 7.99 (s, 1H), 7.77 (d, J=8.0 Hz, 1H), 7.71-7.65 (m, 1H), 7.64 (d, J=0.8 Hz, 1H), 7.25 (s, 1H), 7.08 (d, J=8.5 Hz, 1H), 6.88 (d, J=2.8 Hz, 1H), 6.85-6.77 (m, 2H), 5.46 (s, 1H), 4.65 (d, J=4.5 Hz, 2H), 4.07-4.01 (m, 2H), 3.88 (s, 3H), 2.00 (s, 3H), 1.32 (t, J=6.9 Hz, 3H). MS (ESI) m/z (M+H)⁺ 416.2.

Compound 700: ¹H NMR (DMSO-d₆, 400 MHz) δ 8.56-8.50 (m, 2H), 7.91 (s, 1H), 7.58 (s, 1H), 7.37 (d, J=5.8 Hz, 2H), 7.08-7.01 (m, 2H), 6.85 (d, J=2.5 Hz, 1H), 6.77 (dd, J₁=2.8, J₂=8.5 Hz, 1H), 6.46 (t, J=6.1 Hz, 1H), 5.75 (s, 1H), 5.09 (s, 1H), 4.38 (d, J=6.0 Hz, 2H), 4.02 (q, J=6.9 Hz, 2H), 3.87 (s, 3H), 1.99 (s, 3H), 1.32 (t, J=6.9 Hz, 3H). MS (ESI) m/z (M+H)⁺416.2.

HCl salt of Compound 700: ¹H NMR (DMSO-d₆, 400 MHz) δ 8.85 (d, J=6.5 Hz, 2H), 7.98 (d, J=6.3 Hz, 2H), 7.96 (s, 1H), 7.63 (s, 1H), 7.17 (s, 1H), 7.04 (d, J=8.8 Hz, 1H), 6.86 (d, J=2.8 Hz, 1H), 6.78 (dd, J₁=2.8, J₂=8.5 Hz, 1H), 6.73 (t, J=6.1 Hz, 1H), 5.20 (s, 1H), 4.66 (d, J=6.0 Hz, 2H), 4.03 (d, J=7.0 Hz, 2H), 3.88 (s, 3H), 2.00-1.98 (m, 3H), 1.32 (t, J=6.9 Hz, 3H). MS (ESI) m/z (M+H)⁺ 416.2.

Compound 701: ¹H NMR (DMSO-d₆, 400 MHz) δ 8.59 (d, J=1.8 Hz, 1H), 8.47 (dd, J₁=1.6, J₂=4.9 Hz, 1H), 7.89 (s, 1H), 7.77 (d, J=7.8 Hz, 1H), 7.56 (s, 1H), 7.38 (dd, J₁=4.8, J₂=7.8 Hz, 1H), 7.06-7.01 (m, 2H), 6.85 (d, J=2.5 Hz, 1H), 6.77 (dd, J₁=2.8, J₂=8.5 Hz, 1H), 6.42 (t, J=6.1 Hz, 1H), 5.75 (s, 1H), 5.20 (s, 1H), 4.38 (d, J=6.0 Hz, 2H), 4.02 (q, J=7.0 Hz, 2H), 3.86 (s, 3H), 1.99 (s, 3H), 1.32 (t, J=7.0 Hz, 3H). MS (ESI) m/z (M+H)⁺ 416.2.

HCl salt of Compound 701: ¹H NMR (DMSO-d₆, 400 MHz) δ 8.90 (s, 1H), 8.78 (d, J=5.3 Hz, 1H), 8.46 (d, J=8.0 Hz, 1H), 8.00-7.91 (m, 2H), 7.61 (s, 1H), 7.17 (s, 1H), 7.05 (d, J=8.5 Hz, 1H), 6.87 (d, J=2.5 Hz, 1H), 6.78 (dd, J₁=2.5, J₂=8.5 Hz, 1H), 6.74 (t, J=6.0 Hz, 1H), 5.39 (s, 1H), 4.56 (d, J=5.8 Hz, 2H), 4.06-4.01 (m, 2H), 3.87 (s, 3H), 1.99 (s, 3H), 1.32 (t, J=6.9 Hz, 3H). MS (ESI) m/z (M+H)⁺ 416.2.

Compound 702: ¹H NMR (DMSO-d₆, 400 MHz) δ 7.87 (s., 1H), 7.55 (s, 1H), 7.45-7.40 (m, 1H), 7.30-7.20 (m, 1H), 7.10-7.02 (m, 3H), 6.85 (d, J=2.4 Hz, 1H), 6.79-6.76 (m, 1H), 6.35-6.31 (m, 1H), 5.18 (s, 1H), 4.35 (d, J=5.6 Hz, 2H), 4.02 (q, J=7.2 Hz, 2H), 3.86 (s, 3H), 2.00 (s, 3H), 1.32 (t, J=7.2 Hz, 3H).

HCl salt of Compound 702: ¹H NMR (DMSO-d₆, 400 MHz) δ 7.91 (s, 1H), 7.58 (s, 1H), 7.47-7.43 (m, 1H), 7.30-7.24 (m, 2H), 7.10 (d, J=8.4 Hz, 2H), 6.88 (s., 1H), 6.81 (d, J=8.4 Hz, 1H), 6.73 (s, 1H), 5.42 (s, 1H), 4.39 (d, J=4.8 Hz, 2H), 4.03 (q, J=6.8 Hz, 2H), 3.87 (s, 3H), 2.00 (s, 3H), 1.32 (t, J=6.8 Hz, 3H).

Compound 703: ¹H NMR (DMSO-d₆, 400 MHz) δ 7.92 (s., 1H), 7.57 (s, 1H), 7.12-7.03 (m, 5H), 6.85 (d, J=2.4 Hz, 1H), 6.78 (d, J=2.4 Hz, 1H), 6.46 (t, J=6.0 Hz, 1H), 5.15 (s, 1H), 4.36 (d, J=6.0 Hz, 2H), 4.02 (q, J=7.2 Hz, 2H), 3.87 (s, 3H), 2.00 (s, 3H), 1.32 (t, J=7.2 Hz, 3H).

HCl salt of Compound 703: ¹H NMR (DMSO-d₆, 400 MHz) δ 7.98 (s, 1H), 7.61 (s, 1H), 7.26 (s, 1H), 7.13-7.10 (m, 4H), 6.88 (brs, 2H), 6.80 (d, J=8.4 Hz, 1H), 5.42 (s, 1H), 4.41 (d, J=4.8 Hz, 2H), 4.03 (q, J=6.8 Hz, 2H), 3.88 (s, 3H), 2.0 (s, 3H), 1.32 (t, J=6.8 Hz, 3H).

Compound 704: ¹H NMR (DMSO-d₆, 400 MHz) δ 7.91 (s, 1H), 7.83 (d, J=8.0 Hz, 2H), 7.61-7.52 (m, 3H), 7.06 (s, 1H), 7.03 (d, J=8.8 Hz, 1H), 6.85 (d, J=2.8 Hz, 1H), 6.78 (dd, J=2.8, 8.4 Hz, 1H), 6.50 (t, J=6.0 Hz, 1H), 5.76 (s, 1H), 5.10 (s, 1H), 4.44 (d, J=6.0 Hz, 2H), 4.03 (q, J=7.2 Hz, 2H), 3.87 (s, 3H), 1.99 (s, 3H), 1.32 (t, J=7.2 Hz, 3H).

HCl salt of Compound 704: ¹H NMR (DMSO-d₆, 400 MHz) δ 7.95 (s, 1H), 7.83 (d, J=8.0 Hz, 2H), 7.61 (s, 1H), 7.56 (d, J=8.0 Hz, 2H), 7.27 (s, 1H), 7.09 (d, J=8.8 Hz, 1H), 6.99 (t, J=5.8 Hz, 1H), 6.87 (d, J=2.8 Hz, 1H), 6.79 (dd, J=2.8, 8.8 Hz, 1H), 5.41 (s, 1H), 4.48 (d, J=5.6 Hz, 2H), 4.02 (q, J=7.2 Hz, 2H), 3.87 (s, 3H), 1.98 (s, 3H), 1.31 (t, J=7.2 Hz, 3H).

Compound 705: ¹H NMR (DMSO-d₆, 400 MHz) δ 7.84 (s, 1H), 7.58 (s, 1H), 7.33-7.21 (m, 4H), 7.16 (d, J=7.2 Hz, 2H), 7.16 (d, J=7.2 Hz, 1H), 7.07 (s, 1H), 6.87 (d, J=2.8 Hz, 1H), 5.69 (s, 1H), 4.11 (d, J=8.8 Hz, 2H), 4.02 (q, J=7.2 Hz, 2H), 3.75 (s, 3H), 2.52 (s, 3H), 2.00 (s, 3H), 1.31 (t, J=7.2 Hz, 3H).

HCl salt of Compound 705: ¹H NMR (DMSO-d₆, 400 MHz) δ 7.87 (s, 1H), 7.60 (s, 1H), 7.37-7.24 (m, 4H), 7.19 (d, J=7.0 Hz, 2H), 7.14 (d, J=8.8 Hz, 1H), 6.91 (d, J=2.5 Hz, 1H), 6.83 (dd, J=2.8, 8.5 Hz, 1H), 5.83 (s, 1H), 4.26-4.13 (m, 2H), 4.05 (q, J=7.0 Hz, 2H), 3.78 (s, 3H), 2.58 (s, 3H), 2.03 (s, 3H), 1.34 (t, J=7.0 Hz, 3H).

Compound 706: ¹H NMR (DMSO-d₆, 400 MHz) δ 7.86 (s, 1H), 7.54 (s, 1H), 7.41 (s, 1H), 7.12 (d, J=8.4 Hz, 1H), 7.05 (d, J=6.8 Hz, 1H), 6.86 (d, J=2.8 Hz, 1H), 6.80-6.72 (m, 3H), 5.97 (t, J=5.6 Hz, 1H), 5.15 (s, 1H), 4.22 (d, J=5.2 Hz, 2H), 4.06-3.98 (m, 4H), 3.85 (s, 3H), 2.29 (s, 3H), 2.01 (s, 3H), 1.35-1.29 (m, 6H).

HCl salt of Compound 706: ¹H NMR (DMSO-d₆, 400 MHz) δ 7.97 (s, 1H), 7.62 (s, 1H), 7.41 (s, 1H), 7.16 (dd, J=8.5, 17.3 Hz, 2H), 6.98-6.90 (m, 2H), 6.84 (dd, J=2.8, 8.5 Hz, 1H), 6.80 (s, 1H), 6.74 (dd, J=2.6, 8.4 Hz, 1H), 5.66 (br. s., 1H), 4.31 (d, J=5.3 Hz, 2H), 4.10-3.91 (m, 4H), 3.88 (s, 3H), 2.32 (s, 3H), 2.02 (s, 3H), 1.35-1.29 (m, 6H).

Compound 707: ¹H NMR (DMSO-d₆, 400 MHz) δ 7.85 (s, 1H), 7.53 (s, 1H), 7.26 (d, J=8.4 Hz, 2H), 7.01 (t, J=2.4 Hz, 2H), 6.90 (d, J=8.8 Hz, 2H), 6.83 (d, J=2.8 Hz, 1H), 6.76 (t, J=5.6 Hz, 1H), 5.18 (s, 1H), 4.24 (d, J=5.6 Hz, 2H), 4.06-4.00 (m, 4H), 3.84 (s, 3H), 3.63 (t, J=4.8 Hz, 2H), 3.29 (s, 3H), 1.97 (s, 3H), 1.31 (t, J=6.8 Hz, 3H).

HCl salt of Compound 707: ¹H NMR (DMSO-d₆, 400 MHz) δ 7.97 (s, 1H), 7.61 (s, 1H), 7.36 (d, J=2.5 Hz, 1H), 7.31 (d, J=8.5 Hz, 2H), 7.18-7.06 (m, 2H), 6.96-6.89 (m, 3H), 6.84-6.81 (m, 1H), 5.71 (brs, 1H), 4.34 (brs, 2H), 4.09-4.02 (m, 4H), 3.89 (s, 3H), 3.66-3.64 (m, 2H), 3.30 (s, 3H), 2.00 (s, 3H), 1.33 (t, J=7.0 Hz, 3H).

Compound 708 was prepared by HBr hydrolysis of 2-methoxy-4,5-bis(1-methyl-1H-pyrazol-4-yl)pyridine, followed by standard copper acetate/pyridine/pyridine-N-oxide catalyzed reaction in DMF at 90° C. to afford the final product. ¹H NMR (DMSO-d₆, 400 MHz) δ 7.71 (s, 1H), 7.65-7.63 (m, 3H), 7.56 (s, 1H), 7.52 (d, J=8.0 Hz, 2H), 7.33 (s, 1H), 7.28 (s, 1H), 6.60 (s, 1H), 3.82 (s, 3H), 3.81 (s, 3H).

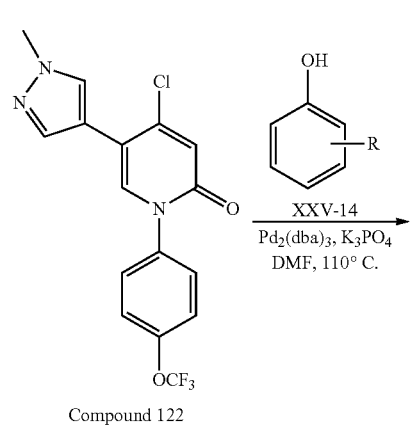

Compound 122

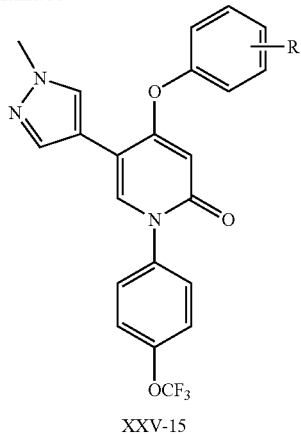

XXV-15

Compound 122 (1 eq.), phenol (XXV-14, 2 eq.) and K$_3$PO$_4$ (3 eq.) were added into DMF. The solution was degassed by nitrogen for three times and then Pd$_2$(dba)$_3$ (0.2 eq.) was added. The reaction mixture was stirred at 110° C. for 14 hrs under N$_2$. After being cooled to rt, the mixture was diluted with EA and filtered; the filtrate was washed with brine. The separated organic phase was dried over Na$_2$SO$_4$, concentrated under reduced pressure. The residue was purified by column chromatography (PE/EA=1/1) to give the final product.

Compounds 408-410 and 412-414 were prepared following the general scheme as illustrated above.

Compound 408: $^1$H NMR (CDCl$_3$, 400 MHz) δ 7.74 (s, 1H), 7.68 (s, 1H), 7.49-7.45 (m, 3H), 7.37-7.33 (m, 2H), 7.30-7.22 (m, 4H), 5.79 (s, 1H), 3.94 (s, 3H). MS (ESI) m/z (M+H)$^+$ 446.1.

Compound 409: $^1$H NMR (CDCl$_3$, 400 MHz) δ 7.70 (s, 1H), 7.67 (s, 1H), 7.50 (s, 1H), 7.47-7.42 (m, 3H), 7.37-7.33 (m, 2H), 7.05-7.00 (m, 1H), 6.98-6.96 (m, 1H), 6.94-6.90 (m, 1H), 5.84 (s, 1H), 3.94 (s, 3H). MS (ESI) m/z (M+H)$^+$ 445.9.

Compound 410: $^1$H NMR (CDCl$_3$, 400 MHz) δ 7.72 (s, 1H), 7.68 (s, 1H), 7.49-7.44 (m, 3H), 7.36-7.34 (m, 2H), 7.17-7.14 (m, 4H), 5.76 (s, 1H), 3.94 (s, 3H). MS (ESI) m/z (M+H)$^+$ 445.9.

Compound 412: $^1$H NMR (CDCl$_3$, 400 MHz) δ 7.70 (s, 1H), 7.67 (s, 1H), 7.49-7.42 (m, 5H), 7.36-7.34 (m, 2H), 7.12-7.10 (m, 2H), 5.78 (s, 1H), 3.94 (s, 3H). MS (ESI) m/z (M+H)$^+$ 462.1.

Compound 413: $^1$H NMR (CDCl$_3$, 400 MHz) δ 7.70 (s, 1H), 7.67 (s, 1H), 7.50 (s, 1H), 7.47-7.35 (m, 5H), 7.32-7.29 (m, 1H), 7.20-7.19 (m, 1H), 7.10-7.06 (m, 1H), 5.82 (s, 1H), 3.94 (s, 3H). MS (ESI) m/z (M+H)$^+$ 462.1.

Compound 414: $^1$H NMR (CDCl$_3$, 400 MHz) δ 7.83 (s, 1H), 7.79 (s, 1H), 7.55-7.45 (m, 4H), 7.40-7.34 (m, 3H), 7.31-7.29 (m, 1H), 7.24-7.21 (m, 1H), 5.74 (s, 1H), 3.97 (s, 3H). MS (ESI) m/z (M+H)$^+$ 462.1.

Compounds 533 and 535 were prepared by reacting Compound 122 with the corresponding substituted phenol in DMF and KOH at 130° C. overnight.

Compound 533: $^1$HNMR (CDCl$_3$, 400 MHz) δ 7.75 (s, 1H), 7.68 (s, 1H), 7.48-7.43 (m, 3H), 7.34 (d, J=8.4 Hz, 2H), 7.06 (d, J=9.2 Hz, 2H), 6.69 (d, J=9.2 Hz, 2H), 5.78 (s, 1H), 4.15 (t, J=4.8 Hz, 1H), 3.94 (s, 3H), 3.78 (t, J=4.8 Hz, 2H), 3.48 (s, 3H).

Compound 535: $^1$H NMR (DMSO-d$_6$, 400 MHz) δ 8.05-8.01 (m, 5H), 7.84 (s, 1H), 7.61 (d, J=8.8 Hz, 2H), 7.53 (d, J=8.4 Hz, 2H), 7.45 (s, 1H), 7.37 (s, 1H), 7.35 (s, 1H), 5.46 (s, 1H), 3.84 (s, 3H). MS (ESI) m/z (M+H)$^+$ 457.2.

Preparation of Compound 664: To a solution of Compound 122 (210 mg, 0.569 mmol) in dioxane (20 mL) were added pyridazin-3-ylmethanamine hydrochloride (165 mg, 1.14 mmol), NaOtBu (218 mg, 2.28 mmol), Xphos (27.2 mg, 0.057 mmol), precatalyst 13 (44.8 mg, 0.057 mmol). The mixture was degassed under in vacuum and purged with N$_2$ three times. The reaction mixture was stirred at 100° C. for 14 h. The mixture was cooled to rt. The mixture was diluted with water and extracted with EA. The combined organic layer was dried over Na$_2$SO$_4$, concentrated in vacuum. The residue was purified by column chromatography on silica gel eluted with DCM:MeOH (50:1-10:1) to give Compound 664 (50 mg, 20% yield) as a pale yellow solid. $^1$H NMR (DMSO-d$_6$, 400 MHz) δ 9.15 (s, 1H), 7.91 (s, 1H), 7.67 (s, 2H), 7.60 (s, 1H), 7.49 (d, J=8.8 Hz, 2H), 7.42 (d, J=8.8 Hz, 2H), 7.33 (s, 1H), 6.67 (t, 1H), 5.25 (s, 1H), 4.62 (t, J=5.6 Hz, 1H), 3.87 (s, 3H).

Compound 696 was prepared by reacting 4-chloro-1-(4-ethoxy-2-methylphenyl)-5-(1-methyl-1H-pyrazol-4-yl)pyridin-2(1H)-one with 2-isopropoxyethanol in the presence of NaH in DMF solution at rt for 12 hrs to afford the final product as a yellow solid. $^1$H NMR (CDCl$_3$, 400 MHz) δ 7.78 (s, 1H), 7.66 (s, 1H), 7.32 (s, 1H), 7.15-7.12 (m, 1H), 6.89-6.81 (m, 2H), 6.08 (s, 1H), 4.22-4.18 (m, 2H), 4.10-4.05 (q, J=6.9 Hz, 2H), 3.93 (s, 3H), 3.87-3.85 (dd, J=3.6, 5.6 Hz, 2H), 3.77-3.74 (td, J=6.1, 12.2 Hz, 1H), 2.16 (s, 3H), 1.45 (t, J=6.9 Hz, 3H), 1.27 (d, J=6.3 Hz, 6H). MS (ESI) m/z (M+H$^+$) 412.3.

Compound 697 was prepared by reacting 4-chloro-1-(4-ethoxy-2-methylphenyl)-5-(1-methyl-1H-pyrazol-4-yl)pyridin-2(1H)-one with 2-(2-methoxyethoxy)ethanol in the presence of NaH in DMF solution at rt for 12 hrs to afford the final product as a light yellow solid. $^1$H NMR (CDCl$_3$, 400 MHz) δ 7.79 (s, 1H), 7.64 (s, 1H), 7.31 (s, 1H), 7.13 (d, J=8.5 Hz, 1H), 6.89-6.81 (m, 2H), 6.07 (s, 1H), 4.25-4.20 (m, 2H), 4.11-4.03 (q, J=6.9 Hz, 2H), 3.96-3.90 (m, 5H), 3.78-3.72 (m, 2H), 3.66-3.60 (m, 2H), 3.45-3.40 (m, 3H), 2.16 (s, 3H), 1.45 (t, J=6.9 Hz, 3H). MS (ESI) m/z (M+H$^+$) 428.3.

Compound 698 was prepared by reacting 4-chloro-1-(4-ethoxy-2-methylphenyl)-5-(1-methyl-1H-pyrazol-4-yl)pyridin-2(1H)-one with tetrahydro-2H-pyran-4-ol in the presence of NaH in DMF solution at rt for 16 hrs to afford the final product as a light yellow solid. $^1$H NMR (CDCl$_3$, 400 MHz) δ 7.63 (s, 1H), 7.60 (s, 1H), 7.31 (s, 1H), 7.13 (d, J=8.5 Hz, 1H), 6.89-6.81 (m, 2H), 6.10 (s, 1H), 4.64 (t t, J=3.9, 8.0 Hz, 1H), 4.07 (q, J=6.9 Hz, 2H), 4.04-3.96 (m, 2H), 3.95 (s, 3H), 3.64 (dt, J=1.8, 8.8 Hz, 2H), 2.21-2.12 (m, 5H), 1.91 (ttd, J=4.0, 8.4, 12.8 Hz, 2H), 1.45 (t, J=7.0 Hz, 3H). MS (ESI) m/z (M+H$^+$) 410.2.

Example 11-D

Synthesis of Compound 154 (Scheme XXVI)

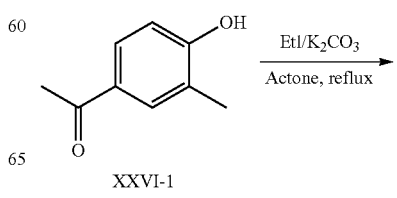

XXVI-1

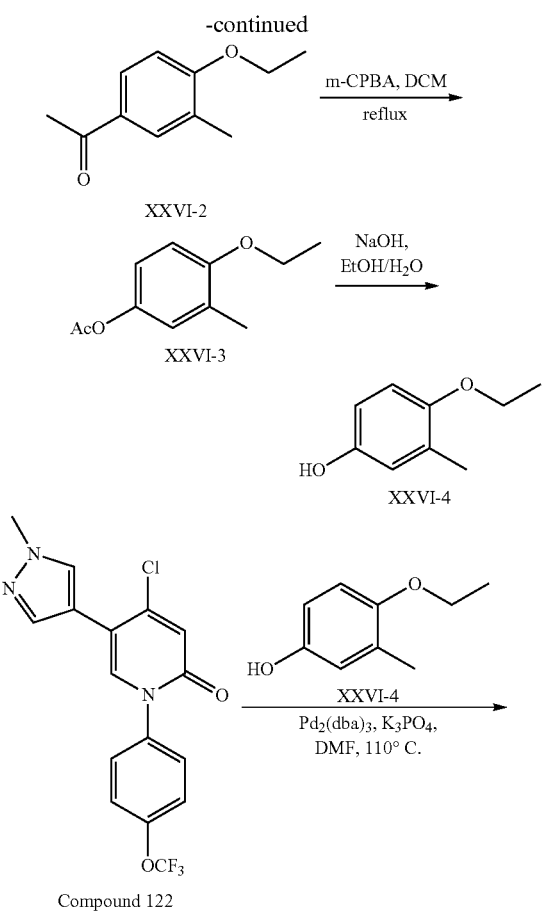

Compound 122

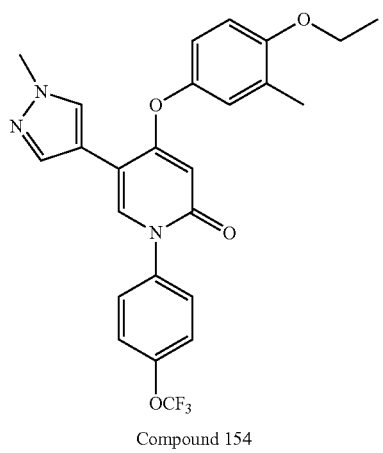

Compound 154

XXVI-1 (1.0 g, 6.67 mmol) and $K_2CO_3$ (1.38 g, 10 mmol) were added into in acetone (25 mL). And then EtI (1.14 g, 7.33 mmol) was added. The mixture was heated to reflux for 24 hrs. The mixture was cooled to rt and removed the solvent. Then the crude product was diluted with EA (100 mL), washed with water and brine, dried over $Na_2SO_4$, concentrated in vacuo to give XXVI-2 (870 mg, 73% yield), which was used directly without further purification.

A mixture of XXVI-2 (1.2 g, 6.74 mmol) and m-CPBA (1.5 g, 8.76 mmol) in DCM (30 mL) was refluxed for 48 hrs. The reaction mixture was cooled to rt, diluted with DCM (100 mL), washed with saturated aq.$Na_2S_2O_3$ and aq. $K_2CO_3$, dried over $Na_2SO_4$. Concentrated in vacuo to give XXVI-3 (1.0 g, 77% crude yield), which was used directly without further purification.

XXVI-3 (1 g, 5 mmol) was dissolved in ethanol (10 mL), then treated with a solution of NaOH (2.6 g) in $H_2O$ (3 mL) slowly. The resultant mixture was stirred at rt for 4 hrs. The resultant mixture was concentrated and residue was diluted with water (10 mL). The mixture was made acidic with diluted HCl (aq.) and extracted with EA (50 mL×3). The organic phases were combined, washed with brine, dried over $Na_2SO_4$, concentrated under reduced pressure to give the crude product. The residue was purification by flash chromatography on silica gel (PE/EA=5:1→2:1) to give XXVI-4 (800 mg, ~100% yield).

Compound 154 was prepared by following the similar procedure described in synthesis of Compound 153 (101 mg, 20% yield). $^1$H NMR (CDCl$_3$, 400 MHz) δ 7.76 (s, 1H), 7.68 (s, 1H), 7.47-7.44 (m, 3H), 7.36-7.34 (m, 2H), 6.93-6.84 (m, 3H), 5.80 (s, 1H), 4.05 (q, J=7.2 Hz, 2H), 3.93 (s, 3H), 2.24 (s, 3H), 1.46 (t, J=7.2 Hz, 3H). MS (ESI) m/z (M+H)$^+$ 486.

Compound 155 was prepared by following the similar procedure for obtaining Compound 154 using 3-chloro-4-ethoxyphenol in place of XXVI-4. $^1$H NMR (CDCl$_3$, 400 MHz) δ 7.71 (s, 1H), 7.67 (s, 1H), 7.48-7.44 (m, 3H), 7.36-7.34 (m, 2H), 7.21 (s, 1H), 7.03-6.96 (m, 2H), 5.80 (s, 1H), 4.14 (q, J=7.2 Hz, 2H), 3.94 (s, 3H), 1.51 (t, J=7.2 Hz, 3H). MS (ESI) m/z (M+H)$^+$505.9.

Compound 157 was prepared by following the similar procedure for obtaining Compound 154 using 2-ethoxy-5-hydroxybenzonitrile in place of XXVI-4. $^1$H NMR (CDCl$_3$, 400 MHz) δ 7.67 (d, J=7.6 Hz, 2H), 7.50-7.44 (m, 3H), 7.39-7.31 (m, 4H), 7.03 (d, J=9.2 Hz, 1H), 5.73 (s, 1H), 4.19 (q, J=6.8 Hz, 2H), 3.94 (s, 3H), 1.52 (t, J=6.8 Hz, 3H). MS (ESI) m/z (M+H)$^+$497.

Compound 162 was prepared following the similar procedure for obtaining Compound 85 using 1-methyl-4-(4,4,5,5-tetramethyl-1,3,2-dioxaborolan-2-yl)-1H-pyrazole in place of XXIII-4 and using (4-ethoxy-2-methylphenyl)boronic acid in place of XXIII-7. $^1$H NMR (DMSO-d$_6$, 400 MHz) δ 7.93 (s, 1H), 7.71 (s, 1H), 7.64 (s, 1H), 7.10 (d, J=8.0 Hz, 1H), 6.90 (d, J=2.8 Hz, 1H), 6.84-6.81 (m, 1H), 5.95 (s, 1H), 4.04 (q, J=7.2 Hz, 2H), 3.86 (s, 3H), 3.79 (s, 3H), 2.00 (s, 3H), 1.33 (t, J=7.2 Hz, 3H). MS (ESI) m/z (M+H)$^+$ 340.1.

Compound 532 was prepared following the similar procedure for obtaining Compound 154 using 4-chloro-1-(4-fluorophenyl)-5-(1-methyl-1H-pyrazol-4-yl)pyridin-2(1H)-one in place of Compound 122 and using phenol in place of XXIV-4. $^1$H NMR (CDCl$_3$, 400 MHz) δ 7.75 (s, 1H), 7.68 (s, 1H), 7.49-7.44 (m, 3H), 7.39-7.36 (m, 2H), 7.32-7.20 (m, 1H), 7.18-7.14 (m, 4H), 5.79 (s, 1H), 3.93 (s, 3H). MS (ESI) m/z [M+H]$^+$ 362.1

Compound 534 was prepared following the similar procedure for the synthesis of Compound 532. $^1$H NMR (Methanol-d$_4$, 400 MHz) δ 8.02 (s, 1H), 7.93 (s, 1H), 7.85 (s, 1H), 7.58-7.54 (m, 4H), 7.45 (d, J=8.8 Hz, 2H), 7.41-7.37 (m, 1H), 7.27 (d, J=8.8 Hz, 2H), 5.67 (s, 1H), 3.93 (s, 3H). MS (ESI) m/z (M+H)$^+$ 378.1.

Example 11-E

Synthesis of Compound 542

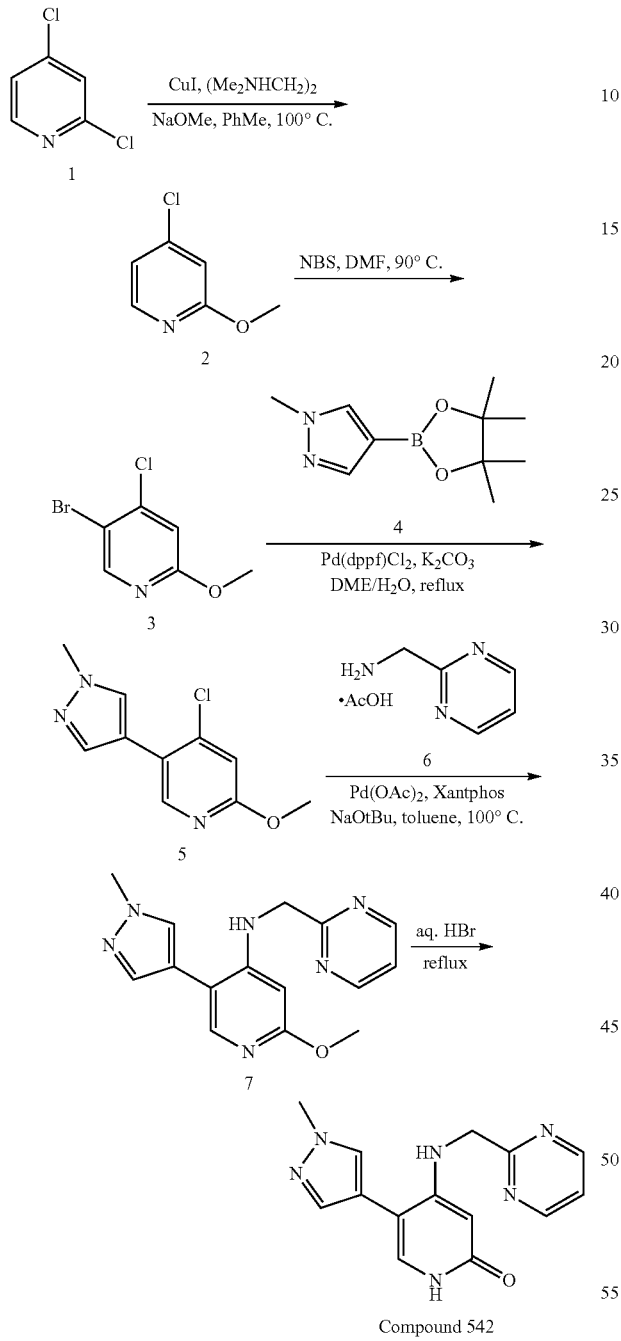

Compound 542

To a mixture of compound 1 (68 g, 0.465 mol) in toluene (250 mL) was added CuI (17.9 g, 0.093 mol), (Me$_2$NHCH$_2$)$_2$ (36.8 g, 0.418 mol) and NaOMe (50.2 g 0.93 mol). The mixture was purged with nitrogen for three times and then heated at 100° C. for 8 hours. The mixture was concentrated to remove toluene, diluted with H$_2$O and extracted with EtOAc. After standard workup, the crude product was chromatographed on silica gel (PE) to give compound 2 (39.5 g, 60% yield).

To a solution of compound 2 (28.7 g. 0.2 mol) in DMF (50 mL) was added NBS (35.5 g, 0.2 mol). The mixture was heated at 90° C. for 8 hours. The crude compound 3 was collected by filtration. (22 g, 50% yield).

To a stirred mixture of compound 3 (4 g, 18.1 mmol), compound 4 (4.52 g 21.72 mmol), and K$_2$CO$_3$ (5 g, 36.2 mmol) in DME/H$_2$O (48 mL, v/v=5/1) was added Pd(dppf)Cl$_2$ (668 mg, 0.91 mmol) under N$_2$ protection. The reaction mixture was degassed with nitrogen again and refluxed overnight. The mixture was concentrated, diluted with H$_2$O and extracted with EtOAc. The combined organic layer was washed with brine, dried over anhydrous Na$_2$SO$_4$, and concentrated in vacuo. The residue was purified by column chromatography (PE/EA=2/1) to give compound 5 (2.8 g, 69% yield) as a pale yellow solid.

To a solution of compound 5 (500 mg, 2.24 mmol) in toluene (20 mL) were added compound 6 (757.1 mg, 4.48 mmol), NaOtBu (860.2 mg, 8.96 mmol), Xantphos (129.5 mg, 0.224 mmol), Pd(OAc)$_2$ (50.2 mg, 0.224 mmol). The mixture was degassed under in vacuum and purged with N$_2$ three times. The reaction mixture was stirred at 100° C. for 14 h. The mixture was cooled to rt, diluted with water and extracted with EA. The combined organic layer was dried over Na$_2$SO$_4$, concentrated in vacuum. The residue was purified by silica gel chromatography eluted with DCM: MeOH (50:1-10:1) to afford compound 7 (300 mg, 45%) as a pale yellow solid.

Compound 7 (300 mg, 1.01 mmol) was dissolved in aq. HBr (40%, 15 mL), the mixture was heated to reflux overnight. After cooling to rt, the mixture was adjusted with aq. NaOH (1 M) to pH=4-5, the resulting precipitate was collected by filtration and dried in vacuo to give Compound 542 (40 mg, 14% yield). $^1$H NMR (DMSO-d$_6$, 400 MHz) δ 10.60 (s, 1H), 8.81 (d, J=4.8 Hz, 2H), 7.85 (s, 1H), 7.55 (s, 1H), 7.43 (t, J=4.8 Hz, 2H), 6.99 (s, 1H), 6.33 (t, J=5.2 Hz, 1H), 5.16 (s, 1H), 4.47 (d, J=5.2 Hz, 1H), 3.89 (s, 3H).

Compound 544 was prepared following the similar procedure for the synthesis of Compound 542 using pyridin-2-ylmethanamine in place of compound 6. $^1$H NMR (DMSO-d$_6$, 400 MHz) δ 10.56 (s, 1H), 8.52-8.51 (m, 1H), 7.85 (s, 1H), 7.90-7.56 (m, 1H), 7.53 (s, 1H), 7.33 (d, J=8.0 Hz, 1H), 7.29-7.26 (m, 1H), 6.95 (s, 1H), 6.33 (t, J=5.6 Hz, 1H), 5.05 (s, 1H), 4.37-4.35 (d, J=5.6 Hz, 2H), 3.88 (s, 3H).

Example 11-E

Synthesis of Compound 536

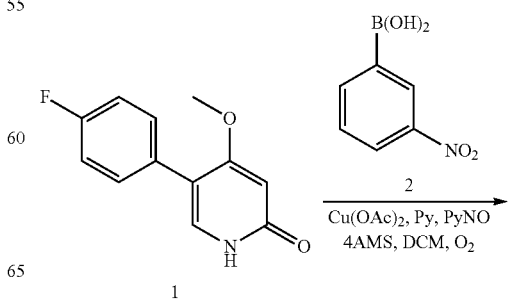

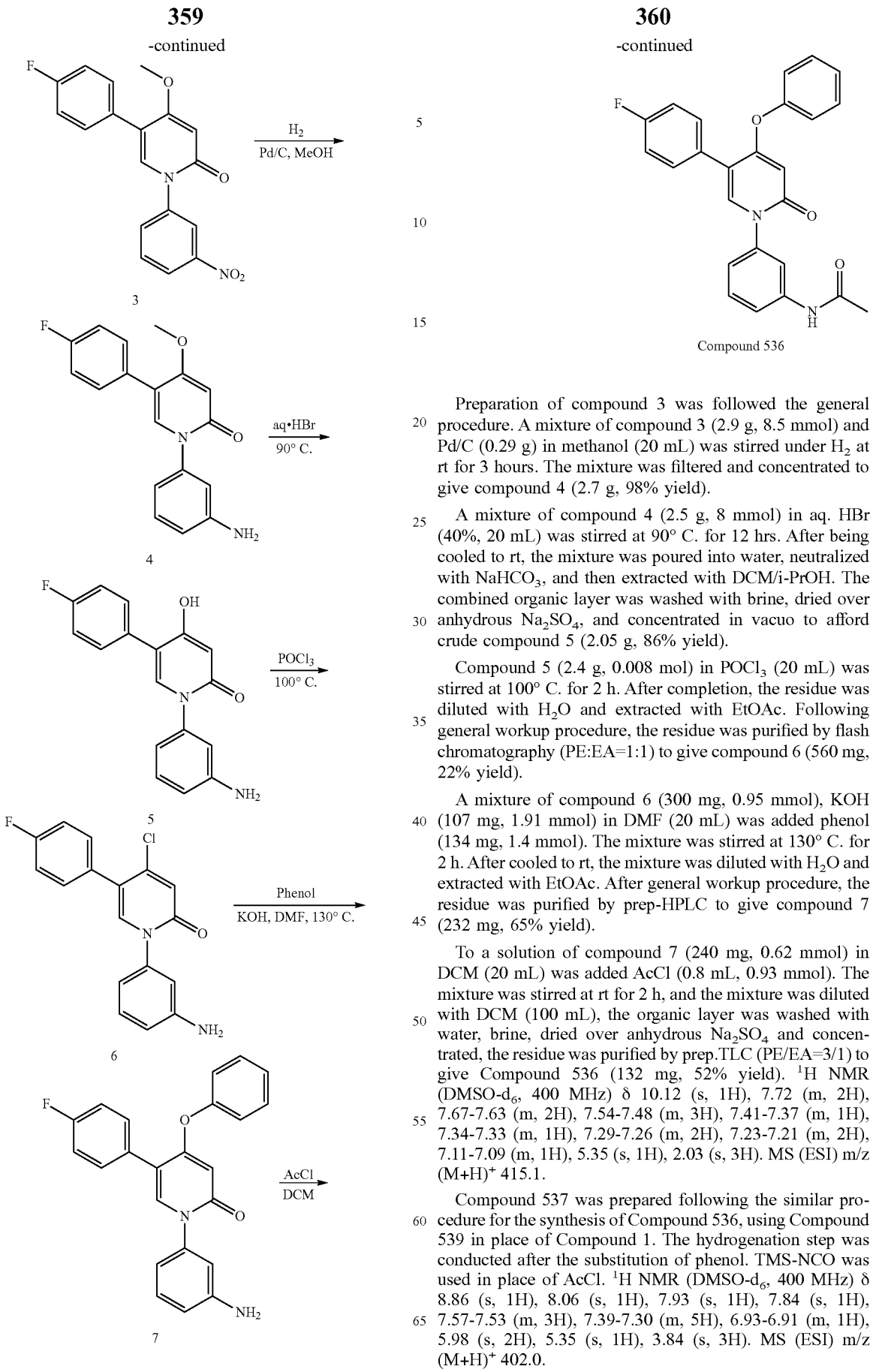

Compound 536

Preparation of compound 3 was followed the general procedure. A mixture of compound 3 (2.9 g, 8.5 mmol) and Pd/C (0.29 g) in methanol (20 mL) was stirred under $H_2$ at rt for 3 hours. The mixture was filtered and concentrated to give compound 4 (2.7 g, 98% yield).

A mixture of compound 4 (2.5 g, 8 mmol) in aq. HBr (40%, 20 mL) was stirred at 90° C. for 12 hrs. After being cooled to rt, the mixture was poured into water, neutralized with $NaHCO_3$, and then extracted with DCM/i-PrOH. The combined organic layer was washed with brine, dried over anhydrous $Na_2SO_4$, and concentrated in vacuo to afford crude compound 5 (2.05 g, 86% yield).

Compound 5 (2.4 g, 0.008 mol) in $POCl_3$ (20 mL) was stirred at 100° C. for 2 h. After completion, the residue was diluted with $H_2O$ and extracted with EtOAc. Following general workup procedure, the residue was purified by flash chromatography (PE:EA=1:1) to give compound 6 (560 mg, 22% yield).

A mixture of compound 6 (300 mg, 0.95 mmol), KOH (107 mg, 1.91 mmol) in DMF (20 mL) was added phenol (134 mg, 1.4 mmol). The mixture was stirred at 130° C. for 2 h. After cooled to rt, the mixture was diluted with $H_2O$ and extracted with EtOAc. After general workup procedure, the residue was purified by prep-HPLC to give compound 7 (232 mg, 65% yield).

To a solution of compound 7 (240 mg, 0.62 mmol) in DCM (20 mL) was added AcCl (0.8 mL, 0.93 mmol). The mixture was stirred at rt for 2 h, and the mixture was diluted with DCM (100 mL), the organic layer was washed with water, brine, dried over anhydrous $Na_2SO_4$ and concentrated, the residue was purified by prep.TLC (PE/EA=3/1) to give Compound 536 (132 mg, 52% yield). $^1$H NMR (DMSO-$d_6$, 400 MHz) δ 10.12 (s, 1H), 7.72 (m, 2H), 7.67-7.63 (m, 2H), 7.54-7.48 (m, 3H), 7.41-7.37 (m, 1H), 7.34-7.33 (m, 1H), 7.29-7.26 (m, 2H), 7.23-7.21 (m, 2H), 7.11-7.09 (m, 1H), 5.35 (s, 1H), 2.03 (s, 3H). MS (ESI) m/z $(M+H)^+$ 415.1.

Compound 537 was prepared following the similar procedure for the synthesis of Compound 536, using Compound 539 in place of Compound 1. The hydrogenation step was conducted after the substitution of phenol. TMS-NCO was used in place of AcCl. $^1$H NMR (DMSO-$d_6$, 400 MHz) δ 8.86 (s, 1H), 8.06 (s, 1H), 7.93 (s, 1H), 7.84 (s, 1H), 7.57-7.53 (m, 3H), 7.39-7.30 (m, 5H), 6.93-6.91 (m, 1H), 5.98 (s, 2H), 5.35 (s, 1H), 3.84 (s, 3H). MS (ESI) m/z $(M+H)^+$ 402.0.

Compound 545 was prepared following the similar procedure for the synthesis of Compound 536 using (4-methoxyphenyl)boronic acid in place of Compound 1. The hydrogenation and reaction with AcCl steps were eliminated.

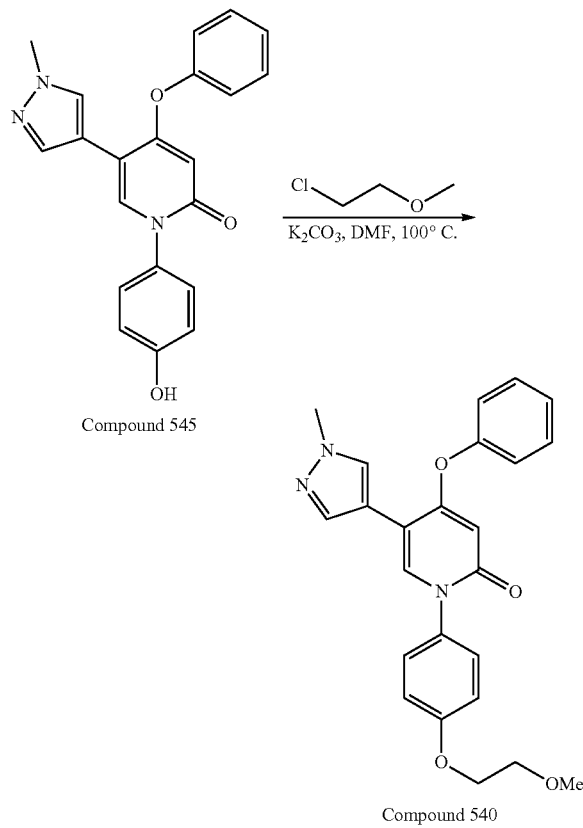

Compound 545

Compound 540

Compound 540: To a solution of Compound 545 (200 mg, 0.56 mmol) in DMF (5 mL), 1-chloro-2-methoxyethane (68 mg, 0.72 mmol) and K$_2$CO$_3$ (155 mg, 1.12 mmol) was added. The mixture was stirred at 100° C. overnight, then diluted with water and extracted with EA. After standard workup procedure, the residue was purified by prep-TLC (PE:EA=1:1) to give Compound 540 (100 mg, yield 43%) $^1$H NMR (CDCl$_3$, 400 MHz) δ 7.74 (s, 1H), 7.68 (s, 1H), 7.51 (s, 1H), 7.45 (t, J=8.0 Hz, 2H), 7.30 (d, J=8.8 Hz, 2H), 7.26 (s, 1H), 7.16 (d, J=8.0 Hz, 2H), 7.03 (d, J=8.8 Hz, 2H), 5.79 (s, 1H), 4.16 (t, J=4.8 Hz, 2H), 3.93 (s, 3H), 3.77 (t, J=4.8 Hz, 2H), 3.46 (s, 3H). MS (ESI) m/z (M+H)$^+$ 418.1.

Example 12-A

Synthesis of 4-Methyl, 5-Phenyl Pirfenidone Analogs (Scheme XXVII)

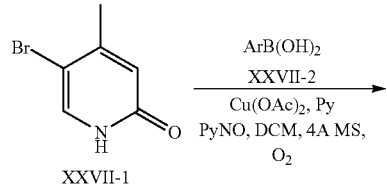

XXVII-1

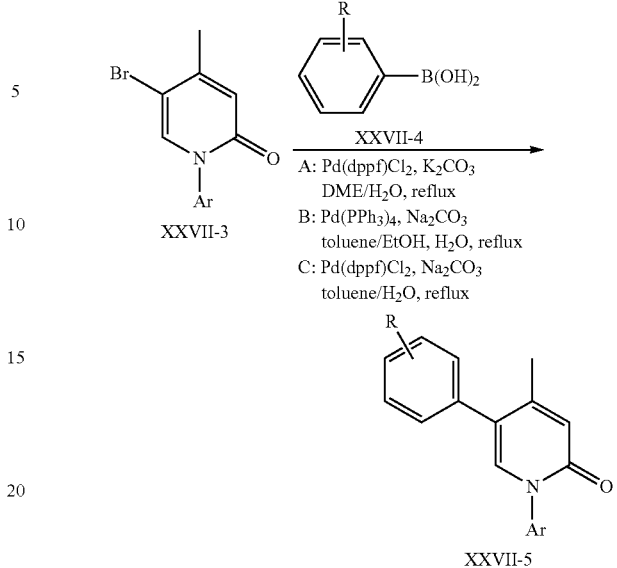

XXVII-3: To a solution of XXVII-1 (1 eq.) in DCM (0.1 mmol/mL) was added the relevant boronic acid XXVII-2 (1.5-2 eq.), Cu(OAc)$_2$ (1~3 eq), Pyridine (10 eq.) and Pyridine-N-Oxide (2-3 eq.), followed by addition of 4 Å molecular sieve (200-500 mg). The reaction mixture was stirred at rt under oxygen atmosphere overnight. After completion of the reaction indicated by TLC, the resulting mixture was filtered and washed with ethyl acetate; the filtrate was washed with brine, dried over Na$_2$SO$_4$ and concentrated. The residue was purified by flash chromatography on silica gel to give the final product.

Three general procedures for the preparation of XXVII-5:

Method A:

To a mixture of XXVII-3 (1 eq.), the relevant boronic acid XXVII-4 (1.2 eq.) and K$_2$CO$_3$ (2 eq.) in DME/H$_2$O (v/v=6/1) was added Pd(dppf)Cl$_2$ (0.1 eq.). The reaction mixture was degassed by purging with nitrogen and then was heated to reflux overnight. After the completion of the reaction, the mixture was cooled to rt, concentrated in vacuo. The residue was diluted with water and extracted with EtOAc. The combined organic layer was washed with brine, dried over Na$_2$SO$_4$, and concentrated under reduced pressure. The residue was purified by flash chromatography on silica gel to afford the final product.

Method B:

To a mixture of XXVII-3 (1 eq.), the relevant boronic acid XXVII-4 (1.2 eq.) and Na$_2$CO$_3$ (2 eq.) in toluene/EtOH/H$_2$O (v/v/v=5/2/1) was added Pd(PPh$_3$)$_4$ (0.1 eq.). The reaction mixture was degassed by purging with nitrogen and then was heated to reflux overnight. After the completion of the reaction, the mixture was cooled to rt, concentrated in vacuo. The residue was diluted with water and extracted with EtOAc. The combined organic layer was washed with brine, dried over Na$_2$SO$_4$, and concentrated under reduced pressure. The residue was purified by flash chromatography on silica gel to afford the final product.

Method C:

To a mixture of XXVII-3 (1 eq.), boronic acid XXVII-4 (1.2 eq.) and Na$_2$CO$_3$ (2 eq.) in toluene/H$_2$O (v/v=5/1) was added Pd(dppf)Cl$_2$ (0.1 eq.). The reaction mixture was degassed by purging with nitrogen and then was heated to reflux overnight. After the completion of the reaction, the mixture was cooled to rt, concentrated in vacuo. The residue was diluted with water and extracted with EtOAc. The combined organic layer was washed with brine, dried over Na$_2$SO$_4$, and concentrated under reduced pressure. The residue was purified by flash chromatography on silica gel to afford the final product.

Compounds 163-171, 191, 194, 201-205, 552 were prepared following the Method A as described above. Compounds 172-177 were prepared following the Method B as described above. Compounds 195-198 were prepared following the Method C as described above.

Compound 163: $^1$H NMR (CDCl$_3$, 400 MHz) δ 7.69-7.60 (m, 4H), 7.44-7.35 (m, 3H), 7.30-7.26 (m, 2H), 7.20 (s, 1H), 6.60 (s, 1H), 2.16 (s, 3H).

Compound 164: $^1$H NMR (CDCl$_3$, 400 MHz) δ 7.50-7.47 (m, 2H), 7.43-7.38 (m, 3H), 7.35-7.31 (m, 2H), 7.30-7.26 (m, 2H), 7.21 (s, 1H), 6.60 (s, 1H), 2.16 (s, 3H).

Compound 165: $^1$H NMR (CDCl$_3$, 400 MHz) δ 7.50-7.35 (m, 8H), 7.30-7.26 (m, 2H), 7.22 (s, 1H), 6.59 (s, 1H), 2.16 (s, 3H).

Compound 166: $^1$H NMR (CDCl$_3$, 400 MHz) δ 7.53-7.49 (m, 1H), 7.44-7.37 (m, 4H), 7.34 (s, 1H), 7.30-7.19 (m, 3H), 7.19 (s, 1H), 6.59 (s, 1H), 2.16 (s, 3H).

Compound 167: $^1$H NMR: (CDCl$_3$, 400 MHz) δ 8.67 (s, 1H), 7.69 (s, 1H), 7.44-7.27 (m, 8H), 7.01 (d, J=7.6 Hz, 1H), 6.66 (s, 1H), 2.21 (s, 3H), 2.01 (s, 3H).

Compound 168: $^1$H NMR: (CDCl$_3$, 400 MHz) δ 7.43-7.35 (m, 3H), 7.32-7.28 (m, 2H), 7.17 (s, 1H), 7.13 (d, J=8.8 Hz, 1H), 6.84-6.78 (m, 3H), 4.04 (q, J=7.6 Hz, 2H), 2.22 (s, 3H), 2.15 (s, 3H), 1.42 (t, J=7.6 Hz, 3H).

Compound 169: $^1$H NMR: (CDCl$_3$, 400 MHz) δ 7.98 (s, 1H), 7.44-7.35 (m, 3H), 7.29-7.25 (m, 3H), 7.22-7.18 (m, 1H), 7.03 (d, J=8.4 Hz, 1H), 6.79 (s, 1H), 2.28 (s, 3H), 2.20 (s, 3H).

Compound 170: $^1$H NMR: (CDCl$_3$, 400 MHz) δ 7.78 (d, J=8.4 Hz, 2H), 7.60 (d, J=8.0 Hz, 2H), 7.45-7.38 (m, 3H), 7.30-7.27 (m, 3H), 6.77 (s, 1H), 2.21 (s, 3H).

Compound 171: $^1$H NMR: (CDCl$_3$, 400 MHz) δ 7.50-7.41 (m, 5H), 7.31-7.25 (m, 5H), 6.87 (s, 1H), 2.24 (s, 3H).

Compound 172: $^1$H NMR (CDCl$_3$, 400 MHz) δ 9.07 (s, 1H), 7.67 (s, 1H), 7.29-7.21 (m, 5H), 7.12-7.07 (m, 2H), 6.95-6.93 (m, 1H), 6.60 (s, 1H), 2.17 (s, 3H), 1.95 (s, 3H). MS (ESI) m/z [M+H]$^+$ 337.0.

Compound 173: $^1$H NMR (CDCl$_3$, 400 MHz) δ 7.75 (d, J=8.4 Hz, 2H), 7.58 (d, J=8.4 Hz, 2H), 7.27-7.24 (m, 2H), 7.18 (s, 1H), 7.13-7.09 (m, 2H), 6.59 (s, 1H), 2.13 (s, 3H). MS (ESI) m/z [M+H]$^+$ 348.0.

Compound 174: $^1$H NMR (CDCl$_3$, 400 MHz) δ 7.54-7.50 (m, 1H), 7.41-7.38 (m, 2H), 7.33 (s, 1H), 7.29-7.24 (m, 3H), 7.17 (s, 1H), 7.10 (t, J=8.4 Hz, 2H), 6.58 (s, 1H), 2.13 (s, 3H). MS (ESI) m/z [M+H]$^+$ 364.0.

Compound 175: $^1$H NMR (CDCl$_3$, 400 MHz) δ 7.26-7.22 (m, 2H), 7.13-7.06 (m, 4H), 6.84-6.78 (m, 2H), 6.58 (s, 1H), 4.04 (q, J=6.8 Hz, 2H), 2.16 (m, 3H), 2.14 (m, 3H), 1.42 (t, J=6.8 Hz, 3H). MS (ESI) m/z [M+H]$^+$ 338.2.

Compound 176: $^1$H NMR (CDCl$_3$, 400 MHz) δ 7.50-7.46 (m, 2H), 7.43-7.41 (m, 3H), 7.26-7.23 (m, 2H), 7.20 (s, 1H), 7.12-7.07 (m, 2H), 6.58 (s, 1H), 2.13 (s, 3H). MS (ESI) m/z [M+H]$^+$ 280.1.

Compound 177: $^1$H NMR (CDCl$_3$, 400 MHz) δ 7.77-7.68 (m, 4H), 7.35-7.31 (m, 2H), 7.26-7.17 (m, 3H), 6.67 (s, 1H), 2.21 (s, 3H). MS (ESI) m/z [M+H]$^+$ 348.1.

Compound 191: $^1$H NMR (CD$_3$OD, 400 MHz) δ 7.61-7.57 (m, 2H), 7.52 (s, 1H), 7.46-7.41 (m, 5H), 7.32-7.30 (m, 1H), 6.59 (s, 1H), 2.22 (s, 3H). MS (ESI) m/z (M+H)$^+$ 380.0.

Compound 194: $^1$H NMR (CDCl$_3$, 400 MHz) δ 7.51-7.48 (m, 2H), 7.41-7.32 (m, 3H), 7.27-7.13 (m, 4H), 6.60 (s, 1H), 2.11 (s, 3H). MS (ESI) m/z (M+H)$^+$ 364.1.

Compound 195: $^1$H NMR (CDCl$_3$, 400 MHz) δ 7.50-7.45 (m, 3H), 7.36-7.32 (m, 2H), 7.24-7.19 (m, 2H), 7.15-7.10 (m, 1H), 6.58 (s, 1H), 2.13 (s, 3H).

Compound 196: $^1$H NMR (CDCl$_3$, 400 MHz) δ 7.49-7.45 (m, 2H), 7.36-7.32 (m, 2H), 7.24-7.19 (m, 2H), 7.15-7.10 (m, 1H), 7.03-6.99 (m, 1H), 6.58 (s, 1H), 2.13 (s, 3H).

Compound 197: $^1$H NMR (CDCl$_3$, 400 MHz) δ 7.50-7.47 (m, 3H), 7.40 (s, 1H), 7.37-7.32 (m, 2H), 7.18 (s, 1H), 7.13 (d, J=8.0 Hz, 1H), 6.60 (s, 1H), 2.15 (s, 3H).

Compound 198: $^1$H NMR (CDCl$_3$, 400 MHz) δ 7.48-7.42 (m, 3H), 7.36-7.32 (m, 2H), 7.20 (s, 1H), 7.10 (m, 1H), 7.02 (m, 1H), 6.59 (s, 1H), 2.15 (s, 3H).

Compound 201: $^1$H NMR (CDCl$_3$, 400 MHz) δ 7.48-7.46 (m, 2H), 7.35-7.30 (m, 2H), 7.16 (s, 1H), 6.90-6.88 (m, 1H), 6.78 (s, 1H), 6.75-6.71 (m, 1H), 6.56 (s, 1H), 4.29 (s, 4H), 2.16 (s, 3H). MS (ESI) m/z (M+H)$^+$ 404.0.

Compound 202: $^1$H NMR (CDCl$_3$, 400 MHz) δ 7.50-7.47 (m, 2H), 7.35-7.31 (m, 2H), 7.17 (s, 1H), 6.85-6.82 (m, 1H), 6.75-6.70 (m, 2H), 6.56 (s, 1H), 6.00 (s, 2H), 2.15 (s, 3H). MS (ESI) m/z (M+H)$^+$ 389.9.

Compound 203: Na$_2$CO$_3$ was used instead of K$_2$CO$_3$. $^1$H NMR (CDCl$_3$, 400 MHz) δ 7.49-7.47 (m, 2H), 7.34-7.30 (m, 2H), 6.90-6.86 (m, 2H), 6.72-6.70 (m, 2H), 6.60 (s, 1H), 5.99 (s, 2H), 2.19 (s, 3H). MS (ESI) m/z [M+H]$^+$ 390.1.

Compound 204: Pd(PPh$_3$)$_4$ was used instead of Pd(dppf)Cl$_2$, and Na$_2$CO$_3$ was used instead of K$_2$CO$_3$. $^1$H NMR (CDCl$_3$, 400 MHz) δ 7.51-7.49 (m, 2H), 7.34-7.30 (m, 2H), 7.18 (s, 1H), 6.93-6.84 (m, 2H), 6.72-6.70 (m, 1H), 6.56 (s, 1H), 4.28 (s, 4H), 2.09 (s, 3H). MS (ESI) m/z [M+H]$^+$ 403.9.

Compound 205: 5-bromo-4-(trifluoromethyl)pyridin-2(1H)-one was used instead of XXVII-1. Na$_2$CO$_3$ was used instead of K$_2$CO$_3$. $^1$H NMR (CDCl$_3$, 400 MHz) δ 7.50-7.48 (m, 2H), 7.37 (d, J=8.4 Hz, 2H), 7.32-7.26 (m, 3H), 7.11-7.07 (m, 3H). MS (ESI) m/z [M+H]$^+$ 417.8.

Compound 552: $^1$H NMR (CDCl$_3$, 400 MHz) δ 9.04 (s, 1H), 8.05 (s, 1H), 7.98 (d, J=8.4 Hz, 1H), 7.39-7.36 (m, 1H), 7.17-7.13 (m, 2H), 6.84 (s, 1H), 6.80 (dd, J=1.6, 4.4 Hz, 1H), 8.16 (dd, J=2.4, 8.4 Hz, 1H), 6.62 (s, 1H), 4.04 (q, J=7.2 Hz, 2H), 2.20 (s, 3H), 2.19 (s, 3H), 1.41 (t, J=7.2 Hz, 3H). MS (ESI) m/z (M+H)$^+$ 377.1.

Example 12-B

Synthesis of 4-Methyl, 5-Phenyl Pirfenidone Analogs (Scheme XXVIII)

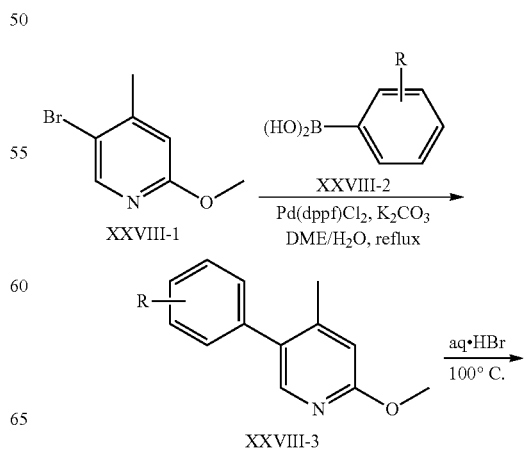

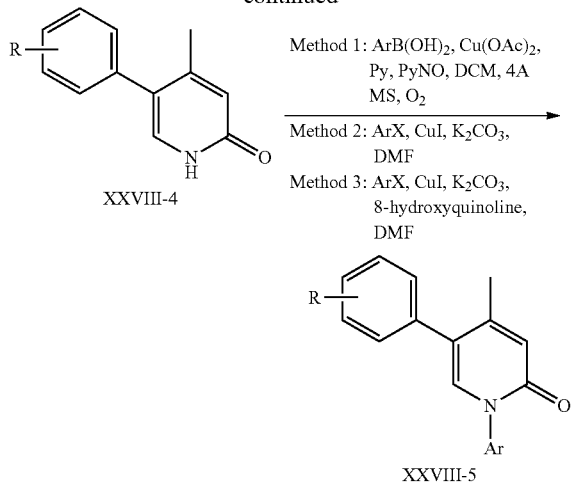

XXVIII-3 was prepared following Method A for obtaining XXVII-5.

XXVIII-4: A mixture of XXVIII-3 in aq. HBr (48%) was stirred at 100° C. overnight. After being cooled to rt, the mixture was concentrated in vacuo. The remaining mixture was neutralized with saturated aq.NaHCO$_3$, and extracted with EtOAc (30 mL×3). The combined organic layer was washed with water and brine, dried over anhydrous Na$_2$SO$_4$, and concentrated in vacuo to afford the crude XXVIII-4.

Three general procedures for the preparation of XXVIII-5:

Method 1:

To a solution of XXVIII-4 (1 eq.) in DCM (0.1 mmol/mL) was added the relevant boronic acid XXVIII-2 (1.5-2 eq.), Cu(OAc)$_2$ (1~3 eq), pyridine (10 eq.) and Pyridine-N-Oxide (2-3 eq.), followed by addition of 4 Å molecular sieve (200~500 mg). The reaction mixture was stirred at rt under oxygen atmosphere overnight. After completion of the reaction indicated by TLC, the resulting mixture was filtered and washed with ethyl acetate; the filtrate was washed with brine, dried over Na$_2$SO$_4$ and concentrated. The residue was purified by flash chromatography on silica gel to give the title compound. Compounds 181-183, 178-180, 192 and 193 were prepared following Method 1.

Compound 178: $^1$H NMR (CDCl$_3$, 400 MHz) δ 7.43-7.39 (m, 2H), 7.28-7.23 (m, 5H), 7.12-7.08 (m, 3H), 6.60 (s, 1H), 2.13 (s, 3H). MS (ESI) m/z [M+H]$^+$ 298.0.

Compound 179: $^1$H NMR (CDCl$_3$, 400 MHz) δ 7.34 (s, 1H), 7.30-7.21 (m, 3H), 7.16 (d, J=8.4 Hz 1H), 7.12-7.07 (m, 2H), 7.02 (s, 1H), 6.59 (s, 1H), 2.19 (s, 3H), 2.15 (s, 3H). MS (ESI) m/z [M+H]$^+$ 327.9.

Compound 180: $^1$H NMR (CDCl$_3$, 400 MHz) δ 7.38-7.33 (m, 2H), 7.18 (s, 1H), 7.09 (t, J=8.8 Hz, 2H), 6.60 (s, 2H), 6.57 (s, 1H), 3.85 (s, 9H), 2.13 (s, 3H). MS (ESI) m/z (M+H)$^+$370.1.

Compound 192: $^1$H NMR (CDCl$_3$, 400 MHz) δ 7.49-7.46 (m, 2H), 7.45-7.32 (m, 3H), 7.20 (s, 1H), 7.09-7.00 (m, 2H), 6.98 (m, 1H), 6.58 (s, 1H), 2.16 (s, 3H). MS (ESI) m/z (M+H)$^+$364.0.

Compound 193: $^1$H NMR (CDCl$_3$, 400 MHz) δ 7.38-7.34 (m, 1H), 7.33-6.98 (m, 5H), 6.84-6.78 (m, 2H), 6.58 (s, 1H), 4.04 (q, J=7.2 Hz, 2H), 2.17 (s, 6H), 1.42 (t, J=7.2 Hz, 3H). MS (ESI) m/z (M+H)$^+$ 338.1.

Compound 181: $^1$H NMR (CDCl$_3$, 400 MHz) δ 7.50 (d, J=8.8 Hz, 2H), 7.38 (d, J=8.8 Hz, 2H), 7.28-7.23 (m, 3H), 7.13 (t, J=8.4 Hz, 2H), 6.86 (s, 1H), 2.21 (s, 3H).

Compound 182: $^1$H NMR (CDCl$_3$, 400 MHz) δ 7.25-7.21 (m, 2H), 7.16 (s, 1H), 7.08 (t, J=8.4 Hz, 2H), 6.95-9.92 (m, 2H), 6.88-6.85 (m, 1H), 6.56 (s, 1H), 4.28 (s, 4H). 2.11 (s, 3H).

Compound 183: $^1$H NMR (CDCl$_3$, 400 MHz) δ 7.26-7.22 (m, 2H), 7.16 (s, 1H), 7.09 (t, J=8.4 Hz, 2H), 6.92 (s, 1H), 6.88-6.80 (m, 2H), 6.56 (s, 1H). 6.02 (s, 2H), 2.12 (s, 3H).

Method 2:

To a stirred mixture of 5-(4-fluorophenyl)-4-methylpyridin-2(1H)-one (203 mg, 1 mmol, 1.0 eq.), 1-bromo-2-methyl-4-(trifluoromethoxy)benzene (382 mg, 1.5 mmol, 1.5 eq.), and K$_2$CO$_3$ (276 mg, 2 mmol, 2.0 eq.) in DMF (5 mL) was added CuI (19 mg, 0.1 mmol, 0.1 eq.). The reaction mixture was stirred at 140° C. for 3 days under N$_2$ protection. The mixture was cooled to rt, diluted with EA (50 mL), washed with water and brine, concentrated. The residue was purified by flash chromatography on silica gel (PE: EA=5:1→1:1) to give Compound 186 (40 mg, 11% yield). $^1$H NMR (CDCl$_3$, 400 MHz) δ 7.27-7.17 (m, 8H), 7.12-7.07 (m, 1H), 6.60 (s, 1H), 2.23 (s, 3H), 2.15 (s, 3H). MS (ESI) m/z [M+H]$^+$ 378.0.

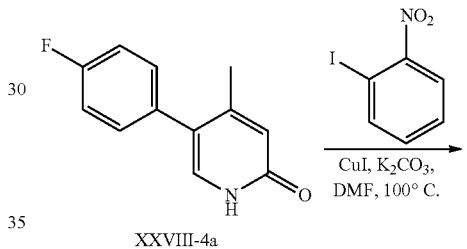

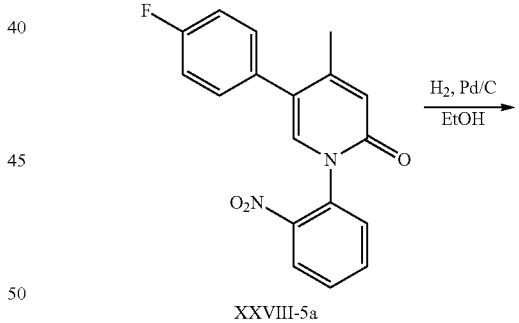

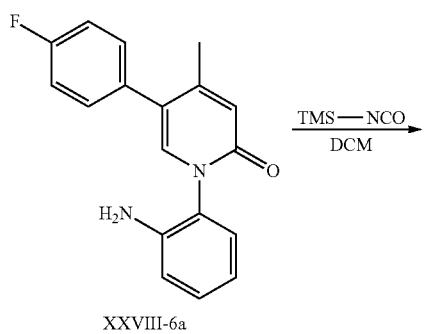

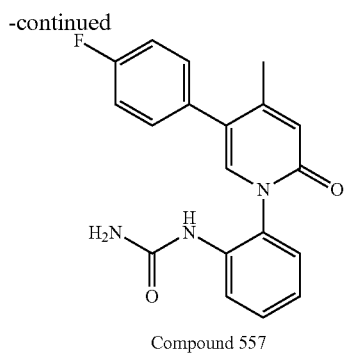

Compound 557

XXVIII-5a was prepared from XXVIII-4a following Method 2 as described above. XXVIII-6a was prepared by hydrogenation (50 Psi) of XXVIII-5a in ethanol at rt for 4 h. Compound 557 was obtained from reacting XXVIII-6a with TMS-NCO. $^1$H NMR (DMSO-$d_6$, 400 MHz) δ 8.21 (d, J=8 Hz, 1H), 7.99 (s, 1H), 7.93 (s, 1H), 7.42-7.39 (m, 2H), 7.30-7.26 (m, 2H), 7.09 (t, J=7.6 Hz, 1H), 7.01 (m, 2H), 6.93 (m, 1H), 6.17 (s, 2H), 2.26 (s, 3H). MS (ESI) m/z [M+H]$^+$ 338.0.

Method 3:

To a stirred mixture of 5-(4-fluorophenyl)-4-methylpyridin-2(1H)-one (2.04 g, 10 mmol, 1.0 eq.), 4-bromobenzo[d][1,3]dioxole (3.0 g, 15 mmol, 1.5 eq.), and K$_2$CO$_3$ (2.76 g, 20 mmol, 2 eq.) in DMF (50 mL) was added CuI (191 mg, 1 mmol, 0.1 eq.) and 8-hydroxyquinoline (140 mg, 1 mmol, 0.1 eq.). The reaction mixture was stirred at 140° C. for 3 days under N$_2$ protection. The mixture was cooled to rt, diluted with EA (250 mL), washed with water and brine, concentrated. The residue was purified by flash chromatography on silica gel (PE:EA=5:1→1:1) to yield Compound 184 (680 mg, 21% yield) as white solid. $^1$H NMR (CDCl$_3$, 400 MHz) δ 7.35-7.32 (m, 2H), 7.26 (s, 1H), 7.18 (t, J=8.8 Hz, 2H), 7.02-6.94 (m, 3H), 6.67 (s, 1H), 6.13 (s, 2H), 2.21 (s, 3H). MS (ESI) m/z [M+H]$^+$ 323.8.

Compound 185 was prepared following the similar procedure for obtaining Compound 184 using 5-bromo-2,3-dihydrobenzo[b][1,4]dioxine in place of 4-bromobenzo[d][1,3]dioxole. $^1$H NMR (CDCl$_3$, 400 MHz) δ 7.28-7.24 (m, 3H), 7.11-7.06 (m, 3H), 6.94-6.88 (m, 3H), 6.57 (s, 1H), 4.30-4.28 (m, 4H), 2.13 (s, 3H). MS (ESI) m/z [M+H]$^+$ 338.1.

Compound 187: To the solution of Compound 172 (378 mg, 1.12 mmol) in EtOH/H$_2$O (10 mL, v/v=2/1) was added aq.H$_2$SO$_4$ (6 M, 2 mL). The mixture was heated to reflux overnight. LCMS showed the reaction was completed. The mixture was concentrated, extracted with EtOAc (30 mL×3). The combined organic layer was washed with brine, dried over anhydrous Na$_2$SO$_4$ and concentrated. The residue was purified by prep-TLC (PE/EA=3/1) to give Compound 187 (200 mg, 60% yield). $^1$H NMR (CDCl$_3$, 400 MHz) δ 7.26-7.21 (m, 3H), 7.18 (s, 1H), 7.11-7.06 (m, 2H), 6.75-6.68 (m, 3H), 6.56 (s, 1H), 2.12 (s, 3H).

Compound 188: To the solution of Compound 187 (80 mg, 0.102 mmol) in THF/H$_2$O (2 mL, v/v=4/1) was added KOCN (10 mg, 0.112 mmol) and AcOH (one drop). The mixture was heated to reflux overnight. LCMS showed the reaction was completed. The mixture was concentrated, diluted with EtOAc (50 mL), washed with brine, dried over anhydrous Na$_2$SO$_4$ and concentrated. The residue was purified by prep-HPLC to give Compound 188 (62.2 mg, 67% yield). $^1$H NMR (CDCl$_3$, 400 MHz) δ 8.12 (s, 1H), 7.62 (s, 1H), 7.24-7.21 (m, 3H), 7.13-7.08 (m, 2H), 6.88 (d, J=8.8 Hz, 1H), 6.81 (d, J=8.0 Hz, 1H), 6.60 (s, 1H), 4.84 (s, 2H), 2.18 (s, 3H).

Compound 559 was prepared reacting XXVIII-4a with 2-fluoro-5-iodoaniline using Method 3 as described above, followed by reacting with TMS-NCO. $^1$H NMR (DMSO-$d_6$, 400 MHz) δ 8.53 (s, 1H), 8.19 (d, J=6.0 Hz, 1H), 7.44-7.40 (m, 3H), 7.29-7.20 (m, 3H), 6.97 (m, 1H), 6.43 (s, 1H), 6.27 (s, 2H), 2.08 (s, 3H).

Example 12-C

Synthesis of Compound 199 (Scheme XXIX)

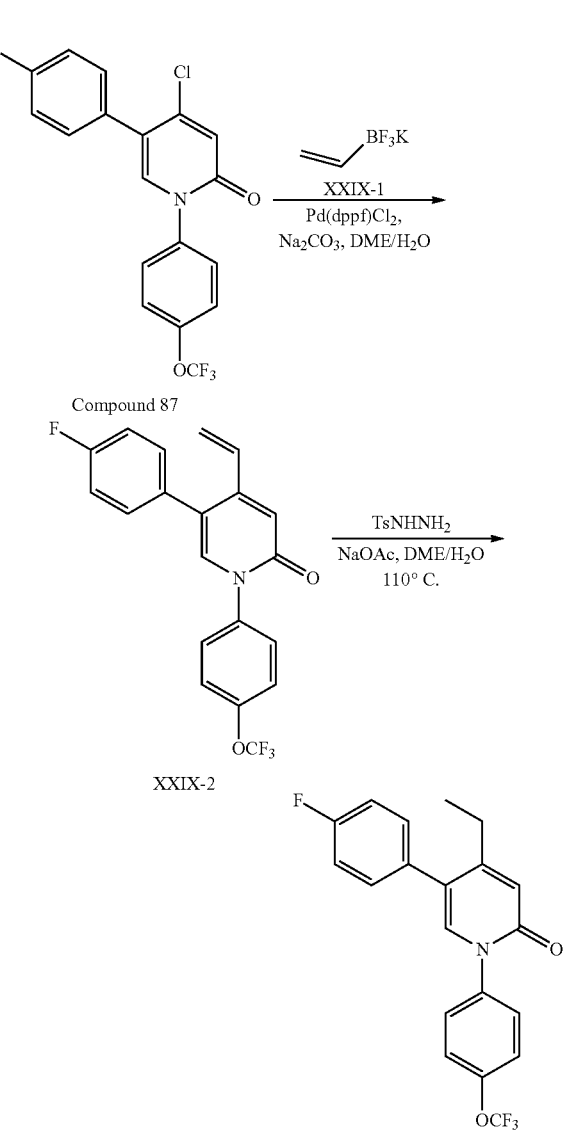

To a stirred mixture of Compound 87 (200 mg, 0.52 mmol), XXIX-1 (92 mg, 0.68 mmol), and Na$_2$CO$_3$ (60 mg, 1.4 mmol) in DME/H$_2$O (18 mL, V/V=8/1) was added Pd(dppf)Cl$_2$ (140 mg, 0.99 mmol) under N$_2$ protection. The reaction mixture was stirred at 110° C. overnight. The mixture was concentrated to remove DME, diluted with H$_2$O, extracted with EtOAc (30 mL×3), the organic layer was washed with water and brine, dried over anhydrous Na$_2$SO$_4$, and concentrated in vacuo, the residue was purified by prep-TLC (PE:EA=2.5:1) to give XXIX-2 (112 mg, yield: 57%) as a white solid. MS (ESI) m/z [M+H]$^+$ 376.09.

XXIX-2 (170 mg, 0.45 mmol), TsNHNH$_2$ (338 mg, 1.81 mmol), and NaOAc (371 mg, 4.53 mmol) were added into DME/H$_2$O (20 mL, v/v=5/1). The reaction mixture was stirred at 110° C. overnight. The mixture was concentrated to remove DME, diluted with H$_2$O, extracted with EtOAc (30 mL×3), the organic layer was washed with water and brine, dried over anhydrous Na$_2$SO$_4$, and concentrated in vacuo, the residue was purified by prep-HPLC to afford Compound 199 (107 mg, yield 64%) as white solid. $^1$H NMR (CDCl$_3$, 400 MHz) δ 7.49-7.46 (m, 2H), 7.33-7.31 (m, 2H), 7.26-7.22 (m, 2H), 7.14 (s, 1H), 7.11-7.06 (m, 2H), 6.60 (s, 1H), 2.46-2.41 (m, 2H), 1.12-1.07 (m, 3H). MS (ESI) m/z [M+H]$^+$ 378.10.

Example 12-D

Synthesis of Compound 200 (Scheme XXX)

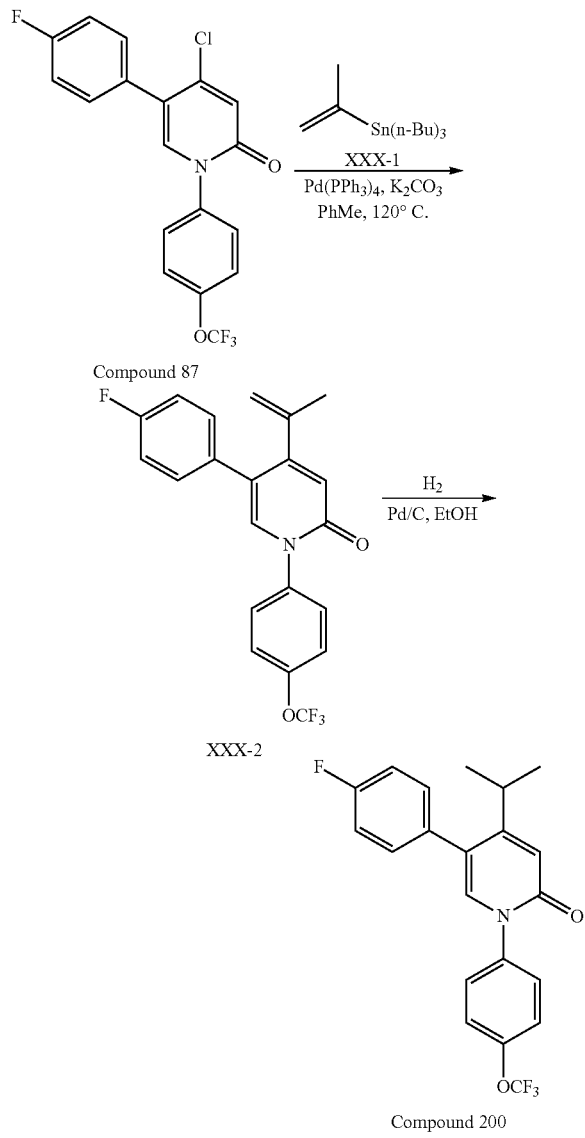

Compound 87

XXX-2

Compound 200

To a stirred mixture of Compound 87 (150 mg, 0.270 mmol), XXX-1 (135 mg, 0.4 mmol), and K$_2$CO$_3$ (186 mg, 1.35 mmol) in toluene (5 mL) was added Pd(PPh$_3$)$_4$ (30 mg, 0.0270 mmol). The mixture was purged with nitrogen for three times and then heated at 120° C. overnight. And then the mixture was concentrated, diluted with H$_2$O, extracted with EtOAc (30 mL×3), the organic layer was washed with water and brine, dried over anhydrous Na$_2$SO$_4$, and concentrated in vacuo. The crude product was purified by prep-TLC (PE:EA=5:1) to yield XXX-2 (135 mg, 88% yield).

A mixture of XXX-2 (100 mg, 0.259 mmol) and dry Pd/C in ethanol (5 mL) was stirred under H$_2$ at rt for 1 h. Filtered the reaction, and concentrated the organic layer to give Compound 200 (61.6 mg, 61% yield). $^1$H NMR (CDCl$_3$, 400 MHz) δ 7.49 (d, J=8.8 Hz, 2H), 7.34 (d, J=8.4 Hz, 2H), 7.25-7.23 (m, 2H), 7.14-7.08 (m, 3H), 6.65 (s, 1H), 2.85-2.77 (m, 1H), 1.14 (d, J=6.8 Hz, 6H).

Compound 629: To a mixture of 5-bromo-1-(4-ethoxy-2-methylphenyl)-4-methylpyridin-2(1H)-one (1.5 g, 4.66 mmol) and 4-(tributylstannyl)pyridazine (3.44 g, 9.31 mmol) in dioxane (20 mL) was added Pd(PPh$_3$)$_2$Cl$_2$ (0.163 g, 0.233 mmol) under N$_2$ at rt. The mixture was refluxed overnight. The mixture was concentrated, diluted with water and extracted with EtOAc. The organic layer were washed with brine, dried over Na$_2$SO$_4$, and concentrated under reduced pressure. The residue was purified by chromatography on silica gel (PE/EA=1:2→EA) to produce Compound 629 as a yellow solid (0.806 g, 54% yield). $^1$H NMR (DMSO-d$_6$, 400 MHz) δ 9.33 (d, J=2.4 Hz, 1H), 9.21 (d, J=5.6 Hz, 1H), 7.78 (dd, J=2.4, 5.2 Hz, 1H), 7.70 (s, 1H), 7.18 (d, J=8.8 Hz, 1H), 6.92 (d, J=2.4 Hz, 1H), 6.85 (dd, J=2.4, 8.4 Hz, 1H), 6.50 (s, 1H), 4.07 (q, J=6.8 Hz, 2H), 2.21 (s, 3H), 2.04 (s, 3H), 1.32 (t, J=6.8 Hz, 3H). MS (ESI) m/z [M+H]$^+$ 322.0.

Example 12-D

Synthesis of Compound 189 (Scheme XXXI)

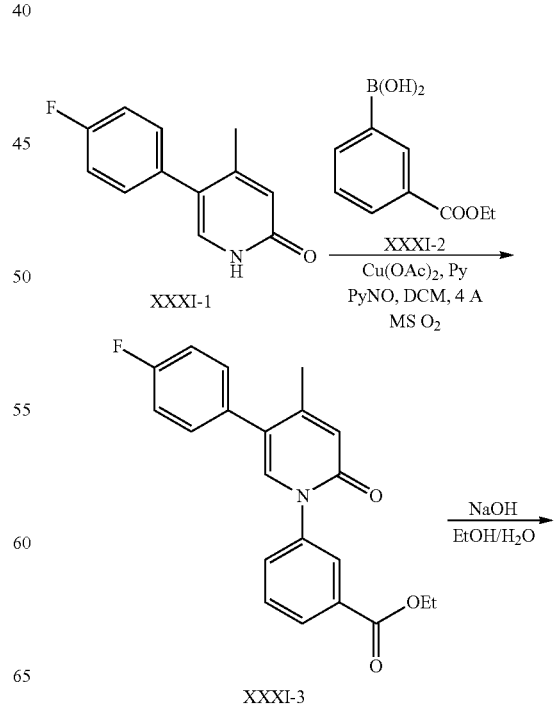

XXXI-1

XXXI-3

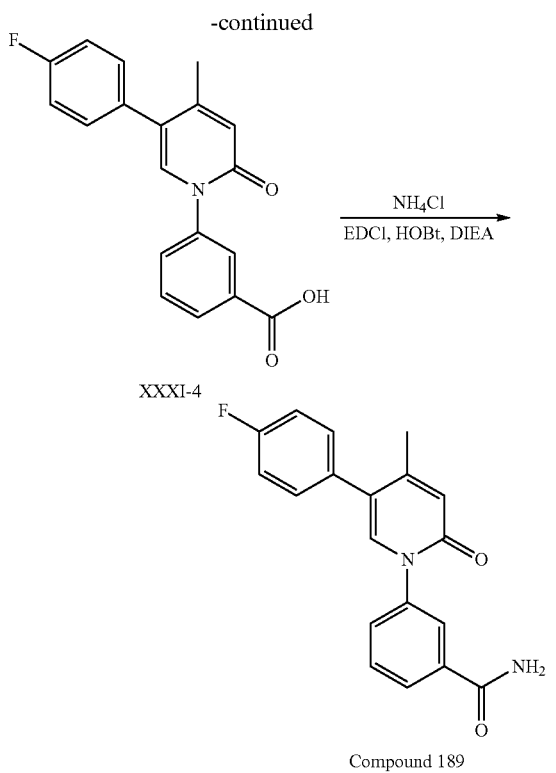

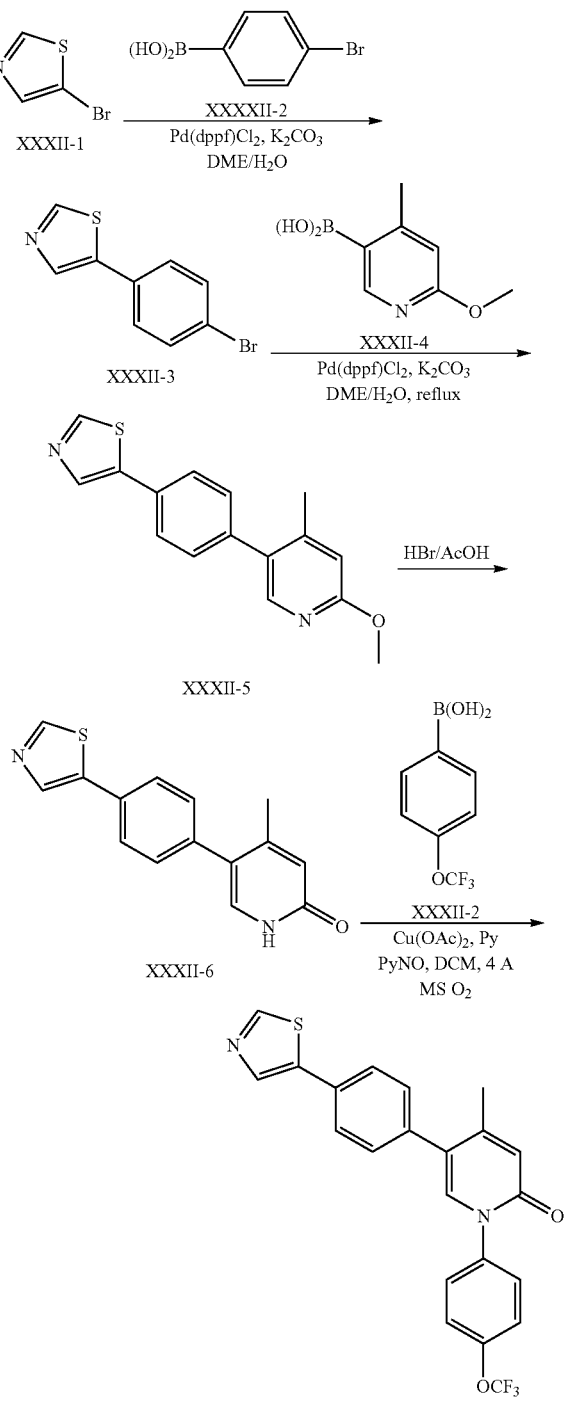

(m, 2H), 7.27-7.21 (m, 3H), 7.13-7.08 (m, 2H), 6.70 (brs, 1H), 6.57 (s, 1H), 2.96 (d, J=4.8 Hz, 3H), 2.14 (s, 3H). MS (ESI) m/z (M+H)+336.9.

Example 12-E

Synthesis of Compound 206 (Scheme XXXII)

XXXI-3 was obtained following the similar procedure for obtaining XXVII-3.

To a solution of XXXI-3 (300 mg, 0.854 mmol) in EtOH (10 mL) was added a solution of NaOH (102 mg, 2.56 mmol) in water (8 mL). The reaction mixture was heated to 100° C. for 4 hrs. After concentration in vacuo, the mixture was acidified with aq. HCl (1N). Then the mixture was extracted with EtOAc (30 mL×3). The combined organic layer was washed with brine, dried over anhydrous $Na_2SO_4$ and concentrated. The crude product was used for next step directly without further purification (200 mg, 72% yield). MS (ESI) m/z [M+H]+ 324.0.

XXXI-4 (150 mg, 0.464 mmol), HOBT (70 mg, 0.51 mmol), EDC.HCl (100 mg, 0.51 mmol) and DIEA (260 mg, 2 mmol) were charged into dry DCM (5 mL), followed by $NH_4Cl$ (75 mg, 1.4 mmol). The reaction mixture was stirred at rt overnight. The mixture was diluted with water (10 mL), extracted with EtOAc (20 mL×3). The combined organic layer was washed with brine, dried over anhydrous $Na_2SO_4$ and concentrated. The residue was purified by prep-HPLC to afford Compound 189 as a pale yellow solid (21.8 mg, 17% yield). $^1$H NMR (CDCl$_3$, 400 MHz) δ 7.89 (s, 1H), 7.84 (m, 1H), 7.59-7.53 (m, 2H), 7.27-7.22 (m, 3H), 7.13-6.99 (m, 2H), 6.56 (s, 1H), 2.14 (s, 3H). MS (ESI) m/z (M+Na)+ 344.9.

Compound 190: To a solution of XXXI-4 (250 mg, 0.77 mmol), HATU (350 mg, 0.92 mmol), and DIEA (300 mg, 2.3 mmol) in dry DCM (8 mL) was added the methylamine hydrochloride (78 mg, 1.16 mmol). The reaction mixture was stirred at rt overnight. The mixture was diluted with water (20 mL), extracted with EtOAc (30 mL×3). The combined organic layer was washed with brine, dried over anhydrous $Na_2SO_4$ and concentrated. The residue was purified by prep-TLC (DCM:MeOH=10:1) to produce Compound 190 as a white solid (159.3 mg, 61% yield). $^1$H NMR (CDCl$_3$, 400 MHz) δ 7.81 (s, 1H), 7.75 (m, 1H), 7.52-7.46

To a stirred mixture of XXXII-1 (1.5 g, 9.15 mmol), XXXII-2 (1.83 g, 9.15 mmol), and $K_2CO_3$ (3.79 g, 27.45 mmol) in DME/H₂O (50 mL, v:v=5:1) was added Pd(dppf)Cl₂ (1.34 g, 1.83 mmol) under N₂ protection. The reaction mixture was heated to reflux overnight. The mixture was poured into water, extracted with EtOAc (150 mL×3). The combined organic layer was washed with brine, dried over anhydrous Na₂SO₄ and concentrated. The residue was purified by flash chromatography on silica gel (PE:EA=10:1→5:1→3:1) to afford XXXII-3 (600 mg, 21% yield).

To a stirred mixture of XXXII-3 (400 mg, 1.7 mmol), XXXII-4 (425.8 mg, 2.55 mmol), and K₂CO₃ (703.8 mg, 5.1 mmol) in DME/H₂O (50 mL, v:v=5:1) was added Pd(dppf)Cl₂ (120 mg, 0.17 mmol) under N₂ protection. The reaction mixture was heated to reflux for 4 hours, then the mixture was poured into water, extracted with EtOAc (30 mL×3), the organic layer was washed with brine, dried over anhydrous Na₂SO₄, and concentrated in vacuo. The residue was purified by column chromatography on silica gel (PE:EA=3:11:1) to afford XXXII-5 (220 mg, 46% yield). MS (ESI) m/z [M+H]⁺ 283.

A mixture of XXXII-5 (100 mg, 0.35 mmol) in AcOH (5 mL) and aq. HBr (40%, 5 mL) was heated to reflux overnight. And then it was neutralized with aq. NaOH (1 M), extracted with EA (30 mL×3). The combined organic layer was washed with brine, dried over Na₂SO₄, and concentrated in vacuo to give XXXII-6 (80 mg, 85% yield). ¹H NMR (DMSO-d₆, 300 MHz) δ 9.12 (s, 1H), 8.36 (s, 1H), 7.73-7.70 (d, J=7.8 Hz, 2H), 7.41-7.39 (d, J=8.1 Hz, 2H), 7.25 (s, 1H), 6.30 (s, 1H), 1.90 (s, 3H).

Compound 206 was prepared by following the similar procedure for obtaining XXVII-3 (150 mg, 58% yield). ¹H NMR (CDCl₃, 400 MHz) δ 8.79 (s, 1H), 8.12 (s, 1H), 7.63 (d, J=8.4 Hz, 2H), 7.49 (d, J=8.8 Hz, 2H), 7.34 (m, 4H), 7.23 (s, 1H), 6.61 (s, 1H), 2.19 (s, 3H). MS (ESI) m/z [M+H]⁺ 429.1.

Example 12-F

Synthesis of Compound 207 (Scheme XXXIII)

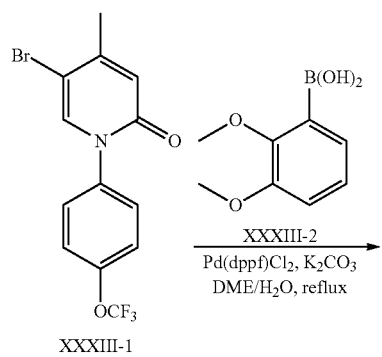

XXXIII-1

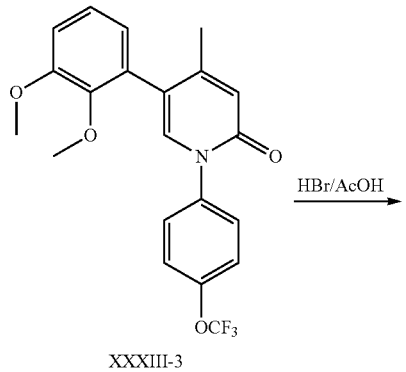

XXXIII-3

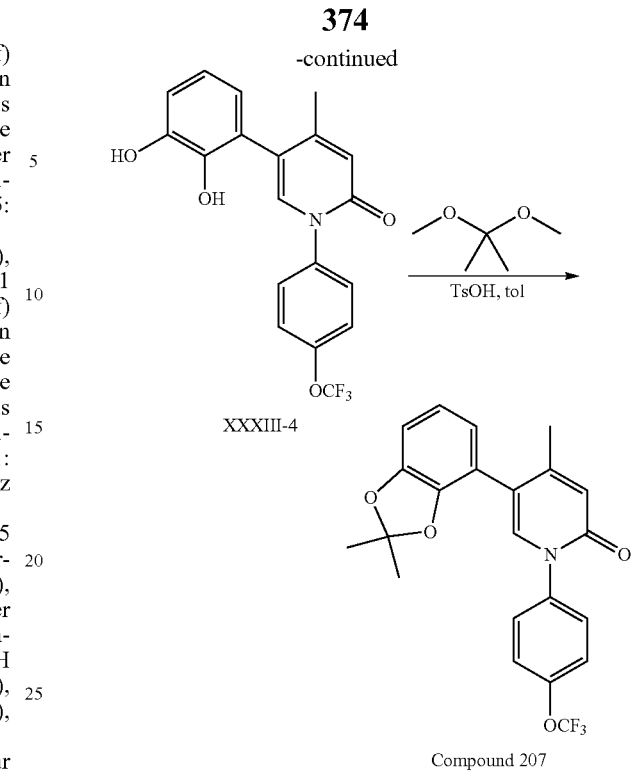

XXXIII-4

Compound 207

XXXIII-3 was prepared following the similar procedure for obtaining XXXII-5.

XXXIII-4 was prepared following the similar procedure for obtaining XXXII-6.

To a solution of XXXIII-3 (450 mg, 1.2 mmol) in toluene (50 mL) was added 2,2-dimethoxypropane (9 mL) and TsOH (45.6 mg, 0.24 mmol), the mixture was heated to reflux overnight. The mixture was poured into water, extracted with EA (50 mL×3). The combined organic layer was washed with brine and concentrated to give crude product, which was purified by prep-HPLC to give Compound 207 (200 mg, 41% yield). ¹H NMR (CDCl₃, 400 MHz) δ 7.49-7.47 (m, 2H), 7.33-7.31 (d, J=8.4 Hz, 2H), 7.24 (s, 1H), 6.83-6.79 (m, 1H), 6.77-6.75 (m, 1H), 6.64-6.62 (m, 1H), 6.57 (s, 1H), 2.18 (s, 3H), 1.70 (s, 6H). MS (ESI) m/z [M+H]+ 418.

Compound 211 was prepared following the similar procedure for obtaining Compound 207 using (3,4-dimethoxyphenyl)boronic acid in place of XXXIII-2. ¹H NMR (CDCl₃, 400 MHz) δ 7.49-7.46 (m, 2H), 7.34-7.31 (m, 2H), 7.16 (s, 1H), 6.75-6.73 (d, J=7.6 Hz, 1H), 6.67-6.64 (m, 2H), 6.56 (s, 1H), 2.16 (s, 3H), 1.70 (s, 6H). MS (ESI) m/z [M+H]+ 417.9.

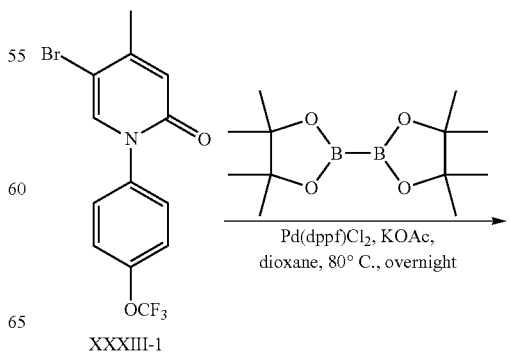

XXXIII-1

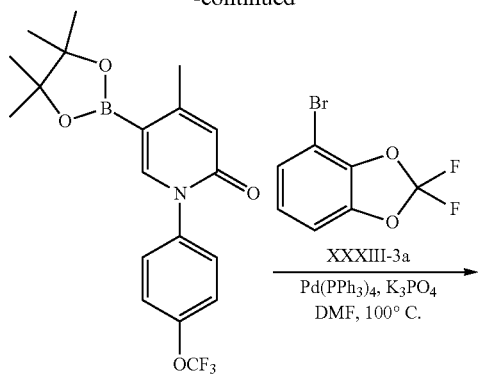

XXXIII-2a

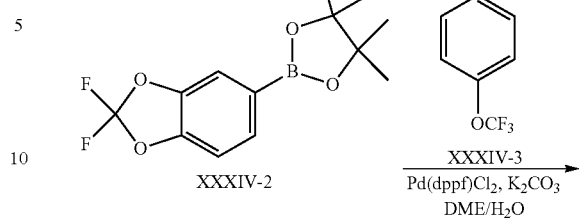

XXXIV-2

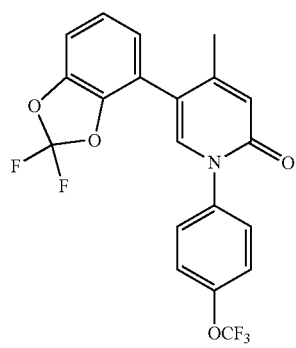

Compound 415

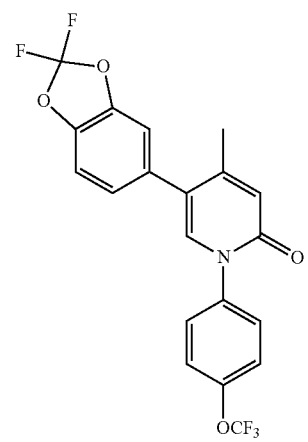

Compound 208

XXXIII-2a was prepared by following the similar procedure for obtaining XXXIII-3 using bis(pinacolato)diboron in place of XXXIII-2 as a white solid.

Compound 415: To a solution of XXXIII-2a (200 mg, 1.06 mmol) in DMF (4 mL) was added K$_3$PO$_4$ (476 mg 2.11 mmol), XXXIII-3a (500 mg, 3.16 mmol), Pd(PPh$_3$)$_4$ (122 mg, 0.106 mmol). The mixture was purged with nitrogen and then heated at 100° C. overnight. The mixture was cooled to rt, diluted with water (20 mL), extracted with EtOAc (30 mL×3). The combined organic layer was washed with brine, dried over anhydrous Na$_2$SO$_4$, and concentrated in vacuo. The residue was purified by prep-TLC (PE/EA=10/1) to give Compound 415 (128 mg, 36% yield). $^1$H NMR (CDCl$_3$, 400 MHz) δ 7.50 (d, J=8.8 Hz, 2H), 7.35 (d, J=8.4 Hz, 2H), 7.29 (s, 1H), 7.15-7.08 (m, 2H), 6.98-6.96 (m, 1H), 6.62 (s, 1H), 2.17 (s, 1H). MS (ESI) m/z (M+H)$^+$ 425.9.

Example 12-G

Synthesis of Compound 208 (Scheme XXXIV)

A flask was charged with XXXIV-2 (1 g, 4.2 mmol), bis(pinacolato)diboron (1.27 g, 5 mmol) and KOAc (0.5 g, 5 mmol) in 1,4-dioxane (30 mL). The flask was purged with nitrogen for three times. And then Pd(dppf)Cl$_2$ (150 mg, 0.21 mmol) was added thereto and then the mixture was purged with nitrogen again. The mixture was stirred at 90° C. for 12 hrs. After the starting material was consumed, the mixture was cooled to rt, the solvent was evaporated in vacuo. The residue was diluted with water (30 mL), extracted with EA (50 mL×3). The combined organic layer was washed with brine, dried over Na$_2$SO$_4$ and concentrated. The residue was purified by column chromatography on silica gel (PE:EA=10:1 to 5:1) to provide XXXIV-2 (800 mg, 67% yield) as a white solid.

Compound 208 was obtaining following the similar procedure for obtaining XXXII-5. $^1$H NMR (CDCl$_3$, 400 MHz) δ 7.48-7.45 (m, 2H), 7.33 (d, J=8.4 Hz, 2H), 7.18 (s, 1H), 7.11-7.09 (m, 1H), 7.02-6.97 (m, 2H), 6.59 (s, 1H), 2.14 (s, 3H). MS (ESI) m/z [M+H]$^+$ 425.9.

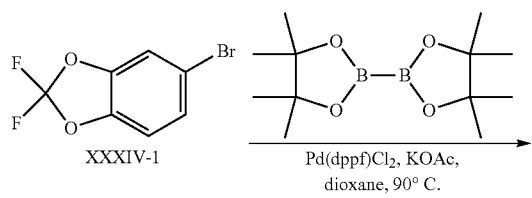

XXXIV-1

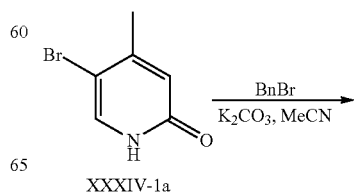

XXXIV-1a

-continued

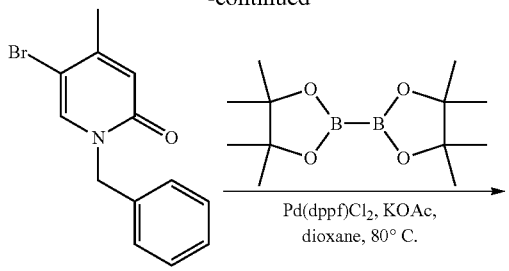

XXXIV-2a

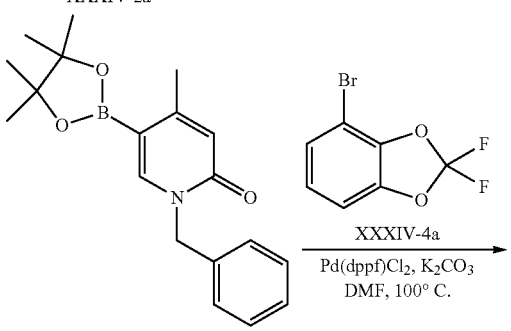

XXXIII-3a

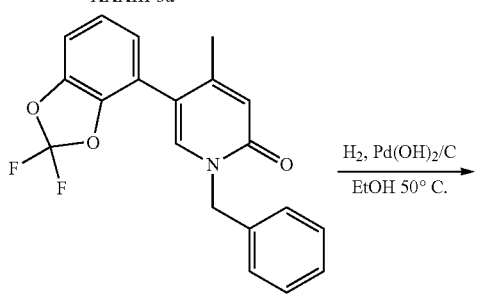

XXXIV-5a

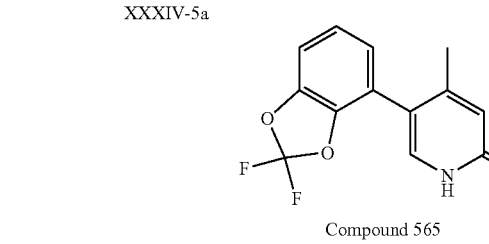

Compound 565 reaction, the mixture was filtered and concentrated, the residue was purified by prep-TLC (PE/EA=5/1) to afford Compound 565 (40 mg, 22% yield). $^1$H NMR (CDCl$_3$, 400 MHz) δ 7.35 (s, 1H), 7.16-7.06 (m, 2H), 6.92 (d, J=7.6 Hz, 1H), 6.52 (s, 1H), 2.16 (s, 3H). MS (ESI) m/z (M+H)$^+$ 266.1.

Example 12-H

Synthesis of Compound 209 (Scheme XXXV)

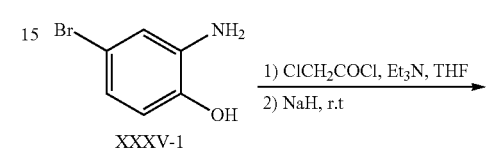

XXXV-1

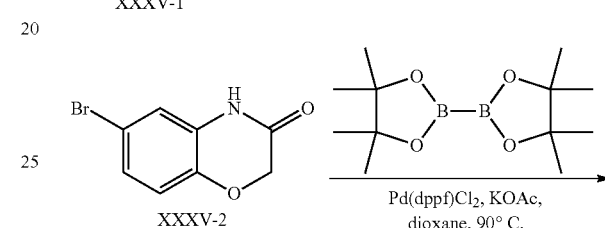

XXXV-2

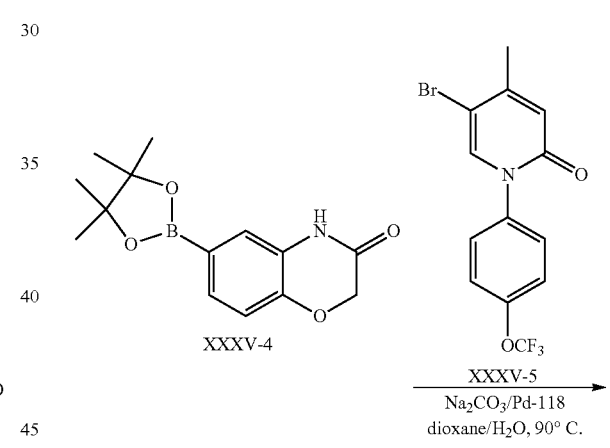

XXXV-4

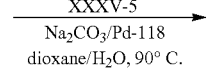

XXXV-5

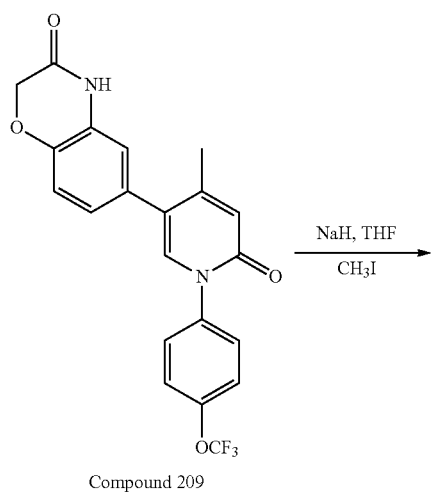

Compound 209

To a mixture of XXXIV-1 (700 mg, 3.763 mmol) in MeCN (20 mL) was added BnBr (954 mg, 15.465 mmol) and K$_2$CO$_3$ (1.349 g, 7.523 mmol). The mixture was stirred at rt overnight, and then it was concentrated to remove MeCN, diluted with H$_2$O, extracted with EtOAc. The organic layer was washed with water and brine, dried over anhydrous Na$_2$SO$_4$, and concentrated in vacuo. The crude product was chromatographed on silica gel (PE:EA=1:1) to give XXXIV-2 (600 mg, yield 58%). MS (ESI) m/z [M+H]$^+$ 278.2.

XXXIV-3a was prepared from Suzuki-Coupling of XXXIV-2a and bis (pinacolato)diboron following the standard procedure described above. XXXIV-5a was prepared by Suzuki-Coupling of XXXIV-3a with XXXIV-4a following the standard procedure described above.

A mixture of XXXIV-5a (250 mg, 0.704 mmol) and Pd(OH)$_2$/C (25 mg) in EtOH (10 mL) was stirred under 1 atm of H$_2$ at 50° C. overnight. After completion of the

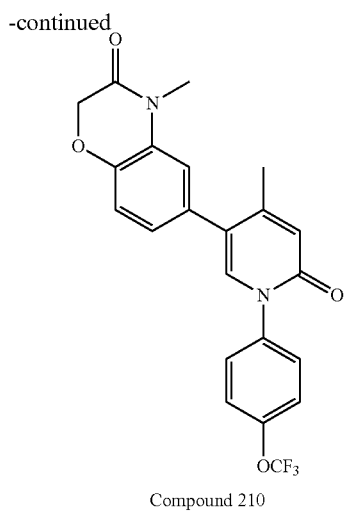

Compound 210

TEA (4.06 g, 0.04 mmol) was added to a solution of XXXV-1 (5 g, 27 mmol) in THF (150 mL). And then 2-chloroacetyl chloride (3.33 g, 0.03 mmol) was added in portions at 0° C. After 20 minutes, the mixture was stirred at rt for 2 hrs. The reaction mixture was cooled to 0° C. and NaH (60%, 2.2 g, 54 mmol) was added in portions. The reaction mixture was stirred at 0° C. for 20 minutes then at rt for 2 h before being quenched with water. The solvent was removed in vacuo and the resulting mixture diluted with water. The precipitate was filtered, washed with water and dried in vacuo to give XXXV-2 (5.5 g, 89% yield).

To the solution of XXXV-2 (2.3 g, 10 mmol) in dioxane (20 mL), bis (pinacolato)diboron (3.05 g, 12 mmol), potassium acetate (2 g, 20 mmol) and Pd(dppf)Cl$_2$ (730 mg, 1 mmol) was added. The mixture was purged with nitrogen and stirred at 90° C. overnight. Then the mixture was diluted with EA (200 mL) and filtrated. The organic phase was washed with brine, dried over Na$_2$SO$_4$, concentrated in vacuo to give the crude product. The residue was purification by column chromatography on silica gel (PE:EA=3:1 to 1:1) to give XXXV-4 (1.9 g, 69% yield).

To the solution of XXXV-4 (1.4 g, 5.1 mmol) in dioxane/H$_2$O (15 mL/3 mL), XXXV-5 (1.47 g, 4.2 mmol), Na$_2$CO$_3$ (890 mg, 8.4 mmol) and Pd-118 (137 mg, 6.21 mmol) were added. The mixture was purged with nitrogen and stirred at 90° C. overnight. Then the mixture was diluted with EA (100 mL) and filtrated. The organic phase was washed with brine, dried over Na$_2$SO$_4$, concentrated in vacuo to give the crude product. The residue was purified by column chromatography on silica gel (PE:EA=2:1 to 1:1) to afford Compound 209 (1.36 g, 64% yield). $^1$H NMR (CDCl$_3$, 400 MHz) δ 9.05 (s, 1H), 7.49-7.45 (m, 2H), 7.35-7.32 (m, 2H), 7.16 (s, 1H), 7.03-7.00 (m, 1H), 6.89-6.87 (m, 1H), 6.74 (s, 1H), 6.58 (s, 1H), 4.65 (s, 2H), 2.13 (s, 3H). MS (ESI) m/z (M+H)$^+$ 416.9.

Compound 210: Compound 209 (400 mg, 0.96 mmol) was dissolved in THF (2 mL), NaH (60%, 60 mg, 1.2 mmol) was added in portions under stirring at 0° C. After about 30 minutes, iodomethane (2.1 g, 14.6 mmol) was added; the mixture was stirred at rt for 14 hrs. Then diluted with water and extracted with EA (30 mL×3). The combined organic phase was washed with brine, dried over Na$_2$SO$_4$, concentrated in vacuo to give the crude product, which was purified by prep-TLC (PE:EA=2:1) to provide Compound 210 (262 mg, 63% yield). $^1$H NMR (CDCl$_3$, 400 MHz) δ 7.50-7.48 (m, 2H), 7.36-7.31 (m, 2H), 7.19 (s, 1H), 7.03-7.00 (m, 1H), 6.91 (d, J=8.0 Hz, 1H), 6.87 (s, 1H), 6.59 (s, 1H), 4.66 (s, 2H), 3.38 (s, 3H), 2.15 (s, 3H). MS (ESI) m/z (M+H)$^+$ 431.0.

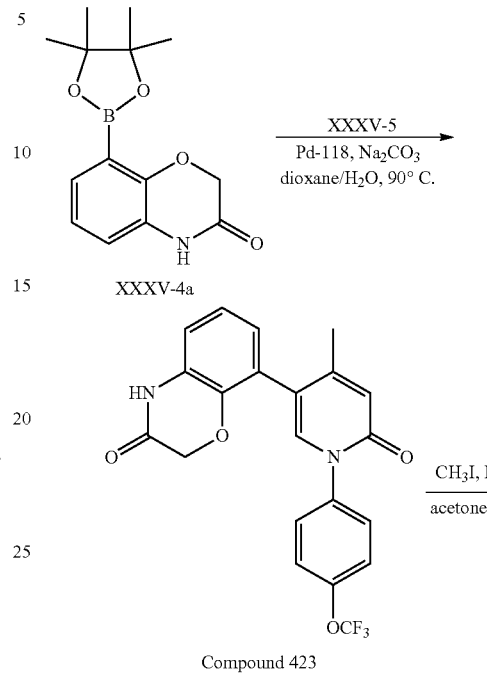

Compound 423

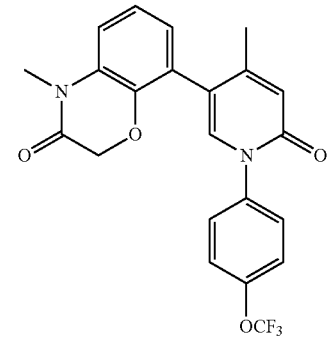

Compound 428

XXXV-4a was prepared by following the similar procedure for obtaining XXXV-4 using 2-amino-6-bromophenol in place of XXXV-1.

To the solution of XXV-4a (450 mg, 1.64 mmol) in dioxane/H$_2$O (10 mL/2 mL), XXV-5 (516 mg, 1.49 mmol), Na$_2$CO$_3$ (316 mg, 2.98 mmol) and Pd-118 (50 mg, 0.08 mmol) was added. The mixture was purged with nitrogen and stirred at 90° C. overnight. Then the mixture was diluted with EA (100 mL) and filtered. The organic phase was washed with brine, dried over Na$_2$SO$_4$, concentrated in vacuo to give the crude product. The residue was purified by column chromatography (PE/EA=2/1) to produce Compound 423 (440 mg, 65% yield). $^1$H NMR (CDCl$_3$, 400 MHz) δ 8.59 (s, 1H), 7.49 (d, J=8.8 Hz, 2H), 7.32 (d, J=8.4 Hz, 2H), 7.18 (s, 1H), 7.02-6.98 (m, 1H), 6.88-6.85 (m, 2H), 6.58 (s, 1H), 4.62 (s, 2H), 2.09 (s, 3H). MS (ESI) m/z (M+H)$^+$ 416.9.

To the stirring mixture of Compound 423 (370 mg, 0.89 mmol) in acetone (5 mL), K$_2$CO$_3$ (180 mg, 1.33 mmol) and iodomethane (139 mg, 0.98 mmol) were added in portions. The mixture was refluxed overnight. The mixture was cooled to rt and filtered. The filtrate was concentrated in vacuo to give the crude product. The residue was purified by column chromatography (PE/EA=2/1) to give Compound 428 (230 mg, 60% yield). $^1$H NMR (CDCl$_3$, 400 MHz) δ 7.49 (d, J=8.8 Hz, 2H), 7.32 (d, J=8.4 Hz, 2H), 7.17 (s, 1H), 7.11-7.07 (m, 1H), 7.04-7.02 (m, 1H), 6.91-6.89 (m, 1H), 6.58 (s, 1H), 4.62 (s, 2H), 3.40 (s, 3H), 2.08 (s, 3H). MS (ESI) m/z (M+H)$^+$ 431.0.

Compounds 424 and 425 were prepared following the similar procedure for obtaining Compounds 423 and 428 using 2-amino-5-bromophenol as starting material.

Compound 424: $^1$H NMR (CDCl$_3$, 400 MHz) δ 8.49 (s, 1H), 7.50-7.46 (m, 2H), 7.35-7.31 (m, 2H), 7.18 (s, 1H), 6.91 (s, 1H), 6.89-6.83 (m, 2H), 6.59 (s, 1H), 4.65 (s, 2H), 2.16 (s, 3H). MS (ESI) m/z (M+H)$^+$ 416.9.

Compound 425: $^1$H NMR (CDCl$_3$, 400 MHz) δ 7.48 (d, J=8.8 Hz, 2H), 7.33 (d, J=8.4 Hz, 2H), 7.19 (s, 1H), 7.01-6.92 (m, 3H), 6.58 (s, 1H), 4.65 (s, 2H), 3.39 (s, 3H), 2.17 (s, 3H). MS (ESI) m/z (M+H)$^+$ 431.0.

Compounds 426 and 427 were prepared following the similar procedure for obtaining Compounds 423 and 428 using 2-amino-3-bromophenol as starting material.

Compound 426: $^1$H NMR (CDCl$_3$, 400 MHz) δ 8.28 (s, 1H), 7.50 (d, J=8.8 Hz, 2H), 7.33 (d, J=8.4 Hz, 2H), 7.23 (s, 1H), 7.02 (d, J=4.8 Hz, 2H), 6.85-6.83 (m, 1H), 6.59 (s, 1H), 4.58 (s, 2H), 1.97 (s, 3H). MS (ESI) m/z (M+H)$^+$ 416.9.

Compound 427: $^1$H NMR (CDCl$_3$, 400 MHz) δ 7.46 (d, J=9.2 Hz, 2H), 7.34 (d, J=8.4 Hz, 2H), 7.24 (s, 1H), 7.10-7.08 (m, 2H), 6.91-6.89 (m, 1H), 6.63 (s, 1H), 4.61-4.50 (m, 2H), 3.04 (s, 3H), 2.07 (s, 3H). MS (ESI) m/z (M+H)$^+$ 431.0.

Compound 566 was obtained by reacting Compound 424 with 2-(2-bromoethoxy)tetrahydro-2H-pyran in DMF with the presence of Cs$_2$CO$_3$, followed by hydroxy group deprotection using TsOH. H$_2$O. $^1$H NMR (CDCl$_3$, 300 MHz) δ 7.47 (d, J=9.0 Hz, 2H), 7.33 (d, J=8.4 Hz, 2H), 7.18-7.13 (m, 2H), 6.94 (d, J=7.2 Hz, 2H), 6.58 (s, 1H), 4.67 (s, 2H), 4.16 (t, J=5.4 Hz, 2H), 3.98 (m, 2H), 2.16 (s, 3H). MS (ESI) m/z (M+H)$^+$ 461.0.

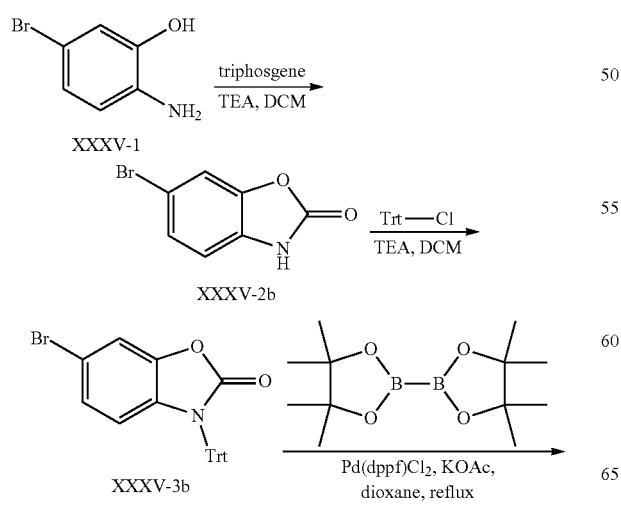

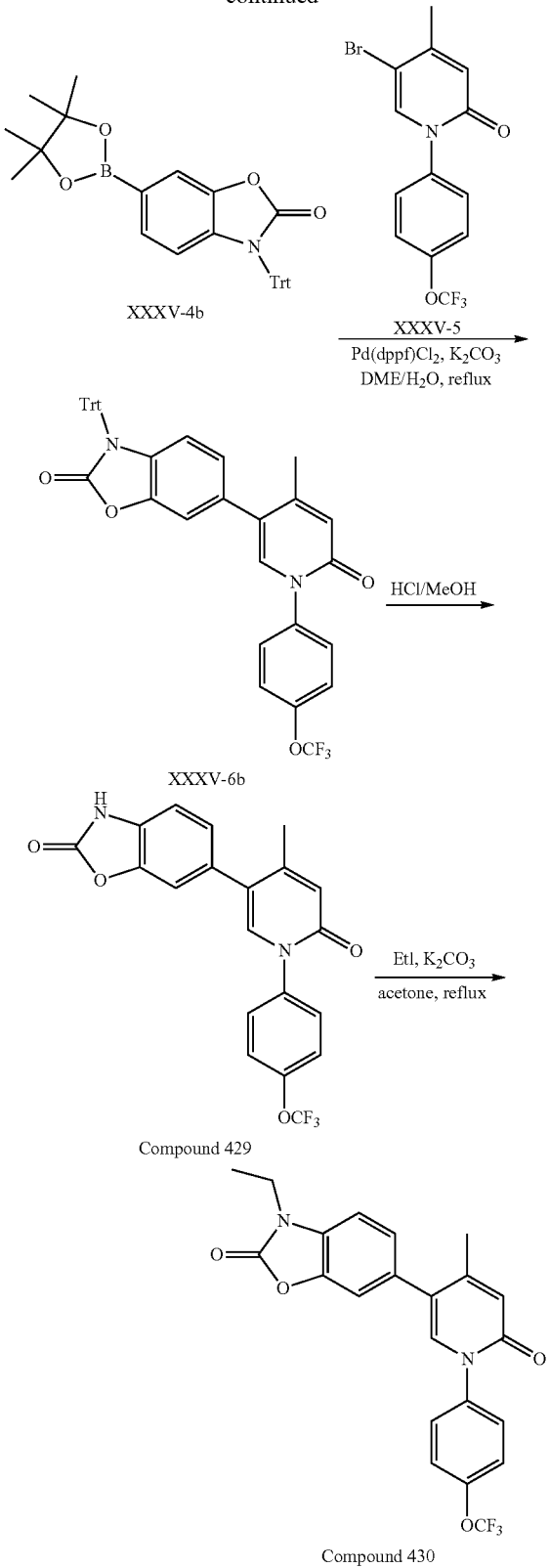

To a solution of XXXV-1 (3 g, 16 mmol) in dry DCM (50 mL) was added TEA (3.2 g, 32 mmol). The reaction mixture was cooled to 0° C., triphosgene (1.6 g, 5.3 mmol) was added slowly. The mixture was stirred overnight at rt, then quenched with water, extracted with DCM (80 mL×3). The combined organic layer was washed with brine, dried over anhydrous Na₂SO₄ and concentrated. The residue was purified by column chromatography on silica gel (PE/EA=10/1) to afford XXXV-2b (2.7 g, 79% yield).

To a solution of XXXV-2b (500 mg, 2.97 mmol) in dry DCM (20 mL) was added TEA (360 mg, 3.56 mmol) and Trt-Cl (992 mg, 3.56 mmol). The mixture was stirred overnight at rt, then poured into water, extracted with DCM (50 mL×3). The combined organic layer was washed with brine, dried over anhydrous Na₂SO₄, and concentrated in vacuo. The residue was purified by column chromatography on silica gel (PE/EA=10/1) to afford XXXV-3b (1.2 g, 89% yield).

XXXV-4b was prepared following the similar procedure for obtaining XXXV-4. MS (ESI) m/z (M+H)⁺ 503.9.

XXXV-6b was prepared following the similar procedure described in Method A. MS (ESI) m/z (M+H)⁺ 645.1.

Compound 429: XXXV-6b (800 mg, 1.24 mmol) was dissolved in a solution of HCl/MeOH (4 M, 50 mL), the mixture was stirred overnight at 70° C. And then the mixture was concentrated, the residue was diluted with water (20 mL) and adjusted to pH=7-8 with saturated aq. NaHCO₃, extracted with EtOAc (80 mL×3). The combined organic layer was washed with brine, dried over anhydrous Na₂SO₄, and concentrated in vacuo. The residue was purified by column chromatography on silica gel (PE/EA=10/1→5/1) to afford Compound 429 (370 mg, 74% yield).

Compound 430 was prepared following the similar procedure for obtaining Compound 428 using ethyl iodide instead of methyl iodide. ¹H NMR (CDCl₃, 400 MHz) δ 7.48-7.46 (m, 2H), 7.34-7.32 (m, 2H), 7.18 (s, 1H), 7.14 (s, 1H), 7.11-7.08 (m, 1H), 7.02-7.00 (m, 1H), 6.59 (s, 1H), 3.92 (q, J=7.2 Hz, 2H), 2.14 (s, 3H), 1.40 (t, J=7.2 Hz, 3H). MS (ESI) m/z (M+H)⁺431.1.

Compound 553 was prepared following the similar procedure described in the synthesis of Compound 429 using 2-amino-4-bromophenol in place of XXXV-1. ¹H NMR (DMSO-d₆, 400 MHz) δ 7.64 (d, J=6.8 Hz, 2H), 7.53-7.49 (m, 3H), 7.32 (d, J=8.0 Hz, 1H), 7.10 (d, J=8.4 Hz, 2H), 6.48 (s, 1H), 2.13 (s, 3H). MS (ESI) m/z [M+H]+ 403.0.

Compound 554 was prepared following the similar procedure described in the synthesis of Compound 430. ¹H NMR (DMSO-d₆, 400 MHz) δ 7.66-7.63 (m, 2H), 7.58 (s, 1H), 7.53-7.51 (m, 2H), 7.40-7.37 (m, 2H), 7.18-7.15 (m, 1H), 6.50 (s, 1H), 3.86 (q, J=6.8 Hz, 2H), 2.16 (s, 3H), 1.26 (t, J=6.8 Hz, 3H). MS (ESI) m/z [M+H]+ 431.1.

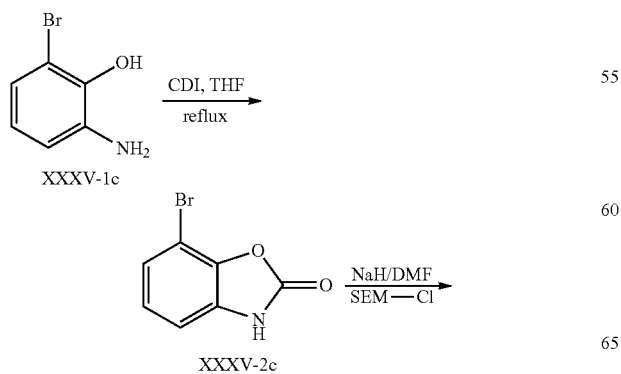

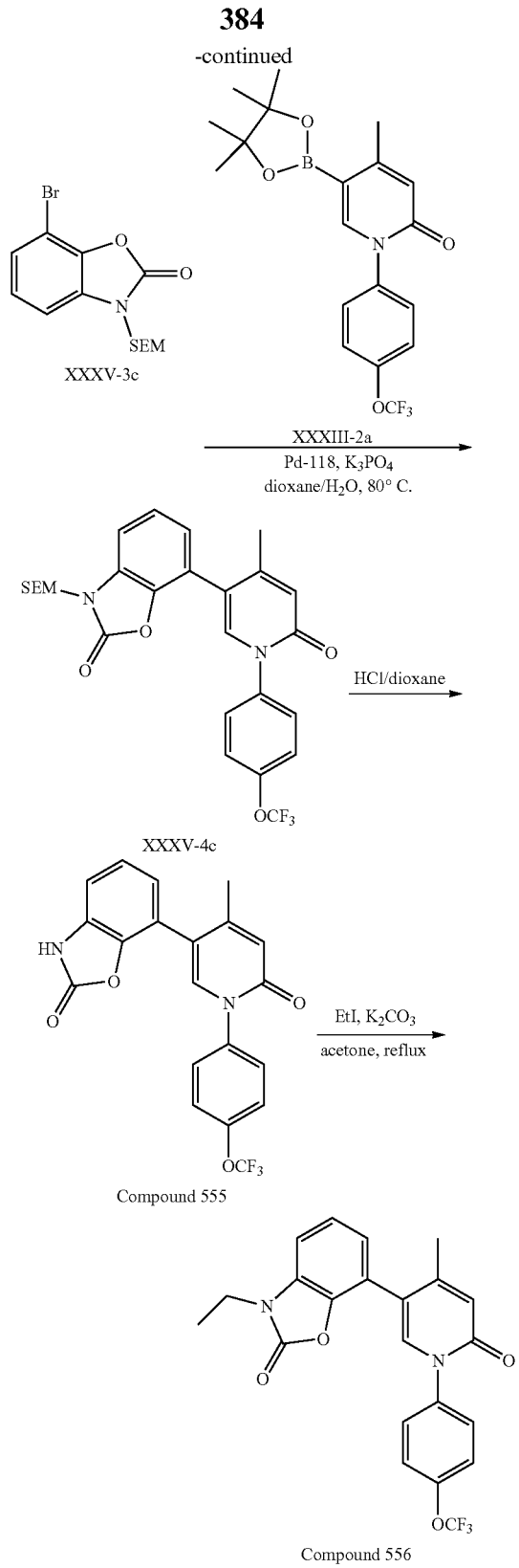

To a solution of XXXV-1c (200 mg, 1.08 mmol) in dry THF (15 ml) was added CDI (262 mg, 1.62 mmol). The reaction mixture was heated to reflux overnight, then quenched with water, extracted with EA, the organic layer was washed with brine, dried over anhydrous Na₂SO₄, and concentrated in vacuo. The residue was purified by chromatography on silica gel (PE:EA=10:1) to afford XXXV-2c (160 mg, yield 70%).

To a solution of XXXV-2c (5.3 g, 25 mmol) in DMF (20 mL) was added NaH (60% dispersion in mineral oil, 1.5 g, 37.5 mmol) at 0° C., The mixture was stirred for 30 mins at rt, then SEM-Cl (6.2 g, 37.5 mmol) was added slowly, and then the reaction mixture was stirred overnight at rt. The mixture was poured into water, extracted with EA, the organic layer was washed with brine, dried over anhydrous $Na_2SO_4$, and concentrated. The residue was purified by chromatography on silica gel (PE:EA=15:15:1) to afford XXXV-3c (2.7 g, yield 31%).

XXXV-4c was prepared following the similar procedure described in the synthesis of Compound 423. Compound 555 was prepared by acid hydrolysis of XXXV-4c. $^1$H NMR (CD$_3$OD, 400 MHz) δ 7.62-7.57 (m, 3H), 7.45 (d, J=8.4 Hz, 2H), 7.22 (d, J=8.0 Hz, 1H), 7.13-7.06 (m, 2H), 6.62 (s, 1H), 2.19 (s, 3H). MS (ESI) m/z [M+H]$^+$ 403.1.

Compound 556 was prepared following the similar procedure described in the synthesis of Compound 430. $^1$H NMR (CD$_3$OD, 400 MHz) δ 7.63-7.57 (m, 3H), 7.46-7.44 (d, J=8.4 Hz, 2H), 7.31-7.26 (m, 2H), 7.13-7.11 (d, J=7.6 Hz, 1H), 6.62 (s, 1H), 3.94 (q, J=7.2 Hz, 2H), 2.18 (s, 3H), 1.36 (t, d=7.2 Hz, 3H). MS (ESI) m/z [M+H]+ 431.0.

Compound 558 was prepared by reacting Compound 429 with (2-bromoethoxy)(tert-butyl)dimethylsilane in acetone with the presence of $K_2CO_3$, followed by deprotection of the TBDMS protecting group using TBAF. $^1$H NMR (CDCl$_3$, 400 MHz) δ 8.19 (s, 1H), 7.47 (d, J=8.8 Hz, 2H), 7.33 (d, J=8.4 Hz, 2H), 7.19 (s, 1H), 7.05 (d, J=8.4 Hz, 1H), 7.00 (s, 1H), 6.88 (d, J=2.0 Hz, 1H), 6.57 (s, 1H), 4.67 (t, J=8.0 Hz, 2H), 4.19 (t, J=8.0 Hz, 2H), 2.17 (s, 3H). MS (ESI) m/z [M+H]$^+$ 447.2

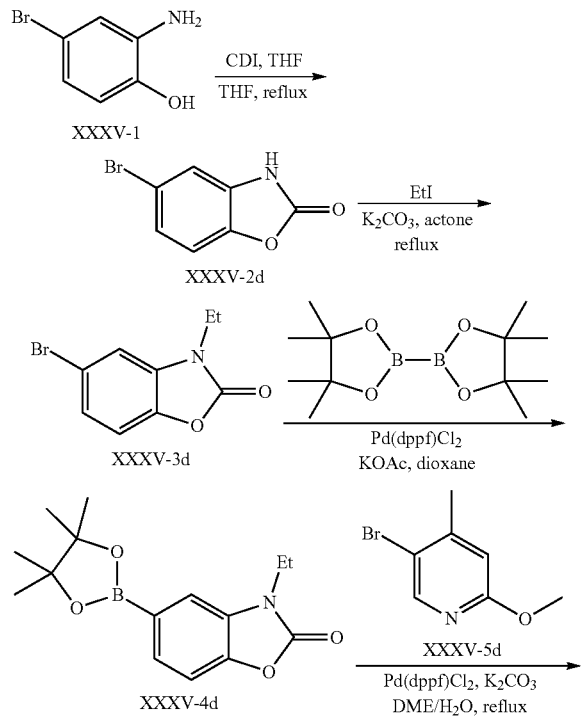

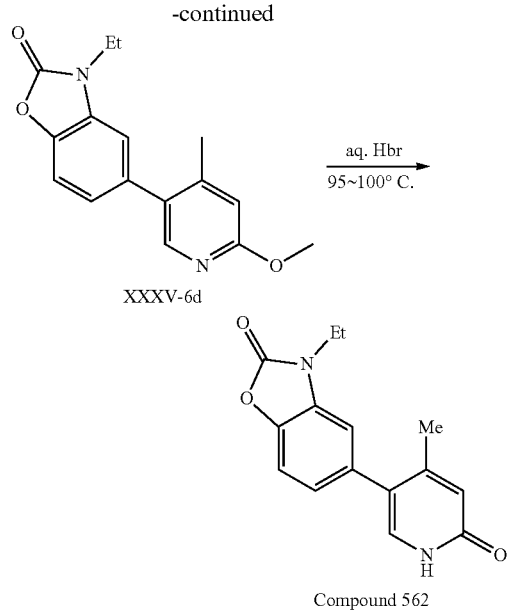

XXXV-2d was prepared following the similar procedure described in the synthesis of XXXV-2c. XXXV-4d was prepared by reacting XXXV-2d with ethyl iodide followed by Suzuki-coupling using the standard procedure described in the synthesis of XXXV-4b.

XXXV-6d was prepared by reacting XXXV-4d with XXXV-5d using Method A as described herein. Compound 562 was obtained from acid hydrolysis of XXXV-6d. 1H NMR (DMSO-d$_6$, 300 MHz) δ 11.65 (s, 1H), 7.35-7.39 (m, 2H), 7.29 (s, 1H), 7.12 (d, J=7.8 Hz, 1H), 6.35 (s, 1H), 3.95 (t, J=6.6 Hz, 2H), 2.14 (s, 3H), 1.32 (t, J=6.6 Hz, 3H). MS (ESI) m/z (M+H)$^+$ 270.9.

Compound 662 was prepared following the similar procedure described in the synthesis of Compound 562 using ClCH$_2$COCl in place of CDI in the reaction with XXXV-1. The subsequent reaction with EtI was eliminated. After the second Suzuki-Coupling reaction, methyl iodide was used to methylate the proton on the benzo[b][1,4]oxazin-3(4H)-one moiety before performing the HBr hydrolysis. $^1$H NMR (DMSO-d$_6$, 400 MHz) δ 7.21 (s, 1H), 7.08 (s, 1H), 7.02 (d, J=8.0 Hz, 1H), 6.96 (d, J=8.0 Hz, 1H), 6.27 (s, 1H), 4.67 (s, 2H), 3.29 (s, 3H), 2.07 (s, 3H). MS (ESI) m/z (M+H)$^+$ 270.9.

Compound 663 was prepared following the similar procedure described in the synthesis of Compound 562 using Trt-Cl in place of EtI in the reaction with XXXV-2d and 5-bromo-4-methyl-1-((2-(trimethylsilyl)ethoxy)methyl) pyridin-2(1H)-one was used in place of XXXV-5d. Finally, the trityl group was removed by HCl in MeOH solution. $^1$H NMR (DMSO-d$_6$, 400 MHz) δ 11.73 (s, 1H), 7.31 (d, J=8.4 Hz, 1H), 7.25 (s, 1H), 7.01 (s, 1H), 7.00 (d, J=6.8 Hz, 1H), 6.33 (s, 1H), 2.05 (s, 3H). MS (ESI) m/z (M+H)$^+$ 243.1.

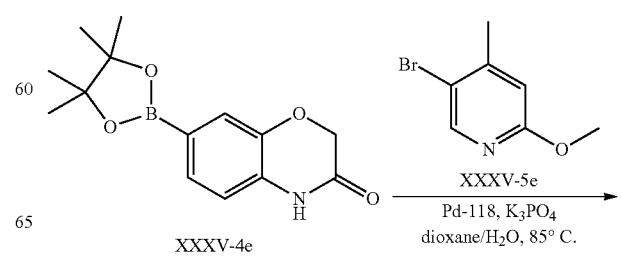

-continued

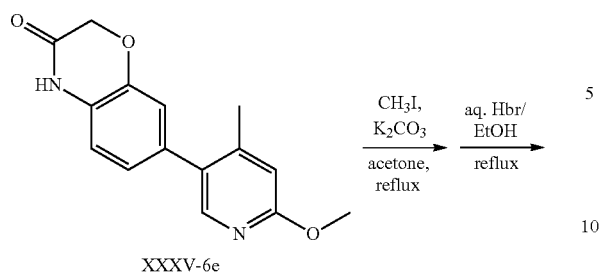

XXXV-6e

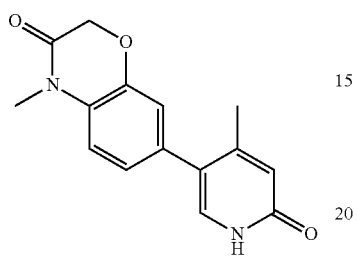

Compound 563

XXXV-4e was prepared by following the similar procedure for obtaining XXXV-4 using 2-amino-5-bromophenol in place of XXXV-1. XXXV-6e was obtained by reacting XXXV-4e with XXXV-5e following the similar procedure described in the synthesis of Compound 423. Compound 563 was obtained by methylation of XXXV-6e followed by HBr hydrolysis. $^1$H NMR (DMSO-d$_6$, 400 MHz) δ 11.54 (s, 1H), 7.17-7.15 (m, 2H), 6.99-6.95 (m, 2H), 6.24 (s, 1H), 4.65 (s, 2H), 3.27 (s, 3H), 2.04 (s, 3H).

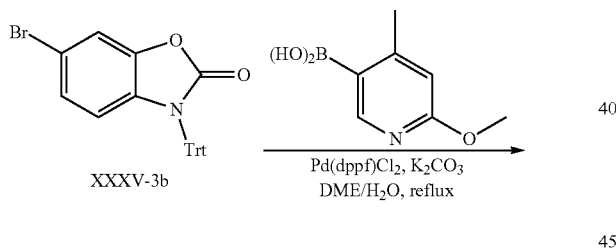

XXXV-3b

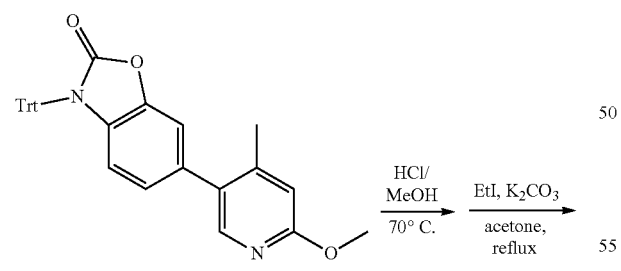

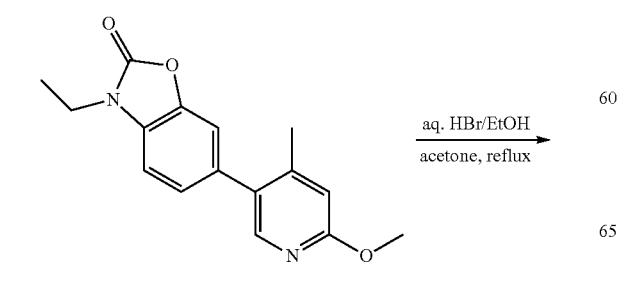

-continued

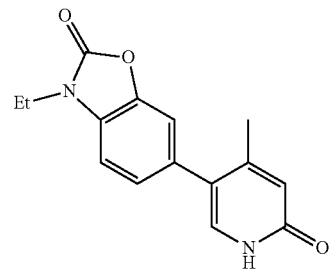

Compound 564

Compound 564 was prepared from XXXV-3b following the synthetic scheme described above. $^1$H NMR (400 MHz, CDCl$_3$) δ 7.26-7.23 (m, 1H), 7.10 (s, 1H), 7.06-7.00 (m, 2H), 6.49 (s, 1H), 3.92 (q, J=7.2 Hz, 2H), 2.13 (s, 3H), 1.42 (t, J=7.2 Hz, 3H). MS (ESI) m/z [M+H]+ 270.9

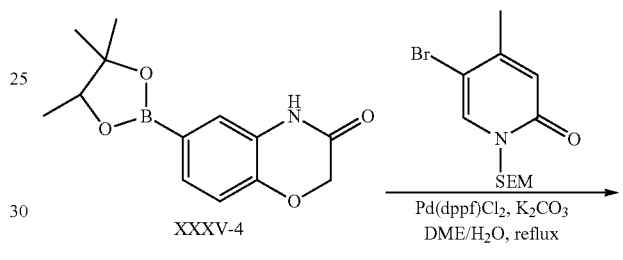

XXXV-4

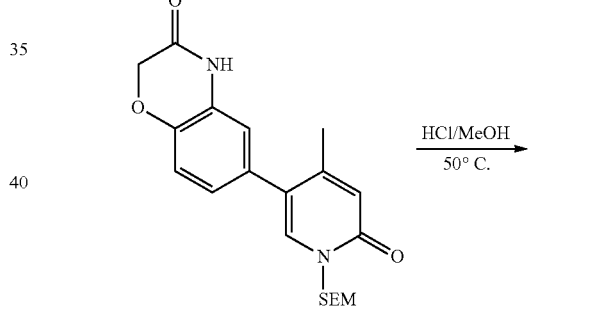

Compound 567

Compound 567 was prepared by Suzuki-Coupling of XXXV-4 with SEM-protected 5-bromo-4-methylpyridin-2 (1H)-one, followed by HCl hydrolysis. $^1$H NMR (DMSO-d$_6$, 300 MHz) δ 11.54 (s, 1H), 10.74 (s, 1H), 7.14 (s, 1H), 6.97 (d, J=8.0 Hz, 1H), 6.85 (d, J=6.0 Hz, 1H), 6.78 (s, 1H), 6.27 (s, 1H), 4.64 (s, 2H), 2.04 (s, 3H). MS (ESI) m/z (M+H)$^+$ 257.0.

Example 13-A

Synthesis of 4-Methyl, 5-Pyrazole analogs (Scheme XXXVI)

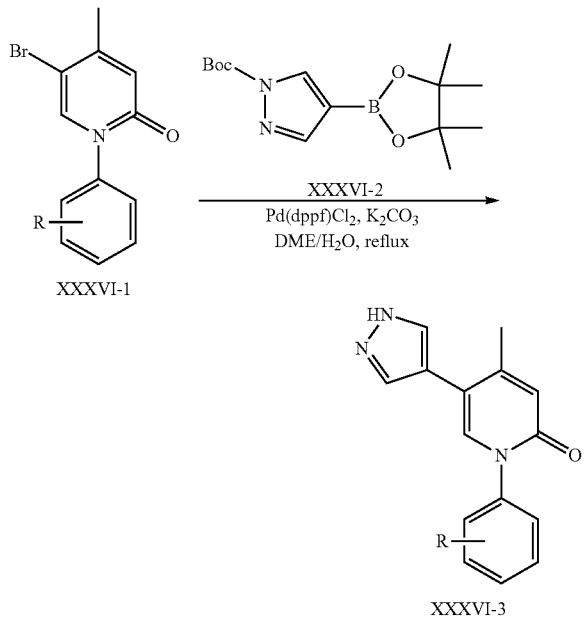

To a solution of XXXVI-1 (1 eq.) in DME/H₂O (v/v=10/1) was added K₂CO₃ (2 eq.), XXXVI-2 (1.5 eq.), Pd(dppf)Cl₂ (0.1 eq.). The mixture was purged with nitrogen and then heated at reflux overnight. The mixture was cooled to rt, diluted with water, extracted with EtOAc. The combined organic layer was washed with brine, dried over anhydrous Na₂SO₄, and concentrated in vacuo. The residue was purified by flash chromatography to give the final product.

Compound 217: $^1$H NMR (CD₃OD, 400 MHz) δ 7.85-7.65 (m, 3H), 7.59-7.55 (m, 2H), 7.48-7.45 (m, 1H), 7.17-7.14 (m, 1H), 6.57 (s, 1H), 2.31 (s, 3H), 2.13 (s, 3H).

Compound 218: $^1$H NMR (CDCl₃, 400 MHz) δ 7.60 (s, 2H), 7.47 (d, J=8.0 Hz, 2H), 7.34 (d, J=8.0 Hz, 2H), 7.24 (s, 1H), 6.59 (s, 1H), 2.22 (s, 3H). MS (ESI) m/z (M+H)⁺ 336.0.

Compound 219: $^1$H NMR (CDCl₃, 400 MHz) δ 7.58 (s, 2H), 7.16-7.10 (m, 2H), 6.84-6.79 (m, 2H), 6.60 (s, 1H), 4.04 (q, J=6.8 Hz, 2H), 2.23 (s, 3H), 2.16 (s, 3H), 1.42 (t, J=6.8 Hz, 3H).

Compound 220: $^1$H NMR (CDCl₃, 400 MHz) δ 7.59 (s, 2H), 7.26 (s, 2H), 6.60 (s, 3H), 3.86 (s, 9H), 2.23 (s, 3H). MS (ESI) m/z (M+H)⁺ 342.1.

The 4-methyl, 5-(1-Me) pyrazole analogs were prepared following the same procedure for obtaining XXXVI-3 using 1-methyl-4-(4,4,5,5-tetramethyl-1,3,2-dioxaborolan-2-yl)-1H-pyrazole in place of XXXVI-2.

Compound 221: $^1$H NMR (CDCl₃, 400 MHz) δ 7.50 (s, 1H), 7.26 (s, 1H), 6.59-6.55 (m, 4H), 3.86 (s, 12H), 2.30 (s, 3H). MS (ESI) m/z (M+H)⁺ 356.0.

Compound 226: $^1$H NMR (CD₃OD, 400 MHz) δ 7.81-7.71 (m, 5H), 7.59-7.57 (m, 2H), 6.57 (s, 1H), 3.91 (s, 3H), 2.31 (s, 3H). MS (ESI) m/z (M+H)⁺ 334.1.

Compound 227: $^1$H NMR (CD₃OD, 400 MHz) δ 7.51-7.47 (m, 2H), 7.38-7.37 (m, 2H), 7.30-7.25 (m, 2H), 7.21 (s, 1H), 6.56 (s, 1H), 3.94 (s, 3H), 2.22 (s, 3H). MS (ESI) m/z (M+H)⁺ 350.1.

Compound 228: $^1$H NMR (CD₃OD, 400 MHz) δ 7.86-7.84 (m, 2H), 7.71 (s, 1H), 7.67-7.65 (m, 2H), 7.61-7.58 (m, 2H), 6.58 (s, 1H), 3.92 (s, 3H), 2.31 (s, 3H). MS (ESI) m/z (M+H)⁺ 334.1.

Compounds 225, 229 and 230 were prepared following Method 1 as described in Example 12-B.

Compound 225: $^1$H NMR (CD₃OD, 400 MHz) δ 9.08 (s, 1H), 8.13 (d, J=2.0 Hz, 1H), 8.08-8.04 (m, 1H), 7.58-7.55 (m, 1H), 7.50 (s, 1H), 7.39 (s, 1H), 7.33 (s, 1H), 6.61 (s, 1H), 3.94 (s, 3H), 2.25 (s, 3H). MS (ESI) m/z (M+H)⁺ 322.9.

Compound 229: $^1$H NMR (CDCl₃, 400 MHz) δ 7.45 (s, 1H), 7.36-7.32 (m, 2H), 7.28-7.25 (m, 1H), 7.14 (d, J=8.0 Hz, 1H), 7.05 (s, 1H), 6.57 (s, 1H), 3.93 (s, 3H), 2.23 (s, 3H), 2.16 (s, 3H). MS (ESI) m/z (M+Na)⁺ 314.1.

Compound 230: $^1$H NMR (CDCl₃, 400 MHz) δ 7.47 (s, 1H), 7.46-7.37 (m, 3H), 7.28-7.23 (m, 1H), 7.15 (s, 1H), 6.58 (s, 1H), 3.93 (s, 3H), 2.22 (s, 3H). MS (ESI) m/z (M+Na)⁺283.9.

Compound 222 was prepared following a modified Method 1 procedure, using DMSO in place of DCM and the molecular sieve was not used. $^1$H NMR (CDCl₃, 300 MHz) δ 7.45 (s, 1H), 7.34 (s, 1H), 7.19 (s, 1H), 6.94-6.91 (m, 2H), 6.85-6.81 (m, 1H), 6.50 (s, 1H), 4.26 (s, 4H), 3.92 (s, 3H), 2.19 (s, 3H). MS (ESI) m/z [M+H]⁺ 324.

Compounds 223 and 224 were prepared following the similar procedure as described in the synthesis of Compound 222. Compound 223: $^1$H NMR (CDCl₃, 300 MHz) δ 7.40 (s, 1H), 7.29 (s, 1H), 7.14 (s, 1H), 6.83-6.79 (m, 2H), 6.74-6.71 (m, 1H), 6.48 (s, 1H), 5.96 (s, 2H), 3.87 (s, 3H), 2.15 (s, 3H). MS (ESI) m/z [M+H]⁺ 310.0. Compound 224: $^1$H NMR (CDCl₃, 400 MHz) δ 8.17 (s, 1H) 7.81 (s, 1H), 7.70-7.67 (d, J=8.8 Hz, 1H), 7.48-7.45 (m, 2H), 7.38 (s, 1H), 7.28 (s, 1H), 6.59 (s, 1H), 3.94 (s, 3H), 2.24 (s, 3H). MS (ESI) m/z [M+H]⁺ 307.1.

Compounds 231 and 232 were prepared following Method 3 as described in Example 12-B.

Compound 231: $^1$H NMR (CDCl₃, 400 MHz) δ 8.06 (s, 1H), 7.57 (s, 1H), 7.43 (s, 1H), 6.87-6.72 (m, 4H), 4.28-4.22 (m, 4H), 3.96 (s, 1H), 2.37 (s, 3H). MS (ESI) m/z [M+H]⁺ 323.9.

Compound 232: $^1$H NMR (CDCl₃, 400 MHz) δ 7.47 (s, 1H), 7.36 (s, 1H), 7.21 (s, 1H), 6.93-6.85 (m, 3H), 6.57 (s, 1H), 6.04 (s, 2H), 3.94 (s, 3H), 2.21 (s, 3H). MS (ESI) m/z [M+H]⁺ 309.8.

Compound 431 was prepared following the similar procedure for obtaining XXXVI-3 using Pd-118 and K₃PO₄ instead of Pd(dppf)Cl₂ and K₂CO₃. The Boc protecting group was subsequently removed in HCl/MeOH solution at rt. $^1$H NMR (CDCl₃, 400 MHz) δ 7.59 (s, 2H), 7.47-7.45 (m, 2H), 7.38-7.35 (m, 2H), 7.23 (s, 1H), 6.59 (s, 1H), 2.22 (s, 3H). MS (ESI) m/z (M+H)⁺ 285.9.

Example 13-B

Synthesis of Compound 233 (Scheme XXXVII)

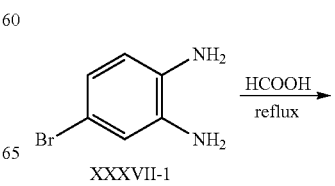

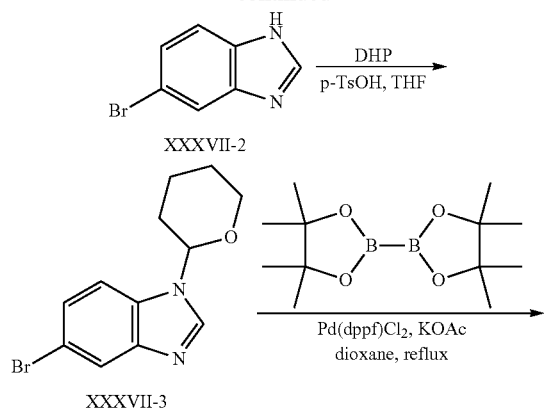

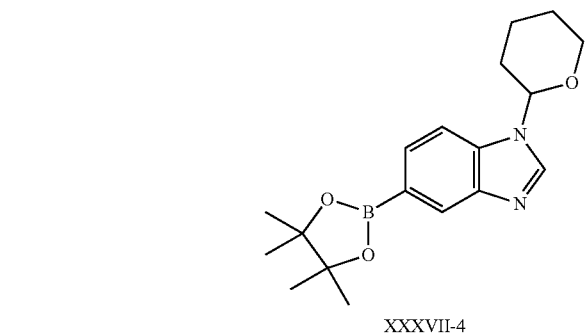

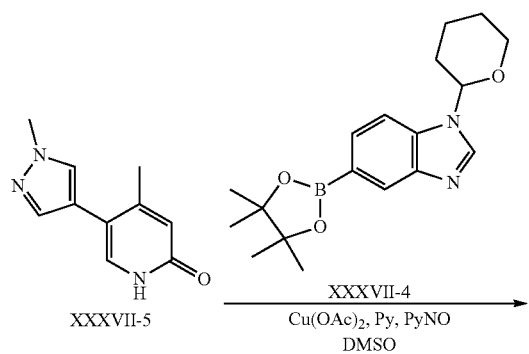

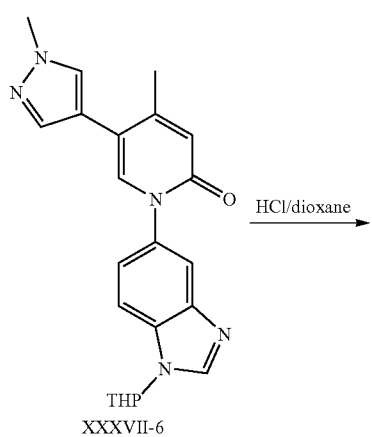

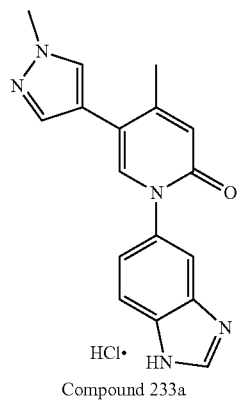

Compound 233a

A solution of XXXVII-1 (10 g, 53.4 mmol) in HCOOH (50 mL) was heated at reflux for 2 hours, after cooled to rt, aq.NaOH (10%) was added slowly until the mixture was basic. Then extracted with EtOAc (100 mL×3), the combined organic layers were washed with brine, dried over Na$_2$SO$_4$, and concentrated in vacuo to give XXXVII-2 (9 g, 85% yield).

To a solution of XXXVII-2 (5 g, 25.4 mmol) in THF (35 mL) was added p-T$_s$OH (1.3 g, 7.6 mmol), DHP (35 ml). The reaction mixture was stirred at 60° C. overnight. The reaction mixture was poured into ice-water, and the aqueous was extracted with EA (50 mL×3), the combined organic layers were washed with brine, dried over Na$_2$SO$_4$, and concentrated in vacuo to give crude XXXVII-3 (4.8 g, 67% yield).

To a solution of XXXVII-3 (1 g, 3.5 mmol) in dioxane (20 mL) was added KOAc (0.69 g, 7 mmol), bis(pinacolato) diboron (0.95 g 3.67 mmol), Pd(dppf)Cl$_2$ (0.25 g, 0.035 mmol) under N$_2$ protection. The reaction mixture was degassed with nitrogen, and then heated to reflux overnight. The reaction mixture was poured into ice-water, and the aqueous was extracted with EA (60 mL×3), the combined organic layers were washed with brine, dried over Na$_2$SO$_4$, and concentrated in vacuo to give crude XXXVII-4 (0.8 g, 70% yield).

XXXVII-6 was prepared following the procedure described in the synthesis of Compound 222. MS (ESI) m/z [M+H]$^+$ 390.1.

XXXVII-6 (200 mg, 0.5 mmol) was dissolved in a solution of HCl/dioxane (4 M, 50 mL), the mixture was stirred overnight at rt, the mixture was concentrated to yield the hydrochloride salt Compound 233a (120 mg, 79% yield). $^1$H NMR (DMSO-d$_6$, 400 MHz) δ 9.66 (s, 1H), 7.99-7.94 (m, 2H), 7.90 (s, 1H), 7.64-7.60 (m, 3H), 6.48 (s, 1H), 3.84 (s, 3H), 2.55 (s, 3H). MS (ESI) m/z [M+H]$^+$ 305.9.

Compound 235 was prepared from Compound 122 following the similar procedure for obtaining Compound 199. $^1$HNMR (CD$_3$OD, 400 MHz) δ 7.76 (s, 1H), 7.59-7.54 (m, 4H), 7.48 (d, J=8.4 Hz, 2H), 6.58 (s, 1H), 3.94 (s, 3H), 2.65 (q, J=7.6 Hz, 2H), 1.19 (t, J=7.6 Hz, 3H). MS (ESI) m/z (M+H)$^+$ 364.0.

Example 13-C

Synthesis of Compound 236 (Scheme XXXVIII)

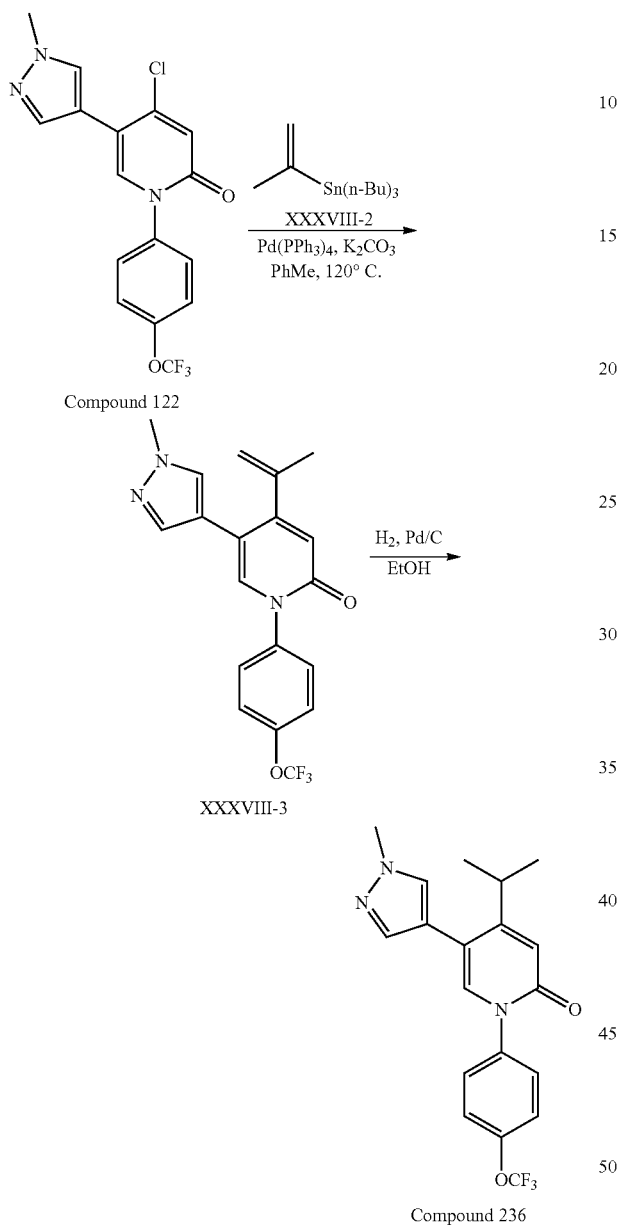

Compound 236

To a stirred mixture of Compound 122 (200 mg, 0.54 mmol), XXXVIII-2 (270 mg, 0.81 mmol), and K$_3$CO$_3$ (150 mg, 1.08 mmol) in toluene (6 mL) was added Pd(PPh$_3$)$_4$ (60 mg, 0.054 mmol). The mixture was purged with nitrogen for three times and then heated at 120° C. overnight. The mixture was concentrated to remove solvent, diluted with H$_2$O (10 mL), extracted with EtOAc (20 mL×3). The combined organic layer was washed with brine, dried over anhydrous Na$_2$SO$_4$, and concentrated in vacuo. The crude product was purified by prep-HPLC to give XXXVIII-3 (130 mg, 64% yield).

A mixture of XXXVIII-3 (130 mg, 0.259 mmol) and Pd/C in ethanol (5 mL) was stirred under H$_2$ at rt for 1 hour. Filtered the mixture, and concentrated to give Compound 236 (86.2 mg, 66% yield). $^1$H NMR (CDCl$_3$, 400 MHz) δ 7.48-7.45 (m, 3H), 7.36-7.31 (m, 3H), 7.17 (s, 1H), 6.63 (s, 1H), 3.95 (s, 3H), 2.97-2.90 (m, 1H), 1.17 (d, J=6.8 Hz, 6H). MS (ESI) m/z (M+H)$^+$ 378.1.

Example 13-D

Synthesis of Compound 238 (Scheme XXXIX)

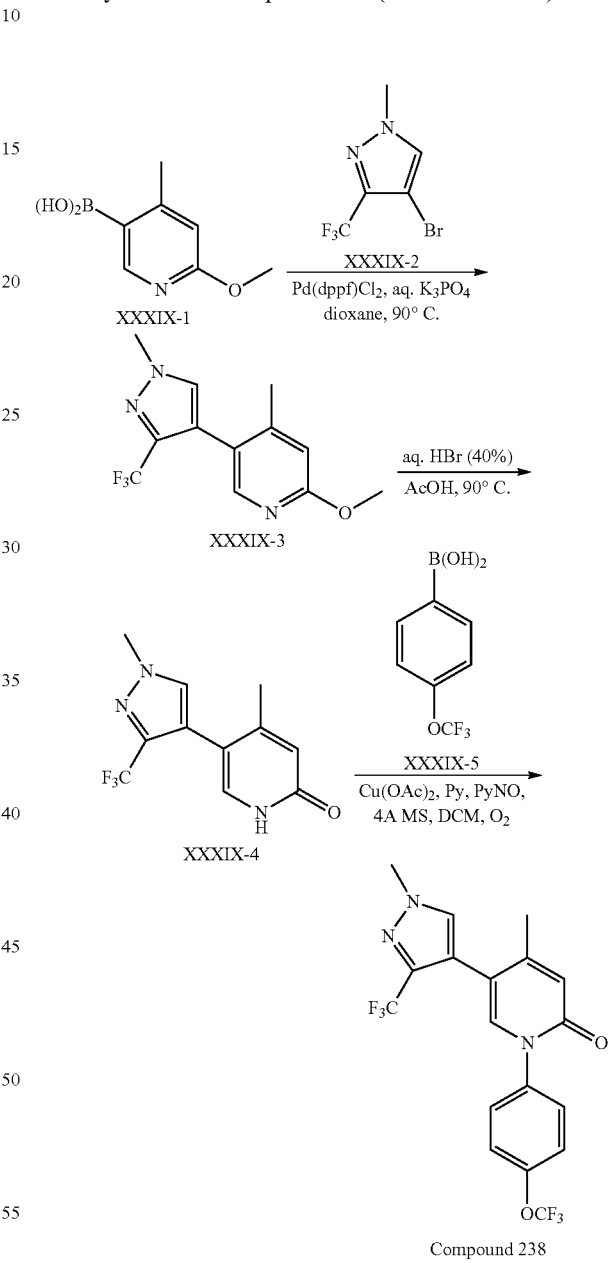

Compound 238

To a stirred mixture of XXXIX-1 (400 mg, 2.4 mmol), XXXIX-2 (500 mg, 2.18 mmol), and K$_3$PO$_4$ (2 M, 1.1 mL, 2.2 mmol) in dioxane (20 mL) was added Pd(dppf)Cl$_2$ (160 mg, 0.218 mmol) under N$_2$ protection. The reaction mixture was degassed with nitrogen again and stirred at 90° C. overnight. The mixture was concentrated, diluted with H$_2$O (20 mL), extracted with EtOAc (30 mL×3). The combined organic layer was washed with brine, dried over anhydrous Na$_2$SO$_4$, and concentrated in vacuo. The residue was purified by column chromatography (PE/EA=2/1) to give XXXIX-3 (400 mg, 67% yield).

A mixture of XXXIX-3 (400 mg, 1.48 mmol) in aq. HBr (40%, 10 mL) and HOAc (5 mL) was stirred at 90° C. for 12 hrs. After being cooled to rt, the mixture was poured into water (20 mL), neutralized with Na$_2$CO$_3$, and then extracted with DCM/i-PrOH (30 mL×3, v/v=9/1). The combined organic layer was washed with brine, dried over anhydrous Na$_2$SO$_4$, and concentrated in vacuo to afford crude XXXIX-4 (220 mg, 58% yield) as light yellow oil. MS (ESI) m/z (M+H)$^+$257.9.

Compound 238 was prepared following the general procedure described in Method 1 as pale yellow solid (80 mg, 24% yield). $^1$H NMR (CDCl$_3$, 400 MHz) δ 7.46-7.40 (m, 3H), 7.34-7.30 (m, 2H), 7.19 (s, 1H), 6.56 (s, 1H), 3.99 (s, 3H), 2.05 (s, 3H). MS (ESI) m/z (M+H)$^+$418.0.

Compound 237 was prepared following the similar procedure for obtaining Compound 238 using (1,3,5-trimethyl-1H-pyrazol-4-yl)boronic acid in place of XXXIX-1 and 5-bromo-2-methoxy-4-methylpyridine in place of XXXIX-2. $^1$H NMR (CDCl$_3$, 400 MHz) δ 7.45-7.41 (m, 2H), 7.31-7.26 (m, 2H), 7.04 (s, 1H), 6.54 (s, 1H), 3.73 (s, 3H), 2.09 (s, 3H), 2.07 (s, 3H), 1.96 (s, 3H). MS (ESI) m/z [M+H]$^+$ 378.2.

Compound 239 was prepared following the similar procedure for obtaining Compound 238 using (4-ethoxy-2-methylphenyl)boronic acid in place of XXXIX-5 as a pale yellow solid. $^1$H NMR (CDCl$_3$, 400 MHz) δ 7.40 (s, 1H), 7.10-7.05 (m, 2H), 6.85-6.75 (m, 2H), 6.55 (s, 1H), 4.02 (q, J=6.8 Hz, 2H), 3.97 (s, 3H), 2.11 (s, 3H), 2.04 (s, 3H), 1.40 (t, J=6.8 Hz, 3H). MS (ESI) m/z (M+H)$^+$ 392.1.

Example 13-E

Synthesis of Compound 234 (Scheme XL)

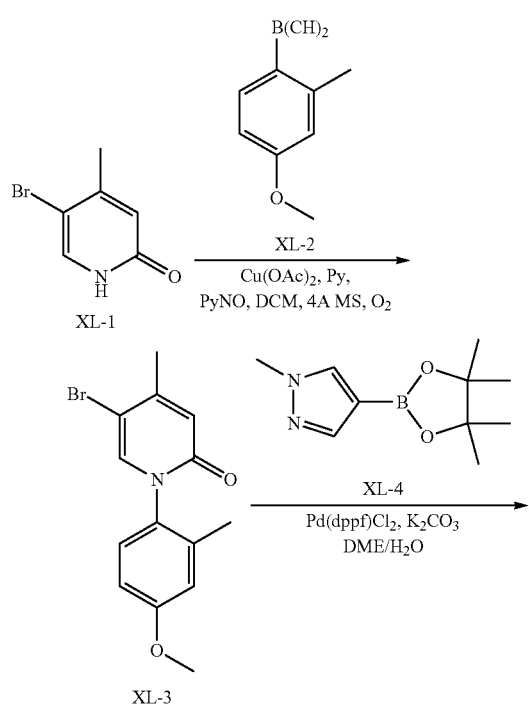

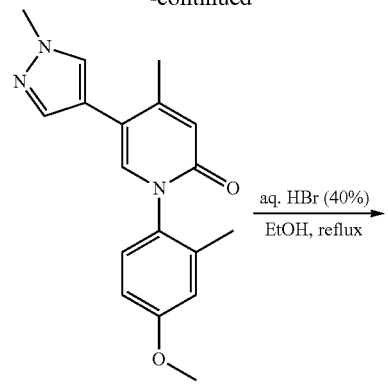

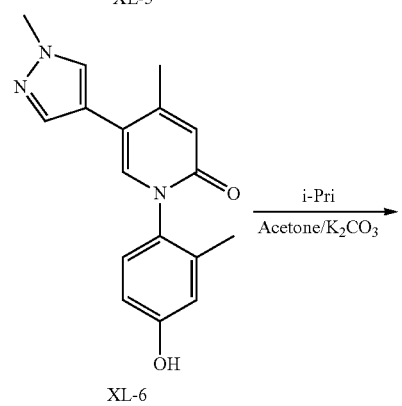

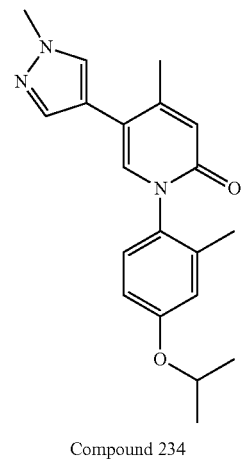

Compound 234

XL-6 was prepared following the synthesis scheme described herewith.

To a solution of XL-6 (100 mg, 0.34 mmol) in acetone (10 mL) was added compound 2-iodopropane (83.7 mg, 0.51 mmol), and K$_2$CO$_3$ (84 mg, 0.68 mmol). The reaction mixture was heated to reflux overnight. After cooling to rt, the mixture was poured into ice-water, extracted with EA (50 mL×3). The combined organic layer was washed with brine and concentrated to give crude product. The residue was purified by prep-HPLC to give Compound 234 (50 mg, 44% yield) as a white solid. $^1$H NMR (CDCl$_3$, 400 MHz) δ 7.46 (s, 1H), 7.35 (s, 1H), 6.98 (s, 1H), 7.10-7.07 (m, 2H), 6.8 (s, 1H), 6.78-6.76 (m, 1H), 6.56 (s, 1H), 4.57-4.51 (m, 1H), 3.92 (s, 3H), 2.23 (s, 3H), 2.13 (s, 3H), 1.34 (d, J=6 Hz, 6H). MS (ESI) m/z [M+H]$^+$ 337.9.

Compound 240 was prepared following the similar procedure for obtaining Compound 234 using 5-bromo-4-(trifluoromethyl)pyridin-2(1H)-one in place of XL-1 and (4-(trifluoromethoxy)phenyl)boronic acid in place of XL-2. $^1$H NMR (CDCl$_3$, 400 MHz) δ 7.48-7.46 (m, 3H), 7.42 (s, 1H), 7.38-7.25 (m, 3H), 7.07 (s, 1H), 3.94 (s, 3H). MS (ESI) m/z [M+H]$^+$ 403.9.

Example 14-A

Synthesis of Compound 243 (Scheme XLI)

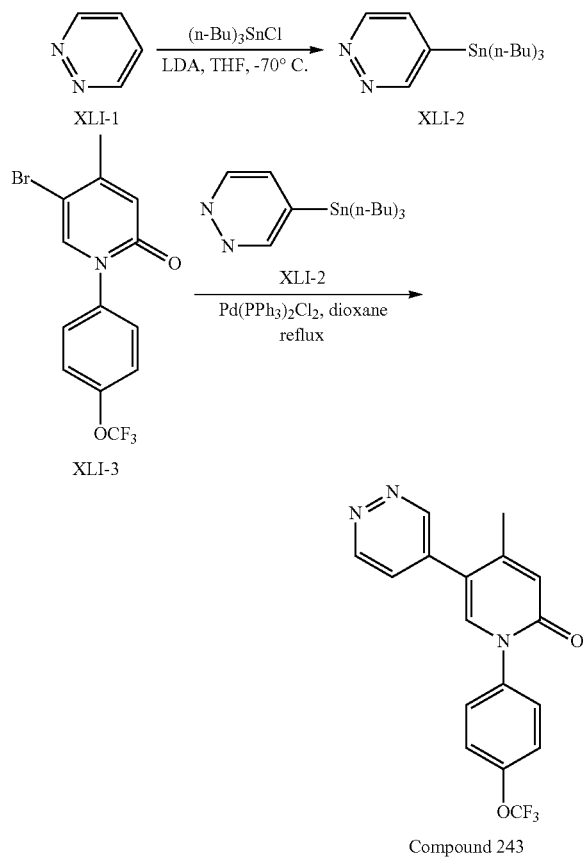

Compound 243

A solution of LDA (1 M in THF, 10 mL, 10 mmol) was added dropwise to a solution of XLI-1 (0.8 g, 10 mmol) and (n-Bu)$_3$SnCl (3.7 g, 11 mmol) in THF (10 mL) at −70° C. under N$_2$. The reaction mixture was stirred at −70° C. for 1 hour. The reaction was quenched with saturated aq. NH$_4$Cl (50 mL) and extracted with EA (50 mL×3), the organic layer dried over Na$_2$SO$_4$, and concentrated under reduced pressure. The residue was purified by column chromatography on silica gel (PE/EA=1/1) to give XLI-2 (1 g, 27% yield).

To a mixture of XLI-3 (0.2 g, 0.58 mmol) and XLI-2 (0.43 g, 1.2 mmol) in dioxane (20 mL) was added Pd(PPh$_3$)$_2$Cl$_2$ (0.04 g, 0.058 mmol) under N$_2$ at rt. The mixture was stirred at reflux overnight. The mixture was diluted with water (20 mL) and extracted with CH$_2$Cl$_2$ (30 mL×3). The combined organic layer was washed with brine, dried over Na$_2$SO$_4$, and concentrated under reduced pressure. The residue was purified by column chromatography on silica gel (eluted with EA) to afford Compound 243 (0.16 g, 80% yield). $^1$H NMR (CDCl$_3$, 400 MHz) δ 9.25-9.20 (m, 2H), 7.47-7.33 (m, 3H), 7.38-7.34 (m, 2H), 7.31 (s, 1H), 6.65 (s, 1H), 2.23 (s, 3H). MS (ESI) m/z (M+H)+348.0.

Compound 241: To a stirred mixture of XLI-3 (300 mg, 0.86 mmol), pyridin-3-ylboronic acid (160 mg, 1.04 mmol), and K$_3$PO$_4$ (0.86 ml, 1.72 mmol) in DMF (10 mL) was added Pd(PPh$_3$)$_4$ (100 mg, 0.086 mmol) under N$_2$ protection. The reaction mixture was stirred at 110° C. overnight. The mixture was concentrated, diluted with H$_2$O, extracted with EtOAc (30 mL×3), the organic layer was washed with brine, dried over anhydrous Na$_2$SO$_4$, and concentrated in vacuo, the residue was purified by prep-HPLC to give Compound 241 (122 mg, 41% yield) as a white solid. $^1$H NMR (DMSO-d$_6$, 400 MHz) δ 8.63 (s, 1H), 8.57-8.56 (m, 1H), 7.90-7.85 (m, 1H), 7.70-7.64 (m, 3H), 7.53-7.51 (m, 2H), 7.48-7.45 (m, 1H), 6.52 (s, 1H), 2.14 (s, 3H). MS (ESI) m/z [M+H]$^+$ 347.1.

Compound 242 was prepared follow the similar procedure for obtaining Compound 241 using pyridin-4-ylboronic acid in place of pyridin-3-ylboronic acid. $^1$H NMR (DMSO-d$_6$, 400 MHz) δ 8.60 (d, J=4.8 Hz, 2H), 7.71 (s, 1H), 7.66-7.64 (m, 2H), 7.53-7.47 (m, 4H), 6.52 (s, 1H), 2.19 (s, 3H). MS (ESI) m/z [M+H]$^+$ 347.1.

Compound 247 was prepared according to Method 4: To a solution of XLI-3 (900 mg, 2.59 mmol) in dioxane/H$_2$O (12 mL, v/v=5/1) was added K$_2$CO$_3$ (720 mg, 5.18 mmol), 1-methyl-5-(4,4,5,5-tetramethyl-1,3,2-dioxaborolan-2-yl)-1H-pyrazole (600 mg, 2.85 mmol), Pd(dppf)Cl$_2$ (180 mg, 0.26 mmol). The mixture was purged with nitrogen and then heated at 100° C. by microwave for 40 min. The mixture was cooled to rt, diluted with water, extracted with EtOAc (30 mL×3). The combined organic layer was washed with brine, dried over anhydrous Na$_2$SO$_4$, and concentrated in vacuo. The residue was purified by flash chromatography on silica gel (PE: EA=10:1→1:1) to give Compound 247 as a yellow solid (175 mg, 20% yield). $^1$H NMR (CDCl$_3$, 400 MHz) δ 7.53 (s, 1H), 7.48-7.45 (m, 2H), 7.36-7.32 (m, 2H), 7.26 (m, 1H), 6.60 (s, 1H), 6.23 (s, 1H), 3.76 (s, 3H), 2.03 (s, 3H).

Compound 254 was prepared following the similar procedure for obtaining XL-5 using 5-(4,4,5,5-tetramethyl-1,3,2-dioxaborolan-2-yl)benzo[d]oxazole in place of XL-4 and using 5-XLI-3 in place of XL-3 as a white solid. $^1$H NMR (CDCl$_3$, 400 MHz) δ 8.16 (s, 1H), 7.71 (s, 1H), 7.63 (d, J=8.4 Hz, 1H), 7.52-7.48 (m, 2H), 7.35-7.29 (m, 3H), 7.25 (d, J=8.4 Hz, 1H), 6.61 (s, 1H), 2.15 (s, 3H). MS (ESI) m/z (M+H)$^+$ 387.0.

Compound 255 was prepared following the similar procedure for obtaining Compound 254 using (1-methyl-1H-indol-5-yl)boronic acid and Na$_2$CO$_3$ instead of K$_2$CO$_3$ as a yellow solid. $^1$H NMR (DMSO-d$_6$, 400 MHz) δ 7.65-7.63 (m, 2H), 7.54-7.45 (m, 5H), 7.35 (d, J=2.8 Hz, 1H), 7.16 (dd, J=1.6, 8.4 Hz, 2H), 6.47 (s, 1H), 6.20 (d, J=2.8 Hz, 1H), 3.81 (s, 3H), 2.13 (s, 3H).

Compound 259 was prepared following the similar procedure for obtaining Compound 255 using 5-(4,4,5,5-tetramethyl-1,3,2-dioxaborolan-2-yl)benzo[c][1,2,5]oxadiazole. $^1$H NMR (CDCl$_3$, 400 MHz) δ 7.90 (dd, J=1.2, 9.6 Hz, 1H), 7.75 (s, 1H), 7.50-7.48 (m, 2H), 7.39-7.34 (m, 4H), 6.64 (s, 1H), 2.22 (s, 3H).

Compound 251 was prepared following the similar procedure for obtaining Compound 255 using 5-(4,4,5,5-tetramethyl-1,3,2-dioxaborolan-2-yl)benzo[d]thiazole. $^1$H NMR (CDCl$_3$, 400 MHz) δ 9.06 (s, 1H), 8.06 (s, 1H), 8.01 (d, J=8.4 Hz, 1H), 7.52-7.49 (m, 2H), 7.39-7.32 (m, 3H), 7.27 (d, J=8.4 Hz, 1H), 6.63 (s, 1H), 2.19 (s, 3H).

Compound 244 was prepared following the similar procedure for obtaining XL-3 by reacting 5-(1H-imidazol-1-yl)-4-methylpyridin-2(1H)-one with (4-(trifluoromethoxy)phenyl) boronic acid. $^1$H NMR (CDCl$_3$, 400 MHz) δ 7.60 (s, 1H), 7.57-7.50 (m, 4H), 7.37-7.33 (m, 2H), 7.25 (m, 1H), 6.58 (s, 1H), 2.01 (s, 1H). MS (ESI) m/z (M+H)+ 336.1.

Compound 245 was prepared following the similar procedure for obtaining XL-5 by reacting XLI-3 with 1-methyl-5-(4,4,5,5-tetramethyl-1,3,2-dioxaborolan-2-yl)-1H-indazole. 1H NMR (CDCl3, 400 MHz) δ 7.99 (s, 1H), 7.62 (s, 1H), 7.51 (d, J=9.2 Hz, 2H), 7.45 (d, J=8.8 Hz, 1H), 7.34-7.23 (m, 4H), 6.61 (s, 1H), 4.11 (s, 3H), 2.15 (s, 3H). MS (ESI) m/z [M+H]+ 400.1.

Compound 246 was prepared following the similar procedure for obtaining XL-5 by reacting XLI-3 with 2-methyl-5-(4,4,5,5-tetramethyl-1,3,2-dioxaborolan-2-yl)-2H-indazole. 1H NMR (CDCl3, 400 MHz) δ 7.97 (s, 1H), 7.80 (d, J=8.8 Hz, 1H), 7.56 (s, 1H), 7.51 (d, J=9.2 Hz, 2H), 7.36 (m, 3H), 7.25 (m, 1H), 6.81 (s, 1H), 4.29 (s, 3H). 2.22 (s, 3H). MS (ESI) m/z [M+H]+ 400.1

Compound 249 was prepared following the similar procedure for obtaining XL-5 by reacting XLI-3 with 1-methyl-6-(4,4,5,5-tetramethyl-1,3,2-dioxaborolan-2-yl)-1H-indazole. 1H NMR (CDCl3, 400 MHz) δ 8.02 (s, 1H), 7.75 (d, J=8.0 Hz, 1H), 7.52-7.50 (m, 2H), 7.35-7.33 (m, 2H), 7.29-7.28 (m, 2H), 7.07 (d, J=8.0 Hz, 1H), 6.62 (s, 1H), 4.09 (s, 3H), 2.18 (s, 3H). MS (ESI) m/z (M+H)+ 400.0.

Compound 250 prepared following the similar procedure for obtaining XL-5 by reacting XLI-3 with 2-methyl-6-(4,4,5,5-tetramethyl-1,3,2-dioxaborolan-2-yl)-2H-indazole. 1H NMR (CDCl3, 400 MHz) δ 7.94 (s, 1H), 7.68 (d, J=8.0 Hz, 1H), 7.58 (s, 1H), 7.53-7.50 (m, 2H), 7.34-7.32 (m, 2H), 7.27 (m, 1H), 7.00 (d, J=8.0 Hz, 1H), 6.61 (s, 1H), 4.25 (s, 3H), 2.19 (s, 3H). MS (ESI) m/z (M+H)+ 400.0.

Compound 258 was prepared following the similar procedure for obtaining XL-5 using 1-methyl-6-(4,4,5,5-tetramethyl-1,3,2-dioxaborolan-2-yl)-1H-indole in place of XL-4 and using XLI-3 in place of XL-3 as a yellow solid. 1H NMR (DMSO-d6, 400 MHz) δ 7.66-7.62 (m, 1H), 7.56-7.48 (m, 4H), 7.44 (s, 1H), 7.33 (s, 1H), 7.02 (d, J=8.0 Hz, 1H), 6.48 (s, 1H), 6.42 (m, 1H), 3.78 (s, 3H), 2.15 (s, 3H). MS (ESI) m/z (M+H)+ 398.9.

Compound 260 was prepared following the similar procedure for obtaining XL-5 using 6-(4,4,5,5-tetramethyl-1,3,2-dioxaborolan-2-yl)benzo[d]thiazole in place of XL-4 and using XLI-3 in place of XL-3. 1H NMR (CDCl3, 400 MHz) δ 9.05 (s, 1H), 8.17 (d, J=8.4 Hz, 1H), 7.88 (s, 1H), 7.52-7.43 (m, 3H), 7.37-7.32 (m, 2H), 7.28-7.26 (m, 1H), 6.63 (s, 1H), 2.19 (s, 3H). MS (ESI) m/z (M+H)+ 403.0.

Compound 432 was prepared following the similar procedure for obtaining compound 243 using Pd-118 and K3PO4 instead of Pd(dppf)Cl2 and K2CO3. 1H NMR (CDCl3, 400 MHz) δ 9.25 (d, J=5.2 Hz, 1H), 9.20 (s, 1H), 7.50-7.47 (m, 2H), 7.44-7.42 (m, 1H), 7.38-7.35 (m, 2H), 7.30 (s, 1H), 6.64 (s, 1H), 2.22 (s, 3H). MS (ESI) m/z (M+H)+ 297.9.

Example 14-B

Synthesis of Compound 248 (Scheme XLII)

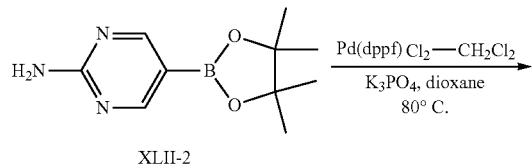

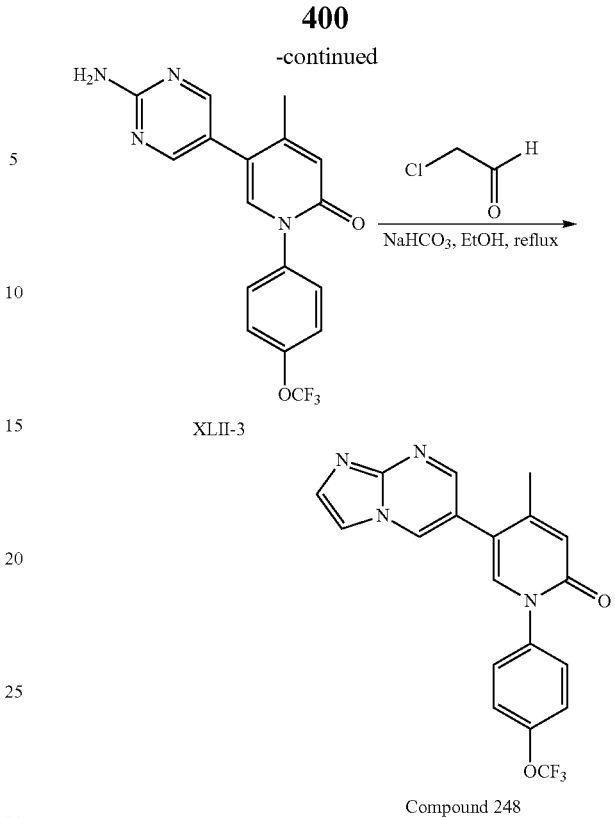

Compound 248

A flask was charged with XLI-3 (0.8 g, 2.30 mmol, 1 eq), XLII-2 (1.02 g, 4.60 mmol, 2 eq), Pd(dppf)Cl2—CH2Cl2 (0.094 g, 0.11 mmol, 0.05 eq), K3PO4 (1.22 g, 4.60 mmol, 2 eq) and 50 mL of dioxane, flushed with nitrogen for three times. The mixture was heated at 80° C. for 8 hrs. LCMS analysis showed the reaction completed. The reaction mixture was cooled down to rt, diluted with water, extracted with ethyl acetate (80 mL×3). The combined organic layer was washed with brine, dried over anhydrous sodium sulfate, filtered and concentrated to give brown oil. Recrystallization from EA gave offwhite solid XLII-3 (0.4 g, 48% yield). MS (ESI) m/z (M+H)+362.9.

A flask was charged with XLII-3 (300 mg, 0.83 mmol, 1 eq), NaHCO3 (139 mg, 1.66 mmol, 2 eq), aq. 2-chloroacetaldehyde (40%, 1.6 g, 8.3 mmol, 10 eq) and 20 mL of EtOH. The mixture was heated to reflux for 18 hrs. LCMS analysis showed the reaction completed. The reaction mixture was cooled down to rt, diluted with water, extracted with ethyl acetate (50 mL×3). The combined organic layer was washed with brine, dried over anhydrous sodium sulfate, filtered and concentrated to give a brown oil. Purification by prep-TLC (PE/EA=2/1) gave Compound 248 as a brown solid (145.5 mg, 45% yield). MS (ESI) m/z (M+H)+ 386.9. 1H NMR (DMSO-d6, 400 MHz) δ 9.05 (d, J=2.4 Hz, 1H), 8.64 (d, J=2.4 Hz, 1H), 7.90 (s, 1H), 7.84 (s, 1H), 7.76 (s, 1H), 7.66 (d, J=8.4 Hz, 2H), 7.54 (d, J=8.4 Hz, 2H), 6.55 (s, 1H), 2.22 (s, 3H).

Compound 252 was prepared following the similar procedure for obtaining Compound 248 using 5-(4,4,5,5-tetramethyl-1,3,2-dioxaborolan-2-yl)pyridin-2-amine in place of XLII-2. MS (ESI) m/z (M+H)+ 386.9. 1H NMR (DMSO-d6, 300 MHz): δ 8.62 (s, 1H), 7.92 (s, 1H), 7.72 (s, 1H), 7.66-7.53 (m, 6H), 7.33 (d, J=6.8 Hz, 1H), 6.52 (s, 1H), 2.19 (s, 3H).

Example 14-C

Synthesis of Compound 253, 256 and 257 (Scheme XLIII)

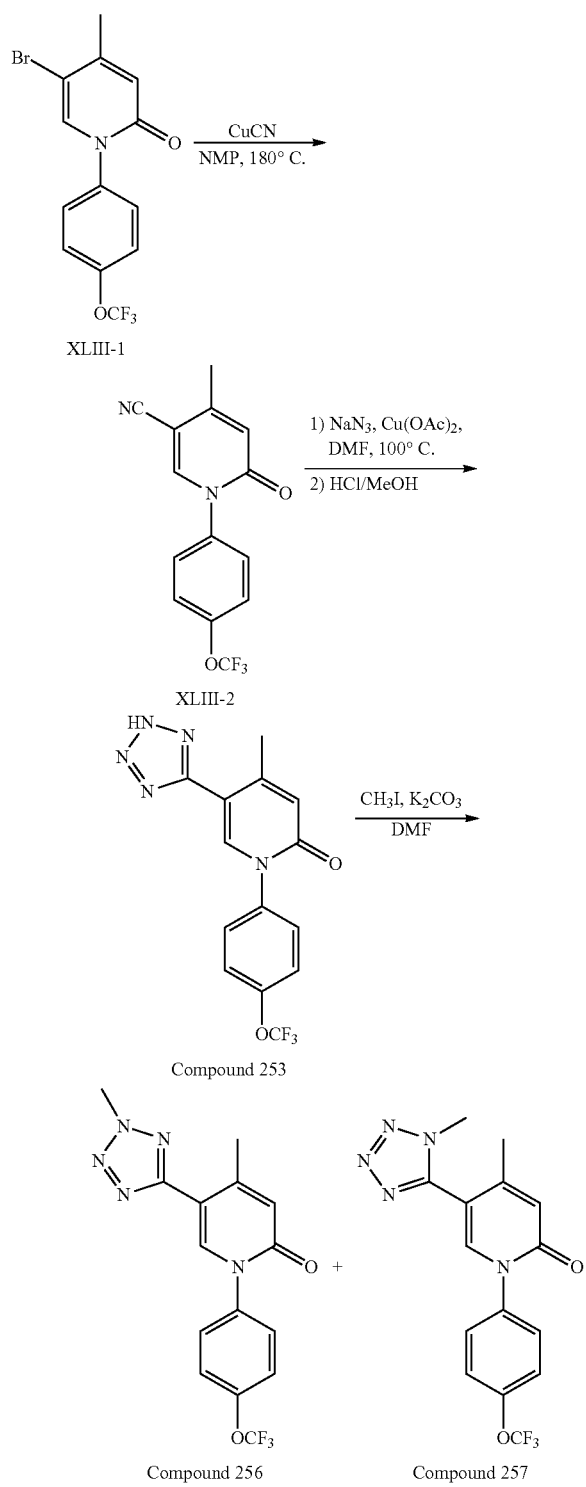

Compound 253

Compound 256          Compound 257

To the solution of XLIII-1 (600 mg, 1.7 mmol) in 5 mL of NMP was added CuCN (462 mg, 5.1 mmol). The mixture was heated to 180° C. for 3 hrs. The mixture was diluted with H$_2$O, extracted with EtOAc (50 mL×3). The combined organic layer was washed with brine, dried over anhydrous Na$_2$SO$_4$, and concentrated in vacuo, the residue was purified by column chromatography on silica gel (PE/EA=5/1) to give XLIII-2 (400 mg, 80% yield) as a white solid.

To the solution of XLIII-2 (300 mg, 1 mmol) in 3 mL of DMF was added NaN$_3$ (130 mg, 2 mmol). and Cu(OAc)$_2$ (360 mg, 2 mmol). The mixture was heated to 100° C. under microwave for 20 minutes. And then the mixture was filtered at 70° C., the filtrate was cooled to rt, the mixture was filtered again. The residual solid was dissolved in HCl/MeOH (4 M), stirred at rt for 1 h. The mixture was concentrated to give Compound 253 (50 mg, 14.5% yield) as black solid. $^1$H NMR (DMSO-d$_6$, 400 MHz) δ 8.17 (s, 1H), 7.60 (m, 2H), 7.51 (m, 2H), 6.51 (s, 1H), 2.36 (s, 3H). MS (ESI) m/z (M+H)$^+$ 338.0.

To the solution of Compound 253 (200 mg, 0.59 mmol) in 2 mL of DMF was added CH$_3$I (100 mg, 0.7 mmol). and K$_2$CO$_3$ (170 mg, 1.2 mmol). The mixture was stirred at rt for 3 hrs. The mixture was diluted with H$_2$O, extracted with EtOAc (50 mL×3). The combined organic layer was washed with brine, dried over anhydrous Na$_2$SO$_4$, and concentrated in vacuo, the residue was purified by prep-TLC (PE/EA=1/1) to give Compound 256 (130 mg, 62% yield) and Compound 257 (40 mg, 19% yield). $^1$H NMR (CDCl$_3$, 400 MHz) δ 8.15 (s, 1H), 7.50 (d, J=8.8 Hz, 2H), 7.36 (d, J=8.8 Hz, 2H), 6.60 (s, 1H), 4.38 (s, 3H), 2.55 (s, 3H). MS (ESI) m/z (M+H)$^+$351.9. $^1$H NMR (CDCl$_3$, 400 MHz) δ 7.48-7.44 (m, 3H), 7.35 (d, J=8.8 Hz, 2H), 6.65 (s, 1H), 4.05 (s, 3H), 2.13 (s, 3H). MS (ESI) m/z (M+H)$^+$ 351.9.

Compounds 261-264 were also prepared following the general procedure as described herein.

Compound 261: $^1$H NMR (CDCl$_3$, 400 MHz) δ 9.04 (s, 1H), 8.03-8.00 (m, 1H), 7.53-7.47 (m, 3H), 7.42-7.28 (m, 4H), 6.65 (s, 1H), 2.07 (s, 3H). MS (ESI) m/z [M+H]$^+$ 402.8.

Compound 262: MS (ESI) m/z [M+H]$^+$ 352.8. $^1$H NMR (CDCl$_3$, 400 MHz) δ 8.87 (m, 1H), 7.70 (s, 1H), 7.51-7.47 (m, 2H), 7.35-7.27 (m, 3H), 6.60 (s, 1H), 2.36 (s, 3H).

Compound 263: $^1$H NMR (DMSO-d$_6$, 400 MHz) δ 9.42 (s, 1H), 8.10 (d, J=8.0 Hz, 1H), 7.78 (s, 1H), 7.64-7.59 (m, 3H), 7.51-7.45 (m, 3H), 6.55 (s, 1H), 1.98 (s, 3H). MS (ESI) m/z [M+H]$^+$ 402.9.

Compound 264: $^1$H NMR (CDCl$_3$, 400 MHz) δ 8.54 (s, 1H), 8.48 (s, 1H), 7.49-7.45 (m, 2H), 7.37-7.32 (m, 2H), 7.29 (s, 1H), 6.61 (s, 1H), 2.19 (s, 3H). MS (ESI) m/z [M+H]$^+$ 353.1.

Example 15

5-Bromo Pyridone Analogs

Compounds 265-273 were prepared following Method 1 in Example 12-B using 5-bromopyridin-2(1H)-one reacting with the relevant boronic acids.

Compound 265: $^1$HNMR (DMSO-d$_6$, 400 MHz) δ 7.97 (s, 1H), 7.63 (d, J=9.6 Hz, 1H), 7.52-7.48 (m, 2H), 7.37-7.32 (m, 2H), 6.48 (d, J=9.6 Hz, 1H). MS (ESI) m/z (M+H)$^+$ 268.1.

Compound 266: $^1$HNMR (DMSO-d$_6$, 400 MHz) δ 8.34 (s, 1H), 8.02 (d, J=9.6 Hz, 1H), 7.85-7.81 (m, 1H), 7.46-7.38 (m, 3H), 6.88 (d, J=9.6 Hz, 1H), 4.21 (s, 3H). MS (ESI) m/z (M+H)$^+$ 280.0.

Compound 267: $^1$HNMR (DMSO-d$_6$, 400 MHz) δ 7.92 (d, J=2.8 Hz, 1H), 7.60 (dd, J=9.6, 2.8 Hz, 1H), 7.32-7.29 (m, 2H), 7.02-6.99 (m, 2H), 6.45 (d, J=9.6 Hz, 1H), 4.70-4.63 (m, 1H), 1.32 (d, J=6.0 Hz, 6H). MS (ESI) m/z (M+H)$^+$ 310.0.

Compound 268: ¹HNMR (DMSO-d₆, 400 MHz) δ 8.07 (d, J=2.8 Hz, 1H), 7.91 (s, 1H), 7.85-7.82 (m, 1H), 7.80-7.73 (m, 2H), 7.65 (dd, J=9.6, 2.8 Hz, 1H), 6.51 (d, J=9.6 Hz, 1H). MS (ESI) m/z (M+H)⁺ 319.9.

Compound 269: ¹HNMR (DMSO-d₆, 400 MHz) δ 7.98 (d, J=2.8 Hz, 1H), 7.63 (dd, J=9.6, 2.8 Hz, 1H), 7.60-7.56 (m, 2H), 7.50-7.47 (m, 2H), 6.48 (d, J=9.6 Hz, 1H). MS (ESI) m/z (M+H)⁺ 285.8.

Compound 270: ¹HNMR (DMSO-d₆, 400 MHz) δ 8.03 (d, J=2.8 Hz, 1H), 7.66-7.59 (m, 3H), 7.53-7.50 (m, 2H), 6.50 (d, J=10 Hz, 1H). MS (ESI) m/z (M+H)⁺ 335.9.

Compound 271: ¹HNMR (DMSO-d₆, 400 MHz) δ 10.17 (s, 1H), 7.96 (d, J=2.8 Hz, 1H), 7.70 (s, 1H), 7.67-7.58 (m, 2H), 7.44 (t, J=8.0 Hz, 1H), 7.10-7.07 (m, 1H), 6.49 (d, J=10 Hz, 1H), 2.07 (s, 3H). MS (ESI) m/z (M+Na)⁺ 328.9.

Compound 272: ¹HNMR (DMSO-d₆, 400 MHz) δ 7.98 (d, J=2.8 Hz, 1H), 7.62 (dd, J=9.6, 2.8 Hz, 1H), 7.58-7.50 (m, 1H), 7.42-7.39 (m, 1H), 7.33-7.27 (m, 2H), 6.47 (d, J=9.6 Hz, 1H). MS (ESI) m/z (M+H)⁺ 267.8.

Compound 273: ¹HNMR (DMSO-d₆, 400 MHz) δ 7.83 (d, J=2.8 Hz, 1H), 7.63 (dd, J=9.6, 2.8 Hz, 1H), 7.15 (d, J=8.4 Hz, 1H), 6.93 (d, J=2.8 Hz, 1H), 6.86-6.83 (m, 1H), 6.47 (d, J=9.6 Hz, 1H), 4.07 (q, J=6.8 Hz, 2H), 2.01 (s, 3H), 1.35 (t, J=6.8 Hz, 3H). MS (ESI) m/z (M+H)⁺ 307.9.

Example 16

5-substituted Pyridone Analogs

Compounds 274-278, 280 and 281 were prepared following Method 1 in Example 12-B by reacting 5-trifluoromethyl pyridin-2(1H)-one reacting with the relevant boronic acids.

Compound 274: ¹H NMR (CDCl₃, 400 MHz) δ 7.73 (s, 1H), 7.58-7.49 (m, 2H), 7.22-7.15 (m, 3H), 6.74 (d, J=9.6 Hz, 1H). MS (ESI) m/z (M+H)⁺ 257.9.

Compound 275: ¹H NMR (CDCl₃, 400 MHz) δ 7.73 (s, 1H), 7.54 (d, J=9.6 Hz, 1H), 7.48-7.42 (m, 2H), 7.38-7.36 (m, 2H), 6.73 (d, J=9.6 Hz, 1H). MS (ESI) m/z (M+H)⁺ 324.1.

Compound 276: ¹H NMR (CDCl₃, 400 MHz) δ 7.74 (s, 1H), 7.54-7.50 (m, 1H), 7.45-7.40 (m, 1H), 7.03-6.99 (m, 1H), 6.94-6.90 (m, 2H), 6.72 (d, J=9.6 Hz, 1H), 3.85 (s, 3H). MS (ESI) m/z (M+H)⁺ 270.1.

Compound 277: ¹HNMR (DMSO-d₆, 400 MHz) δ 10.18 (s, 1H), 8.25 (s, 1H), 7.79-7.75 (m, 1H), 7.71 (s, 1H), 7.63-7.61 (m, 1H), 7.48-7.43 (m, 1H), 7.14-7.11 (m, 1H), 6.66 (d, J=9.6 Hz, 1H), 2.07 (s, 3H). MS (ESI) m/z (M+H)⁺ 296.9.

Compound 278: ¹HNMR (DMSO-d₆, 400 MHz) δ 8.13 (m, 1H), 7.76-7.72 (m, 1H), 7.18 (d, J=8.4 Hz, 1H), 6.91 (s, 1H), 6.84-6.81 (m, 1H), 6.61 (d, J=9.6 Hz, 1H), 4.04 (q, J=6.8 Hz, 2H), 1.97 (s, 3H), 1.31 (t, J=6.8 Hz, 3H). MS (ESI) m/z (M+H)⁺ 298.1.

Compound 280: ¹H NMR: (CDCl₃, 400 MHz) δ 7.67 (s, 1H), 7.55-7.48 (m, 2H), 7.40-7.35 (m, 1H), 7.32-7.28 (m, 2H), 6.75 (d, J=9.6 Hz, 1H). MS (ESI) m/z (M+H)⁺ 258.1.

Compound 281: ¹H NMR: (CDCl₃, 400 MHz) δ 7.61-7.53 (m, 3H), 7.47-7.37 (m, 3H), 6.76 (d, J=9.6 Hz, 1H). MS (ESI) m/z (M+H)⁺ 273.9.

Compound 279 were prepared following Method 2 in Example 12-B by reacting 5-trifluoromethyl pyridin-2(1H)-one with 5-bromopyridine. ¹H NMR (CDCl₃, 400 MHz) δ 9.31 (s, 1H), 8.89 (s, 2H), 7.72 (s, 1H), 7.59 (d, J=9.6 Hz, 1H), 6.78 (d, J=9.6 Hz, 1H). MS (ESI) m/z (M+H)⁺ 242.0.

Compound 282 was prepared following Method 1 in Example 12-B by reacting 5-methyl pyridine-2(1H)-one with (3,4,5-triflurophenyl)boronic acid. ¹H NMR (CDCl₃, 300 MHz) δ 7.28 (d, J=2.4 Hz, 1H), 7.10-7.03 (m, 3H), 6.59 (d, J=9.6 Hz, 1H), 2.10 (s, 3H). MS (ESI) m/z (M+H)⁺ 239.9.

Compound 283 was prepared following Method 2 by reacting 5-methyl pyridine-2(1H)-one with 1-fluoro-2-iodobenzene. ¹H NMR (DMSO-d₆, 300 MHz) δ 7.42-7.31 (m, 2H), 7.30-7.21 (m, 3H), 7.01 (s, 1H), 6.62 (d, J=9.6 Hz, 1H), 2.09 (s, 3H). MS (ESI) m/z (M+H)⁺ 204.1.

Compound 285 was prepared following the general methods described herein. ¹H NMR (CDCl₃, 400 MHz) δ 7.50-7.47 (m, 2H), 7.43-7.35 (m, 4H), 7.10 (d, J=2.4 Hz, 1H), 6.64 (d, J=9.6 Hz, 1H), 2.73-2.65 (m, 1H), 1.20 (d, J=6.8 Hz, 6H). MS (ESI) m/z (M+H)⁺ 214.2.

Compound 287: To a mixture of 5-bromo-1-phenylpyridin-2(1H)-one (0.25 g, 1 mmol) and ethynyltrimethylsilane (5 mL) in DMF (10 mL) and TEA (2 mL) was added CuI (0.02 g, 0.1 mmol) and Pd(PPh₃)₂Cl₂ (0.07 g, 0.1 mmol). The mixture was purged with nitrogen for 5 minutes and stirred under N₂ at 100° C. overnight. The reaction mixture was worked up to afford an intermediate product (0.16 g, 60% yield), which was mixed with TBAF (0.16 g, 0.6 mmol) in CH₂Cl₂ (5 mL) was stirred at rt for 3 hours. The organic layer was concentrated and the residue was purified by column chromatography (PE/EA=10/1) to yield Compound 287 (0.08 g, 68% yield). ¹H NMR (CDCl₃, 400 MHz) δ 7.6 (d, J=2.4 Hz, 1H), 7.54-7.35 (m, 6H), 6.63 (d, J=9.6 Hz, 1H), 3.03 (s, 1H). MS (ESI) m/z (M+H)⁺ 196.1.

Example 17

5-Phenyl Pyridone Analogs

Compounds 288 through 331 were prepared following the similar procedures described herein in Method A through C and Method 1 through 4.

Compound 288: ¹H NMR (DMSO-d₆, 400 MHz) δ 7.91-7.87 (m, 2H), 7.68-7.64 (m, 2H), 7.37 (d, J=8.8 Hz, 2H), 7.22 (t, J=8.8 Hz, 2H), 7.02 (d, J=8.8 Hz, 2H), 6.57 (d, J=9.2 Hz, 1H), 4.70-4.64 (m, 1H), 1.30 (d, J=6.0 Hz, 6H). MS (ESI) m/z [M+H]⁺ 324.1.

Compound 289: ¹H NMR (DMSO-d₆, 400 MHz) δ 8.05 (d, J=2.4 Hz, 1H), 7.96-7.93 (m, 2H), 7.86-7.84 (m, 2H), 7.79-7.77 (m, 1H), 7.72-7.68 (m, 2H), 7.24 (t, J=8.8 Hz, 2H), 6.62 (d, J=9.6 Hz, 1H). MS (ESI) m/z [M+H]⁺ 333.9.

Compound 290: ¹H NMR (DMSO-d₆, 400 MHz) δ 8.02-7.94 (m, 2H), 7.69-7.66 (m, 2H), 7.61-7.53 (m, 2H), 7.46-7.37 (m, 2H), 7.36-7.22 (m, 2H), 6.62 (d, J=9.6 Hz, 1H). MS (ESI) m/z [M+H]⁺ 284.0.

Compound 291: ¹H NMR (CDCl₃, 400 MHz) δ 7.69 (dd, J=2.4, 9.6 Hz, 1H), 7.61-7.58 (m, 1H), 7.48-7.35 (m, 6H), 7.08 (t, J=8.4 Hz, 2H), 6.78 (d, J=9.6 Hz, 1H). MS (ESI) m/z [M+H]⁺ 300.1.

Compound 294: ¹H NMR (CDCl₃, 400 MHz): δ 7.72-7.70 (m, 1H), 7.53 (s, 1H), 7.46-7.39 (m, 6H), 7.37-7.32 (m, 1H), 7.22-7.17 (m, 2H), 6.74 (d, J=9.6 Hz, 1H). MS (ESI) m/z (M+H)⁺ 266.0.

Compound 295: ¹H NMR (CDCl₃, 400 MHz) δ 7.73-7.70 (m, 1H), 7.57 (s, 1H), 7.46-7.39 (m, 5H), 7.36-7.32 (m, 1H), 7.02-6.97 (m, 3H), 6.75 (d, J=9.6 Hz, 1H), 3.84 (s, 3H). MS (ESI) m/z (M+H)⁺ 277.9.

Compound 296: ¹H NMR (CDCl₃, 400 MHz): δ 7.73-7.70 (m, 1H), 7.52-7.40 (m, 6H), 7.36-7.32 (m, 1H), 7.24-7.14 (m, 3H), 6.75 (d, J=9.6 Hz, 1H). MS (ESI) m/z (M+H)⁺ 266.1.

Compound 297: ¹H NMR (CDCl₃, 400 MHz): δ 7.76-7.65 (m, 5H), 7.55 (s, 1H), 7.46-7.40 (m, 4H), 7.38-7.32 (m, 1H), 6.77 (d, J=9.6 Hz, 1H). MS (ESI) m/z (M+H)⁺ 315.2.

Compound 298: $^1$H NMR (CDCl$_3$, 400 MHz): δ 7.76-7.73 (m, 1H), 7.47-7.40 (m, 5H), 7.35-7.31 (m, 1H), 7.15 (d, J=8.4 Hz, 1H), 6.88-6.82 (m, 2H), 6.77 (d, J=9.2 Hz, 1H), 4.06 (q, J=6.8 Hz, 2H), 2.17 (s, 3H), 1.44 (t, J=6.8 Hz, 3H). MS (ESI) m/z (M+H)$^+$ 305.9.

Compound 308: $^1$H NMR (CDCl$_3$, 400 MHz) δ 7.69-7.66 (m, 1H), 7.49-7.45 (m, 2H), 7.35 (d, J=8 Hz, 2H), 7.25-7.15 (m, 3H), 6.97-6.93 (m, 2H), 6.75 (d, J=9.6 Hz, 1H), 3.83 (s, 3H). MS (ESI) m/z (M+H)$^+$ 296.0.

Compound 309: $^1$H NMR (CDCl$_3$, 400 MHz) δ 7.68-7.65 (m, 1H), 7.35 (d, J=2.4 Hz, 1H), 7.43-7.33 (m, 3H), 7.01-6.93 (m, 5H), 6.75 (d, J=9.2 Hz, 1H), 3.83 (s, 6H). MS (ESI) m/z (M+H)$^+$ 308.0.

Compound 310: $^1$H NMR (CDCl$_3$, 300 MHz) δ 7.72-7.69 (m, 1H), 7.60-7.57 (m, 1H), 7.43-7.41 (m, 3H), 7.37-7.33 (m, 3H), 6.96-6.93 (m, 2H), 6.77 (d, J=9.6 Hz, 1H), 3.83 (s, 3H). MS (ESI) m/z (M+H)$^+$ 311.9.

Compound 314: $^1$H NMR (CDCl$_3$, 400 MHz) δ 7.68 (dd, J=2.8, 9.6 Hz, 1H), 7.52-7.49 (m, 3H), 7.41-7.29 (m, 6H), 6.75 (d, J=9.6 Hz, 1H). MS (ESI) m/z (M+H)$^+$ 315.9.

Compound 315: $^1$H NMR (CDCl$_3$, 400 MHz) δ 7.68-7.65 (m, 1H), 7.56 (d, J=4.0 Hz, 1H), 7.42-7.28 (m, 6H), 7.04-7.00 (m, 2H), 6.76 (d, J=9.2 Hz, 1H), 3.86 (s, 3H). MS (ESI) m/z (M+H)$^+$ 312.0.

Compound 316: $^1$H NMR: (CDCl$_3$, 400 MHz) δ 7.67-7.64 (m, 1H), 7.56 (s, 1H), 7.42 (s, 1H), 7.34-7.28 (m, 5H), 7.00-6.97 (m, 2H), 6.76 (d, J=9.2 Hz, 1H), 4.63-4.55 (m, 1H), 1.38 (s, 3H), 1.36 (s, 3H). MS (ESI) m/z (M+H)$^+$ 340.1.

Compound 317: $^1$H NMR: (DMSO-d$_6$, 400 MHz) δ 8.09 (m, 1H), 7.96 (dd, J=2.8, 9.6 Hz, 1H), 7.75 (s, 1H), 7.62-7.53 (m, 3H), 7.43-7.33 (m, 4H), 6.59 (d, J=9.6 Hz, 1H). MS (ESI) m/z (M+H)$^+$ 299.9.

Compound 318: $^1$H NMR: (CDCl$_3$, 400 MHz) δ 7.73-7.66 (m, 5H), 7.54 (s, 1H), 7.43-7.30 (m, 4H), 6.78 (d, J=9.6 Hz, 1H). MS (ESI) m/z (M+H)$^+$ 349.9.

Compound 319: $^1$H NMR: (CDCl$_3$, 400 MHz) δ 7.68-7.65 (m, 1H), 7.56 (s, 1H), 7.43-7.39 (m, 2H), 7.34-7.28 (m, 3H), 7.01-6.96 (m, 3H), 6.75 (d, J=9.6 Hz, 1H), 3.84 (s, 3H). MS (ESI) m/z (M+H)$^+$ 311.9.

Compound 320: $^1$H NMR: (CDCl$_3$, 400 MHz) δ 8.11 (s, 1H), 7.97-7.94 (m, 1H), 7.78 (s, 1H), 7.61-7.32 (m, 7H), 6.60 (d, J=9.6 Hz, 1H). MS (ESI) m/z (M+H)$^+$ 299.9

Compound 321: $^1$H NMR: (CDCl$_3$, 400 MHz) δ 7.42 (d, J=4.0 Hz, 1H), 7.43-7.38 (m, 2H), 7.29-7.27 (m, 1H), 7.12 (d, J=8.0 Hz, 1H), 6.84-6.80 (m, 2H), 6.75 (d, J=9.6 Hz, 1H), 4.03 (q, J=6.8 Hz, 2H), 2.13 (s, 3H), 1.41 (t, J=6.8 Hz, 3H). MS (ESI) m/z (M+H)$^+$ 340.1

Compound 322: $^1$H NMR: (CDCl$_3$, 400 MHz) δ 7.73-7.69 (m, 1H), 7.60-7.58 (m, 1H), 7.46-7.29 (m, 8H), 6.79 (d, J=9.6 Hz, 1H). MS (ESI) m/z (M+H)$^+$ 316.0.

Compound 292: $^1$H NMR (CDCl$_3$, 400 MHz) δ 8.36-8.31 (m, 2H), 7.86-7.85 (m, 1H), 7.74-7.68 (m, 2H), 7.50 (s, 1H), 7.42-7.38 (m, 2H), 7.15-7.11 (m, 2H), 6.78 (d, J=9.2 Hz, 1H). MS (ESI) m/z [M+H]$^+$ 310.8.

Compound 299: $^1$HNMR (CDCl$_3$, 400 MHz) δ 8.77 (brs, 2H), 7.73-7.68 (m, 1H), 7.51-7.32 (m, 8H), 6.77-6.72 (m, 1H). MS (ESI) m/z (M+H)$^+$ 249.2.

Compound 302: $^1$HNMR (CDCl$_3$, 400 MHz) δ 7.78-7.75 (m, 1H), 7.62-7.58 (m, 1H), 7.47-7.40 (m, 8H), 7.35-7.32 (m, 1H), 6.79 (d, J=9.6 Hz, 1H). MS (ESI) m/z (M+H)$^+$ 282.2.

Compound 300: $^1$HNMR (CDCl$_3$, 400 MHz) δ 9.27 (s, 1H), 8.95 (s, 2H), 7.80-7.75 (m, 1H), 7.51-7.35 (m, 6H), 6.79 (d, J=9.6 Hz, 1H). MS (ESI) m/z (M+H)$^+$ 250.0.

Compound 301: $^1$HNMR (CDCl$_3$, 400 MHz) δ 7.76-7.72 (m, 1H), 7.50-7.39 (m, 7H), 7.38-7.27 (m, 3H), 6.78 (d, J=9.6 Hz, 1H). MS (ESI) m/z (M+H)$^+$ 265.9.

Compound 311: $^1$H NMR (CDCl$_3$, 400 MHz) δ 9.26 (s, 1H), 8.94 (s, 2H), 7.72 (dd, J=2.8, 9.6 Hz, 1H), 7.41 (d, J=2.0 Hz, 1H), 7.35-7.33 (m, 2H), 6.97-6.95 (m, 2H), 6.77 (d, J=9.6 Hz, 1H), 3.84 (s, 3H). MS (ESI) m/z (M+H)$^+$ 279.9.

Compound 323: $^1$H NMR: (CDCl$_3$, 400 MHz) δ 8.82 (brs, 2H), 7.72-7.68 (m, 1H), 7.52 (d, J=2.4 Hz, 1H), 7.47-7.42 (m, 2H), 7.39-7.30 (m, 4H), 6.79 (d, J=9.6 Hz, 1H). MS (ESI) m/z (M+H)$^+$ 283.1.

Compound 312: $^1$H NMR (CDCl$_3$, 400 MHz) δ 7.71-7.68 (m, 1H), 7.48-7.39 (m, 3H), 7.37-7.27 (m, 4H), 6.96-6.93 (m, 2H), 6.76 (d, J=9.6 Hz, 1H), 3.83 (s, 3H). MS (ESI) m/z (M+H)$^+$ 296.0.

Compound 324: $^1$H NMR: (CDCl$_3$, 400 MHz) δ 7.70-7.67 (m, 1H), 7.48-7.41 (m, 4H), 7.37-7.28 (m, 5H), 6.79 (d, J=9.6 Hz, 1H). MS (ESI) m/z (M+H)$^+$ 300.1.

Compound 303: $^1$HNMR (DMSO-d$_6$, 400 MHz) δ 7.90-7.86 (m, 2H), 7.59-7.51 (m, 6H), 6.97-6.94 (m, 2H), 6.59 (d, J=9.6 Hz, 1H), 3.76 (s, 3H). MS (ESI) m/z z (M+H)$^+$ 312.0.

Compound 304: $^1$HNMR (DMSO-d$_6$, 400 MHz) δ 7.95-7.76 (m, 6H), 7.59-7.54 (m, 2H), 6.98-6.95 (m, 2H), 6.60 (d, J=9.6 Hz, 1H), 3.76 (s, 3H). MS (ESI) m/z (M+H)$^+$ 345.9.

Compound 305: $^1$HNMR (DMSO-d$_6$, 400 MHz) δ 7.89-7.82 (m, 2H), 7.66-7.54 (m, 4H), 7.43-7.39 (m, 2H), 7.08-7.03 (m, 2H), 6.98-6.96 (m, 2H), 6.56 (d, J=9.2 Hz, 1H), 3.82 (s, 3H), 3.77 (s, 3H). MS (ESI) m/z (M+H)$^+$ 308.0.

Compound 306: $^1$HNMR (DMSO-d$_6$, 400 MHz) δ 7.91-7.87 (m, 2H), 7.59-7.53 (m, 4H), 7.39-7.33 (m, 2H), 6.99-6.96 (m, 2H), 6.59 (d, J=9.2 Hz, 1H), 3.78 (s, 3H). MS (ESI) m/z (M+H)$^+$ 296.1.

Compound 307: $^1$HNMR (DMSO-d$_6$, 400 MHz) δ 7.88-7.82 (m, 2H), 7.56-7.54 (m, 2H), 7.39-7.36 (m, 2H), 7.04-6.95 (m, 4H), 6.56 (d, J=9.2 Hz, 1H), 4.71-4.66 (m, 1H), 3.78 (s, 3H), 1.31 (d, J=6.0 Hz, 6H). MS (ESI) m/z (M+H)$^+$ 336.1.

Compound 313: $^1$H NMR (CDCl$_3$, 400 MHz) δ 7.69-7.66 (m, 1H), 7.58-7.51 (m, 3H), 7.49-7.42 (m, 4H), 7.36-7.29 (m, 3H), 6.77 (d, J=9.6 Hz, 1H). MS (ESI) m/z (M+H)$^+$ 281.9.

Compound 293: $^1$H NMR (DMSO-d$_6$, 400 MHz) δ 7.90-7.87 (m, 2H), 7.68-7.64 (m, 2H), 7.26-7.13 (m, 3H), 6.65-6.54 (m, 4H), 5.40 (brs, 2H). MS (ESI) m/z [M+H]$^+$ 280.9.

Compound 325: $^1$H NMR (DMSO-d$_6$, 400 MHz) δ 8.13 (d, J=2.8 Hz, 1H), 8.02-7.99 (m, 1H), 7.86-7.81 (m, 4H), 7.60-7.56 (m, 2H), 7.40-7.35 (m, 4H), 6.64 (d, J=9.6 Hz, 1H). MS (ESI) m/z (M+H)$^+$ 344.9.

Compound 326: $^1$H NMR (DMSO-d$_6$, 400 MHz) δ 7.88 (d, J=2.4 Hz, 1H), 7.75-7.72 (m, 1H), 7.60-7.54 (m, 4H), 7.34-7.29 (m, 1H), 7.25-7.22 (m, 2H), 7.13-7.05 (m, 4H), 6.37 (d, J=9.6 Hz, 1H). MS (ESI) m/z (M+H)$^+$ 345.2.

Compound 327: $^1$H NMR (DMSO-d$_6$, 400 MHz) δ 8.15 (d, J=2.8 Hz, 1H), 8.04-8.01 (m, 1H), 7.87-7.82 (m, 4H), 7.64-7.57 (m, 4H), 7.38 (s, 2H), 6.65 (d, J=9.6 Hz, 1H). MS (ESI) m/z (M+H)$^+$ 360.9.

Compound 328: $^1$H NMR (DMSO-d$_6$, 400 MHz) δ 8.09 (d, J=2.8 Hz, 1H), 8.00-7.97 (m, 1H), 7.85-7.80 (m, 4H), 7.44-7.41 (m, 2H), 7.37 (s, 2H), 7.08-7.02 (m, 2H), 6.62 (d, J=9.6 Hz, 1H), 3.82 (s, 3H). MS (ESI) m/z (M+H)$^+$ 356.9.

Compound 329: $^1$HNMR (DMSO-d$_6$, 400 MHz) δ 8.21 (s, 1H), 8.02 (dd, J=2.4, 9.6 Hz, 1H), 7.96 (s, 1H), 7.87-7.65 (m, 7H), 7.40 (s, 2H), 6.65 (d, J=9.6 Hz, 1H). MS (ESI) m/z (M+H)$^+$ 394.9.

Compound 330: $^1$H NMR (DMSO-d$_6$, 400 MHz) δ 8.08 (d, J=2.8 Hz, 1H), 7.98-7.95 (m, 1H), 7.84-7.76 (m, 4H), 7.39-7.36 (m, 4H), 7.02 (d, J=8.8 Hz, 2H), 6.60 (d, J=9.6 Hz, 1H), 4.70-4.64 (m, 1H), 1.29 (d, J=6.0 Hz, 6H). MS (ESI) m/z (M+H)$^+$ 384.8.

Compound 331: $^1$H NMR (DMSO-d$_6$, 400 MHz) δ 8.11 (d, J=2.4 Hz, 1H), 8.03-8.00 (m, 1H), 7.87-7.81 (m, 4H), 7.49-7.42 (m, 1H), 7.39 (s, 2H), 7.11-7.04 (m, 3H), 6.63 (d, J=9.6 Hz, 1H), 3.81 (s, 3H). MS (ESI) m/z (M+H)$^+$ 356.9.

Example 18

2(1H)-Thione Analogs

Compounds 332-339 and 341-343 were prepared according to the general procedure: To a solution of Pirfenidone analog (1 eq.) in toluene was added Lawesson reagent (0.6 eq.). The reaction mixture was refluxed under nitrogen overnight. After being cooled to rt, the mixture was concentrated under reduced pressure. The residue was purified by flash chromatography on silica gel (eluenting with petroleum ether/EtOAc) to provide final thione analogs.

Compound 332: $^1$H NMR (DMSO-d$_6$, 400 MHz) δ 7.83 (s, 1H), 7.47-7.44 (m, 1H), 7.32-7.25 (m, 3H), 7.08-7.04 (m, 2H), 3.82 (s, 3H), 2.13 (s, 3H). MS (ESI) m/z (M+H)$^+$ 231.9.

Compound 333: $^1$H NMR (CDCl$_3$, 300 MHz) δ 7.67 (d, J=8.7 Hz, 1H), 7.41-7.38 (m, 5H), 7.15 (d, J=9.0 Hz, 1H), 2.17 (s, 3H). MS (ESI) m/z (M+H)$^+$ 285.9.

Compound 334: $^1$H NMR (CDCl$_3$, 300 MHz) δ 7.67 (d, J=9.0 Hz, 1H), 7.41 (s, 1H), 7.25-7.20 (m, 2H), 7.09 (d, J=9.0 Hz, 1H), 6.96 (d, J=9.0 Hz, 2H), 4.60-4.52 (m, 1H), 2.15 (s, 3H), 1.35 (d, J=6.0 Hz, 6H). MS (ESI) m/z (M+H)$^+$ 259.9.

Compound 335: $^1$H NMR (CDCl$_3$, 300 MHz) δ 7.68 (d, J=9.0 Hz, 1H), 7.51-7.47 (m, 2H), 7.37 (s, 1H), 7.30 (d, J=1.8 Hz, 1H), 7.28 (s, 1H), 7.12 (dd, J=2.1, 9.0 Hz, 1H), 2.18 (s, 3H). MS (ESI) m/z (M+H)$^+$ 236.2.

Compound 336: $^1$H NMR (CDCl$_3$, 300 MHz) δ 7.67 (d, J=9.0 Hz, 1H), 7.39 (s, 1H), 7.37-7.10 (m, 5H), 2.17 (s, 3H). MS (ESI) m/z (M+H)$^+$ 219.9.

Compound 337: $^1$H NMR (CDCl$_3$, 400 MHz) δ 7.75-7.57 (m, 5H), 7.37 (s, 1H), 7.13 (d, J=8.8 Hz, 1H), 2.17 (s, 3H). MS (ESI) m/z (M+H)$^+$ 270.0.

Compound 338: $^1$H NMR (CDCl$_3$, 300 MHz) δ 7.67 (d, J=9.0 Hz, 1H), 7.53-7.48 (m, 1H), 7.39 (s, 1H), 7.21-7.08 (m, 4H), 2.17 (s, 3H). MS (ESI) m/z (M+H)$^+$ 219.9.

Compound 339: $^1$H NMR (CDCl$_3$, 300 MHz) δ 7.67 (d, J=9.0 Hz, 1H), 7.42-7.40 (m, 2H), 7.11 (d, J=8.7 Hz, 1H), 7.01 (d, J=8.7 Hz, 1H), 6.90 (d, J=9.0 Hz, 1H), 6.86-6.84 (m, 1H), 3.82 (s, 3H), 2.17 (s, 3H). MS (ESI) m/z (M+H)$^+$ 231.9.

Compound 341: $^1$H NMR (DMSO-d$_6$, 400 MHz) δ 7.84 (s, 1H), 7.69-7.67 (m, 1H), 7.54-7.38 (m, 4H), 7.37 (dd, J=2.0, 9.2 Hz, 1H), 2.14 (s, 3H). MS (ESI) m/z (M+H)$^+$ 236.1.

Compound 342: $^1$H NMR (DMSO-d$_6$, 400 MHz) δ 7.73 (s, 1H), 7.44 (d, J=8.8 Hz, 1H), 7.30 (dd, J=2.0, 8.8 Hz, 1H), 7.04 (d, J=8.4 Hz, 1H), 6.91 (d, J=2.8 Hz, 1H), 6.84 (dd, J=2.8, 8.4 Hz, 1H), 4.04 (q, J=6.8 Hz, 2H), 2.11 (s, 3H), 1.94 (s, 3H), 1.33 (t, J=6.8 Hz, 3H). MS (ESI) m/z (M+H)$^+$ 260.1.

Compound 343: $^1$H NMR (DMSO-d$_6$, 400 MHz) δ 10.17 (s, 1H), 7.83 (s, 1H), 7.63 (d, J=1.6 Hz, 1H), 7.54 (d, J=8.0 Hz, 1H), 7.45-7.41 (m, 2H), 7.31 (dd, J=2.0, 8.8 Hz, 1H), 6.96 (t, J=6.4 Hz, 1H), 2.11 (s, 3H), 2.05 (s, 3H). MS (ESI) m/z (M+H)$^+$ 258.9.

Example 19

5-Heterocycle Substituted Analogs

Compounds 344-346 were prepared following the similar procedure in Scheme XXVIII, Method 1.

Compound 344: $^1$H NMR (DMSO-d$_6$, 400 MHz) δ 9.11-9.09 (m, 3H), 8.26 (m, 1H), 8.05-8.02 (m, 1H), 7.58-7.55 (m, 2H), 7.39-7.35 (m, 2H), 6.64 (d, J=9.6 Hz, 1H). MS (ESI) m/z (M+H)$^+$ 267.8.

Compound 345: $^1$H NMR (DMSO-d$_6$, 400 MHz) δ 9.13 (m, 3H), 8.31 (m, 1H), 8.08-8.05 (m, 1H), 7.61-7.57 (m, 1H), 7.54-7.50 (m, 1H), 7.42-7.36 (m, 2H), 6.68 (d, J=9.6 Hz, 1H). MS (ESI) m/z (M+H)$^+$ 267.7.

Compound 346: $^1$H NMR (CDCl$_3$, 400 MHz) δ 9.20 (s, 1H), 8.86 (s, 2H), 7.70-7.67 (m, 1H), 7.54 (d, J=2.4 Hz, 1H), 7.52-7.43 (m, 2H), 7.34-7.29 (m, 2H), 6.86 (d, J=9.6 Hz, 1H). MS (ESI) m/z (M+H)$^+$ 289.9.

Compound 347 was prepared following the similar synthetic procedure for obtaining Compound 243: $^1$H NMR (CDCl$_3$, 400 MHz) δ 9.34 (d, J=2.4 Hz, 1H), 9.20 (d, J=5.6 Hz, 1H), 7.79-7.74 (m, 2H), 7.52-7.49 (m, 2H), 7.41-7.39 (m, 2H), 6.85 (d, J=9.6 Hz, 1H). MS (ESI) m/z (M+H)$^+$ 334.9.

Compound 348 was prepared following the similar procedure in Scheme XXVIII, Method 1, except that the first step intermediate was formed by reacting imidazole with 5-bromo-2-methoxypyridine in DMSO with the presence of L-proline, CuI, K$_2$CO$_3$ and 4 Å molecular sieve. $^1$H NMR (400 MHz, CDCl$_3$) δ 7.69 (s, 1H), 7.53-7.47 (m, 4H), 7.39-7.36 (m, 2H), 7.21 (s, 1H), 7.11 (s, 1H), 6.78 (d, J=8.0 Hz, 1H). MS (ESI) m/z (M+H)$^+$ 321.9.

Example 20

3-Methyl Substituted Analogs (Scheme XLIV)

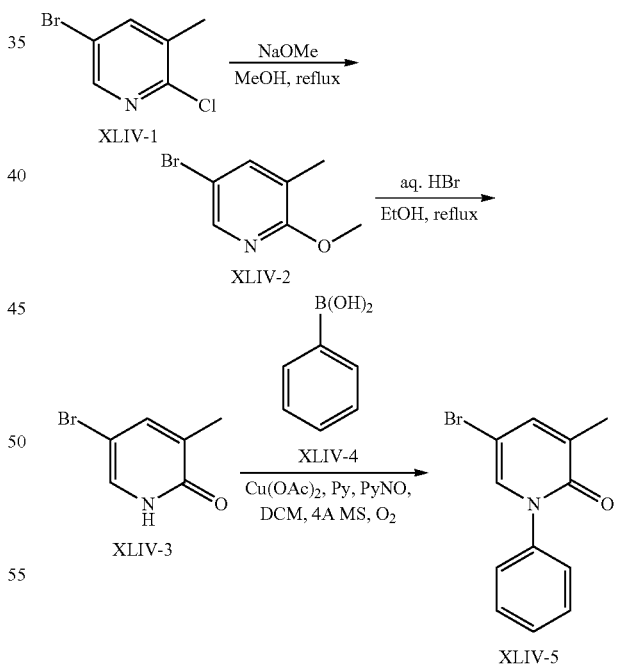

To a solution of NaOMe (5.29 g, 98 mmol) in MeOH (500 mL) was added XLIV-1 (10 g, 49 mmol) by portionwise. The reaction mixture was heated to reflux overnight. The solution was cooled, quenched with water slowly, extracted with PE (100 mL×3). The combined organic layer was washed with brine and concentrated to give XLIV-2 (8.0 g, 81% yield) as a white solid.

XLIV-5 was prepared following the similar procedure in Method 1 for obtaining XXVIII-5. $^1$H NMR (CDCl$_3$, 300 MHz) δ 7.51-7.35 (m, 7H), 2.19 (s, 3H). MS (ESI) m/z [M+H]$^+$ 265.8.

Compounds 349, 351 and 353 were prepared by reacting XLIV-5 with the relevant boronic acid or ester following the similar procedure described in Method A.

Compound 349: $^1$H NMR (CDCl$_3$, 400 MHz) δ 7.68-7.52 (m, 2H), 7.48-7.35 (m, 3H), 7.20-7.16 (m, 1H), 6.96 (s, 1H), 2.17 (s, 3H), 2.08 (s, 3H). MS (ESI) m/z [M+H]$^+$ 200.0.

Compound 351: $^1$H NMR (DMSO-d$_6$, 300 MHz) δ 7.80 (m, 2H), 7.78-7.62 (m, 2H), 7.52-7.44 (m, 5H), 7.23-7.17 (m, 2H), 2.09 (s, 3H). MS (ESI) m/z [M+H]$^+$ 280.1.

Compound 353: $^1$H NMR (DMSO-d$_6$, 300 MHz) δ 7.99 (s, 1H), 7.74-7.68 (m, 3H), 7.49-7.39 (m, 5H), 3.78 (s, 3H), 2.06 (s, 3H). MS (ESI) m/z [M+H]$^+$ 265.9.

Compound 350: To a mixture of 5-bromo-3-methyl-1-(4-(trifluoromethoxy)phenyl)pyridin-2(1H)-one (300 mg, 0.86 mmol, 1 eq.) in 12 mL of toluene/EtOH/H$_2$O (v/v/v=4/1/1) were added (4-fluorophenyl)boronic acid (242 mg, 1.73 mmol, 2 eq.) and K$_2$CO$_3$ (357 mg, 2.59 mmol, 3 eq.). The mixture was degassed by N$_2$ for three times and then Pd(PPh$_3$)$_4$ (100 mg, 0.08 mmol, 0.1 eq.) was added. The reaction vessel was sealed and heated in microwave at 100° C. for 1 h. After being cooled to rt, the mixture was diluted with EA (100 mL), washed with water and brine, dried over anhydrous Na$_2$SO$_4$ and concentrated. The resulting residue was purified by prep-TLC (PE/EA=3/2) to afford Compound 350 (210 mg, 67% yield) as a white solid. $^1$H NMR (CDCl$_3$, 400 MHz) δ 7.55 (s, 1H), 7.51-7.47 (m, 2H), 7.41-7.34 (m, 5H), 7.11 (t, J=8.8 Hz, 2H), 2.27 (s, 3H). MS (ESI) m/z [M+H]$^+$ 364.0.

Compound 352 was prepared by following the similar procedure for obtaining Compound 350 using 1-methyl-4-(4,4,5,5-tetramethyl-1,3,2-dioxaborolan-2-yl)-1H-pyrazole in place of (4-fluorophenyl)boronic acid as a white solid. $^1$H NMR (CDCl$_3$, 400 MHz) δ 7.58 (s, 1H), 7.48-7.43 (m, 4H), 7.36-7.32 (m, 3H), 3.93 (s, 3H), 2.24 (s, 3H). MS (ESI) m/z [M+H]$^+$ 350.1.

Example 21

Pirfenidone Analogs with Heterocyclic Core

Compound 354 was prepared following the similar procedure described in Method 1 by reacting isoquinolin-3(2H)-one with phenyl boronic acid. $^1$H NMR (DMSO-d$_6$, 400 MHz) δ 8.75 (s, 1H), 7.60-7.50 (m, 6H), 7.35-7.28 (m, 2H), 6.92-6.88 (m, 1H), 6.59 (s, 1H). MS (ESI) m/z (M+H)$^+$ 222.0.

Compounds 355 and 356 were prepared following the similar procedure described in Scheme XXVII and Method A using 5-bromopyrimidin-2(1H)-one in place of XXVII-1 and Pd(PPh$_3$)$_4$ in place of Pd(dppf)Cl$_2$.

Compound 355: $^1$H NMR (CDCl$_3$, 400 MHz) δ 8.83 (d, J=3.6 Hz, 1H), 7.77 (d, J=3.6 Hz, 1H), 7.61 (s, 1H), 7.56-7.44 (m, 6H), 3.96 (s, 3H). MS (ESI) m/z [M+H]$^+$ 253.0.

Compound 356: $^1$H NMR (CDCl$_3$, 400 MHz) δ 8.95 (d, J=3.2 Hz, 1H), 7.85 (d, J=3.6 Hz, 1H), 7.57-7.40 (m, 7H), 7.17 (t, J=8.4 Hz, 2H). MS (ESI) m/z [M+H]$^+$ 267.0.

Compound 357 was prepared following the similar procedure described in Scheme XXVIII and Method A using 5-bromo-2-methoxypyrimidine in place of XXVIII-1 and Pd(PPh$_3$)$_4$ in place of Pd(dppf)Cl$_2$ $^1$H NMR (DMSO-d$_6$, 400 MHz) δ 9.11 (d, J=2.8 Hz, 1H), 8.58 (d, J=3.6 Hz, 1H), 7.79-7.74 (m, 4H), 7.58 (d, J=8.4 Hz, 2H), 7.30 (t, J=8.4 Hz, 2H).

Compound 358 was prepared following the general procedure described in Method 1 by reacting 5-methylpyrimidin-2(1H)-one with phenyl boronic acid. $^1$H NMR (CDCl$_3$, 400 MHz) δ 8.60 (brs, 1H), 7.52-7.40 (m, 6H), 2.16 (s, 3H). MS (ESI) m/z [M+H]$^+$ 187.1.

Compounds 359 and 360 were prepared following the general procedure described in Method 1 by reacting 6-methylpyridazin-3(2H)-one with the relevant boronic acid.

Compound 359: $^1$H NMR (CDCl$_3$, 300 MHz) δ 7.58 (d, J=7.8 Hz, 2H), 7.49-7.44 (m, 2H), 7.39-7.34 (m, 1H), 7.11 (d, J=9.6 Hz, 1H), 6.68 (d, J=9.3 Hz, 1H), 2.38 (s, 3H). MS (ESI) m/z [M+H]$^+$ 187.1.

Compound 360: $^1$H NMR (DMSO-d$_6$, 300 MHz) δ 7.66 (d, J=9.0 Hz, 2H), 7.47-7.40 (m, 3H), 6.99 (d, J=9.6 Hz, 1H), 2.28 (s, 3H). MS (ESI) m/z [M+H]$^+$ 271.1.

Compound 361 was prepared following the general procedure described in Method A by reacting 6-chloro-2-phenylpyridazin-3(2H)-one with 1-methyl-4-(4,4,5,5-tetramethyl-1,3,2-dioxaborolan-2-yl)-1H-pyrazole. $^1$H NMR (DMSO-d$_6$, 400 MHz) δ 8.25 (s, 1H), 7.90-7.85 (m, 2H), 7.60-7.59 (m, 2H), 7.51-7.50 (m, 2H), 7.41 (t, J=7.6 Hz, 1H), 7.11 (d, J=10.0 Hz, 1H), 3.86 (s, 3H). MS (ESI) m/z [M+H]$^+$ 252.8. Compounds 362 and 363 were prepared similarly starting with 6-chloro-2-(4-(trifluoromethoxy)phenyl)pyridazin-3(2H)-one.

Compound 362: $^1$H NMR (CDCl$_3$, 400 MHz) δ 7.82-7.71 (m, 5H), 7.35 (d, J=8.0 Hz, 2H), 7.18-7.14 (m, 3H). MS (ESI) m/z (M+H)$^+$ 351.0.

Compound 363: $^1$H NMR (CDCl$_3$, 400 MHz) δ 7.84 (s, 1H), 7.78 (s, 1H), 7.75 (d, J=6.8 Hz, 2H), 7.49 (d, J=10 Hz, 1H), 7.34-7.31 (m, 2H), 7.08 (d, J=9.6 Hz, 1H), 3.96 (s, 3H). MS (ESI) m/z (M+H)$^+$ 337.1.

Compound 364 was prepared following the similar procedure for obtaining Compound 355 using (4-(trifluoromethoxy)phenyl)boronic acid in place of phenyl boronic acid. $^1$H NMR (CDCl$_3$, 400 MHz) δ 8.85 (s, 1H), 7.75 (s, 1H), 7.60-7.52 (m, 4H), 7.40-7.35 (m, 2H), 3.97 (s, 3H). MS (ESI) m/z (M+H)$^+$ 337.2.

Compound 365: To a solution of 1-phenylpyrimidin-2(1H)-one (250 mg, 1.45 mmol) in dry THF (20 mL) was added a solution of NaBH$_4$ (58 mg, 1.5 mmol) in 20 mL MeOH by dropwise at 0° C. The reaction mixture was stirred at rt for 1 h. The mixture was concentrated to remove DCM, the residue was purified by SFC to give 1-phenyl-3,4-dihydropyrimidin-2(1H)-one and Compound 365 (74.8 mg, 30% yield) as a white solid. $^1$H NMR (CDCl$_3$, 400 MHz) δ 7.41-7.33 (m, 4H), 7.23-7.21 (m, 1H), 6.53 (brs, 1H), 6.14-6.11 (m, 1H), 4.88-4.84 (m, 1H), 4.32-4.31 (m, 2H). MS (ESI) m/z [M+H]$^+$ 174.9.

Example 22

4-Methyl Substituted Analogs

Compound 366: To a stirred mixture of 5-bromo-4-methyl-1-phenylpyridin-2(1H)-one (300 mg, 1.15 mmol) and Pd(dppf)Cl$_2$ (83 mg, 0.1 mmol) in 10 mL of anhydrous dioxane was added Zn(Me)$_2$ (1.2 M in toluene, 3.8 mL, 4.56 mmol) under N$_2$ protection. The reaction mixture was refluxed overnight. After being cooled to rt, the mixture was filtered, concentrated. The resulting residue was diluted with H$_2$O (30 mL), extracted with EtOAc (50 mL×3). The combined organic layer was washed with brine, dried over anhydrous Na₂SO₄, and concentrated in vacuo. The residue was purified by prep-TLC (PE/EA=3/1) to produce Compound 366 (60 mg, 26% yield) as a white solid. ¹H NMR (CDCl₃, 400 MHz) δ 7.49-7.45 (m, 2H), 7.41-7.36 (m, 3H), 7.07 (s, 1H), 6.49 (s, 1H), 2.18 (s, 3H), 2.03 (s, 3H). MS (ESI) m/z [M+H]⁺ 200.1.

Compound 367 was prepared following the similar procedure for obtaining Compound 366 using 5-bromo-4-methyl-1-(4-(trifluoromethoxy)phenyl)pyridin-2(1H)-one instead of 5-bromo-4-methyl-1-phenylpyridin-2(1H)-one. ¹H NMR (CDCl₃, 400 MHz) δ 7.42-7.39 (m, 2H), 7.33-7.30 (m, 2H), 7.03 (s, 1H), 6.48 (s, 1H), 2.17 (s, 3H), 2.03 (s, 3H). MS (ESI) m/z (M+H)⁺284.1.

Compound 368 was prepared following the similar procedure described in Method 1 by reacting 4-methyl-5-(trifluoromethyl)pyridin-2(1H)-one with (4-(trifluoromethoxy)phenyl)boronic acid as a yellow solid. ¹H NMR (CDCl₃, 400 MHz) δ 7.70 (s, 1H), 7.44-7.41 (m, 2H), 7.39-7.36 (m, 2H), 6.61 (s, 1H), 2.38 (s, 3H). MS (ESI) m/z (M+H)⁺ 337.9.

Example 23

5-Pyrazole Substituted Analogs (Scheme XLV)

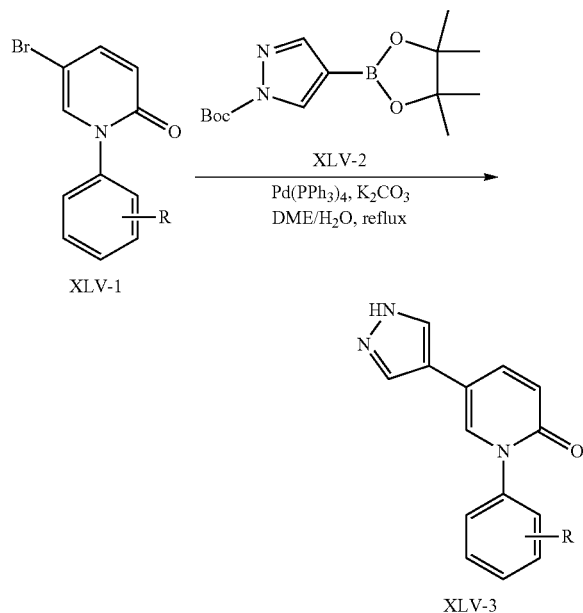

To a mixture of XLV-1 (1 eq.), XLV-2 (1.3 eq.) and K₂CO₃ (2 eq.) in DME/H₂O (v/v=6/1) was added Pd(PPh₃)₄ (0.1 eq.). The reaction mixture was degassed by purging with nitrogen and then was heated to reflux overnight. After the completion of the reaction, the mixture was cooled to rt, diluted with water and extracted with CH₂Cl₂. The combined organic layer was washed with brine, dried over Na₂SO₄, and concentrated under reduced pressure. The residue was purified by flash chromatography on silica gel (PE/EA=1/1 to EA) to afford XLV-3. Compounds 369-377 were prepared following the general procedure discussed above.

Compound 369: ¹H NMR (DMSO-d₆, 400 MHz) δ 12.8 (brs, 1H), 8.09-8.01 (m, 1H), 7.90-7.78 (m, 2H), 7.33 (d, J=8.8 Hz, 1H), 7.01 (d, J=8.8 Hz, 1H), 6.50 (d, J=9.6 Hz, 1H), 4.68-4.62 (m, 1H), 1.28 (d, J=6.0 Hz, 6H).

Compound 370: ¹H NMR (CDCl₃, 400 MHz) δ 7.67 (s, 2H), 7.58-7.55 (m, 1H), 7.48 (s, 1H), 7.33 (d, J=8.8 Hz, 2H), 7.00 (d, J=8.8 Hz, 2H), 6.73 (d, J=9.2 Hz, 1H), 3.85 (s, 3H).

Compound 371: ¹H NMR (DMSO-d₆, 400 MHz) δ 8.10 (brs, 1H), 7.91 (s, 1H), 7.86-7.82 (m, 2H), 7.60-7.57 (m, 2H), 7.60-7.57 (m, 2H), 6.54 (d, J=9.2 Hz, 1H).

Compound 372: ¹H NMR (DMSO-d₆, 400 MHz) δ 8.11 (brs, 1H), 7.96 (s, 1H), 7.89-7.85 (m, 2H), 7.61-7.57 (m, 1H), 7.46 (d, J=8.0 Hz, 1H), 7.37-7.31 (m, 2H), 6.58 (d, J=8.0 Hz, 1H).

Compound 373: ¹H NMR (DMSO-d₆, 400 MHz) δ 12.87 (brs, 1H), 8.10 (brs, 1H), 7.99 (s, 1H), 7.90-7.77 (m, 6H), 6.58 (d, J=8.4 Hz, 1H).

Compound 374: ¹H NMR (DMSO-d₆, 400 MHz) δ 12.87 (brs, 1H), 8.10 (brs, 1H), 7.99 (s, 1H), 7.87 (d, J=8.4 Hz, 2H), 7.63-7.60 (m, 2H), 7.54-7.50 (m, 2H), 6.55 (d, J=9.6 Hz, 1H).

Compound 375: ¹H NMR (DMSO-d₆, 400 MHz) δ 12.86 (brs, 1H), 8.10 (brs, 1H), 7.90-7.80 (m, 3H), 7.44-7.39 (m, 1H), 7.03-6.98 (m, 3H), 6.53 (d, J=9.2 Hz, 1H), 3.78 (s, 3H).

Compound 376: ¹H NMR (DMSO-d₆, 400 MHz) δ 12.86 (brs, 1H), 8.10 (s, 1H), 7.87-7.79 (m, 3H), 7.18 (d, J=8.8 Hz, 1H), 6.95-6.86 (m, 2H), 6.55 (d, J=7.2 Hz, 1H), 4.07 (q, J=6.8 Hz, 2H), 2.03 (s, 3H), 1.35 (t, J=6.8 Hz, 3H). MS (ESI) m/z (M+H)⁺ 295.9.

Compound 377: ¹H NMR (DMSO-d₆, 400 MHz) δ 12.86 (brs, 1H), 8.09 (brs, 1H), 7.91 (d, J=2.4 Hz, 1H), 7.85-7.82 (m, 2H), 7.53-7.49 (m, 2H), 7.37-7.33 (m, 2H), 6.53 (d, J=9.6 Hz, 1H).

Compound 627 was obtained from the corresponding non-Boc protected boronic ester following the general procedure described in Method A: ¹H NMR (CDCl₃, 400 MHz) δ 7.45-7.39 (m, 3H), 7.37-7.30 (m, 3H), 7.18 (s, 1H), 6.51 (s, 1H), 3.91 (s, 3H), 2.19 (s, 3H). MS (ESI) m/z (M+H)⁺ 300.1.

Compound 628: ¹H NMR (DMSO-d₆, 400 MHz) δ 8.83 (s, 1H), 7.87 (s, 1H), 7.57 (s, 1H), 7.55 (m, 1H), 7.46 (s, 1H), 7.34-7.31 (m, 2H), 6.93-6.89 (m, 1H), 6.40 (s, 1H), 5.95 (s, 2H), 3.81 (s, 3H), 2.21 (s, 3H). MS (ESI) m/z (M+H)⁺ 324.1.

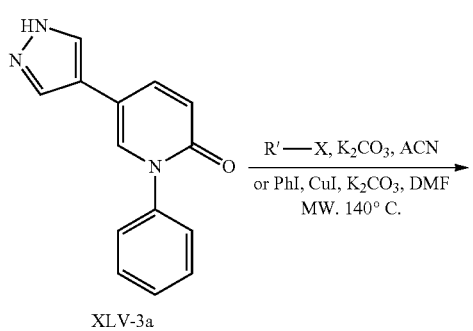

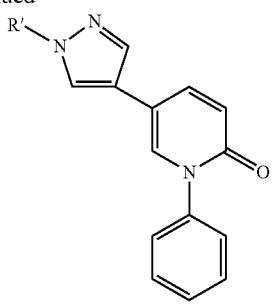

XLV-4

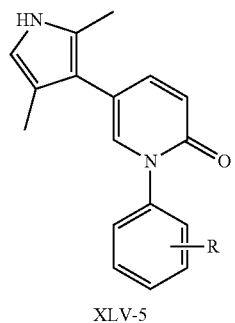

XLV-5

Compound 385: To a solution of XLV-3a (0.2 g, 0.8 mmol) in CH₃CN (15 mL) was added K₂CO₃ (0.5 g, 3.6 mmol), benzyl chloride (0.37 g, 2.9 mmol). The mixture was purged with nitrogen and then heated to reflux overnight. The mixture was cooled to rt, diluted with water, extracted with EtOAc (20 mL×3). The combined organic layer was washed with brine, dried over anhydrous Na₂SO₄, and concentrated in vacuo. The residue was purified by column chromatography on silica gel (PE:EA=1:2) to give Compound 385 (112.8 mg, 46% yield). $^1$H NMR (DMSO-d$_6$, 400 MHz) δ 8.18 (s, 1H), 7.91 (d, J=2.4 Hz, 1H), 7.85 (s, 1H), 7.80 (d, J=8.8 Hz, 1H), 7.53-7.42 (m, 5H), 7.33-7.21 (m, 5H), 6.53 (d, J=9.6 Hz, 1H), 5.28 (s, 2H). MS (ESI) m/z (M+H)⁺ 328.2.

Compound 388 was prepared following the similar procedure for obtaining Compound 385 using isopropyl iodide in place of benzyl chloride. $^1$H NMR (CDCl₃, 400 MHz) δ 7.58-7.50 (m, 5H), 7.47-7.40 (m, 4H), 6.72 (d, J=9.6 Hz, 1H), 4.54-4.48 (m, 1H), 1.52 (d, J=6.8 Hz, 6H). MS (ESI) m/z (M+H)⁺ 280.0.

Compound 389: To a stirred mixture of XLV-3a (0.2 g, 0.8 mmol), iodobenzene (2 g, 9.8 mmol), and K₂CO₃ (0.89 g, 6.4 mmol) in DMF (2 mL) was added CuI (0.12 g, 0.8 mmol). The mixture was purged with nitrogen for three times and then heated at 140° C. under microwave for 2 hrs. The mixture was diluted with H₂O, extracted with EtOAc (20 mL×3). The combined organic layer was washed with water and brine, dried over anhydrous Na₂SO₄, and concentrated in vacuo. The crude product was chromatographed on silica gel (PE: EA=1:2) to give Compound 389 (50.3 mg, 25% yield). $^1$H NMR (CDCl₃, 400 MHz) δ 8.01 (s, 1H), 7.81 (s, 1H), 7.69 (d, J=8.0 Hz, 2H), 7.63-7.60 (m, 1H), 7.55-7.42 (m, 8H), 7.33-7.29 (m, 1H), 6.76 (d, J=8.0 Hz, 1H). MS (ESI) m/z (M+H)⁺ 314.2.

Compounds 378, 379, 381, 387 and 390 were prepared following the similar procedure for obtaining XLV-3 using XLV-2a in place of XLV-2.

Compound 378: $^1$H NMR (DMSO-d$_6$, 400 MHz) δ 12.30 (brs, 1H), 7.54-7.51 (m, 1H), 7.44-7.40 (m, 2H), 7.03-7.00 (m, 3H), 6.54 (d, J=9.2, 1H), 3.80 (s, 3H), 2.18 (s, 6H). MS (ESI) m/z (M+H)⁺ 295.9.

Compound 379: $^1$H NMR (DMSO-d$_6$, 400 MHz) δ 12.30 (brs, 1H), 7.44-7.36 (m, 3H), 7.21-7.17 (m, 3H), 6.72 (d, J=9.6 Hz, 1H), 2.27 (s, 6H).

Compound 381: $^1$H NMR (CDCl₃, 400 MHz) δ 7.50-7.43 (m, 1H), 7.40-7.36 (m, 1H), 7.23-7.10 (m, 4H), 6.73 (d, J=9.6 Hz, 1H), 2.27 (s, 6H). MS (ESI) m/z (M+H)⁺ 283.1.

Compound 387: $^1$H NMR (DMSO-d$_6$, 400 MHz) δ 7.53 (d, J=9.2 Hz, 1H), 7.32 (s, 1H), 7.53 (d, J=8.4 Hz, 1H), 6.94 (s, 1H), 6.87-6.84 (m, 1H), 6.54 (d, J=9.2 Hz, 1H), 4.05 (q, J=6.8 Hz, 2H), 2.17 (s, 6H), 2.05 (s, 3H), 1.35 (t, J=6.8 Hz, 3H). MS (ESI) m/z (M+H)⁺ 323.4.

Compound 390: $^1$H NMR (CDCl₃, 400 MHz) δ 8.79-8.78 (m, 2H), 7.46-7.45 (m, 2H), 7.40-7.38 (m, 1H), 7.18 (s, 1H), 6.74 (d, J=9.6 Hz, 1H), 2.28 (s, 6H). MS (ESI) m/z (M+H)⁺ 267.1.

Compound 380 were prepared following the similar procedure for obtaining XLV-3 using XLV-2a in place of XLV-2 and using Pd(dppf)Cl₂ in place of Pd(PPh₃)₄. $^1$H NMR (DMSO-d$_6$, 400 MHz): δ 12.25 (s, 1H), 7.60-7.47 (m, 6H), 6.51 (d, J=9.2 Hz, 1H), 2.16 (s, 6H). MS (ESI) m/z (M+H)⁺ 299.8.

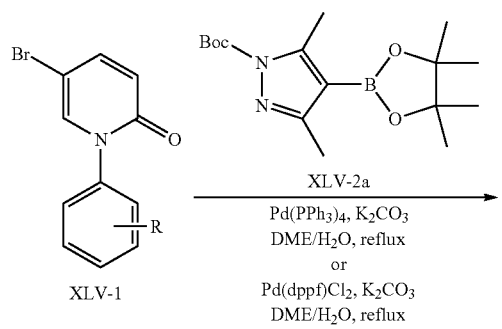

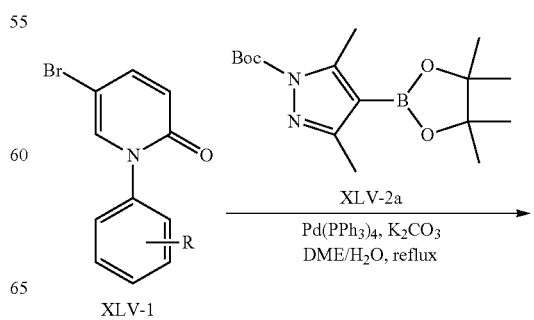

-continued

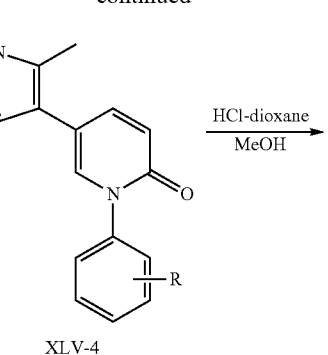

XLV-4

Additional Boc-deprotection procedure: To a solution of XLV-4a (1 eq.) in MeOH (0.1-0.2 mmol/mL) was added a solution of HCl (gas) in dioxane (4 M, volume was two times of MeOH). The mixture was stirred at rt for 1 h. After the completion of the reaction, the mixture was concentrated in vacuo. The crude product was purified by prep-HPLC to yield XLV-5. The preparation of Compounds 382-384 and 386 followed the above deprotection procedure.

Compound 382: $^1$H NMR (DMSO-$d_6$, 400 MHz) δ 12.28 (s, 1H), 7.50 (dd, J=9.6, 2.8 Hz, 1H), 7.42 (d, J=2.4 Hz, 1H), 7.33 (dd, J=6.8, 2.0 Hz, 1H), 7.02 (d, J=9.2 Hz, 1H), 5.52 (d, J=9.2 Hz, 1H), 4.70-4.64 (m, 1H), 2.17 (s, 6H), 1.30 (s, 6H).

Compound 383: $^1$H NMR (DMSO-$d_6$, 400 MHz) δ 12.27 (s, 1H), 7.61 (dd, J=6.8, 2.4 Hz, 1H), 7.54-7.50 (m, 5H), 6.55 (dd, J=8.8, 1.2 Hz, 1H), 2.16 (s, 6H).

Compound 384: $^1$H NMR (DMSO-$d_6$, 400 MHz) δ 12.27 (s, 1H), 7.88 (s, 1H), 7.82-7.73 (m, 3H), 7.55-7.52 (m, 2H), 6.56 (dd, J=8.8, 0.8 Hz, 1H), 2.16 (s, 6H).

Compound 386: $^1$H NMR (DMSO-$d_6$, 400 MHz) δ 12.27 (s, 1H), 7.88 (s, 1H), 7.49 (dd, J=9.6, 2.8 Hz, 1H), 7.40-7.34 (m, 3H), 7.04-7.02 (m, 2H), 6.50 (d, J=9.2 Hz, 1H), 3.79 (s, 3H), 2.15 (s, 6H).

Compound 391 was prepared by following the similar procedure for obtaining Compound 238 (Scheme XXXIX) by using 4-bromo-1,5-dimethyl-1H-pyrazole in place of XXXIX-2. $^1$H NMR (CDCl$_3$, 400 MHz) δ 7.49-7.42 (m, 4H), 7.38-7.33 (m, 2H), 7.26-7.24 (m, 1H), 6.71 (d, J=9.2 Hz, 1H), 3.83 (s, 3H), 2.32 (s, 3H). MS (ESI) m/z [M+H]$^+$ 349.9.

Compounds 420-422 were prepared following Scheme XLV using 5-(4,4,5,5-tetramethyl-1,3,2-dioxaborolan-2-yl)benzo[d]thiazole or 5-(4,4,5,5-tetramethyl-1,3,2-dioxaborolan-2-yl)benzo[d]oxazole as XLV-2 and 5-bromo-1-(4-ethoxy-2-methylphenyl)-4-methylpyridin-2(1H)-one or 5-bromo-1-(4-chlorophenyl)-4-methylpyridin-2(1H)-one as XLV-1.

Compound 420: $^1$H NMR (CDCl$_3$, 400 MHz) δ 8.14 (s, 1H), 7.70 (s, 1H), 7.62-7.59 (m, 1H), 7.32-7.30 (m, 1H), 7.15-7.12 (m, 2H), 6.85-6.79 (m, 2H), 6.61 (s, 1H), 4.03 (q, J=6.8 Hz, 2H), 2.18 (s, 3H), 2.16 (s, 3H), 1.41 (t, J=6.8 Hz, 3H). MS (ESI) m/z (M+H)$^+$ 361.1.

Compound 421: $^1$H NMR (CDCl$_3$, 400 MHz) δ 9.07 (s, 1H), 8.05 (s, 1H), 8.00 (d, J=8.0 Hz, 1H), 7.48-7.43 (m, 2H), 7.42-7.37 (m, 3H), 7.26 (s, 1H), 6.62 (s, 1H), 2.18 (s, 3H). MS (ESI) m/z (M+H)$^+$ 352.9.

Compound 422: $^1$H NMR (CDCl$_3$, 400 MHz) δ 8.16 (s, 1H), 7.70 (s, 1H), 7.62 (d, J=8.0 Hz, 1H), 7.48-7.43 (m, 2H), 7.41-7.38 (m, 2H), 7.32-7.28 (m, 2H), 6.60 (s, 1H), 2.14 (s, 3H). MS (ESI) m/z (M+H)$^+$ 337.2.

Example 24

5-Phenyl, 4-Alkyl Substituted Analogs (Scheme XLVI)

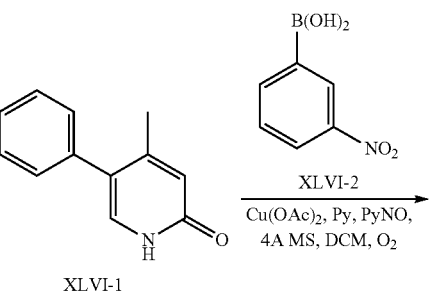

XLVI-1

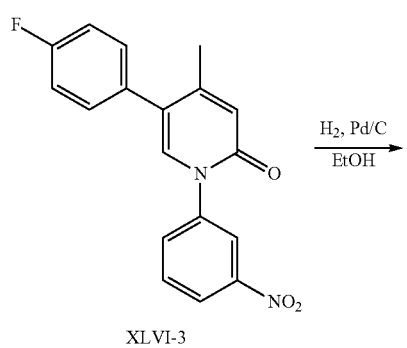

XLVI-3

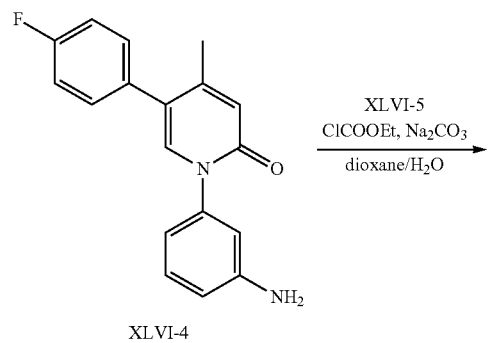

XLVI-4

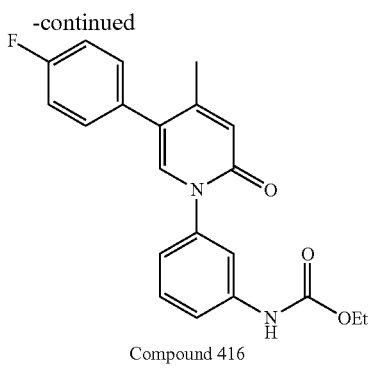

Compound 416

XLVI-3 was prepared following the general procedure described in Method 1. MS (ESI) m/z (M+H)+ 325.1.

A mixture of XLVI-3 (2.3 g, 7.08 mmol) and Pd/C (~0.2 g) in ethanol (30 mL) was stirred under $H_2$ at rt overnight. Filtered the mixture, and concentrated the filtrate to give XLVI-4 (1.6 g, 77% yield). MS (ESI) m/z (M+H)+ 294.9.

To a solution of XLVI-4 (400 mg, 1.36 mmol) in dioxane/$H_2O$ (11 mL, v/v=10:1) was added $Na_2CO_3$ (288 mg, 2.72 mmol) with stirring at 0° C. Then ethyl chloroformate (XLVI-5) (443 mg, 4.08 mmol) was added dropwise. The mixture was stirred at rt for 5 hours. The reaction was evaporated to dryness. The residue was diluted with water (20 mL), extracted with EtOAc (30 mL×3). The combined organic layer was washed with brine, dried over anhydrous $Na_2SO_4$ and concentrated. The crude was purified by prep-TLC (PE/EA=1/1) to give Compound 416 (389 mg, 78% yield) as a white solid. $^1$H NMR (DMSO-$d_6$, 400 MHz) δ 9.81 (s, 1H), 7.54 (s, 1H), 7.47-7.34 (m, 5H), 7.24-7.20 (m, 2H), 7.05 (d, J=8.0 Hz, 1H), 6.44 (s, 1H), 4.11 (q, J=7.2 Hz, 2H), 2.08 (s, 3H), 1.22 (t, J=7.2 Hz, 3H). MS (ESI) m/z [M+H]+ 366.9.

Compound 417: To the solution of XLVI-4 (500 mg, 1.7 mmol) in Py (2 mL) was added dimethylcarbamic chloride (365 mg, 3.4 mmol). The mixture was stirred at rt overnight. The reaction was partitioned between EA (100 mL) and $H_2O$ (20 mL). The organic layer was separated, washed with aq. HCl (2N) and brine, dried over anhydrous $Na_2SO_4$ and concentrated. The residue was purified by prep-TLC (PE/EA=1/3) to give Compound 417 (160 mg, 26% yield). $^1$H NMR (DMSO-$d_6$, 400 MHz) δ 8.46 (s, 1H), 7.57 (s, 1H), 7.53 (d, J=8.4 Hz, 1H), 7.44-7.41 (m, 2H), 7.39 (s, 1H), 7.31 (t, J=8.0 Hz, 1H), 7.22 (t, J=8.8 Hz, 2H), 7.00-6.98 (m, 1H), 6.44 (s, 1H), 2.91 (s, 6H), 2.09 (s, 3H). MS (ESI) m/z [M+H]+ 365.9.

Compound 419: To the solution of XLVI-4 (500 mg, 1.7 mmol) in Py (2 mL) was added methylcarbamic chloride (317 mg, 3.4 mmol). The mixture was stirred at rt overnight. The reaction was partitioned between EA (100 mL) and $H_2O$ (20 mL). The organic layer was separated, washed with aq. HCl (2N) and brine, dried over anhydrous $Na_2SO_4$ and concentrated. The residue was purified by prep-TLC (PE/EA=1/3) to give Compound 419 (209 mg, 35% yield). $^1$H NMR (DMSO-$d_6$, 400 MHz) δ 8.73 (s, 1H), 7.57 (s, 1H), 7.47-7.42 (m, 3H), 7.38-7.30 (m, 2H), 7.27-7.22 (m, 2H), 6.96 (d, J=7.2 Hz, 1H), 6.46 (s, 1H), 6.11-6.07 (m, 1H), 2.64 (d, J=4.8 Hz, 3H), 2.11 (s, 3H). MS (ESI) m/z [M+H]+ 351.9.

XLVI-4a was prepared following the similar procedure for obtaining XLVI-4 by using (4-nitrophenyl)boronic acid in place of XLVI-2. MS (ESI) m/z (M+H)+ 294.9.

Compound 418: To the solution of XLVI-4a (500 mg, 1.7 mmol) in DCM (15 mL) was added TMSNCO (978 mg, 8.5 mmol). The mixture was stirred at rt overnight. LCMS showed the reaction was completed. The mixture was filtered and concentrated. The residue was purified by prep-TLC (PE/EA=1/3) to afford Compound 418 (101 mg, 18% yield). $^1$H NMR (DMSO-$d_6$, 400 MHz) δ 8.70 (s, 1H), 7.48-7.39 (m, 5H), 7.28-7.20 (m, 4H), 6.41 (s, 1H), 5.89 (s, 2H), 2.08 (s, 3H). MS (ESI) m/z [M+H]+ 337.9.

Compound 560 was prepared by reacting XLVI-4 with isocyanatoethane in DCM at rt overnight. $^1$H NMR (DMSO-$d_6$, 400 MHz) δ 8.50 (s, 1H), 7.58 (s, 1H), 7.46-7.41 (m, 3H), 7.33-7.24 (m, 4H), 6.95 (d, J=7.2 Hz, 1H), 6.45 (s, 1H), 6.08 (d, J=7.2 Hz, 1H), 3.74 (m, 1H), 2.11 (s, 3H), 1.10 (d, J=6.4 Hz, 6H).

Compound 561 was prepared by reacting XLVI-4 with 2-isocyanatopropane in DCM at rt overnight. $^1$H NMR (DMSO-$d_6$, 400 MHz) δ 8.62 (s, 1H), 7.56 (s, 1H), 7.44-7.39 (m, 3H), 7.32-7.30 (m, 2H), 7.22 (t, J=8.8 Hz, 2H), 6.94-6.92 (m, 1H), 6.43 (s, 1H), 6.15 (t, J=5.6 Hz, 1H), 3.11-3.04 (m, 2H), 2.08 (s, 3H), 7.02 (t, J=7.2 Hz, 3H).

Additional compounds as shown in Table 1 were also prepared. Those skilled in the art will be able to recognize modifications of the disclosed syntheses and to devise alternate routes based on the disclosures herein.

Compound 666: $^1$H NMR (CDCl$_3$, 400 MHz) δ 8.20-8.10 (m, 4H), 7.42-7.40 (m, 2H), 7.27 (m, 2H). MS (ESI) m/z [M+H]+ 337.0.

Compound 667: $^1$H NMR (CDCl$_3$, 400 MHz) δ 8.04-8.00 (m, 2H), 7.51-7.49 (m, 1H), 7.20-7.15 (m, 2H), 6.90-6.85 (m, 2H), 4.14-4.09 (q, J=7.2 Hz, 2H), 2.30 (s, 3H), 1.48-1.44 (t, J=7.2 Hz, 3H). MS (ESI) m/z [M+H]+ 311.0.

Compound 668: $^1$H NMR (CDCl$_3$, 400 MHz) δ 8.26 (s, 1H), 7.90 (s, 1H), 6.79 (t, J=8.0 Hz, 2H), 5.40 (s, 1H), 4.72 (d, J=8.0 Hz, 1H), 4.49-4.38 (m, 2H), 3.94-3.90 (q, J=6.4 Hz, 1H), 3.81-3.66 (m, 4H), 2.75-2.65 (m, 1H), 2.28-2.16 (m, 4H), 2.05-1.97 (m, 2H), 1.52-1.44 (m, 3H), 1.31-1.25 (m, 3H). MS (ESI) m/z (M+H)+ 449.1. EE %: 95.5%.

Example 25

5-Haloalkyl Substituted Analogs (Scheme XLVII)

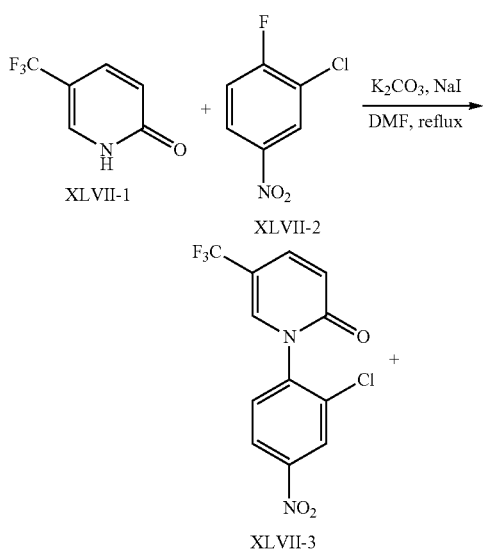

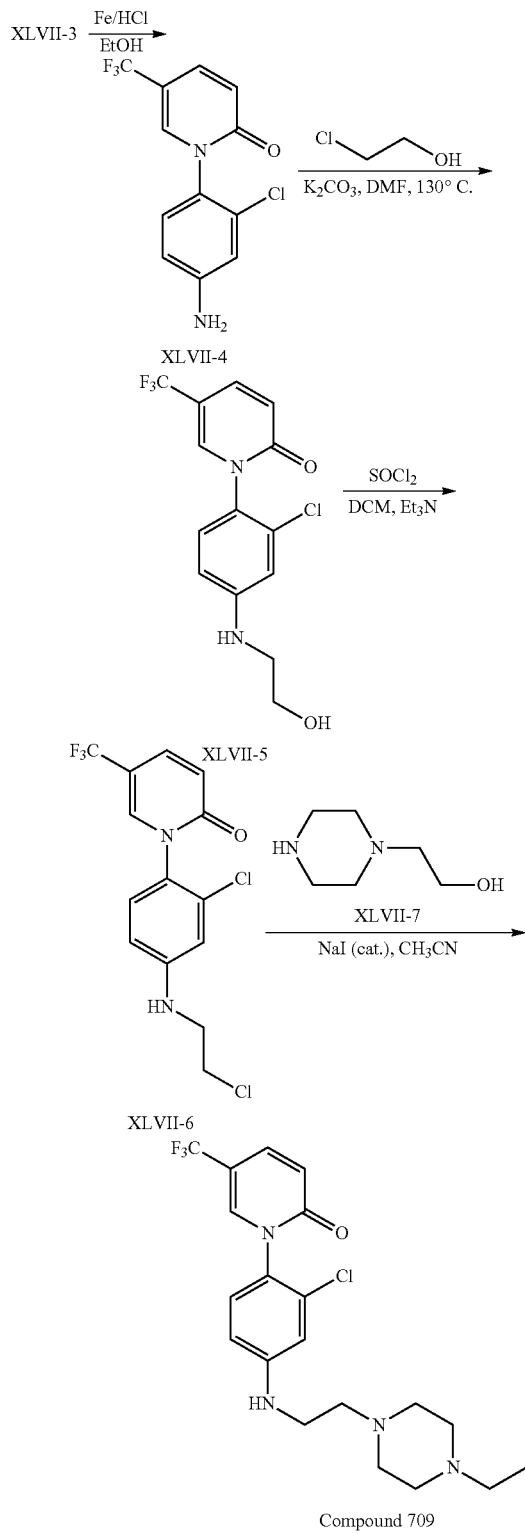

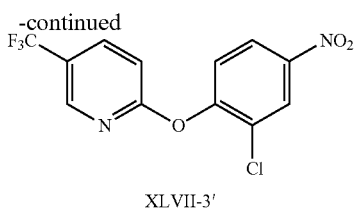

To a mixture of XLVII-1 (8.2 g, 50 mmol, 1 eq) in DMF (60 mL) was added XLVII-2 (13.1 g, 75 mmol, 1.5 eq), $K_2CO_3$ (11.0 g, 80 mmol, 1.6 eq) and NaI (1.4 g, 9.3 mmol, 0.18 eq). The resulting mixture was refluxed for 4 h under $N_2$. Then the mixture was cooled to rt and diluted with $H_2O$ and extracted with EA. The combined organic phase was washed with brine, dried over $Na_2SO_4$, and filtrated. EA was evaporated to allow solid precipitate out. The solid was filtered, and the filter cake was washed with PE to give the pure XLVII-3 (11.2 g, 70%) as a brown solid. The filtrate was concentrated and purified by flash column chromatography (PE:EA=10:1~1:1) to afford the XLVII-3'(1.7 g, 10.6%) as a yellow oil.

The mixture of XLVII-3 (9.85 g, 31 mmol, 1 eq) and reductive iron power (5.2 g, 93 mmol, 3 eq) in 80 mL of 50% EtOH was heated to reflux, conc.HCl (0.34 mL, 4 mmol) was added dropwise, then the mixture was refluxed for 4 h. Then the mixture was cooled to rt, filtered, washed the filter cake with EA, the filtrate was washed with brine, dried over $Na_2SO_4$, and concentrated to afford XLVII-4 (8.9 g, crude yield 100%).

The mixture of XLVII-4 (6.0 g, 20.8 mmol, 1 eq), chloroethanol (20 mL, 300 mmol, 14.4 eq) and $K_2CO_3$ (5.75 g, 41.6 mmol, 2 eq) in DMF (50 mL) was stirred at 130° C. for 28 h. After the mixture was cooled to rt, diluted with $H_2O$, and extracted with EA, the filtrate was concentrated and the residue was purified to afford XLVII-5 (2.5 g, 36%) as a yellow solid.

The mixture of XLVII-5 (2.0 g, 6 mmol, 1 eq), $SOCl_2$ (0.65 mL, 9 mmol, 1.5 eq) and $Et_3N$ (1.3 mL, 9 mmol, 1.5 eq) in DCM (50 mL) was stirred at rt for 28 h under $N_2$. The reaction was then quenched with $H_2O$, extracted with EA, the filtrate was concentrated and the residue was purified to produce XLVII-6 (1.5 g, 71%) as a yellow solid.

The mixture of XLVII-6 (900 mg, 2.6 mmol, 1 eq), XLVII-7 (1.2 g, 7.8 mmol, 3 eq) and NaI (30 mg, catalytic amount) in $CH_3CN$ (50 mL) was refluxed for 16 h under $N_2$. The solvent was then removed and the resulting residue was purified to give Compound 709 (420 mg, 37%) as a yellow colloid substance. $^1$H NMR ($CDCl_3$, 400 MHz) δ 7.61 (s, 1H), 7.51 (dd, J=2.6, 9.7 Hz, 1H), 7.11 (d, J=8.5 Hz, 1H), 6.76-6.70 (m, 2H), 6.58 (dd, J=2.6, 8.7 Hz, 1H), 4.74 (t, J=4.5 Hz, 1H), 3.66-3.60 (m, 2H), 3.16 (q, J=5.3 Hz, 2H), 2.72-2.44 (m, 12H). MS (ESI) m/z (M+H$^+$) 445.1.

Example 26

ET-1 Assay

Assay of Inhibitory Effect on TGF-b induced Endothelin-1 Production

Fibroblasts (primary human lung and dermal, HFL-1, 3T3 etc) are seeded in 96-well plates at ~15000 cells/well and serum starved for 0-48 hours. After media exchange, compounds serially diluted in DMSO are added to the cells. After a brief incubation of ~30 min, stimulants (TGFb, serum, LPA etc) are added followed by further incubation for 16-48 hours. Media is then harvested and stored frozen in plate format for later endothelin-1 (ET-1) determination by ELISA. Toxicity measurements are made using the ATPlite kit (Perkin-Elmer). ET-1 is quantified using an ELISA kit (R&D Systems). The amount of ET-1 produced in the assay wells are back-calculated using the ELISA standard. The ability of a compound to inhibit ET-1 production is typically analyzed by fitting dose-response curves to a 4-parameter logistic function to obtain an EC50 value. A measure of cytotoxicity (CC50) is likewise reported from the same experiment using the ATPlite data.

Assay Data for Compounds

Compounds of some embodiments were prepared according to synthetic methods described herein and assay data obtained for $EC_{50}$ against ET-1. The assay data obtained is presented in Table 2, in which A=less than 50 μM, B=greater than or equal to 50 μM and less than or equal to 200 μM; and C=greater than 200 μM.

TABLE 2

| Compd. # | $EC_{50}$ ET-1 |
|---|---|
| 10 | C |
| 11 | C |
| 12 | C |
| 13 | C |
| 14 | C |
| 15 | C |
| 17 | C |
| 18 | C |
| 19 | B |
| 21 | C |
| 22 | C |
| 23 | B |
| 24 | C |
| 25 | C |
| 26 | A |
| 27 | C |
| 28 | B |
| 29 | B |
| 31 | A |
| 32 | C |
| 33 | A |
| 34 | A |
| 35 | A |
| 36 | A |
| 37 | B |
| 38 | C |
| 39 | A |
| 40 | C |
| 42 | C |
| 43 | A |
| 44 | C |
| 45 | C |
| 46 | A |
| 47 | A |
| 49 | A |
| 50 | C |
| 51 | C |
| 52 | C |
| 53 | C |
| 54 | C |
| 55 | C |
| 56 | C |
| 57 | C |
| 58 | A |
| 59 | A |
| 60 | A |
| 61 | A |
| 62 | C |
| 63 | A |
| 64 | B |
| 65 | C |
| 66 | B |
| 67 | C |
| 68 | C |
| 71 | C |
| 73 | A |
| 74 | B |
| 75 | B |
| 77 | B |
| 78 | C |
| 79 | A |
| 80 | B |
| 81 | B |
| 82 | C |
| 83 | C |
| 84 | C |
| 85 | C |
| 86 | B |
| 87 | A |
| 88 | B |
| 89 | C |
| 90 | C |
| 91 | C |
| 92 | B |
| 93 | A |
| 94 | C |
| 95 | A |
| 96 | C |
| 97 | C |
| 98 | B |
| 99 | A |
| 100 | A |
| 101 | C |
| 102 | C |
| 103 | C |
| 104 | C |
| 105 | C |
| 106 | C |
| 107 | C |
| 108 | C |
| 110 | C |
| 111 | C |
| 112 | C |
| 113 | C |
| 114 | C |
| 115 | C |
| 116 | C |
| 118 | C |
| 119 | A |
| 120 | A |
| 121 | C |
| 122 | C |
| 123 | A |
| 124 | C |
| 125 | C |
| 126 | A |
| 127 | C |
| 128 | A |
| 129 | B |
| 130 | C |
| 131 | C |
| 132 | C |
| 133 | B |
| 134 | A |
| 135 | B |
| 136 | B |
| 137 | C |
| 138 | C |
| 139 | C |
| 140 | B |
| 141 | C |
| 143 | C |
| 144 | C |
| 145 | B |
| 146 | C |
| 147 | C |
| 148 | C |
| 149 | B |
| 150 | B |
| 151 | A |
| 152 | B |
| 153 | A |
| 154 | C |
| 156 | C |
| 157 | A |
| 158 | C |
| 159 | C |
| 160 | B |
| 161 | A |
| 162 | A |
| 163 | A |
| 164 | A |

TABLE 2-continued

| Compd. # | EC$_{50}$ ET-1 |
|---|---|
| 165 | B |
| 166 | A |
| 167 | C |
| 168 | B |
| 169 | B |
| 170 | A |
| 171 | B |
| 172 | C |
| 173 | C |
| 174 | A |
| 175 | B |
| 176 | B |
| 177 | B |
| 178 | B |
| 180 | B |
| 181 | C |
| 182 | C |
| 183 | C |
| 184 | B |
| 185 | B |
| 186 | A |
| 187 | B |
| 188 | A |
| 189 | C |
| 190 | B |
| 191 | B |
| 192 | A |
| 193 | B |
| 194 | A |
| 195 | A |
| 196 | B |
| 197 | B |
| 198 | B |
| 199 | B |
| 200 | B |
| 201 | B |
| 202 | B |
| 203 | A |
| 204 | A |
| 205 | B |
| 206 | B |
| 207 | B |
| 208 | B |
| 209 | A |
| 210 | A |
| 211 | C |
| 212 | B |
| 213 | C |
| 214 | B |
| 216 | B |
| 217 | C |
| 218 | A |
| 219 | B |
| 220 | C |
| 221 | C |
| 222 | C |
| 223 | C |
| 224 | C |
| 225 | C |
| 226 | C |
| 227 | C |
| 228 | B |
| 229 | B |
| 230 | C |
| 231 | B |
| 232 | C |
| 233 | C |
| 234 | C |
| 235 | B |
| 236 | B |
| 237 | B |
| 238 | B |
| 240 | C |
| 241 | C |
| 242 | C |
| 243 | B |
| 244 | C |

TABLE 2-continued

| Compd. # | EC$_{50}$ ET-1 |
|---|---|
| 247 | C |
| 248 | C |
| 250 | B |
| 251 | A |
| 252 | B |
| 253 | C |
| 254 | A |
| 255 | C |
| 256 | C |
| 257 | C |
| 258 | A |
| 259 | B |
| 260 | B |
| 261 | C |
| 262 | B |
| 263 | A |
| 264 | C |
| 265 | C |
| 266 | C |
| 267 | C |
| 268 | C |
| 269 | C |
| 270 | C |
| 271 | C |
| 272 | C |
| 273 | C |
| 274 | C |
| 275 | C |
| 276 | C |
| 277 | C |
| 278 | B |
| 279 | C |
| 281 | C |
| 282 | C |
| 283 | C |
| 285 | C |
| 287 | C |
| 288 | B |
| 289 | B |
| 290 | B |
| 291 | C |
| 294 | B |
| 296 | C |
| 298 | B |
| 299 | C |
| 300 | C |
| 302 | B |
| 303 | B |
| 309 | B |
| 310 | B |
| 311 | C |
| 312 | C |
| 313 | B |
| 314 | A |
| 315 | A |
| 316 | A |
| 318 | A |
| 319 | A |
| 320 | A |
| 321 | A |
| 322 | A |
| 323 | C |
| 324 | B |
| 327 | C |
| 328 | C |
| 329 | C |
| 330 | C |
| 331 | C |
| 332 | C |
| 333 | B |
| 334 | C |
| 336 | C |
| 338 | C |
| 344 | C |
| 345 | C |
| 346 | C |
| 347 | B |

TABLE 2-continued

| Compd. # | EC$_{50}$ ET-1 |
|---|---|
| 349 | C |
| 350 | B |
| 351 | A |
| 352 | B |
| 353 | B |
| 354 | B |
| 355 | C |
| 356 | B |
| 357 | C |
| 359 | C |
| 360 | A |
| 361 | C |
| 362 | C |
| 363 | C |
| 364 | C |
| 365 | C |
| 366 | C |
| 367 | C |
| 368 | C |
| 369 | B |
| 370 | C |
| 371 | C |
| 372 | C |
| 373 | C |
| 374 | A |
| 375 | C |
| 376 | A |
| 377 | B |
| 378 | B |
| 379 | C |
| 380 | C |
| 381 | C |
| 382 | B |
| 383 | B |
| 384 | B |
| 385 | B |
| 387 | B |
| 388 | C |
| 390 | C |
| 391 | A |
| 392 | C |
| 393 | C |
| 394 | A |
| 395 | B |
| 396 | C |
| 397 | C |
| 398 | C |
| 399 | C |
| 400 | A |
| 401 | C |
| 402 | A |
| 403 | A |
| 404 | A |
| 405 | A |
| 406 | B |
| 407 | A |
| 408 | C |
| 409 | A |
| 410 | A |
| 411 | B |
| 412 | C |
| 413 | A |
| 414 | A |
| 415 | A |
| 416 | A |
| 417 | A |
| 418 | B |
| 419 | B |
| 420 | B |
| 421 | B |
| 422 | C |
| 423 | C |
| 424 | B |
| 425 | A |
| 426 | C |
| 427 | C |
| 429 | C |
| 430 | A |
| 431 | C |
| 432 | C |
| 438 | C |
| 439 | C |
| 440 | C |
| 442 | C |
| 526 | C |
| 527 | A |
| 528 | A |
| 529 | C |
| 530 | A |
| 531 | A |
| 532 | A |
| 533 | B |
| 534 | A |
| 535 | A |
| 536 | A |
| 537 | A |
| 540 | A |
| 541 | C |
| 542 | A |
| 543 | A |
| 544 | B |
| 545 | C |
| 546 | C |
| 547 | A |
| 550 | A |
| 552 | C |
| 553 | A |
| 554 | C |
| 555 | C |
| 556 | C |
| 557 | A |
| 558 | B |
| 559 | A |
| 562 | A |
| 563 | A |
| 565 | A |
| 566 | C |
| 568 | C |
| 569 | A |
| 570 | C |
| 571 | C |
| 573 | C |
| 574 | A |
| 575 | A |
| 577 | B |
| 579 | C |
| 580 | A |
| 581 | C |
| 582 | A |
| 583 | A |
| 584 | A |
| 585 | C |
| 586 | A |
| 587 | A |
| 588 | C |
| 591 | A |
| 593 | A |
| 594 | A |
| 595 | A |
| 596 | A |
| 597 | C |
| 598 | A |
| 599 | A |
| 600 | A |
| 601 | A |
| 602 | A |
| 603 | A |
| 604 | A |
| 605 | A |
| 606 | A |
| 607 | A |
| 608 | B |
| 609 | A |
| 610 | A |

TABLE 2-continued

| Compd. # | EC$_{50}$ ET-1 |
|---|---|
| 611 | A |
| 612 | A |
| 614 | A |
| 615 | A |
| 617 | A |
| 618 | B |
| 619 | A |
| 620 | A |
| 622 | C |
| 623 | C |
| 624 | A |
| 625 | A |
| 626 | A |
| 628 | A |
| 629 | A |
| 631 | A |
| 634 | A |
| 636 | C |
| 647 | A |
| 648 | A |
| 649 | A |
| 650 | A |
| 651 | A |
| 657 | A |
| 665 | A |
| 666 | A |
| 667 | A |
| 669 | A |
| 670 | A |
| 671 | A |
| 672 | A |
| 673 | A |
| 674 | B |
| 675 | A |
| 676 | A |
| 677 | B |
| 678 | B |
| 679 | A |
| 680 | C |
| 681 | B |
| 682 | A |
| 683 | A |
| 684 | B |
| 685 | A |
| 686 | B |
| 687 | A |
| 688 | B |
| 689 | A |
| 690 | A |
| 691 | A |
| 692 | A |
| 693 | B |
| 694 | A |
| 695 | A |
| 696 | B |
| 697 | B |
| 698 | B |
| 699 | B |
| 700 | B |
| 701 | A |
| 702 | A |
| 703 | A |
| 704 | A |
| 705 | A |
| 706 | A |
| 707 | A |
| 708 | B |
| 709 | B |

Example 27

Cell Proliferation Assay

Assay of Inhibitory Effect on Cell Proliferation (BrdU Incorporation)

Fibroblasts (primary human lung and dermal, HFL-1, 3T3 etc) were plated on a 96-well plate and serum starved for 24-48 hours. The media were then exchanged for media containing stimulants (LPA, TGFb, serum etc) and cultured further for 16-24 hours before BrdU addition. After culturing for another 8 hours, cells were washed with PBS and the amount of BrdU incorporated into the cells was assayed by absorbance at 450 nm using the Cell proliferation ELISA system (RPN250, Amersham LIFE SCIENCE). The difference between the amount of BrdU incorporated in the stimulant-added well and the amount of BrdU incorporated in the well containing no stimulant represented the amount of BrdU incorporation accelerated by stimulant. The increase of BrdU incorporation without the addition of test compounds was set as 100% and the concentration of compound with 50% inhibition in the increase of BrdU incorporation (IC$_{50}$ value) was determined. The test compounds were added 0-30 min before stimulant addition.

Assay Data for Compounds

Compounds of some embodiments were prepared according to synthetic methods described herein and assay data obtained for IC$_{50}$ for BrdU inhibition. The assay data obtained is presented in Table 3, in which A=less than 50 μM, B=greater than or equal to 50 μM and less than or equal to 200 μM; and C=greater than 200 μM.

TABLE 3

| Compd. # | IC$_{50}$ BRDU |
|---|---|
| 13 | C |
| 21 | C |
| 28 | B |
| 29 | C |
| 31 | B |
| 41 | A |
| 43 | C |
| 46 | A |
| 47 | A |
| 49 | A |
| 50 | A |
| 51 | C |
| 52 | C |
| 53 | C |
| 58 | A |
| 59 | A |
| 60 | A |
| 61 | A |
| 63 | A |
| 68 | C |
| 71 | C |
| 73 | C |
| 75 | B |
| 80 | C |
| 86 | A |
| 87 | A |
| 101 | B |
| 119 | A |
| 120 | A |
| 123 | A |
| 126 | A |
| 133 | B |
| 134 | A |
| 153 | A |
| 155 | A |
| 157 | C |
| 160 | A |
| 161 | A |

TABLE 3-continued

| Compd. # | IC$_{50}$ BRDU |
|---|---|
| 162 | A |
| 175 | A |
| 180 | A |
| 184 | A |
| 185 | A |
| 188 | A |
| 189 | C |
| 192 | A |
| 195 | A |
| 196 | A |
| 198 | A |
| 201 | A |
| 202 | A |
| 203 | A |
| 204 | A |
| 206 | A |
| 207 | A |
| 208 | B |
| 209 | A |
| 210 | C |
| 216 | A |
| 218 | A |
| 219 | C |
| 229 | A |
| 234 | C |
| 237 | A |
| 238 | A |
| 239 | A |
| 243 | C |
| 251 | A |
| 252 | B |
| 254 | A |
| 258 | A |
| 259 | A |
| 260 | A |
| 261 | A |
| 262 | A |
| 263 | A |
| 276 | C |
| 278 | B |
| 282 | C |
| 285 | C |
| 290 | C |
| 300 | C |
| 316 | A |
| 333 | C |
| 350 | B |
| 351 | B |
| 353 | C |
| 360 | B |
| 374 | B |
| 376 | C |
| 383 | B |
| 385 | A |
| 387 | B |
| 391 | B |
| 394 | A |
| 395 | B |
| 399 | A |
| 400 | A |
| 402 | C |
| 403 | A |
| 404 | A |
| 405 | A |
| 406 | A |
| 407 | A |
| 410 | A |
| 411 | A |
| 413 | A |
| 414 | A |
| 415 | A |
| 416 | A |
| 417 | A |
| 418 | B |
| 419 | B |
| 424 | A |
| 425 | A |
| 430 | A |
| 431 | B |
| 432 | B |
| 531 | A |
| 535 | A |
| 538 | B |
| 542 | A |
| 543 | A |
| 544 | A |
| 547 | A |
| 550 | A |
| 551 | A |
| 553 | A |
| 557 | A |
| 562 | A |
| 563 | A |
| 564 | A |
| 565 | A |
| 569 | A |
| 570 | C |
| 574 | A |
| 575 | A |
| 583 | A |
| 584 | A |
| 588 | A |
| 591 | C |
| 594 | A |
| 595 | B |
| 600 | C |
| 601 | A |
| 602 | A |
| 603 | A |
| 604 | A |
| 605 | A |
| 606 | A |
| 607 | A |
| 609 | A |
| 610 | A |
| 615 | A |
| 617 | B |
| 618 | B |
| 619 | A |
| 620 | A |
| 624 | A |
| 625 | A |
| 626 | A |
| 629 | C |
| 631 | C |
| 636 | C |
| 640 | C |
| 647 | A |
| 648 | A |
| 649 | B |
| 650 | A |
| 651 | A |
| 657 | A |
| 658 | C |
| 662 | C |
| 664 | A |
| 665 | B |
| 681 | A |
| 682 | A |
| 683 | A |
| 684 | A |
| 685 | A |
| 686 | A |
| 687 | A |
| 688 | B |
| 689 | A |

While the disclosure has been illustrated and described in detail in the foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' preferred, 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of treating a fibrotic condition selected from pulmonary fibrosis, dermal fibrosis, pancreatic fibrosis, liver fibrosis, and renal fibrosis, comprising administering a therapeutically effective amount of a compound having the structure of Formula (III):

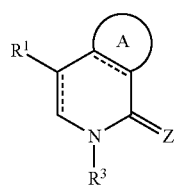

(III)

or a pharmaceutically acceptable salt thereof to a subject in need thereof, wherein $R^1$ is selected from the group consisting of $C_{6-10}$ aryl optionally substituted with one or more $R^4$, 5-10 membered heteroaryl optionally substituted with one or more $R^4$, $C_{3-10}$ carbocyclyl optionally substituted with one or more $R^4$, and 3-10 membered heterocyclyl optionally substituted with one or more $R^4$;

$R^3$ is selected from the group consisting of hydrogen, —(CH$_2$)$_n$—(C$_{6-10}$ aryl), —(CH$_2$)$_n$-(5-10 membered heteroaryl), —(CH$_2$)$_n$—(C$_{3-10}$ carbocyclyl), and —(CH$_2$)$_n$-(3-10 membered heterocyclyl), each optionally substituted with one or more $R^9$;

ring A is

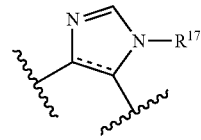

optionally substituted with one or more $R^4$, wherein $R^{17}$ is independently selected from hydrogen, optionally substituted $C_{1-6}$ alkyl, optionally substituted $C_{3-6}$ cycloalkyl, optionally substituted $C_{2-8}$ alkoxyalkyl, optionally substituted C-carboxy, acyl, $C_{6-10}$ aryl optionally substituted with one or more $R^{11}$, or $C_{7-14}$ aralkyl optionally substituted with one or more $R^{11}$, each $R^4$ is independently selected from the group consisting of halogen, —CN, —OH, —C(O)R$^8$, —SO$_2$R$^{16}$, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{6-10}$ aryl optionally substituted with one or more $R^{11}$, $C_{7-14}$ aralkyl optionally substituted with one or more $R^{11}$, 5-10 membered heteroaryl optionally substituted with one or more $R^{11}$, or independently two geminal $R^4$ together are oxo;

each $R^5$ is independently selected from the group consisting of hydrogen, optionally substituted $C_{1-6}$ alkyl, optionally substituted $C_{2-6}$ alkenyl, optionally substituted $C_{2-6}$ alkynyl, optionally substituted $C_{2-8}$ alkoxyalkyl, $C_{6-10}$ aryl optionally substituted with one or more $R^{11}$, $C_{7-14}$ aralkyl optionally substituted with one or more $R^{11}$, and —(CH$_2$)$_n$-(3-10 membered heterocyclyl) optionally substituted with one or more $R^{10}$;

each $R^8$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —NR$^{12}$R$^{13}$, and —OR$^5$;

each $R^9$ is independently selected from the group consisting of hydroxy, halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, —OR$^5$, —NR$^{14}$R$^{15}$, —C(O)R$^8$, —SO$_2$R$^{16}$, —CN, and —NO$_2$;

each $R^{10}$ is independently selected from the group consisting of optionally substituted $C_{1-6}$ alkyl, optionally substituted $C_{2-6}$ alkenyl, and optionally substituted $C_{2-6}$ alkynyl, or independently two geminal $R^{10}$ together are oxo;

each $R^{11}$ is independently selected from the group consisting of halogen, —CN, optionally substituted $C_{1-6}$ alkyl, optionally substituted $C_{2-6}$ alkenyl, optionally substituted $C_{2-6}$ alkynyl, and optionally substituted $C_{1-6}$ alkoxy;

each $R^{12}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

each $R^{13}$ is independently selected from the group consisting of hydrogen, optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, and $C_{7-14}$ aralkyl optionally substituted with one or more $R^{11}$;

$R^{14}$ is selected from the group consisting of hydrogen, optionally substituted $C_{1-6}$ alkyl, optionally substituted $C_{6-10}$ aryl, and —C(O)R$^8$;

$R^{15}$ is selected from the group consisting of hydrogen, optionally substituted $C_{1-6}$ alkyl, optionally substituted $C_{6-10}$ aryl, and —C(O)R$^8$;

each $R^{16}$ is independently selected from the group consisting of optionally substituted $C_{1-6}$ alkyl, optionally substituted $C_{2-6}$ alkenyl, optionally substituted $C_{2-6}$ alkynyl, $C_{6-10}$ aryl optionally substituted with one or more $R^{11}$, $C_{7-14}$ aralkyl optionally substituted with one or more $R^{11}$, —NR$^{12}$R$^{13}$, and —OR$^5$;

Z is selected from oxygen and sulfur;

each n is 0; and the bonds represented by a solid and dashed line are independently selected from the group consisting of a single bond and a double bond.

2. The method of claim 1, wherein $R^3$ is selected from the group consisting of —(CH$_2$)$_n$—(C$_{6-10}$ aryl), —(CH$_2$)$_n$-(5-10 membered heteroaryl), —(CH$_2$)$_n$—(C$_{3-10}$ carbocyclyl), and —(CH$_2$)$_n$-(3-10 membered heterocyclyl), each optionally substituted with one or more $R^9$; and each $R^9$ is independently selected from the group consisting of halogen, optionally substituted $C_{1-6}$ alkyl, optionally substituted $C_{2-6}$ alkenyl, optionally substituted $C_{2-6}$ alkynyl, optionally substituted $C_{1-6}$ alkylthio, optionally substituted $C_{2-8}$ alkoxyalkyl, optionally substituted $C_{3-10}$ carbocyclyl, optionally substituted $C_{6-10}$ aryl, —OR$^5$, —NR$^{14}$R$^{15}$, —C(O)R$^8$, —SO$_2$R$^{16}$, and —NO$_2$.

3. The method of claim 1, wherein $R^1$ is selected from $C_{6-10}$ aryl optionally substituted with one or more $R^4$, or 5 to 6 membered heteroaryl optionally substituted with one or more $R^4$.

4. The method of claim 3, wherein $R^1$ is phenyl optionally substituted with one or more $R^4$.

5. The method of claim 3, wherein $R^1$ is pyridazinyl optionally substituted with one or more $R^4$.

6. The method of claim 3, wherein $R^1$ is pyrazolyl or 1-methyl pyrazolyl optionally substituted with one or more $R^4$.

7. The method of claim 1, wherein $R^3$ is $-(CH_2)_n-(C_{6-10}$ aryl) optionally substituted with one or more $R^9$.

8. The method of claim 7, wherein $R^3$ is phenyl, optionally substituted with one or more $R^9$.

9. The method of claim 7, wherein $R^3$ is unsubstituted.

10. The method of claim 8, wherein $R^9$ is selected from cyano, halogen, optionally substituted $C_{1-6}$ alkyl, or optionally substituted $C_{1-6}$ alkoxy.

11. The method of claim 10, wherein $R^9$ is selected from cyano, fluoro, chloro, methyl, ethyl, ethoxy, methoxy, trifluoromethyl, trifluoromethoxy or difluoromethoxy.

12. The method of claim 1, wherein $R^{17}$ is selected from hydrogen, methyl, ethyl, isopropyl, cyclopropyl, $-(CH_2)_2F$, $-(CH_2)_2OH$, $-(CH_2)_2OCH_3$, $-(CH_2)_2OC_2H_5$, $-(CH_2)_2OC_3H_7$, $-C(O)O$-t-Bu, $-C(O)CH_3$ or benzyl.

13. The method of claim 1, wherein $R^4$ is selected from halogen, optionally substituted $C_{1-6}$ alkyl, or $C_{7-14}$ aralkyl optionally substituted with one or more $R^{11}$, or two geminal $R^4$ together are oxo.

14. The method of claim 13, wherein $R^4$ is selected from fluoro, methyl, trifluoromethyl, $-(CH_2)_2OH$, benzyl, or two geminal $R^4$ together are oxo.

15. The method of claim 1, wherein ring A is unsubstituted.

16. The method of claim 1, wherein Z is oxygen.

17. The method of claim 1, wherein the bonds represented by a solid and dashed line are double bonds.

18. The method of claim 1, wherein the compound is selected from the group consisting of

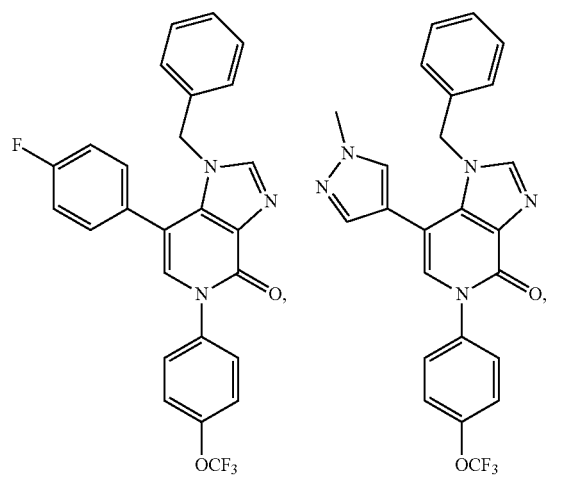

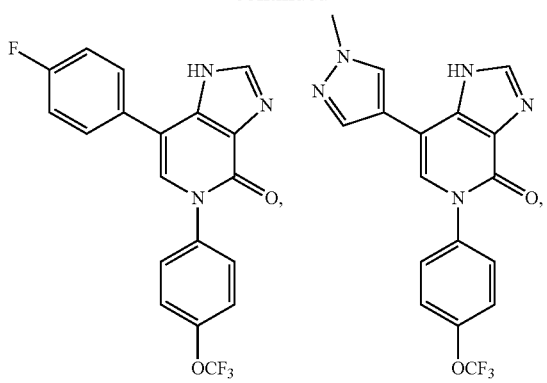

-continued

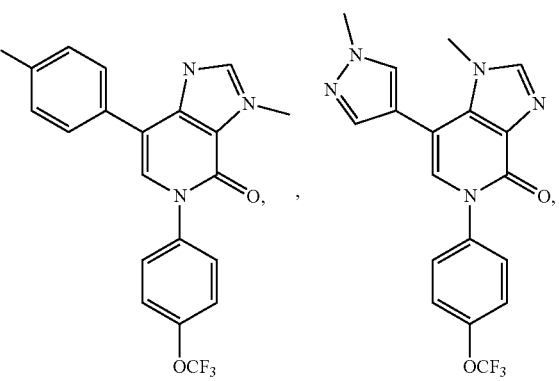

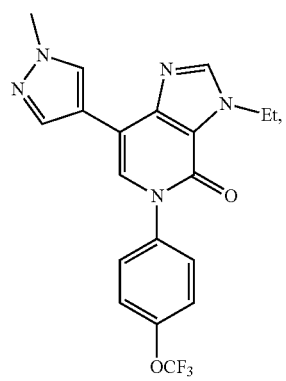

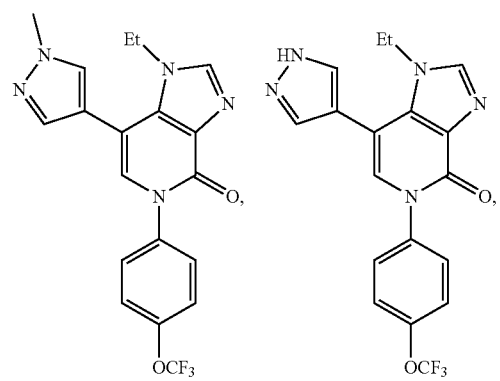

-continued
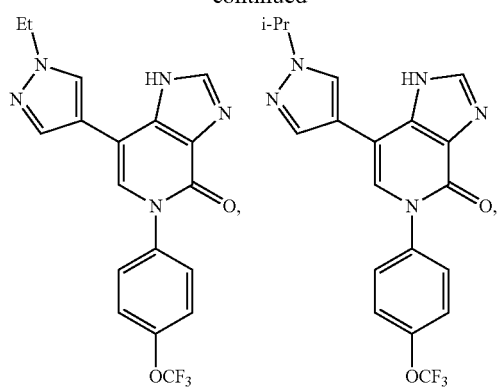
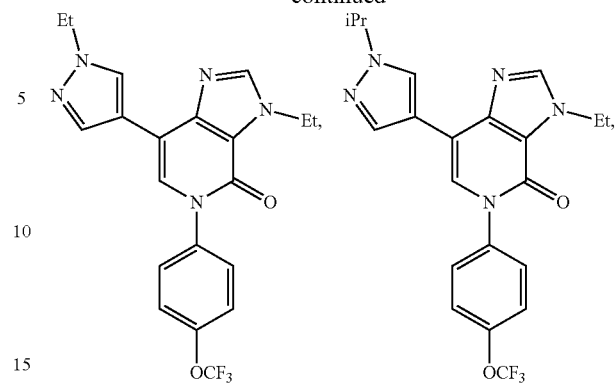
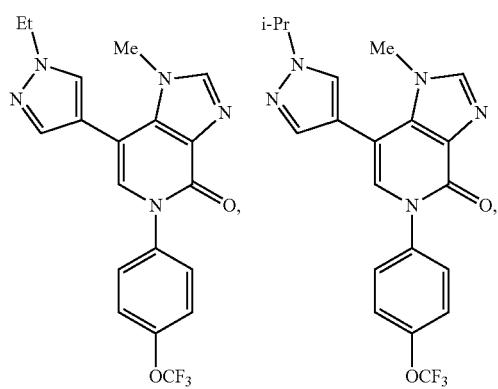
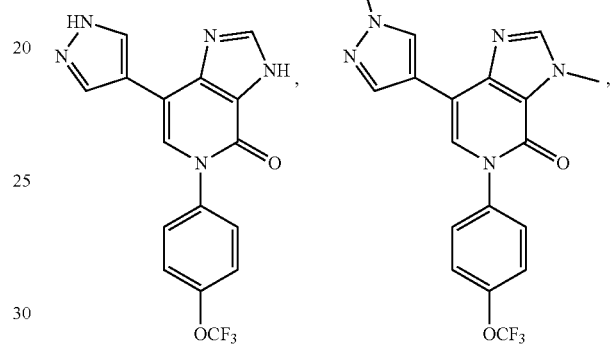
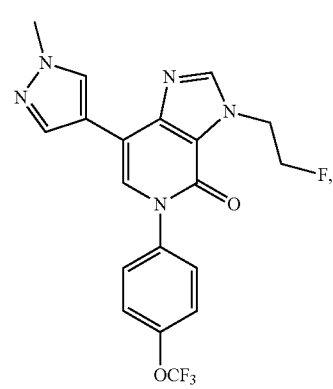
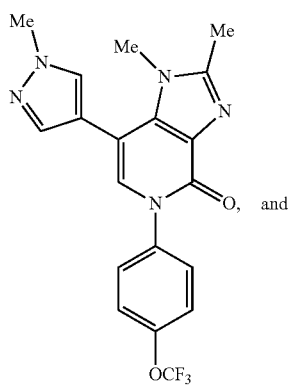
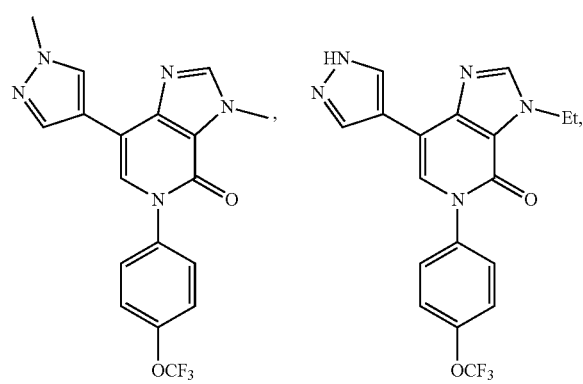
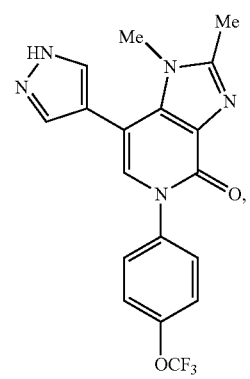
or pharmaceutically acceptable salts thereof.

19. The method of claim 18, wherein the compound is

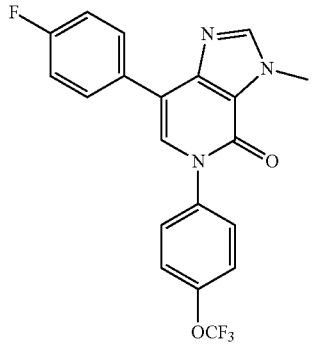

or a pharmaceutically acceptable salt thereof.

20. The method of claim 18, wherein the compound is

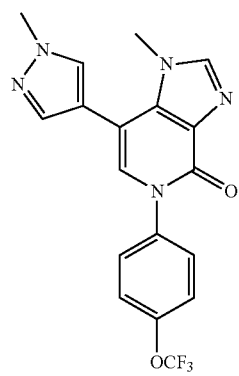

or a pharmaceutically acceptable salt thereof.

21. The method of claim 18, wherein the compound is

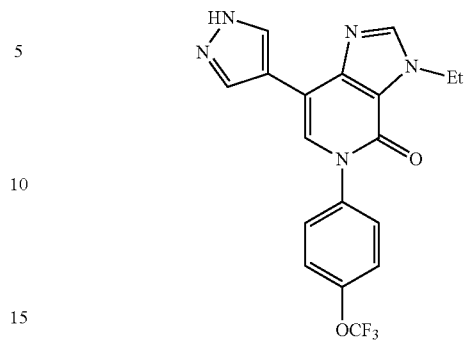

or a pharmaceutically acceptable salt thereof.

22. The method of claim 18, wherein the compound is

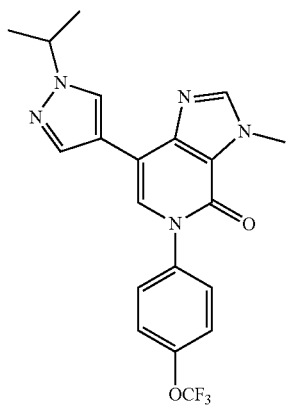

or a pharmaceutically acceptable salt thereof.

23. The method of claim 1, wherein the fibrotic condition is idiopathic pulmonary fibrosis.

24. The method of claim 1, wherein the compound is administered by inhalation.

* * * * *

UNITED STATES PATENT AND TRADEMARK OFFICE
CERTIFICATE OF CORRECTION

PATENT NO. : 9,675,593 B2
APPLICATION NO. : 15/162214
DATED : June 13, 2017
INVENTOR(S) : Brad Owen Buckman et al.

It is certified that error appears in the above-identified patent and that said Letters Patent is hereby corrected as shown below:

In the Claims

At Column 433, Line 49, "$R^{11}$," should be -- $R^{11}$; --.

At Column 436, Lines 20-33, " 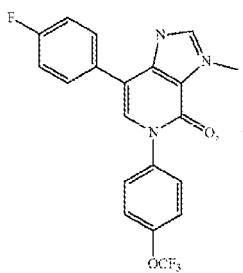 " should be -- 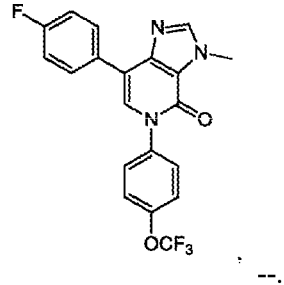 --.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*